(12) United States Patent
Shinozaki et al.

(10) Patent No.: US 7,368,630 B2
(45) Date of Patent: May 6, 2008

(54) ENVIRONMENTAL STRESS-RESPONSIVE PROMOTER AND A GENE ENCODING ENVIRONMENTAL STRESS-RESPONSIVE TRANSCRIPTIONAL FACTOR

(75) Inventors: Kazuo Shinozaki, Ibaraki (JP); Motoaki Seki, Kanagawa (JP); Miki Fujita, Ibaraki (JP)

(73) Assignee: Riken, Wako-shi, Saitama (JP)

( * ) Notice: Subject to any disclaimer, the term of this patent is extended or adjusted under 35 U.S.C. 154(b) by 0 days.

(21) Appl. No.: 11/470,154

(22) Filed: Sep. 5, 2006

(65) Prior Publication Data

US 2007/0094752 A1    Apr. 26, 2007

Related U.S. Application Data

(62) Division of application No. 10/495,918, filed as application No. PCT/JP02/11955 on Nov. 5, 2002, now abandoned.

(30) Foreign Application Priority Data

Nov. 19, 2001  (JP) .............................. 2001-353038
Jan. 29, 2002  (JP) .............................. 2002-20329

(51) Int. Cl.
C12N 15/82  (2006.01)
A01H 1/00   (2006.01)

(52) U.S. Cl. ..................... 800/289; 435/468
(58) Field of Classification Search ............. None
See application file for complete search history.

(56) References Cited

FOREIGN PATENT DOCUMENTS

| EP | 1 033 405 A2 | 6/2000 |
|---|---|---|
| EP | 1 209 228 A2 | 5/2002 |
| JP | 2000-60558 A | 2/2000 |
| JP | 2000-116259 A | 4/2000 |
| JP | 2000-116260 A | 4/2000 |
| JP | 2000-287685 A | 10/2000 |
| WO | WO-90 09447S A | 8/1990 |
| WO | WO-02/16655 A2 | 2/2002 |

OTHER PUBLICATIONS

Bevan et al. (NCBI, GenBank, Accession No. AL162508, Published Mar. 28, 2000).*
Kasuga et al. (Nature Biotechnology, vol. 17, pp. 287-291, Mar. 1999).*
Guarente et al. (TIG, 8:27-32, 1992).*
Lee et al. (Biochem. Biophys. Res. Commun. 284:133-41, 2001).*
Yamaguchi-Shinozaki et al. (Trends in Plant Science, 10:88-94, 2005).*
Logemann et al. (PNAS, 99:2428-2432, 2002).*
Liu et al. (European Journal of Biochemistry 262:247-257, 1999).*
Theologis, A. et al.; Nature 408 (6814) Accession No. E96497 (2000), Abstract.
XP 002321693 "*Arabidopsis thaliana*DNA chromosome 4, contig fragment No. 50"; Mar. 2000 EMBL-EBI Accession No. ATCHRIV50.
International Preliminary Examination Report issued in corresponding PCT Application No. PCT/JP2002/011955 (dated Aug. 27, 2004).
Li, Y., database EMBL/GenBank/DDBJ, Jun. 19, 2002.
Seki, M. et al., The plant cell, (Jan. 2001), vol. 13, No. 1, pp. 61 to 72.
Kasuga, M. et al., Nature Biotechnology, (Mar. 1999), vol. 17, No. 3, pp. 287 to 291.
Shinwari, Z. K. et al., Biochemical and Biophysical Research Communication, Sep. 8, 1998 vol. 250, No. 1, pp. 161 to 170.
Bevan et al. (NCBI, GenBank, Accession No. AL 162508), Published Mar. 18, 2000).
Kim et al. (Plant Molecular Biology, 24: 105:117, 1994).
Yamaguchi-Shinozaki et al. (The Plant Cell, 6:251-264, 1994).
Velvekens et al. (PNAS, 85:5536-5540, 1988).
Grover et al. (Current Science, 80:206-216, Jan. 2001).

* cited by examiner

Primary Examiner—Phuong T. Bui
Assistant Examiner—Vinod Kumar
(74) Attorney, Agent, or Firm—Birch, Stewart, Kolasch and Birch, LLP

(57) ABSTRACT

The present invention provides a method of regulating expression of a gene by (a) preparing a recombinant plant cell line, plant tissue or plant with an expression vector having an abiotic environmental stress-responsive promoter of SEQ ID NO: 27 and the gene downstream thereof; and (b) culturing and cultivating the recombinant plant cell, plant tissue or plant under an abiotic environmental stress, wherein the promoter regulates the expression of the gene under the abiotic environmental stress.

4 Claims, 162 Drawing Sheets

Dry treatment

Dry treatment

Dry treatment

Dry treatment

Cold treatment

Dry treatment

Cold treatment

Dry treatment

NaCl treatment

Dry treatment

Dry treatment

Dry treatment

NaCl treatment

NaCl treatment

NaCl treatment

NaCl treatment

Dry treatment

NaCl treatment

NaCl treatment

ENVIRONMENTAL STRESS-RESPONSIVE PROMOTER AND A GENE ENCODING ENVIRONMENTAL STRESS-RESPONSIVE TRANSCRIPTIONAL FACTOR

This application is a Divisional of application Ser. No. 10/495,918 filed on May 18, 2004 now abandoned, and for which priority is claimed under 35 U.S.C. 120; and this application claims priority of International Application No. PCT/JP02/11955 filed on Nov. 5, 2002 under 35 U.S.C. 119; the entire contents of all are hereby incorporated by reference.

TECHNICAL FIELD

The present invention relates to an environmental stress-responsive promoter and a gene encoding environmental stress-responsive transcriptional factor.

BACKGROUND ART

Large quantities of genomic and cDNA sequences have been determined with respect to a number of organisms by gene sequencing projects. In a plant model, *Arabidopsis thaliana*, the complete genomic sequences of two chromosomes have been determined (Lin, X. et al., (1999), Nature 402, 761-768; and Mayer, K. et al., (1999), Nature 402, 769-777).

The expressed sequence tag (EST) project also has greatly contributed to the discovery of expression genes (Hofte, H. et al., (1993), Plant J. 4, 1051-1061; Newman, T. et al., (1994), Plant Physiol. 106, 1241-1255; and Cooke, R. et al., (1996), Plant J. 9, 101-124; and Asamizu, E. et al., (2000), DNA Res. 7, 175-180). For example, the database of EST (dbEST) of the National Center for Biotechnology Information(NCBI) includes partial cDNA sequences, in which more than half (about 28,000 genes) of the total genes are reproduced, (as estimated from the gene content of *Arabidopsis thaliana* chromosome 2 completely sequenced [Lin. X. et al., (1999), Nature 402, 761-768]).

Recently, microarray (DNA chip) technology has become a useful tool for analyzing genome-scale gene expression (Schena, M. et al., (1995), Science 270, 467-470; Eisen M. B. and Brown, P. O. (1999), Methods Enzymol. 303, 179-205). In the technology using a DNA chip, cDNA sequences are arrayed on a slide glass in a density of not smaller than 1,000 genes/cm$^2$. The cDNA sequences thus arrayed are hybridized simultaneously with a pair of cDNA probes tagged with two color fluorescent labels, which have been prepared from RNA samples of different types of cells or tissues. In this manner, a large amount of genes can be directly analyzed and compared for gene expression. This technology was demonstrated for the first time by analyzing 48 *Arabidopsis* genes for differential expression in root and shoots (Schene, M. et al., (1995), Science 270, 467-470). Furthermore, a microarray was used in investigating 1,000 clones randomly taken from a human cDNA library in order to identify a novel gene responsive to heat shock and protein kinase C activation (Schena, M. et al., (1996), Proc. Natl. Acad. Sci. USA, 93, 10614-10619).

In another method, a DNA chip is used in analyzing the expression profile of an inflammatory-disease associated gene under various induction conditions (Heller, R. A. et al., (1997), Proc. Natl. Acad. Sci. USA, 94, 2150-2155). Furthermore, using a microarray, a yeast genome having more than 6,000 coding sequences has been analyzed for dynamic expression (DeRisi, J. L. et al., (1997) Science, 278, 680-686; and Wodicka, L. et al., (1997), Nature Biotechnol. 15, 1359-1367).

However, in the field of plant science, only a few reports have been made on microarray analysis (Schena, M. et al., (1995), Science 270, 467-470; Ruan, Y. et al., (1998), Plant J. 15, 821-833; Abaroni. A, et al., (2000), Plant Cell 12, 647-661; and Reymond, P. et al., (2000), Plant Cell 12, 707-719).

The growth of plants is significantly affected by environmental stresses such as drought, high salinity and low temperature. Of the stresses, drought or water deficiency is the most critical factor that limits growth of plants and productions of crops. Such a drought stress causes various biochemical and physiological responses in plants.

To survive under these conditions of stress, plants acquire responsivity and adaptability to the stresses. Recently, several types of genes responsive to drought at a transcriptional level have been reported (Bohnert, H. J. et al., (1995), Plant Cell 7, 1099-1111; Ingram J., and Bartels, D. (1996), Plant Mol. Biol. 47, 377-403; Bray, E. A. (1997), Trends Plant Sci. 2, 48-54; Shinozaki, K., and Yamaguchi-Shinozaki, K. (1997), Plant Physiol. 115, 327-334; Shinozaki, K., and Yamaguchi-Shinozaki, K. (1999), "Molecular responses to drought stress. Molecular responses to cold, drought, heat and salt stress in higher plants", edited by Shinozaki, K. and Yamaguchi-Shinozaki, K. R. G. Landes Company; and Shinozaki, K., and Yamaguchi-Shinozaki, K. (2000), Curr. Opin. Plant Biol. 3, 217-223).

On the other hand, in an attempt to improve stress resistance of plants by introducing a gene, stress-inducible genes have been used (Holmberg, J., and Bulow, L., (1998), Trends Plant Sci. 3, 61-66; and Bajaj, S. et al., (1999), Mol. Breed. 5, 493-503). Not only to further clarify the mechanism of stress resistance and stress responsivity of a higher plant at a molecular level but also to improve the stress resistance of a crop by gene manipulation, it is important to analyze the function of a stress-inducible gene.

Dehydration responsive element and C-repeat sequence (DRE/CRT) has been identified as an important cis-acting element when drought, high salt and cold stress-responsive genes are expressed in an ABA independent manner, where ABA refers to abscisic acid, a kind of plant hormone and serves as a signal transmission factor of seed dormancy and environmental stress (Yamaguchi-Shinozaki, K., and Shinozaki, K. (1994), Plant Cell 6, 251-264; Thomashow, M. F. et al., (1999), Plant Mol. Biol. 50, 571-599; and Shinozaki, K., and Yamaguchi-Shinozaki, K. (2000), Curr. Opin. Plant Biol. 3, 217-223). Furthermore, a transcriptional factor (DREB/CBF) involved in DRE/CRT responsive gene expression has been closed (Stockinger, E. J. et al., (1997), Proc. Natl. Acad. Sci. USA 94, 1035-1040; Liu, Q. et al., (1998), Plant Cell 10, 1391-1406; Shinwari, Z. K. et al., (1998), Biochem. Biophys. Res. Commun. 250, 161-170; and Gilmour, S. J. et al., (1998), Plant J. 16, 433-443). DREB1/CBF is considered to function in cold-responsive gene expression, whereas DREB2 is involved in drought-responsive gene expression. Strong resistance to freezing stress was observed in a transgenic *Arabidopsis* plant that overexpresses CBF1 (DREB1B) cDNA under the control of a cauliflower mosaic virus (CaMV) 35S promoter (Jaglo-Ottosen, K. R. et al., (1998), Science 280, 104-106).

The present inventors have reported that when DREB1A (CBF3) cDNA molecules are overexpressed in transgenic plants under the control of a CaMV 35S promoter or a stress-inducible rd29A promoter, strong constitutive expression of stress-inducible DREB1A target genes are induced to improve resistance to freezing, drought and salt stresses (Liu, Q. et al., (1998), Plant Cell 10, 1391-1406; and Kasuga, M. et al., (1999), Nature Biotechnol. 17, 287-291). Furthermore, the present inventors have already identified six DREB1A target genes such as rd29A/lti78/cor78, kin1, kin2/cor6.6, cor15a, rd17/cor47, and erd10 (Kasuga, M. et al., (1999), Nature Biotechnol. 17, 287-291). However, it has not yet been sufficiently elucidated how the overexpressed DREB1A cDNA improves stress resistance to freezing, drought and salt in a transgenic plant. To investigate the molecular mechanisms of drought and freezing resistance, it is important to identify and analyze as many genes controlled by DREB1A as possible.

DISCLOSURE OF THE INVENTION

The present invention is directed to providing an environmental stress-responsive promoter and a gene encoding an environmental stress-responsive transcriptional factor.

The present inventors have intensively studied to solve the aforementioned problems. As a result, they succeeded in identifying novel genes responsive to cold, drought and salt stresses and isolating promoter regions thereof by using cDNA microarray analysis, thereby accomplishing the present invention.

More specifically, the present invention is directed to an environmental stress-responsive promoter comprising DNA of the following (a), (b) or (c):
(a) DNA consisting of any nucleotide sequence selected from SEQ ID NOS: 1 to 90;
(b) DNA consisting of a nucleotide sequence comprising a deletion, substitution or addition of one or more nucleotides relative to any nucleotide sequence selected from SEQ ID NOS: 1 to 90, and functioning as an environmental stress responsive promoter; and
(c) DNA hybridizing under stringent conditions to DNA consisting of any nucleotide sequence selected from SEQ ID NOS: 1 to 90, and functioning as an environmental stress responsive promoter.

Examples of environmental stress include at least one selected from the group consisting of cold stress, drought stress, and salt stress.

The present invention is also directed to an expression vector comprising the promoter mentioned above, or an expression vector having an arbitrary gene integrated therein.

Furthermore, the present invention is directed to a transformant comprising the expression vector.

Moreover, the present invention is directed to a transgenic plant, such as a plant body, plant organ, plant tissue or plant culture cell, comprising the expression vector.

The present invention is still further directed to a method for producing a stress-resistant plant, comprising culturing or cultivating the transgenic plant.

On the other hand, the present invention identified novel genes encoding cold, drought and salt stress-responsive transcriptional factors by use of cDNA microarray analysis, thereby accomplishing the present invention.

More specifically, the present invention is directed to a gene encoding an environmental stress-responder transcriptional factor comprising an amino acid of the following (a) or (b):
(a) any amino acid sequence selected from SEQ ID NOS: 2n (n is an integer from 47 to 82);
(b) an amino acid sequence comprising a deletion, substitution or addition of one or more amino acids relative to any amino acid sequence selected from SEQ ID NOS: 2n (n is an integer from 47 to 82), functioning as an environmental stress-responsive transcriptional factor.

Also, the present invention is directed to a gene according to claim 1, comprising DNA of the following (a), (b) or (c):
(a) DNA consisting of any nucleotide sequence selected from SEQ ID NOS: 2n−1 (n is an integer from 47 to 82);
(b) DNA consisting of a nucleotide sequence comprising a deletion, substitution or addition of one or more nucleotides relative to any nucleotide sequence selected from SEQ ID NOS: 2n−1 (n is an integer from 47 to 82), and encoding an environmental stress-responsive transcriptional factor; and
(c) DNA hybridizing under stringent conditions to DNA consisting of any nucleotide sequence selected from SEQ ID NOS: 2n−1 (n is an integer from 47 to 82), and encoding an environmental stress-responsive transcriptional factor.

In the present invention, examples of environmental stress include at least one selected from the group consisting of cold stress, drought stress, and salt stress.

The present invention is also directed to an expression vector containing the gene, a transformant containing the expression vector, and a transgenic plant containing the expression vector.

Furthermore, the present invention is directed to a transgenic plant, such as a plant body, plant organ, plant tissue or plant culture cell.

Moreover, the present invention is directed to a method for producing a stress-resistant plant, comprising culturing or cultivating the transgenic plant.

Hereinafter, the present invention will be described in detail.

The present invention constructed full-length cDNA libraries from *Arabidopsis* plants placed under different conditions, such as dehydration-treated plants and cold-treated plants (Seki. M. et al., (1998), Plant J. 15, 707-720), by the biotinylated CAP trapper method (Carninci, P. et al., (1996), Genomics, 37, 327-336). Then, *Arabidopsis* full-length cDNA microarrays were respectively prepared using about 1,300 full-length cDNA molecules and about 7,000 full-length cDNA molecules both containing stress-inducible genes. Besides using these dehydration and cold-inducible full-length cDNA molecules, another cDNA microarray was prepared using a DREB1A target gene, a transcriptional regulator for controlling expression of a stress-responsive gene. Thereafter, expression patterns of genes under drought and cold stress were monitored to exhaustively analyze stress-responsive genes. As a result, from the full-length cDNA microarray containing about 1,300 of full-length cDNA molecules, novel environmental stress-responsive genes, that is, 44 drought-inducible genes and 19 cold-inducible genes were isolated. 30 out of the 44 drought-inducible genes, and 10 out of the 19 cold-inducible genes were novel stress-inducible genes. Moreover, it was found that 12 stress-inducible genes were DREB1A target genes and 6 out of the 12 stress-inducible genes were novel genes. As a result of the analysis, 301 drought-inducible genes, 54 cold-inducible genes and 211 high salt-stress inducible genes were isolated from a cDNA microarray containing about 7,000 full-length cDNA molecules.

Thereafter, not only promoter regions but also environmental genes encoding environmental stress-responsive transcriptional factors were successfully isolated from these environmental stress-responsive genes.

As described above, a full-length cDNA microarray is useful tool for analyzing the expression manner of *Arabi-*

*dopsis thaliana* drought- and cold-stress inducible genes and analyzing the target gene of a stress associated transcriptional regulator.

1. Isolation of Promoter

The promoter of the present invention contains a cis-element which is present upstream of a gene encoding a stress-responsive protein expressed by an environmental stress such as a cold, drought, or high salt stress and which activates the transcription of a gene present downstream thereof by binding of a transcriptional factor. Examples of such a cis-element include a dehydration responsive element (DRE), an abscisic acid responsive element (ABRE), and a cold-stress responsive element. Examples of genes encoding proteins binding to these elements include a DRE binding protein 1A gene (referred to also as a "DREB1A gene"), DRE binding protein 1C gene (referred to also as a "DREB1C gene"), DRE binding protein 2A gene (referred to also as a "DREB2A gene"), and DRE binding protein 2B gene (referred to also as a "DREB2B gene").

In isolating a promoter of the present invention, first, stress-responsive genes are isolated by using a microarray. In constructing a microarray, use may be made of about 1,300 cDNA molecules in total including genes isolated from *Arabidopsis* full-length cDNA libraries, responsive to dehydration (RD) genes, early responsive to dehydration (ERD) genes, kin1 genes, kin2 genes, and cor15a genes; and furthermore, α-tubulin genes as an internal standard; and moreover, mouse nicotinic acetylcholine receptor epsilon subunit (nAChRE) genes and mouse glucocorticoid receptor homologous genes, as negative controls.

As a microarray used in isolating the promoter of the present invention, use may be made of about 7,000 cDNA molecules in total including genes isolated from an *Arabidopsis* full-length cDNA library, responsive to dehydration (RD) genes, early responsive to dehydration(ERD) genes, and PCR amplification fragments as an internal standard obtained from λ control template DNA fragments (TX803, manufactured by Takara Shuzo); and mouse nicotinic acetylcholine receptor epsilon subunit (nAChRE) genes and mouse glucocorticoid receptor homologous genes, as negative controls.

A plasmid DNA extracted with a plasmid preparation device (manufactured by Kurabo) is sequenced by sequence analysis using a DNA sequencer (ABI PRISM 3700, PE Applied Biosystems, CA, USA). Based on the GenBank/EMBL database, the obtained sequence is screened for homology by using the BLAST program.

After poly A selection is performed, reverse transcription is carried out to synthesize double-standard DNA molecules and a cDNA molecule is inserted into a vector.

The cDNA molecule inserted into a vector for constructing cDNA libraries is amplified by PCR using complementary primers to the sequences of vectors on both sides of the cDNA molecule. Examples of such vectors include λZAPII and λPS.

A microarray can be prepared according to a conventional method, which is not particularly limited. For example, using a gene tip microarray stamp machine GTMASS SYSTEM (manufactured by Nippon Laser & Electronics Lab.), the above obtained PCR product is loaded from a microtiter plate and spotted on a microslide glass at predetermined intervals. Then, to prevent a non-specific signal from being expressed, the slide is immersed into a blocking solution.

Examples of plant materials include a plant strain obtained by destroying specific genes as well as wild type plants. A transgenic plant having cDNA of DREB1A introduced therein may be used. Examples of plant species include *Arabidopsis thaliana*, tobacco and rice. Of them, *Arabidopsis thaliana* is preferable.

Dehydration- and cold-stress treatments can be carried out according to a known method (Yamaguchi-Shinozaki, K., and Shinozaki, K. (1994), Plant Cell 6, 251-264).

After plant bodies (wild type plants and DREB1A overexpression transformants) are exposed to stress, they are sampled and stored in cryogenic conditions with liquid nitrogen. The wild type and DREB1A overexpression transformants are used in an experiment to identify a DREB1A target gene. From plant bodies, mRNA is isolated and purified by a known method or a kit.

In the presence of Cy3 dUTP or Cy5 dUTP for labeling (Amersham Pharmacia), each of mRNA samples is subjected to reverse transcription and then used in hybridization.

After the hybridization, the microarray is scanned with a scanning laser microscope or the like. As a program for analyzing data of a microarray, Imagene Ver 2.0 (BioDiscovery) and QuantArray (GSI Lumonics) etc. may be used.

After the scanning, a plasmid having a target gene is prepared. In this way, the target genes are isolated.

A promoter region is determined by analyzing the nucleotide sequence of the gene isolated above and using a gene analysis program based on the genomic information of database (GenBank/EMBL, ABRC). The isolated genes can be classified into ones inducible by both dehydration and cold stress, ones inducible specifically by drought stress, and one inducible specifically by cold stress. According to the gene analysis program, from the genes mentioned above, 90 types of genes below can be identified.

(FL03-07-F12, FL04-12-F24, FL04-14-N10, FL04-14-P24, FL04-17-I03, FL04-17-M08, FL04-17-M22, FL05-05-A17, FL05-05-F20, FL05-05-G20, FL05-09-N09, FL05-10-J09, FL05-10-M08, FL05-11-H09, FL05-12-H13, FL05-13-120, FL05-14-E15, FL05-14-E16, FL05-16-F03, FL05-16-H23, FL05-18-M07, FL05-18-O21, FL05-19-F21, FL05-19-O22, FL05-21-K17, FL06-10-F03, FL06-12-H12, FL07-12-I23, FL08-08-H23, FL08-08-O14, FL08-09-M05, FL08-10-K08, FL08-11-P07, FL08-13-F10, FL08-19-D04, FL08-19-G15, FL09-06-B11, FL09-07-G17, FL09-10-A12, FL09-13-P15, FL02-05-I05, FL04-12-N15, FL04-16-P21, FL04-17-N22, FL04-20-P19, FL02-09-H01, FL05-01-D08, FL05-02-G08, FL05-02-O17, FL05-07-L13, FL05-08-B14, FL05-09-N10, FL05-11-L01, FL05-12-J09, FL05-14-D24, FL05-14-F20, FL05-14-I08, FL05-15-C04, FL05-15-E19, FL05-18-A06, FL05-18-H15, FL05-19-C02, FL05-20-M16, FL05-20-N18, FL05-21-E06, FL05-21-L12, FL06-07-B08, FL06-08-H20, FL06-09-N04, FL06-11-K21, FL07-07-G15, FL07-12-D17, FL08-11-C23, FL08-13-G20, FL08-15-M21, FL08-18-N19, FL08-19-C07, FL08-19-P05, FL09-07-G09, FL09-07-G15, FL09-10-J18, FL09-11-I12, FL09-12-B03, FL09-16-I11, FL09-16-M04, FL11-01-J18, FL11-07-D13, FL11-07-F02, FL11-07-N15 and FL11-10-D10). The promoter regions of these genes are represented by SEQ ID NOS: 1 to 90, respectively.

As long as a promoter of the present invention acts as an environmental stress-responsive promoter, use may be made of any promoter having a nucleotide sequence selected from SEQ ID NOS: 1 to 90 wherein one or more nucleotides, preferably one or several nucleotides (for example 1 to 10, preferably 1 to 5) may be deleted, substituted or added. Furthermore, DNA hybridizing with the DNA comprising any nucleotide sequence selected from SEQ ID NOS: 1 to 90 under stringent conditions and acting as an environmental stress-responsive promoter is also included in the promoter of the present invention.

Once the nucleotide sequence of a promoter according to the present invention is determined, the promoter can be obtained by chemical synthesis, PCR using a cloned probe as a template, or hybridization using a DNA fragment having the nucleotide sequence as a probe. Furthermore, a mutant of the promoter of the present invention, which has the same functions as those of a non-mutated promoter, can be also synthesized by a site-specific mutagenesis or the like.

To introduce a mutation into a promoter sequence, a known method such as the Kunkel method. Gapped duplex method or an equivalent method may be employed. A mutation may be introduced by using a mutation-introducing kit (for example, Mutant-K manufactured by Takara or Mutant-G manufactured by Takara) which uses a site-specific mutagenesis or by using the LA PCR in vitro mutagenesis series kit (manufactured by Takara).

The term "functioning as an environmental stress-responsive promoter" used herein refers to a function of activating transcription caused by binding RNA polymerase to the promoter when the promoter is exposed to a predetermined environmental stress condition.

The term "environmental stress" used herein generally refers to an abiotic stress such as drought stress, cold stress, high salt stress, or intensive light stress. The term "drought" used herein refers to a state of water deficiency, and the term "cold" used herein refers to a state where an object is exposed to a lower temperature than the optimum living temperature for each organism (e.g., in the case of *Arabidopsis thaliana*, it is exposed to a temperature of −20 to +21° C. continuously for one hour to several weeks). The term "high salt" used herein refers to a state where a plant is treated with NaCl of 50 mM to 600 mM in concentration continuously for 0.5 hours to several weeks. The term "intensive light stress" used herein refers to a state where too intensive light to use for photosynthesis is applied to a plant, and corresponds to a case where, for example, light of 5,000 to 10,000 Lx or more is applied. These environmental stresses may be applied singly or in combination.

The plant promoter of the present invention includes a promoter having a nucleotide sequence represented by SEQ ID NOS: 1 to 90 wherein a nucleotide sequence may be added to the 3' end in order to increase transcriptional efficiency or a nucleotide sequence may be deleted from the 5' end to the extent not to lose the activity of a promoter.

Furthermore, the promoter of the present invention includes DNA which hybridizes with DNA consisting of any nucleotide sequence selected from SEQ ID NOS: 1 to 90 under stringent conditions and acts as an environmental stress-responsive promoter. The term "stringent conditions" used herein refers to the conditions of sodium concentration of 25 to 500 mM, preferably 25 to 300 mM, and a temperature of 42 to 68° C., preferably 42 to 65° C.; more preferably, conditions of 5×SSC (83 mM NaCl, 83 mM sodium citrate) and a temperature 42° C.

2. Construction of Expression Vector

An expression vector of the present invention can be obtained by ligating (inserting) a promoter according to the present invention to an appropriate vector. The vector into which a promoter of the present invention is to be inserted is not particularly limited as long as it can be replicated in a host. Examples of such a vector include a plasmid, shuttle vector and helper plasmid.

Examples of such a plasmid DNA include plasmids derived from *Escherichia coli* (e.g., pBR322, pBR325, pUC118, pUC119, pUC18, pUC19, and pBluescript); plasmids derived from *Bacillus subtilis* (e.g., pUB110 and pTP5); and plasmids derived from yeasts (e.g., YEp13 and YCp50). Examples of a phage DNA include λ phages (Charon4A, Charon21A EMBL3, EMBL4, λgt10, λgt11, and λZAP). Further animal virus vectors such as retrovirus and a vaccinia virus and insect virus vectors such as a baculovirus can be also used.

To insert a promoter according to the present invention into a vector, use may be made of a method of digesting a purified DNA with appropriate restriction enzymes, inserting the obtained DNA fragment into the restriction site of a suitable vector DNA or a multi-cloning site, and ligating it to the vector.

In the present invention, to express an arbitrary gene, the arbitrary gene can be further inserted into the aforementioned expression vector. The technique inserting an arbitrary gene is the same as the method inserting a promoter into a vector. An arbitrary gene is not particularly limited. Examples of the gene include genes shown in Table 1 and known genes other than those.

In a case where a reporter gene, for example, a GUS gene, widely used in plants is linked to the 3' end of a promoter of the present invention, the strength of the promoter can be easily evaluated by checking GUS activity. As such a reporter gene other than the GUS gene, luciferase and a green fluorescent protein can be used.

As described above, various types of vectors can be used in the present invention. Further, a desired gene is ligated to the promoter of the present invention in a sense or antisense direction and then, the construction can be inserted into a vector such as pB1101 (Clontech) called a binary vector.

3. Isolation of Transcriptional Factor

A transcriptional factor binds to a cis element which is present upstream of a gene and activates the transcription of the gene present downstream thereof. The transcriptional factors isolated in the present invention are induced by environmental stresses such as a low temperature, dehydration, and high salt concentration.

Environmental stress-responsive transcriptional factors are roughly divided into those belonging to a DREB family, ERF family, zinc finger family, WRKY family, MYB family, bHLH family, NAC family, homeo domain family and bZIP family.

In isolating a transcriptional factor, first, stress responsive genes are isolated by using a microarray. As a microarray, use may be made of about 7,000 cDNA molecules in total including genes isolated from *Arabidopsis* full-length cDNA libraries, responsive to dehydration (RD) genes, early responsive to dehydration (ERD) genes; PCR amplification fragments obtained from a λ control template DNA fragment (TX803, manufactured by Takara Shuzo), as an internal standard; and mouse nicotinic acetylcholine receptor epsilon subunit (nAChRE) genes and mouse glucocorticoid receptor homologous genes, a negative controls.

A plasmid DNA extracted by a plasmid preparation device (manufactured by Kurabo) is sequenced by sequence analysis using a DNA sequencer (ABI PRISM 3700, PE Applied Biosystems, CA, USA). Based on the GenBank/EMBL database, the obtained sequence is screened for homology by using the BLAST program.

After poly A selection is performed, reverse transcription is carried out to synthesize a double-stranded DNA molecule and a cDNA molecule is inserted into a vector.

The cDNA molecule inserted into a vector for constructing cDNA libraries is amplified by PCR using complementary primers to the sequences of vectors on both sides of the cDNA molecule. Examples of such vectors include λZAPII and λPS.

A microarray can be prepared according to a conventional method, which is not particularly limited. For example, using a gene tip microarray stamp machine GTMASS SYSTEM (manufactured by Nippon Laser & Electronics Lab.), the above obtained PCR product is loaded from the microtiter plate and spotted on a microslide glass at predetermined intervals. Then, to prevent a non-specific signal from being expressed, the slide is immersed into a blocking solution.

Examples of plant materials include a plant strain obtained by destroying a specific gene as well as wild type plants. A transgenic plant having a cDNA of DREB1A introduced therein may be used. Examples of plant species include *Arabidopsis thaliana*, tobacco and rice. Of them, *Arabidopsis thaliana* is preferable.

Dehydration- and cold-stress treatments can be carried out according to a known method (Yamaguchi-Shinozaki, K., and Shinozaki, K. (1994), Plant Cell 6, 251-264).

After plant bodies (wild type plants and DREB1A overexpression transformants) are exposed to stress, they are sampled and stored in cryogenic conditions with liquid nitrogen. The wild type and DREB1A overexpression transformants are used in an experiment to identify a DREB1A target gene. From plant bodies, mRNA is isolated and purified by a known method or a kit.

In the presence of Cy3 dUTP or Cy5 dUTP for labeling (Amersham Pharmacia), each of mRNA samples is subjected to reverse transcription and then used in hybridization.

After hybridization, the microarray is scanned with a scanning laser microscope or the like. As a program for analyzing data of a microarray, Imagene Ver 2.0 (BioDiscovery) and QuantArray (GSI Lumonics) etc., may be used.

After the scanning, a plasmid having a target gene is prepared. In this way, the target genes are isolated.

A transcriptional factor is determined by analyzing the nucleotide sequence of the gene isolated above and using a gene analysis program based on the genomic information of database (GenBank/EMBL, ABRC). The isolated genes can be classified into ones inducible by both drought and cold stress, ones inducible specifically by drought stress, and one inducible specifically by cold stress. According to the gene analysis program, from the genes mentioned above, genes encoding 36 types of transcriptional factors can be identified. The nucleotide sequences of the genes encoding 36 types of transcriptional factors are represented by SEQ ID NOS: 2n−1 (n is an integer of 47 to 82) and amino acid sequences of the transcriptional factors are represented by SEQ ID NOS: 2n (n is an integer of 47 to 82). Sequence ID numbers and the names of genes encoding transcriptional factors are shown in Table 1.

TABLE 1

| Name of gene | SEQ ID NO: |
| --- | --- |
| RAFL05-11-M11 | SEQ ID NO: 93 |
| RAFL06-11-K21 | SEQ ID NO: 95 |
| RAFL05-16-H23 | SEQ ID NO: 97 |
| RAFL08-16-D06 | SEQ ID NO: 99 |
| RAFL08-16-G17 | SEQ ID NO: 101 |
| RAFL06-08-H20 | SEQ ID NO: 103 |
| RAFL07-10-G04 | SEQ ID NO: 105 |
| RAFL04-17-D16 | SEQ ID NO: 107 |

TABLE 1-continued

| Name of gene | SEQ ID NO: |
| --- | --- |
| RAFL05-19-M20 | SEQ ID NO: 109 |
| RAFL08-11-M13 | SEQ ID NO: 111 |
| RAFL04-15-K19 | SEQ ID NO: 113 |
| RAFL05-11-L01 | SEQ ID NO: 115 |
| RAFL05-14-C11 | SEQ ID NO: 117 |
| RAFL05-19-G24 | SEQ ID NO: 119 |
| RAFL05-20-N02 | SEQ ID NO: 121 |
| RAFL05-18-H12 | SEQ ID NO: 123 |
| RAFL06-10-D22 | SEQ ID NO: 127 |
| RAFL06-12-M01 | SEQ ID NO: 129 |
| RAFL05-14-D24 | SEQ ID NO: 131 |
| RAFL05-20-N17 | SEQ ID NO: 133 |
| RAFL04-17-F21 | SEQ ID NO: 135 |
| RAFL09-12-N16 | SEQ ID NO: 137 |
| RAFL05-19-I05 | SEQ ID NO: 139 |
| RAFL05-21-I22 | SEQ ID NO: 141 |
| RAFL08-11-H20 | SEQ ID NO: 143 |
| RAFL05-21-C17 | SEQ ID NO: 145 |
| RAFL05-08-D06 | SEQ ID NO: 147 |
| RAFL05-20-M16 | SEQ ID NO: 149 |
| RAFL11-01-J18 | SEQ ID NO: 151 |
| RAFL11-09-C20 | SEQ ID NO: 153 |
| RAFL05-18-N16 | SEQ ID NO: 155 |
| RAFL11-10-D10 | SEQ ID NO: 157 |
| RAFL04-17-N22 | SEQ ID NO: 159 |
| RAFL05-09-G15 | SEQ ID NO: 161 |
| RAFL05-21-L12 | SEQ ID NO: 163 |

Note that as long as a transcriptional factor of the present invention functions as an environmental stress-responsive transcriptional factor, use may be made of any transcriptional factor having a nucleotide sequence selected from SEQ ID NOS: 2n−1 (n is an integer of 47 to 82) wherein one or more nucleotides, preferably one or several nucleotides (for example 1 to 10, preferably 1 to 5) have been deleted, substituted or added. Furthermore, DNA hybridizing with the DNA comprising any nucleotide sequence selected from SEQ ID NOS. 2n−1 (n is an integer of 47 to 82) under stringent conditions and encoding an environmental stress-responsive transcriptional factor is also included in the transcriptional factor of the present invention. The term "stringent conditions" used herein refers to the conditions of sodium concentration of 25 to 500 mM, preferably 25 to 300 mM, and a temperature of 42 to 68° C., preferably 42 to 65° C.; more preferably, conditions of 5×SSC (83 mM NaCl, 83 mM sodium citrate) and a temperature of 42° C.

36 types of transcriptional factors isolated in the present invention may be classified as follows.

(1) DREB family: RAFL05-11-M11, RAFL06-11-K21, RAFL05-16-H23, RAFL08-16-D16;
(2) ERF family: RAFL08-16-G17, RAFL06-08-H20;
(3) Zinc finger family: RAFL07-10-G04, RAFL04-17-D16, RAFL05-19-M20, RAFL08-11-M13, RAFL04-15-K19, RAFL05-11-L01, RAFL05-14-C11, RAFL05-19-G24, RAFL05-20-N02;
(4) WRKY family: RAFL05-18-H12, RAFL05-19-E19, RAFL06-10-D22, RAFL06-12-M01;
(5) MYB family: RAFL05-14-D24, RAFL05-20-N17, RAFL04-17-F21;
(6) bHLH family: RAFL09-12-N16;
(7) NAC family: RAFL05-19-I05, RAFL05-21-I22, RAFL08-11-H20, RAFL05-21-C17, RAFL05-08-D06;
(8) Homeo domain family: RAFL05-20-M16, RAFL11-01-J18, RAFL11-09-C20; and
(9) bZIP family: RAFL05-18-N16, RAFL11-10-D10, RAFL04-17-N22, RAFL05-09-G15.

Note that RAFL05-21-L12 cannot be classified into (1) to (9).

Once the nucleotide sequence of a gene encoding a transcriptional factor according to the present invention is determined, the gene encoding a transcriptional factor according to the present invention can be obtained by chemical synthesis, PCR using a cloned probe as a template, or hybridizing a DNA fragment having the nucleotide sequence as a probe. Furthermore, a mutant of the gene encoding a transcriptional factor according to the present invention, and having the same functions as those of a non-mutated transcriptional factor, can be also synthesized by a site-specific mutagenesis or the like.

To introduce a mutation into a nucleotide sequence of a gene encoding a transcriptional factor, a known method such as the Kunkel method, Gapped duplex method, or an equivalent method may be employed. A mutation may be introduced by using a mutation-introducing kit (for example, Mutant-K manufactured by Takar and Mutant-G manufactured by Takura) which uses a site-specific mutagenesis or by using the LA PCR in vitro mutagenesis series kit (manufactured by Takara).

The term "environmental stress" used herein generally refers to an abiotic stress such as drought stress, cold stress, high salt stress, or intensive light stress. The term "drought" used herein refers to a state of water deficiency, the term "cold" used herein refers to a state where an object is exposed to a lower temperature than the optimum living temperature of each organism (e.g., in the case of *Arabidopsis thaliana*, e.g., in the case of *Arabidopsis thaliana*, it is exposed to a temperature of −20 to +21° C. continuously for one hour to several weeks). The term "high salt" used herein refers to a state where a plant is treated with NaCl of 50 mM to 600 mM in concentration continuously for 0.5 hours to several weeks. The term "intensive light stress" used herein refers to a state where too intensive light to use for photosynthesis is applied to a plant, and corresponds to a case where, for example, light of 5,000 to 10,000 Lx or more is applied. These environmental stresses may be applied singly or in combination.

4. Construction or Expression Vector

The expression vector of the present invention can be obtained by ligating (inserting) a gene encoding a transcriptional factor according to the present invention to an appropriate vector. The vector into which a gene encoding a transcriptional factor of the present invention is inserted is not particularly limited as long as it can be replicated in a host. Examples of such a vector include a plasmid, shuttle vector and helper plasmid.

Examples of such a plasmid DNA include plasmids derived from *Escherichia coli* (e.g., pBR322, pBR325, pUC118, pUC119, pUC18, pUC19, and pBluescript), plasmids derived from *Bacillus subtilis* (e.g., pUB110 and pTP5); and plasmids derived from yeasts (e.g., YEp13 and YCp50). Examples of a phage DNA include λ phages (Charon4A, Charon21A EMBL3, EMBL4, λgt10, λgt11, and λZAP). Further animal virus vectors such as retrovirus and a vaccinia virus and insect virus vectors such as a baculovirus can be also used.

To insert a transcriptional factor of the present invention into a vector, use may be made of a method of digesting a purified DNA with appropriate restriction enzymes, inserting the obtained DNA fragment into the restriction site of a suitable vector DNA or a multi-cloning site, and ligating it to the vector.

In a case where a reporter gene, for example, a GUS gene, widely used in plants is linked to the 3' end of the gene encoding a transcriptional factor of the present invention, the strength of the gene expression can be easily evaluated by checking GUS activity. As such a reporter gene other than the GUS gene, luciferase and a green fluorescent protein can be used.

5. Preparation of Transformant

A transformant of the present invention can be obtained by introducing an expression vector of the present invention into a host. The host used herein is not particularly limited as long as it can express a promoter, a gene of interest, or an environmental stress-responsive transcriptional factor. Of them, a plant is preferable. In a case of a plant host, a transformant plant (transgenic plant) can be obtained as follows.

A plant to be transformed in the present invention refers to an entire plant, a plant organ (such as leaf, petal, stem, root, or seed), a plant tissue (such as the epidermis, phloem, parenchyma, xylem, or vascular bundle), or a plant culture cell. Examples of plants used for transformation include plants belonging to the Brassicaceae, Gramineae, Solanaceae and Leguminosae (see below); however they are to limited to these plants.

Brassiczceae: *Arabidopsis thaliana*
Gramineae: *Nicotiana tabacum*
Solanaceae: *Zea mays, Oryza sativa*
Leguminosae: *Glycine max*

The aforementioned recombinant vector can be introduced into a plant by a conventional transformation method such as electroporation, *Agrobacterium* method, particle gun method, or PEG method.

For example, where electroporation is used, a gene is introduced into a host by treating a vector by an electroporation device equipped with a pulse controller under conditions: a voltage of 500 to 1,600 V, 25 to 1,000 μF, and 20 to 30 msec.

When a particle gun method is used, a plant body, organ and tissue may be directly used. Alternatively, they may be used after they are sectioned to pieces or after protoplasts of them are prepared. The samples thus prepared may be processed by a gene-introduction device (for example, PDS-1000/He manufactured by Bio-Rad). Processing conditions vary depending upon a plant or sample. Generally, processing is performed at a pressure of about 1,000 to 1800 psi and a distance of about 5 to 6 cm.

Furthermore, a gene of interest can be introduced into a plant by using a plant virus as a vector. Examples of available plant viruses include a cauliflower mosaic virus. More specifically, a virus genome is inserted into a vector derived from *Escherichia coli* to prepare a recombinant and then such a gene of interest is inserted into the virus genome. The virus genome thus modified is excised out from the recombinant with restriction enzymes and inoculated into a plant host. In this manner the gene of interest can be introduced into the plant host.

In the method using a Ti plasmid of the *Agrobacterium*, when bacteria belonging to the *Agrobacterium* are transfected to a plant, a portion of plasmid DNA of the bacteria is transferred into a plant genome. Using such a characteristic, a gene of interest is introduced into a plant host. Of bacteria belonging to the *Agrobacterium*, *Agrobacterium tumefaciens*, when it is introduced into a plant by transfection, produces a tumor called a crown gall. Also, a plant when it is transfected with *Agrobacterium rhizogenes*, it produces hairy roots. These phenomena are caused by transferring a region called a T-DNA region (transferred DNA region) present in a plasmid such as a Ti plasmid or Ri plasmid present in each bacterium into a plant and incorporating the region into a plant genome at a time of transfection.

By inserting desired DNA, which is to be incorporated into a plant genome, into the T-DNA region on a Ti or Ri plasmid, the desired DNA can be incorporated into a plant genome, when the host is transfected with *Agrobacterium* bacteria.

Tumoral tissues, shoots and hairy roots obtained as a result of transformation can be directly used in cell culture, tissue culture, or organ culture. Also, when a plant hormone such as auxin, cytokinin, gibberellin, abscisic acid, ethylene, or brassinoride, is administered to them in an appropriate concentration by using a conventional plant tissue culture method, a plant body can be regenerated from them.

A vector according to the present invention can be not only incorporated into the plant hosts mentioned above but also introduced into bacteria belonging to the *Escherichia* such as *Escherichia coli*, the *Bacillus* such as *Bacillus subtilis* and the *Pseudomonas* such as *Pseudomonas putida*; yeasts such as *Saccharomyces cerevisiae* and *Schizosaccharomyces pombe*; animal cells such as COS cells and CHO cells; and insect cells such as Sf9 cells, to obtain a transformant. Where a bacterium such as *Escherichia coli* or yeast is used as a host, it is preferably that a recombinant vector according to the present invention can be self-replicated in the bacterium and, at the same time, is comprised of a promoter of the present invention, a ribosome binding sequence, a gene of interest and a transcription termination sequencer. Furthermore, a gene regulating the promoter may be included in the bacterium.

A method for introducing a recombinant vector into bacteria is not particularly limited as long as it is a method which can introduce DNA into bacteria. Examples of such a method include a method of using calcium ions and an electroporation method.

When a yeast is used as a host, *Saccharomyces cerevisiae* and *Schizosaccharomyces pombe* may be used. A method for introducing a recombinant vector is not particularly limited as long as it is a method for introducing DNA into a yeast. Examples of such a method include electroporation, spheroplast method, and lithium acetate method.

Where a animal call is used as a host, a monkey COS-7 cell, Vero, Chinese hamster ovary cell (CHO cell), and mouse L cell etc. are used. Examples of methods for introducing a recombinant vector into an animal cell include electroporation, calcium phosphate method, and lipofection method.

When an insect cell is used as a host, a Sf9 cell and the like may be used. Examples of method for introducing a recombinant vector into an insect cell include a calcium phosphate method, lipofection method, and electroporation method.

Whether a gene is incorporated into a host or not is confirmed by a PCR method, Southern hybridization, Northern hybridization method or the like. For example, PCR is performed by preparing DNA from a transformant, and designing DNA specific primers. PCR is carried out under the same conditions as used for preparing the plasmid mentioned above. Thereafter, the obtained amplified product is subjected to agarose gel electrophoresis, polyacrylamide gel electrophoresis or capillary electrophoresis, and stained with ethidium bromide, or SYBR Green solution, etc. If the amplified product is found as a single band, it is confirmed that a transformant is obtained. Alternatively, the amplified product can be also detected by PCR using primers previously stained with a fluorescent dye or the like. Furthermore, there may be employed a method in which the amplified product is bound to a solid phase such a microplate and confirmed by fluorescent or an enzymatic reaction.

4. Production of Plant

In the present invention, a transformed plant body can be regenerated from the above transformed plant cell or the like. As a regeneration method, use is made of one in which callus-form transformed cells are transferred to a medium having a different hormone in a different concentration and cultured to form an adventitious embryo, from which an entire plant body is obtained. Examples of the medium to be used herein include an LS medium and an MS medium.

The "method for producing a plant body" of the present invention comprises steps of: introducing a plant expression vector, into which the above plant promoter or a gene encoding an environmental stress-responsive transcriptional factor is inserted, into a host cell to obtain a transformed plant cell; regenerating a transformed plant body from the transformed plant cell; obtaining a plant seed from the transformed plant body; and producing a plant body from the plant seed.

To obtain plant seeds from a transformed plant body, for example, the transformed plant body is collected from a rooting medium and transferred to a pot having soil containing water placed therein. Then, the transformed plant body is grown at constant temperature to form flowers. Finally seeds are obtained. To produce a plant body from a seed, for example, when a seed formed on a transformed plant body has matured, the seed is isolated and seeded in soil containing water, followed by growing at constant temperature under illumination. The plant thus bred becomes an environmental stress-resistant plant exhibiting the stress resistance corresponding to the responsivity of a promoter introduced therein or a gene encoding the environmental stress-responsive transcriptional factor introduced therein.

BRIEF DESCRIPTION OF THE DRAWINGS

FIG. 120 is a characteristic graph showing the relationship between drought stress and expression ratio regarding RAFL04-15-K19;

FIG. 121 is a characteristic graph showing the relationship between cold stress and expression ratio regarding RAFL04-15-K19;

FIG. 122 is a characteristic graph showing the relationship between drought stress and expression ratio regarding RAFL05-11-L01;

FIG. 123 is a characteristic graph showing the relationship between high salt stress and expression ratio regarding RAFL05-11-L01;

FIG. 124 is a characteristic graph showing the relationship between drought stress and expression ratio regarding RAFL05-14-C11;

FIG. 125 is a characteristic graph showing the relationship between high salt stress and expression ratio regarding RAFL05-19-G24;

FIG. 126 is a characteristic graph showing the relationship between drought stress and expression ratio regarding RAFL05-19-G24;

FIG. 127 is a characteristic graph showing the relationship between cold stress and expression ratio regarding RAFL05-19-G24;

FIG. 128 is a characteristic graph showing the relationship between drought stress and expression ratio regarding RAFL05-20-N02;

FIG. 129 is a characteristic graph showing the relationship between drought stress and expression ratio regarding RAFL05-18-H12;

FIG. 130 is a characteristic graph showing the relationship between high salt stress and expression ratio regarding RAFL05-18-H12;

FIG. 131 is a characteristic graph showing the relationship between drought stress and expression ratio regarding RAFL05-19-E19;

Figure 132:
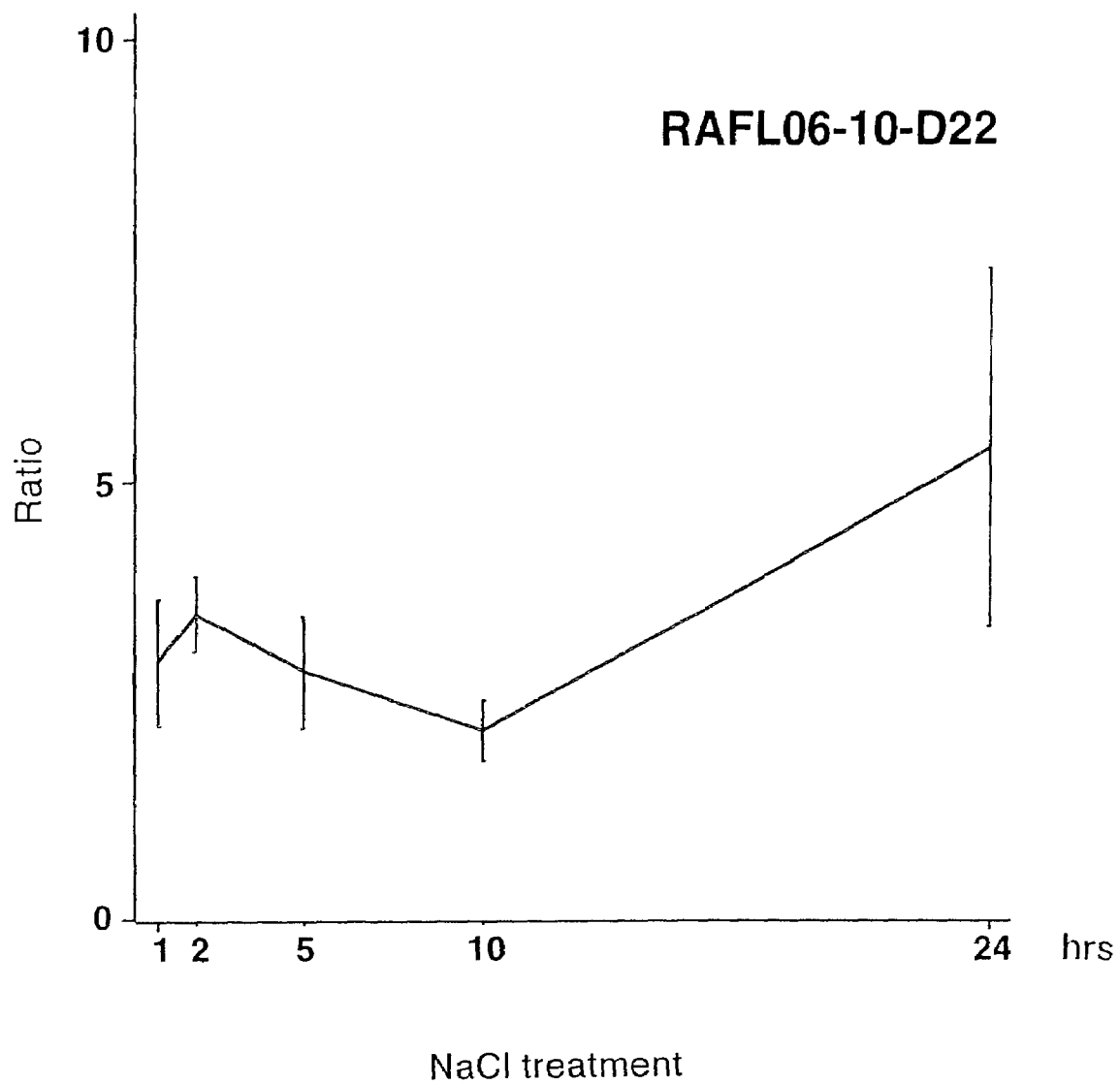
Figure 133:
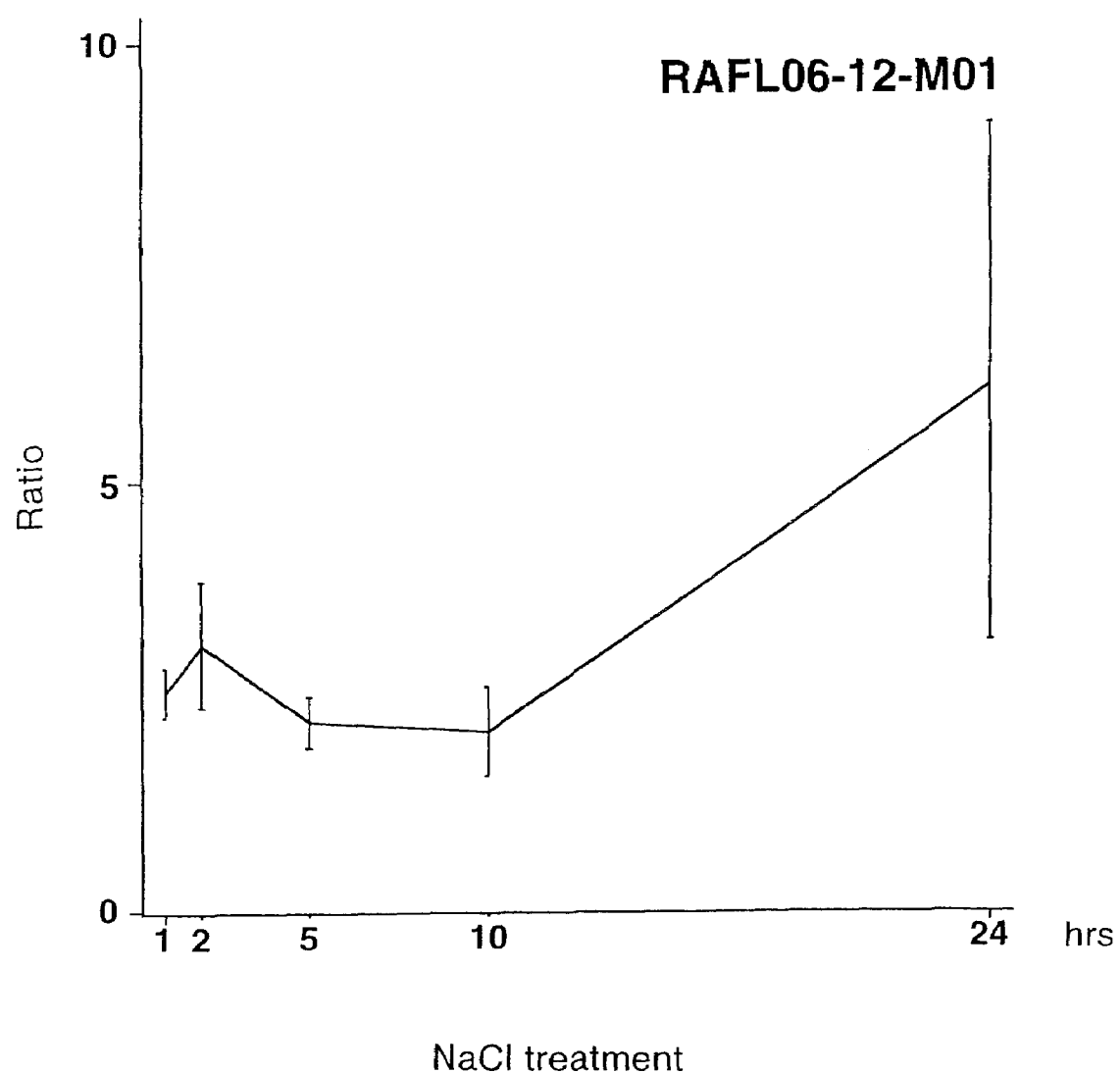
Figure 134:
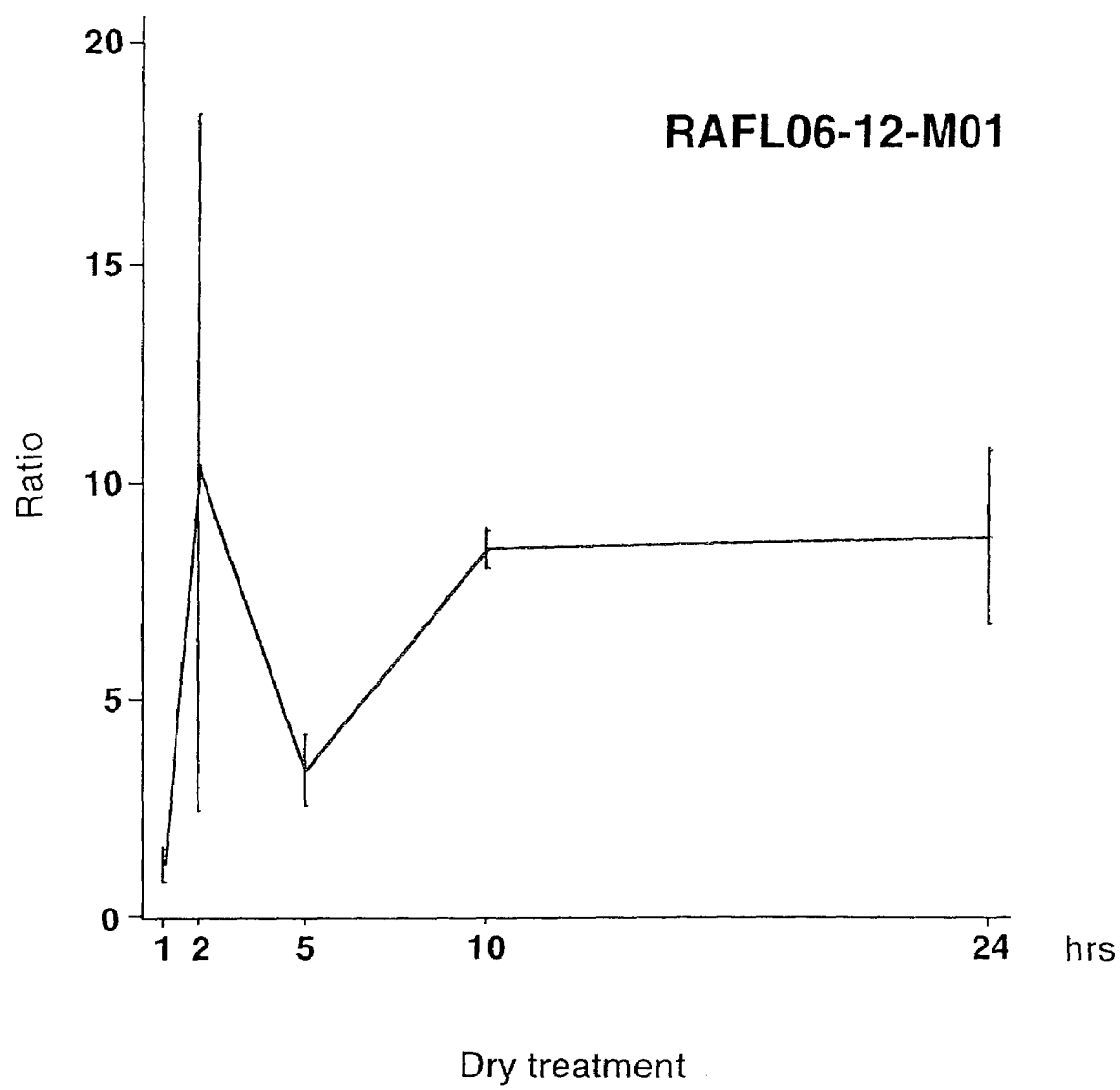
Figure 135:
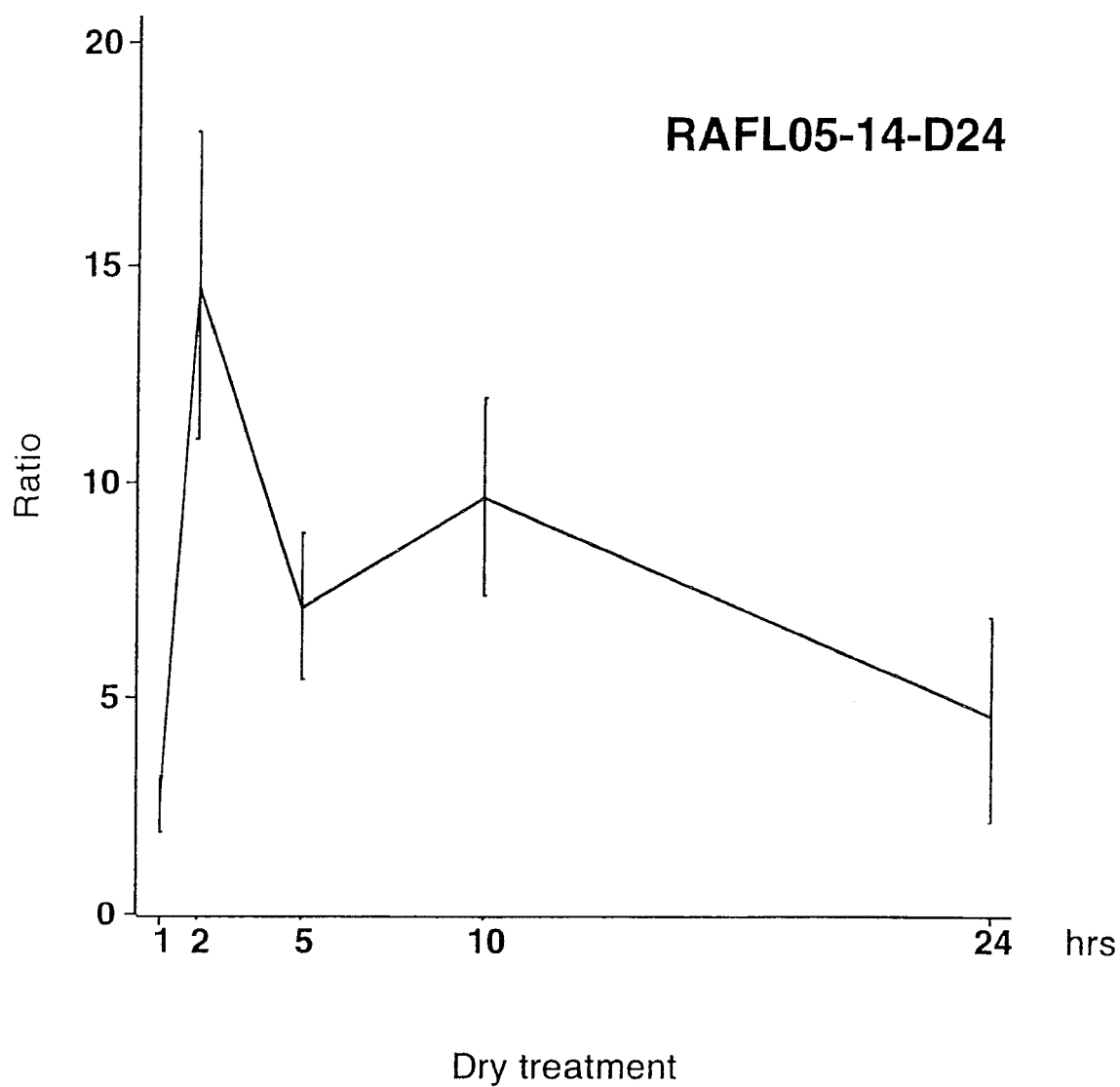
Figure 136:
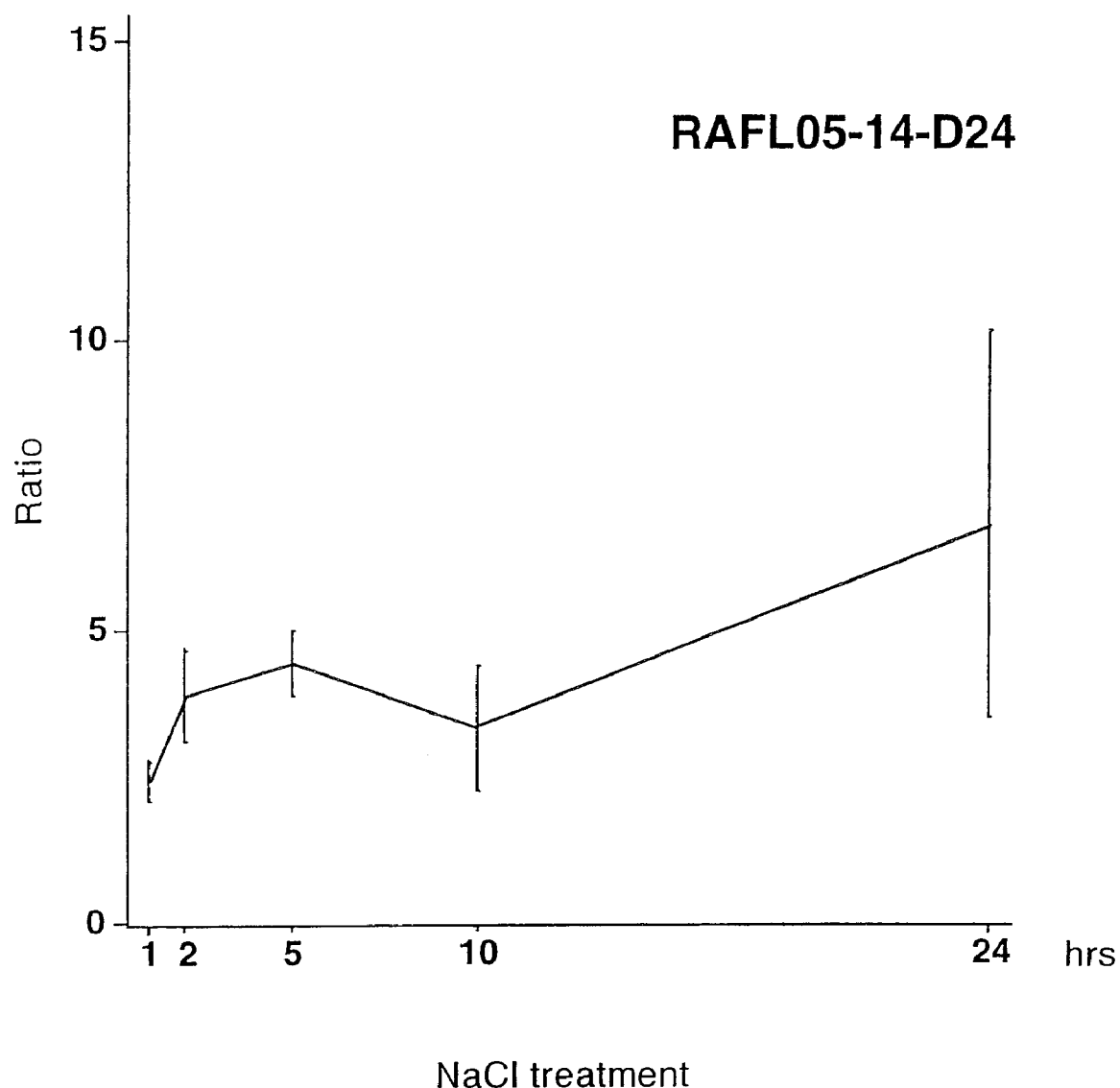
Figure 137:
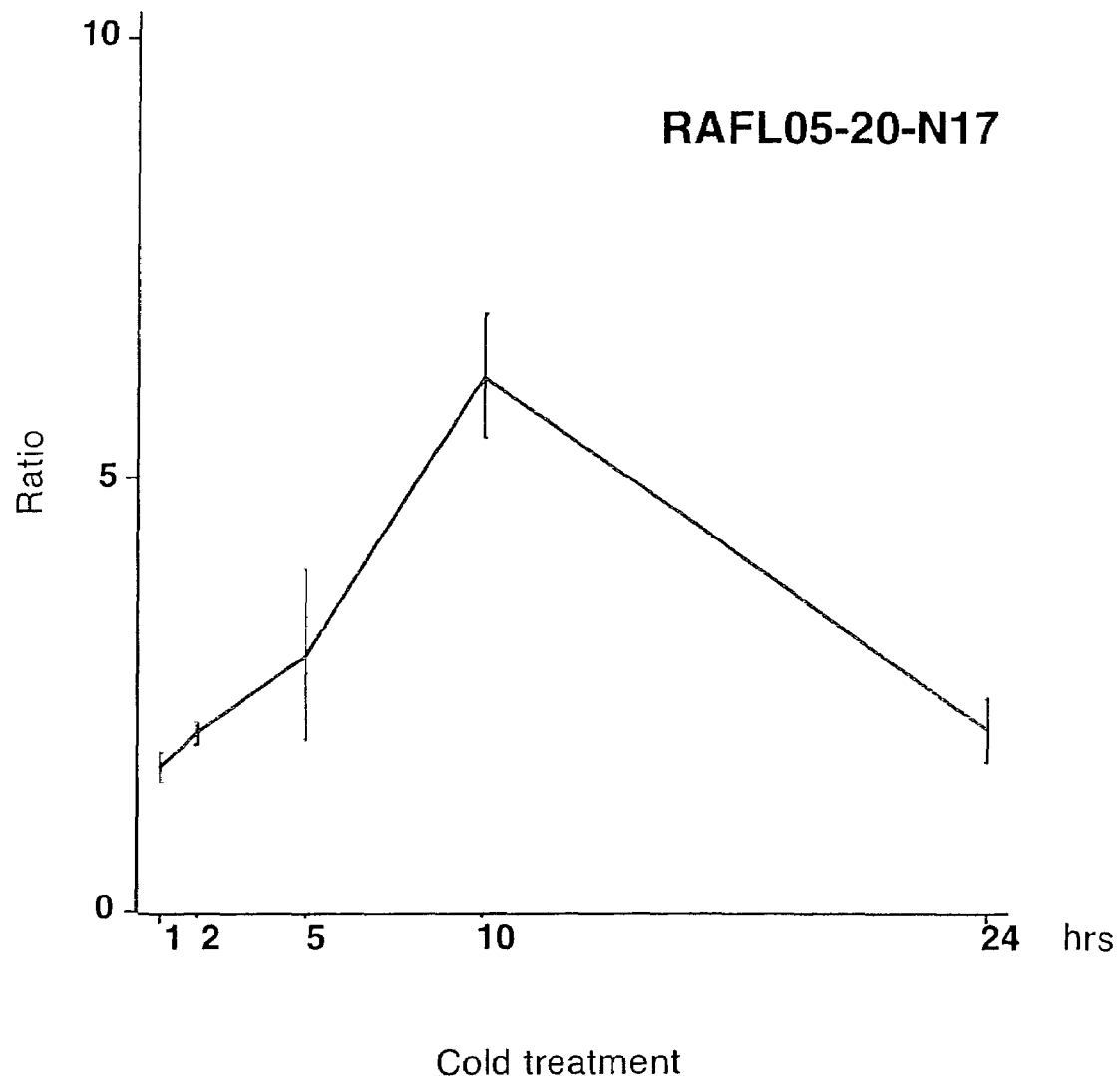
Figure 138:
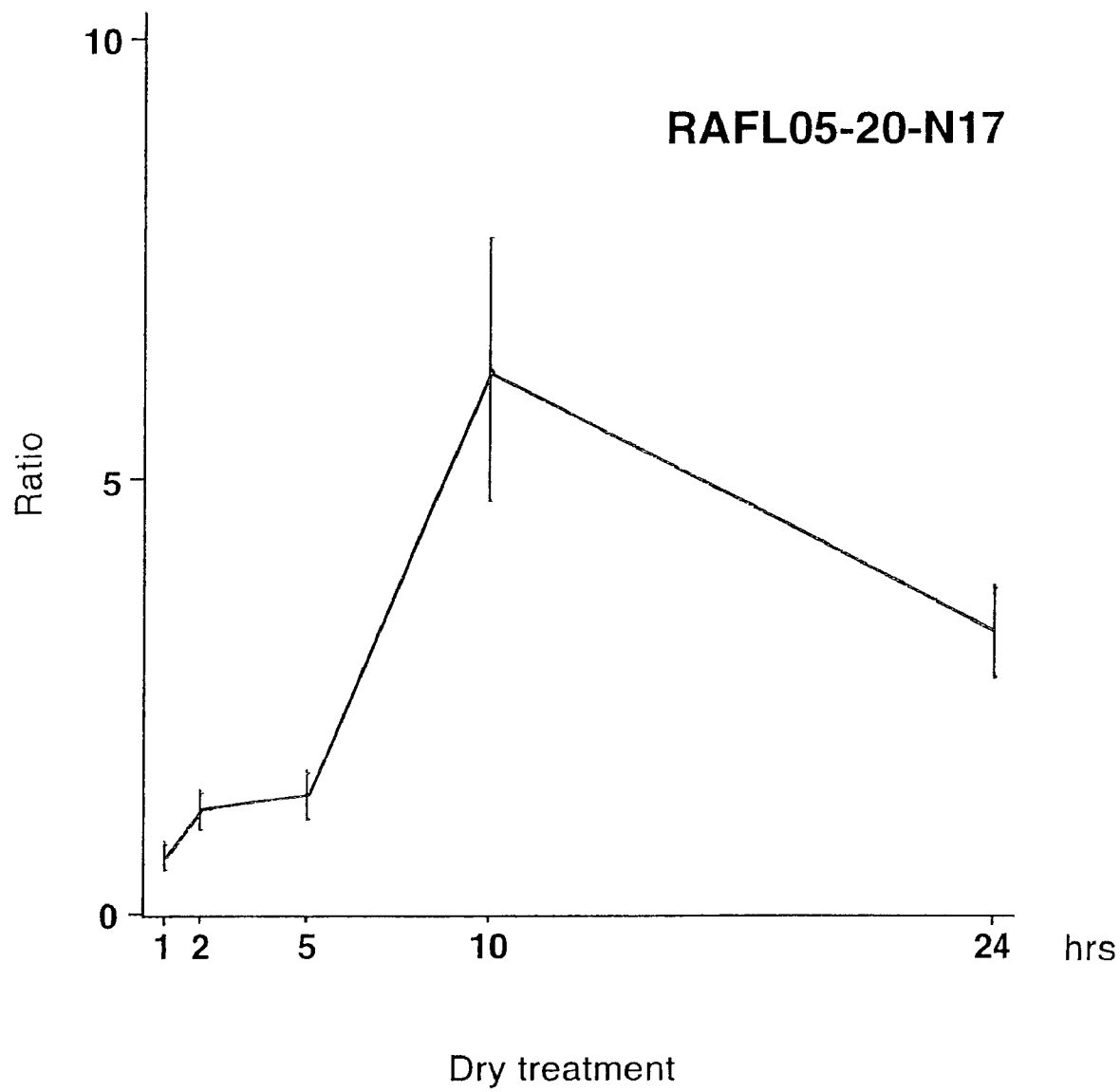
Figure 139:
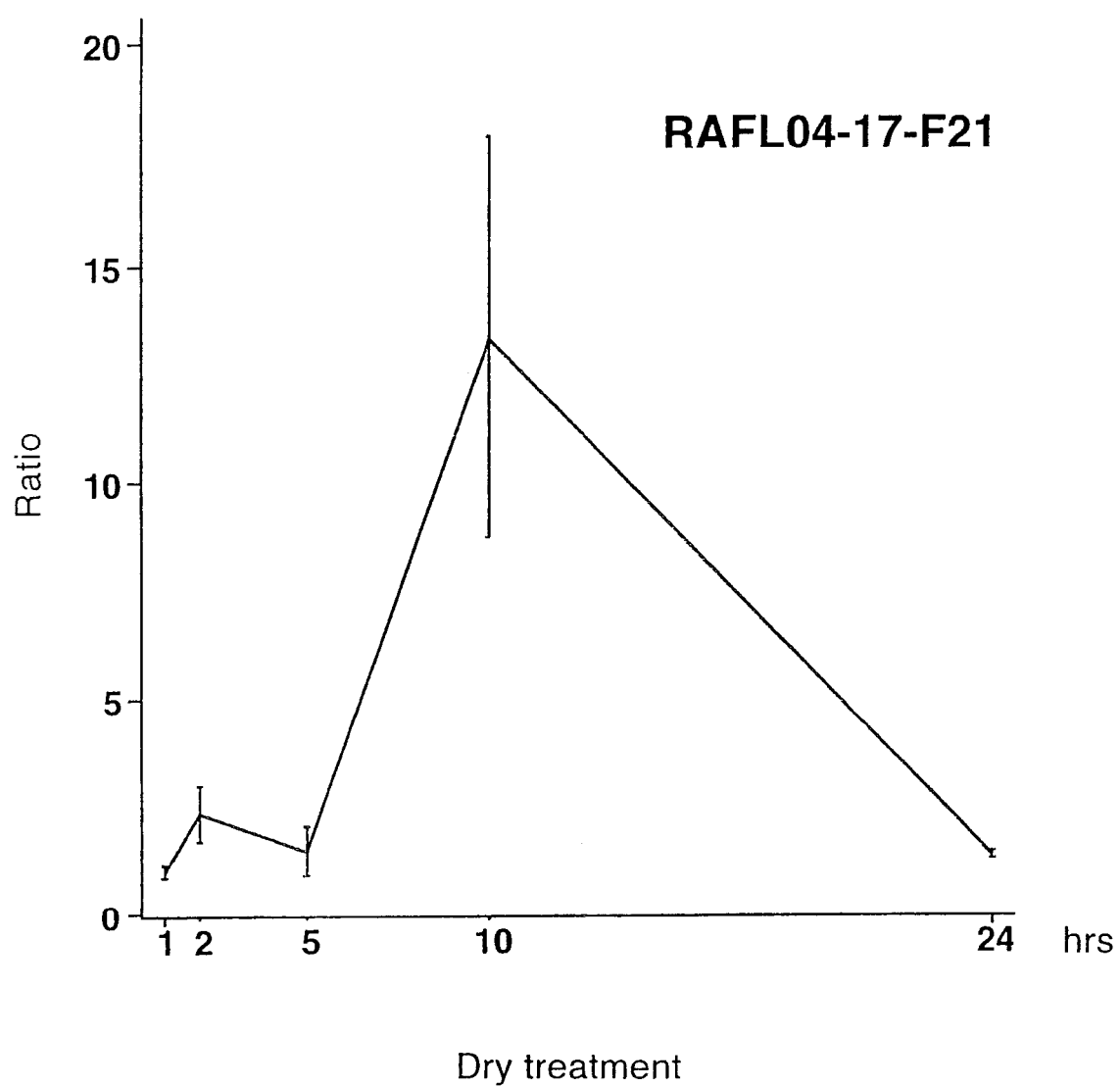
Figure 140:
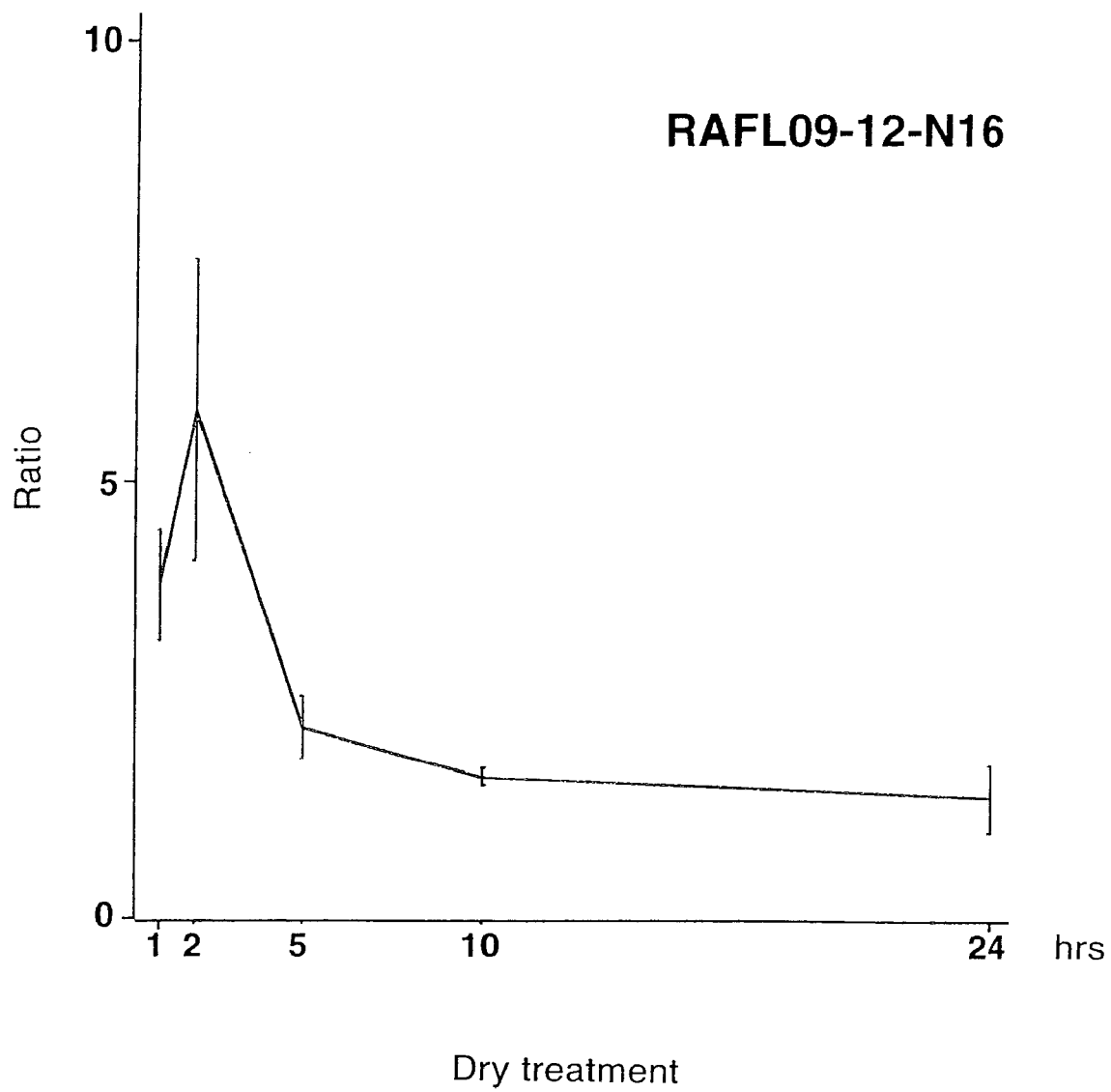
Figure 141:
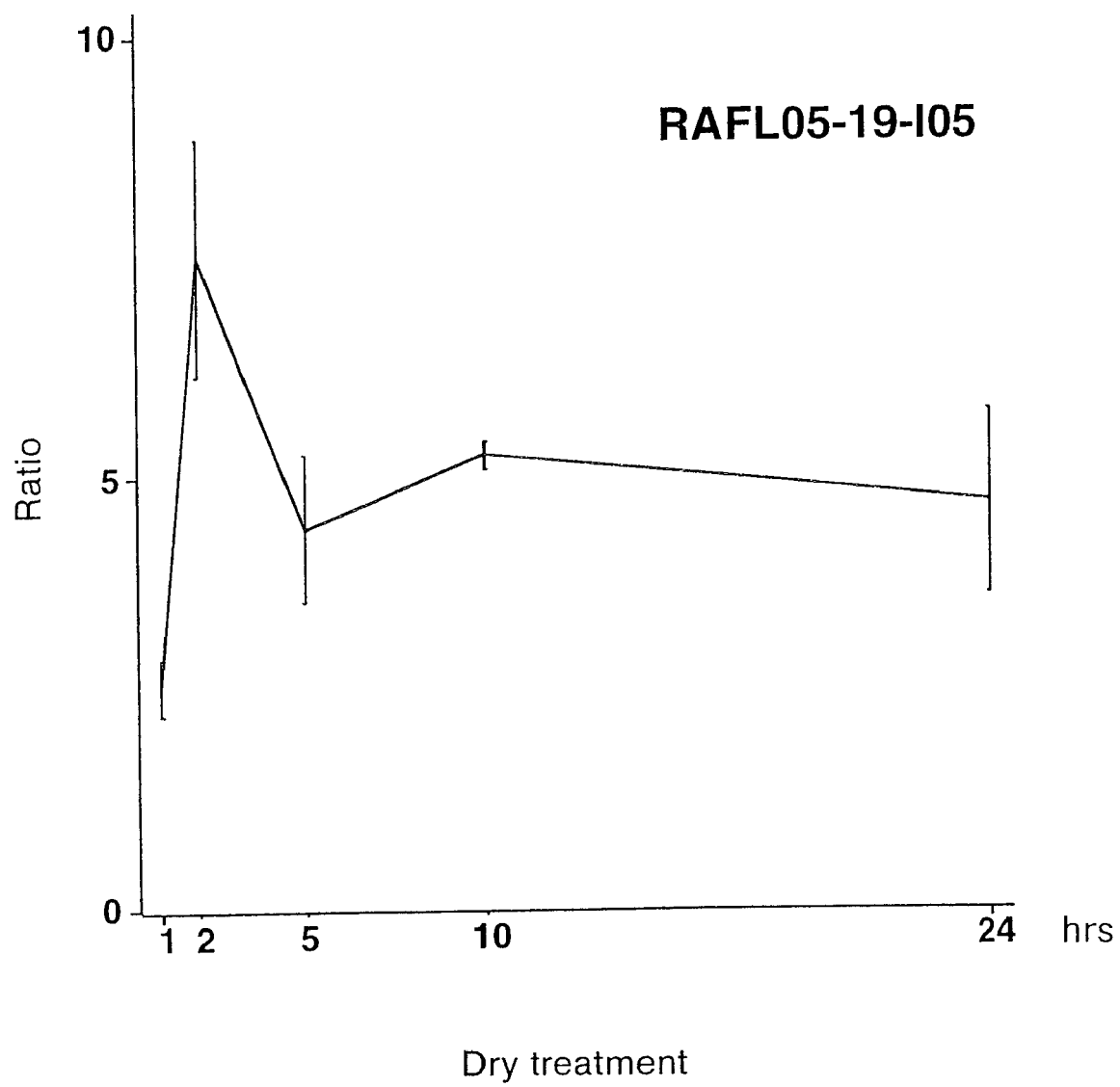
Figure 142:
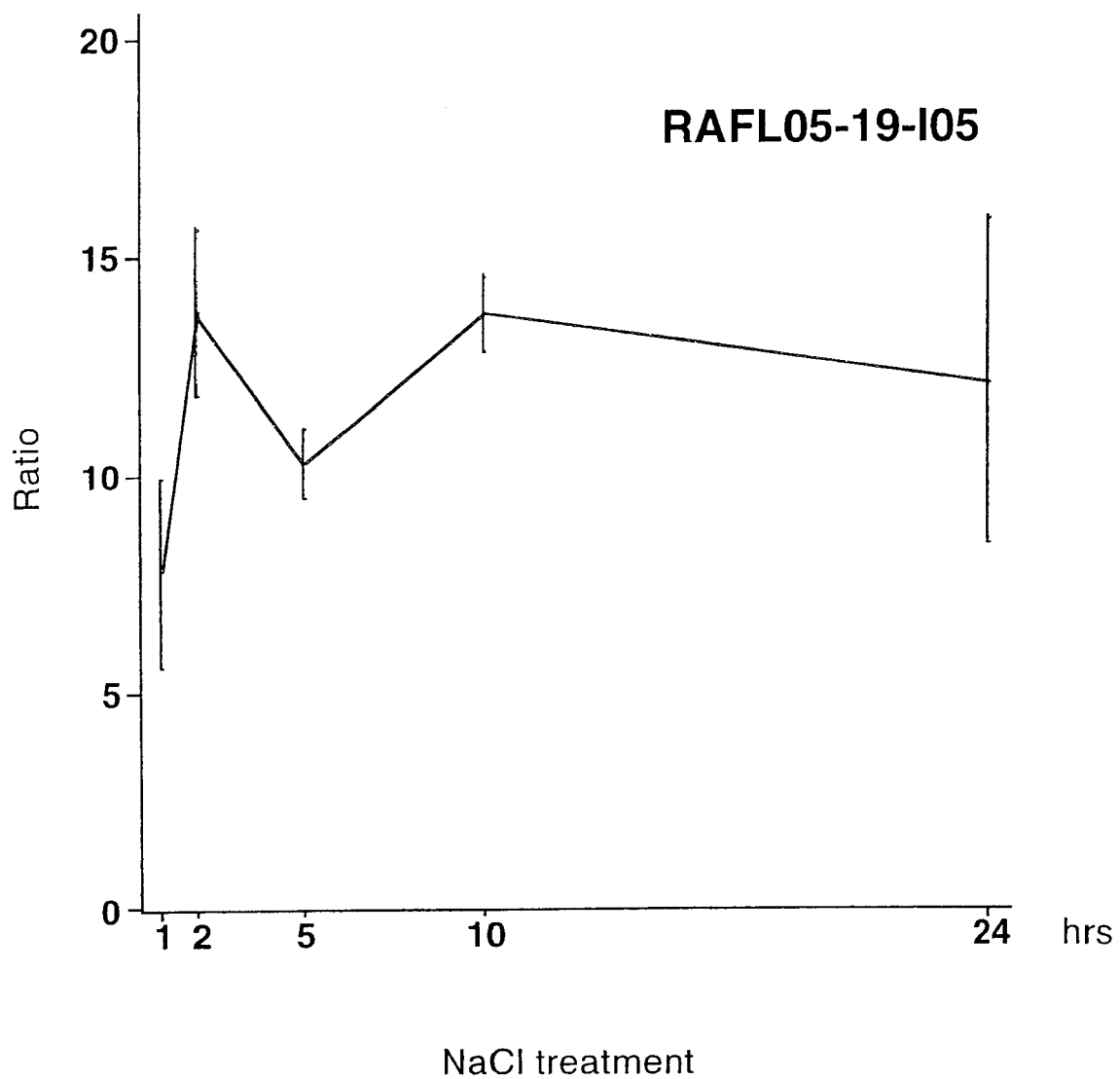
Figure 143:
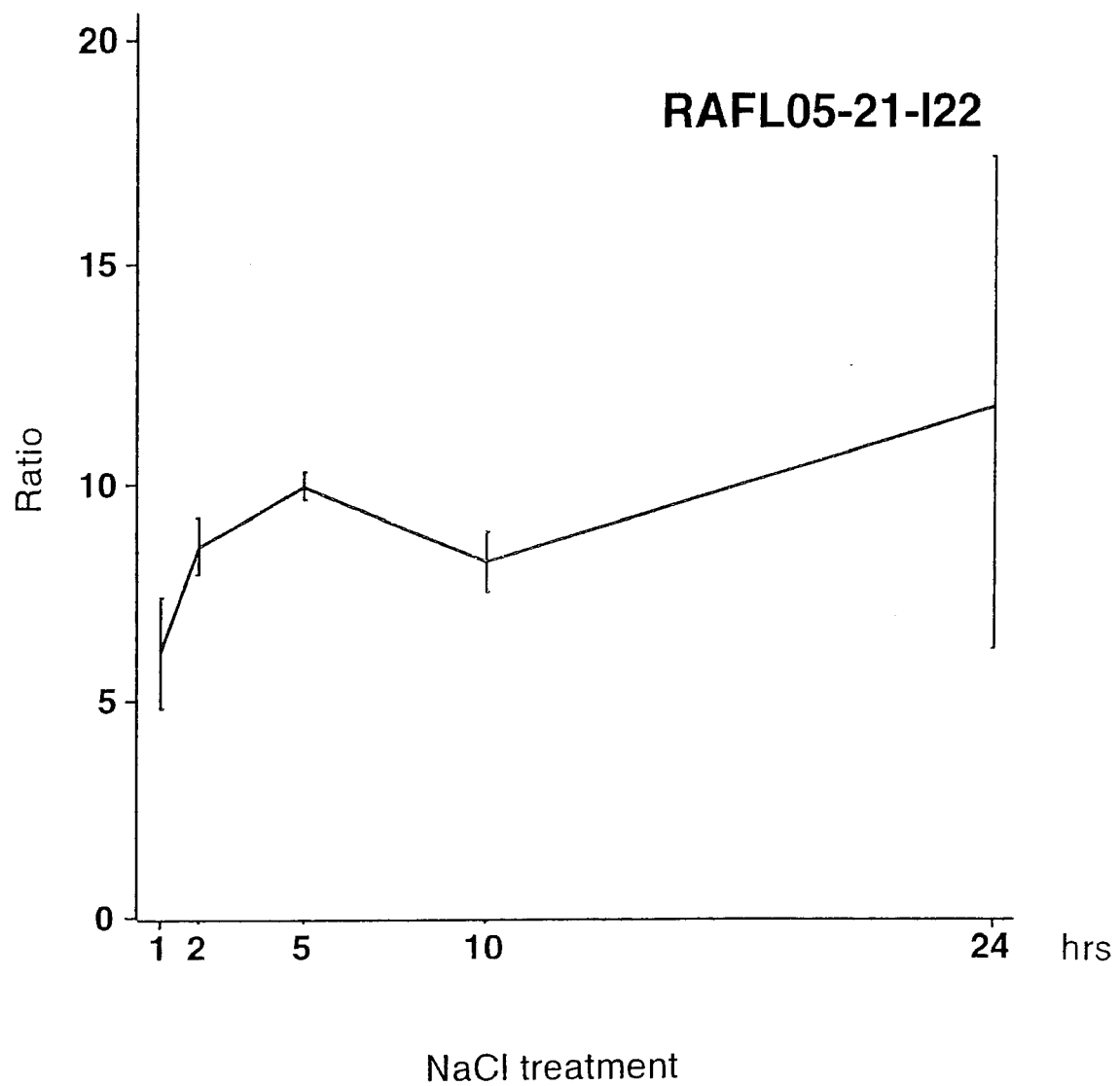
Figure 144:
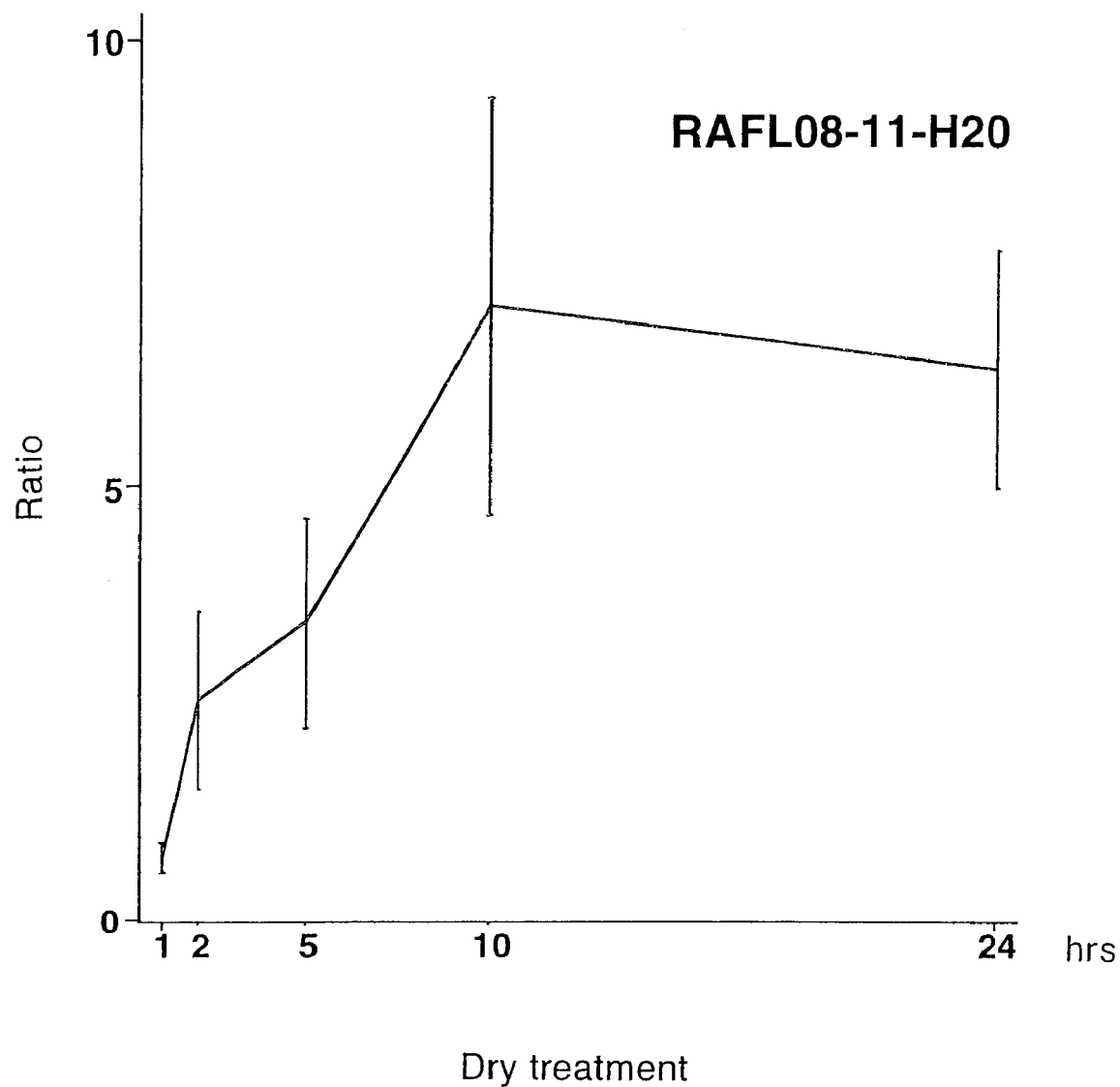
Figure 145:
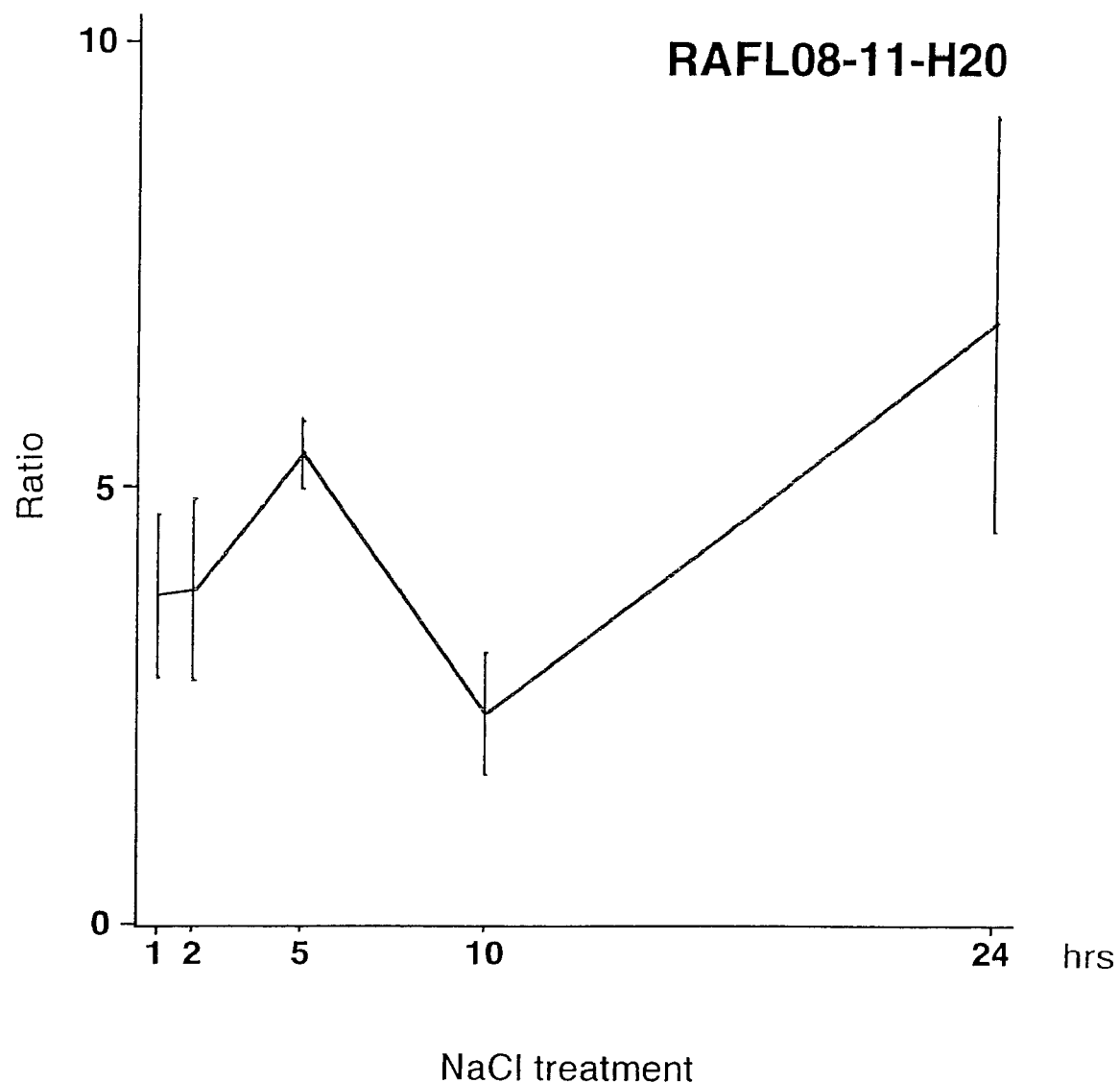
Figure 146:
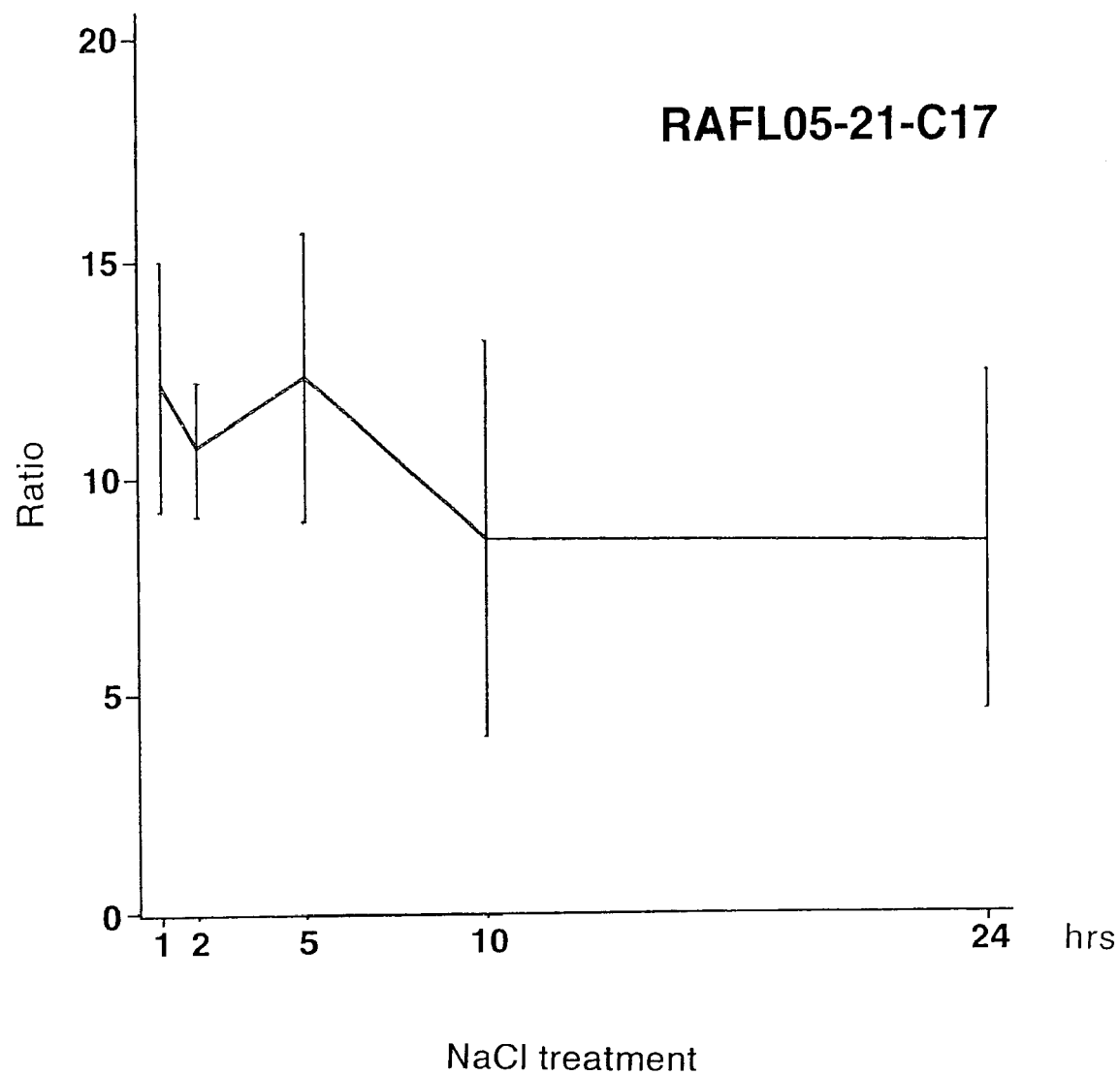
Figure 147:
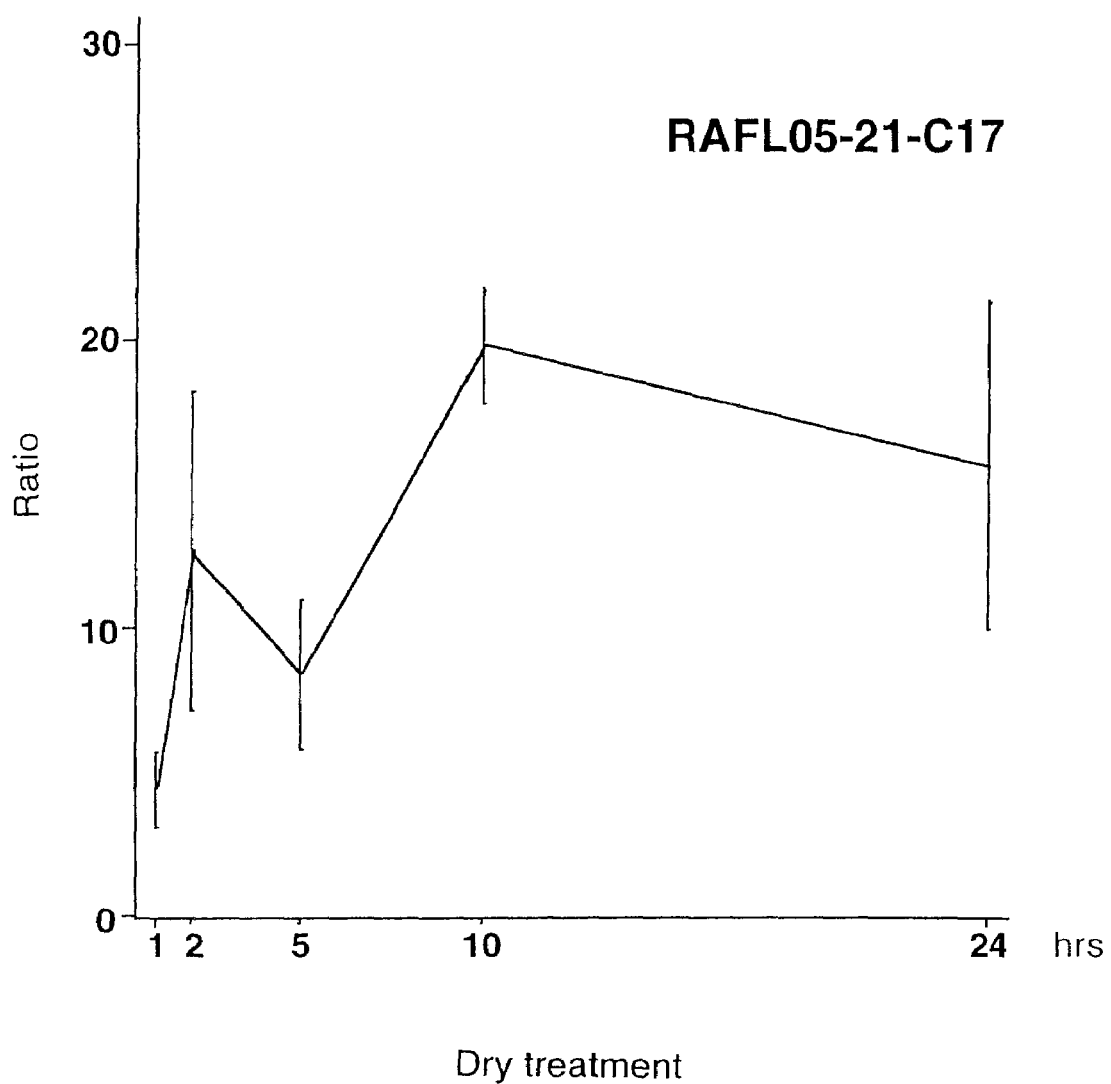
Figure 148:
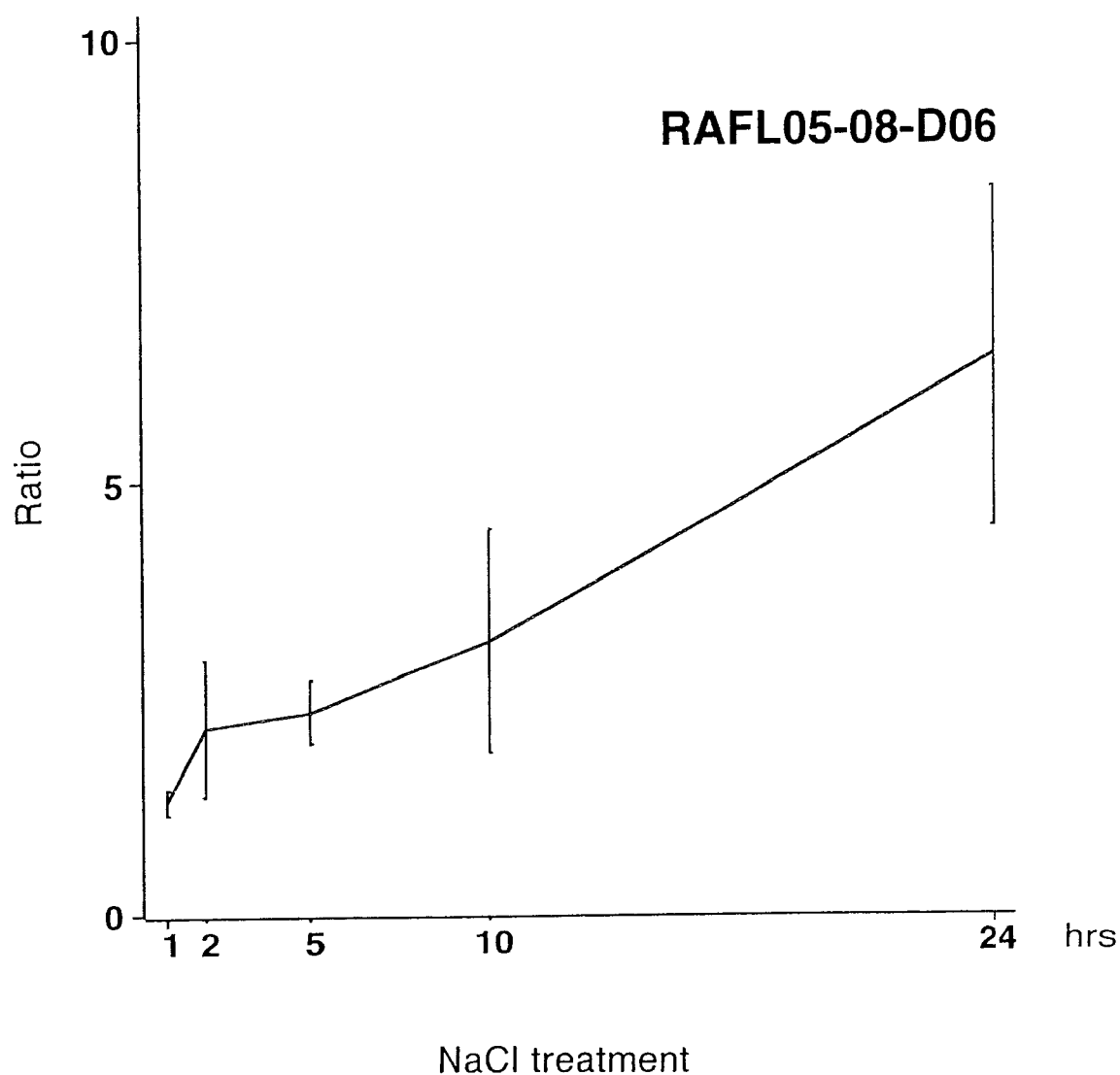
Figure 149:
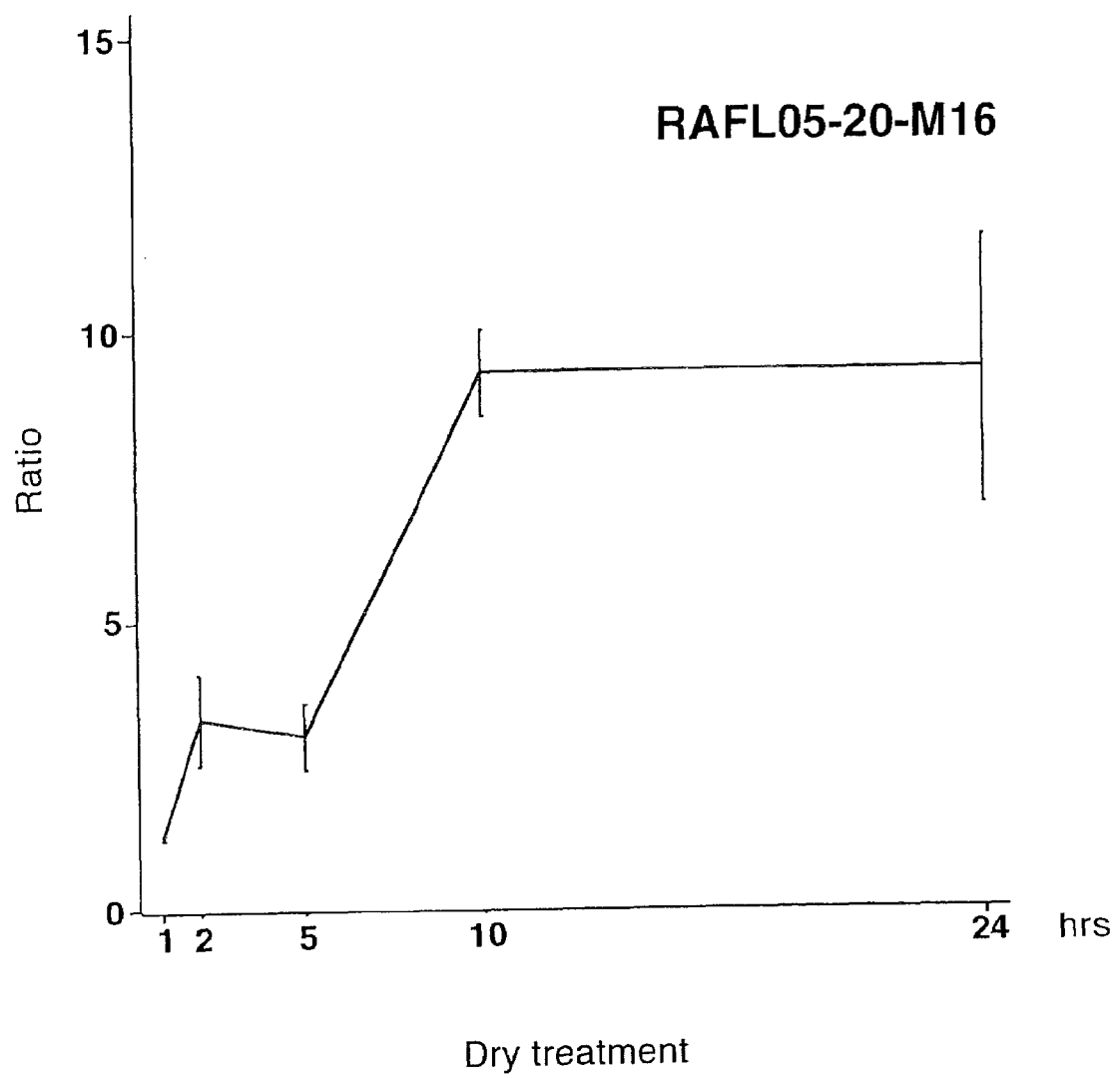
Figure 150:
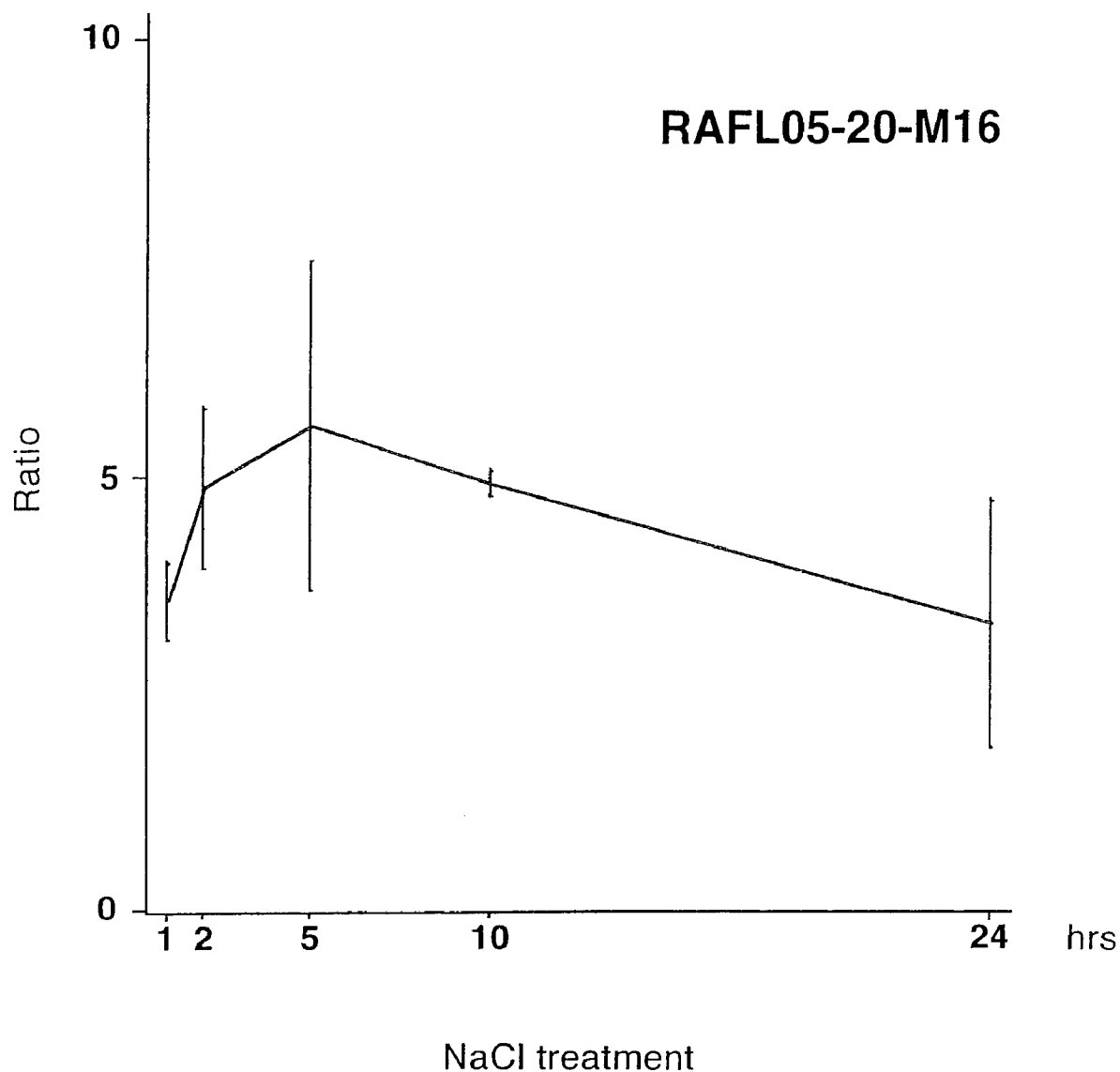
Figure 151:
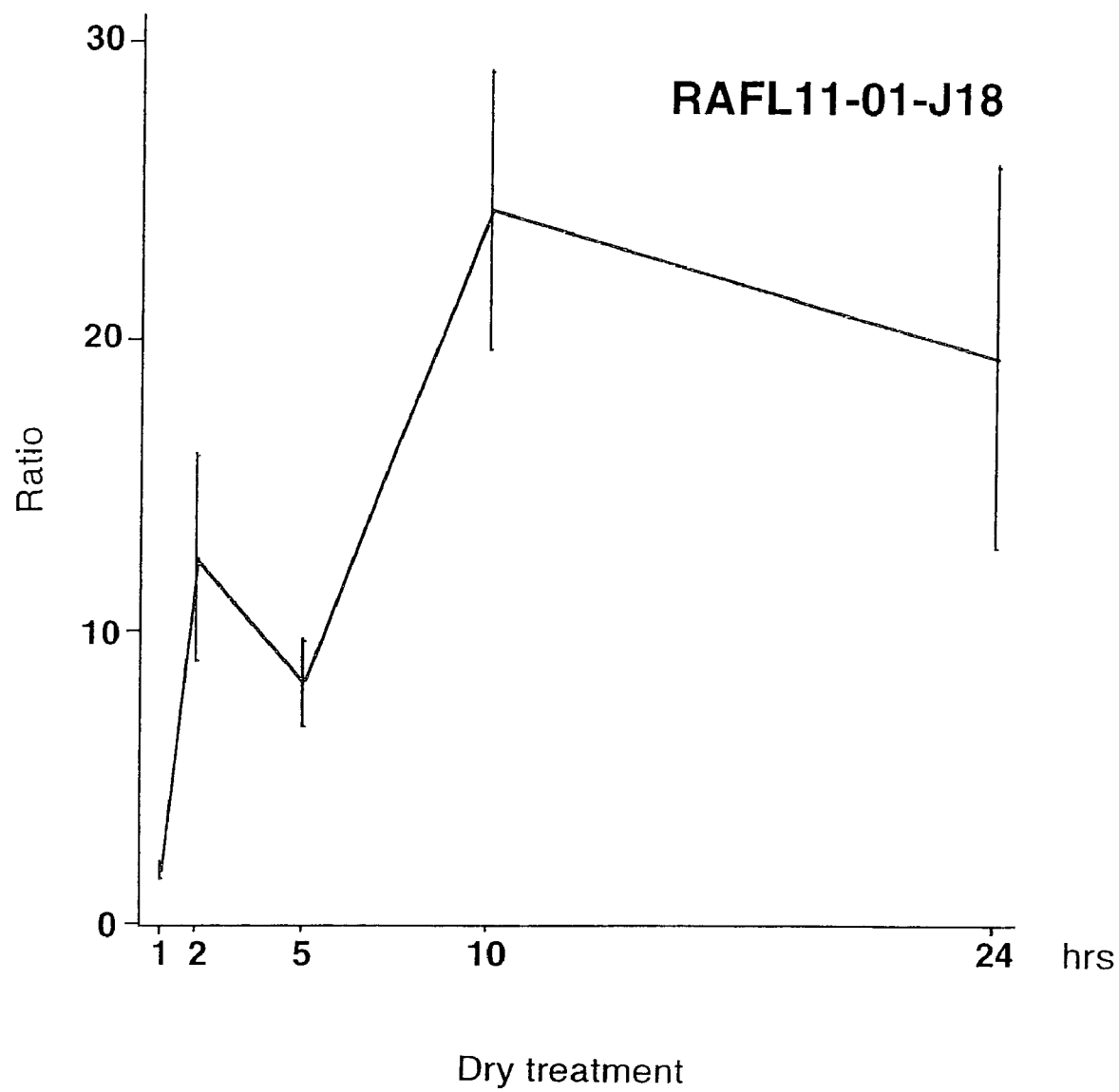
Figure 152:
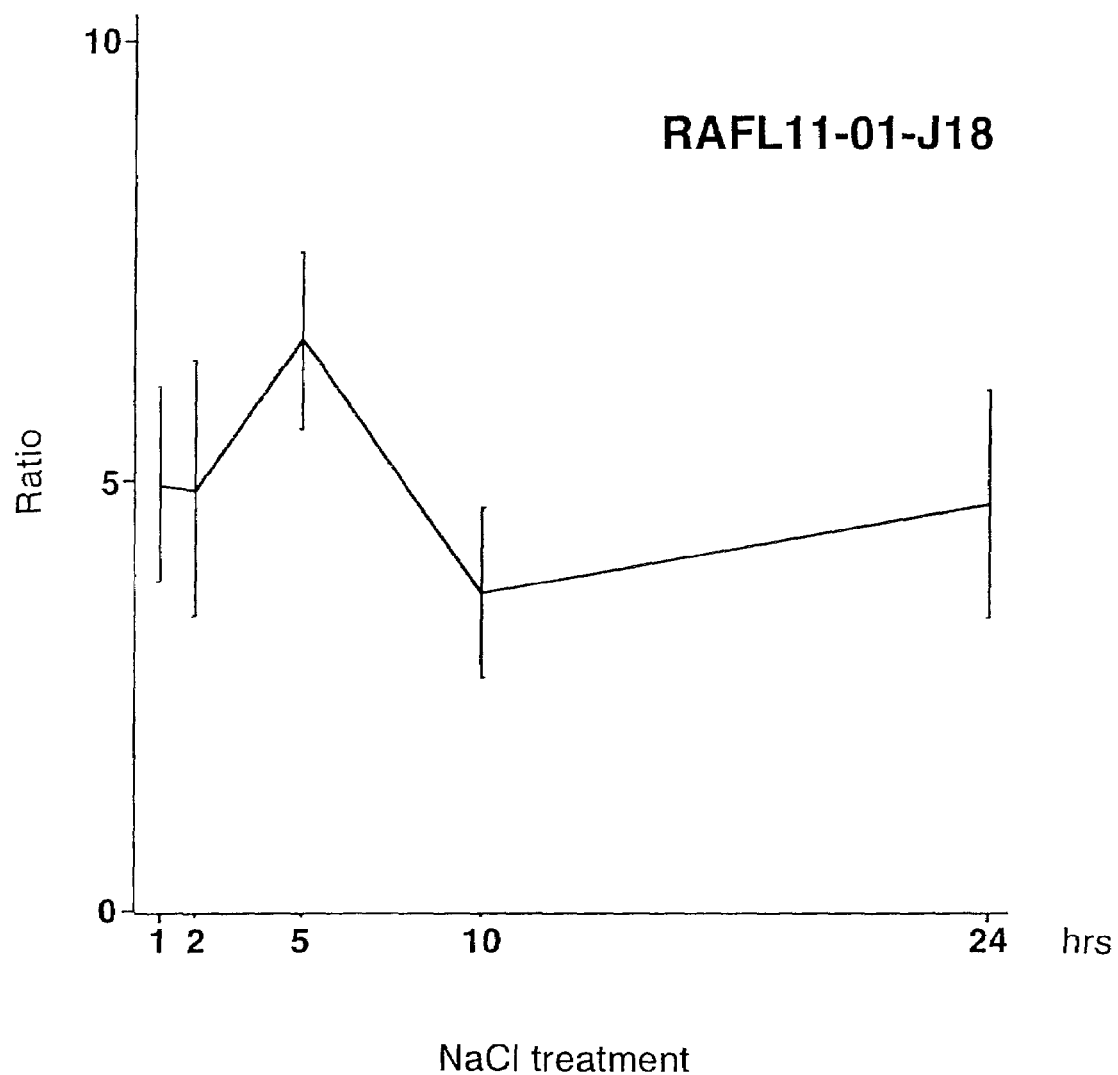
Figure 153:
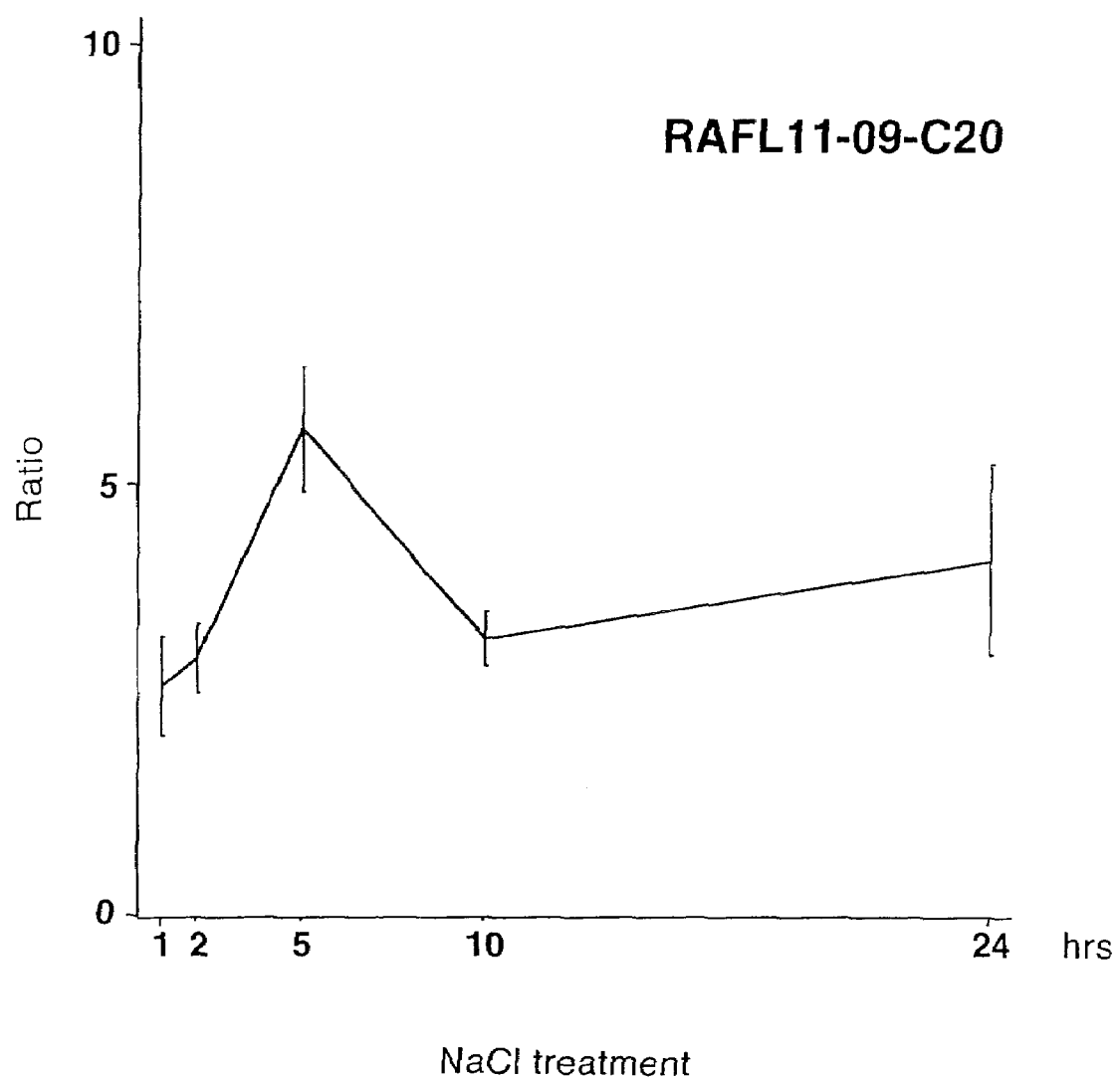
Figure 154:
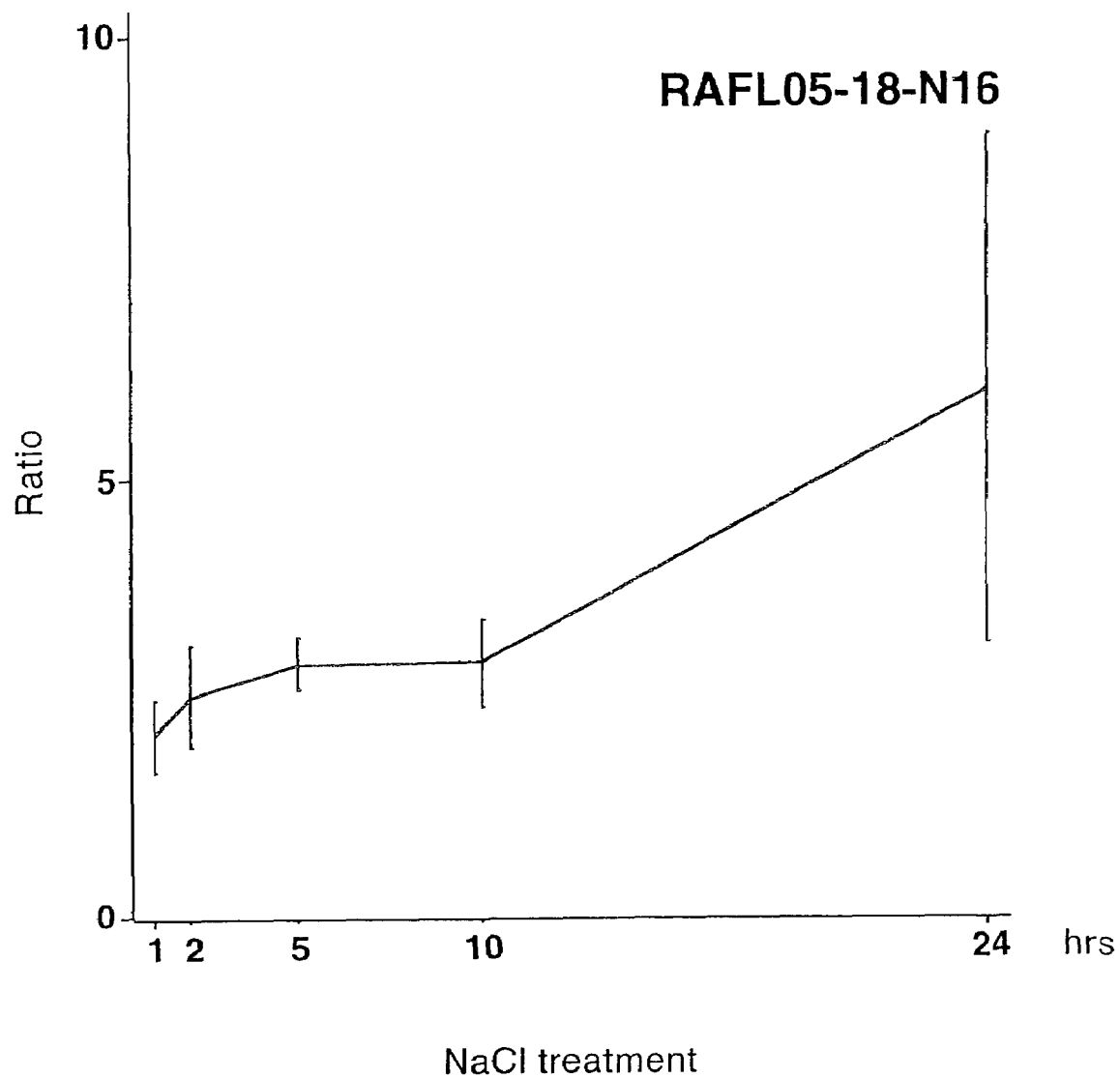
Figure 155:
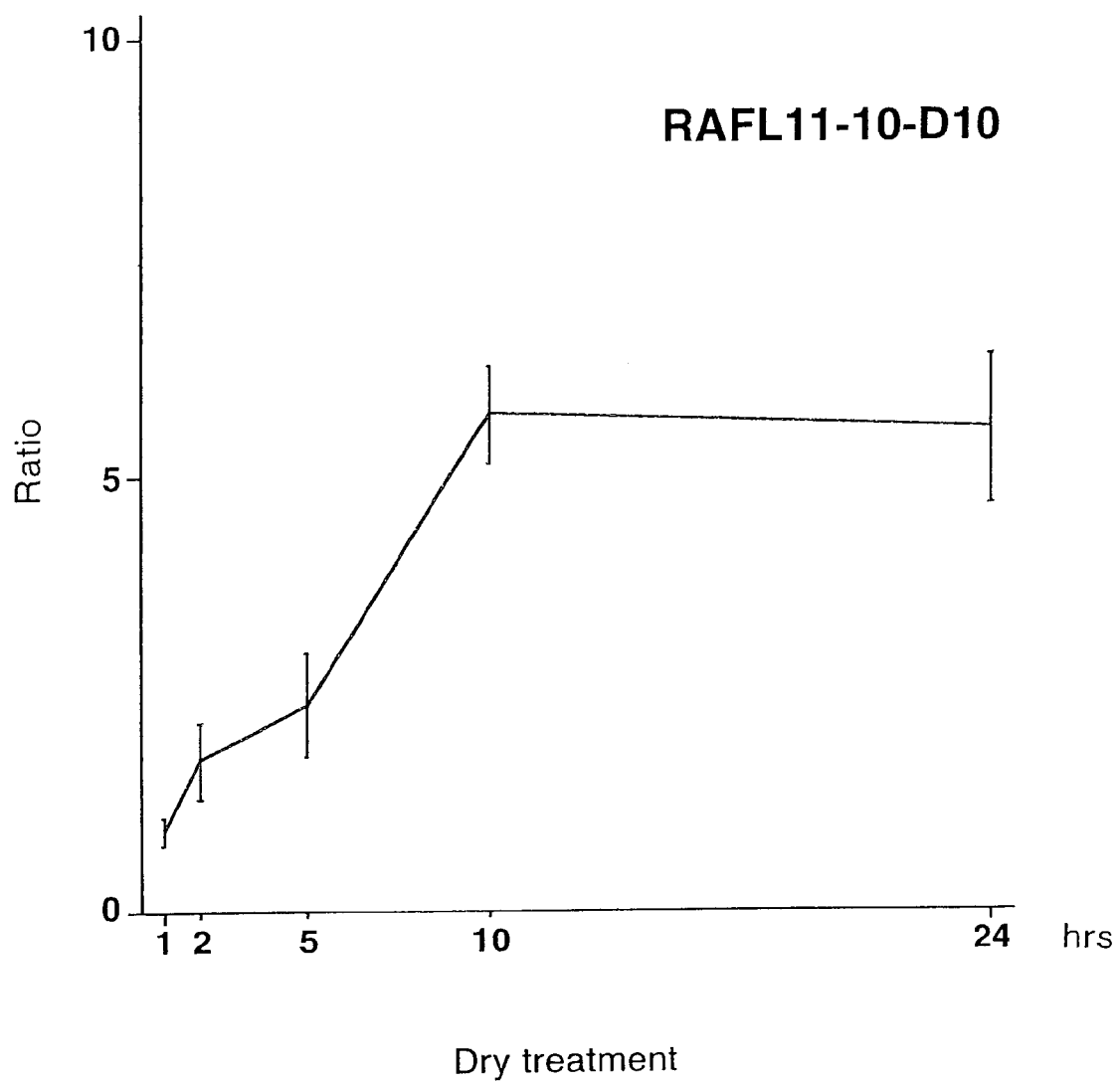
Figure 156:
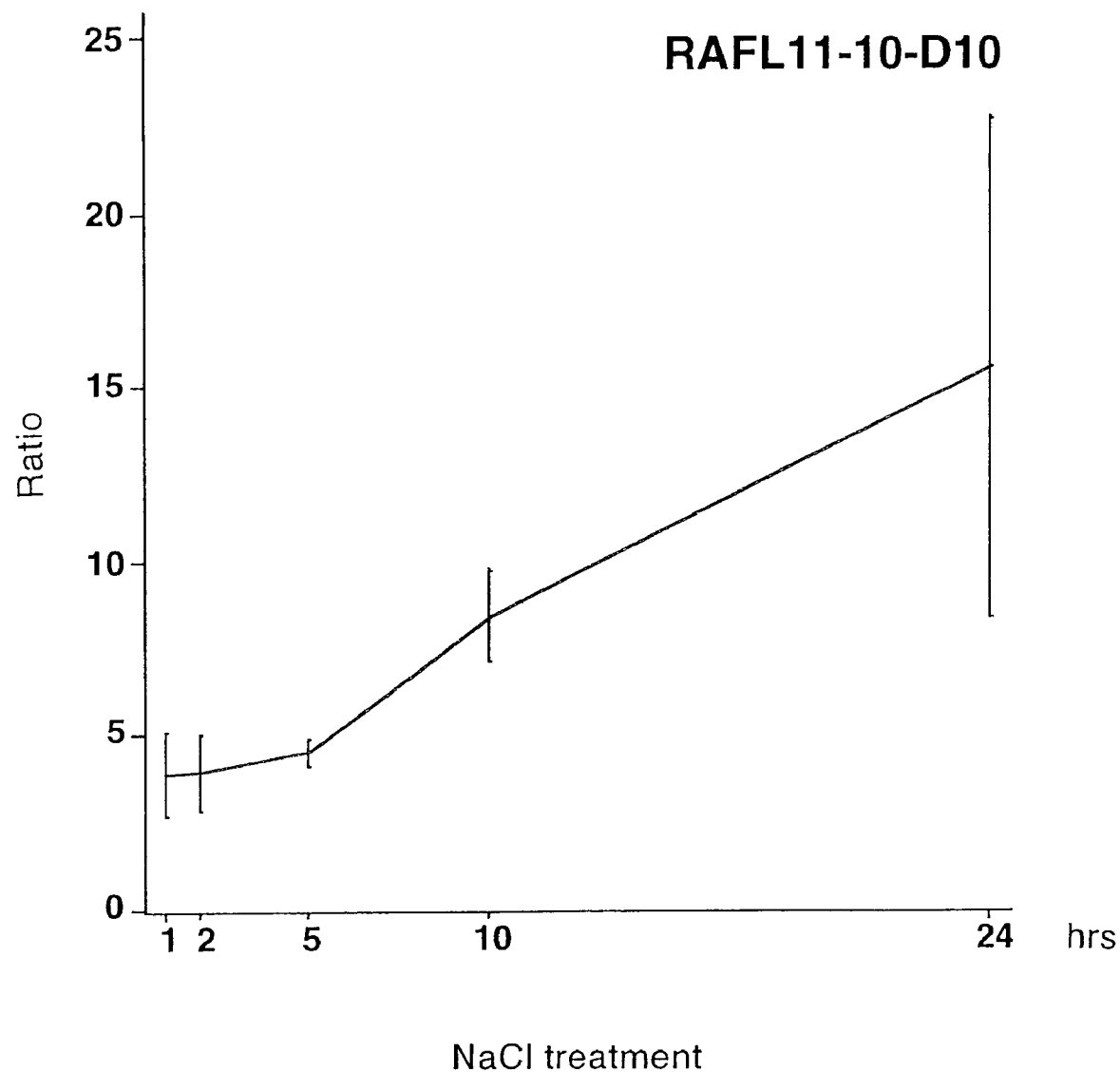
Figure 157:
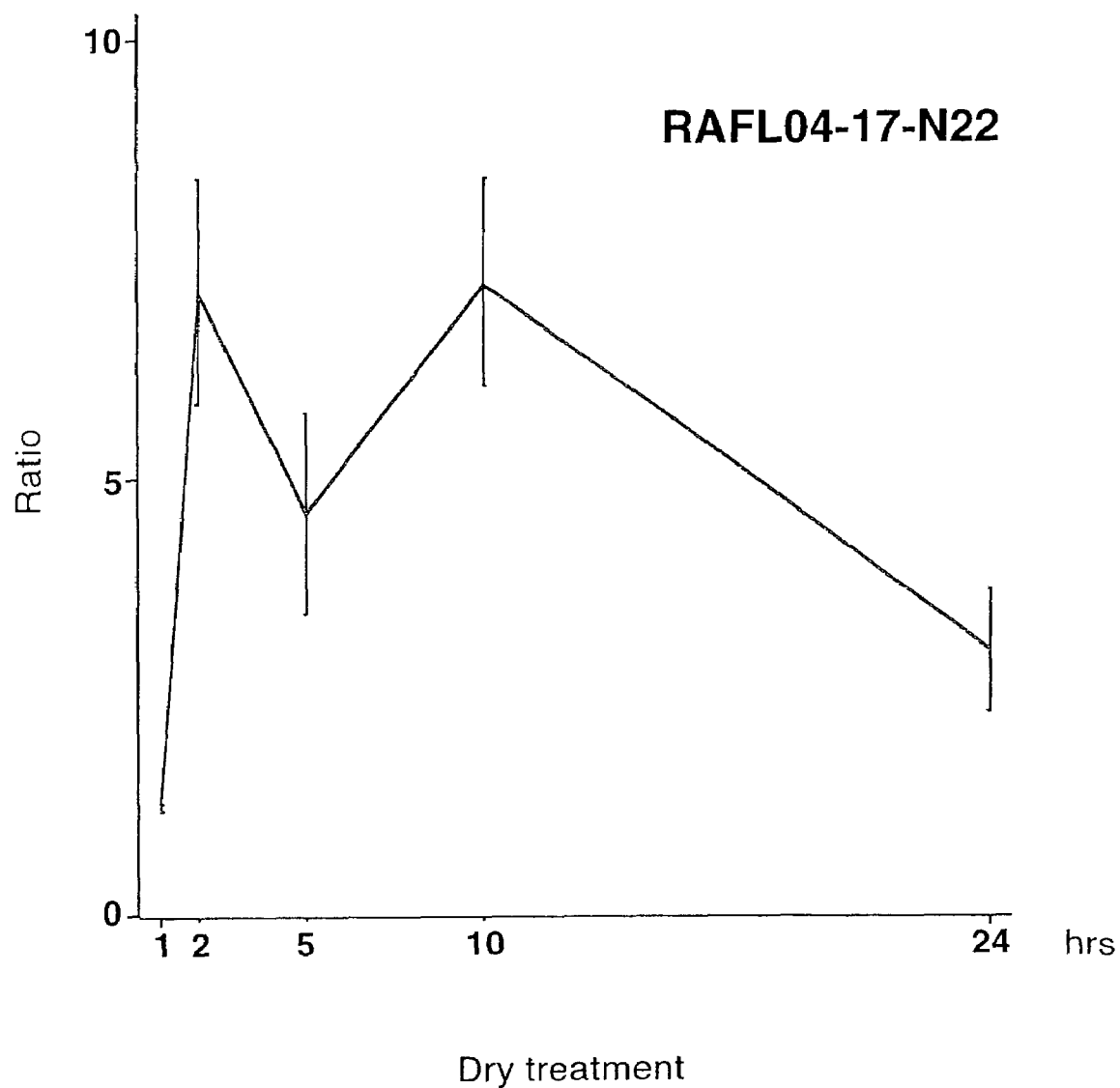
Figure 158:
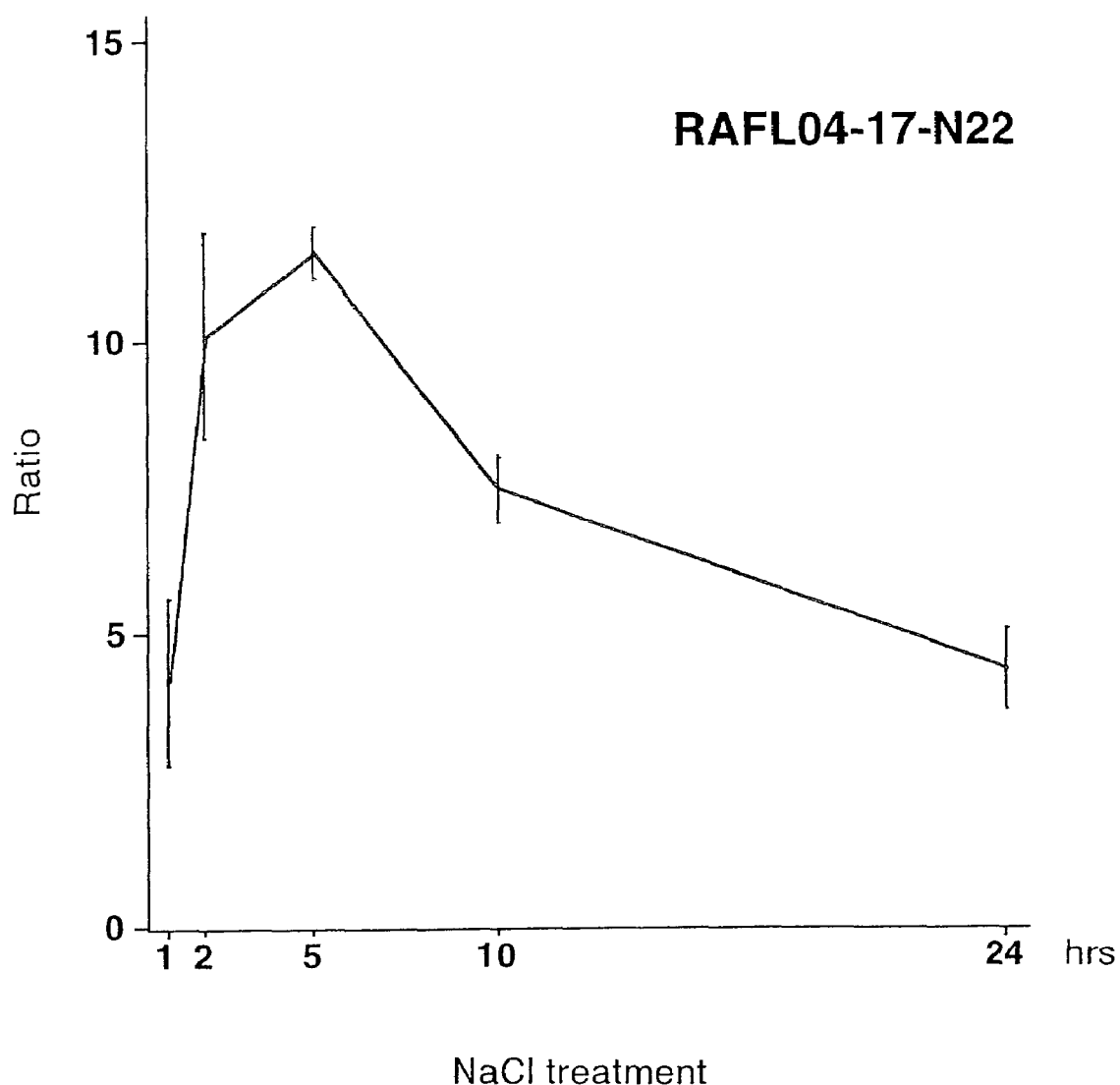
Figure 159:
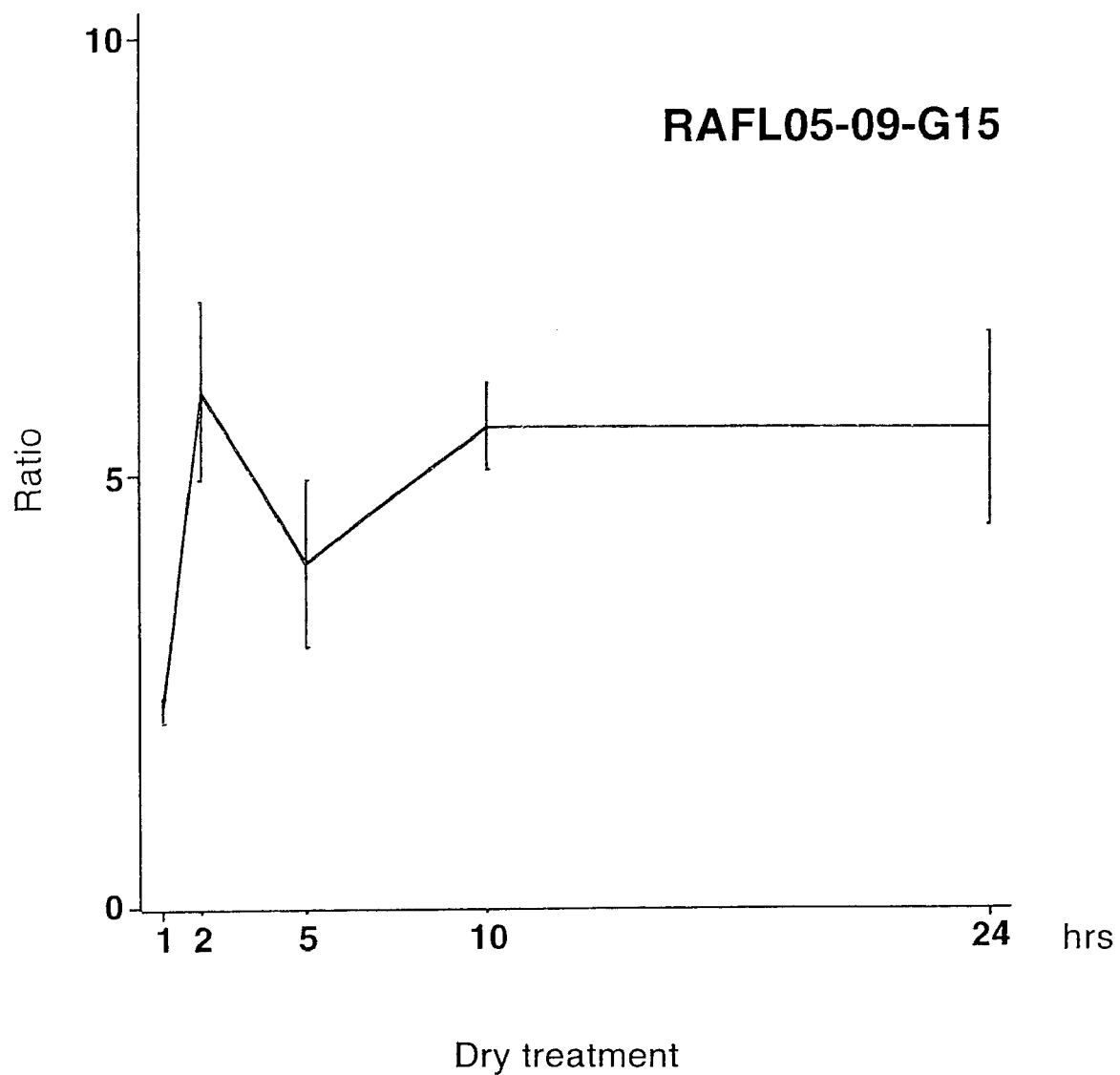
Figure 160:
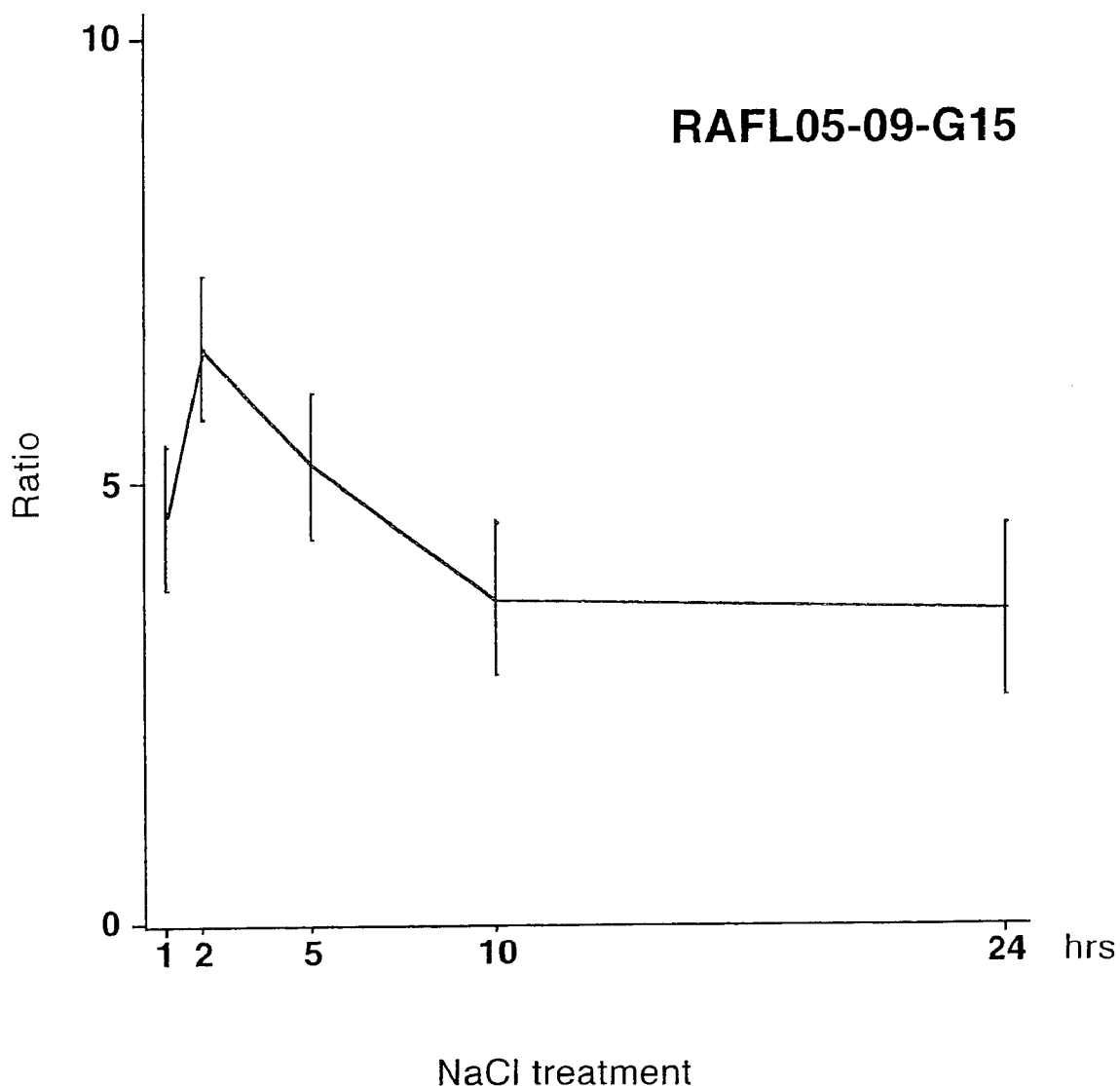
Figure 161:
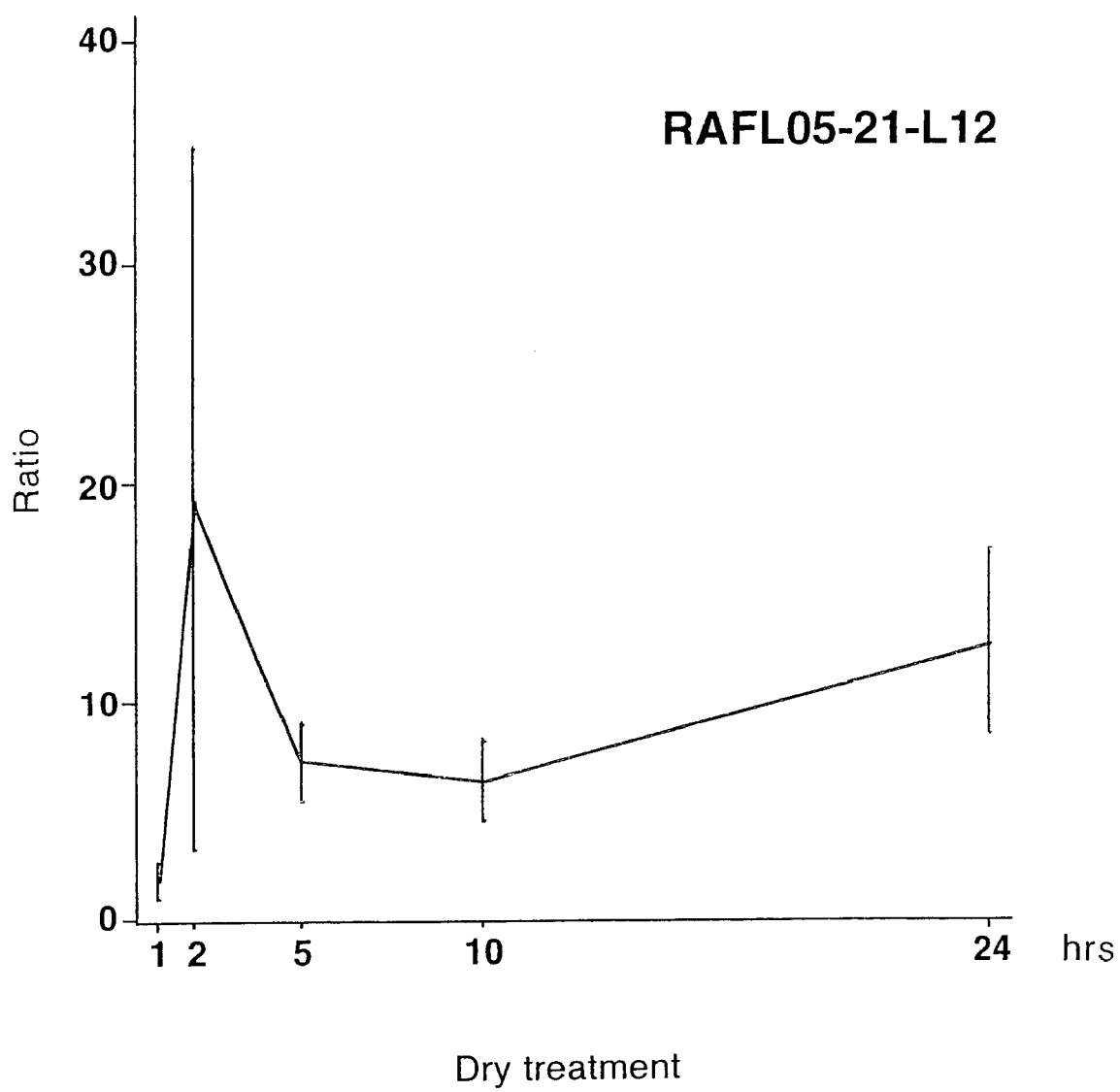
Figure 162:
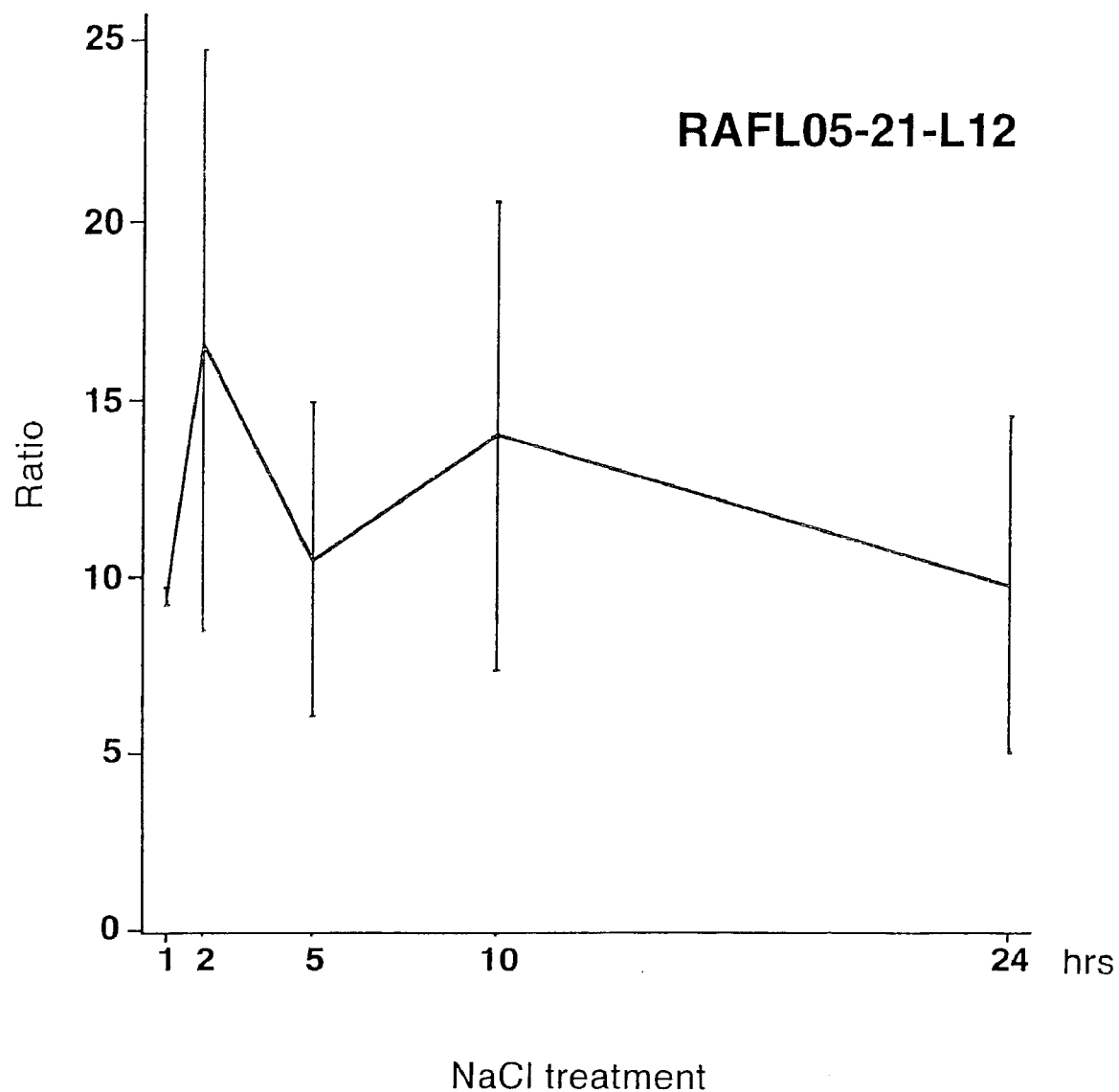

FIG. 132 is a characteristic graph showing the relationship between high salt stress and expression ratio regarding RAFL06-10-D22;

FIG. 133 is a characteristic graph showing the relationship between high salt stress and expression ratio regarding RAFL06-12-M01;

FIG. 134 is a characteristic graph showing the relationship between drought stress and expression ratio regarding RAFL06-12-M01;

FIG. 135 is a characteristic graph showing the relationship between drought stress and expression ratio regarding RAFL05-14-D24;

FIG. 136 is a characteristic graph showing the relationship between high salt stress and expression ratio regarding RAFL05-14-D24;

FIG. 137 is a characteristic graph showing the relationship between cold stress and expression ratio regarding RAFL05-20-N17;

FIG. 138 is a characteristic graph showing the relationship between drought stress and expression ratio regarding RAFL05-20-N17;

FIG. 139 is a characteristic graph showing the relationship between drought stress and expression ratio regarding RAFL04-17-F21;

FIG. 140 is a characteristic graph showing the relationship between drought stress and expression ratio regarding RAFL09-12-N16;

FIG. 141 is a characteristic graph showing the relationship between drought stress and expression ratio regarding AFL05-19-I05;

FIG. 142 is a characteristic graph showing the relationship between high salt stress and expression ratio regarding RAFL05-19-I05;

FIG. 143 is a characteristic graph showing the relationship between high salt stress and expression ratio regarding RAFL05-21-I22;

FIG. 144 is a characteristic graph showing the relationship between drought stress and expression ratio regarding RAFL08-11-H20;

FIG. 145 is a characteristic graph showing the relationship between high salt stress and expression ratio regarding RAFL08-11-H20;

FIG. 146 is a characteristic graph showing the relationship between high salt stress and expression ratio regarding RAFL05-21-C17;

FIG. 147 is a characteristic graph showing the relationship between drought stress and expression ratio regarding RAFL05-21-C17;

FIG. 148 is a characteristic graph showing the relationship between high salt stress and expression ratio regarding RAFL05-08-D06;

FIG. 149 is a characteristic graph showing the relationship between drought stress and expression ratio regarding RAFL05-20-M16;

FIG. 150 is a characteristic graph showing the relationship between high salt stress and expression ratio regarding RAFL05-20-M16;

FIG. 151 is a characteristic graph showing the relationship between drought stress and expression ratio regarding RAFL11-01-J18;

FIG. 152 is a characteristic graph showing the relationship between high salt stress and expression ratio regarding RAFL11-01-J18;

FIG. 153 is a characteristic graph showing the relationship between high salt stress and expression ratio regarding RAFL11-09-C20;

FIG. 154 is a characteristic graph showing the relationship between high salt stress and expression ratio regarding RAFL05-18-N16;

FIG. 155 is a characteristic graph showing the relationship between drought stress and expression ratio regarding RAFL11-10-D10;

FIG. 156 is a characteristic graph showing the relationship between high salt stress and expression ratio regarding RAFL11-10-D10;

FIG. 157 is a characteristic graph showing the relationship between drought stress and expression ratio regarding RAFL04-17-N22;

FIG. 158 is a characteristic graph showing the relationship between high salt stress and expression ratio regarding RAFL04-17-N22;

FIG. 159 is a characteristic graph showing the relationship between drought stress and expression ratio regarding RAFL05-09-G15;

FIG. 160 is a characteristic graph showing the relationship between high salt stress and expression ratio regarding RAFL05-09-G15;

FIG. 161 is a characteristic graph showing the relationship between drought stress and expression ratio regarding RAFL05-21-L12; and FIG. 162 is a characteristic graph showing the relationship between high salt stress and expression ratio regarding RAFL05-21-L21.

BEST MODE FOR CARRYING OUT THE INVENTION

Hereinafter, the present invention will be further explained in detail by way of examples, which should not be construed as limiting the scope of the present invention.

EXAMPLE 1

Isolation of Promoter

1. Materials and Methods (1) *Arabidopsis* cDNA Clone

A microarray was constructed by using about 7,000 cDNA molecules in total including genes isolated from an *Arabidopsis* full-length cDNA libraries, responsive-to-dehydration (RD) genes, early responsive-to-dehydration (ERD) genes, kin 1 genes kin2 genes, and cor15a genes; α-tubulin genes as an internal standard; and mouse nicotinic acetylcholine receptor epsilon subunit (nAChRE) genes and mouse glucocorticoid receptor homologous genes, as negative controls.

Positive control: dehydration-inducible genes (responsive-to-dehydration genes: rd, and early responsive-to-dehydration genes; erd)

Internal standard: α-tubulin gene

Negative control: mouse nicotinic acetylcholine receptor epsilon subunit (nAChRE) genes and mouse glucocorticoid receptor homologous genes, which do not substantially have homology with any given sequence in an *Arabidopsis* database for analyzing non-specific hybridization.

(2) *Arabidopsis* Full-length cDNA Microarray

The present inventors have constructed full-length cDNA libraries from an *Arabidopsis* plant body under different conditions (e.g., dehydration treatment, cold treatment and non-treatment in different growth stages from budding to maturation of seeds) by the biotinylated CAP trapper method. From the full-length cDNA libraries, the present inventors isolated individually about 7,000 independent *Arabidopsis* full-length cDNA molecules. The cDNA fragments, which were amplified by PCR, were arranged on a slide glass in accordance with a known method (Eisen and Brown, 1999). The present inventors prepared a full-length cDNA microarray containing about 7,000 *Arabidopsis* full-length cDNA molecules, which contain the genes below.

(3) Isolation of Dehydration-, Cold-, High Salt-, and ABA-inducible Genes Using cDNA Microarray In this example, dehydration-, cold-, high salt-, and ABA-inducible genes were isolated by using a full-length cDNA microarray containing about 7,000 *Arabidopsis* full-length cDNA molecules.

Probes of a plant treated with different stresses and an untreated plant with stress and labeled with Cy3 and Cy5 fluorescent dyes were mixed. The probes were hybridized with the full-length cDNA microarray containing about 7,000 *Arabidopsis* full-length cDNA molecules. By such a double labeling of a pair of cDNA probes wherein one of the mRNA samples was labeled with Cy3-dUTP and the other was labeled with Cy5-dUTP, hybridization with DNA elements on a microarray can be performed simultaneously, with the result that quantitative determination of gene expression under two different conditions (that is, stressed and unstressed conditions) can be directly and easily performed. The hybridized microarray was scanned by two discrete laser channels for Cy3 and Cy5 emission from each of DNA elements. Subsequently, the intensity ratio between two fluorescent signals from each DNA element was determined. Based on the relative value of the intensity ratio, a change of differential expression of genes represented as a cDNA spot on the microarray was determined. In this example, an α-tubulin gene, whose expression level was almost equivalent under two different experimental conditions was used, as an internal control gene.

In the full-length cDNA microarray containing about 7,000 *Arabidopsis* full-length cDNA molecules, a procedure for identifying dehydration-, cold-, high salt-, and ABA-inducible genes will be explained.

1) Both mRNA molecules derived from a plant treated with one of the stresses mentioned above and mRNA molecules derived from a wild-type plant unstressed were used to prepare Cy3-labeled cDNA and Cy5-labeled cDNA probes, respectively. These cDNA probes were mixed and hybridized with the cDNA microarray. In this example, an α-tubulin gene, which exhibits almost the same expression level under two type conditions, was as used as an internal control gene. A gene that exhibits the expression ratio of dehydration:unstressed, cold:unstressed, or high salt:unstressed more than double of that of the α-tubulin gene was defined as an inducible gene by a stress given to the gene.

2) Both mRNA molecules derived from a 35S:DREB1A transgenic plant and mRNA molecules derived from a wild-type plant unstressed were used to prepare Cy3-labeled cDNA and Cy5-labeled cDNA probes, respectively. These cDNA probes were mixed and hybridized with a cDNA microarray. In this example, an α-tubulin gene exhibiting almost the same expression level under two type conditions was used as an internal control gene. A gene of 35S:DREB1A transgenic plant exhibiting an expression ratio more than double of that of a gene of the wild type plant unstressed was defined as a DREB1A target gene.

Both mRNA molecules derived from a plant treated with a stress and mRNA molecules derived from a wild-type plant unstressed were used to prepare Cy3-labeled cDNA and Cy5-labeled cDNA probes, respectively. These cDNA probes were mixed and hybridized with a cDNA microarray. The same experiment was repeated three times to evaluate the reproducibility of microarray analysis. When the same mRNA sample was hybridized with various microarrays, a good correlation was observed. A gene that exhibits an expression ratio (dehydration/unstressed, cold-unstressed) more than double of that of the α-tubulin gene was defined as an inducible gene by a stress given to the gene.

(4) Analysis of Sequence

Plasmid DNA extracted by a plasmid preparation device (NA 100) manufactured by Kurabo was sequenced to find homology of gene sequences. The DNA sequence was determined by a dye terminator cycle sequencing method using a DNA sequencer (ABI PRISM 3700. PE Applied Biosystems, CA, USA). Based on the GenBank/EMBL database, homology of sequences was found by using the BLAST program.

(5) Amplification of cDNA

λZAPII (Carninci et all, 1996) was used as a vector for constructing a cDNA library. The cDNA inserted in a vector for the library was amplified by PCR using complementary primers to the sequences of both sides of the cDNA.

The sequence of primers are as follows:

```
FL forward 1224:
5'-CGCCAGGGTTTTCCCAGTCACGA    (SEQ ID NO: 91)

FL reverse 1233:
5'-AGCGGATAACAATTTCACACAGGA   (SEQ ID NO: 92)
```

To 100 µl of a PCR solution mixture (0.25 mM dNTP, 0.2 µM PCR primer, 1×Ex Taq Buffer, and 1.25 U Ex Taq polymerase (manufactured by Takura Shuzo)), a plasmid (1 to 2 ng) was added as a template. PCR was performed under the following conditions: an initial reaction at 94° C. for 3 minutes, 35 cycles each consisting of 95° C. for one minute, 60° C. for 30 seconds and 72° C. for 3 minutes, and a final reaction at 72° C. for 3 minutes. After a PCR product was precipitated with ethanol, the precipitate was dissolved in 25 µl of 3×SSC and then subjected to electrophoresis using 0.7% agarose gel. The quality of the DNA obtained and amplification efficiency of PCR were confirmed.

(6) Construction of cDNA Microarray

Using a gene tip microarray stamp machine GTMASS SYSTEM (manufactured by Nippon Laser & Electronics Lab.), 0.5 µl of a PCR product (100 to 500 ng/ml) was loaded from a 384-well microtiter plate to form spots of the PCR product (5 nl for each) at intervals of 280 µm of 6 micro slide glasses (S7444, manufactured Matsunami) coated with poly-L lysine. To spot DNA in an equivalent amount, the slide after printing was placed in a beaker containing heated distilled water to moisten it and placed at 100° C. for 3 seconds to dry it. After the slide was placed on a slide rack, the rack was transferred into a glass chamber. To the glass chamber, a blocking solution (15 ml of 1M sodium borate salt (pH 8.0), 5.5 g succinic anhydrous compound (Wako), and 335 ml of 1-methyl-2-pyrrolidon (Wako)) was poured. After the glass chamber housing the slide rack was shaken up and down 5 times and gently shaking for 15 minutes, the slide rack was transferred to a glass chamber containing boiling water, shaken 5 times, and allowed to stand alone for 2 minutes. Thereafter, the slide rack was transferred to a glass chamber containing 95% ethanol, shaken 5 times, and centrifuged at 800 rpm for 30 minutes.

(7) Plant Material and Isolation of RNA

As a plant material, use was made of a wild type *Arabidopsis thaliana* plant body which was seeded on an agar medium and grown for 3 weeks (Yamaguchi-Shinozaki and Shinozaki, 1994) and an *Arabidopsis thaliana* (Colombian species) plant body into which DREB1A cDNA (Kasuga et al., 1999) connected to a 35S promoter of a cauliflower mosaic virus was introduced. Dehydration- and cold-stress treatments were performed in accordance with the method of Yamaguchi-Shinozaki and Shinozaki (1994). More specifically, dehydration treatment was performed by pulling a plant body out of the agar medium, placing it on a filter, and dried at a temperature of 22° C. and a relative humidity of 60%. The cold treatment was performed by transferring a plant body grown at 22° C. to 4° C. High salt stress treatment was performed by growing a plant body at an aqueous solution containing 250 mM NaCl.

After wild type plant bodies were exposed to stress-treatment for 2 or 10 hours, a sample was taken from each of plant bodies and stored in cryogenic conditions with liquid nitrogen. Furthermore, wild type and DREB1A overexpression-type transformants cultured in an agar medium without kanamycin were subjected to an experiment for identifying a DREB1A target gene. The DREB1A overexpression-type transformant was not treated with stresses.

The total RNA was isolated from a plant body by using ISOGEN (Nippon gene, Tokyo, Japan) and mRNA was isolated and purified by Oligotex-dT30 mRNA purification kit (Takara, Tokyo, Japan).

(8) Fluorescent Labeling of Probe

Each of the mRNA samples was subjected to a reverse transcription reaction in the presence of Cy3 dUTP or Cy5 dUTP (Amersham Pharmacia). The composition of the buffer (30 μl) used in the reverse transcription reaction is shown in Table 2.

TABLE 2

| | |
|---|---|
| poly(A)$^+$ RNA with 6 μg oligo(dT) 18-mer | 1 μg |
| 10 mM DTT | |
| 500 μM dATP, dCTP and dGTP | |
| 200 μM dTTP | |
| 100 μM Cy3 dUTP or Cy5 dUTP | |
| 400 units of SuperScript II Reverse Transcriptase (Life technologies) | |
| 1X Superscript First Strand Synthesis Buffer (Life technologies) | |
| | Total 30 μL |

After reaction was performed at 42° C. for one hour, two samples (labeled with Cy3 and Cy5) were mixed to obtain a reaction mixture. To this reaction mixture, 15 μl of 0.1 M NaOH and 1.5 μl of 20 mM EDTA were added and treated at 70° C. for 10 minutes. Further, 15 μl of 0.1 M HCl was added to the reaction mixture, a sample was taken and transferred to a Micro con 30 micro concentrator (Amicon). 400 μl of TE buffer was added to the sample and centrifuged until the volume of the buffer reached 10 to 20 μl. The effluent was discarded. 400 μl of TE buffer and 20 μl of 1 mg/ml human Cot-1 DNA (Gibco BRL) were added to the resultant mixture and the mixture was again centrifuged. The labeled samples were centrifugally collected and several μl of distilled water was added thereto. The obtained probes, 2 μl of 10 μg/μl yeast tRNA, 2 μl of 1 μg/μl pd(A)$_{12-18}$ (Amersham Pharmacia), 3.4 ml of 20×SSC, and 0.6 μl of 10% SDS were added. Further, the samples were denatured at 100° C. for 1 minute and placed at room temperature for 30 minutes and thereafter used in hybridization.

(9) Microarray Hybridization and Scanning

A probe was subjected to high-speed centrifugation for one minute by a benchtop micro centrifuge. To avoid generation of bubbles, the probe was placed at the center of an array and a cover slip was placed thereon. Four drops of 5 μl of 3×SSC were dropped on a slide glass and a chamber was kept at a suitable humidity to prevent the probe from being dried during hybridization. After the slide glass was placed in a cassette for hybridization (THC-1, BM machine) and the cassette was sealed, hybridization treatment was performed at 65° C. for 12 to 16 hours. The slide glass was taken out from the cassette and placed on the slide rack. After the cover slip was carefully removed in solution 1 (2×SSC, 0.1% SDS), the rack was washed while shaking and transferred into solution 2 (1×SSC) to wash for 2 minutes. The rack was further transferred to solution 3 (0.2×SSC), allowed to stand for 2 minutes, and centrifuged at 800 rpm for 1 min to dry.

The microarray was scanned at a resolution of 10 μm per pixel by use of a scanning laser microarray (ScanArray 4000; GSI Lumonics, Watertown, Mass.). As a program for analyzing microarray data, Imagine Ver 2.0 (BioDiscovery) and QuantArray (GSI Lumonics) were used.

(10) Northern Analysis

Northern analysis was performed using total RNA, (Yamaguchi-Shinozaki and Shinozaki, 1994). DNA fragments were isolated from the *Arabidopsis thaliana* full-length cDNA library by a PCR method and used as probes for Northern hybridization.

(11) Determination of Promoter Region

Based on the genomic information of *Arabidopsis thaliana* in a data base (GenBank/EMBL, ABRC), a promoter region was analyzed by using the BLAST program for gene analysis.

2. Results (1) Stress-inducible Gene

Fluorescent-labeled cDNA was prepared by subjecting mRNA isolated from an unstressed *Arabidopsis thaliana* plant to a reverse transcription reaction in the presence of Cy5-dUTP. A second probe labeled with Cy3-dUTP was prepared from a plant treated at low temperature for 2 hours. Both probes were simultaneously hybridized with a cDNA microarray comprising about 7,000 *Arabidopsis thaliana* cDNA clones and then a pseudo color image was created.

Genes induced and suppressed by a stress are presented by a red signal and green signal, respectively. Genes expressed at virtually the same level in both treatments are represented by a yellow signal. The intensity of each spot corresponds to the absolute value of the expression level of each gene. It is shown that a cold-inducible gene (rd29A) is represented by a red signal whereas an α-tubulin gene (an internal control) is represented by a yellow signal.

(2) Identification of Promoter Region

As a result of identifying a promoter region, the promoter gene regions of 90 types of genes were obtained in a full-length cDNA microarray containing about 7,000 of *Arabidopsis* full-length cDNA molecules. The name of these 90 types of genes and their promoter sequences are summarized in Table 3.

TABLE 3

| Name of gene | SEQ ID NO: |
|---|---|
| FL03-07-F12 | SEQ ID NO: 1 |
| FL04-12-F24 | SEQ ID NO: 2 |
| FL04-14-N10 | SEQ ID NO: 3 |
| FL04-14-P24 | SEQ ID NO: 4 |
| FL04-17-I03 | SEQ ID NO: 5 |
| FL04-17-M08 | SEQ ID NO: 6 |
| FL04-17-M22 | SEQ ID NO: 7 |
| FL05-05-A17 | SEQ ID NO: 8 |
| FL05-05-F20 | SEQ ID NO: 9 |
| FL05-05-G20 | SEQ ID NO: 10 |
| FL05-09-N09 | SEQ ID NO: 11 |
| FL05-10-J09 | SEQ ID NO: 12 |
| FL05-10-M08 | SEQ ID NO: 13 |
| FL05-11-H09 | SEQ ID NO: 14 |
| FL05-12-H13 | SEQ ID NO: 15 |
| FL05-13-I20 | SEQ ID NO: 16 |
| FL05-14-E15 | SEQ ID NO: 17 |
| FL05-14-E16 | SEQ ID NO: 18 |
| FL05-16-F03 | SEQ ID NO: 19 |
| FL05-16-H23 | SEQ ID NO: 20 |
| FL05-18-M07 | SEQ ID NO: 21 |
| FL05-18-O21 | SEQ ID NO: 22 |
| FL05-19-P21 | SEQ ID NO: 23 |
| FL05-19-O22 | SEQ ID NO: 24 |
| FL05-21-K17 | SEQ ID NO: 25 |
| FL06-10-F03 | SEQ ID NO: 26 |
| FL06-12-H12 | SEQ ID NO: 27 |
| FL07-12-I23 | SEQ ID NO: 28 |
| FL08-08-H23 | SEQ ID NO: 29 |

TABLE 3-continued

| Name of gene | SEQ ID NO: |
|---|---|
| FL08-08-O14 | SEQ ID NO: 30 |
| FL08-09-M05 | SEQ ID NO: 31 |
| FL08-10-K08 | SEQ ID NO: 32 |
| FL08-11-P07 | SEQ ID NO: 33 |
| FL08-13-F10 | SEQ ID NO: 34 |
| FL08-19-D04 | SEQ ID NO: 35 |
| FL08-19-G15 | SEQ ID NO: 36 |
| FL09-06-B11 | SEQ ID NO: 37 |
| FL09-07-G17 | SEQ ID NO: 38 |
| FL09-10-A12 | SEQ ID NO: 39 |
| FL09-13-P15 | SEQ ID NO: 40 |
| FL02-05-I05 | SEQ ID NO: 41 |
| FL04-12-N15 | SEQ ID NO: 42 |
| FL04-16-P21 | SEQ ID NO: 43 |
| FL04-17-N22 | SEQ ID NO: 44 |
| FL04-20-P19 | SEQ ID NO: 45 |
| FL02-09-H01 | SEQ ID NO: 46 |
| FL05-01-D08 | SEQ ID NO: 47 |
| FL05-02-G08 | SEQ ID NO: 48 |
| FL05-02-O17 | SEQ ID NO: 49 |
| FL05-07-L13 | SEQ ID NO: 50 |
| FL05-08-B14 | SEQ ID NO: 51 |
| FL05-09-N10 | SEQ ID NO: 52 |
| FL05-11-L01 | SEQ ID NO: 53 |
| FL05-12-J09 | SEQ ID NO: 54 |
| FL05-14-D24 | SEQ ID NO: 55 |
| FL05-14-F20 | SEQ ID NO: 56 |
| FL05-14-I08 | SEQ ID NO: 57 |
| FL05-15-C04 | SEQ ID NO: 58 |
| FL05-15-E19 | SEQ ID NO: 59 |
| FL05-18-A06 | SEQ ID NO: 60 |
| FL05-18-H15 | SEQ ID NO: 61 |
| FL05-19-C02 | SEQ ID NO: 62 |
| FL05-20-M16 | SEQ ID NO: 63 |
| FL05-20-N18 | SEQ ID NO: 64 |
| FL05-21-E06 | SEQ ID NO: 65 |
| FL05-21-L12 | SEQ ID NO: 66 |
| FL06-07-B08 | SEQ ID NO: 67 |
| FL06-08-H20 | SEQ ID NO: 68 |
| FL06-09-N04 | SEQ ID NO: 69 |
| FL06-11-K21 | SEQ ID NO: 70 |
| FL07-07-G15 | SEQ ID NO: 71 |
| FL07-12-D17 | SEQ ID NO: 72 |
| FL08-11-C23 | SEQ ID NO: 73 |
| FL08-13-G20 | SEQ ID NO: 74 |
| FL08-15-M21 | SEQ ID NO: 75 |
| FL08-18-N19 | SEQ ID NO: 76 |
| FL08-19-C07 | SEQ ID NO: 77 |
| FL08-19-P05 | SEQ ID NO: 78 |
| FL09-07-G09 | SEQ ID NO: 79 |
| FL09-07-G15 | SEQ ID NO: 80 |
| FL09-10-J18 | SEQ ID NO: 81 |
| FL09-11-I12 | SEQ ID NO: 82 |
| FL09-12-B03 | SEQ ID NO: 83 |
| FL09-16-I11 | SEQ ID NO: 84 |
| FL09-16-M04 | SEQ ID NO: 85 |
| FL11-01-J18 | SEQ ID NO: 86 |
| FL11-07-D13 | SEQ ID NO: 87 |
| FL11-07-F02 | SEQ ID NO: 88 |
| FL11-07-N15 | SEQ ID NO: 89 |
| FL11-10-D10 | SEQ ID NO: 90 |

(3) The Relationship Between Stress Treatment Time and Expression Ratio

Figure 1:
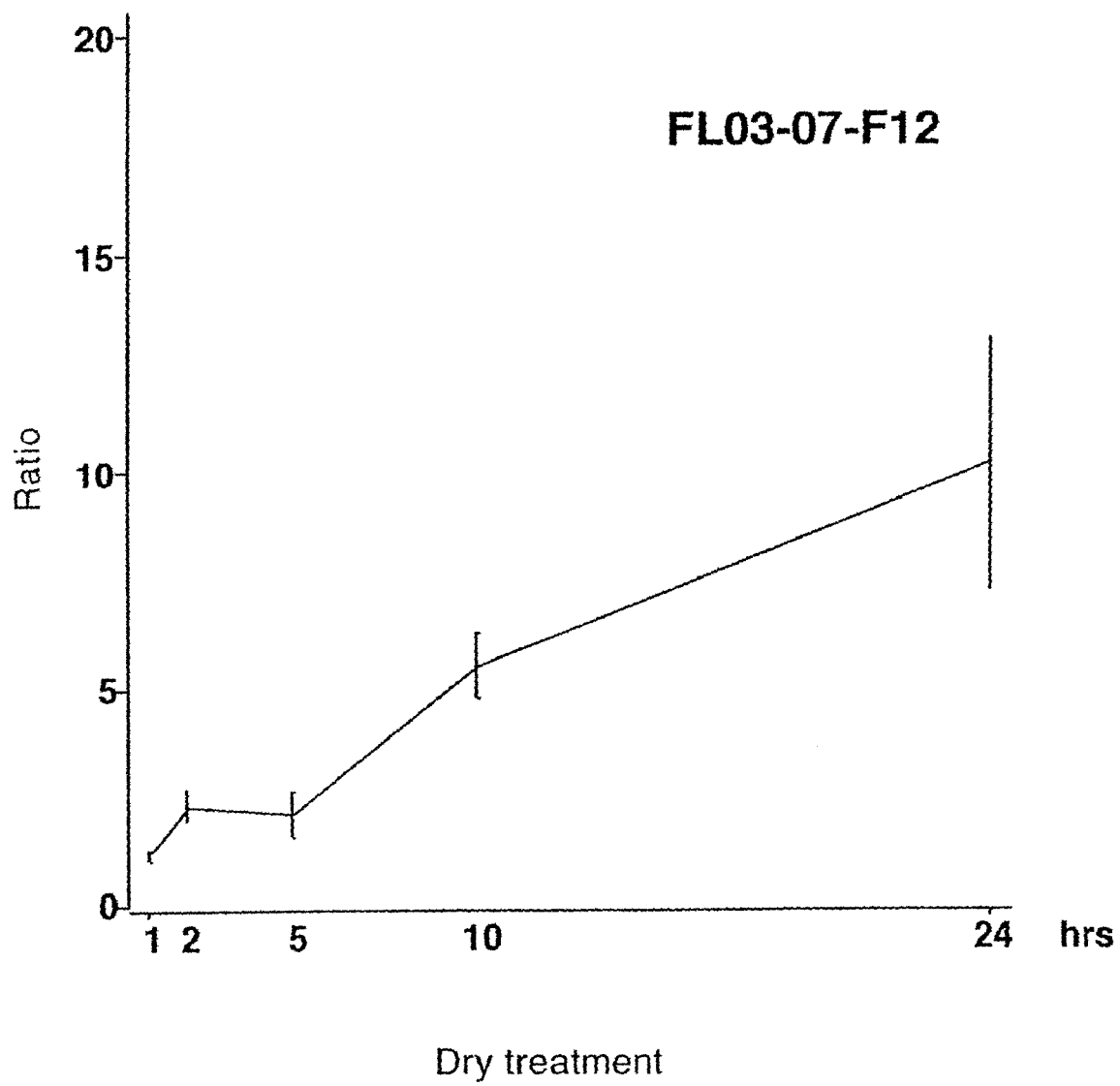
FIG. 1 is a characteristic graph showing the relationship between dehydration treatment time and expression ratio regarding FL03-07-F12.
Figure 105:
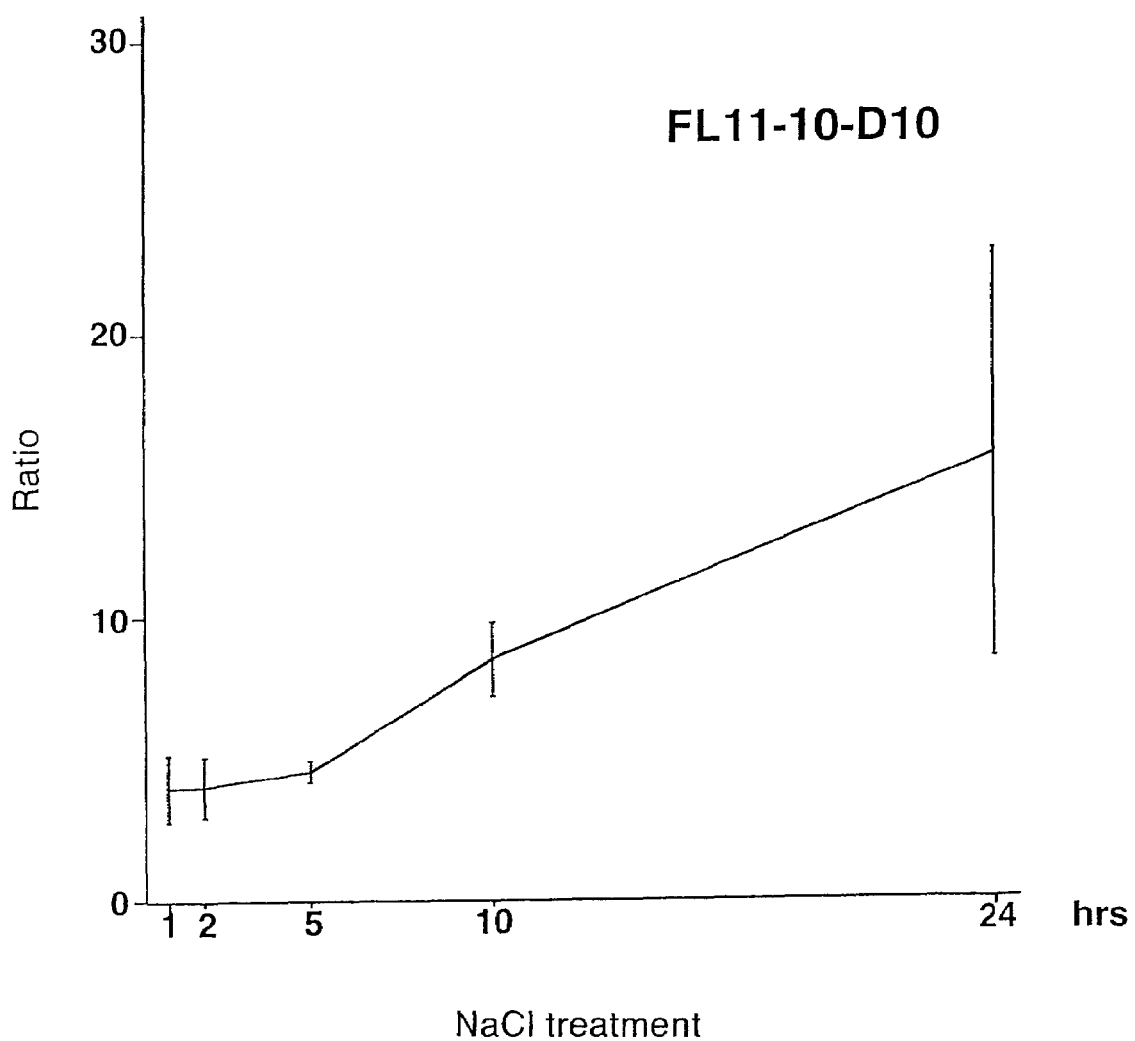
FIG. 105 is a characteristic graph showing the relationship between high salt treatment time and expression ratio regarding FL11-10-D10.

The 90 types of stress inducible genes isolated above were analyzed for the relationship between stress treatment time and expression ratio. The results are shown in FIGS. 1 to 105. The relationship between 90 types of genes and stress treatment are shown in Table 4.

TABLE 4

Figure 2:
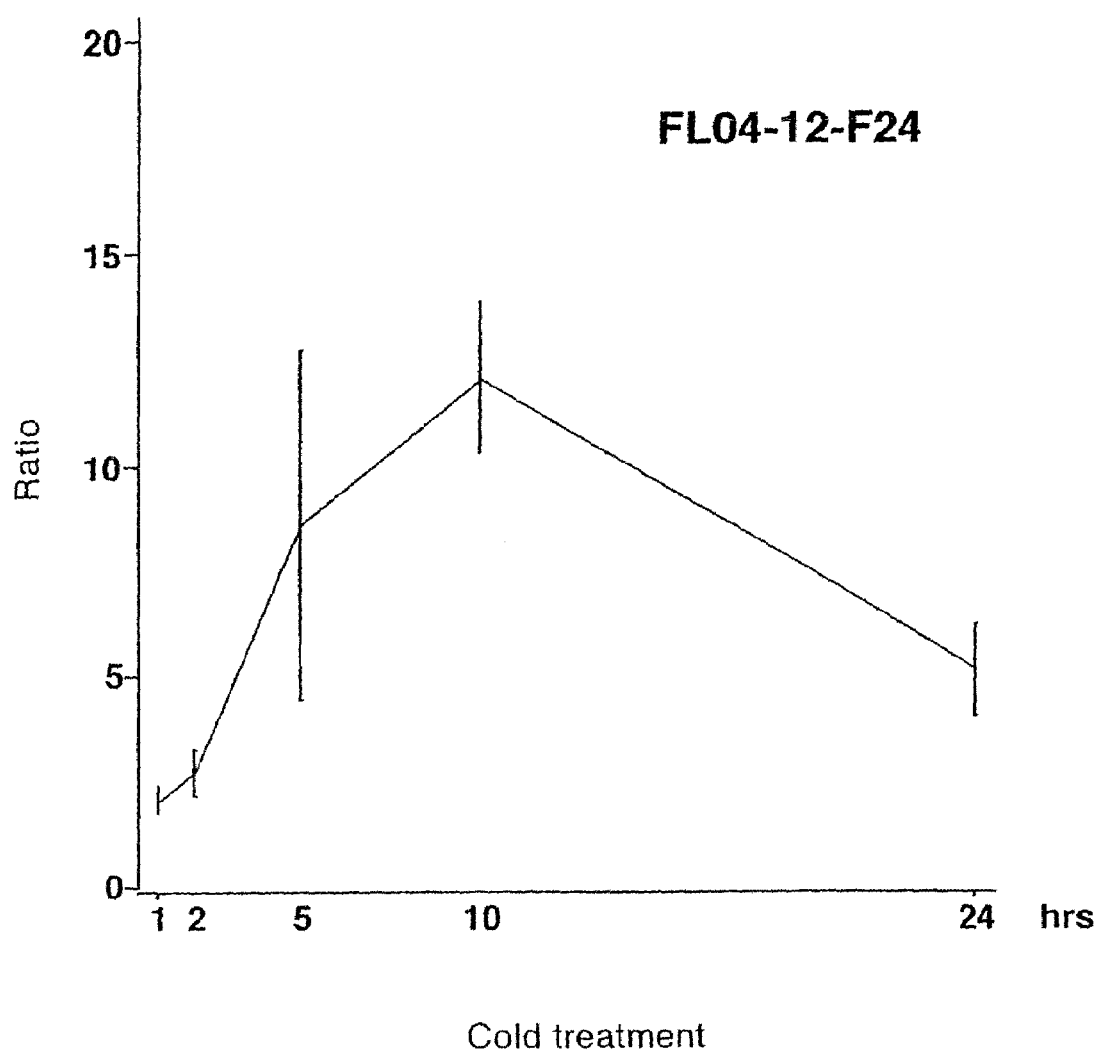
FIG. 2 is a characteristic graph showing the relationship between cold treatment time and expression ratio regarding FL04-12-F24.
Figure 3:
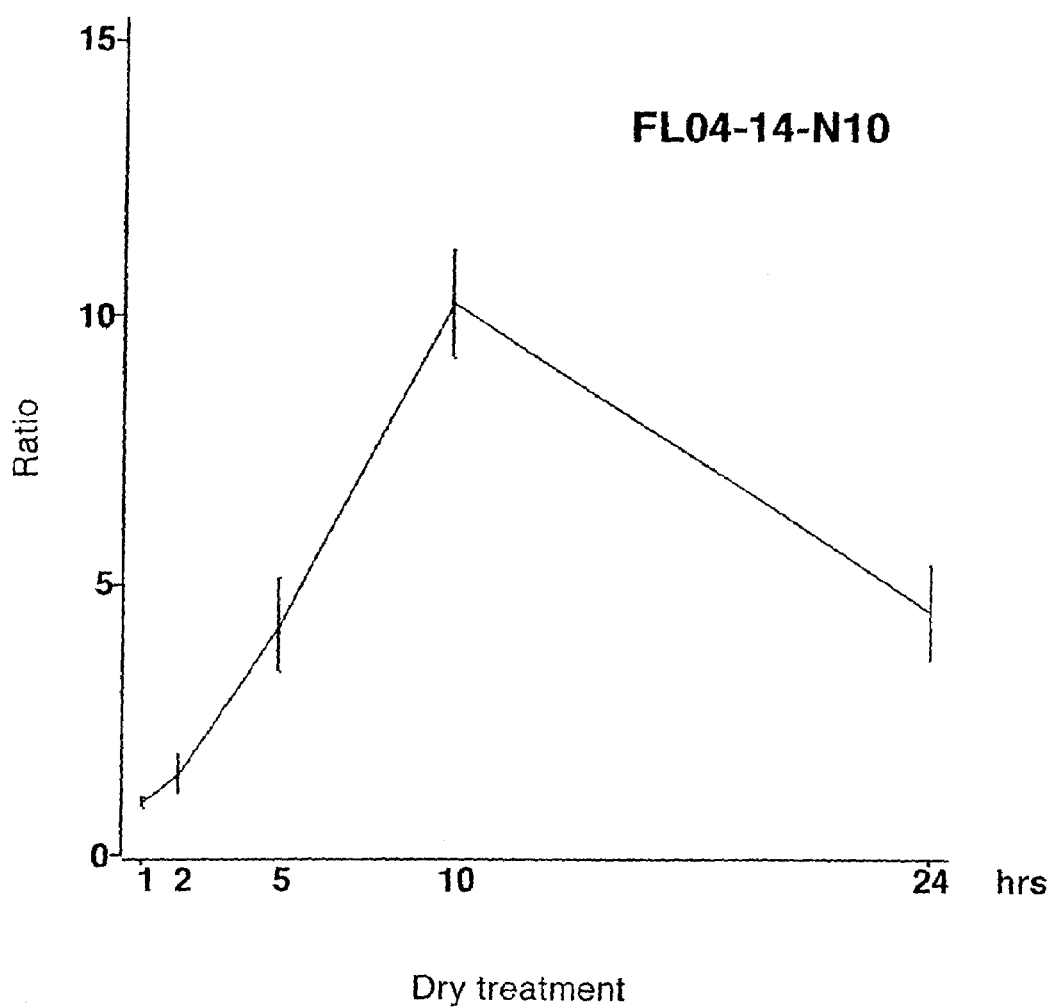
FIG. 3 is a characteristic graph showing the relationship between dehydration treatment time and expression ratio regarding FL04-14-N10.
Figure 4:
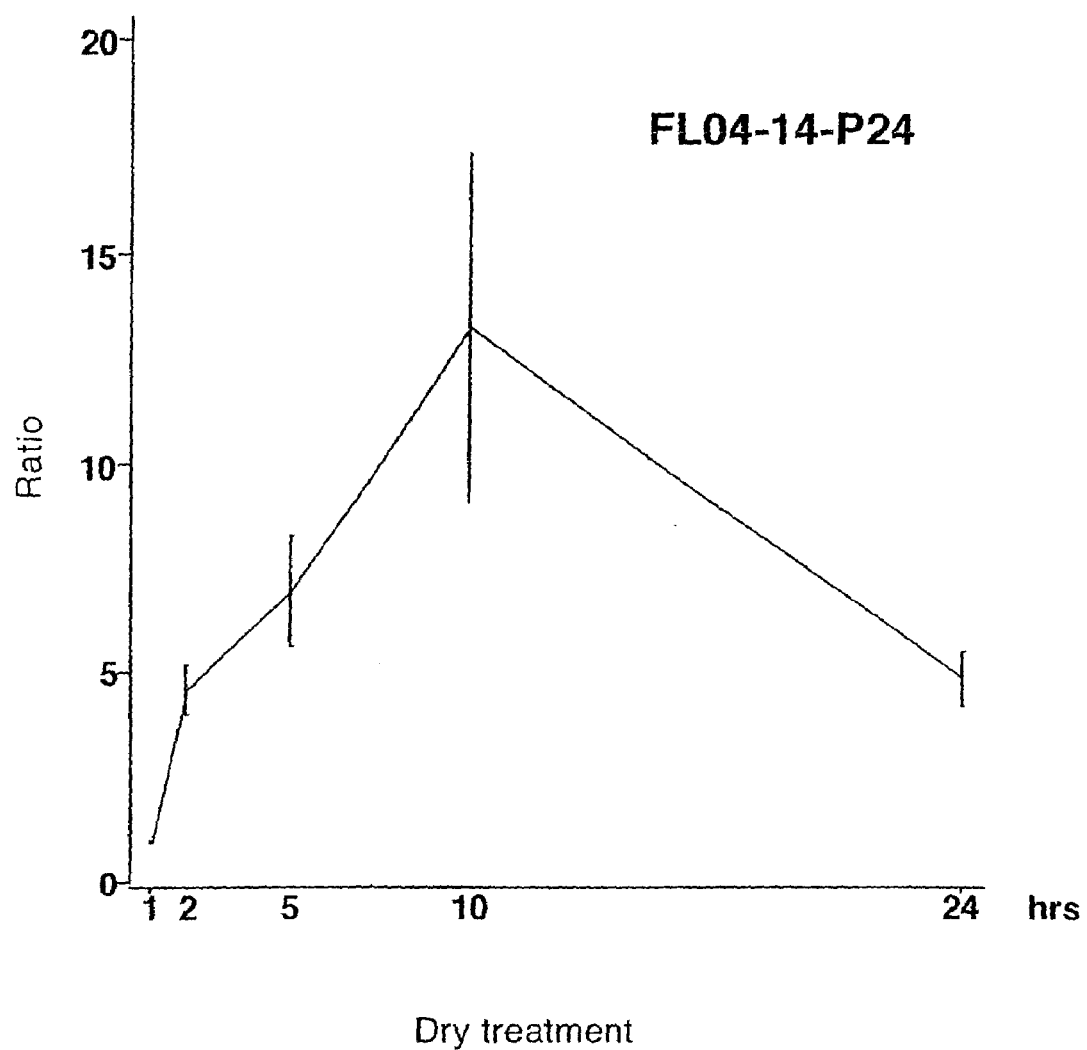
FIG. 4 is a characteristic graph showing the relationship between dehydration treatment time and expression ratio regarding FL04-14-P24.
Figure 5:
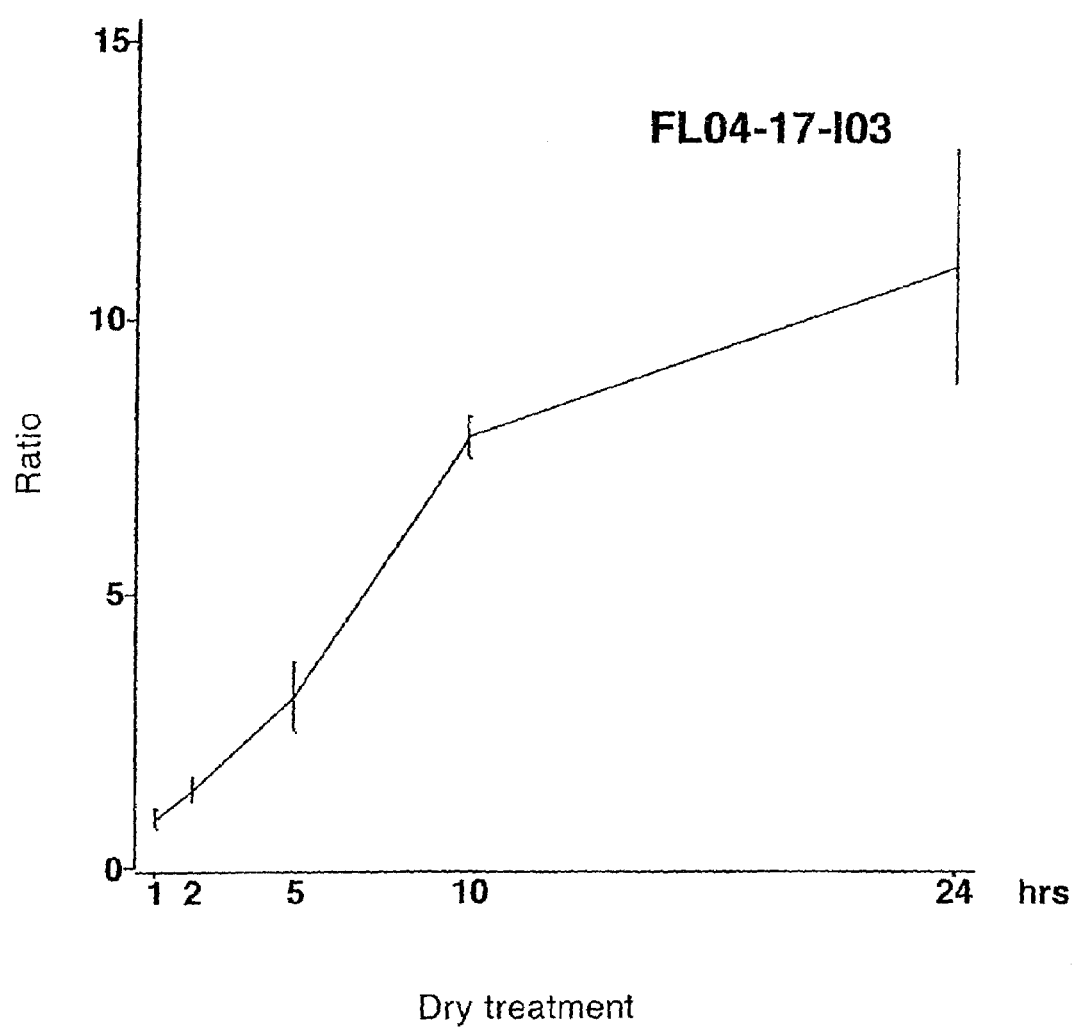
FIG. 5 is a characteristic graph showing the relationship between dehydration treatment time and expression ratio regarding FL04-17-I03.
Figure 6:
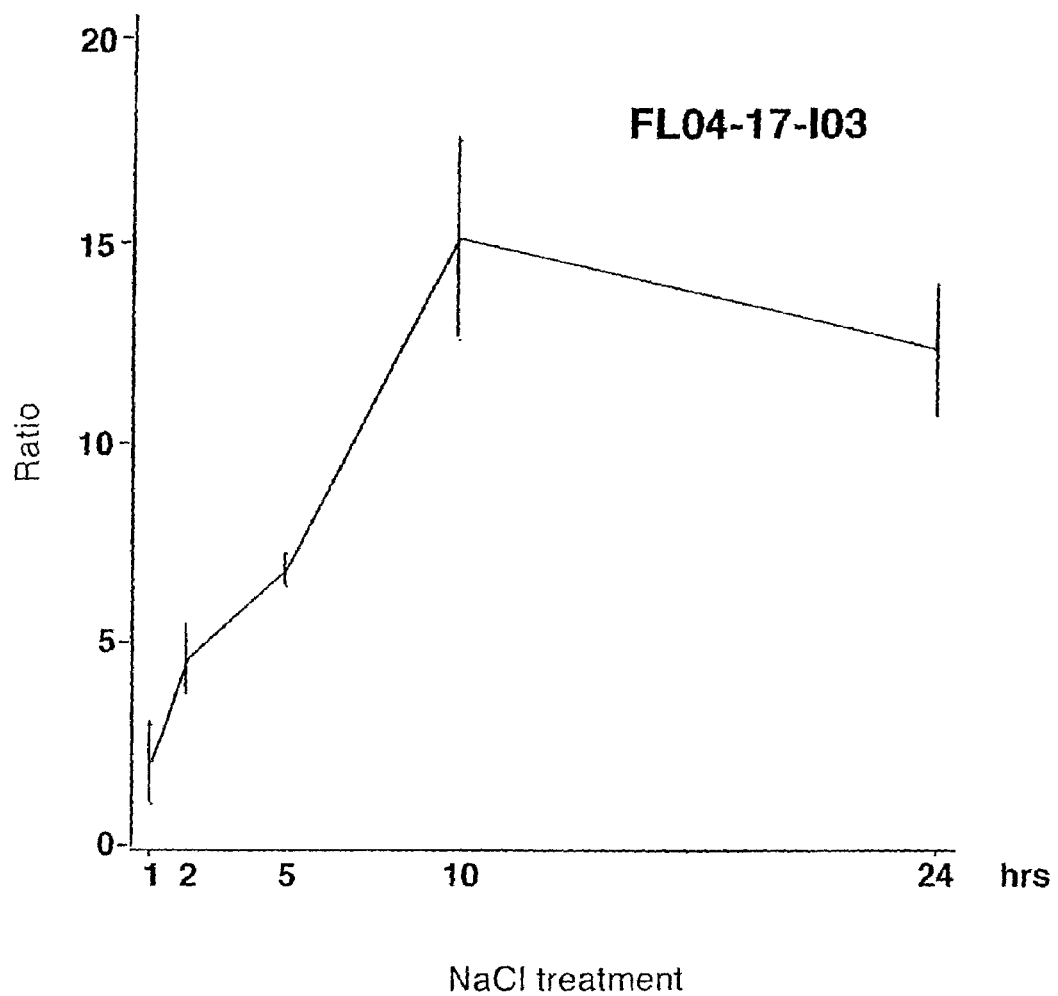
FIG. 6 is a characteristic graph showing the relationship between high salt treatment time and expression ratio regarding FL04-17-I03.
Figure 7:
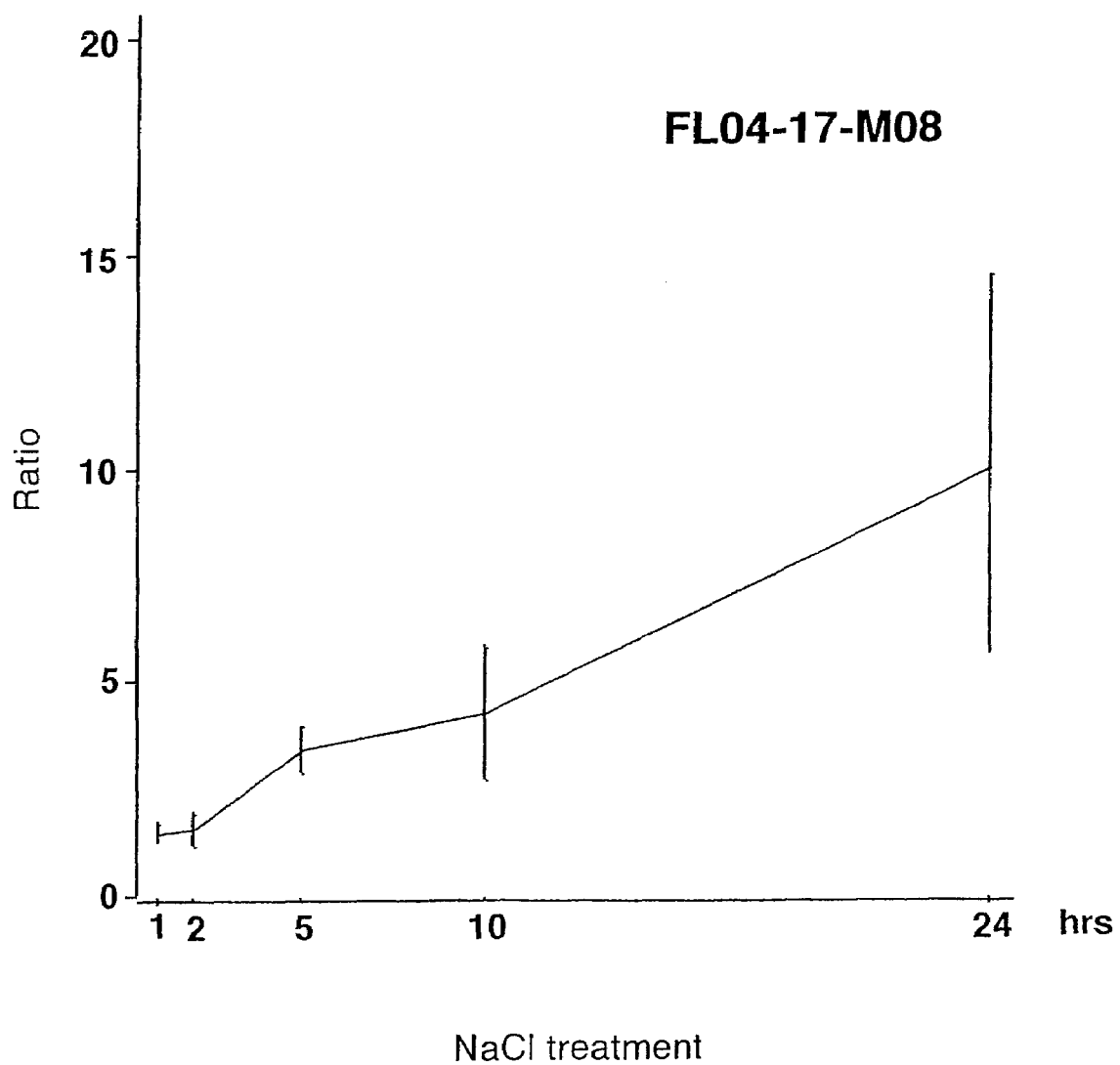
FIG. 7 is a characteristic graph showing the relationship between high salt treatment time and expression ratio regarding FL04-17-M08.
Figure 8:
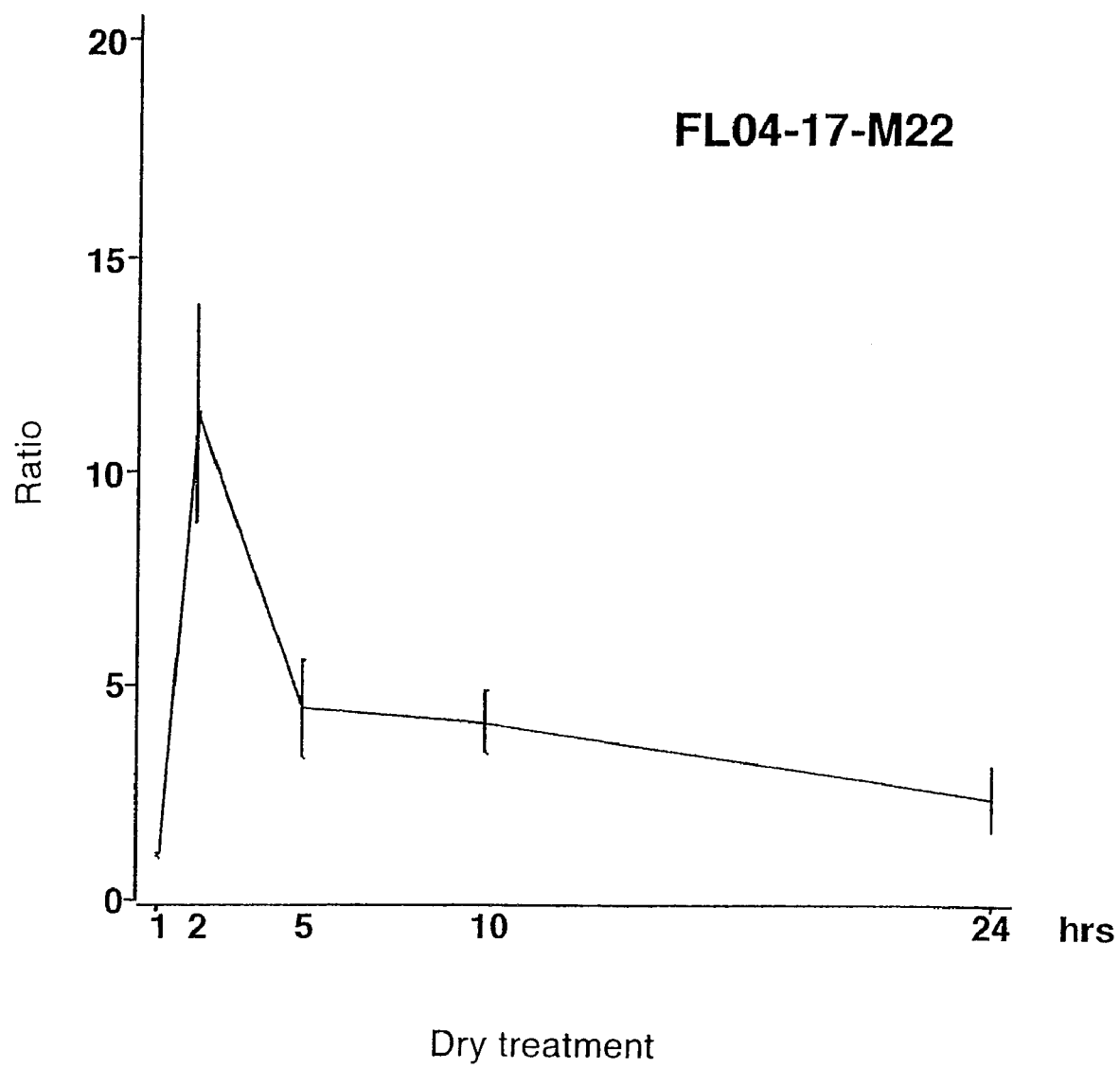
FIG. 8 is a characteristic graph showing the relationship between dehydration treatment time and expression ratio regarding FL04-17-M22.
Figure 9:
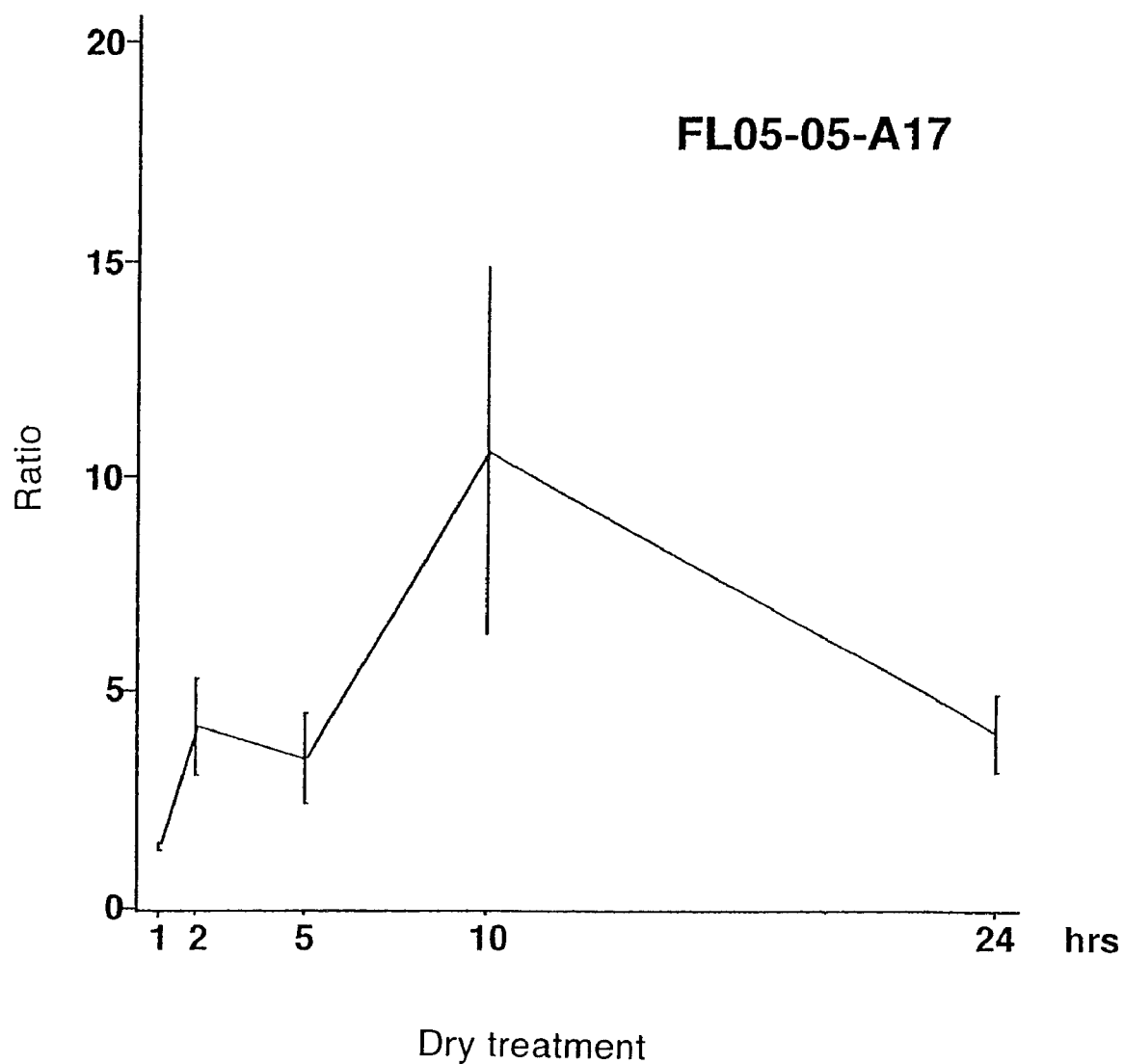
FIG. 9 is a characteristic graph showing the relationship between dehydration treatment time and expression ratio regarding FL05-05-A17.
Figure 10:
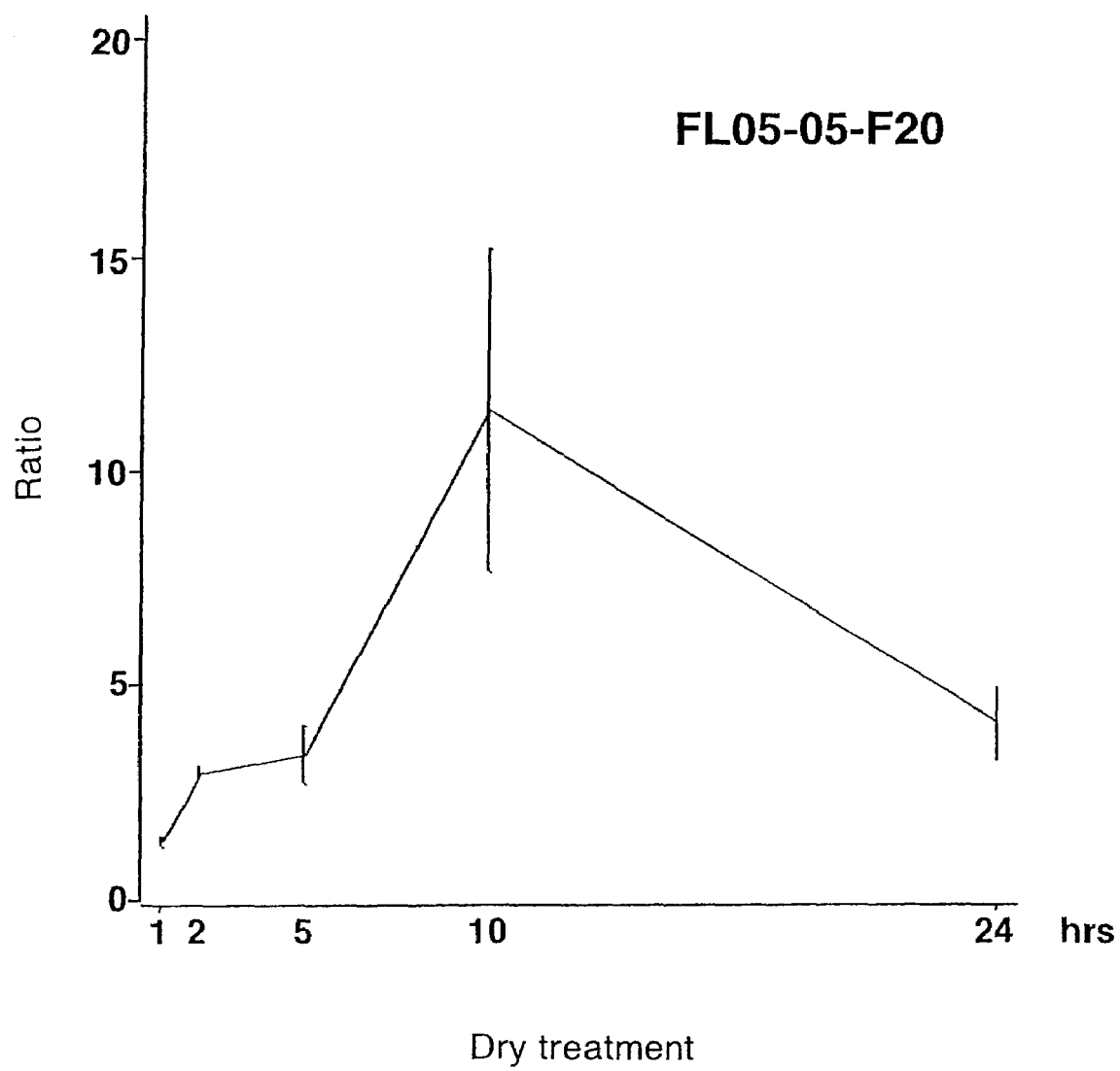
FIG. 10 is a characteristic graph showing the relationship between dehydration treatment time and expression ratio regarding FL05-05-F20.
Figure 11:
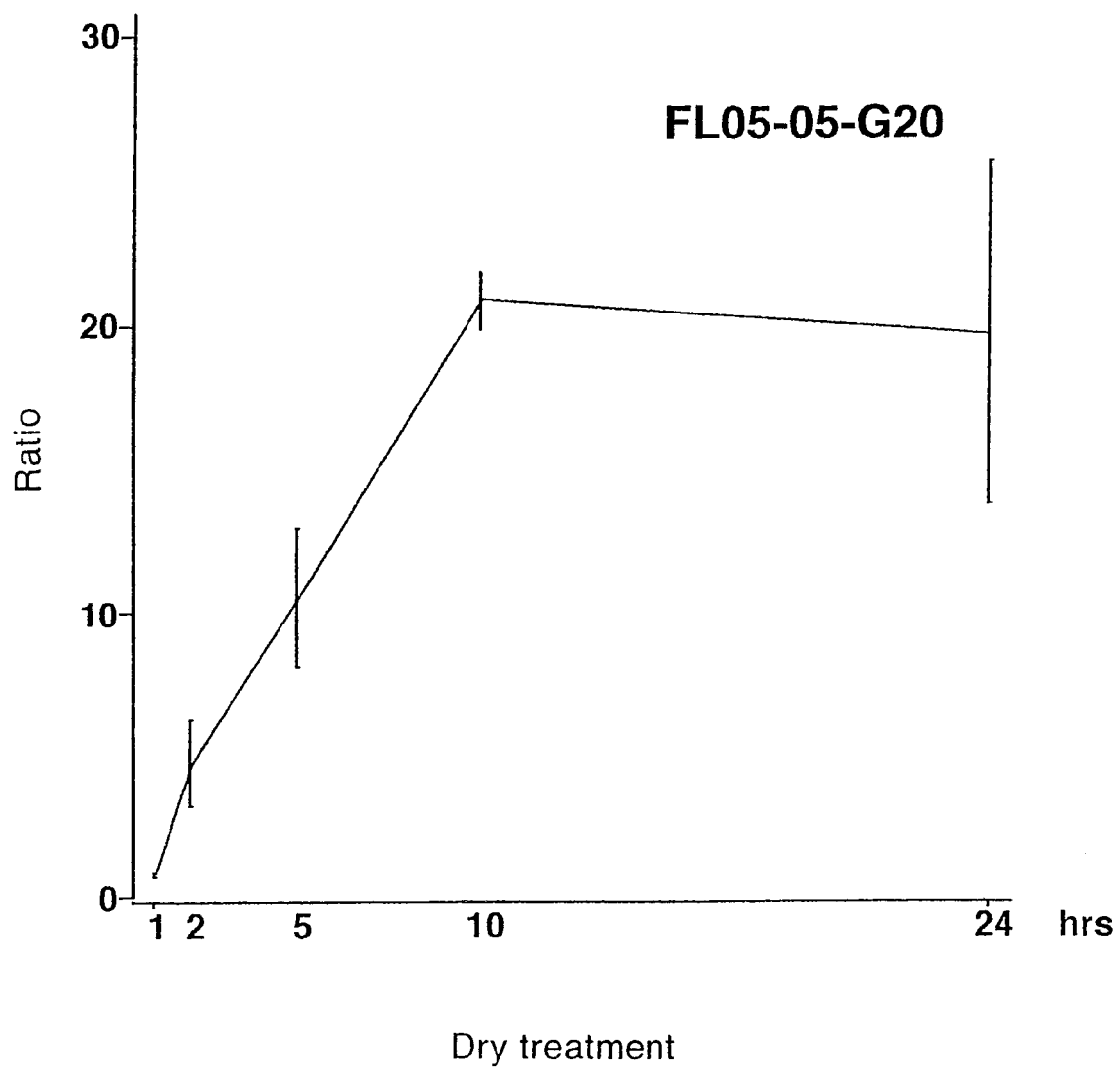
FIG. 11 is a characteristic graph showing the relationship between dehydration treatment time and expression ratio regarding FL05-05-G20.
Figure 12:
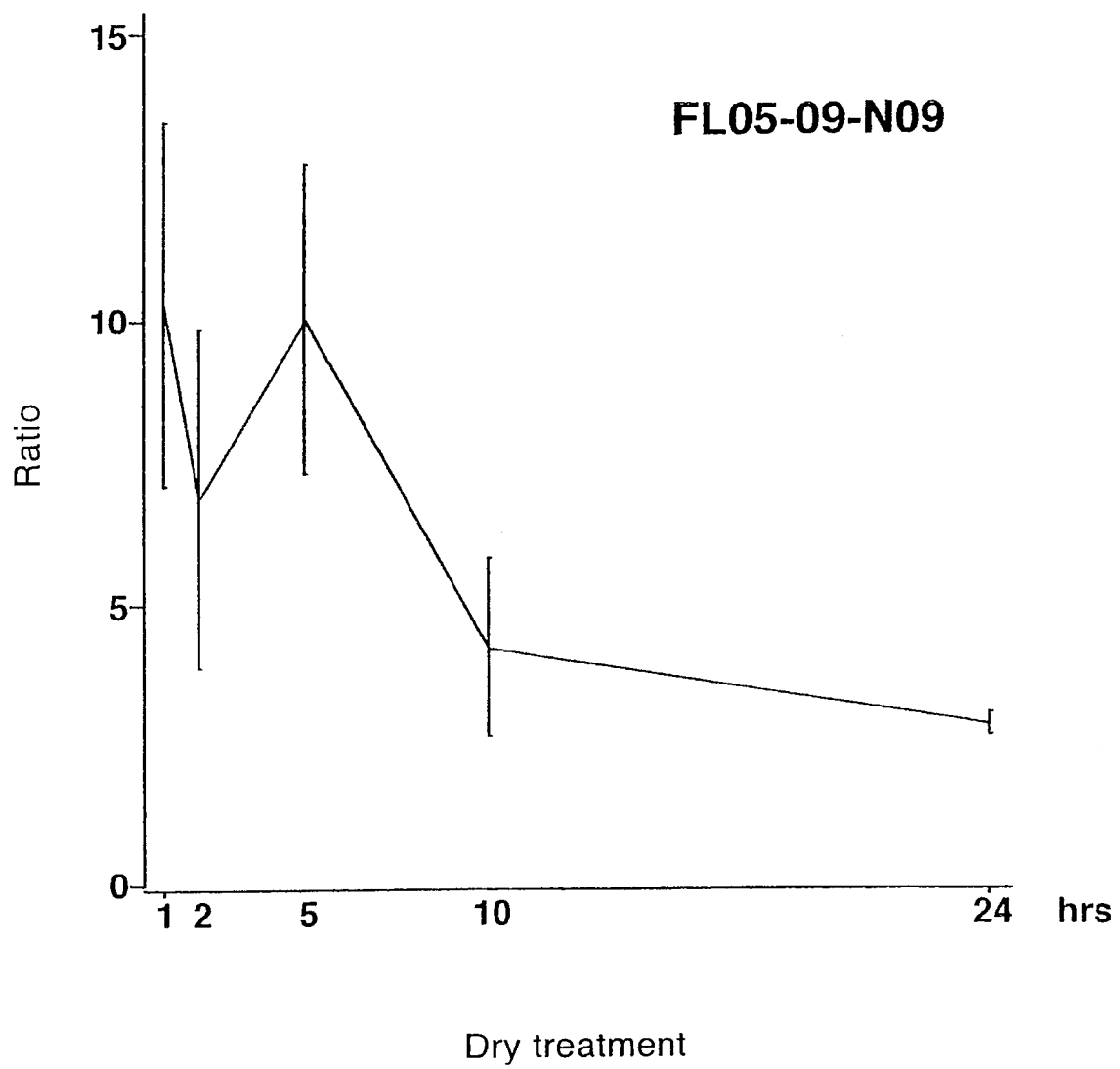
FIG. 12 is a characteristic graph showing the relationship between dehydration treatment time and expression ratio regarding FL05-09-N09.
Figure 13:
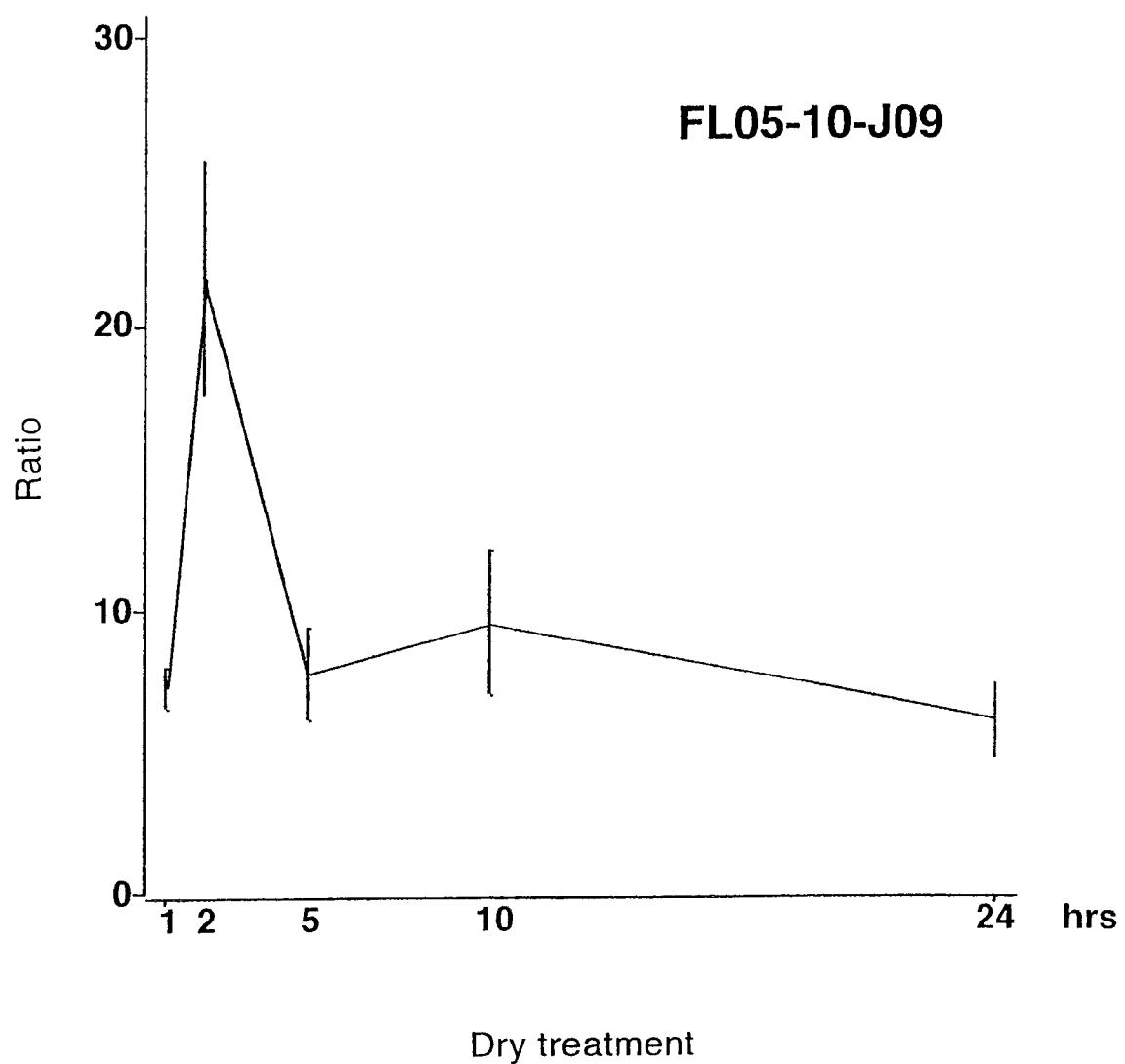
FIG. 13 is a characteristic graph showing the relationship between dehydration treatment time and expression ratio regarding FL05-10-J09.
Figure 14:
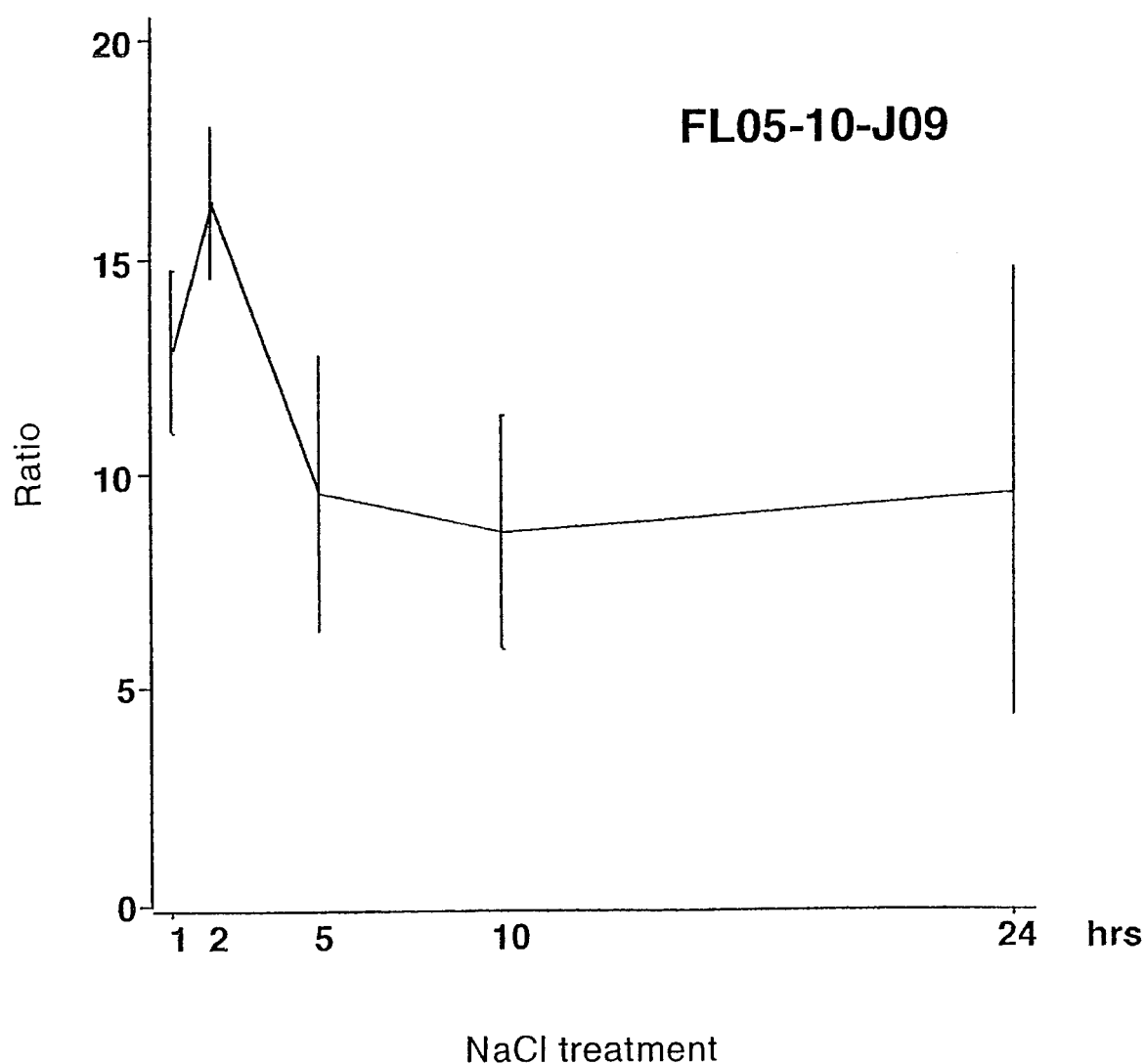
FIG. 14 is a characteristic graph showing the relationship between high salt treatment time and expression ratio regarding FL05-10-J09.
Figure 15:
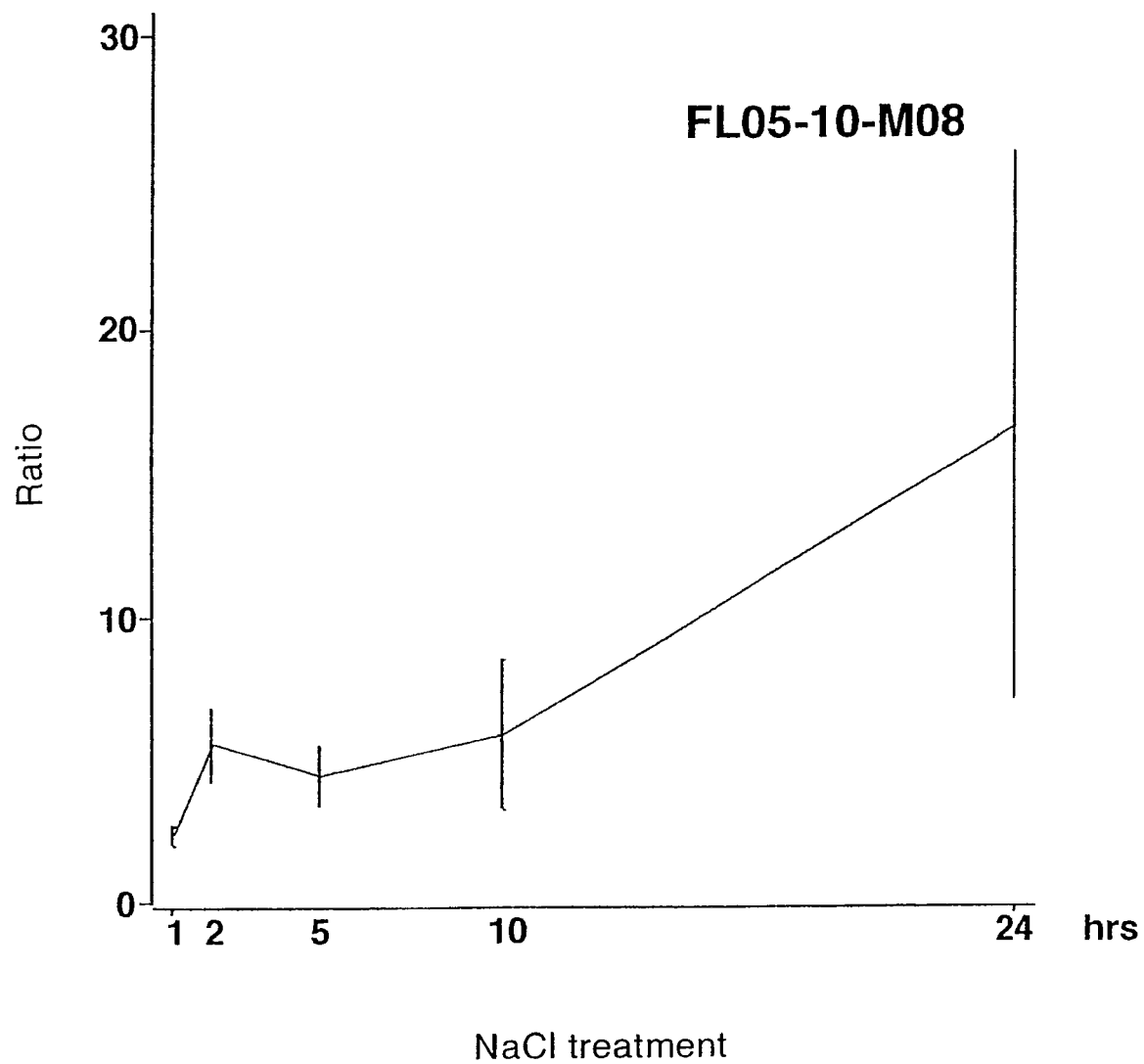
FIG. 15 is a characteristic graph showing the relationship between high salt treatment time and expression ratio regarding FL05-10-M08.
Figure 16:
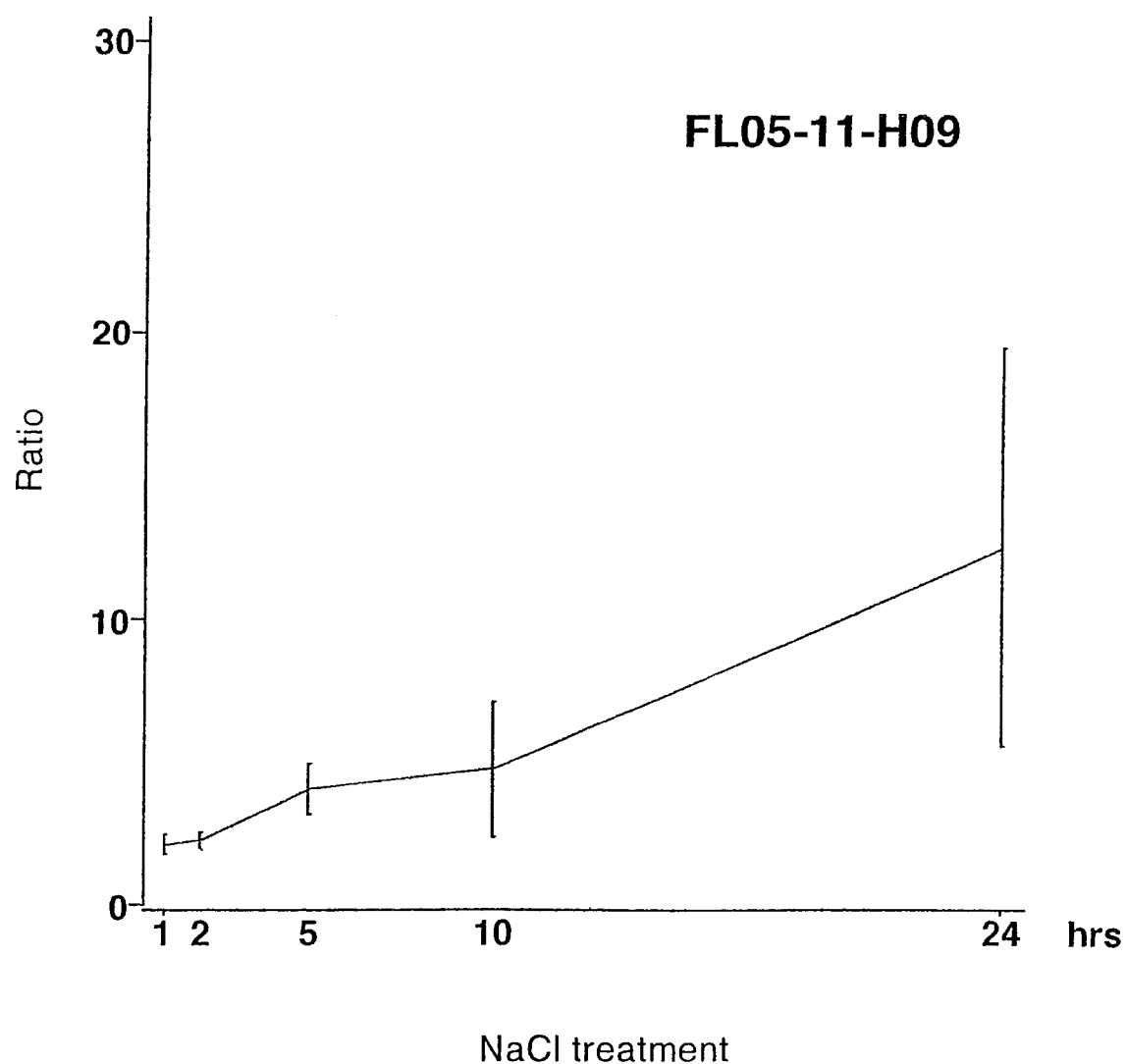
FIG. 16 is a characteristic graph showing the relationship between high salt treatment time and expression ratio regarding FL05-11-H09.
Figure 17:
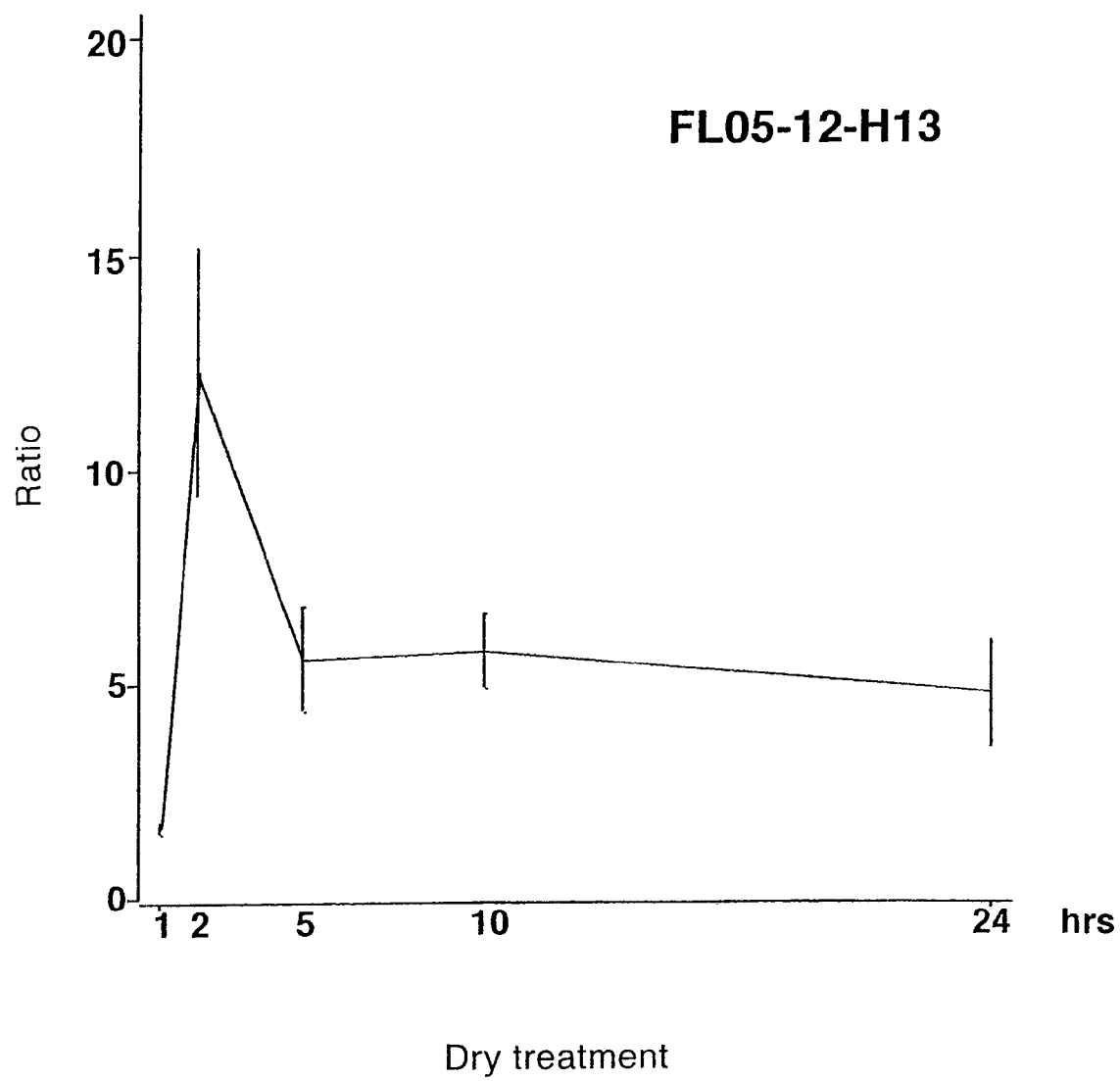
FIG. 17 is a characteristic graph showing the relationship between dehydration treatment time and expression ratio regarding FL05-12-H13.
Figure 18:
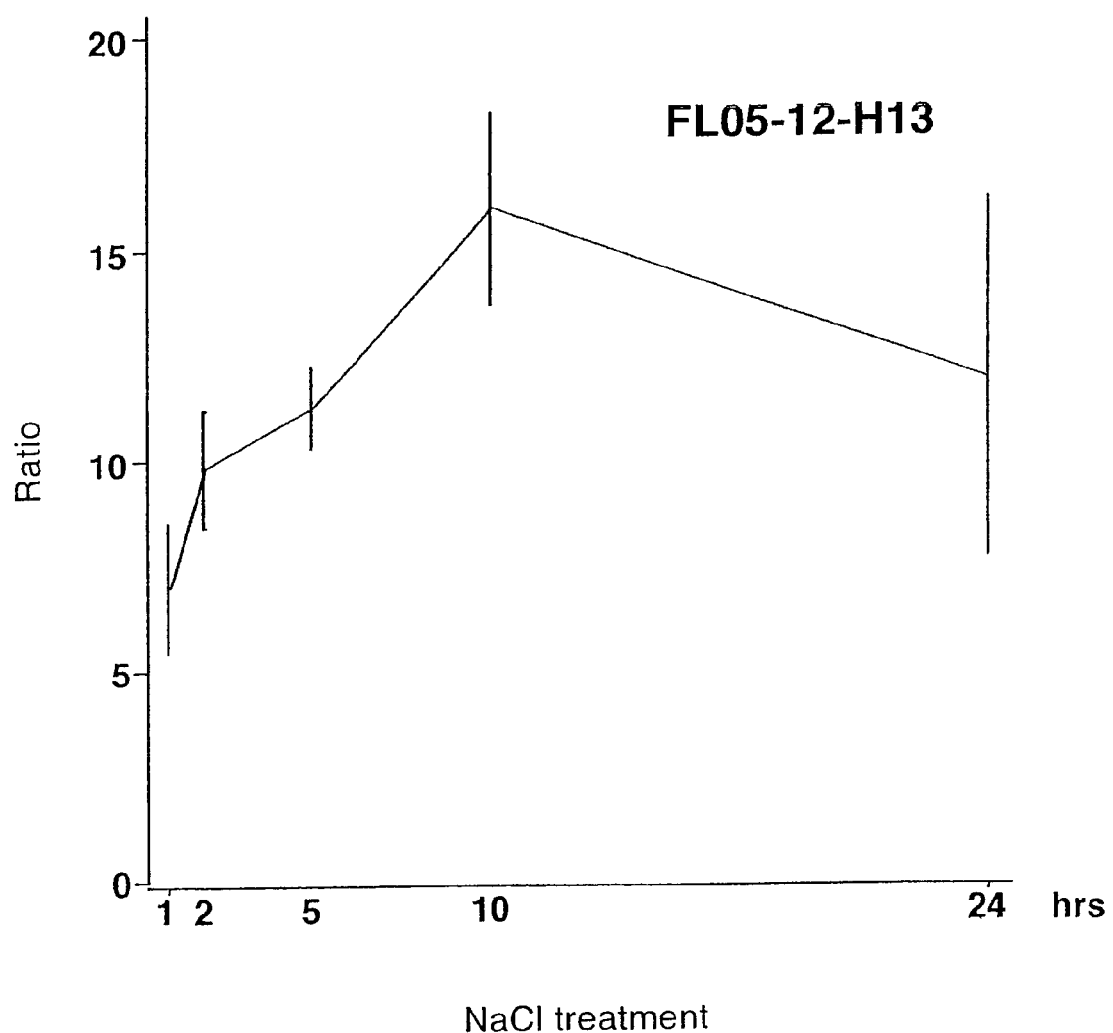
FIG. 18 is a characteristic graph showing the relationship between high salt treatment time and expression ratio regarding FL05-12-H13.
Figure 19:
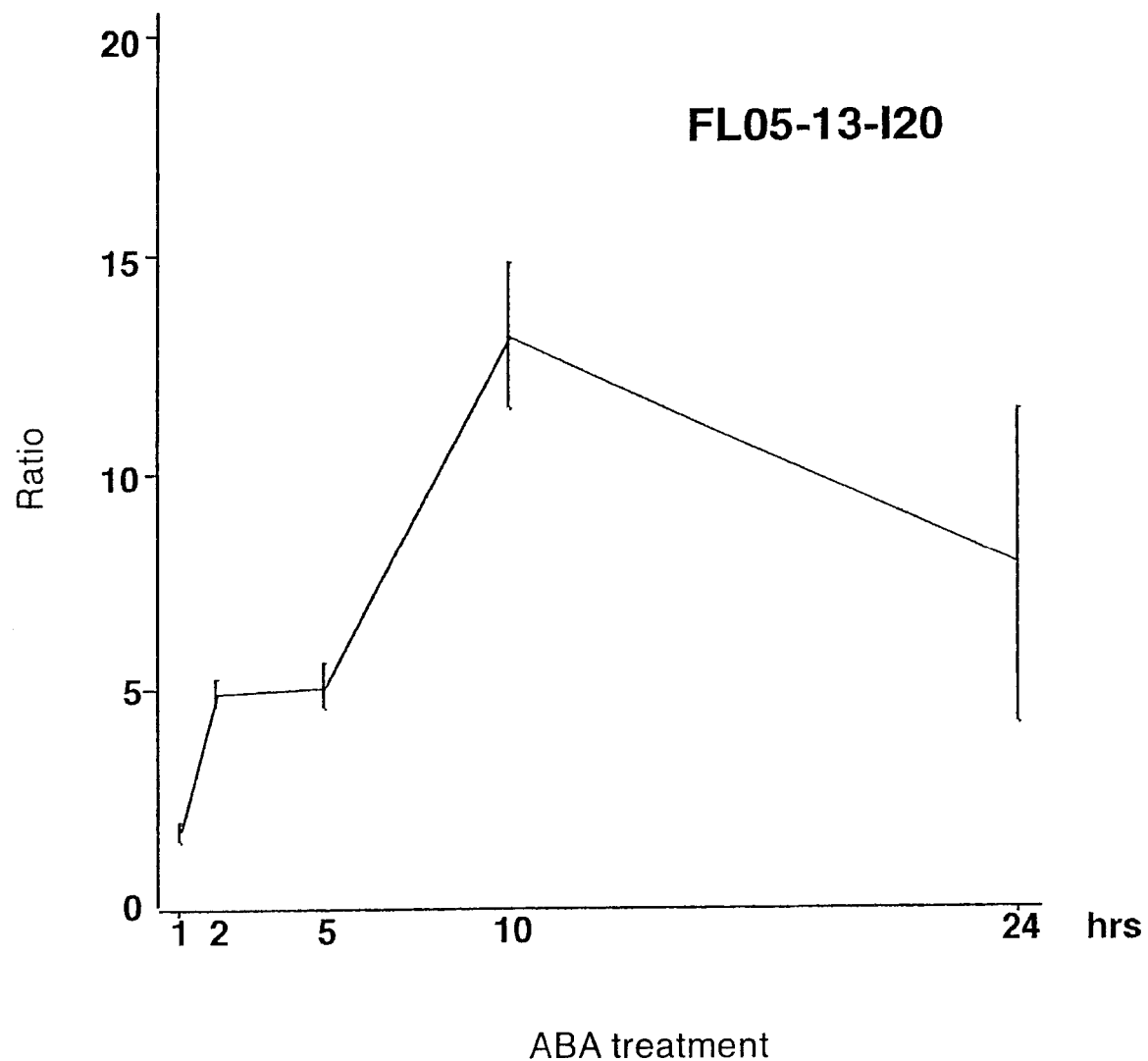
FIG. 19 is a characteristic graph showing the relationship between ABA treatment time and expression ratio regarding FL05-13-I20.
Figure 20:
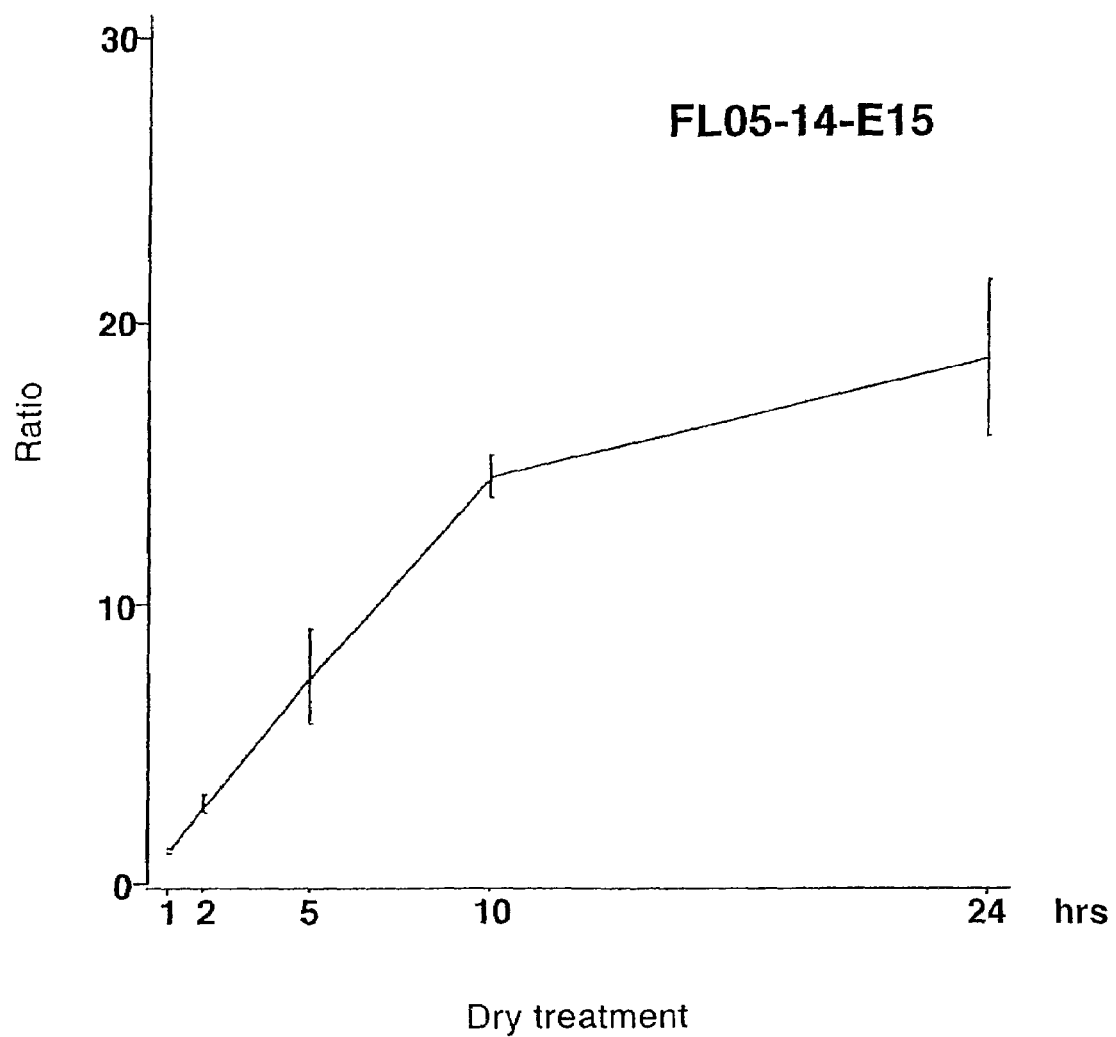
FIG. 20 is a characteristic graph showing the relationship between dehydration treatment time and expression ratio regarding FL05-14-E15.
Figure 21:
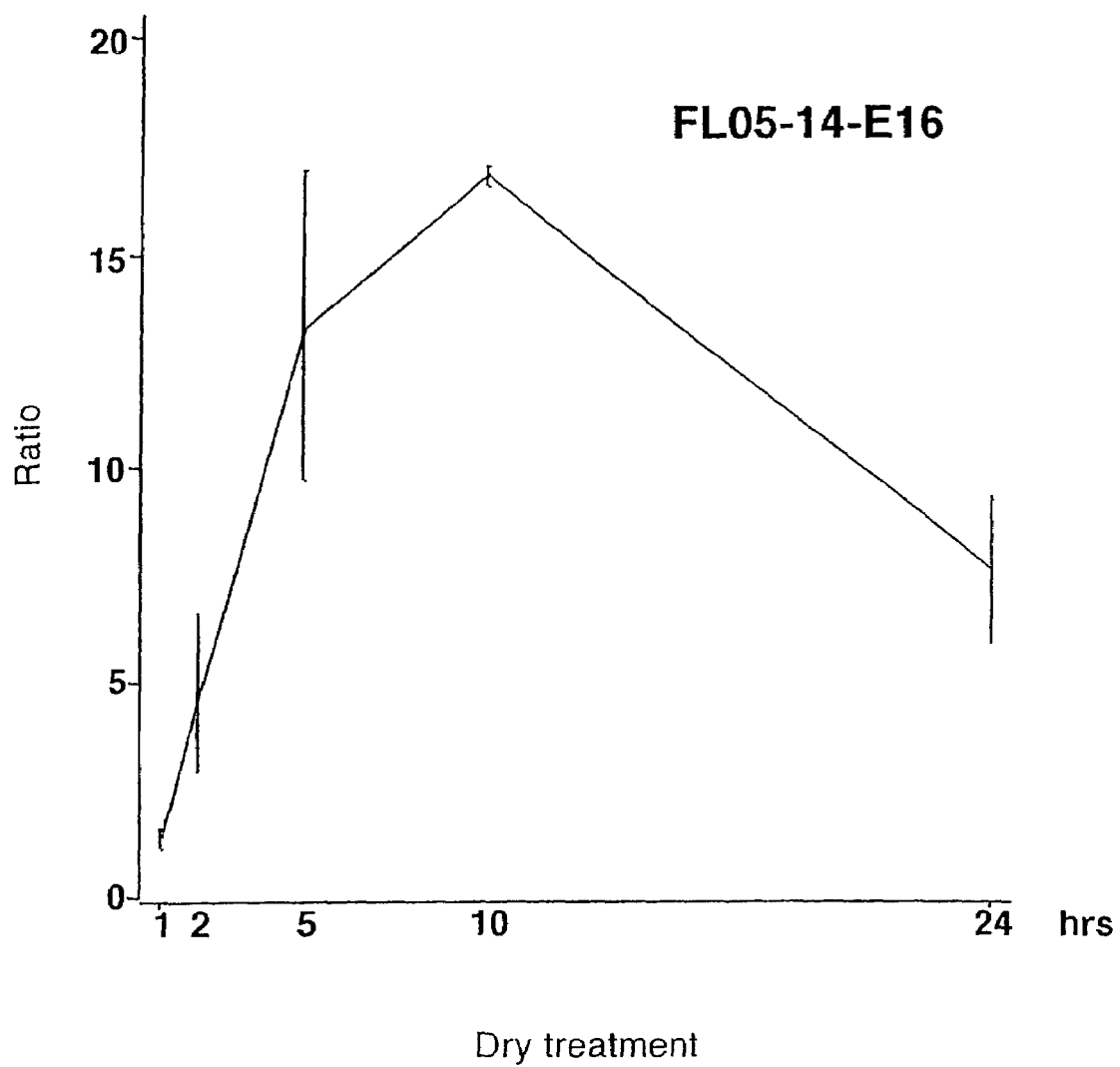
FIG. 21 is a characteristic graph showing the relationship between dehydration treatment time and expression ratio regarding FL05-14-E16.
Figure 22:
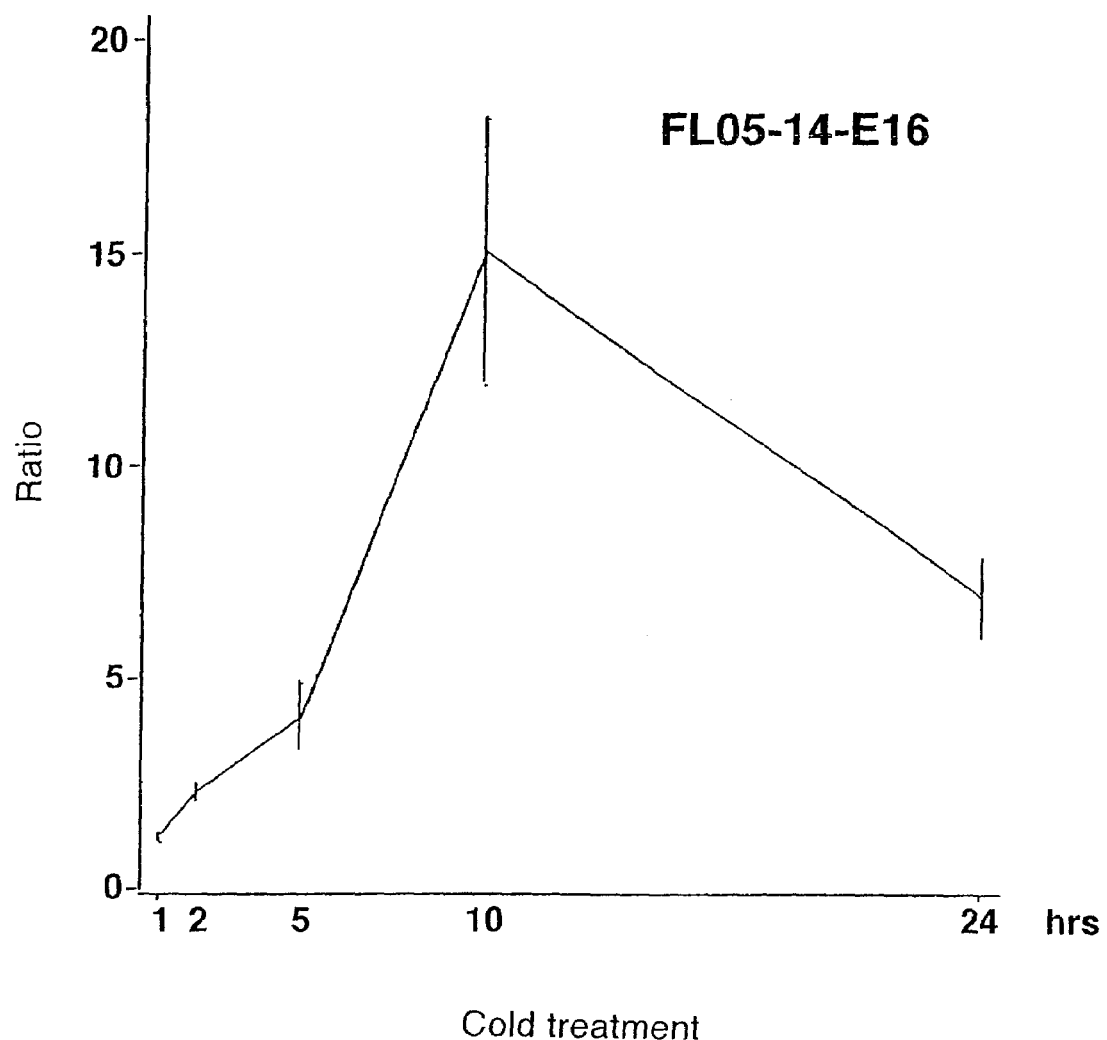
FIG. 22 is a characteristic graph showing the relationship between cold treatment time and expression ratio regarding FL05-14-E16.
Figure 23:
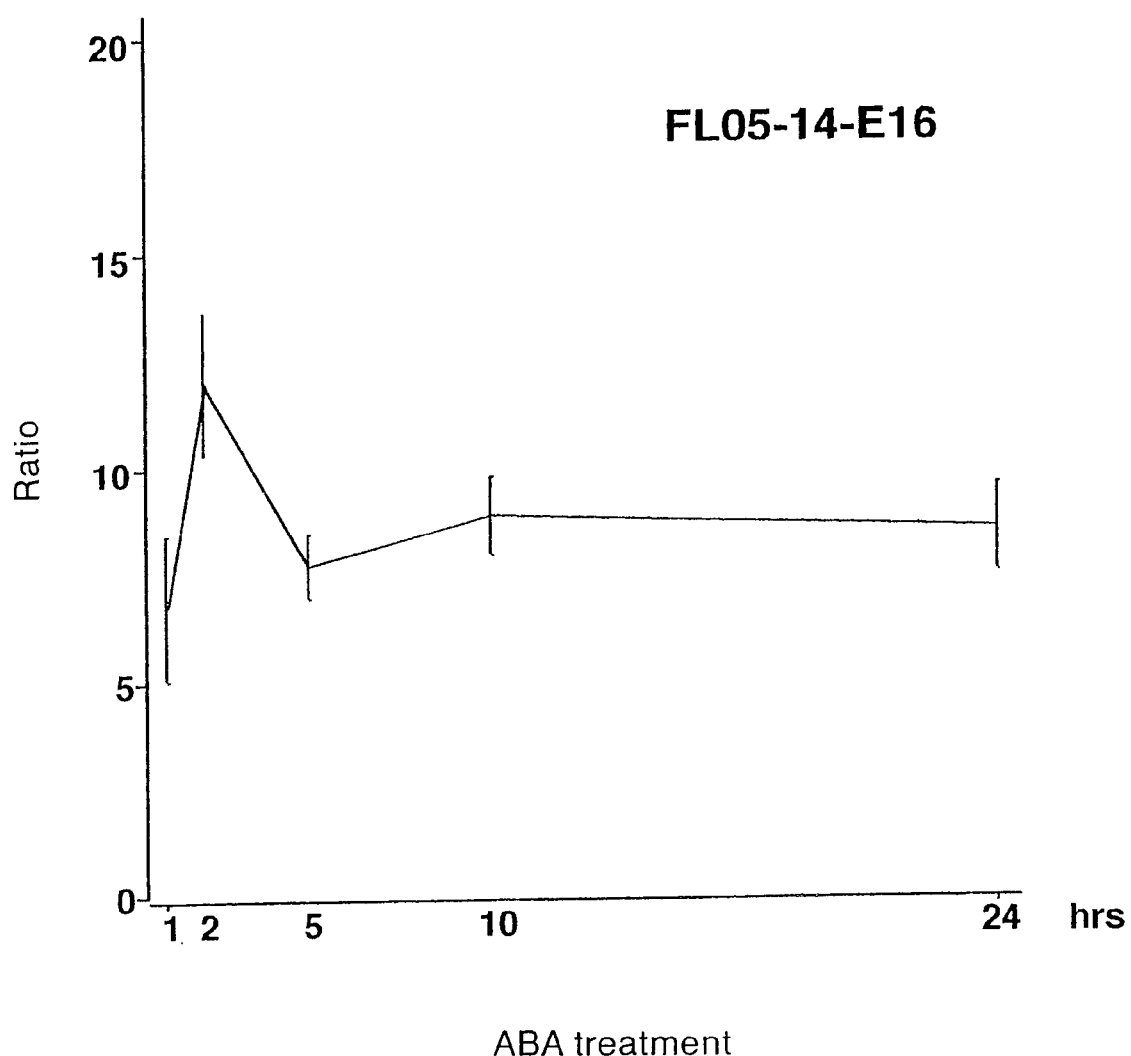
FIG. 23 is a characteristic graph showing the relationship between ABA treatment time and expression ratio regarding FL05-14-E16.
Figure 24:
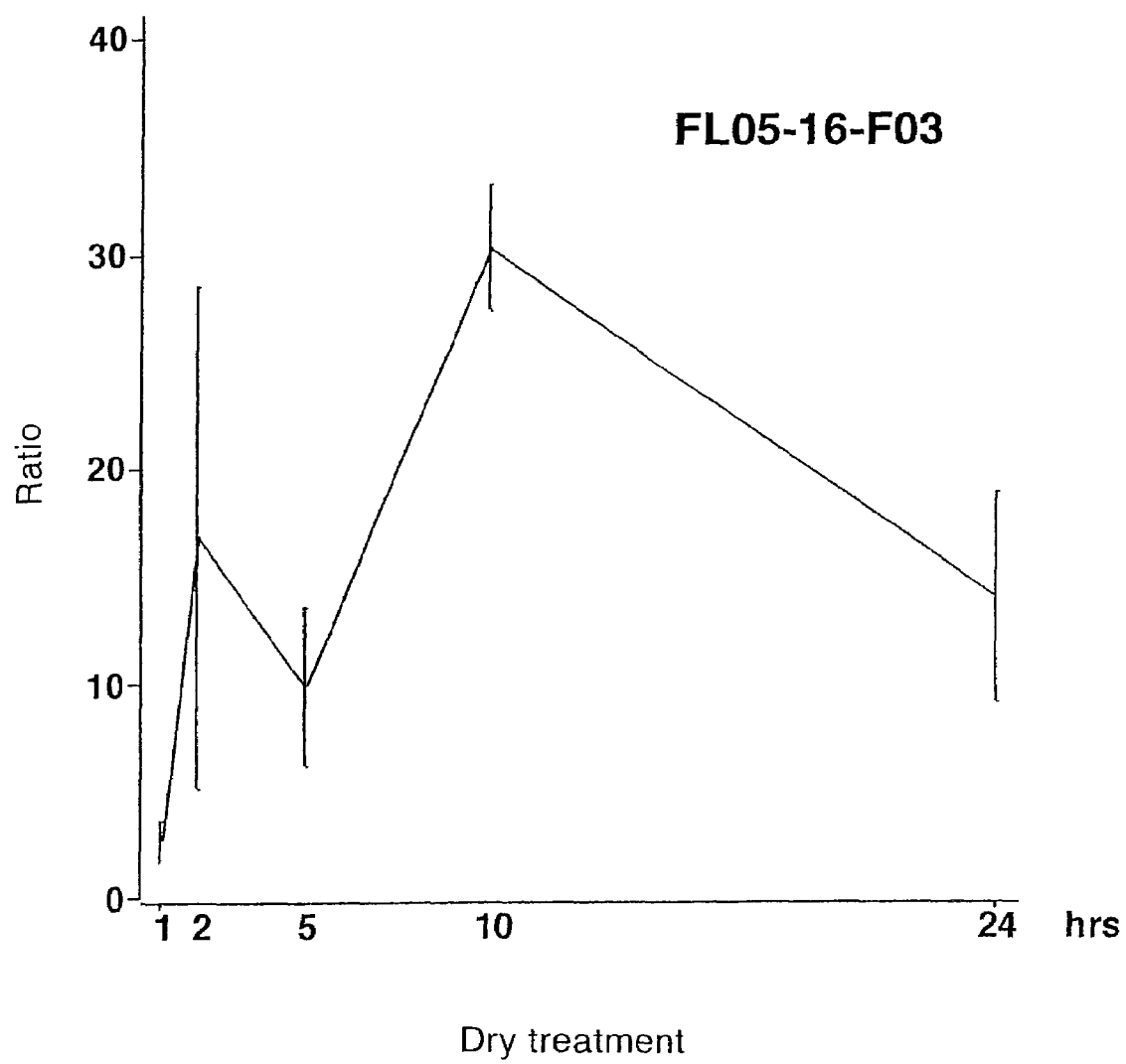
FIG. 24 is a characteristic graph showing the relationship between dehydration treatment time and expression ratio regarding FL05-16-F03.
Figure 25:
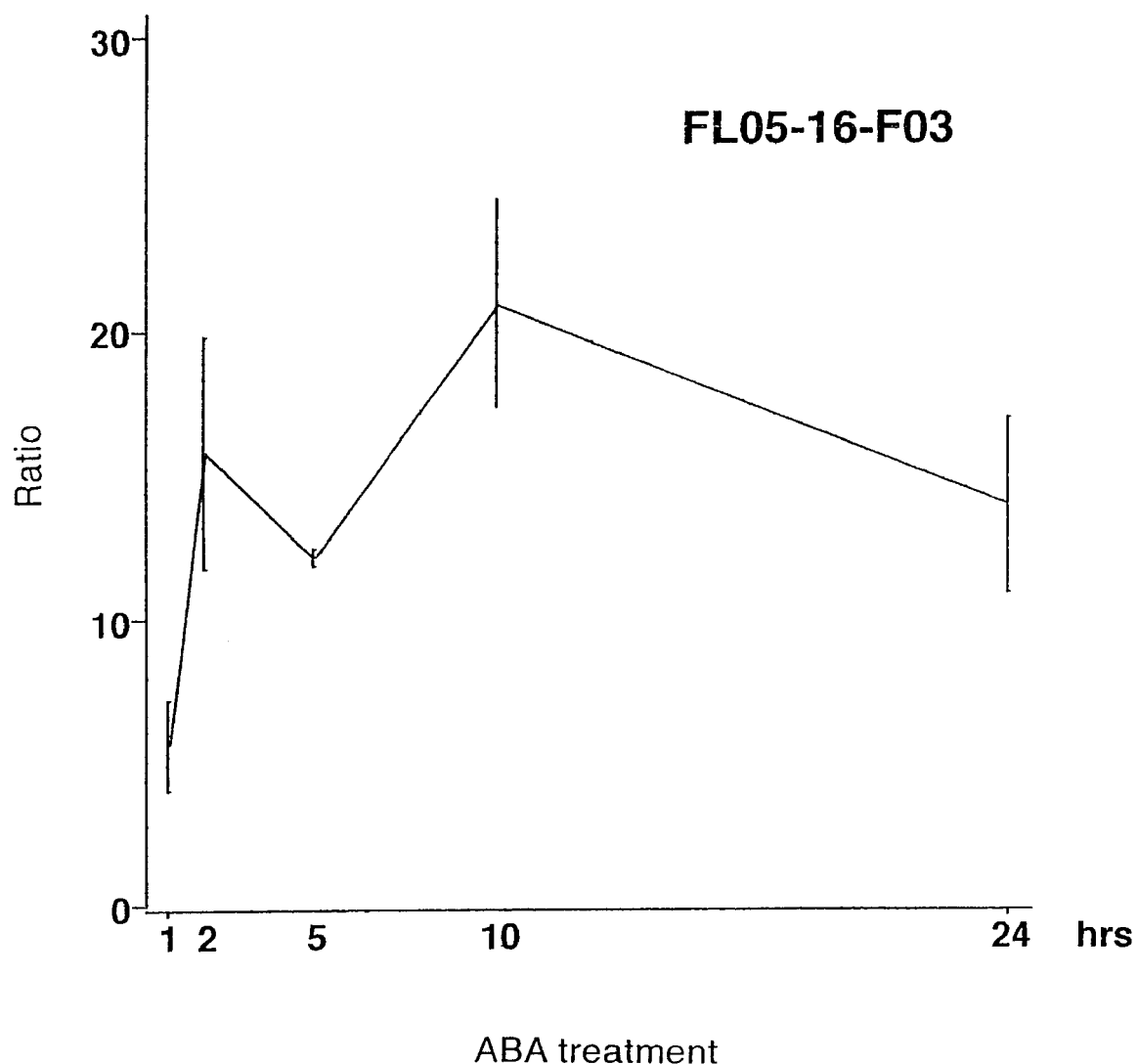
FIG. 25 is a characteristic graph showing the relationship between ABA treatment time and expression ratio regarding FL05-16-F03.
Figure 26:
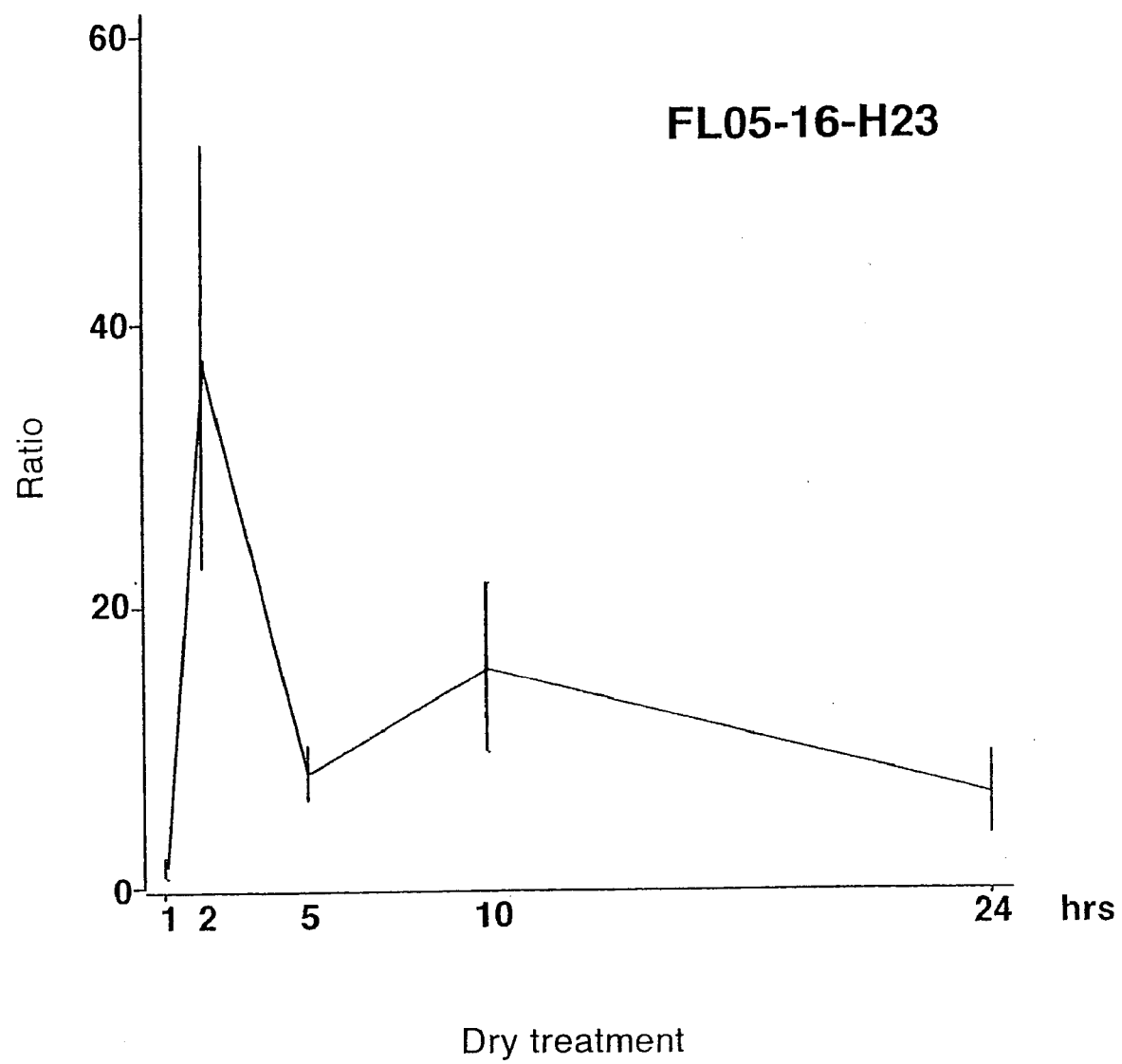
FIG. 26 is a characteristic graph showing the relationship between dehydration treatment time and expression ratio regarding FL05-16-H23.
Figure 27:
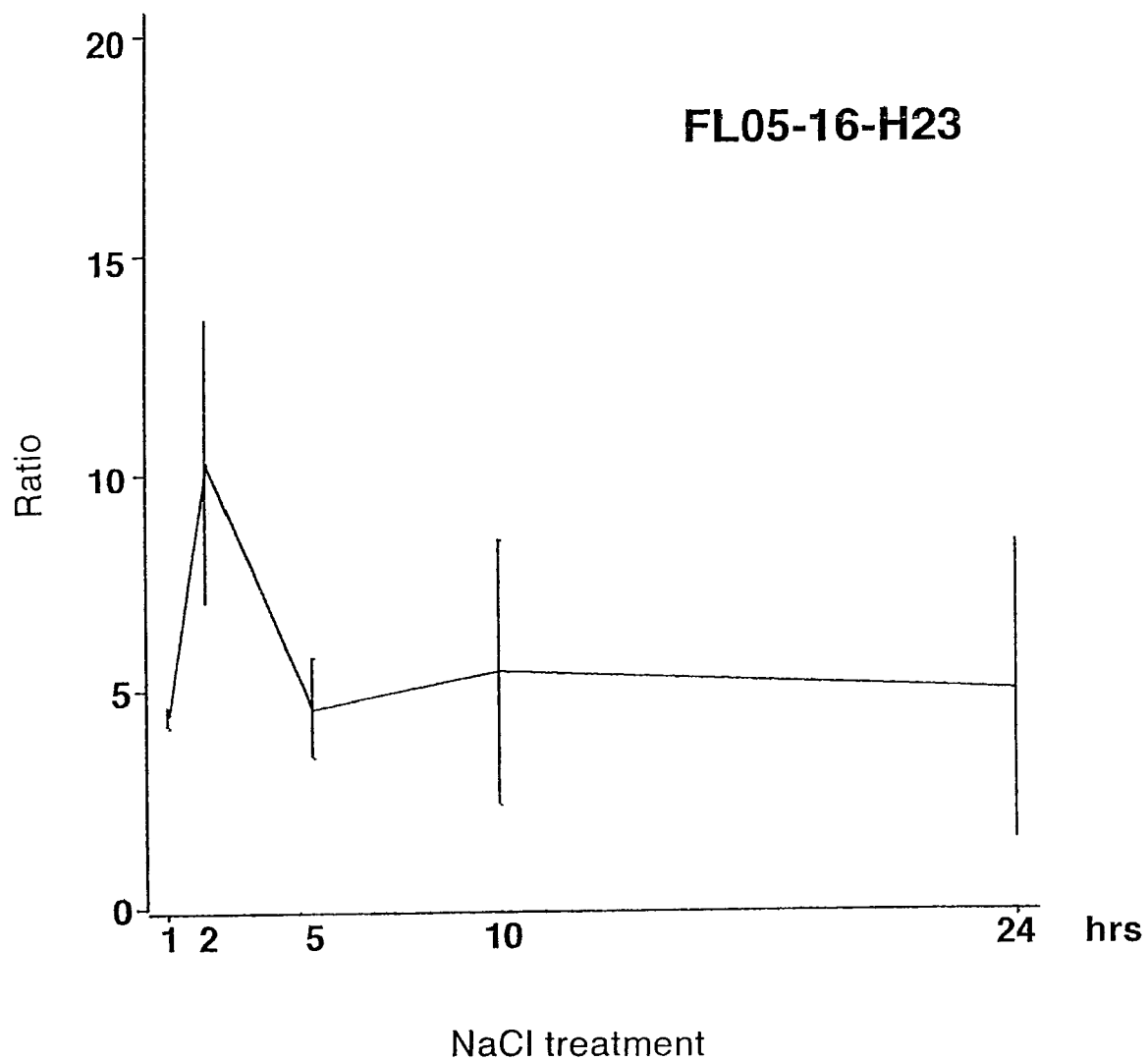
FIG. 27 is a characteristic graph showing the relationship between high salt treatment time and expression ratio regarding FL05-16-H23.
Figure 28:
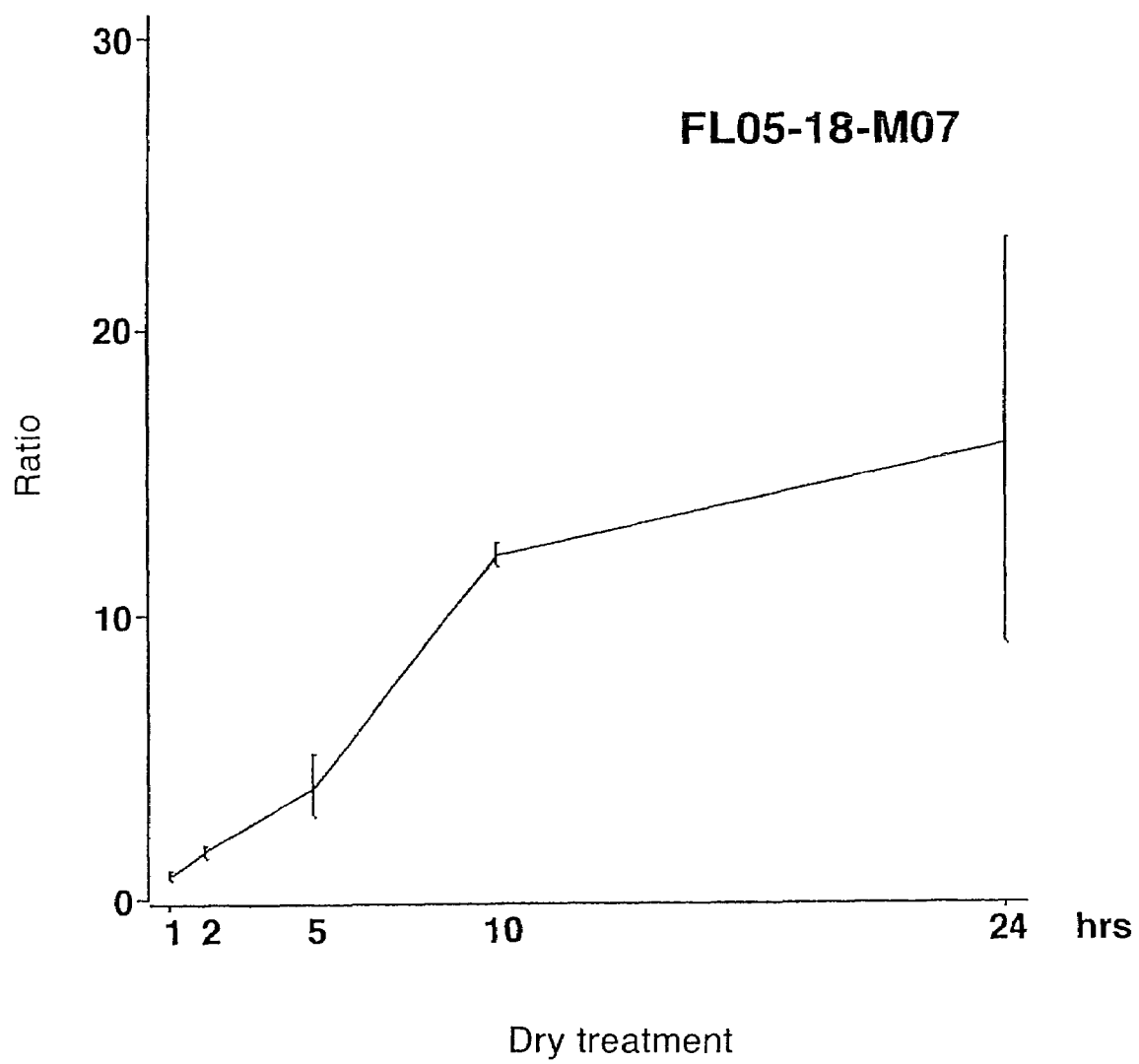
FIG. 28 is a characteristic graph showing the relationship between dehydration treatment time and expression ratio regarding FL05-18-M07.
Figure 29:
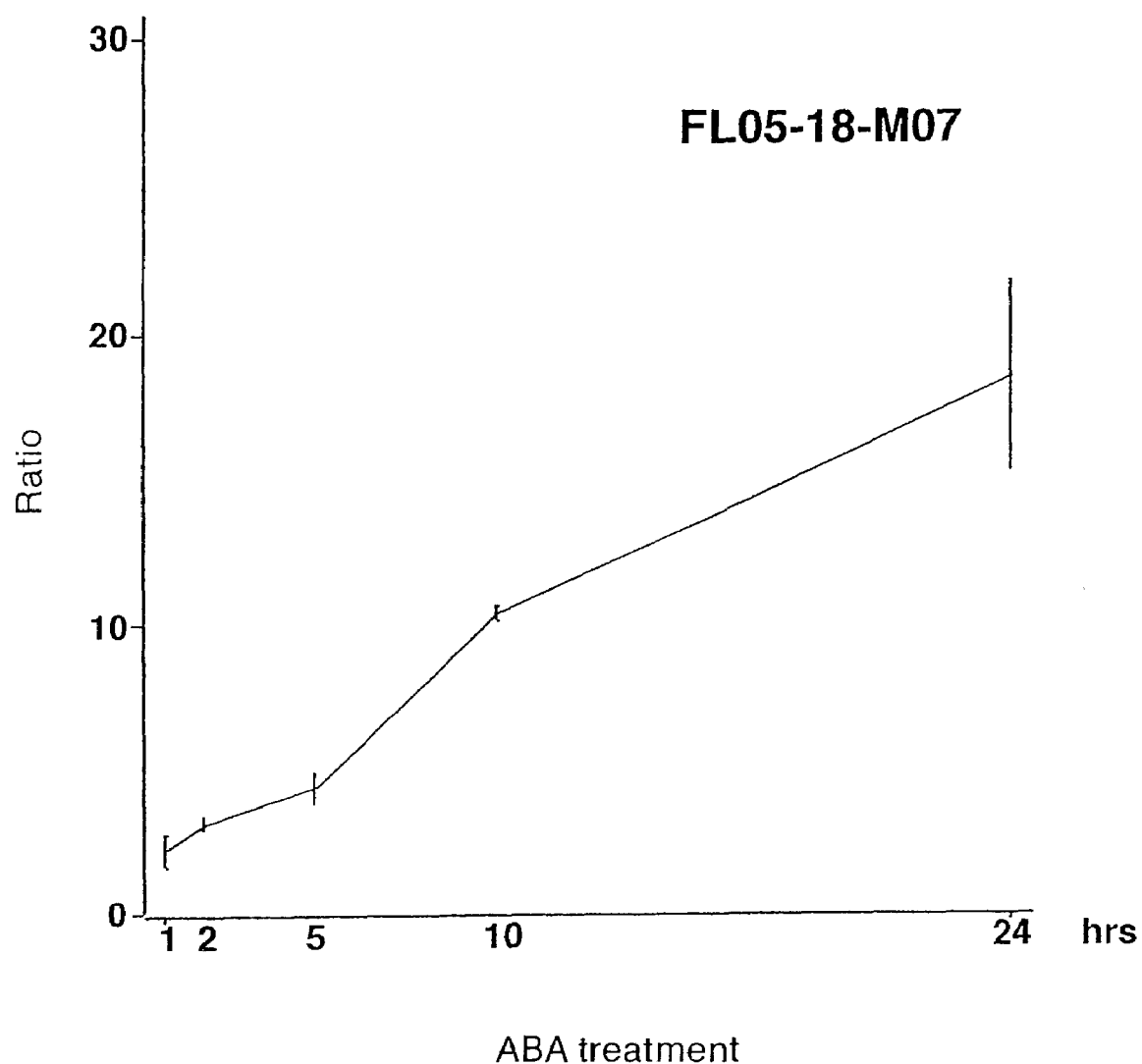
FIG. 29 is a characteristic graph showing the relationship between ABA treatment time and expression ratio regarding FL05-18-M07.
Figure 30:
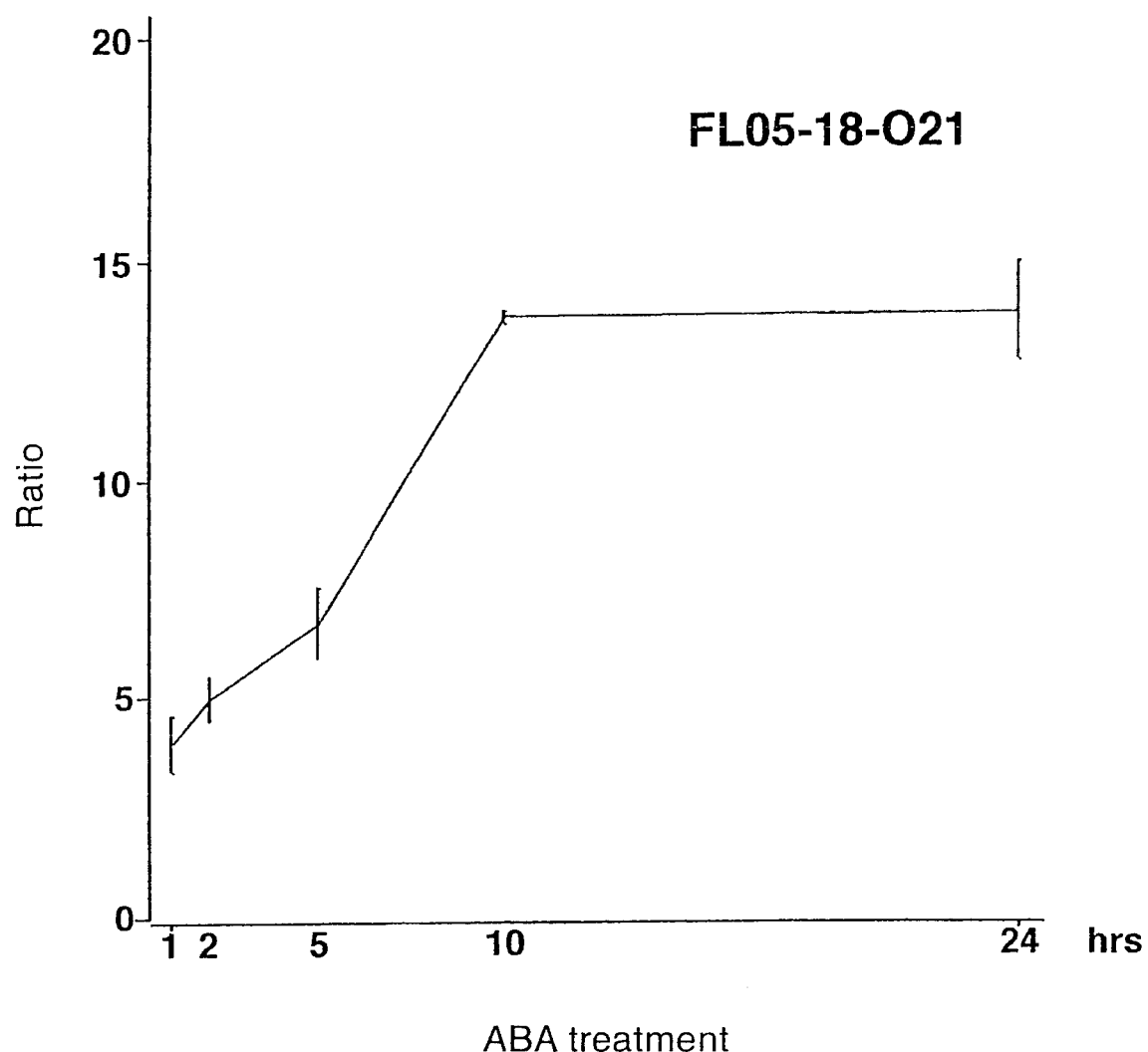
FIG. 30 is a characteristic graph showing the relationship between ABA treatment time and expression ratio regarding FL05-18-O21.
Figure 31:
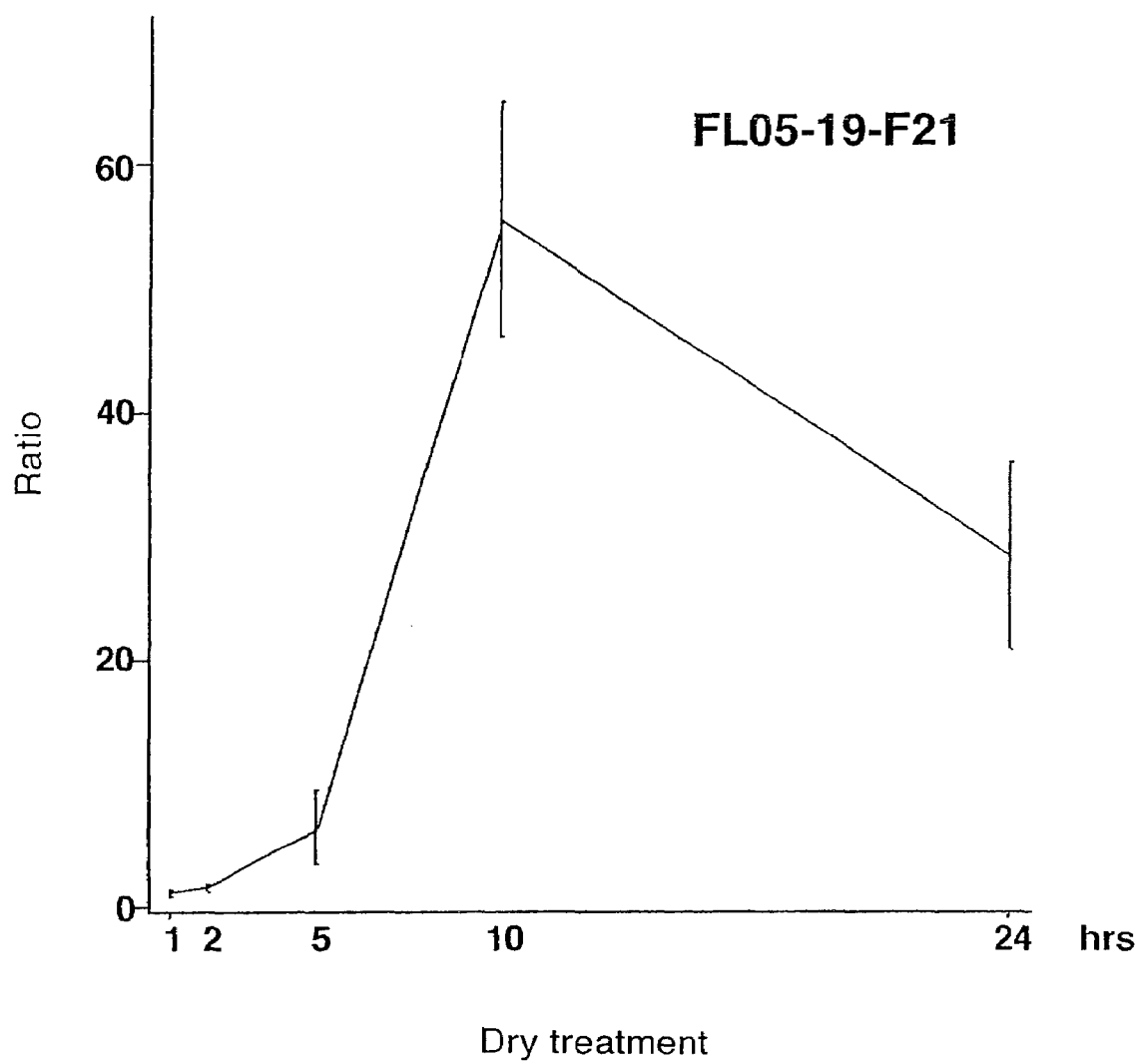
FIG. 31 is a characteristic graph showing the relationship between dehydration treatment time and expression ratio regarding FL05-19-F21.
Figure 32:
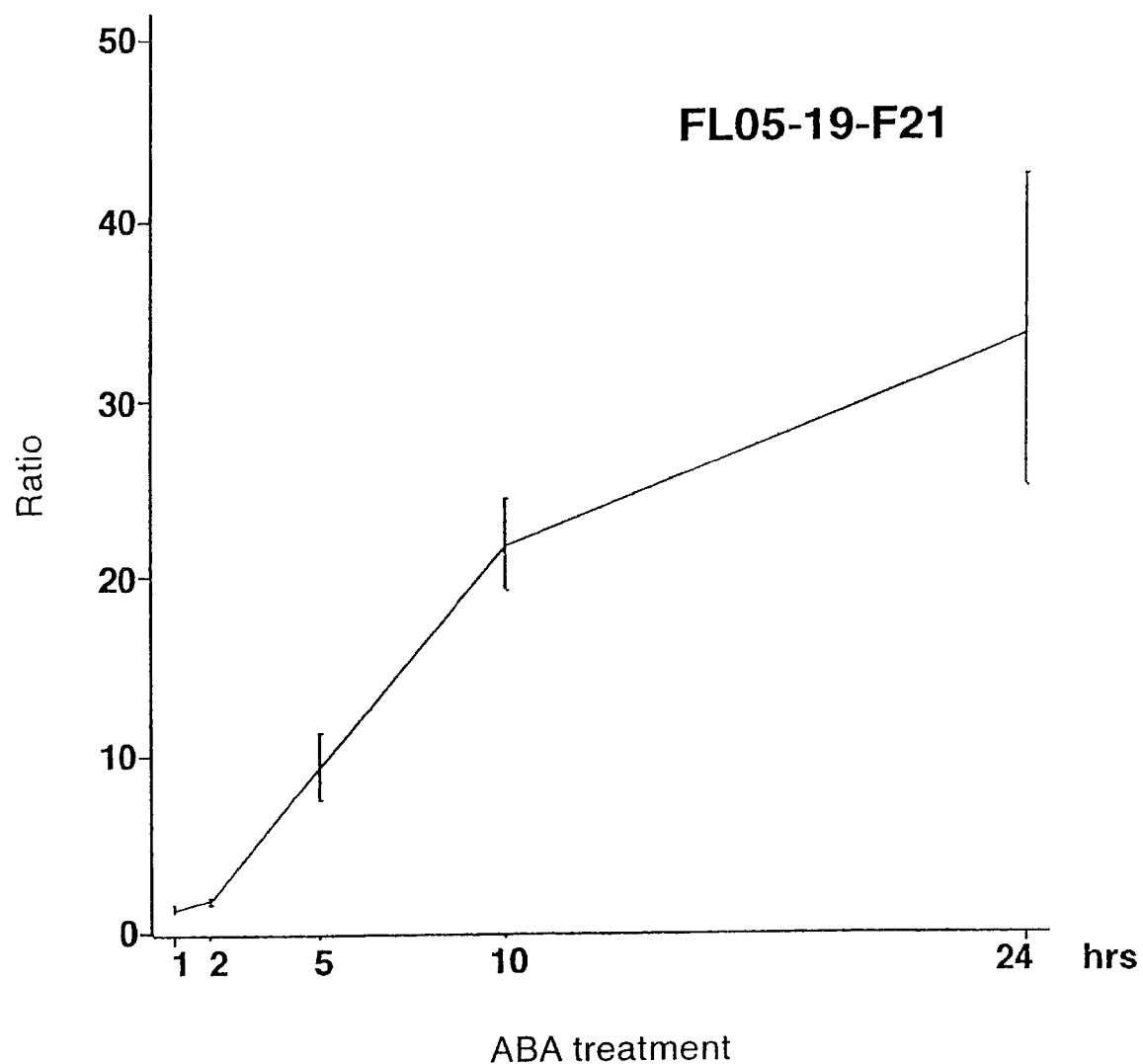
FIG. 32 is a characteristic graph showing the relationship between ABA treatment time and expression ratio regarding FL05-19-F21.
Figure 33:
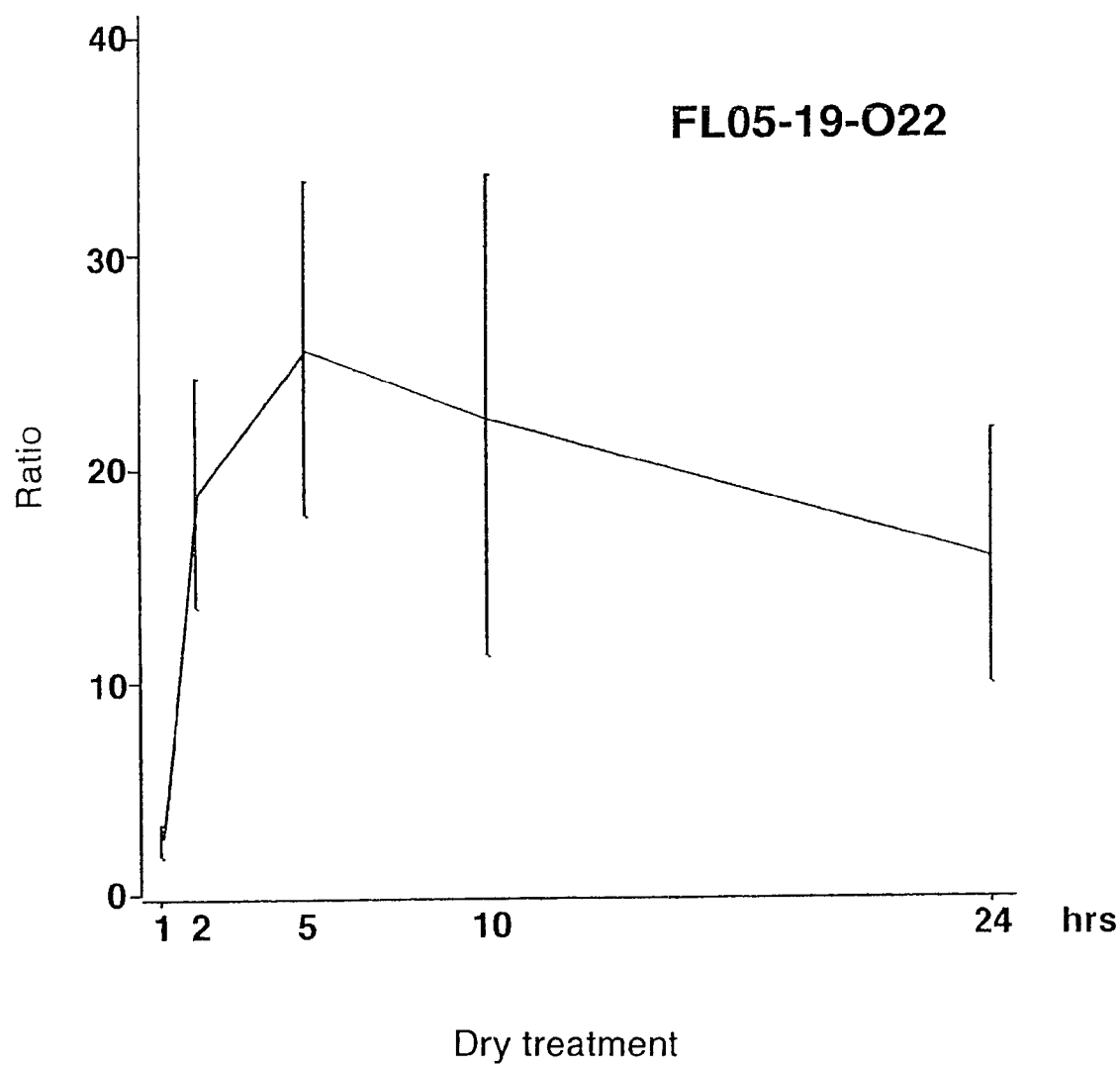
FIG. 33 is a characteristic graph showing the relationship between dehydration treatment time and expression ratio regarding FL05-19-O22.
Figure 34:
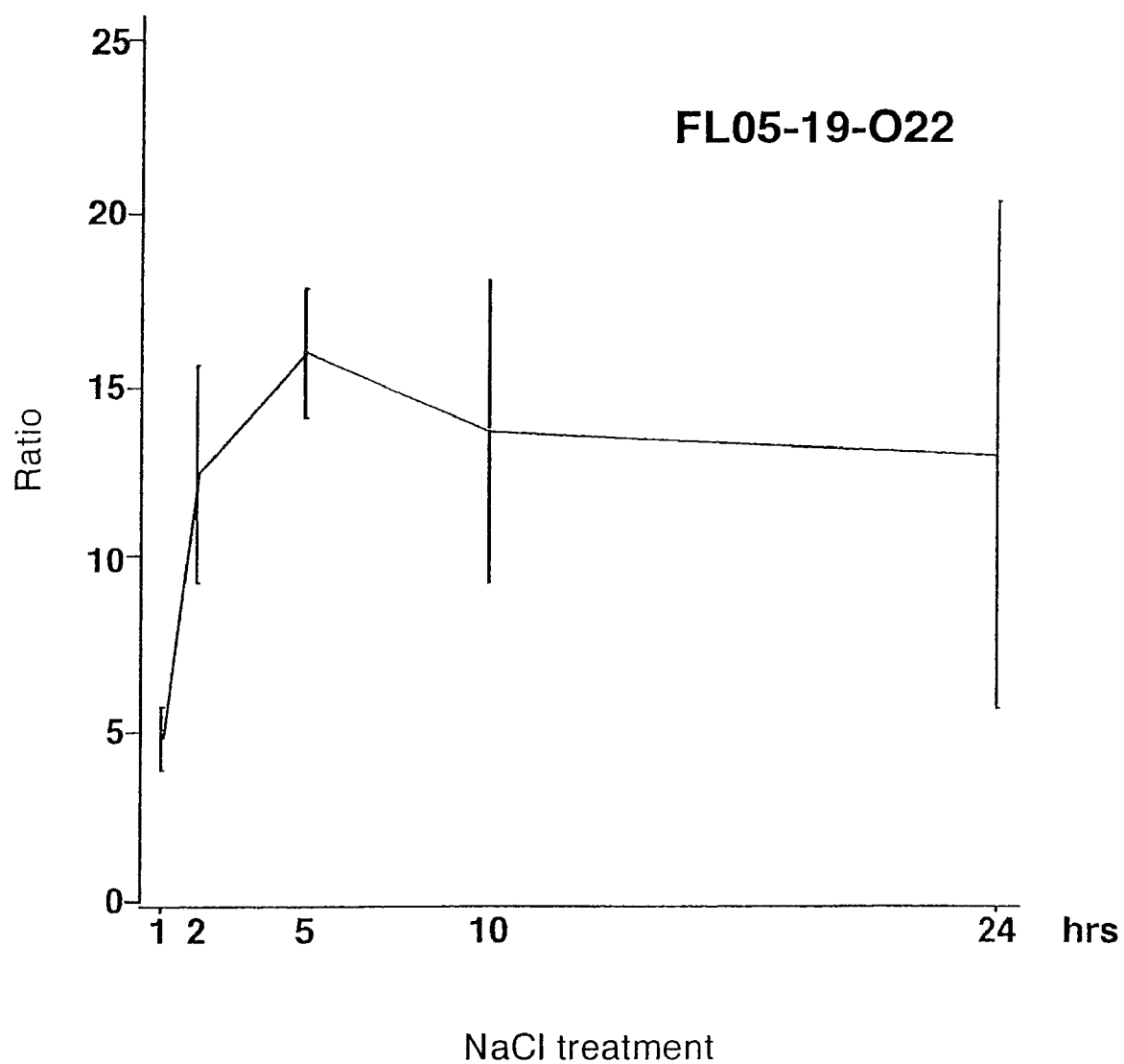
FIG. 34 is a characteristic graph showing the relationship between high salt treatment time and expression ratio regarding FL05-19-O22.
Figure 35:
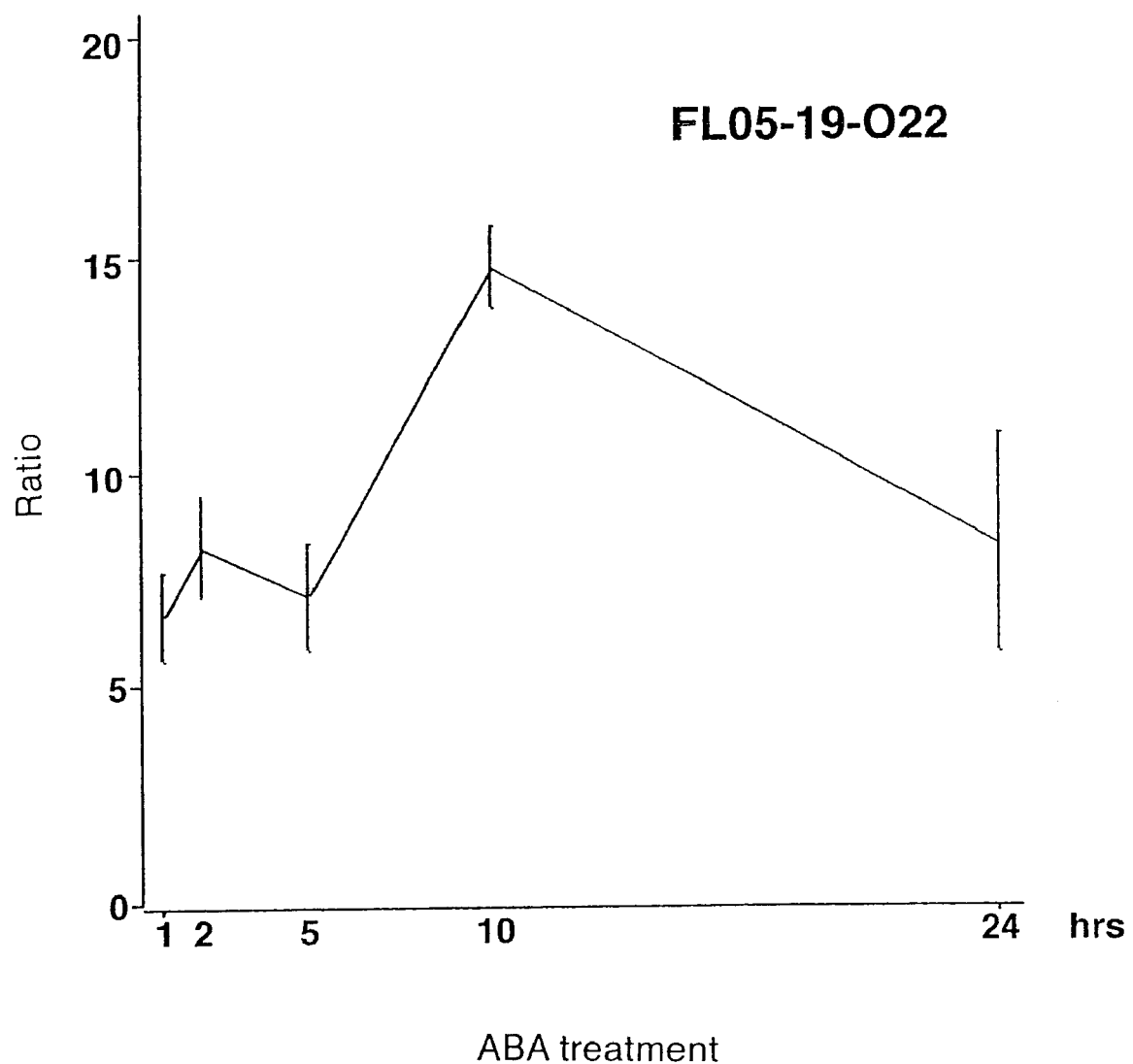
FIG. 35 is a characteristic graph showing the relationship between ABA treatment time and expression ratio regarding FL05-19-O22.
Figure 36:
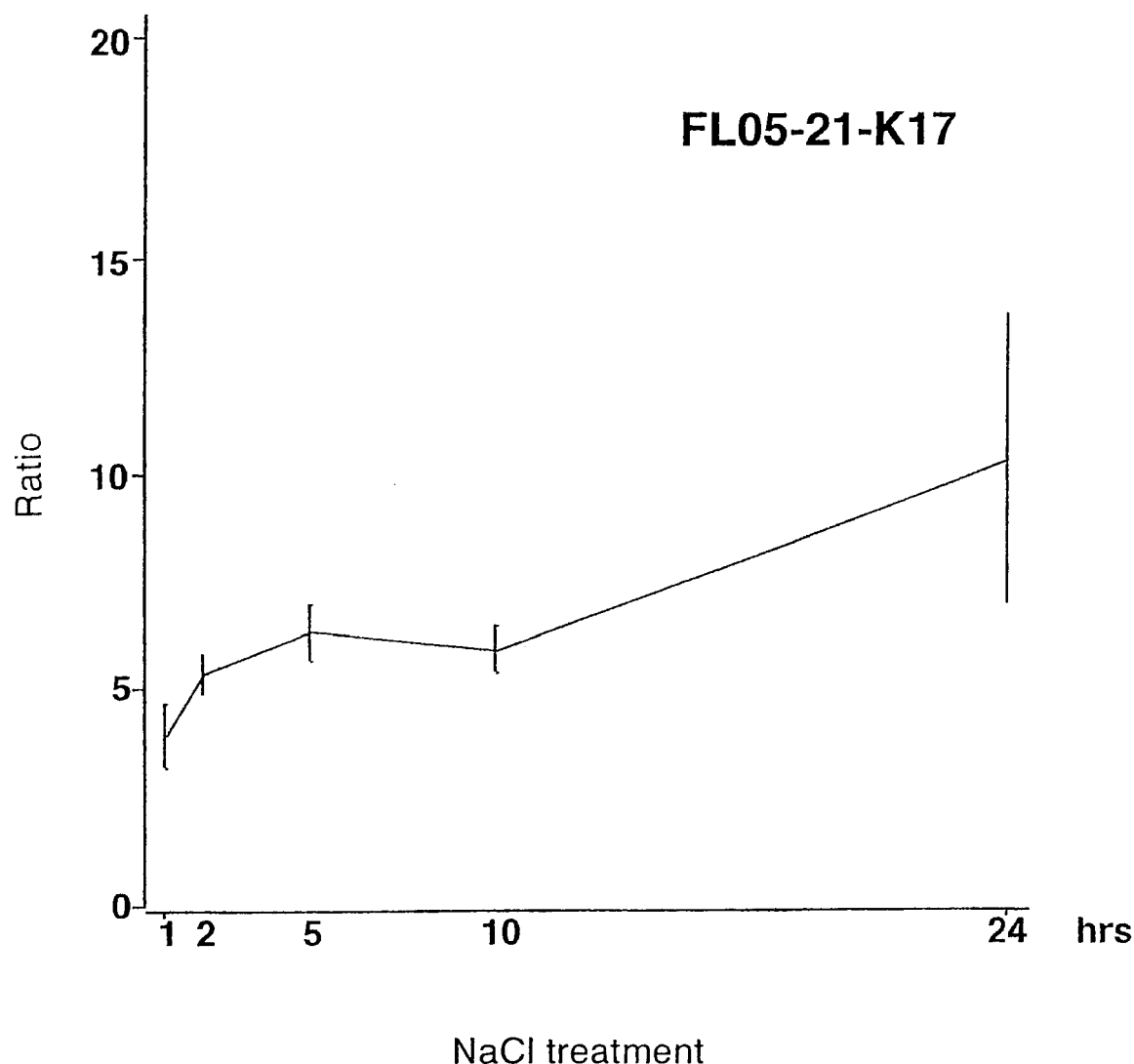
FIG. 36 is a characteristic graph showing the relationship between high salt treatment time and expression ratio regarding FL05-21-K17.
Figure 37:
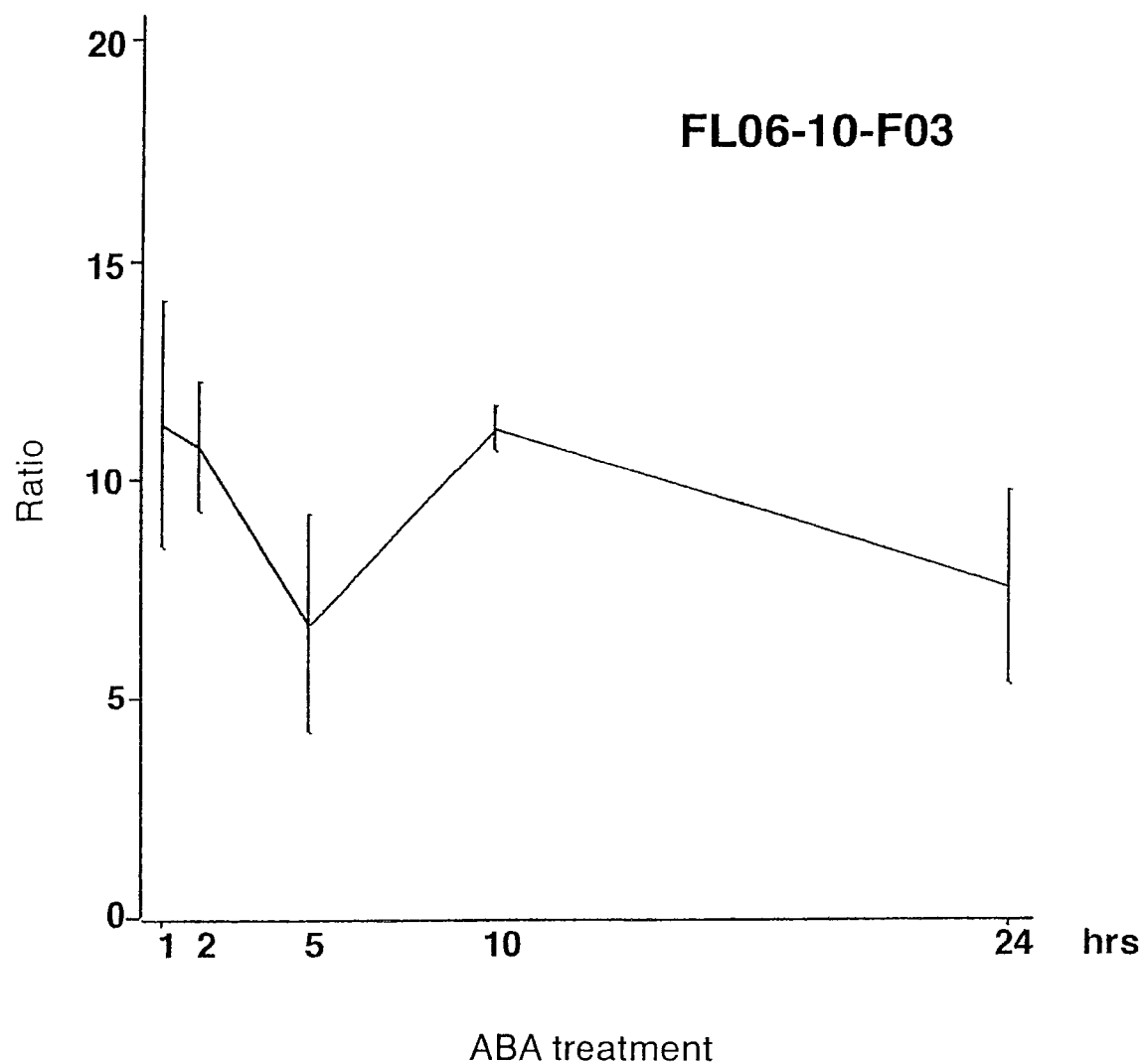
FIG. 37 is a characteristic graph showing the relationship between ABA treatment time and expression ratio regarding FL06-10-F03.
Figure 38:
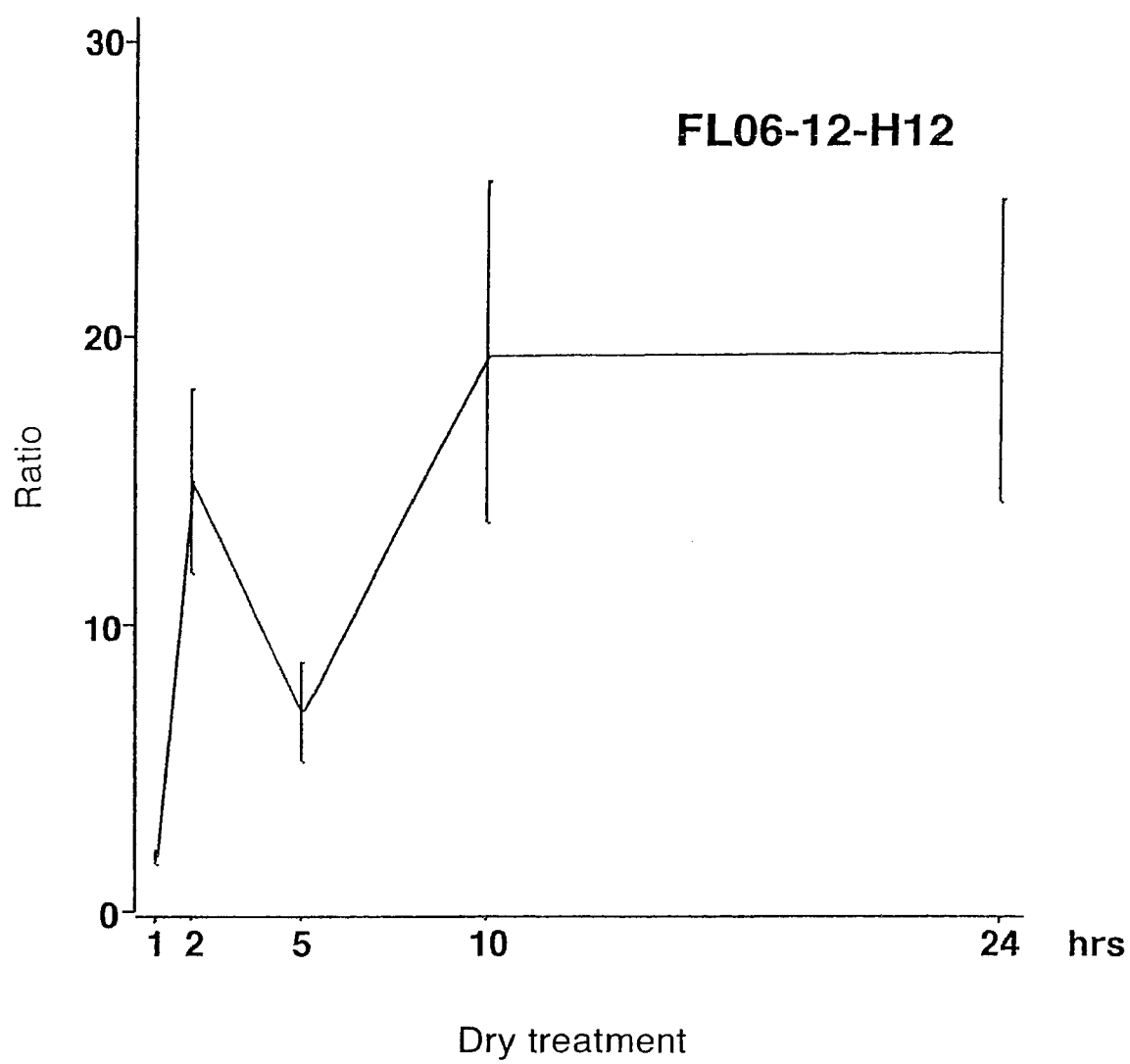
FIG. 38 is a characteristic graph showing the relationship between dehydration treatment time and expression ratio regarding FL06-12-H12.
Figure 39:
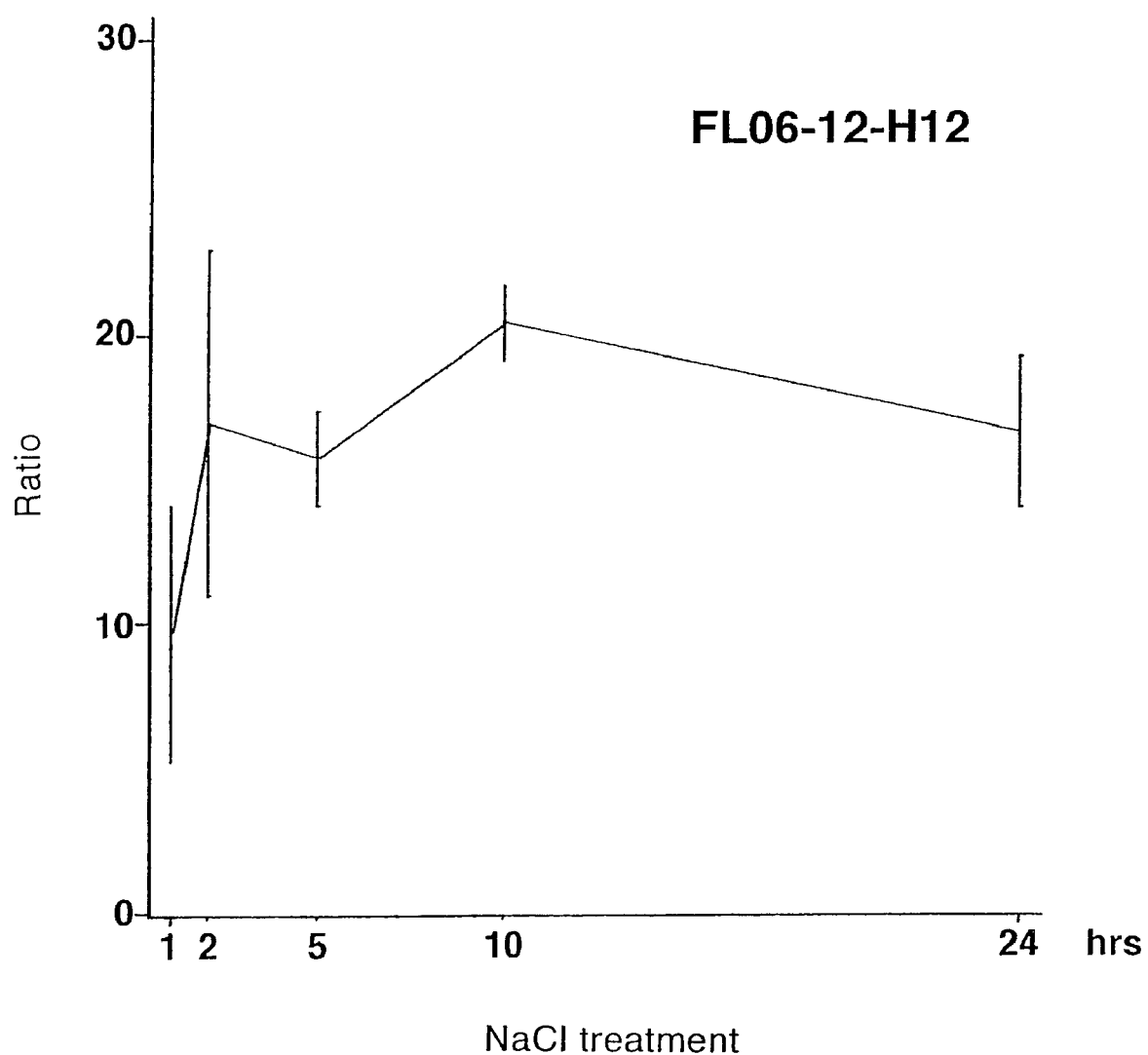
FIG. 39 is a characteristic graph showing the relationship between high salt treatment time and expression ratio regarding FL06-12-H12.
Figure 40:
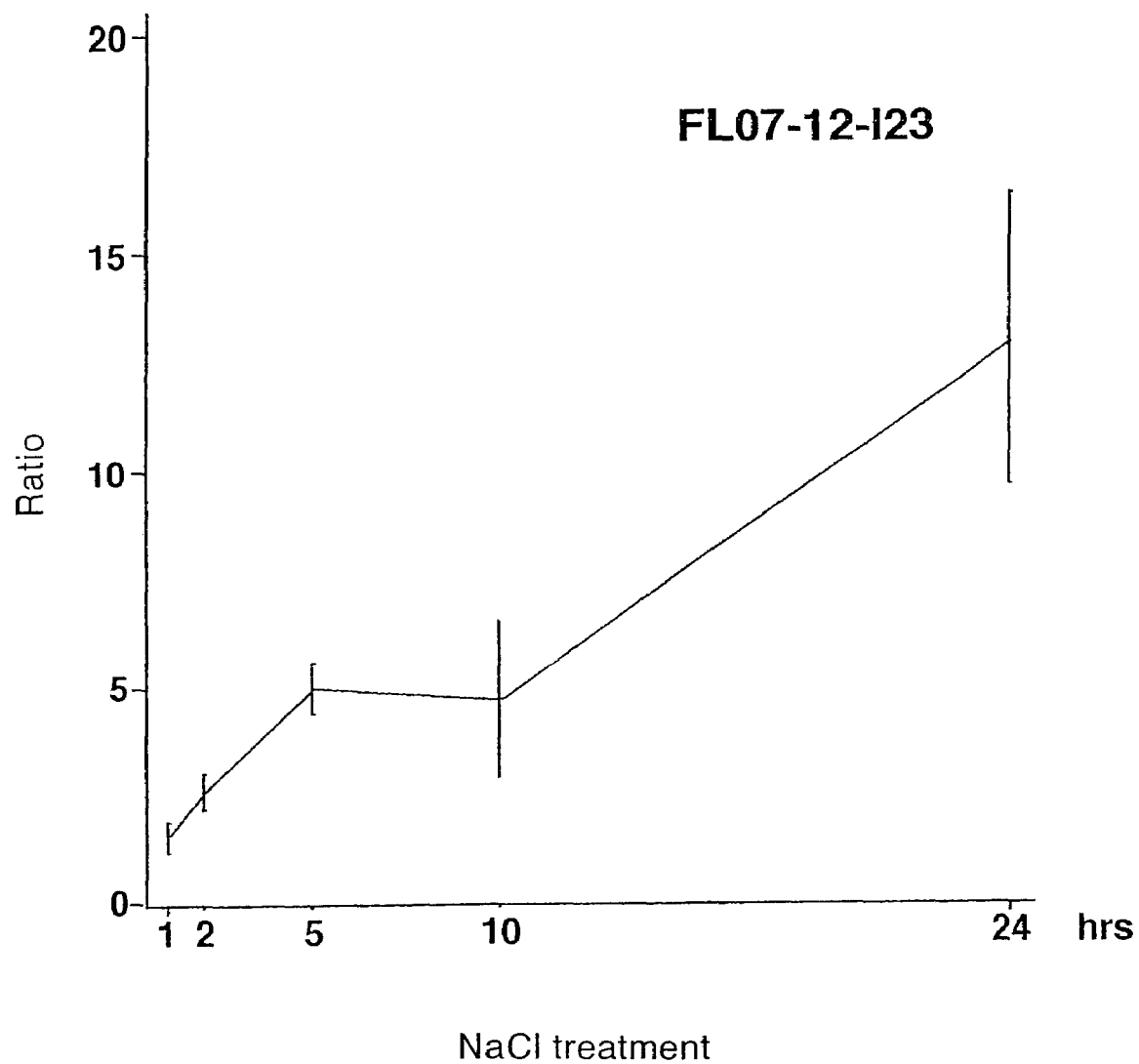
FIG. 40 is a characteristic graph showing the relationship between high salt treatment time and expression ratio regarding FL07-12-I23.
Figure 41:
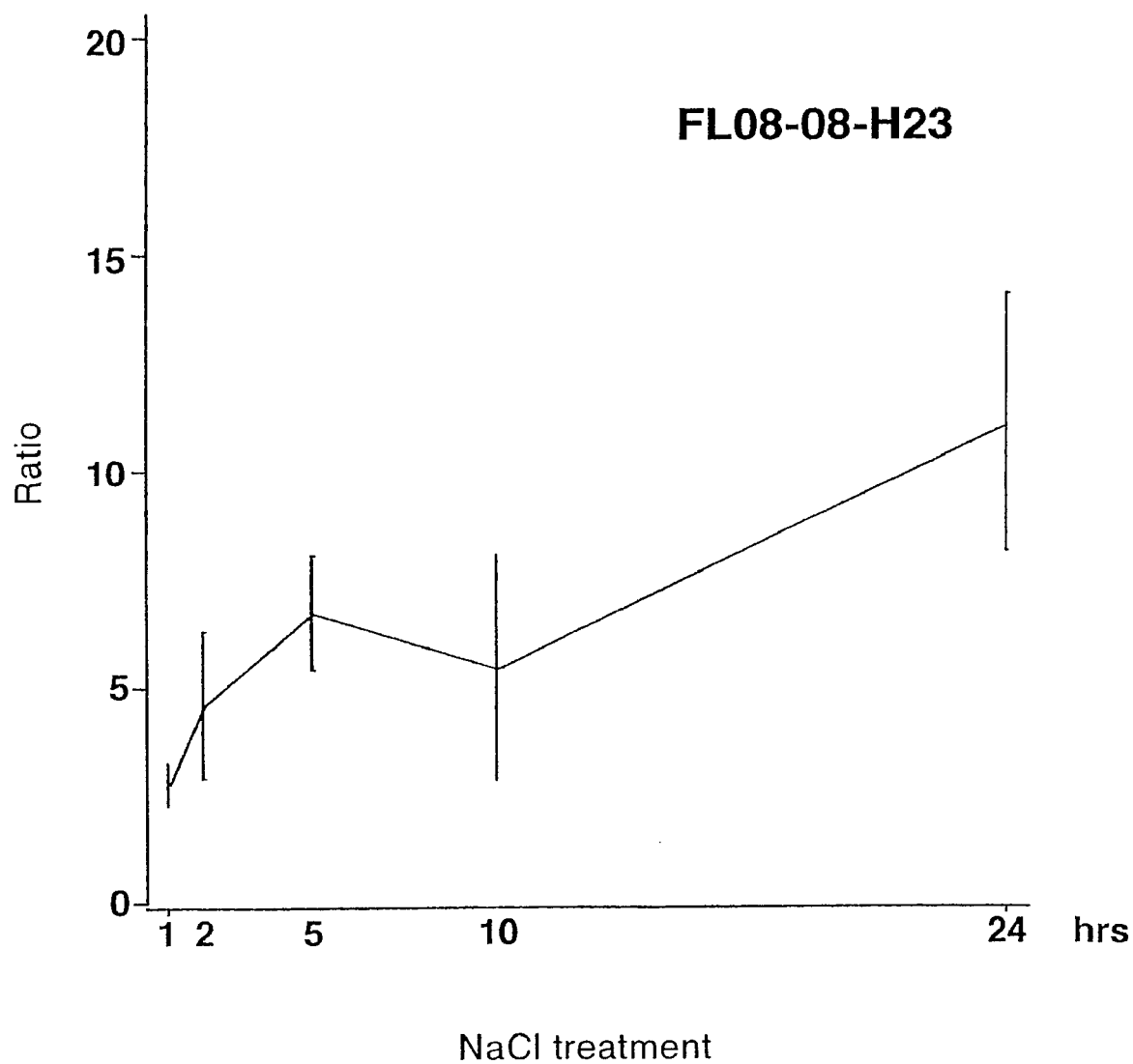
FIG. 41 is a characteristic graph showing the relationship between high salt treatment time and expression ratio regarding FL08-08-H23.
Figure 42:
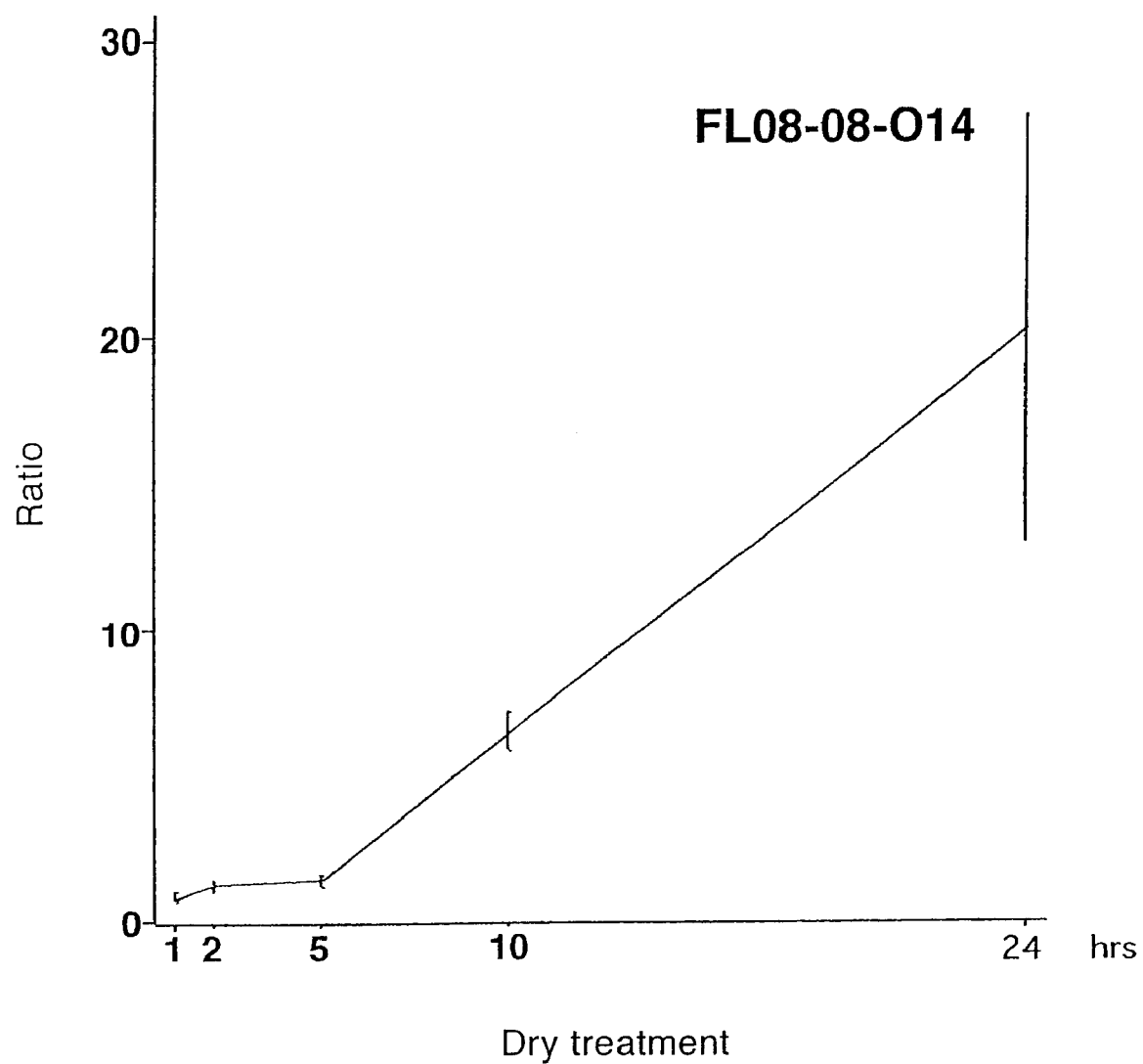
FIG. 42 is a characteristic graph showing the relationship between dehydration treatment time and expression ratio regarding FL08-08-O14.
Figure 43:
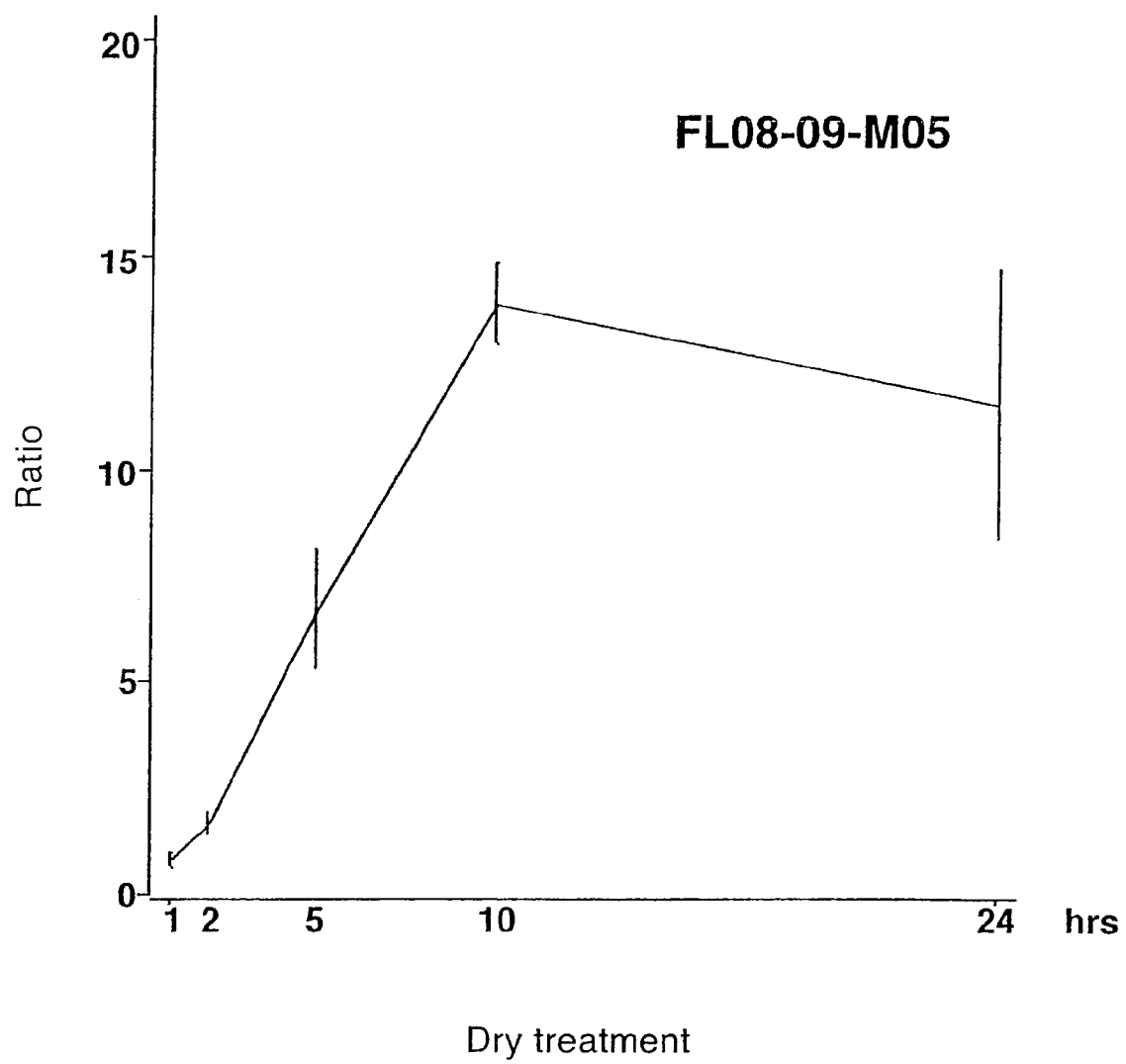
FIG. 43 is a characteristic graph showing the relationship between dehydration treatment time and expression ratio regarding FL08-09-M05.
Figure 44:
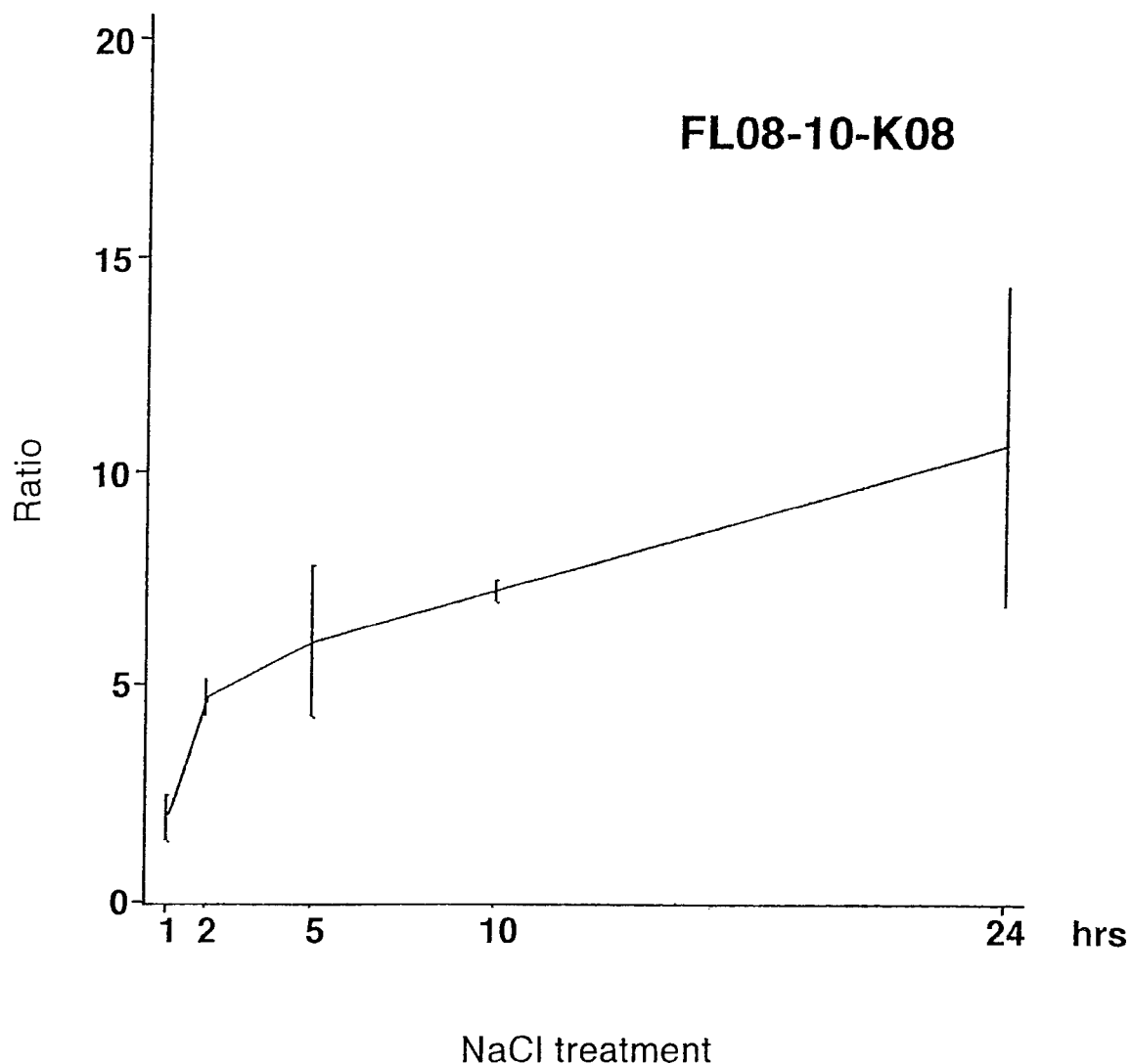
FIG. 44 is a characteristic graph showing the relationship between high salt treatment time and expression ratio regarding FL08-10-K08.
Figure 45:
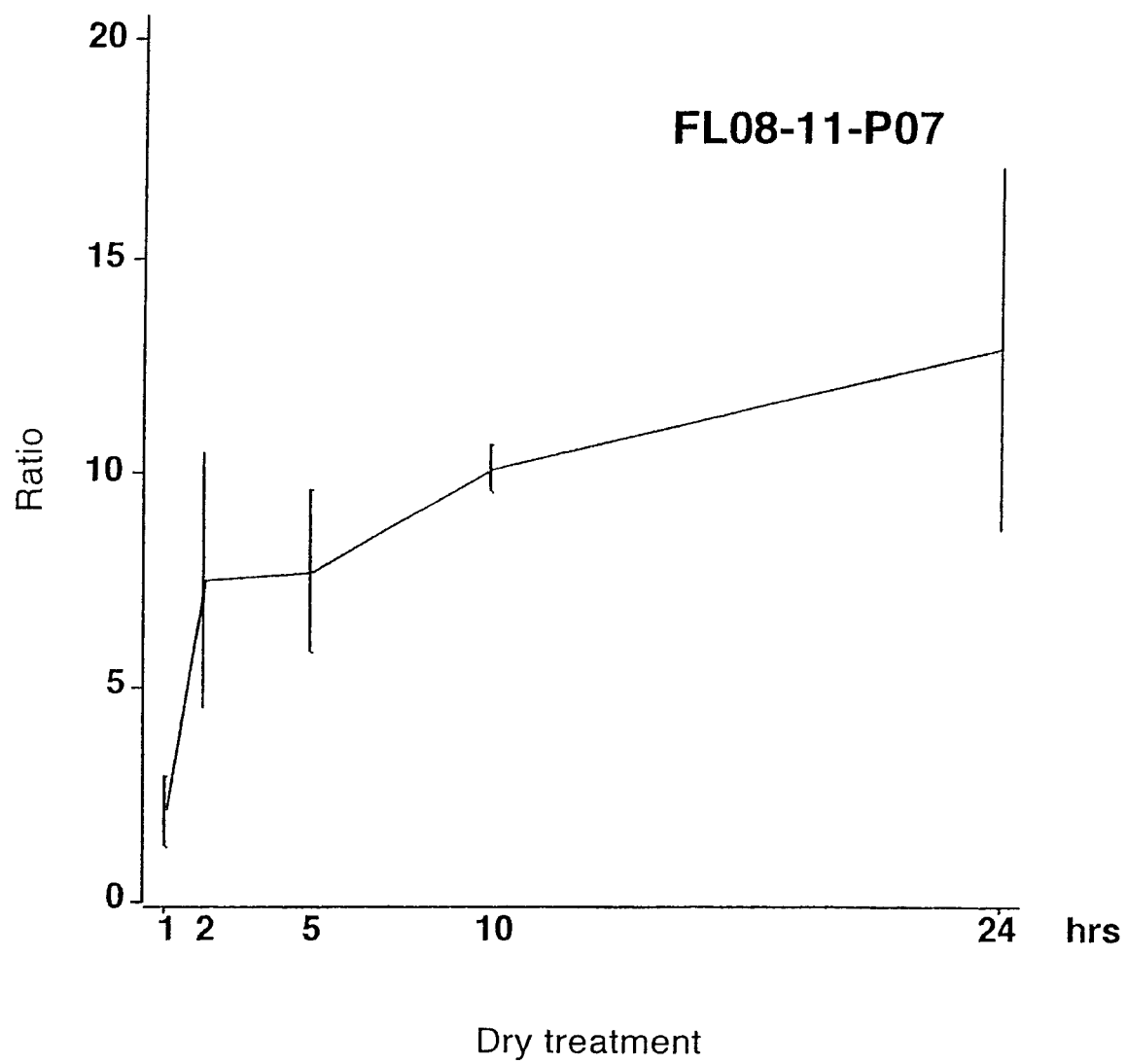
FIG. 45 is a characteristic graph showing the relationship between dehydration treatment time and expression ratio regarding FL08-11-P07.
Figure 46:
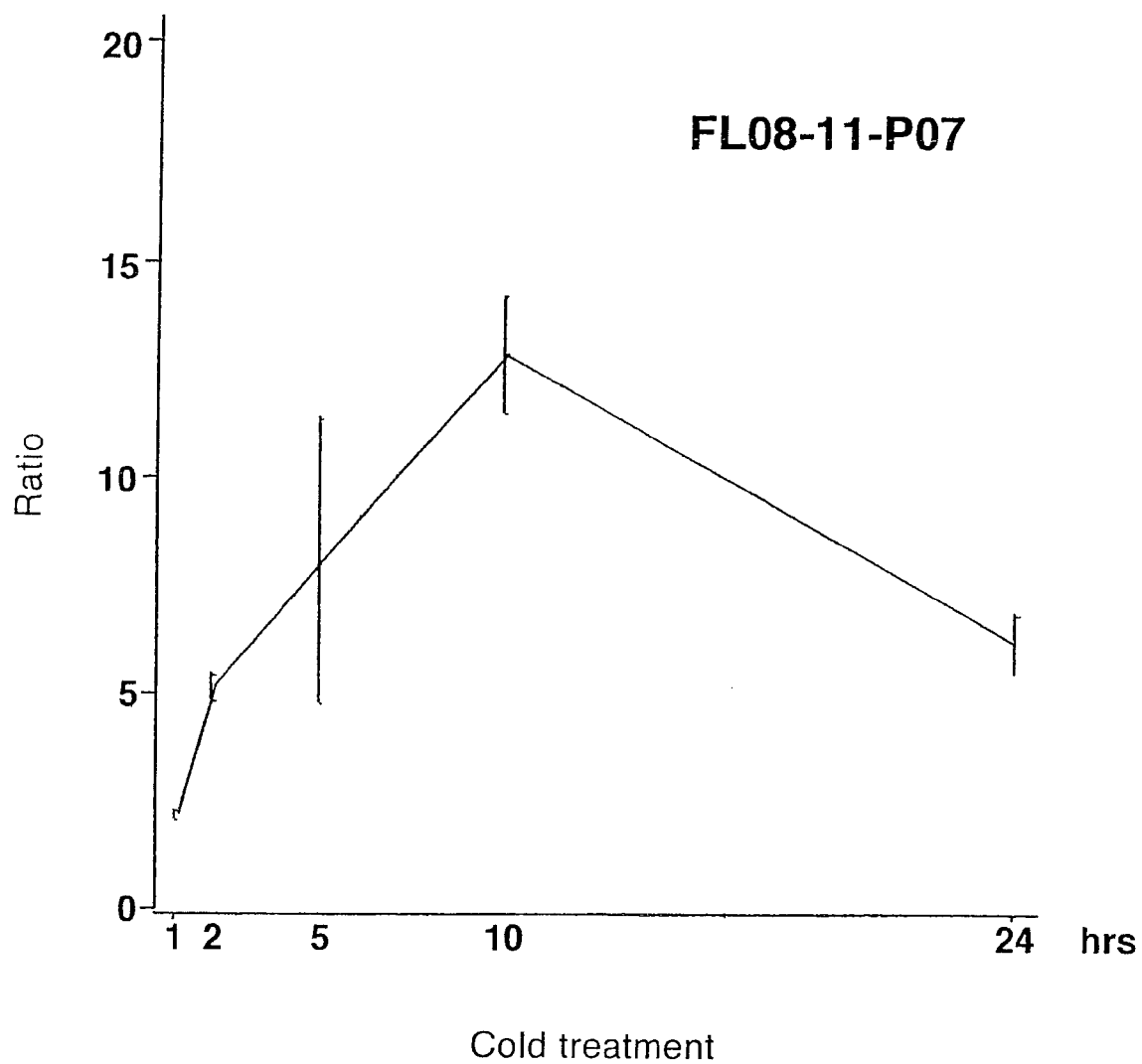
FIG. 46 is a characteristic graph showing the relationship between cold treatment time and expression ratio regarding FL08-11-P07.
Figure 47:
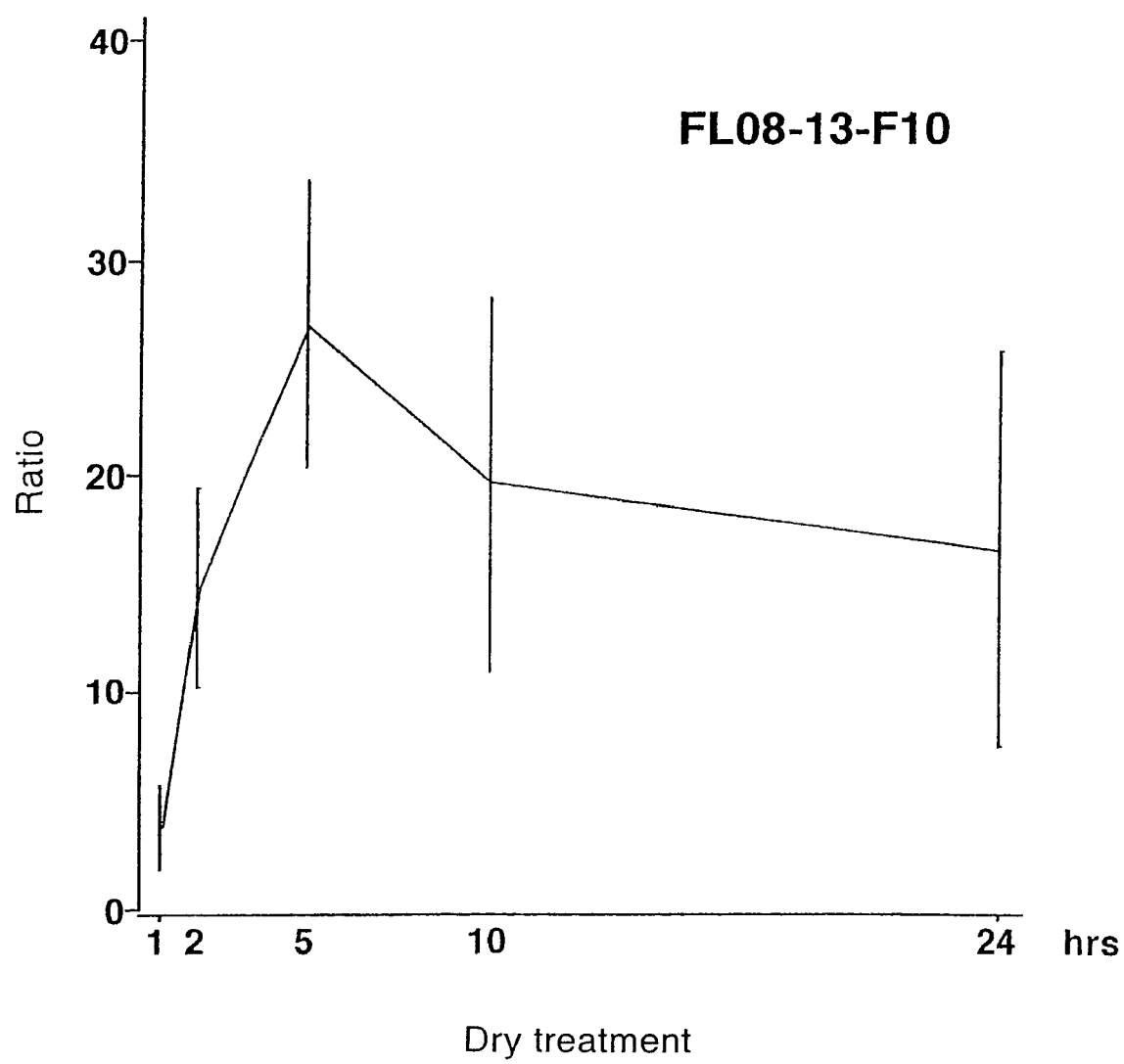
FIG. 47 is a characteristic graph showing the relationship between dehydration treatment time and expression ratio regarding FL08-13-F10.
Figure 48:
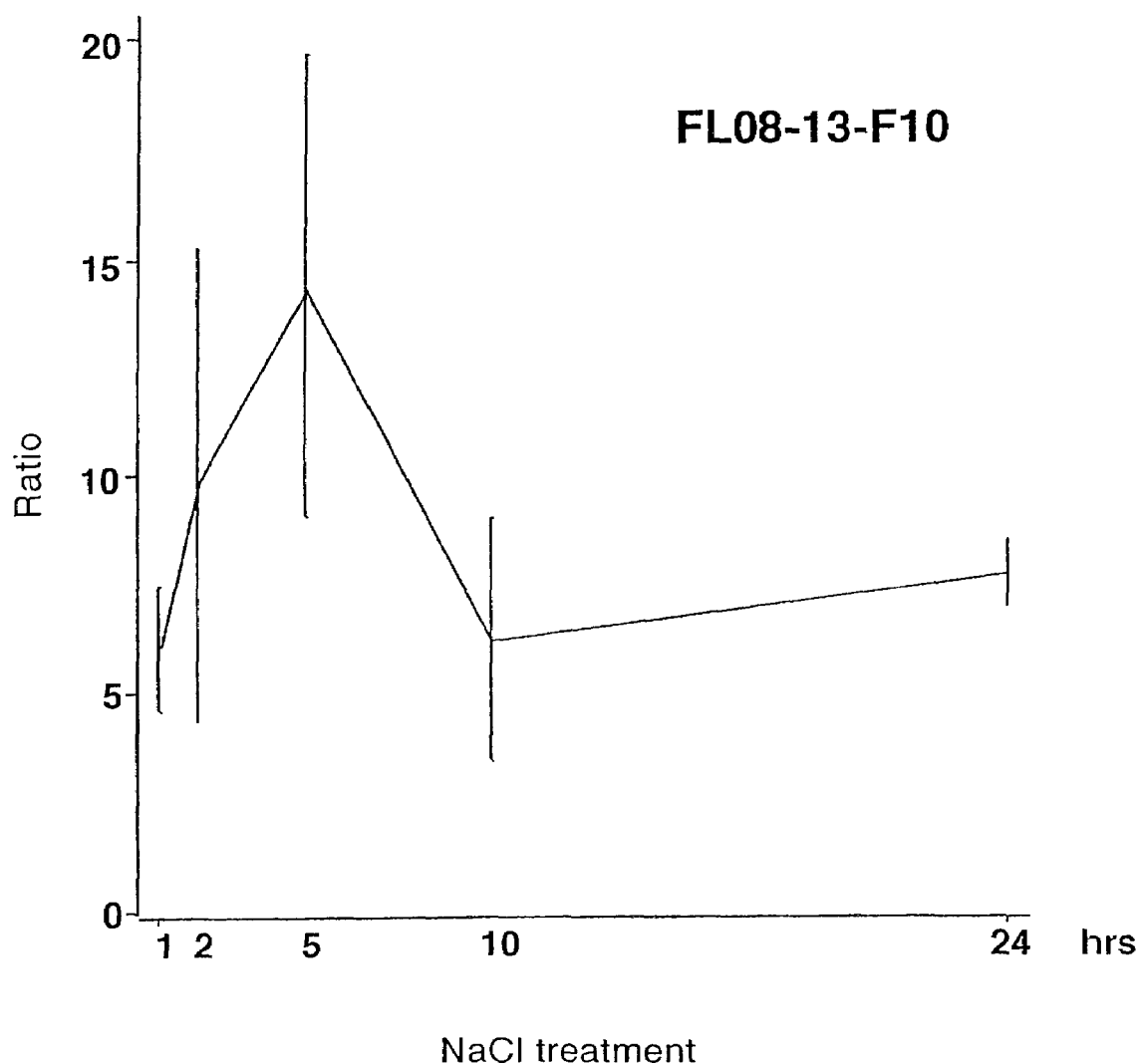
FIG. 48 is a characteristic graph showing the relationship between high salt treatment time and expression ratio regarding FL08-13-F10.
Figure 49:
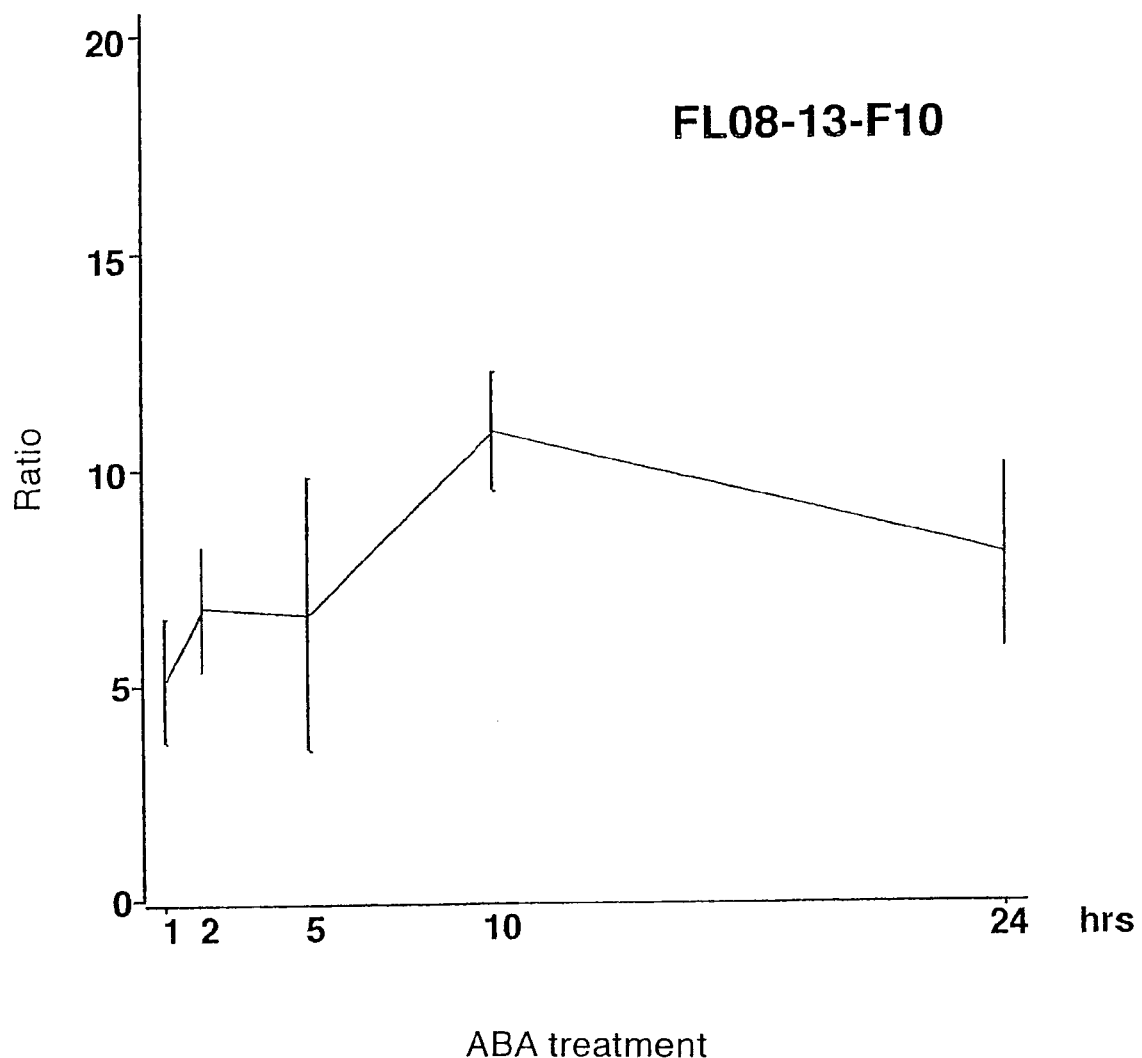
FIG. 49 is a characteristic graph showing the relationship between ABA treatment time and expression ratio regarding FL08-13-F10.
Figure 50:
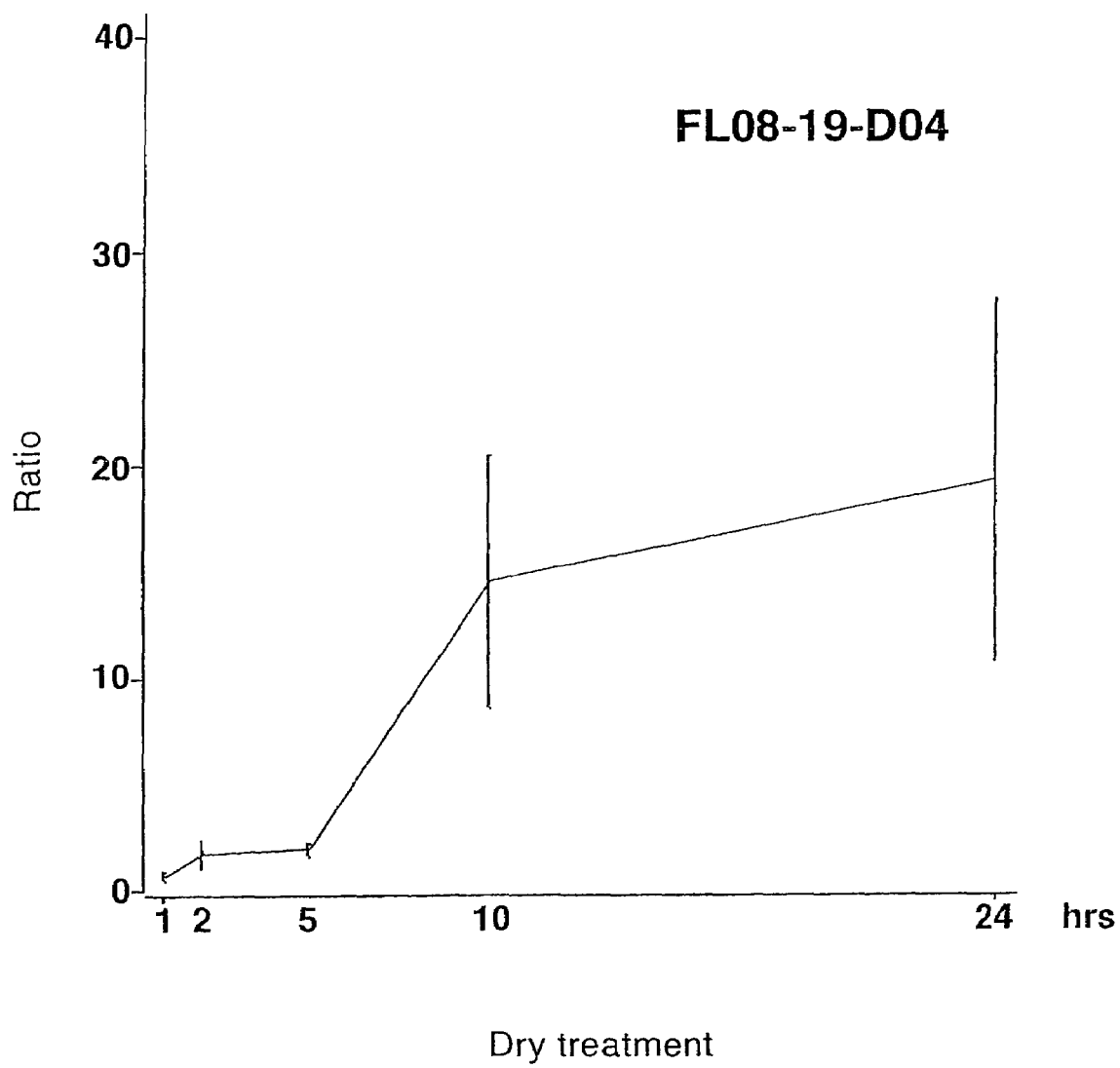
FIG. 50 is a characteristic graph showing the relationship between dehydration treatment time and expression ratio regarding FL08-19-D04.
Figure 51:
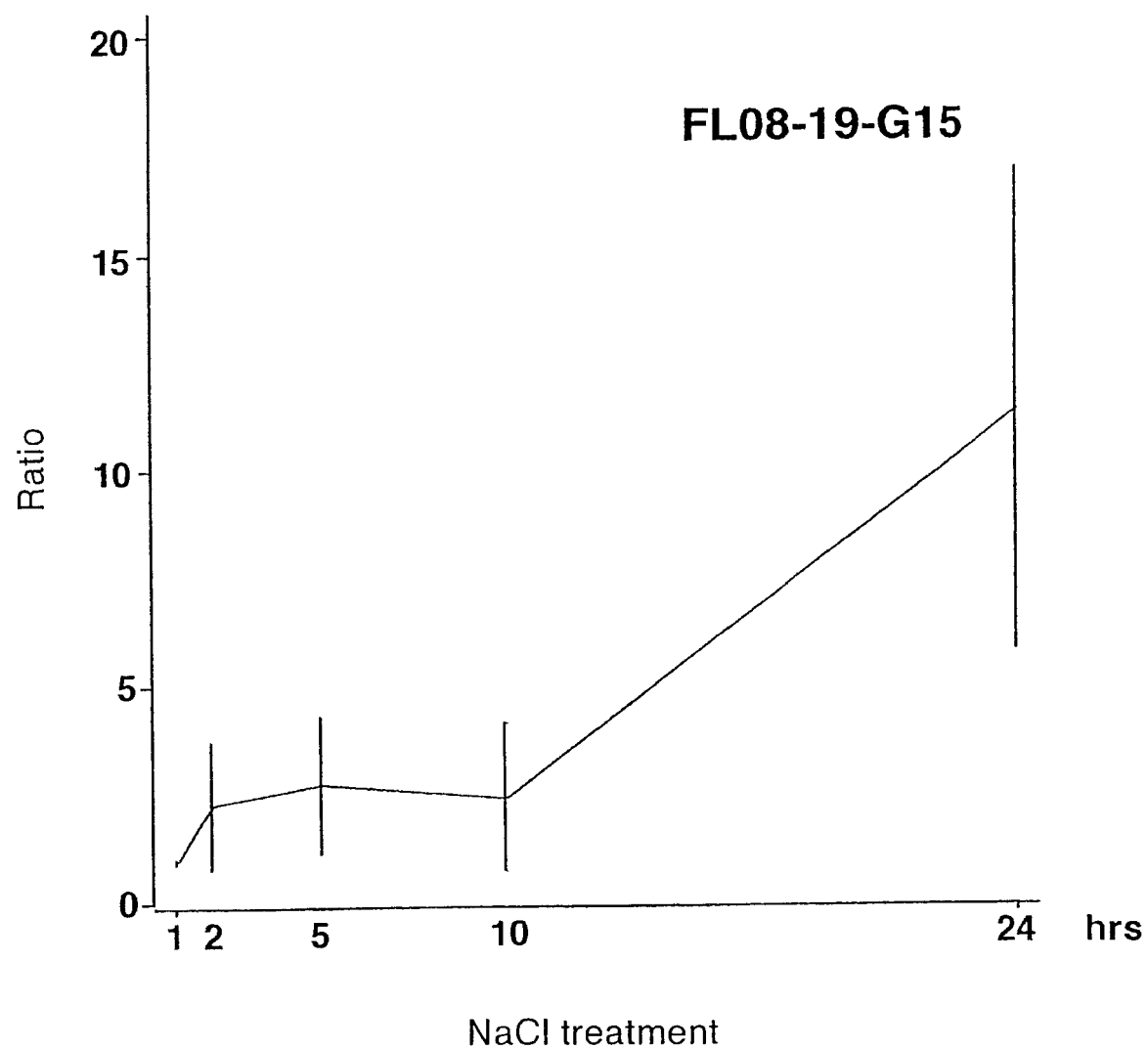
FIG. 51 is a characteristic graph showing the relationship between high salt treatment time and expression ratio regarding FL08-19-G15.
Figure 52:
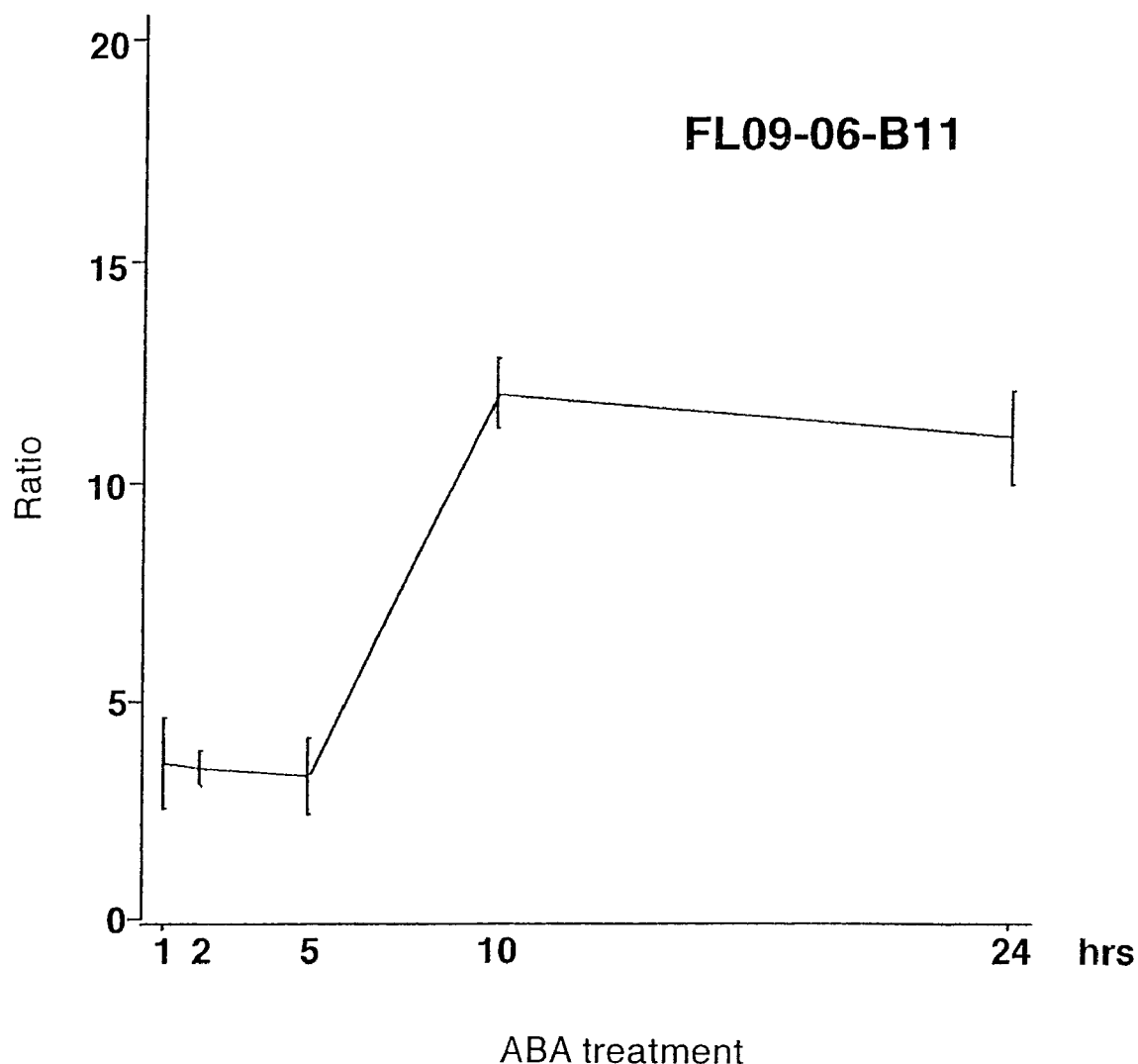
FIG. 52 is a characteristic graph showing the relationship between ABA treatment time and expression ratio regarding FL09-06-B11.
Figure 53:
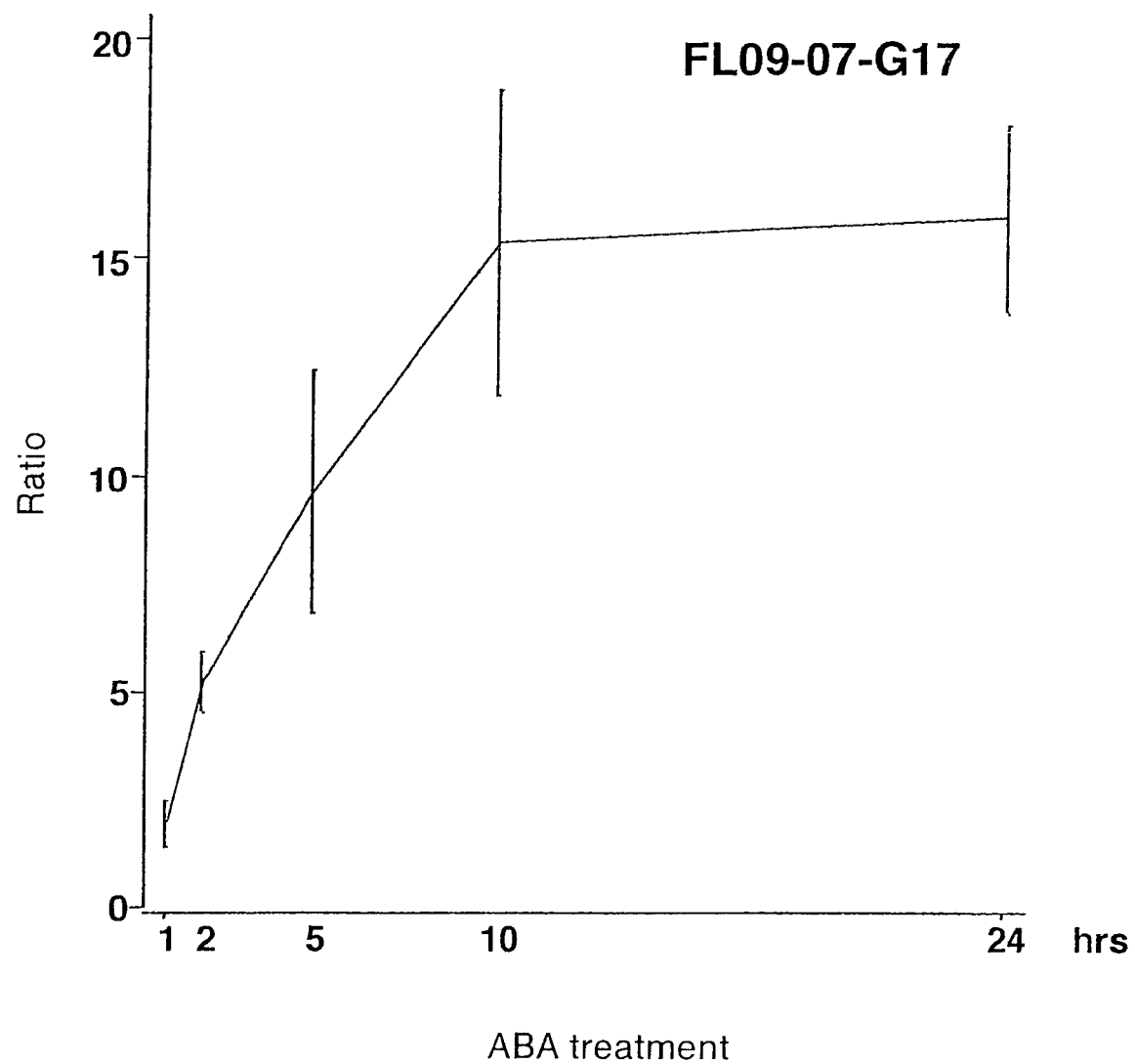
FIG. 53 is a characteristic graph showing the relationship between ABA treatment time and expression ratio regarding FL09-07-G17.
Figure 54:
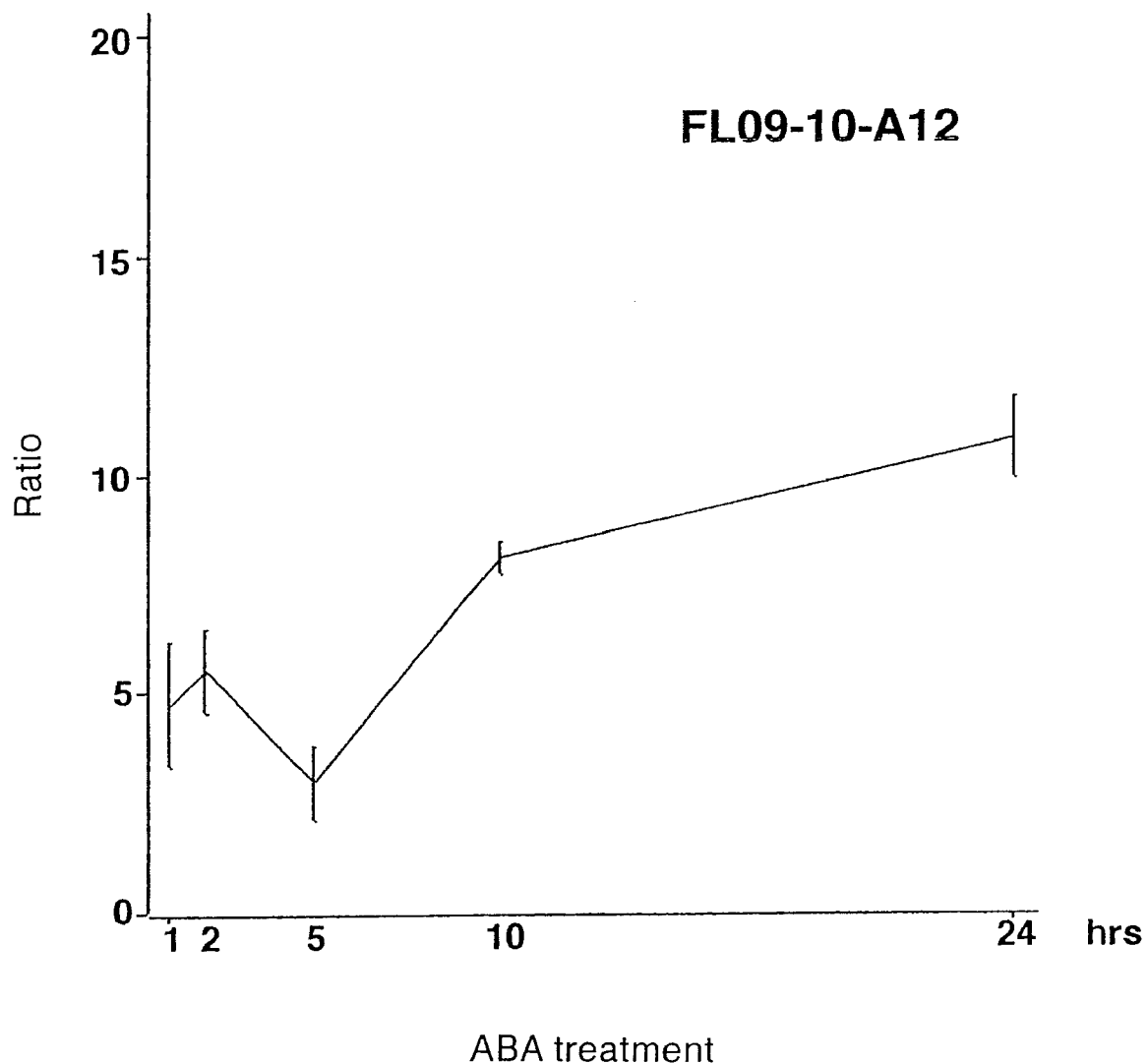
FIG. 54 is a characteristic graph showing the relationship between ABA treatment time and expression ratio regarding FL09-10-A12.
Figure 55:
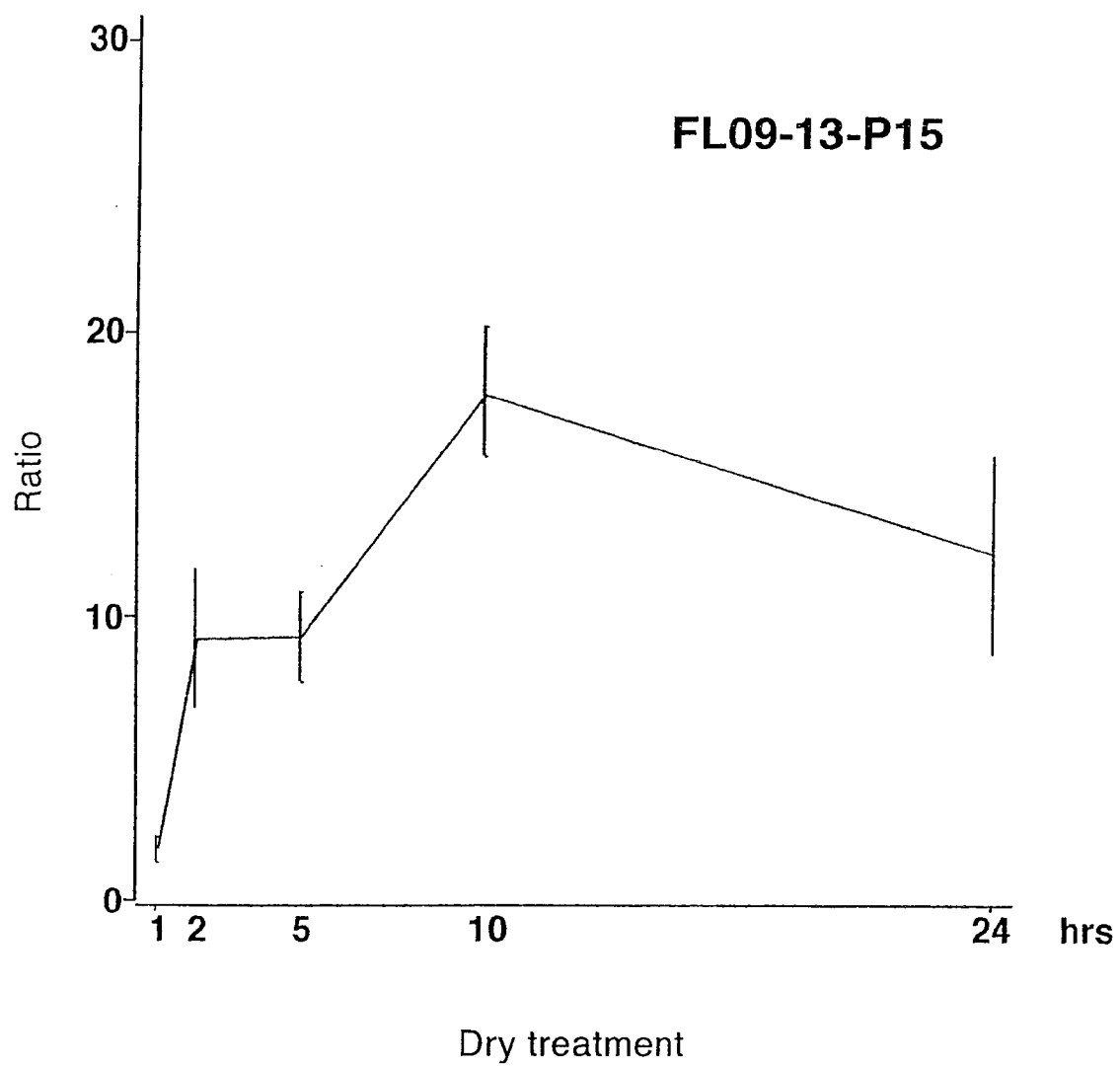
FIG. 55 is a characteristic graph showing the relationship between dehydration treatment time and expression ratio regarding FL09-13-P15.
Figure 56:
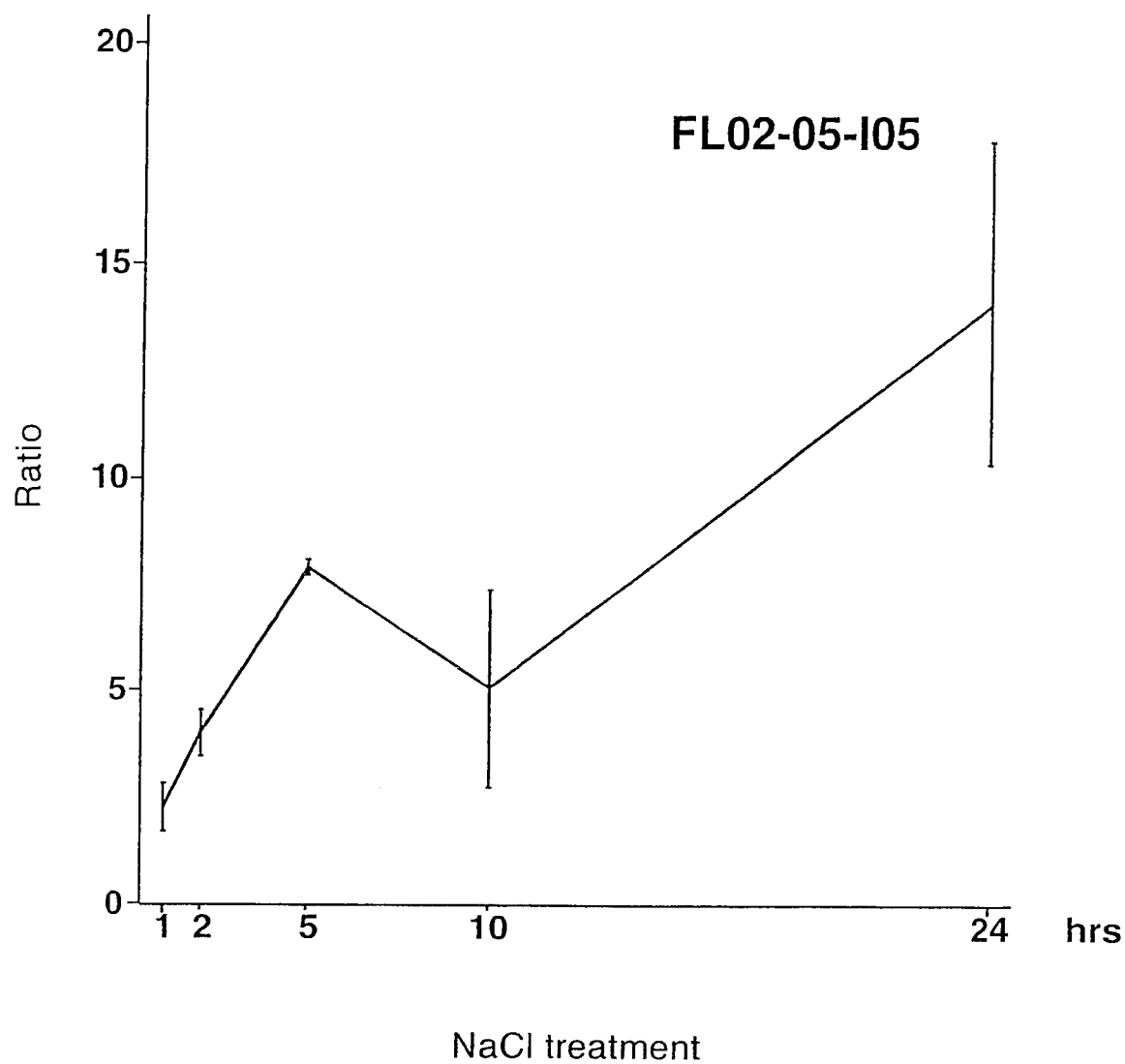
FIG. 56 is a characteristic graph showing the relationship between high salt treatment time and expression ratio regarding FL02-05-I05.
Figure 57:
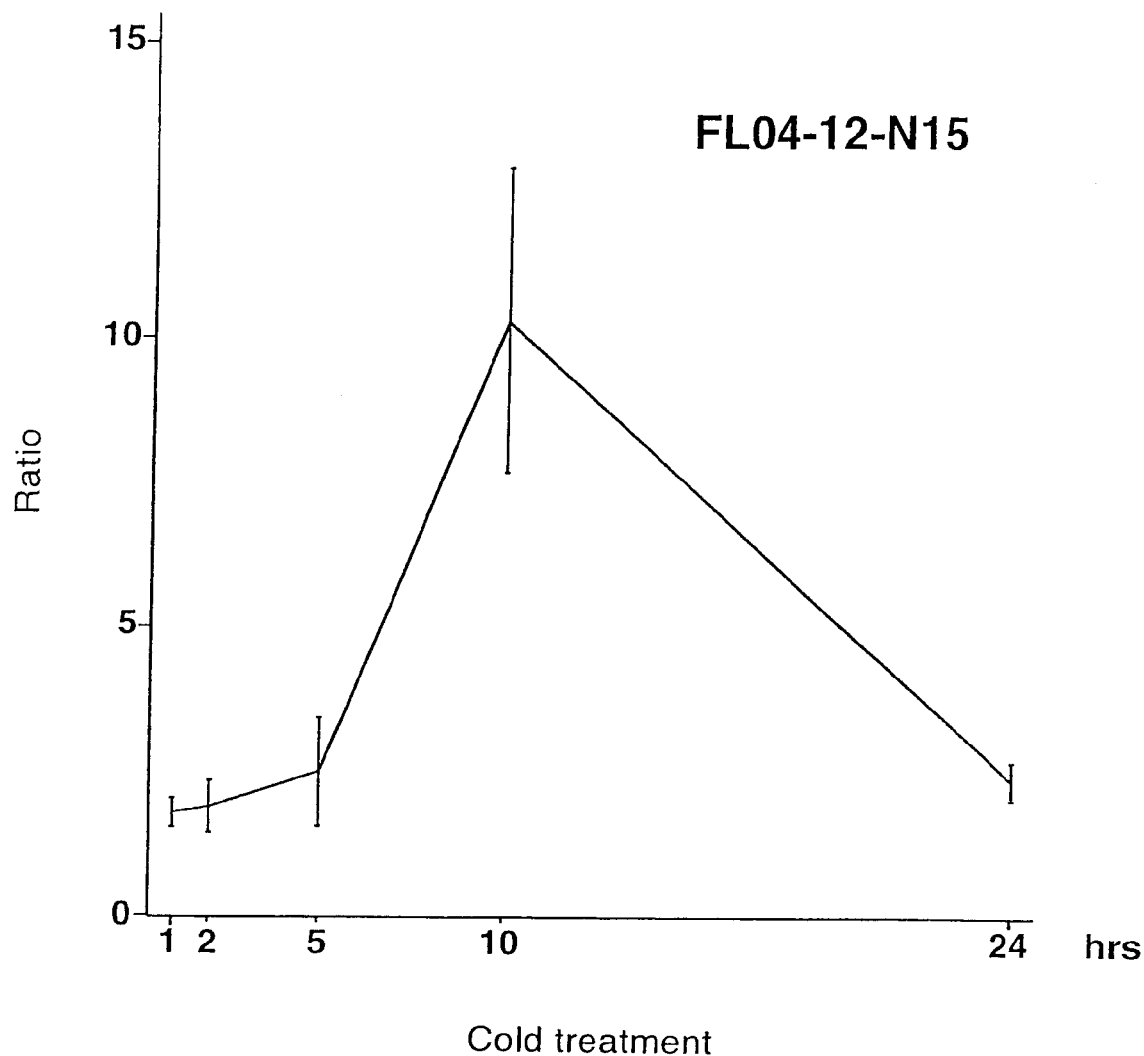
FIG. 57 is a characteristic graph showing the relationship between cold treatment time and expression ratio regarding FL04-12-N15.
Figure 58:
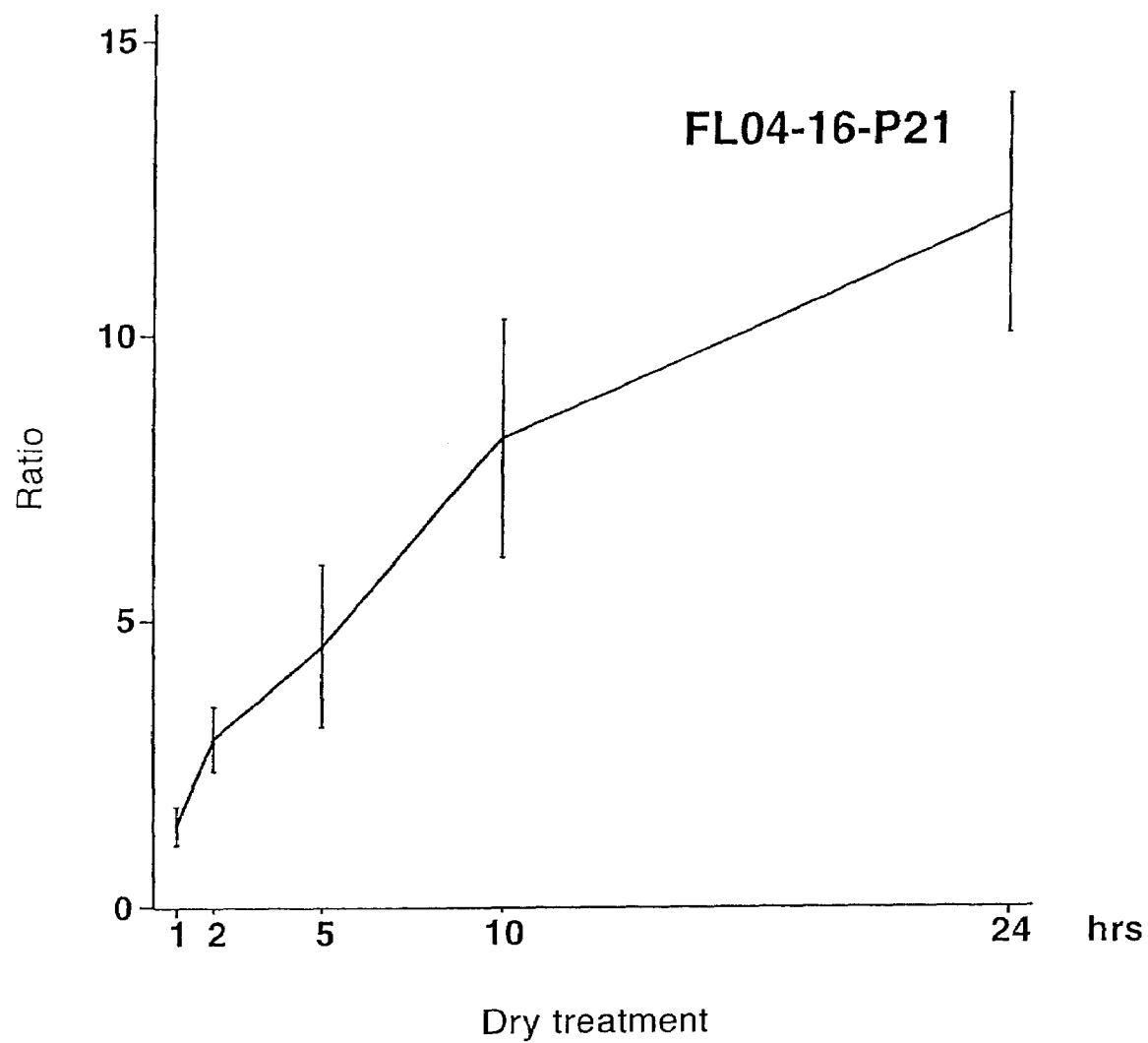
FIG. 58 is a characteristic graph showing the relationship between dehydration treatment time and expression ratio regarding FL04-16-P21.
Figure 59:
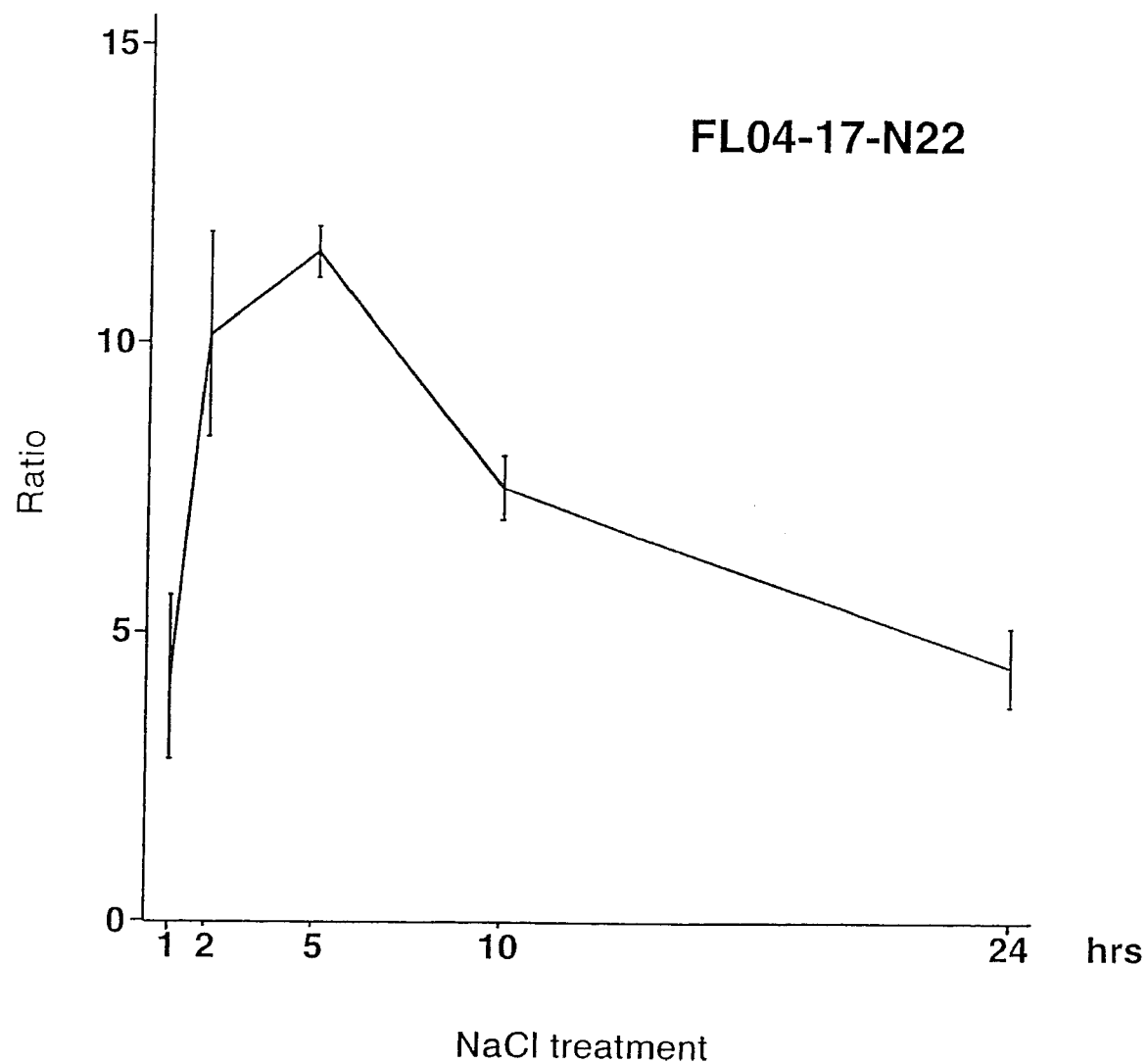
FIG. 59 is a characteristic graph showing the relationship between high salt treatment time and expression ratio regarding FL04-17-N22.
Figure 60:
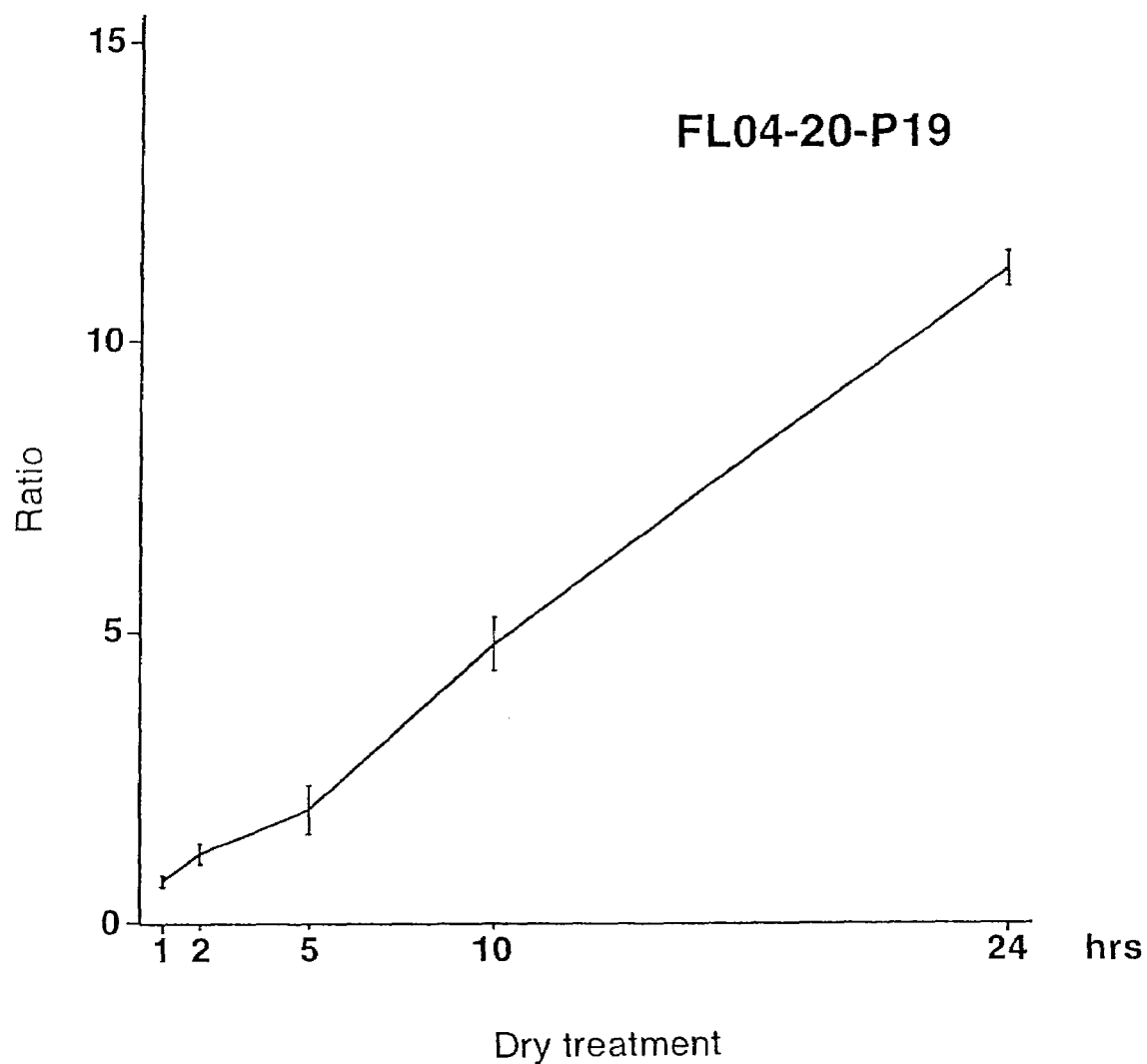
FIG. 60 is a characteristic graph showing the relationship between dehydration treatment time and expression ratio regarding FL04-20-P19.
Figure 61:
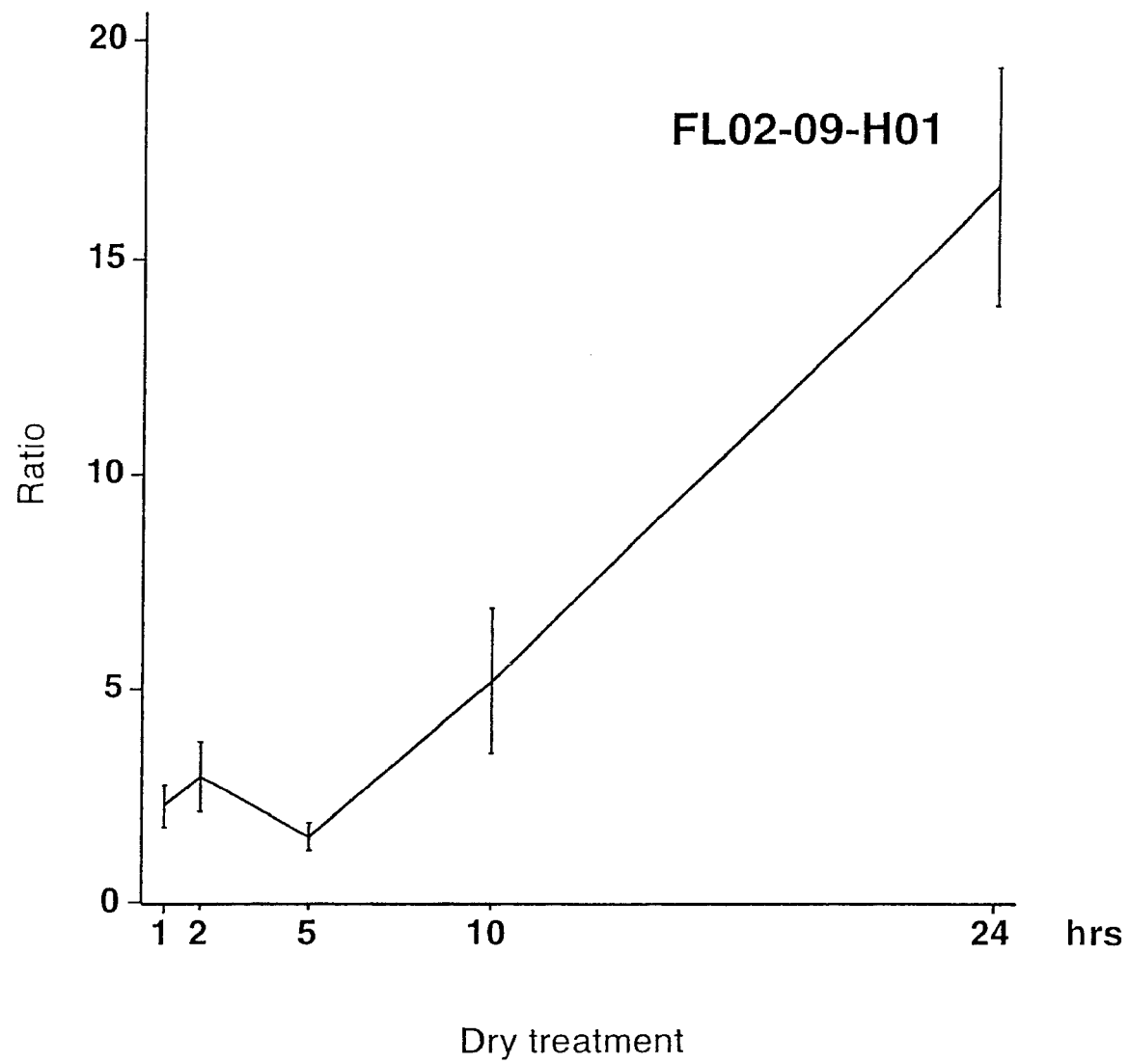
FIG. 61 is a characteristic graph showing the relationship between dehydration treatment time and expression ratio regarding FL02-09-H01.
Figure 62:
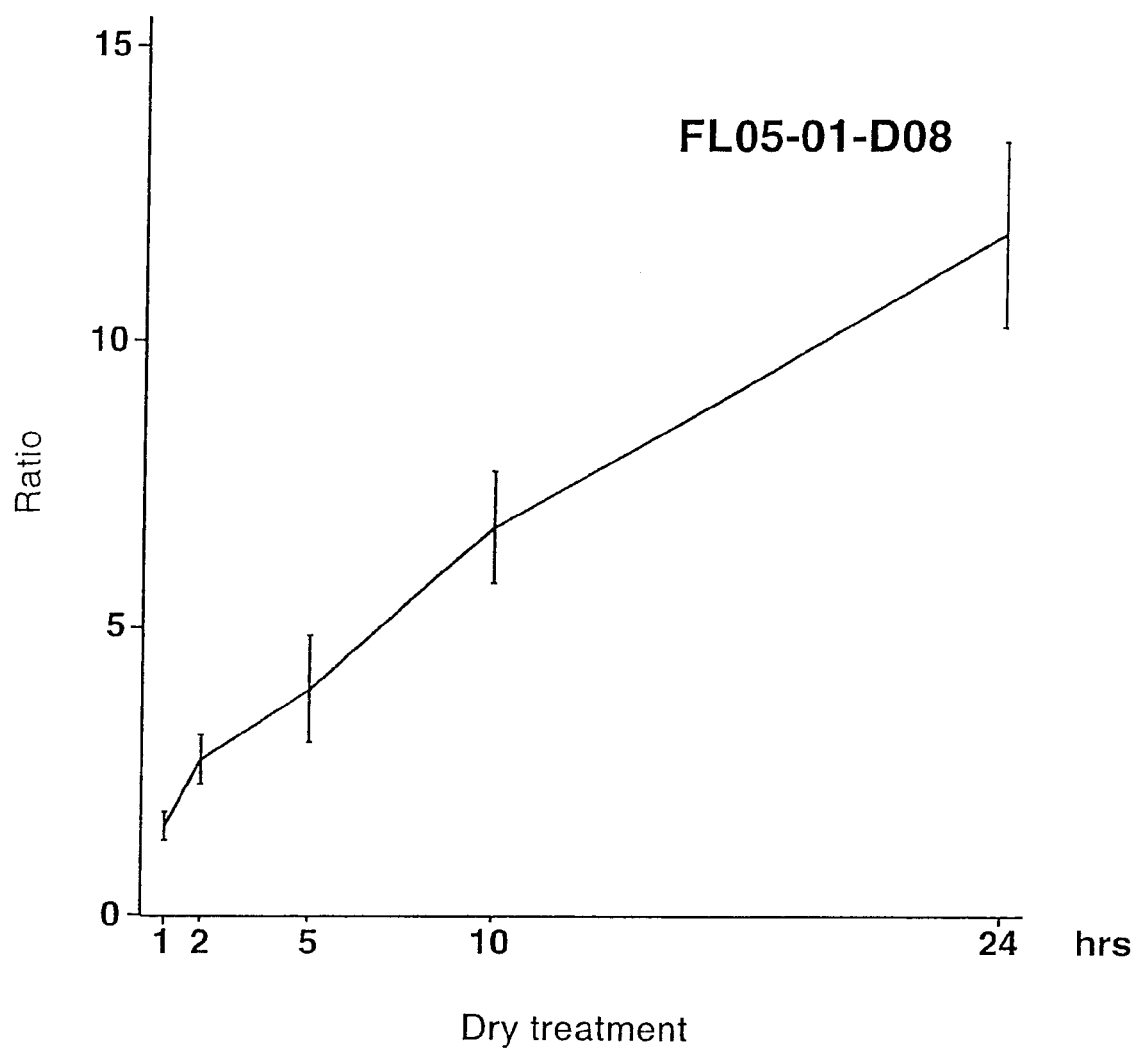
FIG. 62 is a characteristic graph showing the relationship between dehydration treatment time and expression ratio regarding FL05-01-D08.
Figure 63:
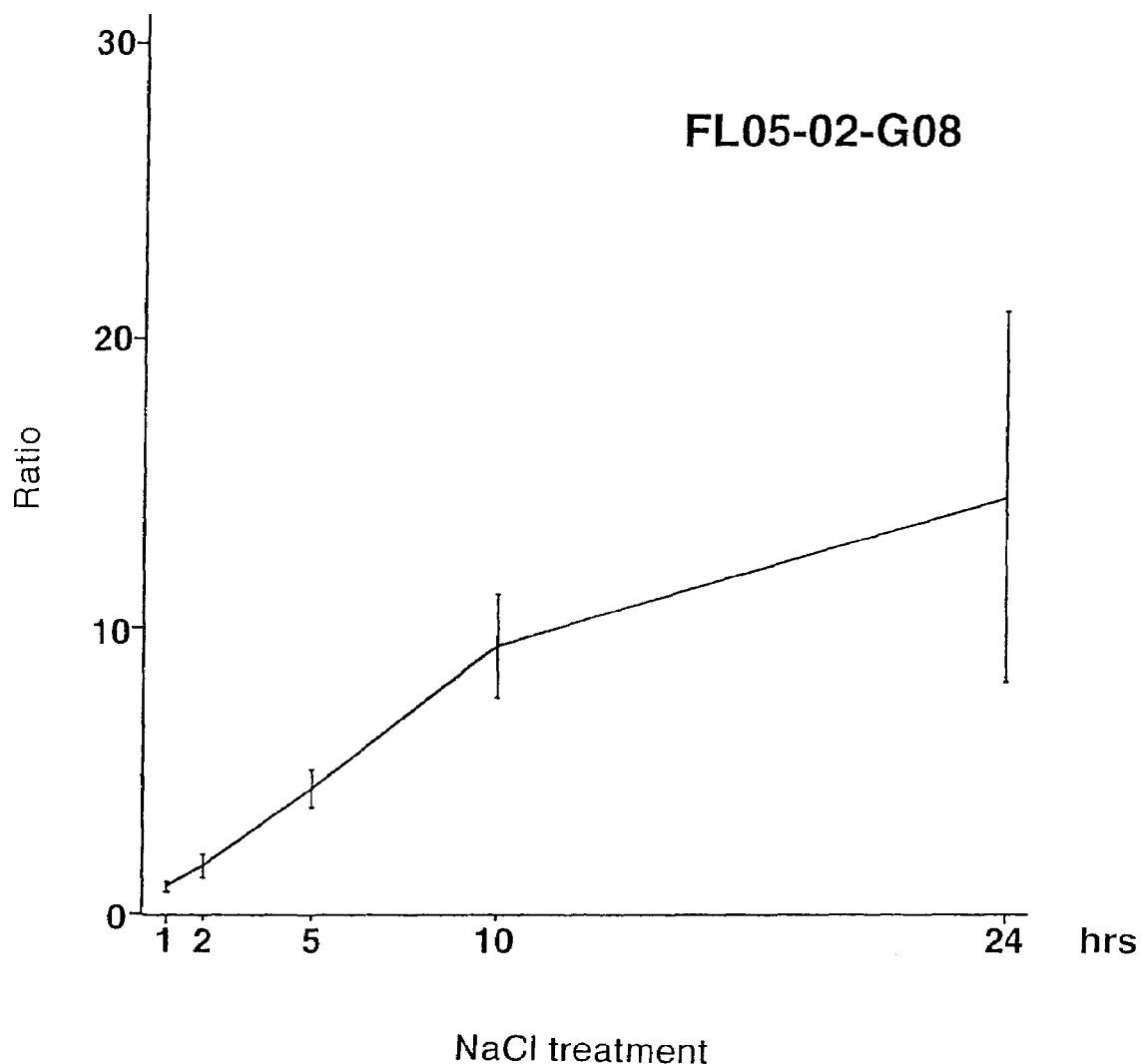
FIG. 63 is a characteristic graph showing the relationship between high salt treatment time and expression ratio regarding FL05-02-G08.
Figure 64:
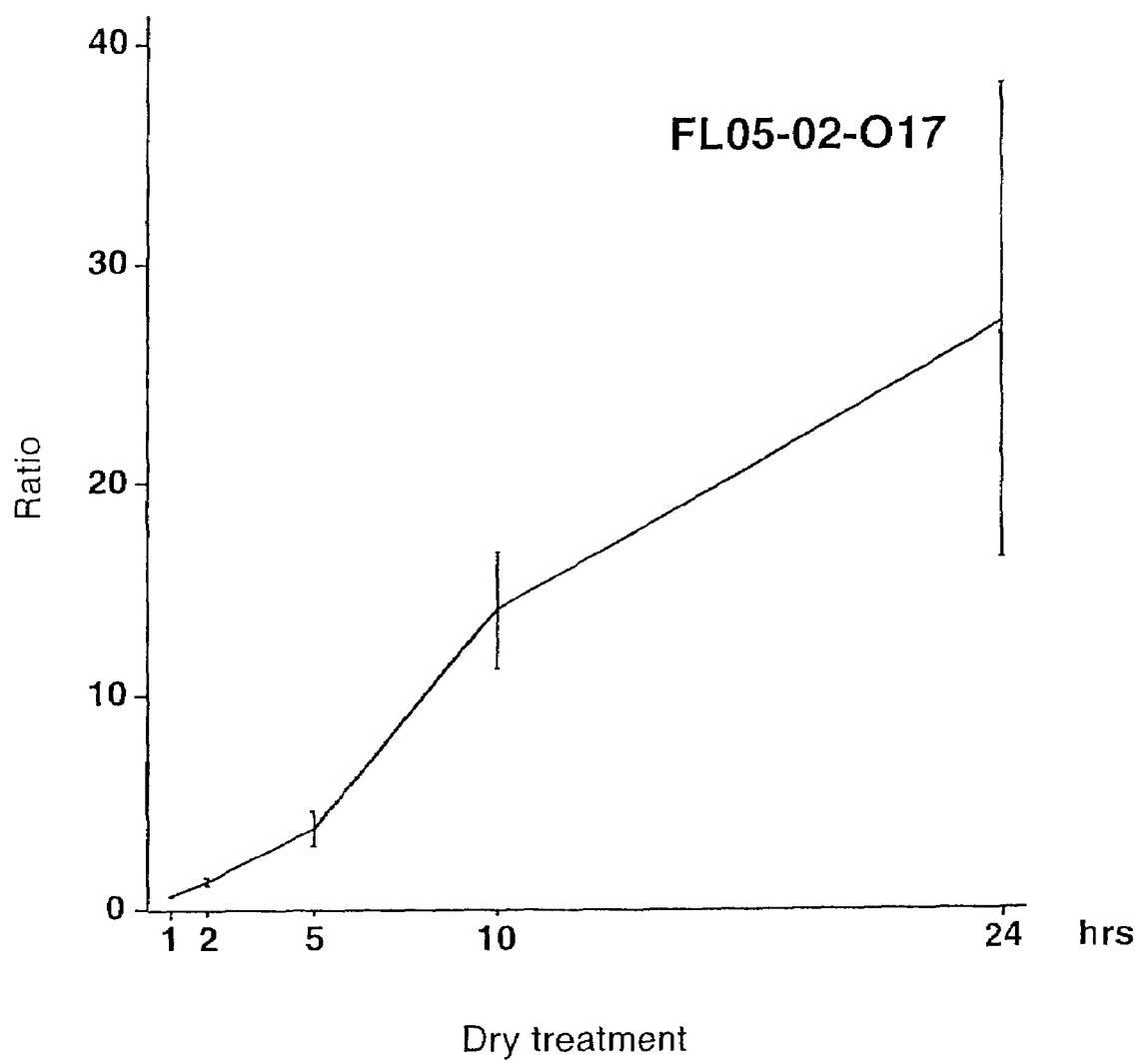
FIG. 64 is a characteristic graph showing the relationship between dehydration treatment time and expression ratio regarding FL05-02-O17.
Figure 65:
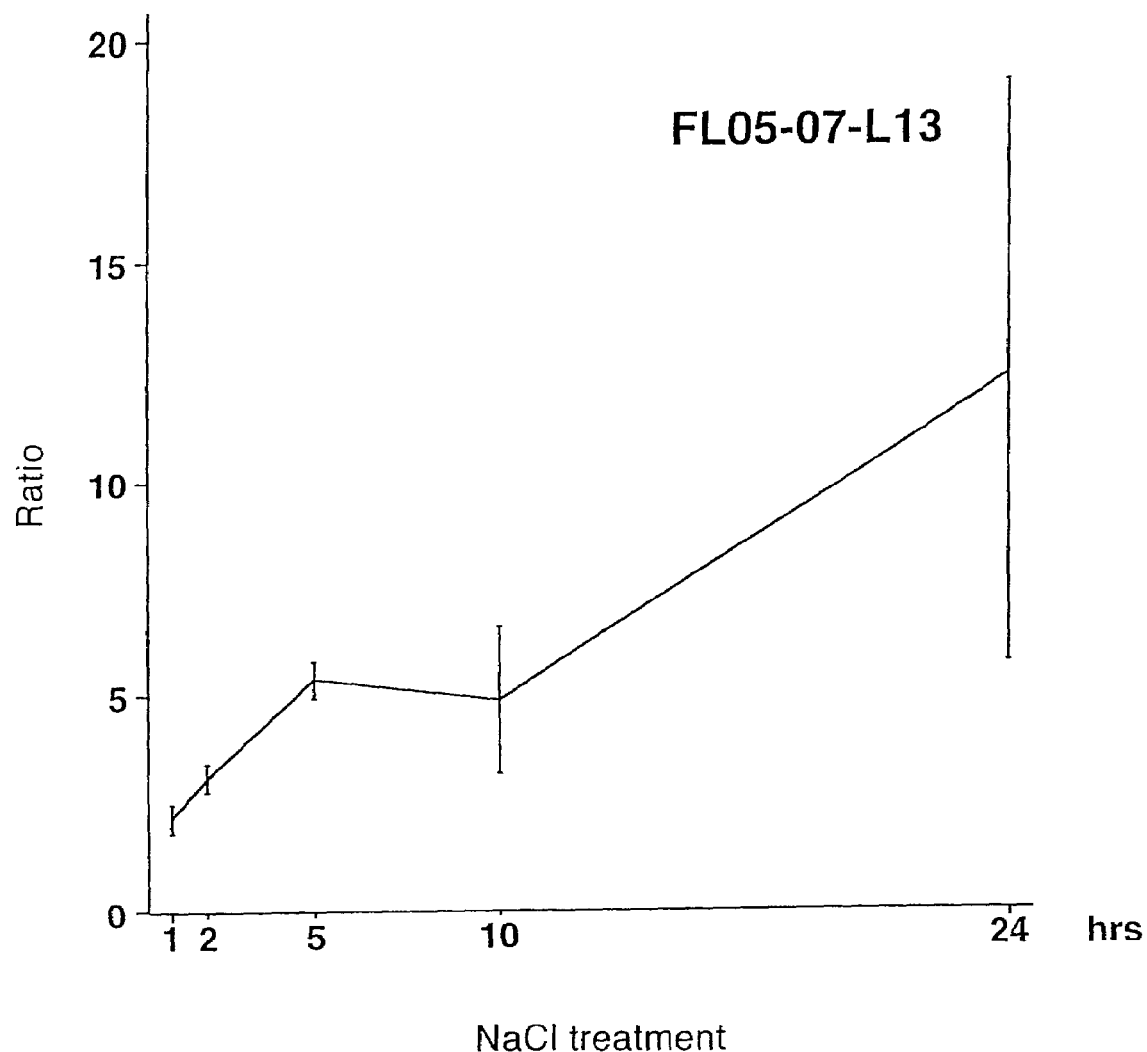
FIG. 65 is a characteristic graph showing the relationship between high salt treatment time and expression ratio regarding FL05-07-L13.
Figure 66:
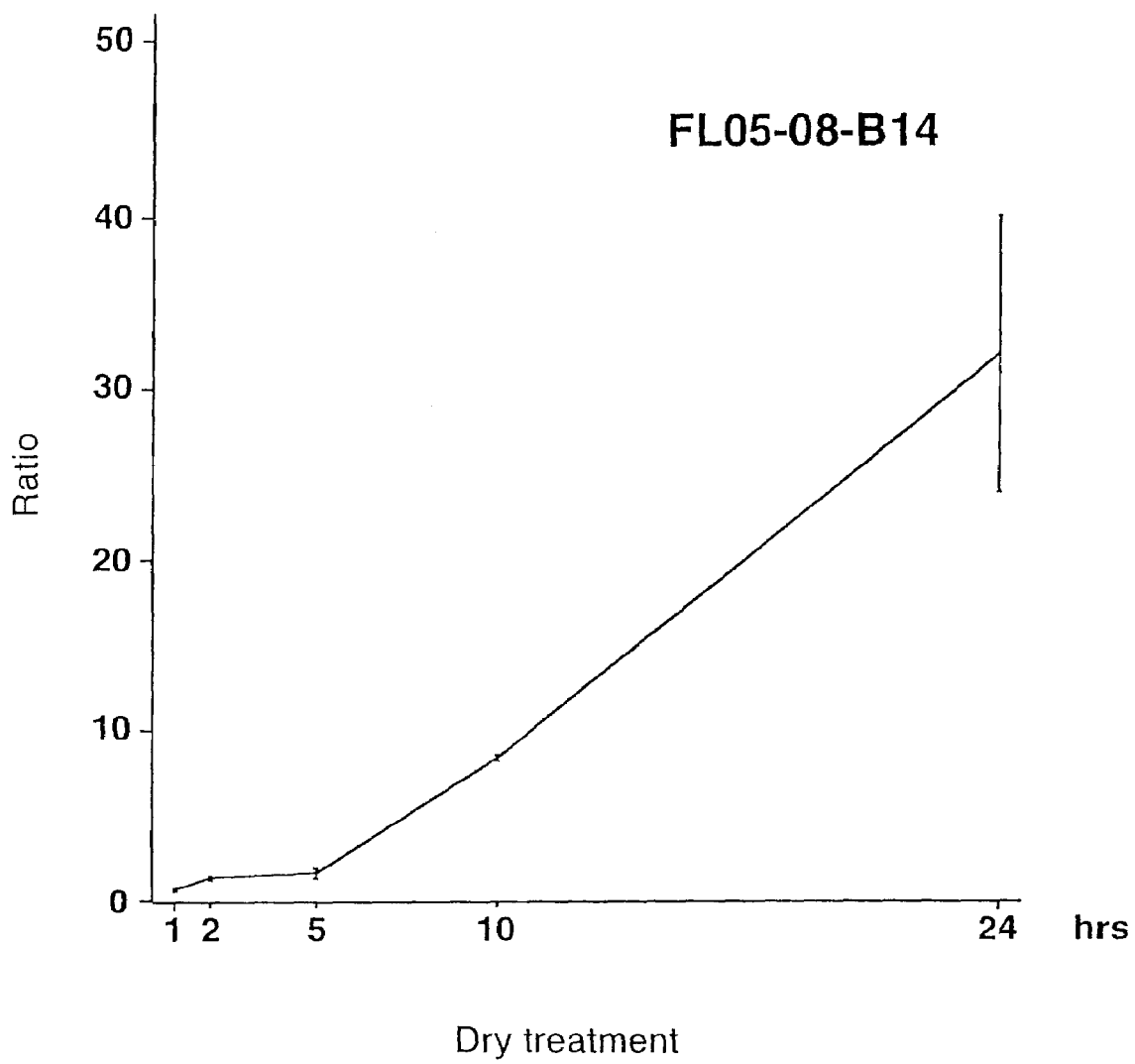
FIG. 66 is a characteristic graph showing the relationship between dehydration treatment time and expression ratio regarding FL05-08-B14.
Figure 67:
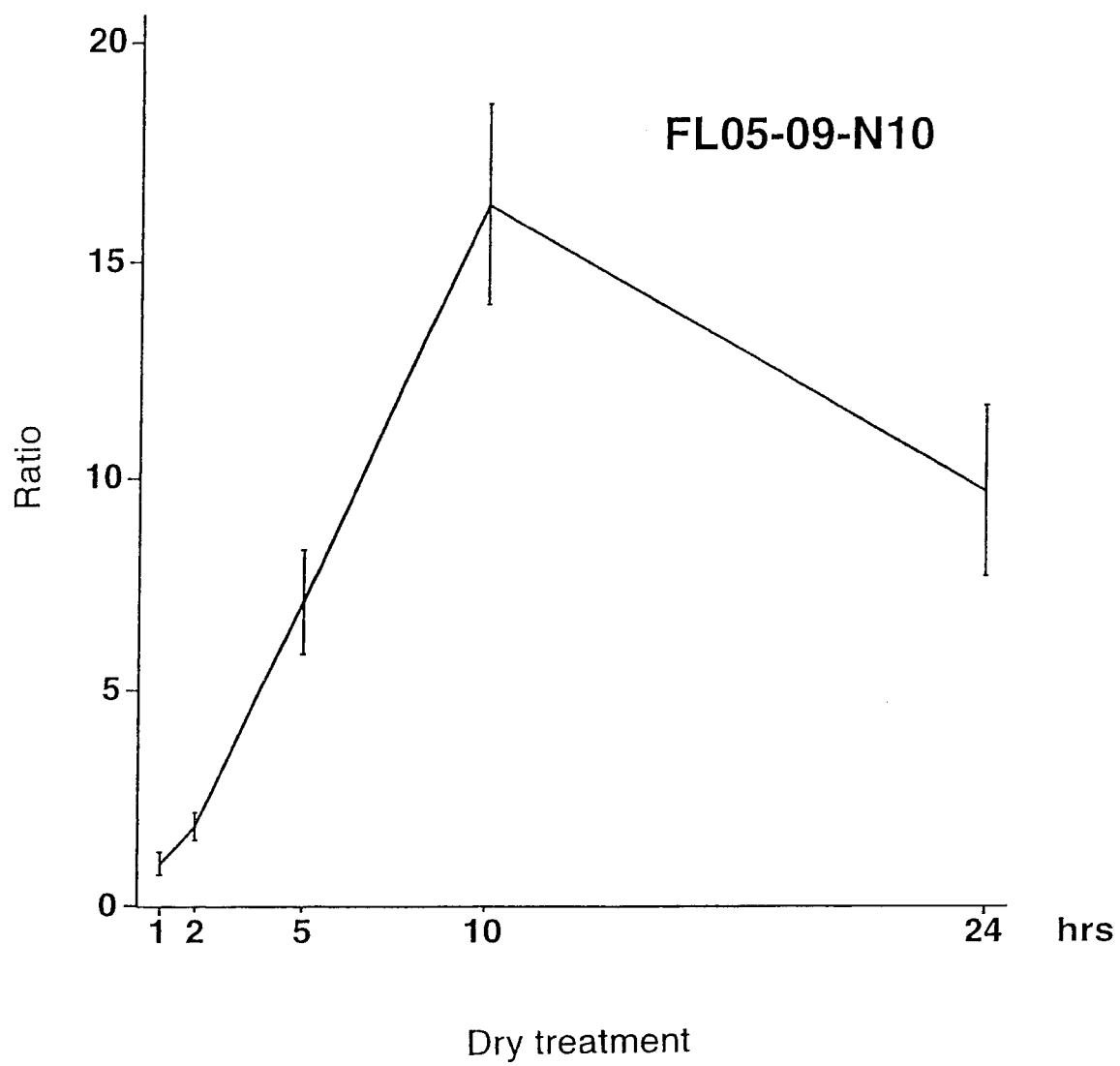
FIG. 67 is a characteristic graph showing the relationship between dehydration treatment time and expression ratio regarding FL05-09-N10.
Figure 68:
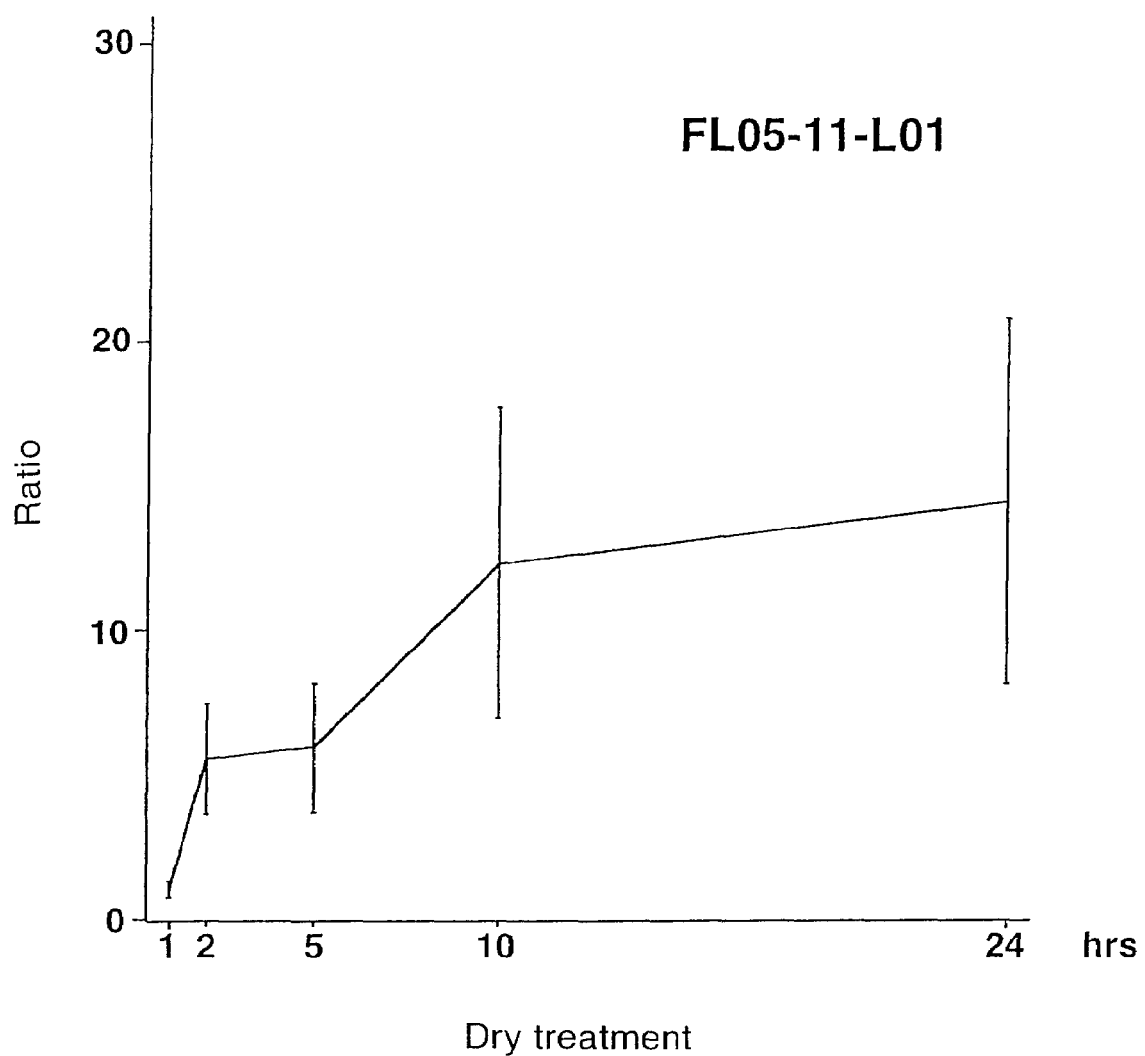
FIG. 68 is a characteristic graph showing the relationship between dehydration treatment time and expression ratio regarding FL05-11-L01.
Figure 69:
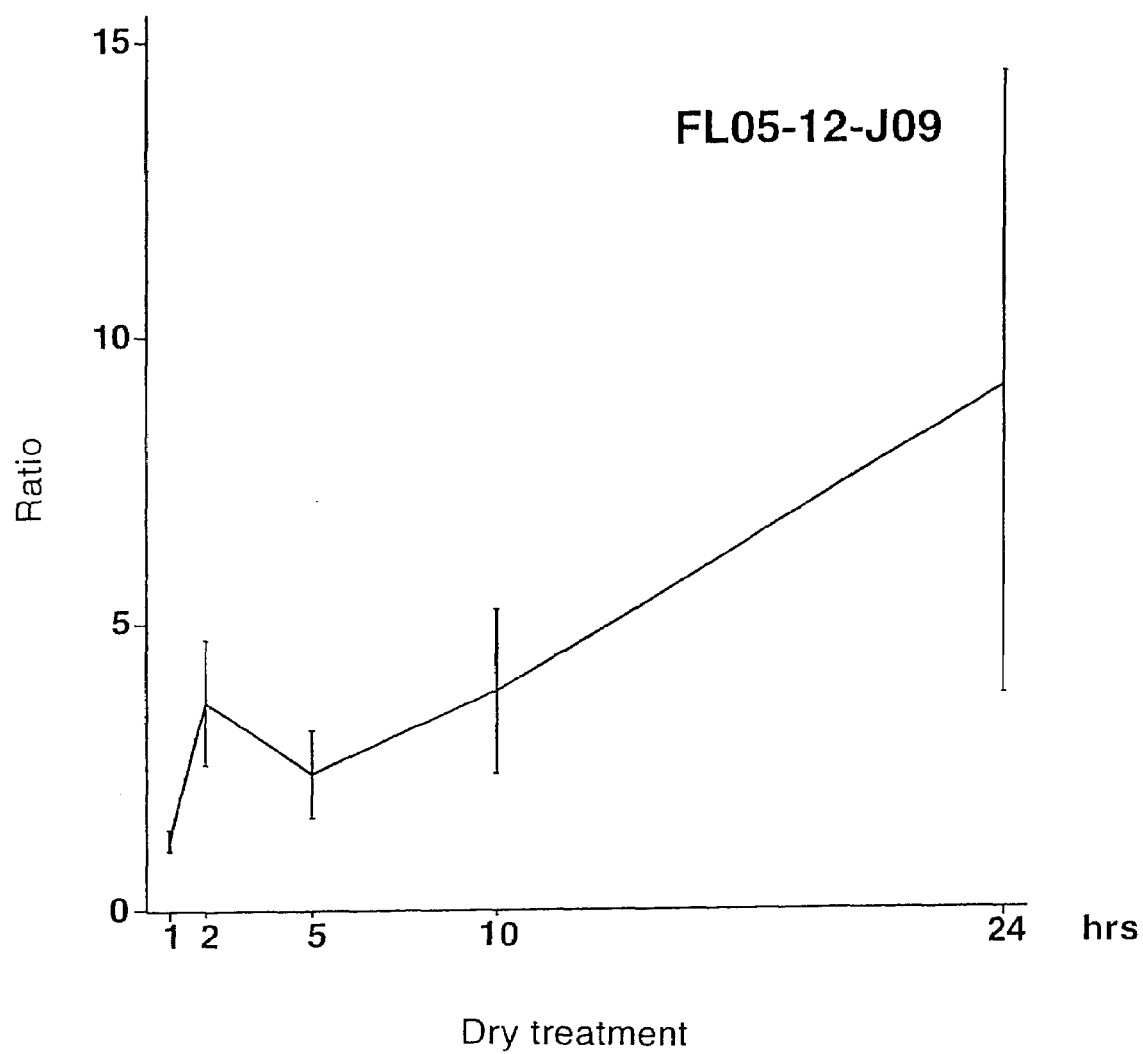
FIG. 69 is a characteristic graph showing the relationship between dehydration treatment time and expression ratio regarding FL05-12-J09.
Figure 70:
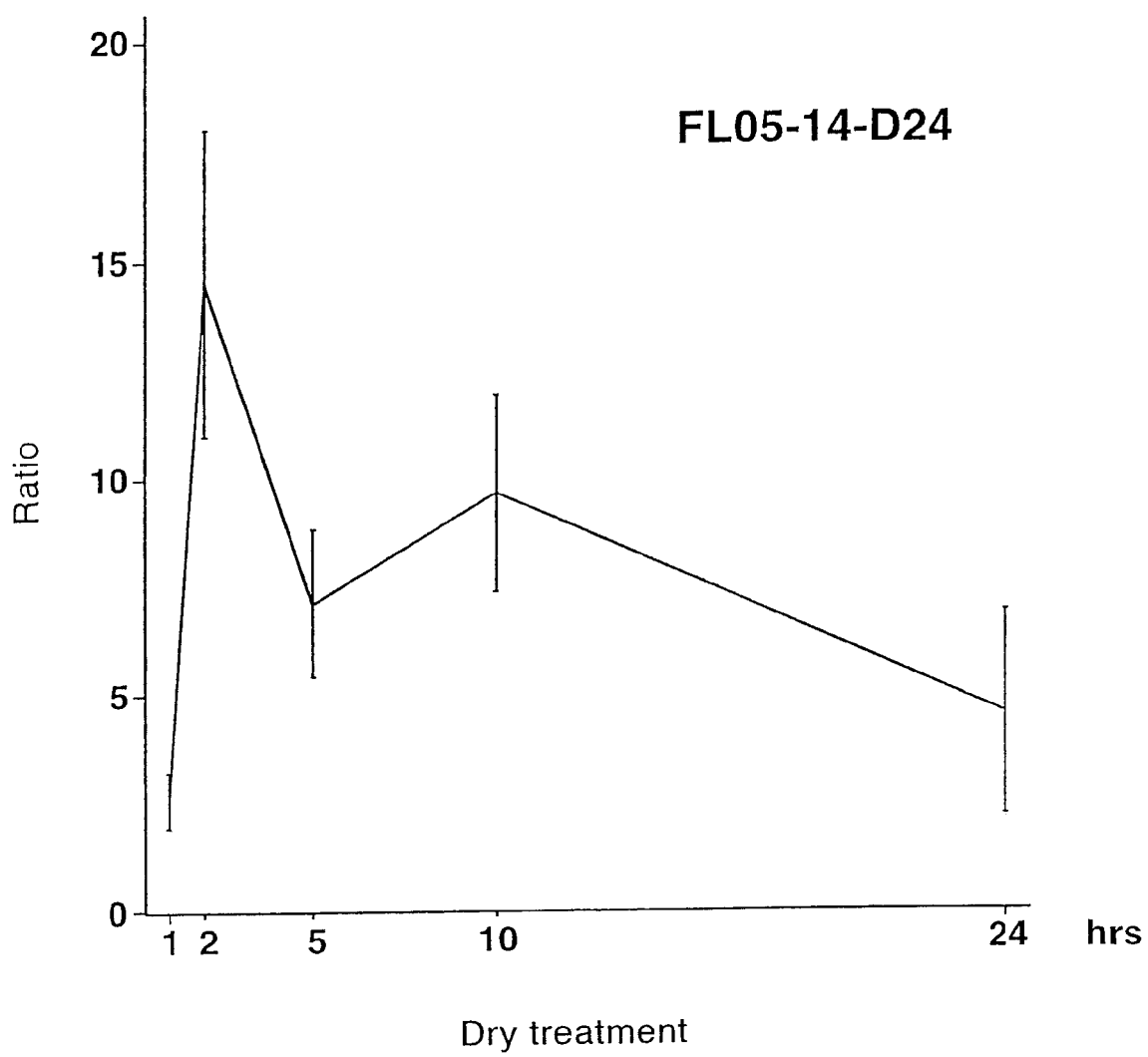
FIG. 70 is a characteristic graph showing the relationship between dehydration treatment time and expression ratio regarding FL05-14-D24.
Figure 71:
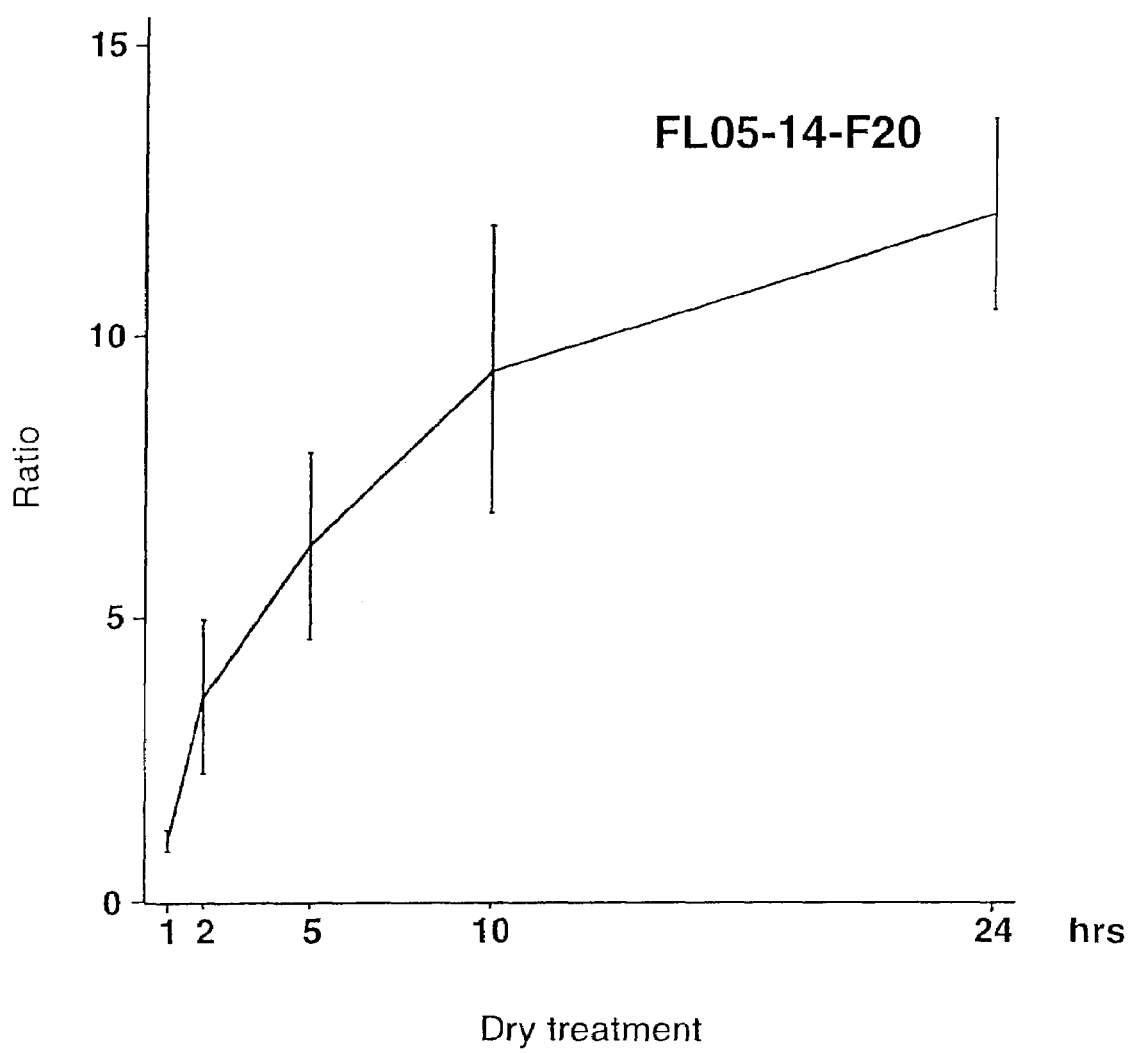
FIG. 71 is a characteristic graph showing the relationship between dehydration treatment time and expression ratio regarding FL05-14-F20.
Figure 72:
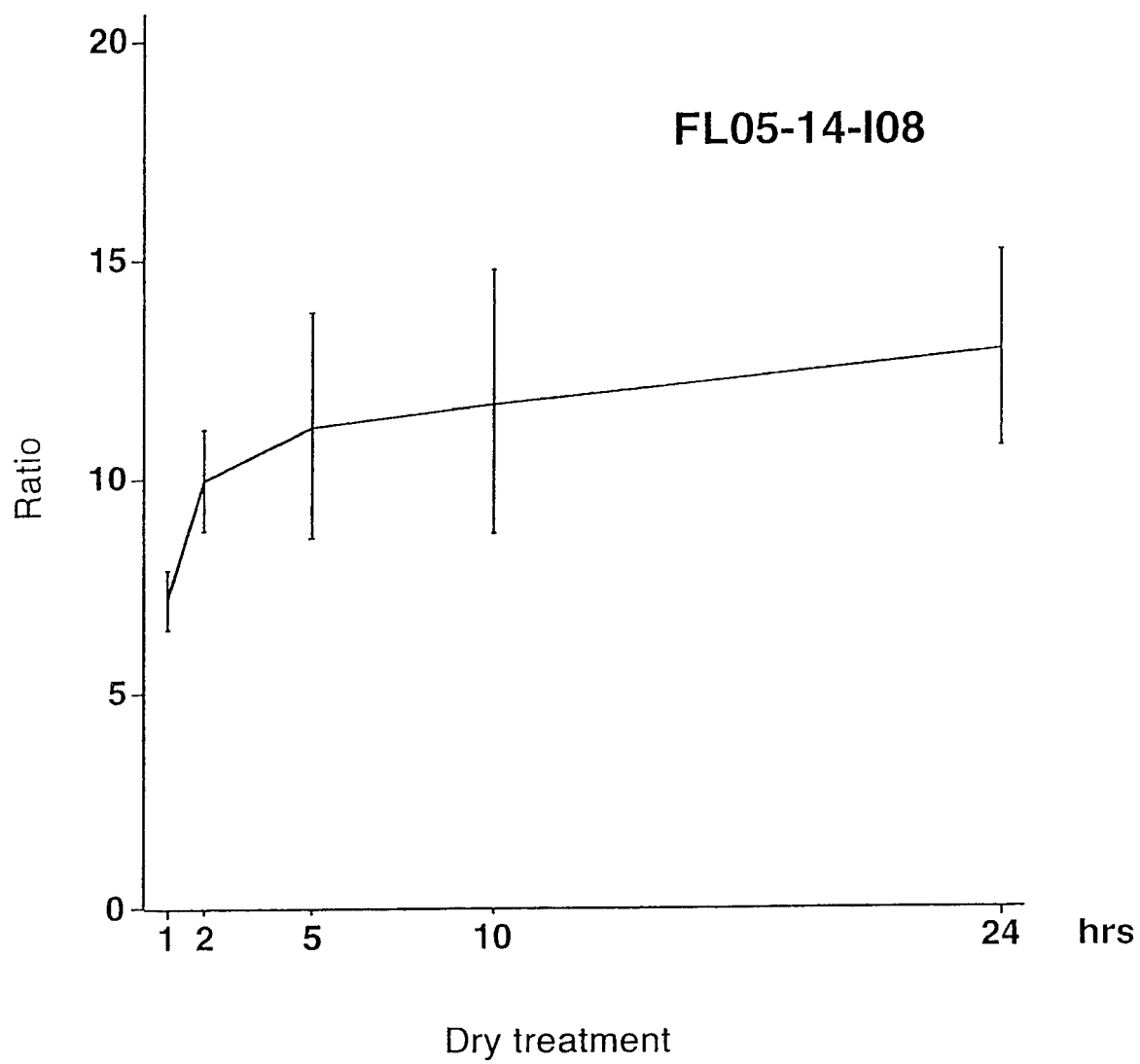
FIG. 72 is a characteristic graph showing the relationship between dehydration treatment time and expression ratio regarding FL05-14-I08.
Figure 73:
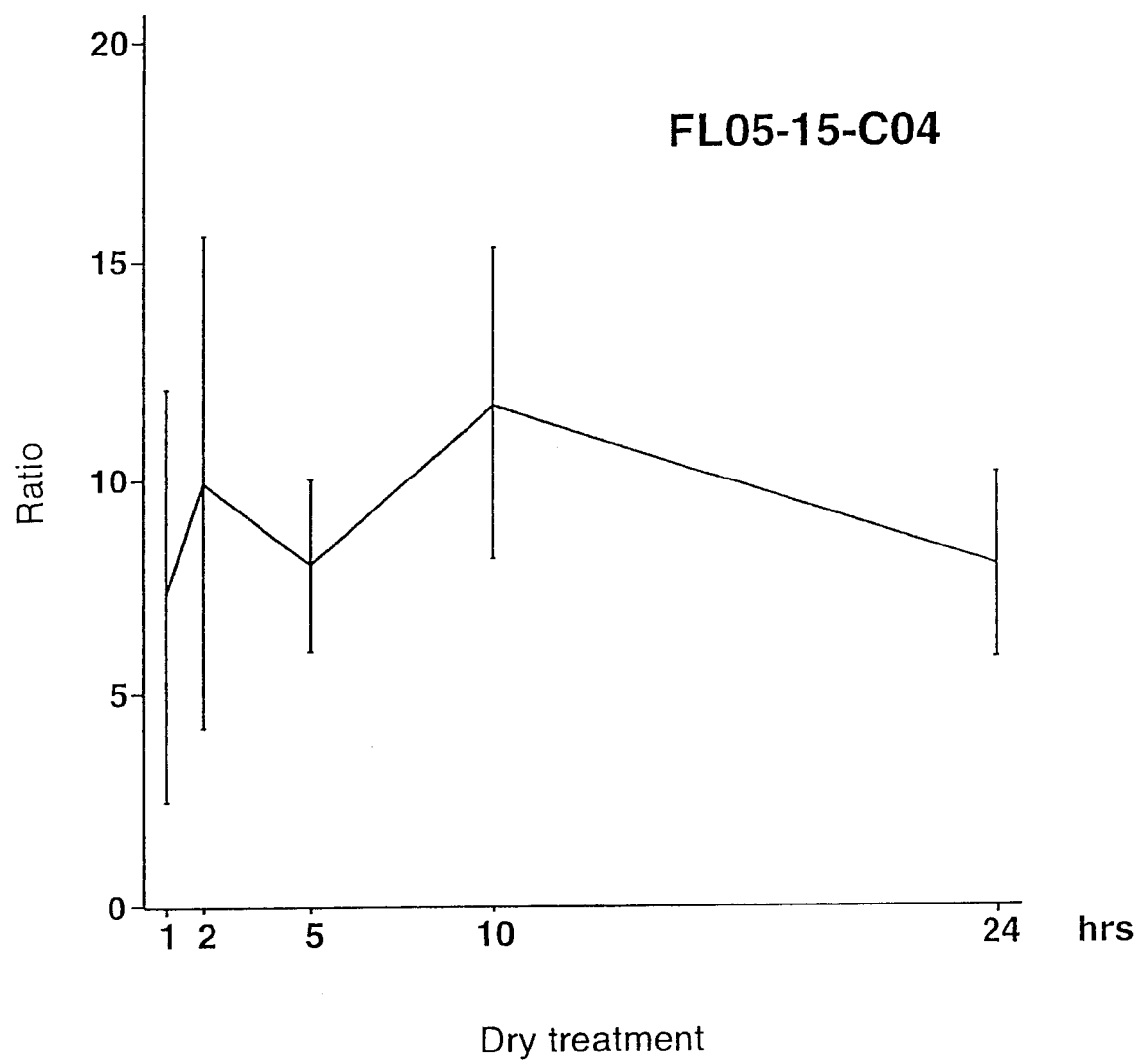
FIG. 73 is a characteristic graph showing the relationship between dehydration treatment time and expression ratio regarding FL05-15-C04.
Figure 74:
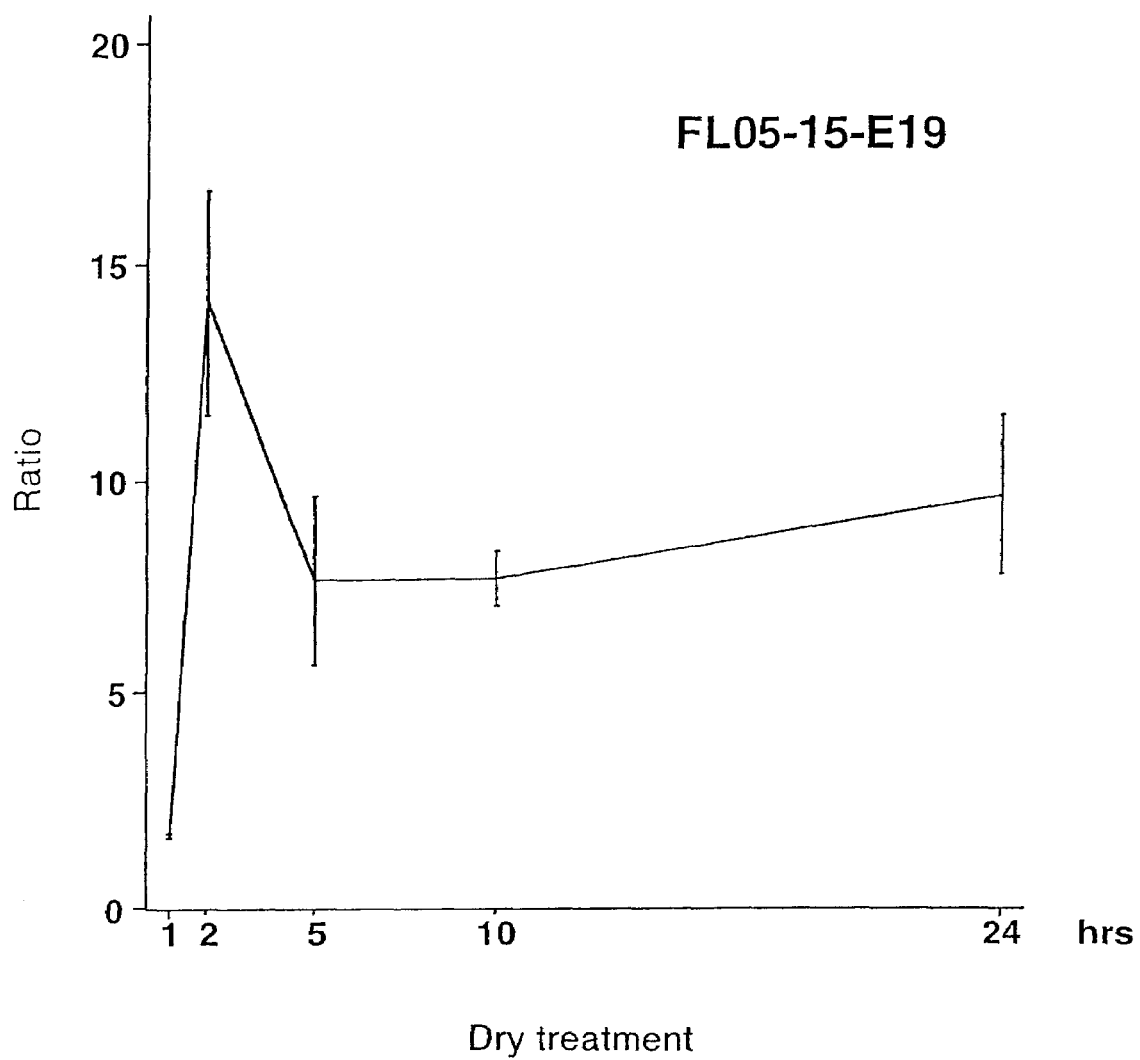
FIG. 74 is a characteristic graph showing the relationship between dehydration treatment time and expression ratio regarding FL05-15-E19.
Figure 75:
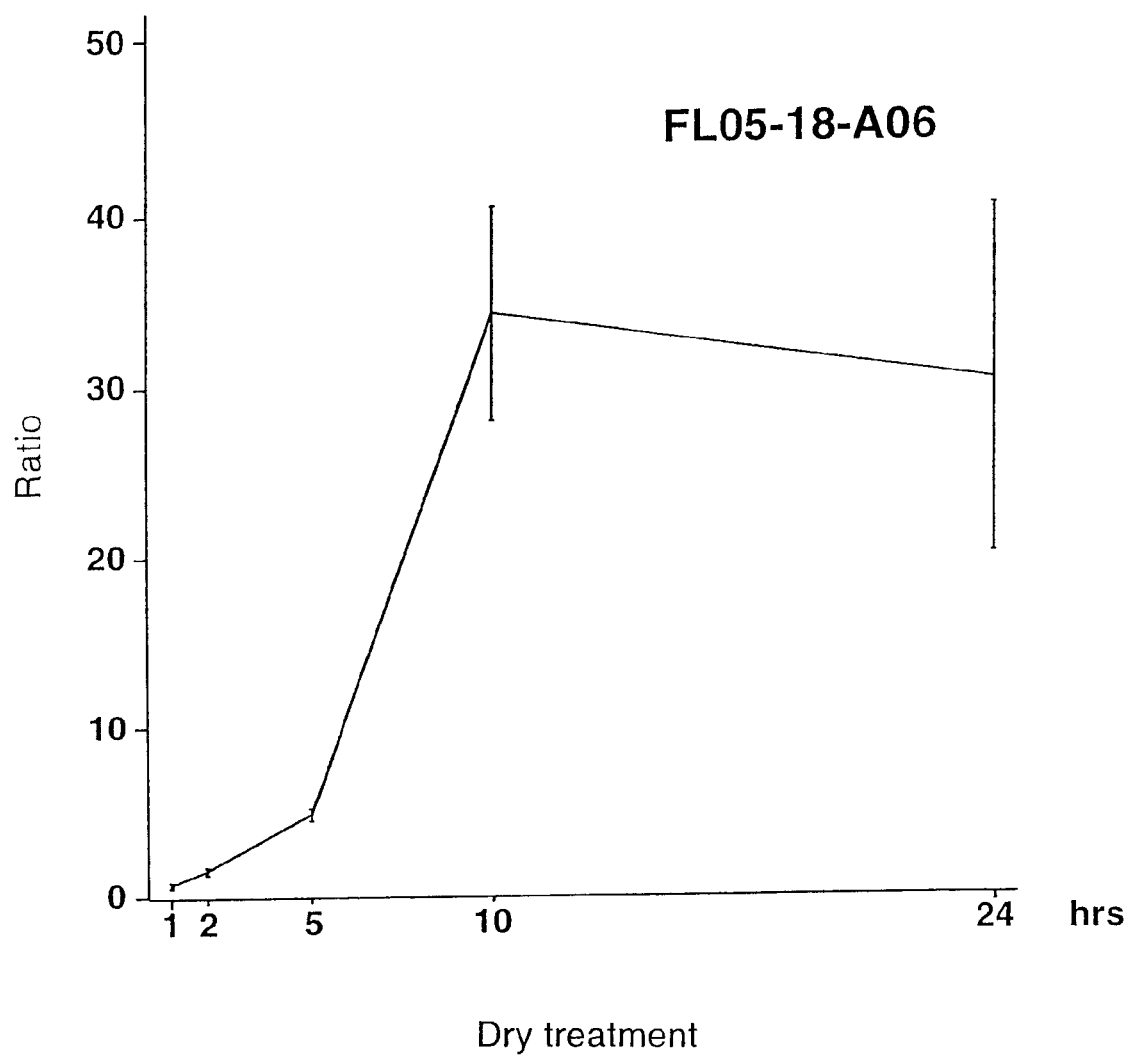
FIG. 75 is a characteristic graph showing the relationship between dehydration treatment time and expression ratio regarding FL05-18-A06.
Figure 76:
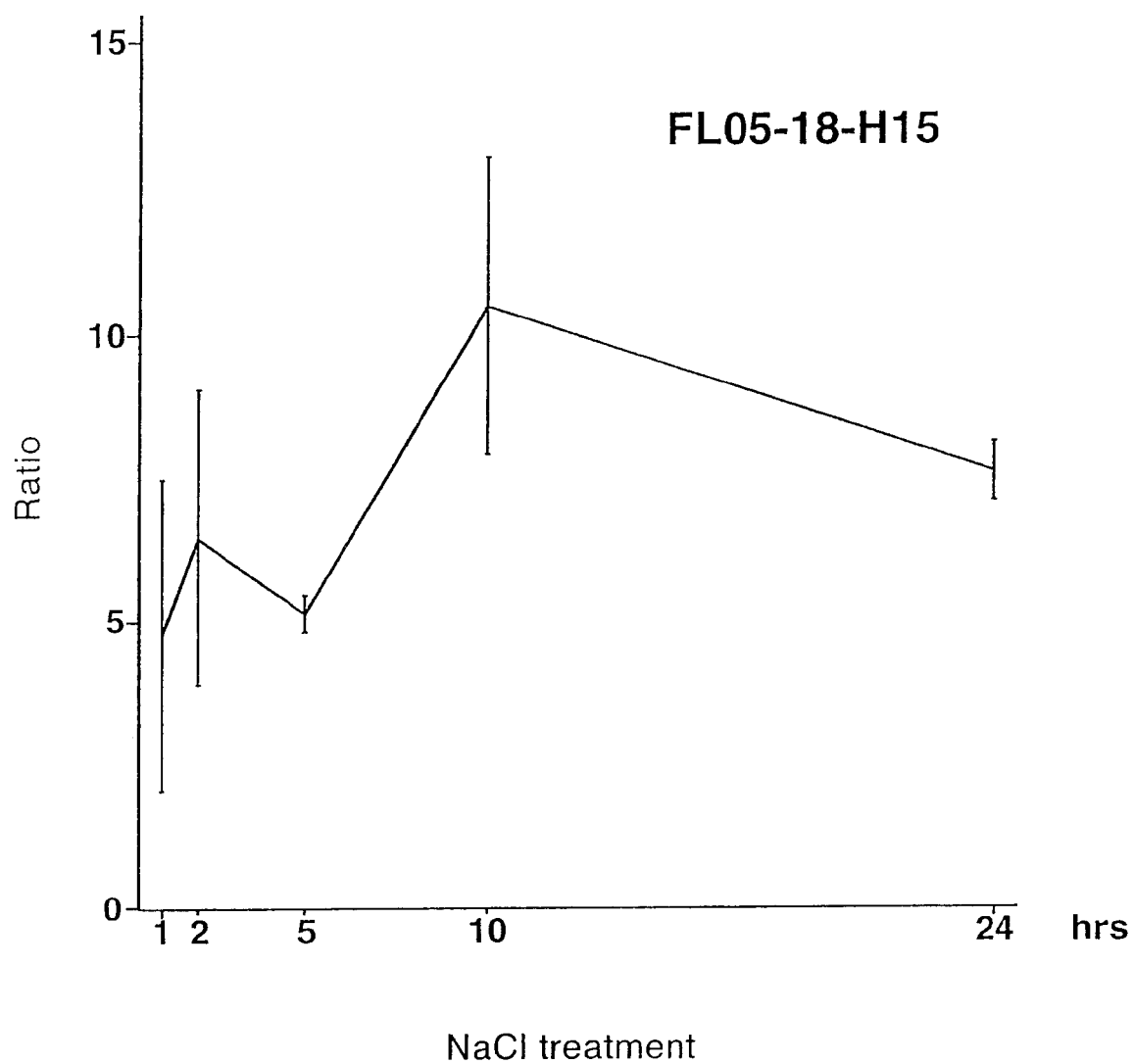
FIG. 76 is a characteristic graph showing the relationship between high salt treatment time and expression ratio regarding FL05-18-H15.
Figure 77:
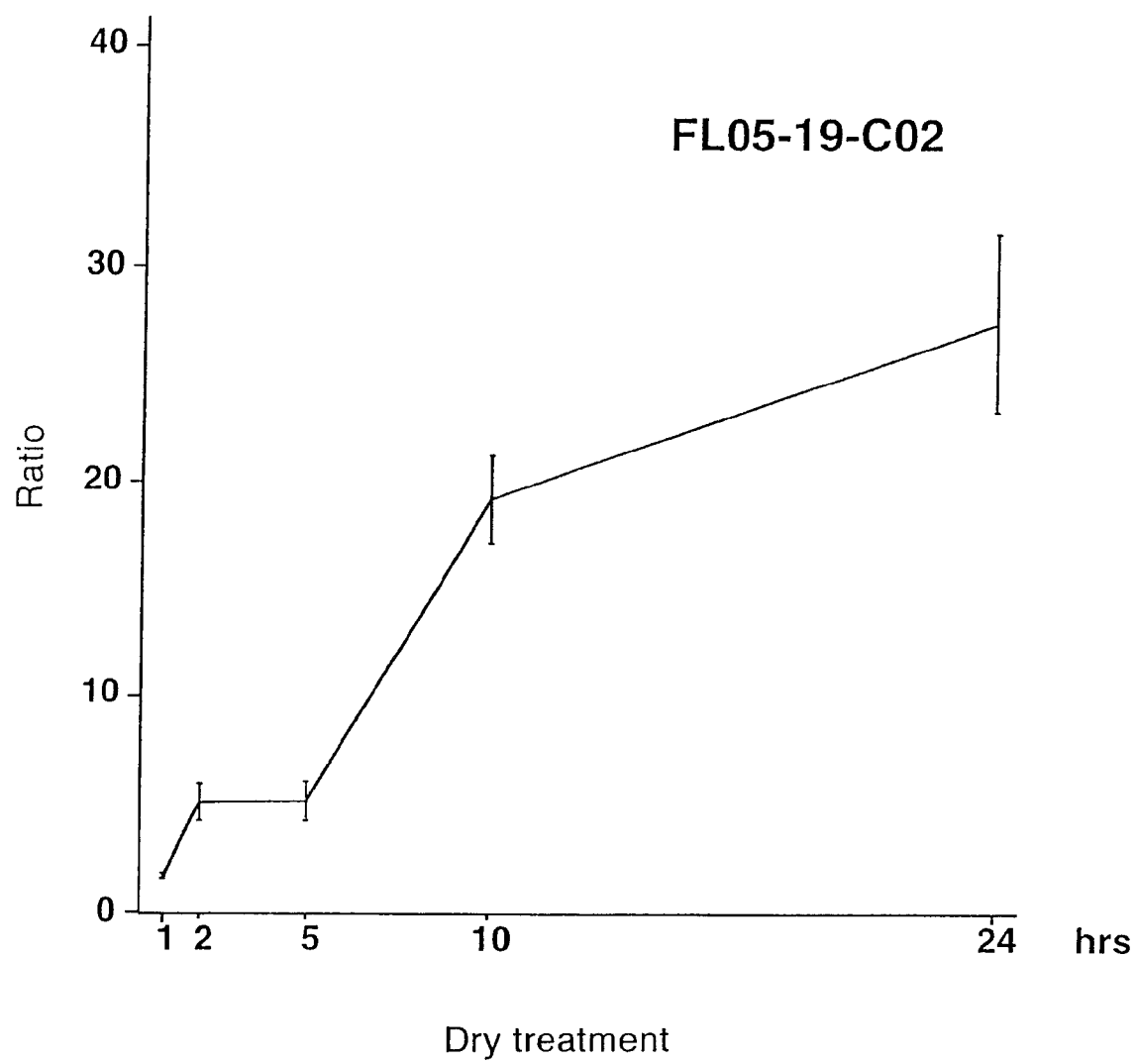
FIG. 77 is a characteristic graph showing the relationship between dehydration treatment time and expression ratio regarding FL05-19-C02.
Figure 78:
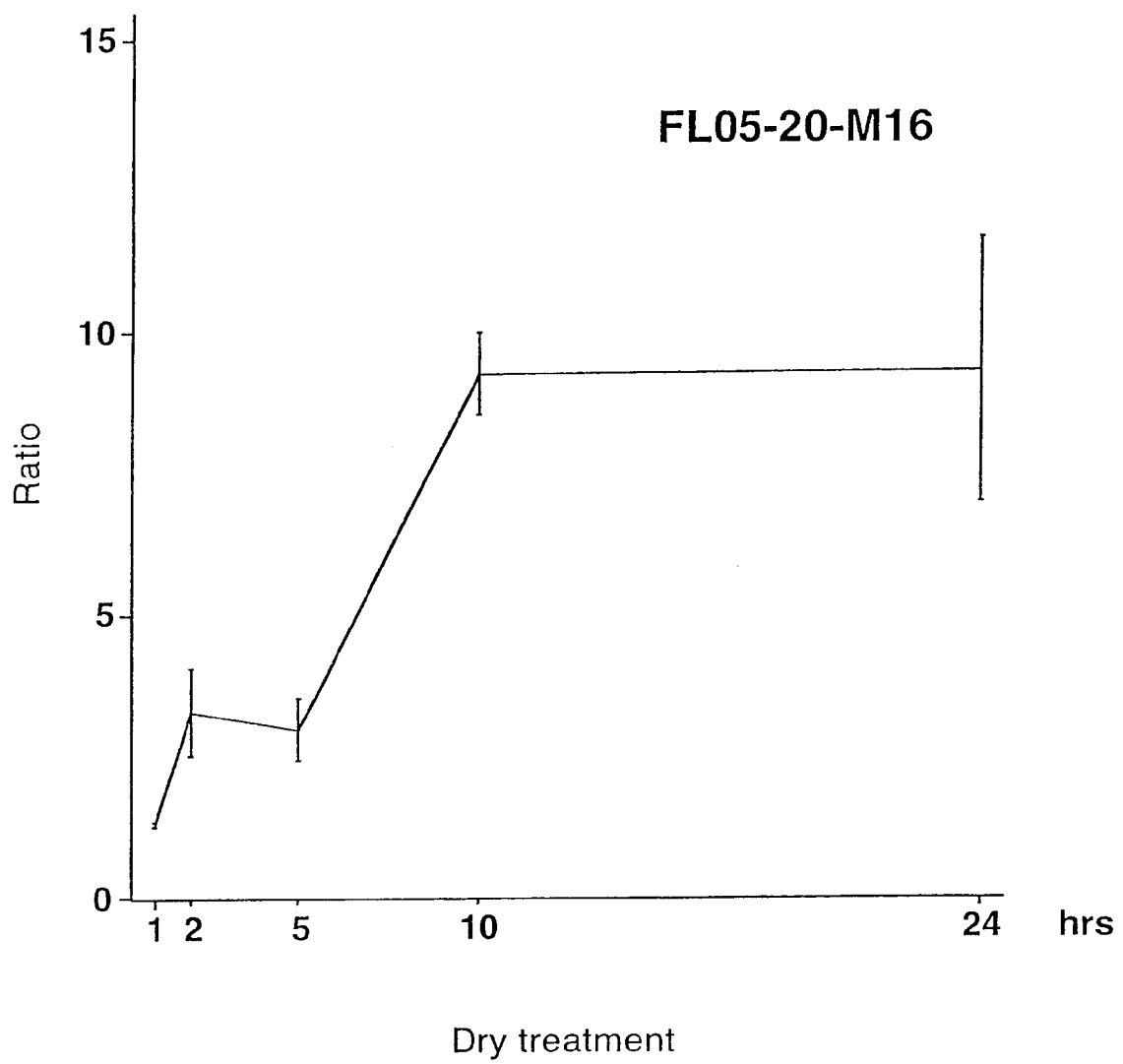
FIG. 78 is a characteristic graph showing the relationship between dehydration treatment time and expression ratio regarding FL05-20-M16.
Figure 79:
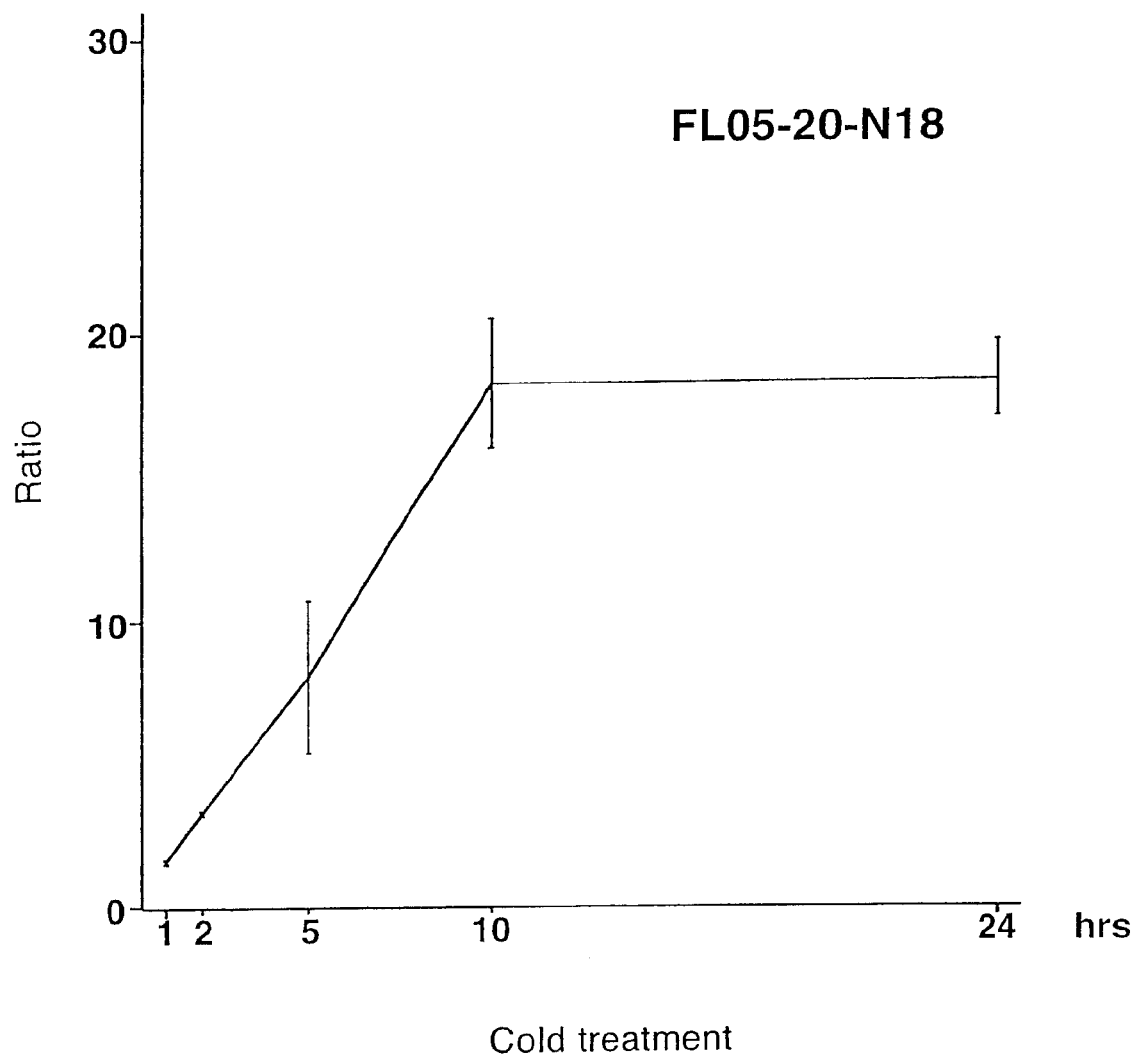
FIG. 79 is a characteristic graph showing the relationship between cold treatment time and expression ratio regarding FL05-20-N18.
Figure 80:
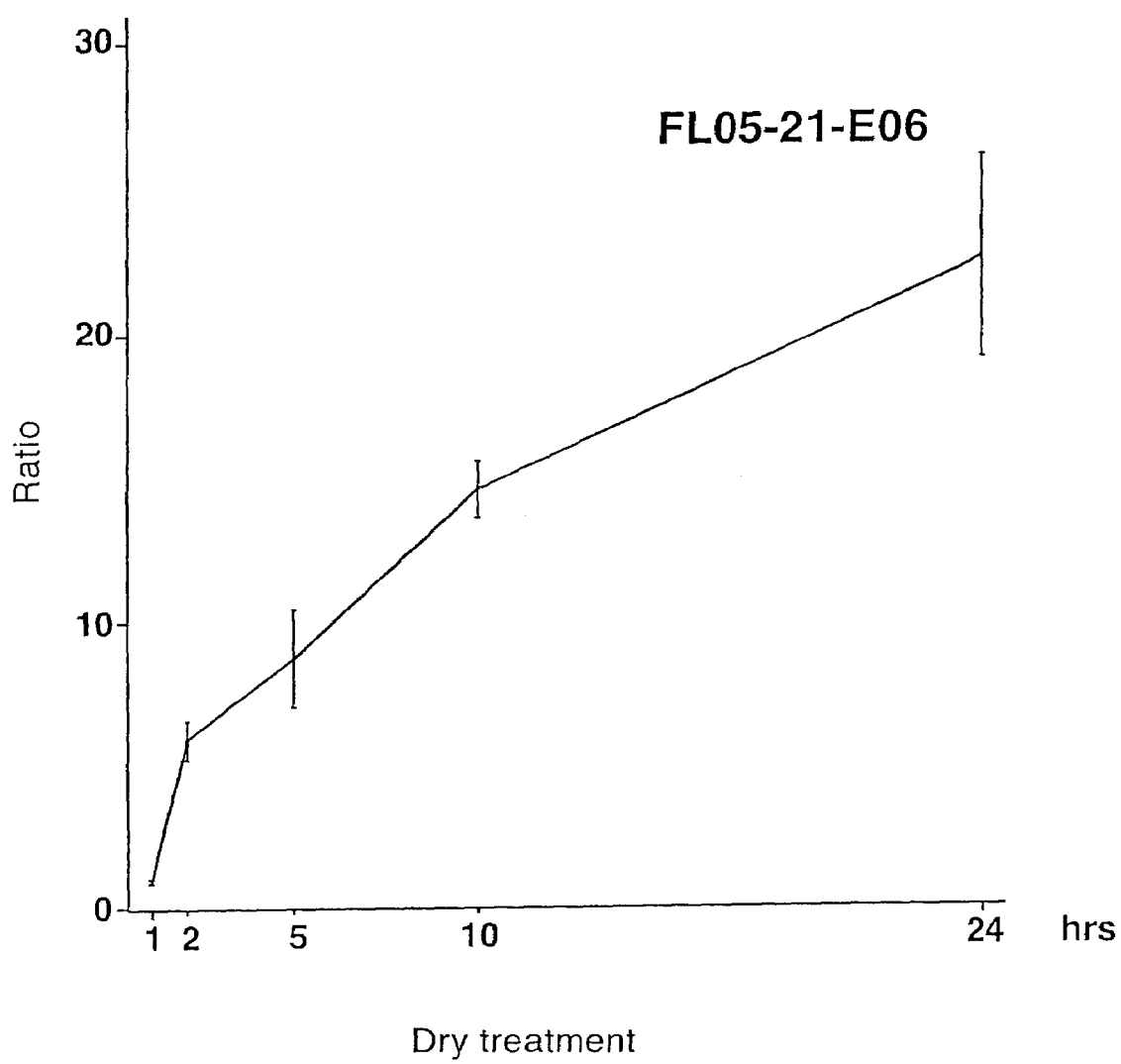
FIG. 80 is a characteristic graph showing the relationship between dehydration treatment time and expression ratio regarding FL05-21-E06.
Figure 81:
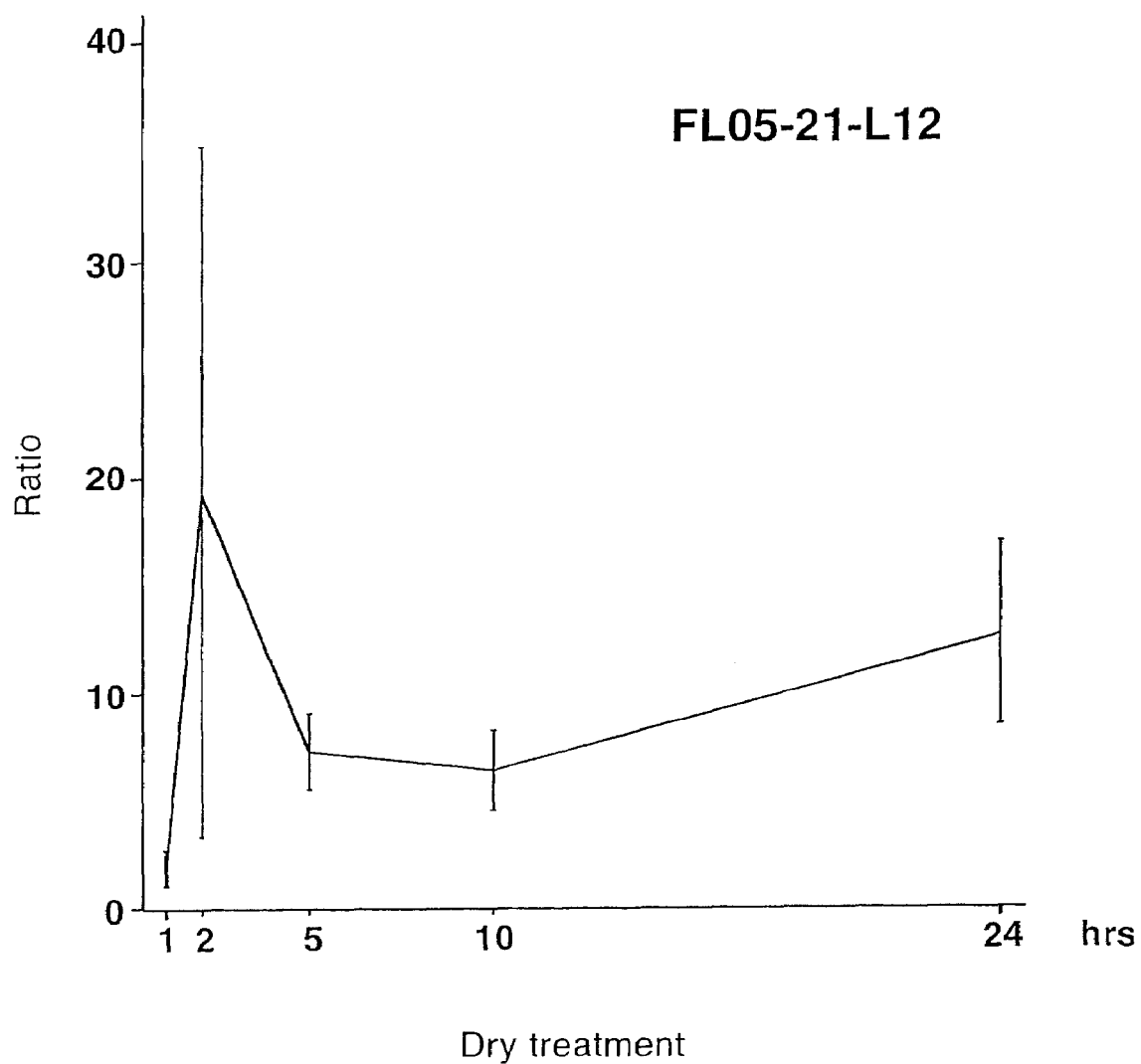
FIG. 81 is a characteristic graph showing the relationship between dehydration treatment time and expression ratio regarding FL05-21-L12.
Figure 82:
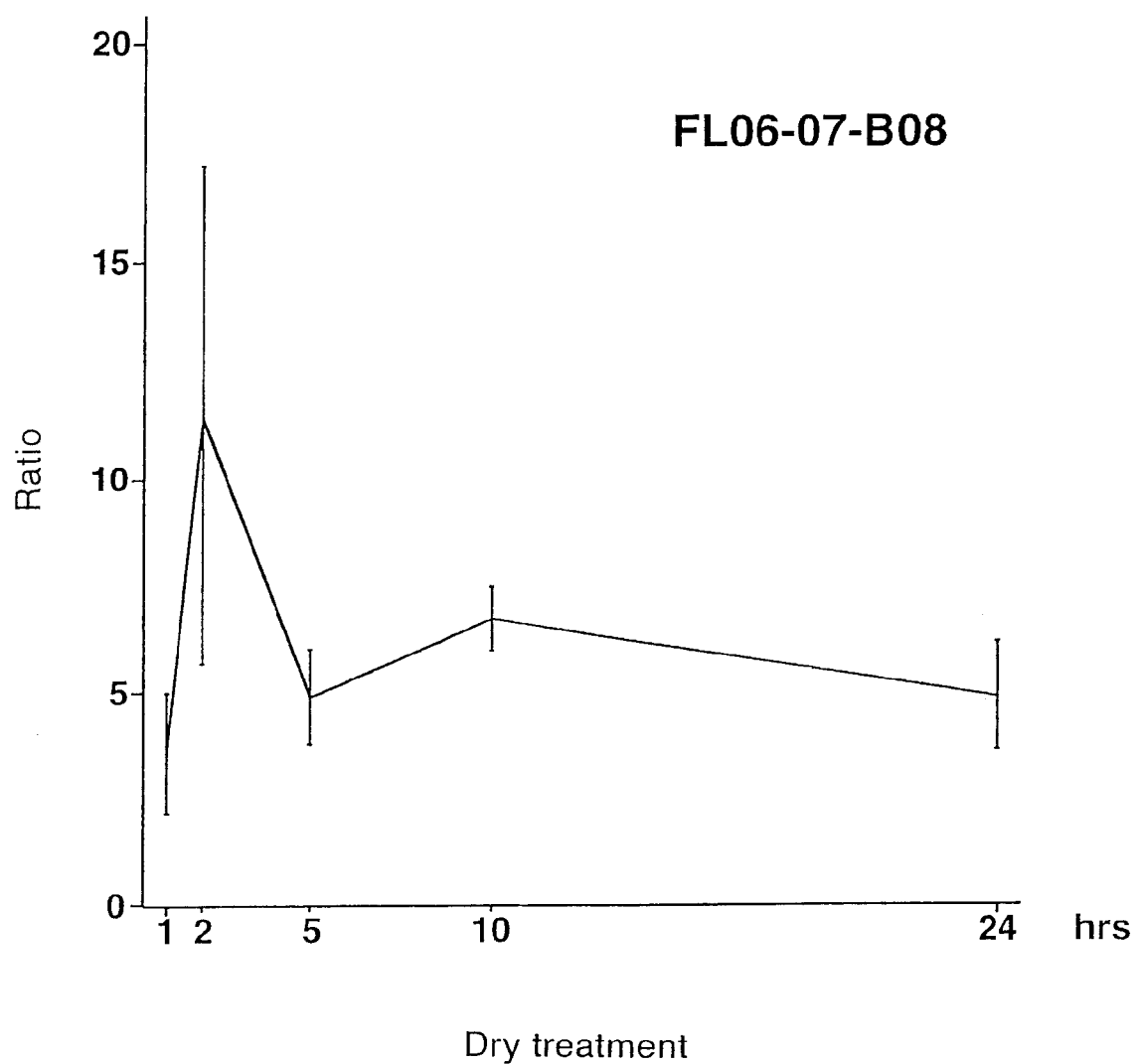
FIG. 82 is a characteristic graph showing the relationship between dehydration treatment time and expression ratio regarding FL06-07-B08.
Figure 83:
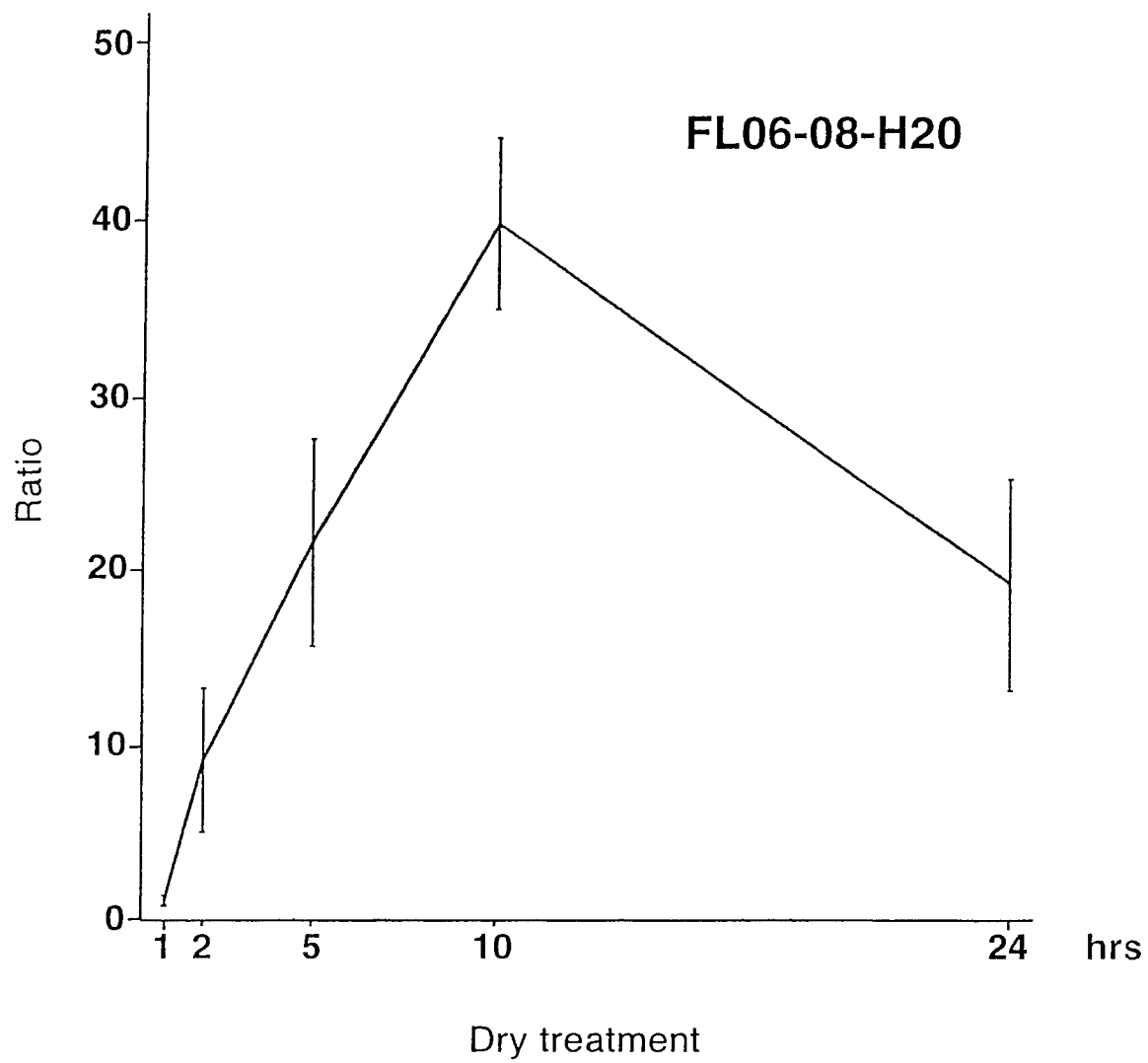
FIG. 83 is a characteristic graph showing the relationship between dehydration treatment time and expression ratio regarding FL06-08-H20.
Figure 84:
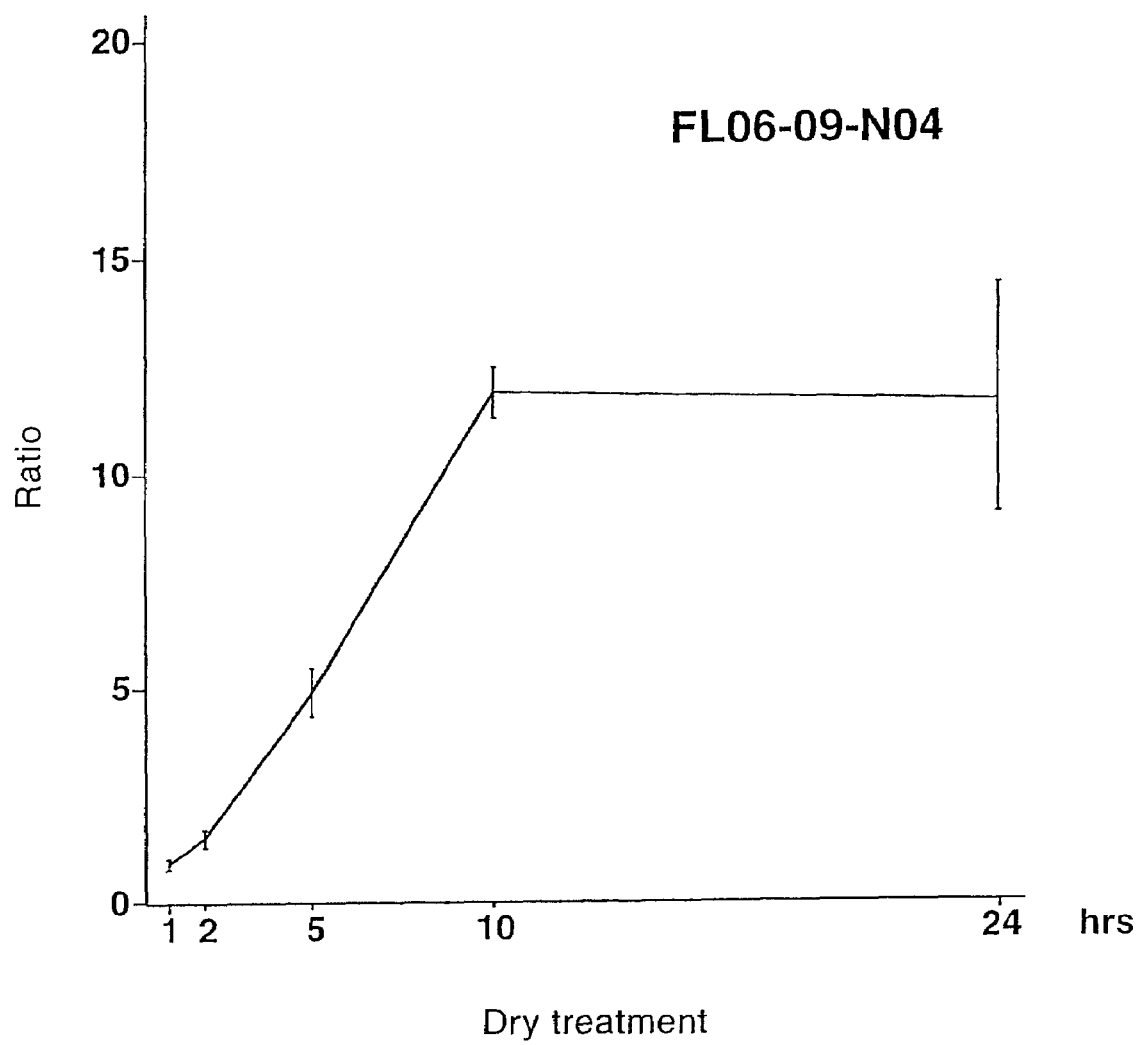
FIG. 84 is a characteristic graph showing the relationship between dehydration treatment time and expression ratio regarding FL06-09-N04.

| Name of gene | Type of applied stress | Drawing |
|---|---|---|
| FL03-07-F12 | Dehydration | FIG. 1 |
| FL04-12-F24 | Exposure to cold | FIG. 2 |
| FL04-14-N10 | Dehydration | FIG. 3 |
| FL04-14-P24 | Dehydration | FIG. 4 |
| FL04-17-I03 | Dehydration, Exposure to a high level salt solution | FIGS. 5, 6 |
| FL04-17-M08 | Exposure to a high level salt solution | FIG. 7 |
| FL04-17-M22 | Dehydration | FIG. 8 |
| FL05-05-A17 | Dehydration | FIG. 9 |
| FL05-05-F20 | Dehydration | FIG. 10 |
| FL05-05-G20 | Dehydration | FIG. 11 |
| FL05-09-N09 | Dehydration | FIG. 12 |
| FL05-10-J09 | Dehydration, Exposure to a high level salt solution | FIGS. 13, 14 |
| FL05-10-M08 | Exposure to a high level salt solution | FIG. 15 |
| FL05-11-H09 | Exposure to a high level salt solution | FIG. 16 |
| FL05-12-H13 | Dehydration, Exposure to a high level salt solution | FIGS. 17, 18 |
| FL05-13-I20 | ABA treatment | FIG. 19 |
| FL05-14-E15 | Dehydration | FIG. 20 |
| FL05-14-E16 | Dehydration, Exposure to cold, ABA treatment | FIGS. 21-23 |
| FL05-16-F03 | Dehydration, ABA treatment | FIGS. 24, 25 |
| FL05-16-H23 | Dehydration, Exposure to a high level salt solution | FIGS. 26, 27 |
| FL05-18-M07 | Dehydration, ABA treatment | FIGS. 28, 29 |
| FL05-18-O21 | ABA treatment | FIG. 30 |
| FL05-19-F21 | Dehydration, ABA treatment | FIGS. 31, 32 |
| FL05-19-O22 | Dehydration, Exposure to a high level salt solution, ABA treatment | FIGS. 33-35 |
| FL05-21-K17 | Exposure to a high level salt solution | FIG. 36 |
| FL06-10-F03 | ABA treatment | FIG. 37 |
| FL06-12-H12 | Dehydration, Exposure to a high level salt solution | FIGS. 38, 39 |
| FL07-12-I23 | Exposure to a high level salt solution | FIG. 40 |
| FL08-08-H23 | Exposure to a high level salt solution | FIG. 41 |
| FL08-08-O14 | Dehydration | FIG. 42 |
| FL08-09-M05 | Dehydration | FIG. 43 |
| FL08-10-K08 | Exposure to a high level salt solution | FIG. 44 |
| FL08-11-P07 | Dehydration Exposure to cold | FIGS. 45, 46 |
| FL08-13-F10 | Dehydration, Exposure to a high level salt solution, ABA treatment | FIGS. 47-49 |
| FL08-19-D04 | Dehydration | FIG. 50 |
| FL08-19-G15 | Exposure to a high level salt solution | FIG. 51 |
| FL09-06-B11 | ABA treatment | FIG. 52 |
| FL09-07-G17 | ABA treatment | FIG. 53 |
| FL09-10-A12 | ABA treatment | FIG. 54 |
| FL09-13-P15 | Dehydration | FIG. 55 |
| FL02-05-I05 | Exposure to a high level salt solution | FIG. 56 |
| FL04-12-N15 | Exposure to cold | FIG. 57 |
| FL04-16-P21 | Dehydration | FIG. 58 |
| FL04-17-N22 | Exposure to a high level salt solution | FIG. 59 |
| FL04-20-P19 | Dehydration | FIG. 60 |
| FL02-09-H01 | Dehydration | FIG. 61 |
| FL05-01-D08 | Dehydration | FIG. 62 |
| FL05-02-G08 | Exposure to a high level salt solution | FIG. 63 |
| FL05-02-O17 | Dehydration | FIG. 64 |
| FL05-07-L13 | Exposure to a high level salt solution | FIG. 65 |
| FL05-08-B14 | Dehydration | FIG. 66 |
| FL05-09-N10 | Dehydration | FIG. 67 |
| FL05-11-L01 | Dehydration | FIG. 68 |
| FL05-12-J09 | Dehydration | FIG. 69 |
| FL05-14-D24 | Dehydration | FIG. 70 |
| FL05-14-F20 | Dehydration | FIG. 71 |
| FL05-14-I08 | Dehydration | FIG. 72 |
| FL05-15-C04 | Dehydration | FIG. 73 |
| FL05-15-E19 | Dehydration | FIG. 74 |
| FL05-18-A06 | Dehydration | FIG. 75 |
| FL05-18-H15 | Exposure to a high level salt solution | FIG. 76 |
| FL05-19-C02 | Dehydration | FIG. 77 |
| FL05-20-M16 | Dehydration | FIG. 78 |
| FL05-20-N18 | Exposure to cold | FIG. 79 |
| FL05-21-E06 | Dehydration | FIG. 80 |
| FL05-21-L12 | Dehydration | FIG. 81 |
| FL06-07-B08 | Dehydration | FIG. 82 |
| FL06-08-H20 | Dehydration | FIG. 83 |
| FL06-09-N04 | Dehydration | FIG. 84 |

TABLE 4-continued

Figure 85:
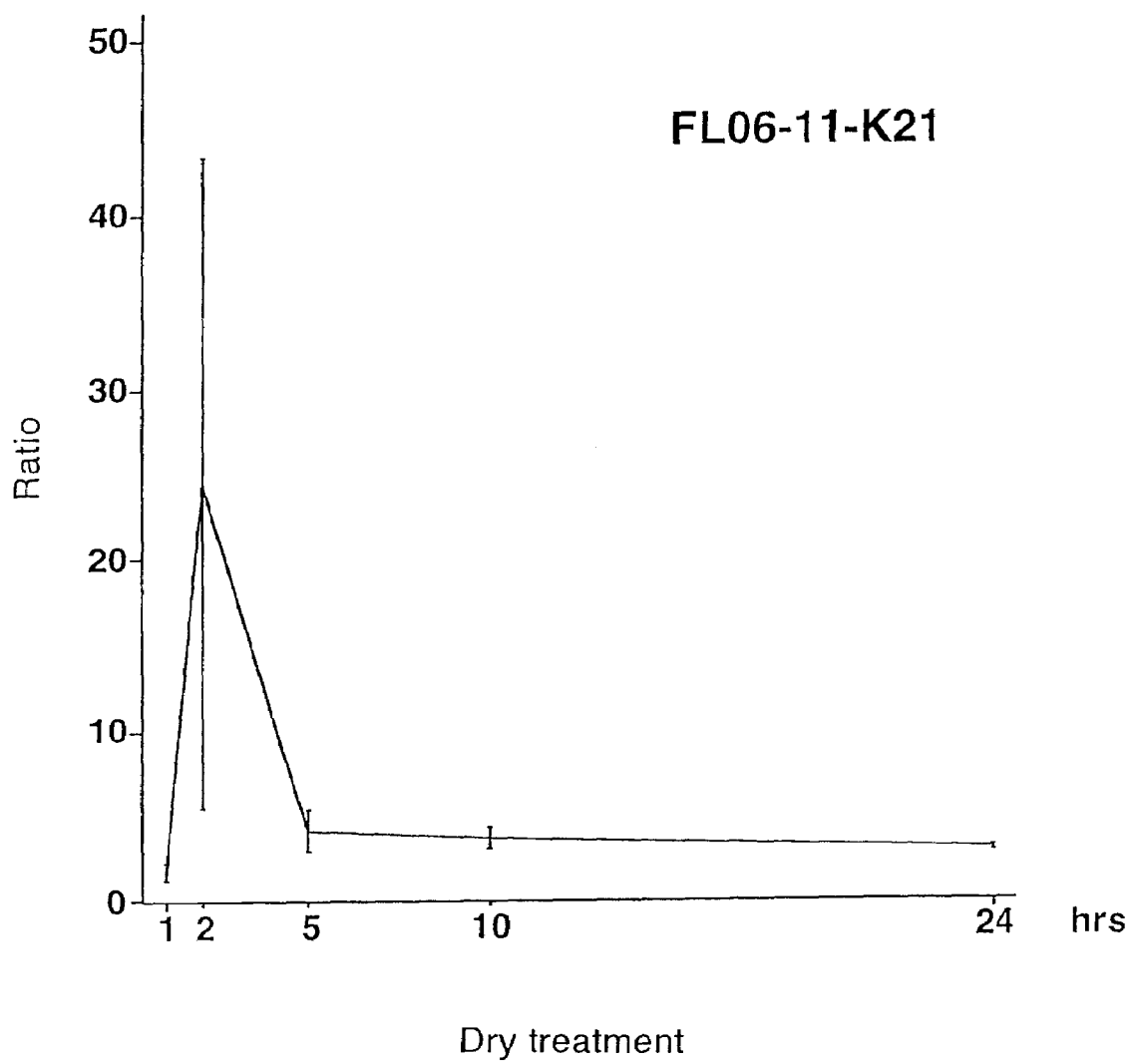
FIG. 85 is a characteristic graph showing the relationship between dehydration treatment time and expression ratio regarding FL06-11-K21.
Figure 86:
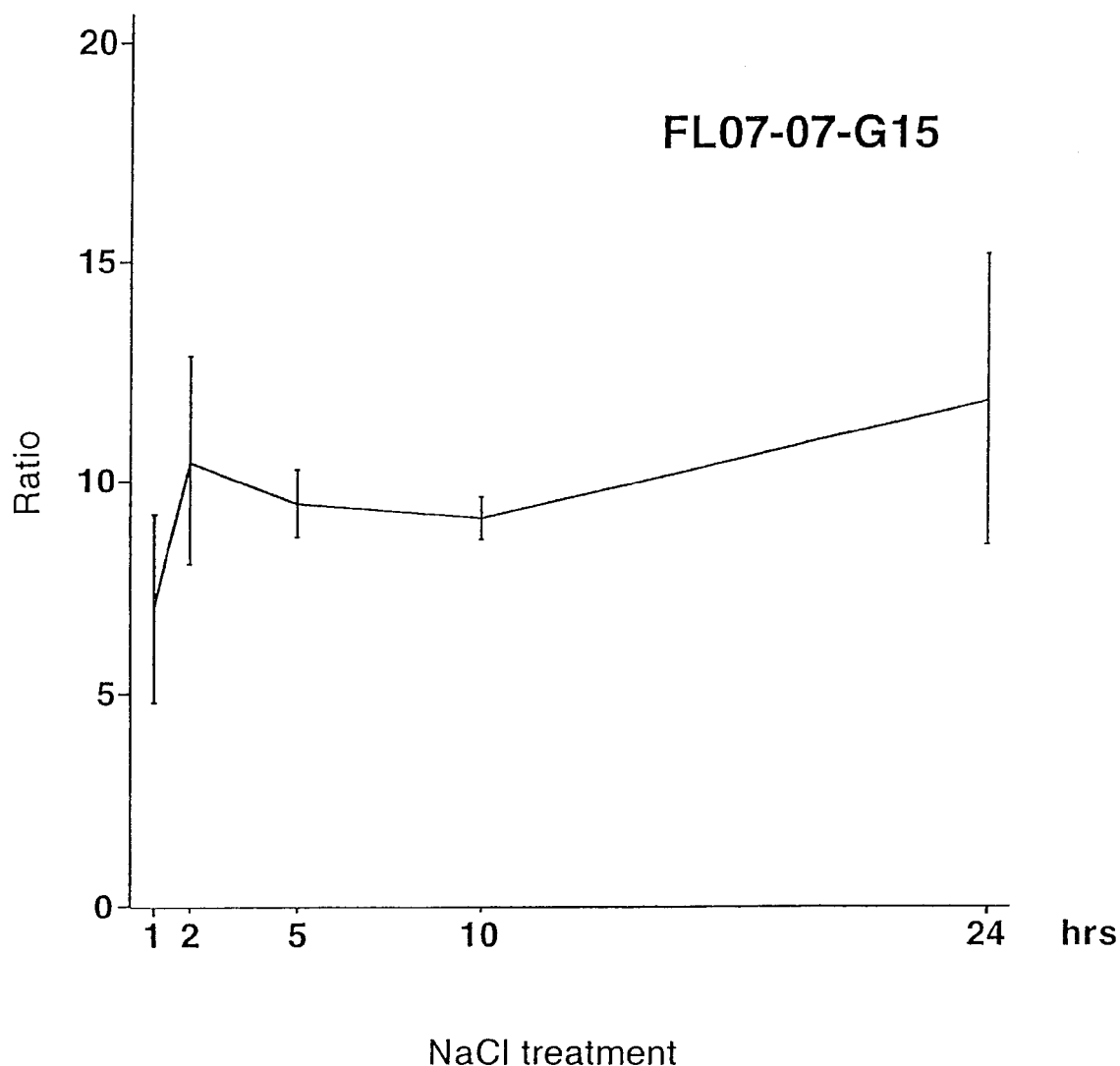
FIG. 86 is a characteristic graph showing the relationship between high salt treatment time and expression ratio regarding FL07-07-G15.
Figure 87:
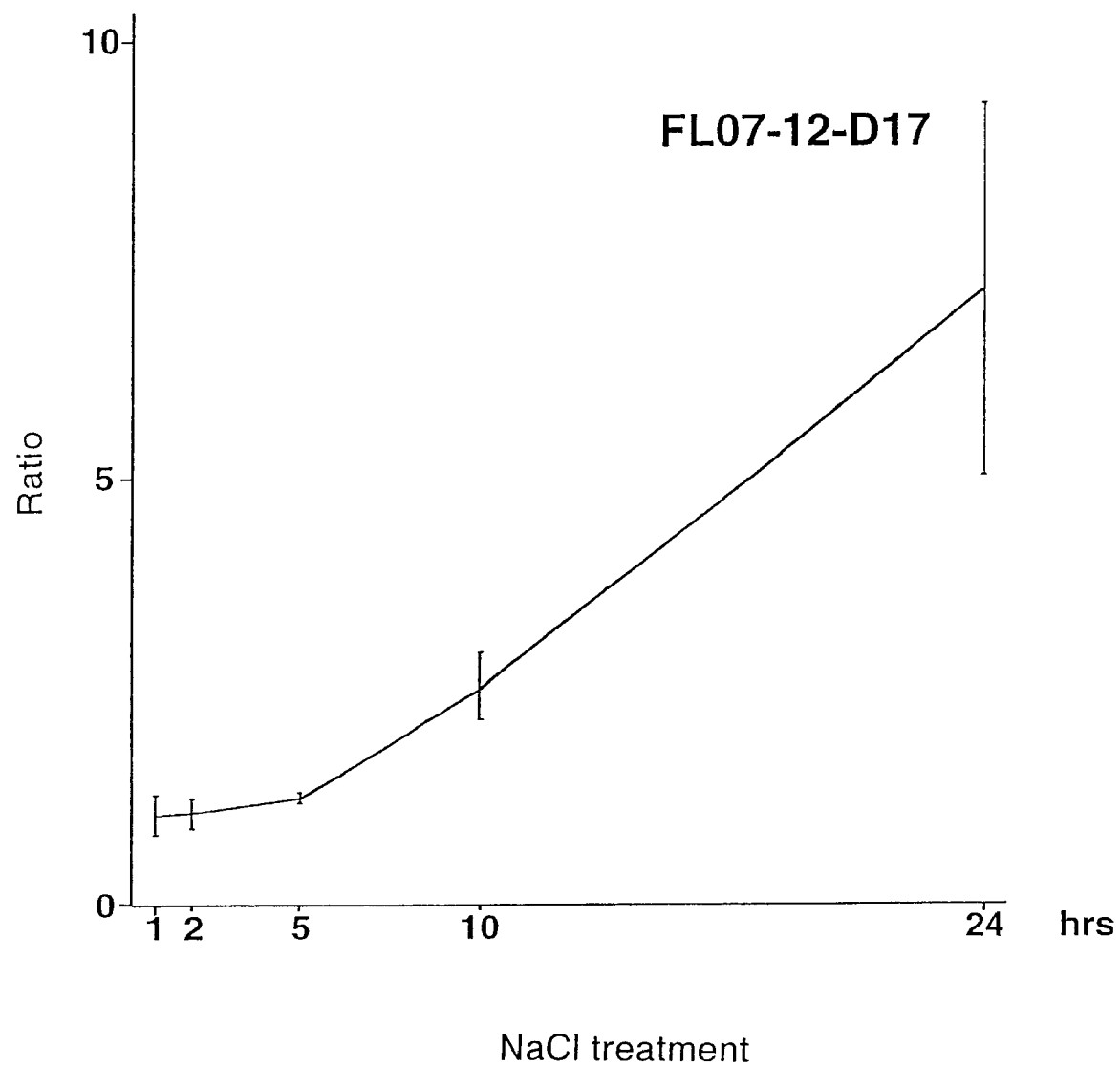
FIG. 87 is a characteristic graph showing the relationship between high salt treatment time and expression ratio regarding FL07-12-D17.
Figure 88:
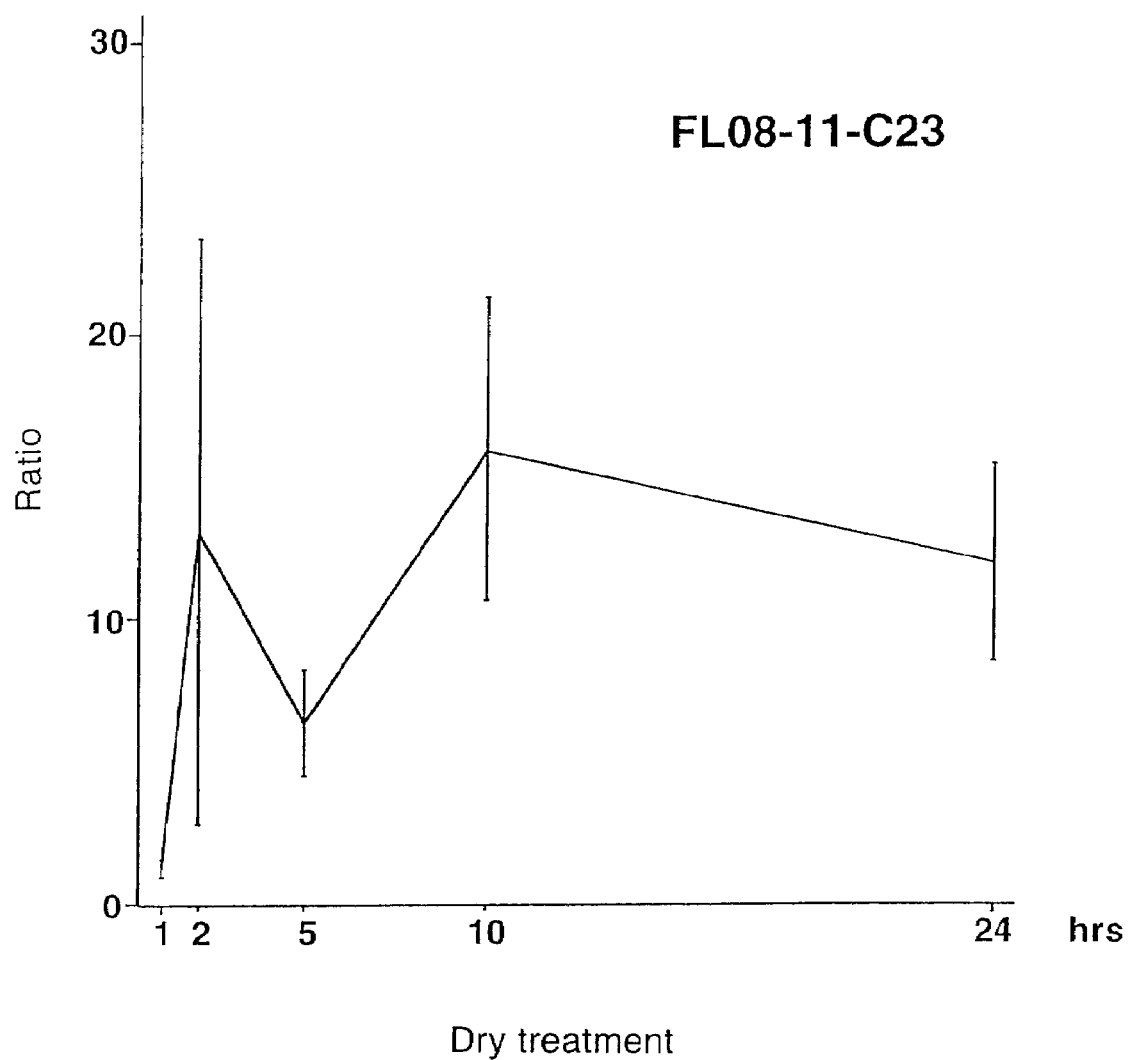
FIG. 88 is a characteristic graph showing the relationship between dehydration treatment time and expression ratio regarding FL08-11-C23.
Figure 89:
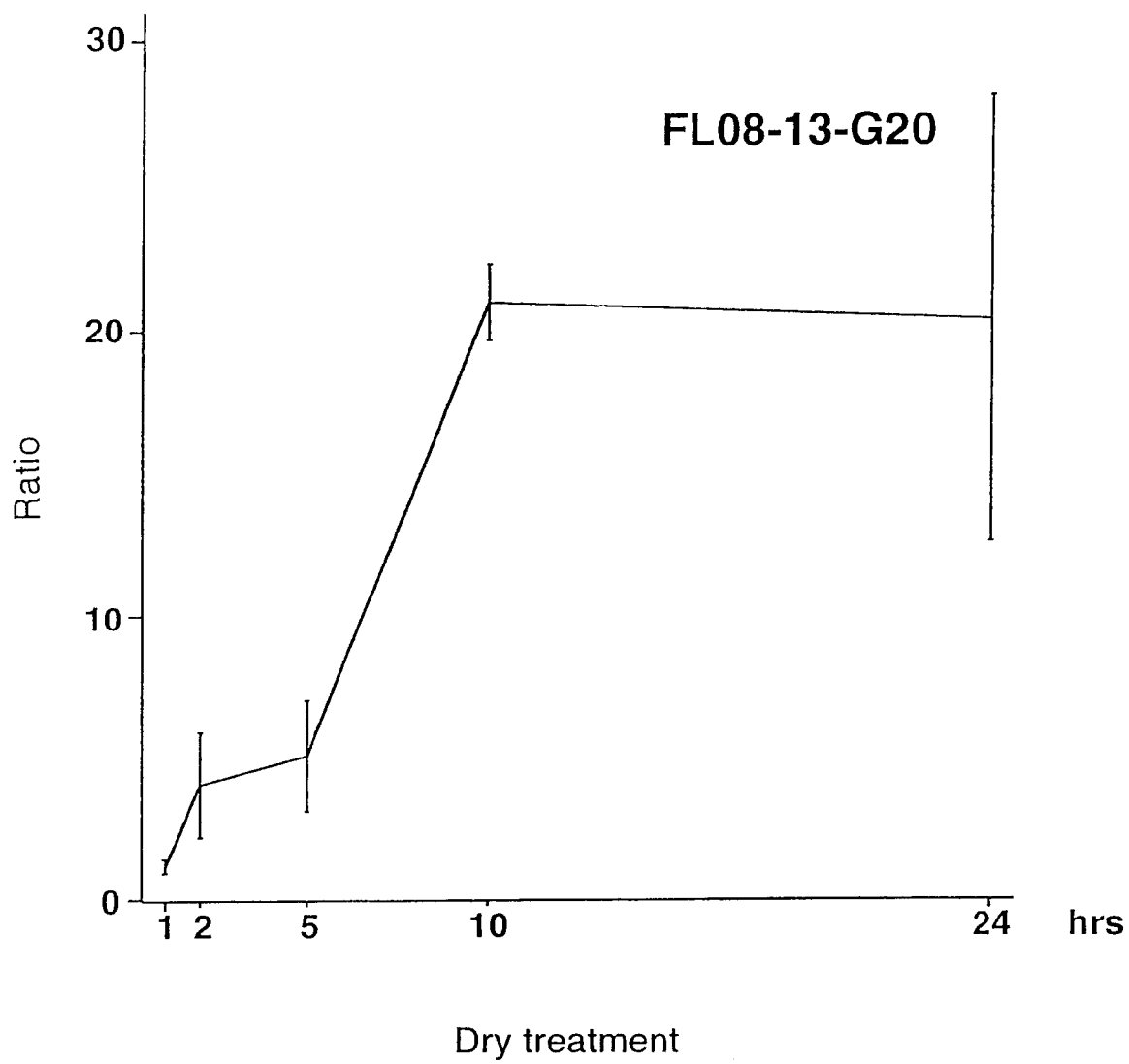
FIG. 89 is a characteristic graph showing the relationship between dehydration treatment time and expression ratio regarding FL08-13-G20.
Figure 90:
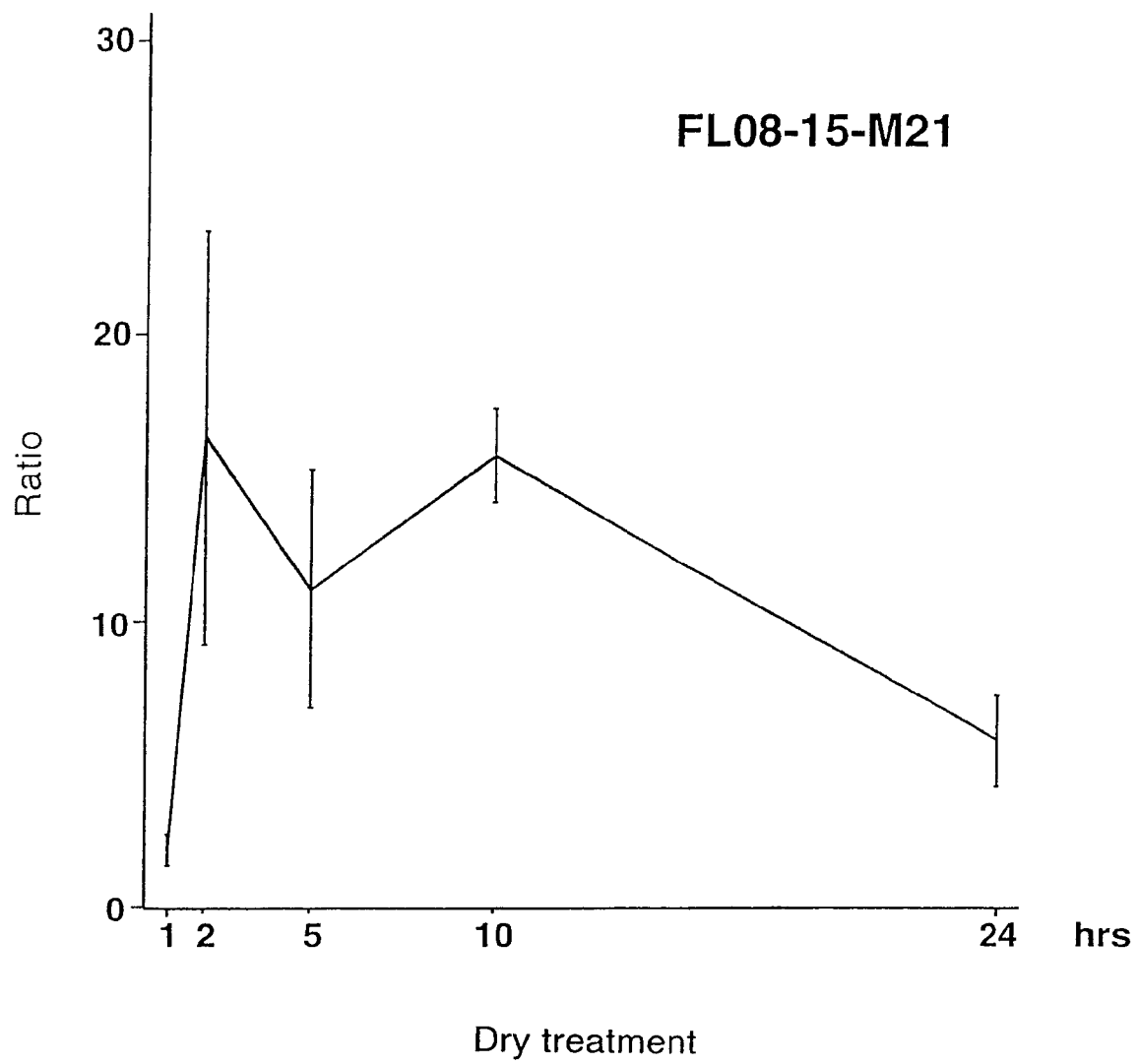
FIG. 90 is a characteristic graph showing the relationship between dehydration treatment time and expression ratio regarding FL08-15-M21.
Figure 91:
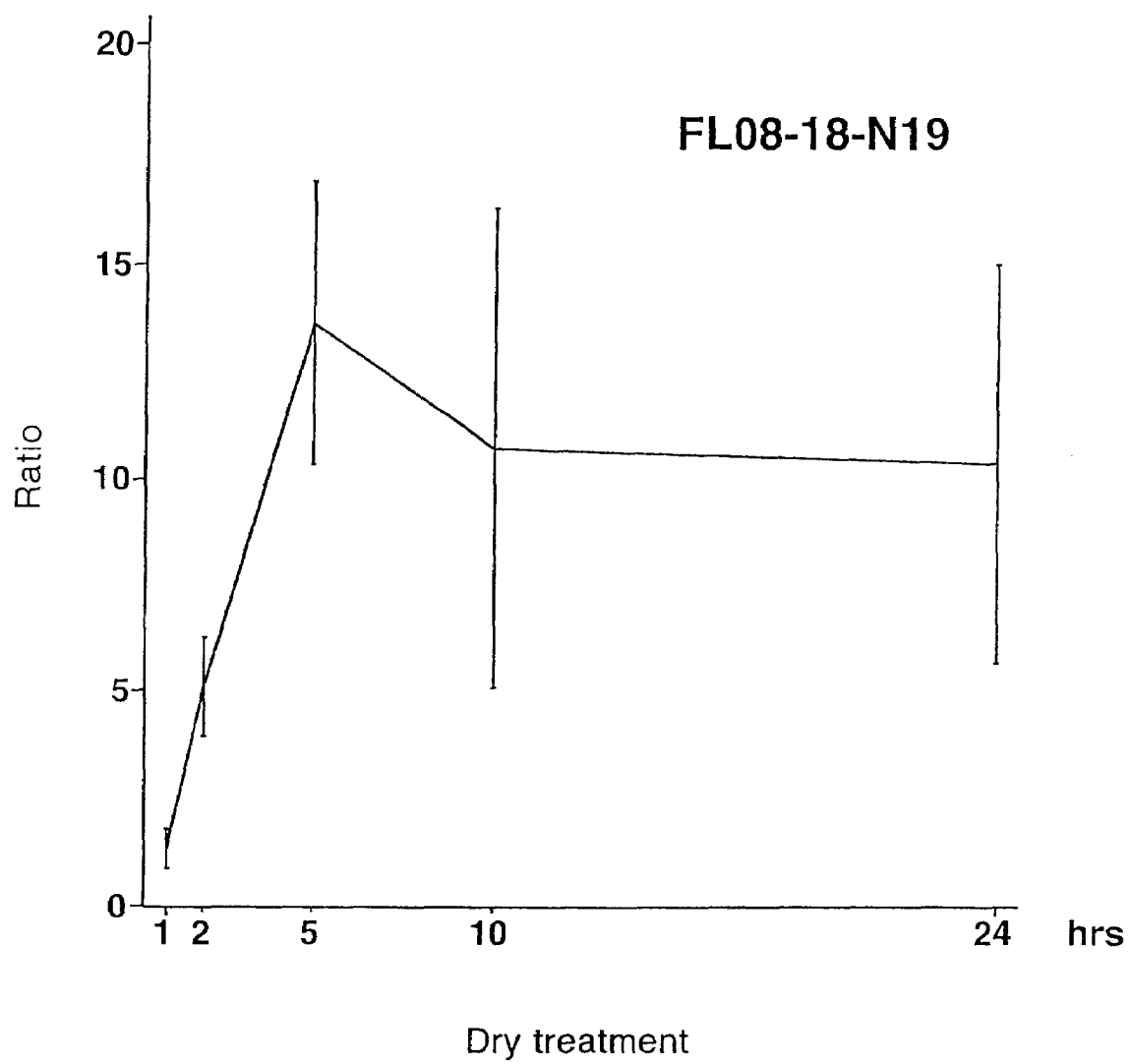
FIG. 91 is a characteristic graph showing the relationship between dehydration treatment time and expression ratio regarding FL08-18-N19.
Figure 92:
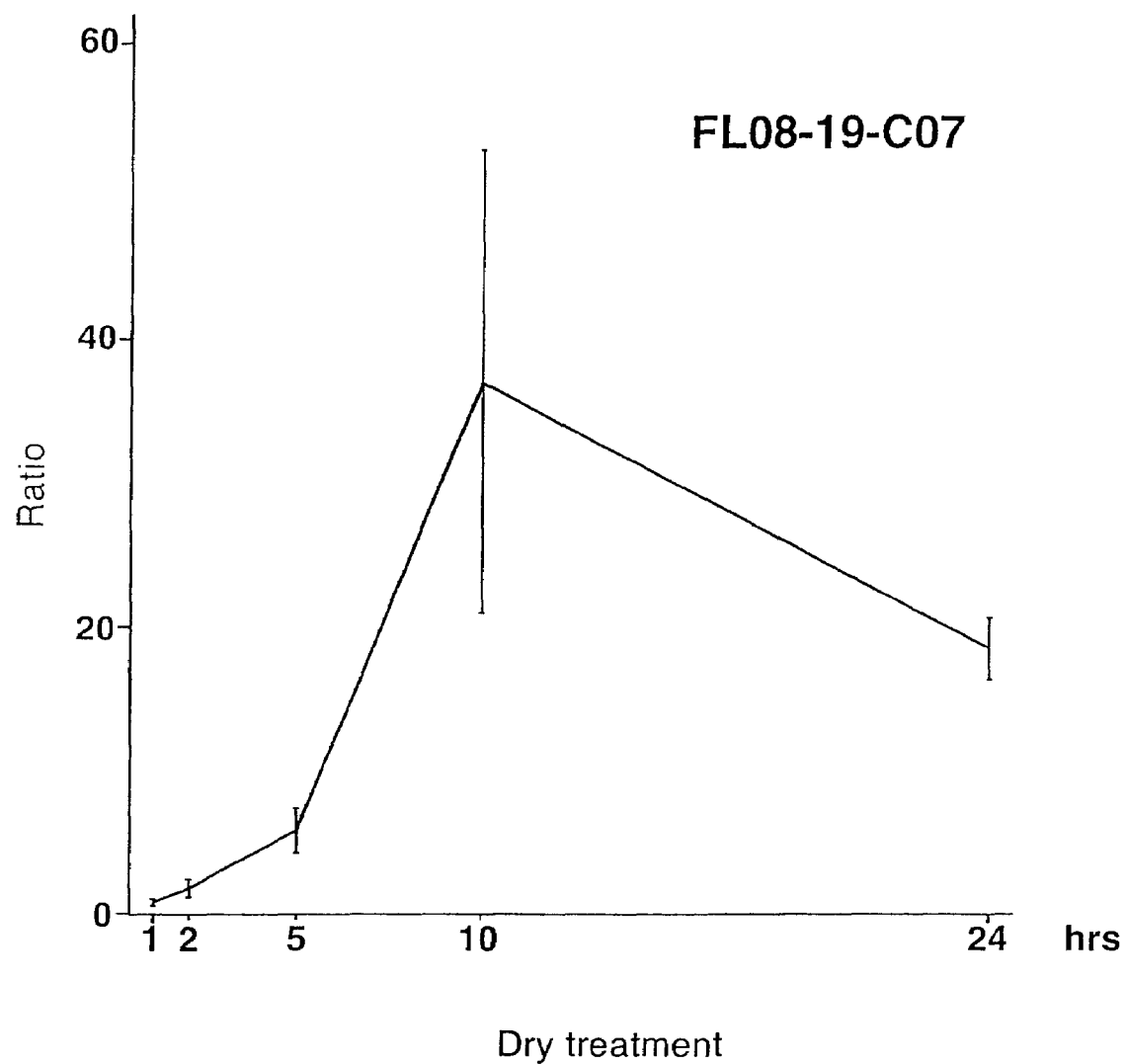
FIG. 92 is a characteristic graph showing the relationship between dehydration treatment time and expression ratio regarding FL08-19-C07.
Figure 93:
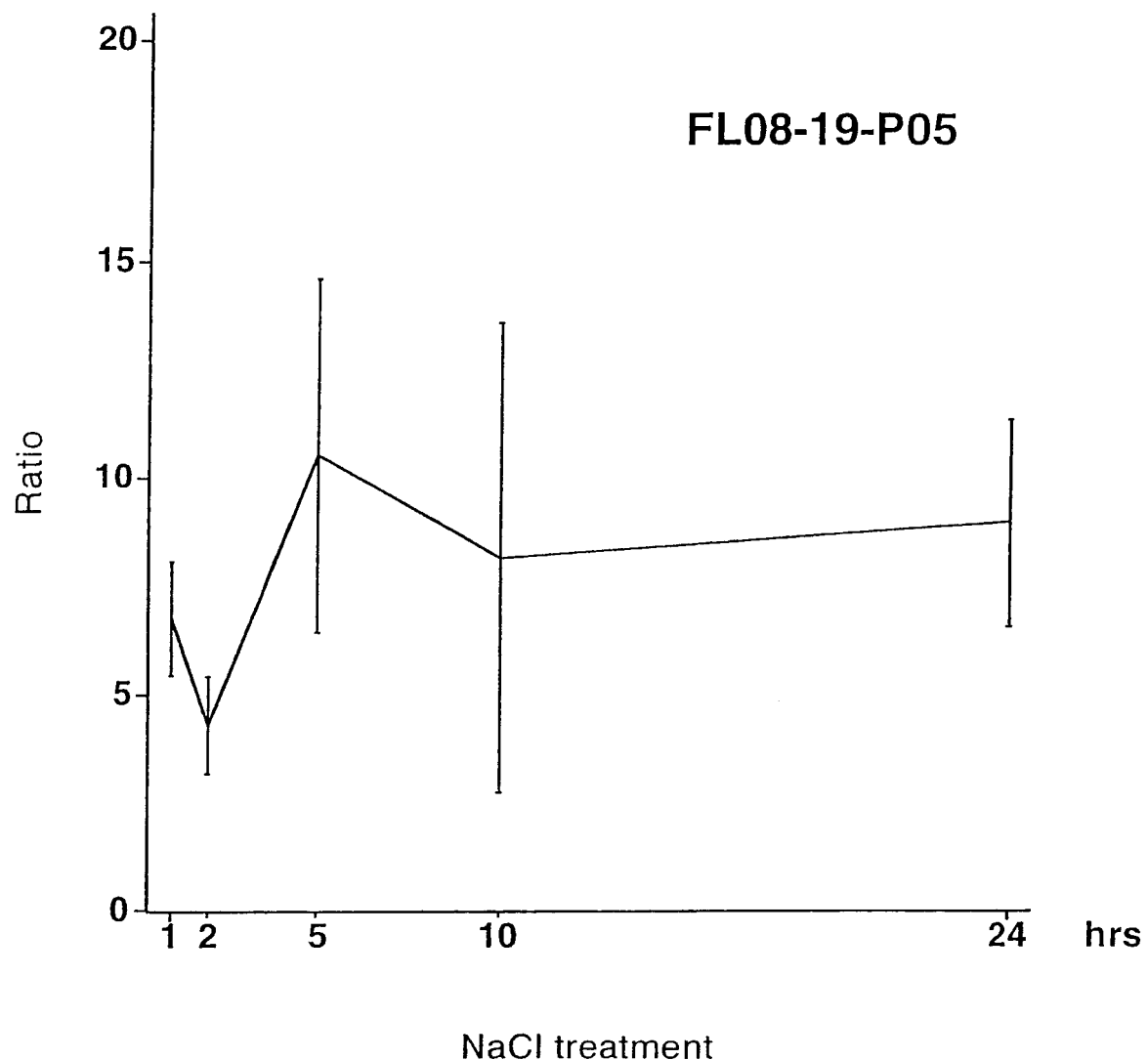
FIG. 93 is a characteristic graph showing the relationship between high salt treatment time and expression ratio regarding FL08-19-P05.
Figure 94:
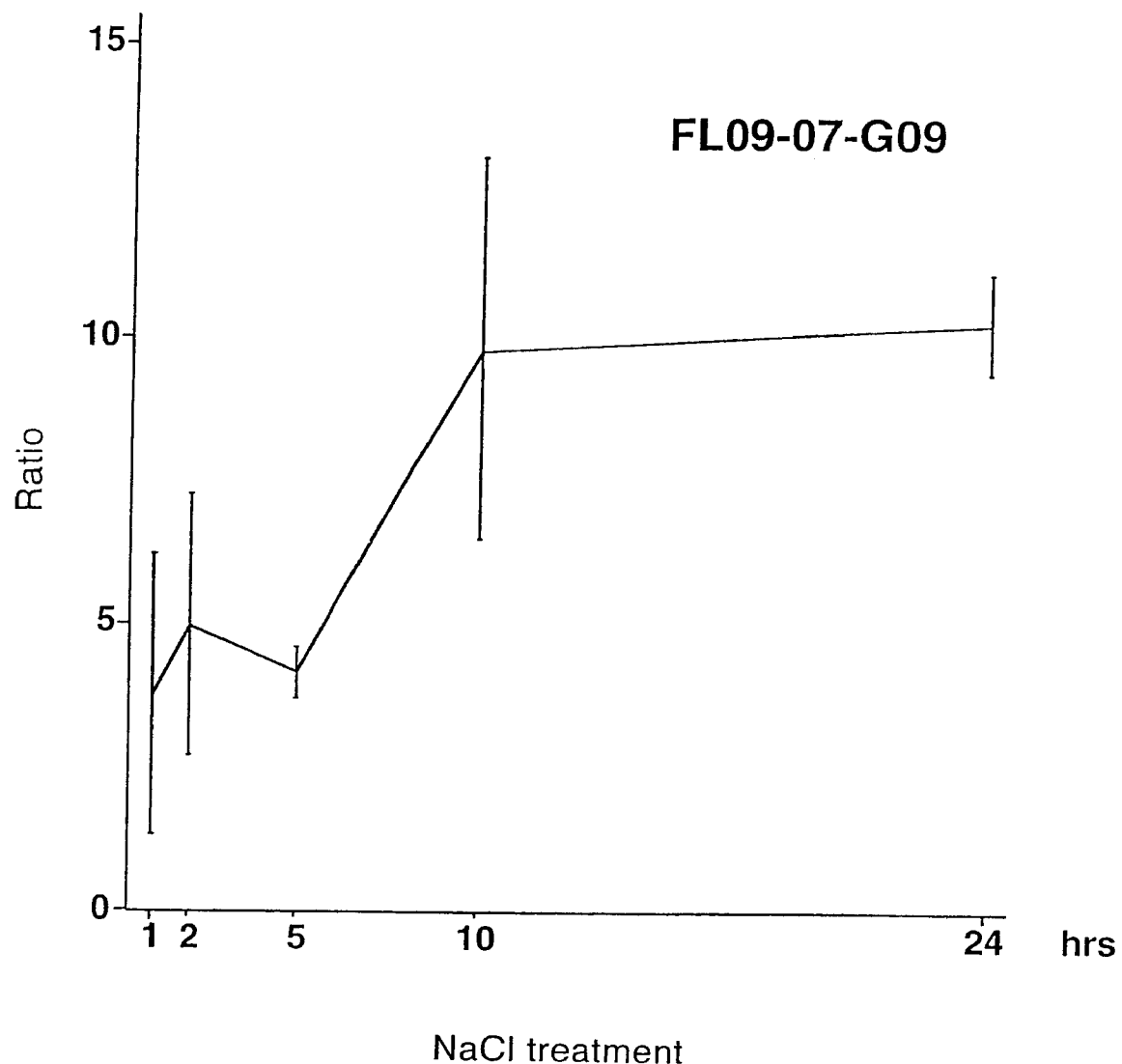
FIG. 94 is a characteristic graph showing the relationship between high salt treatment time and expression ratio regarding FL09-07-G09.
Figure 95:
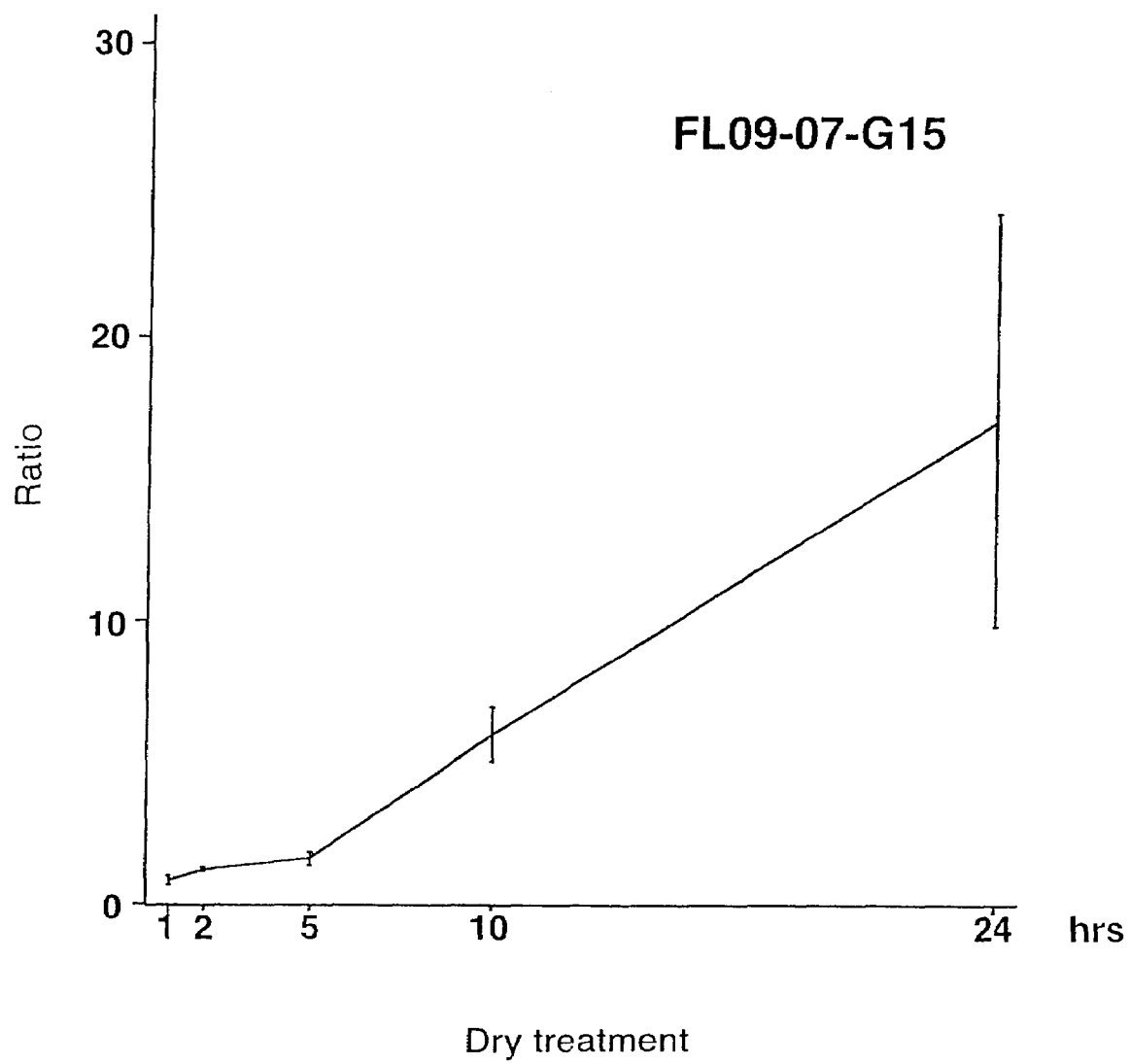
FIG. 95 is a characteristic graph showing the relationship between high salt treatment time and expression ratio regarding FL09-07-G15.
Figure 96:
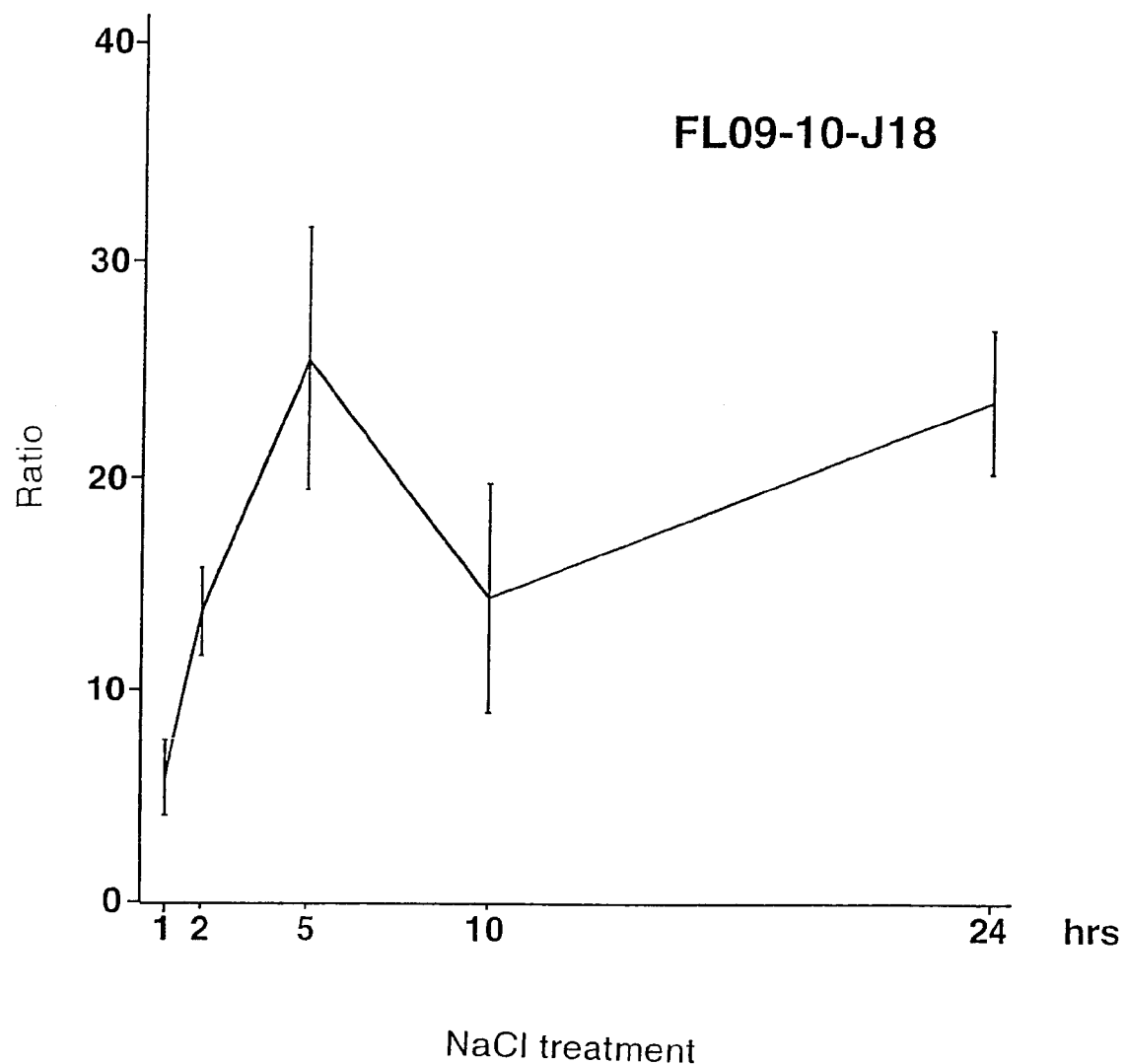
FIG. 96 is a characteristic graph showing the relationship between high salt treatment time and expression ratio regarding FL09-10-J18.
Figure 97:
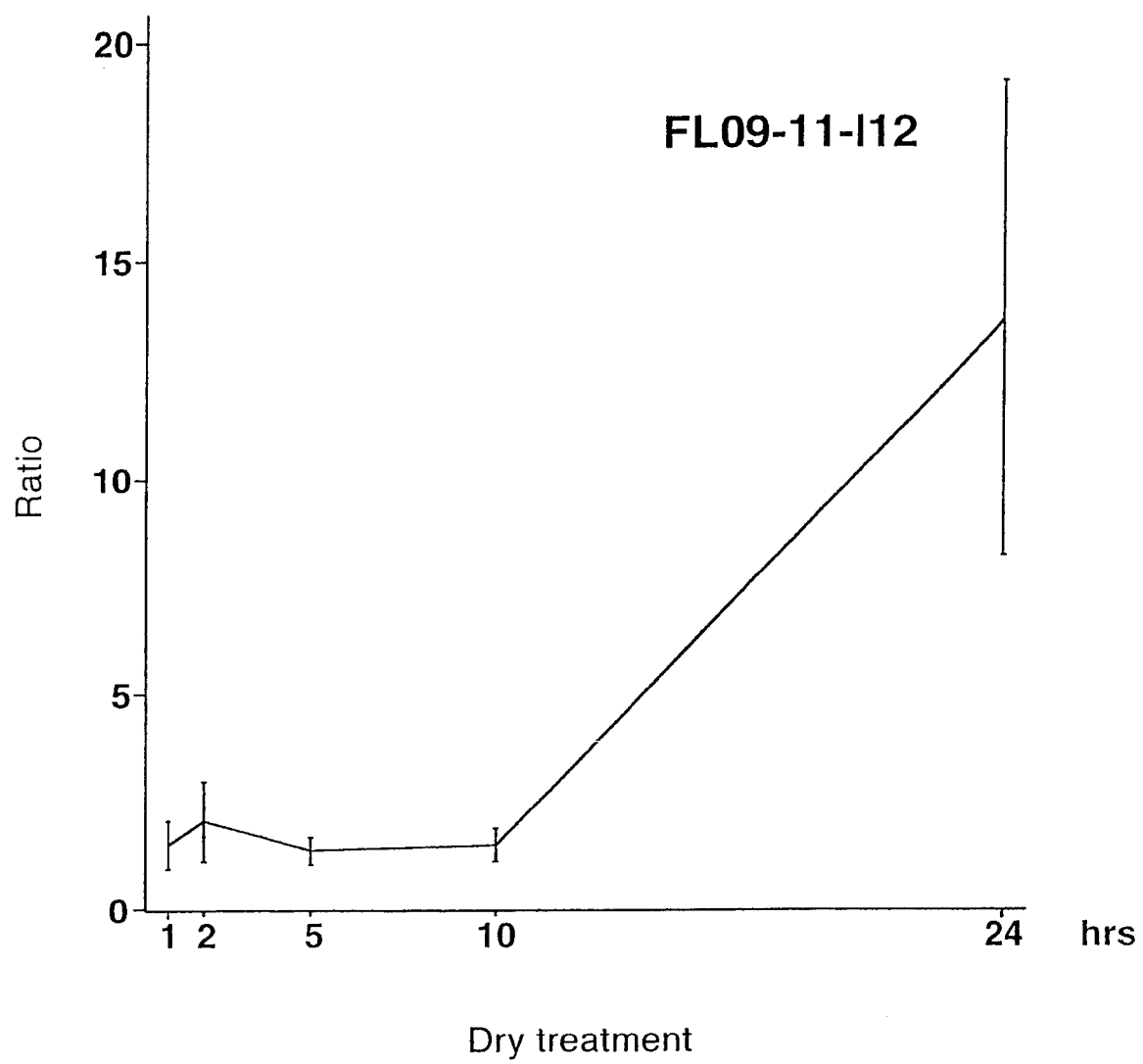
FIG. 97 is a characteristic graph showing the relationship between dehydration treatment time and expression ratio regarding FL09-11-I12.
Figure 98:
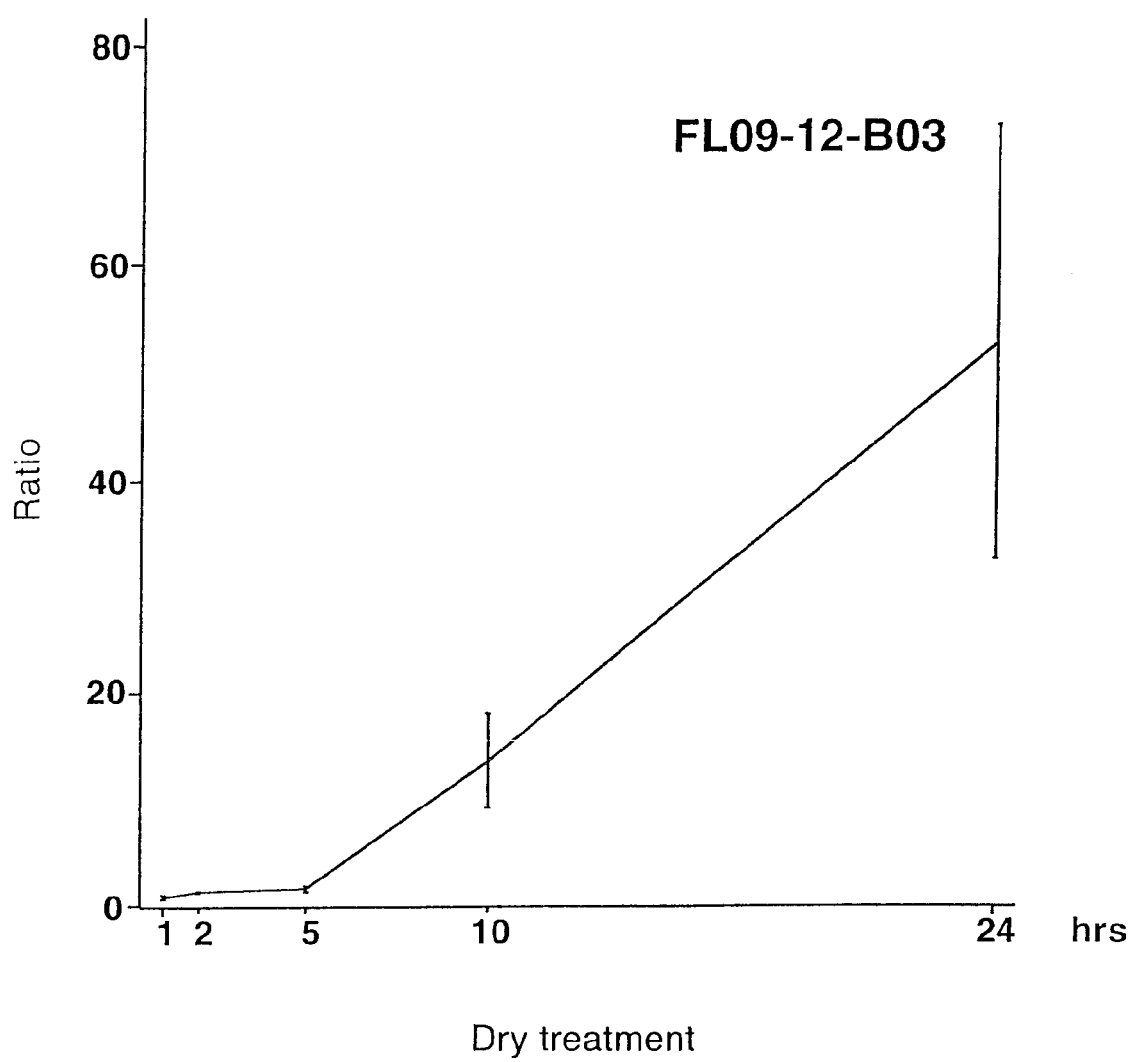
FIG. 98 is a characteristic graph showing the relationship between dehydration treatment time and expression ratio regarding FL09-12-B03.
Figure 99:
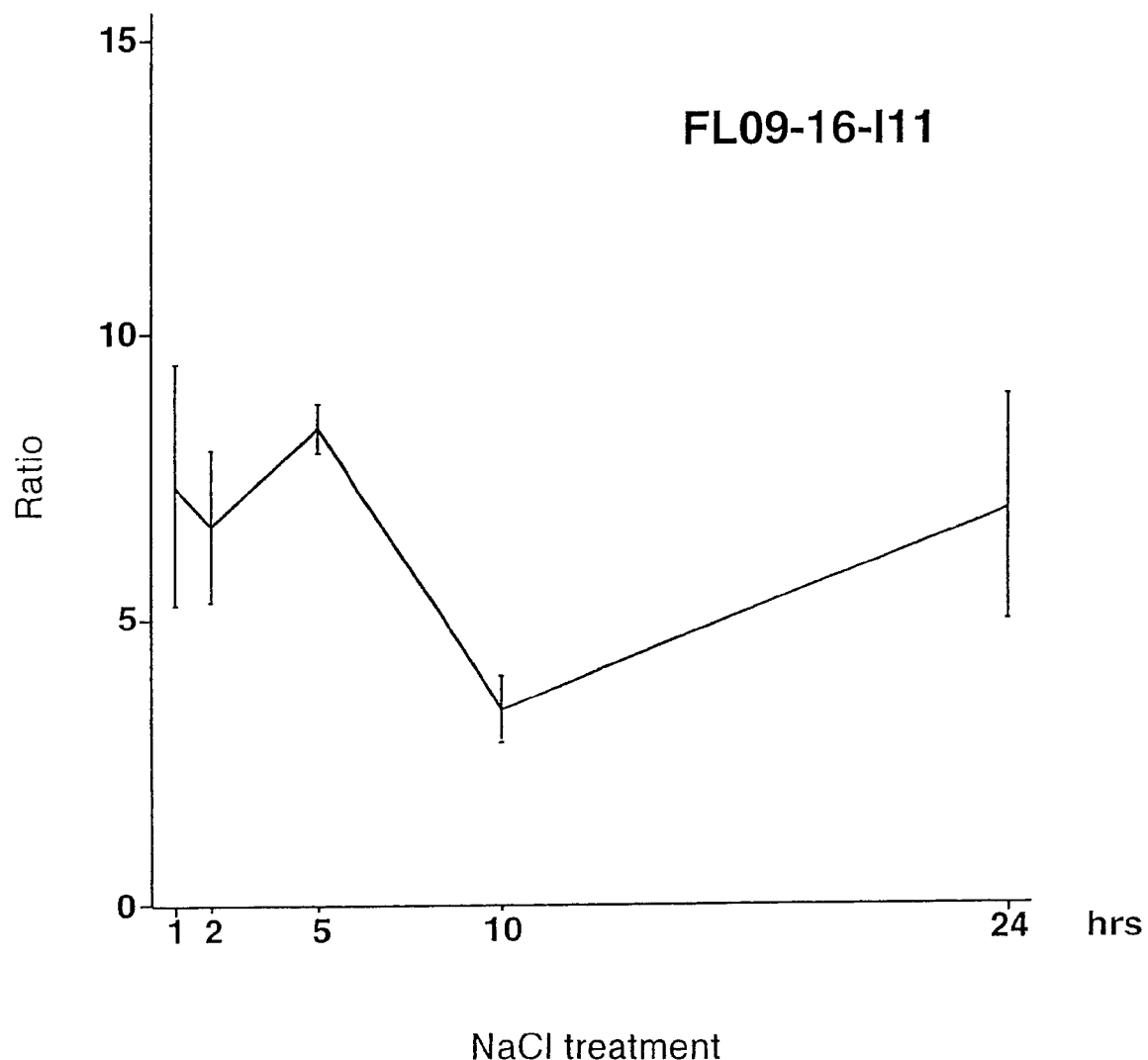
FIG. 99 is a characteristic graph showing the relationship between high salt treatment time and expression ratio regarding FL09-16-I11.
Figure 100:
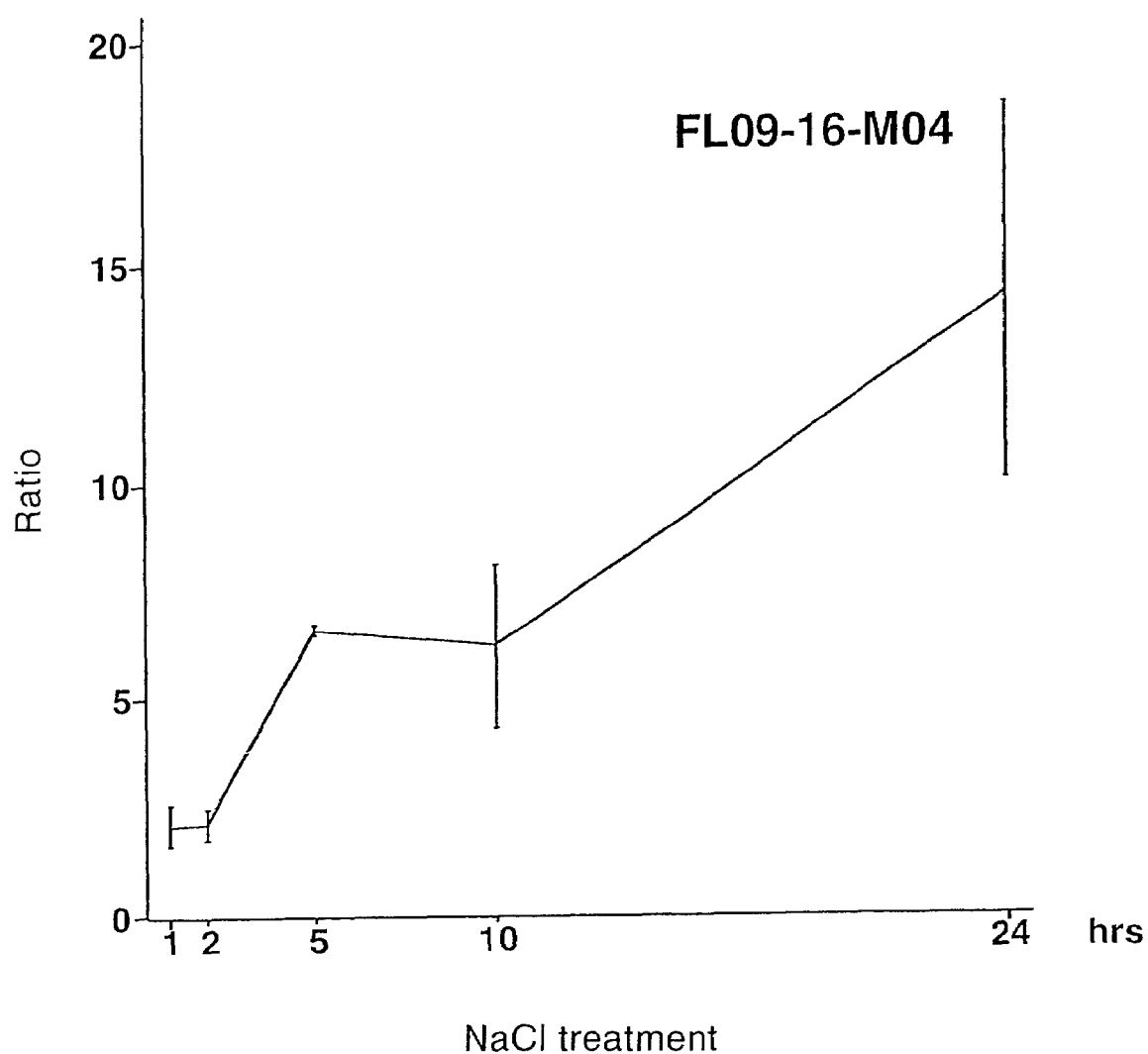
FIG. 100 is a characteristic graph showing the relationship between high salt treatment time and expression ratio regarding FL09-16-M04.
Figure 101:
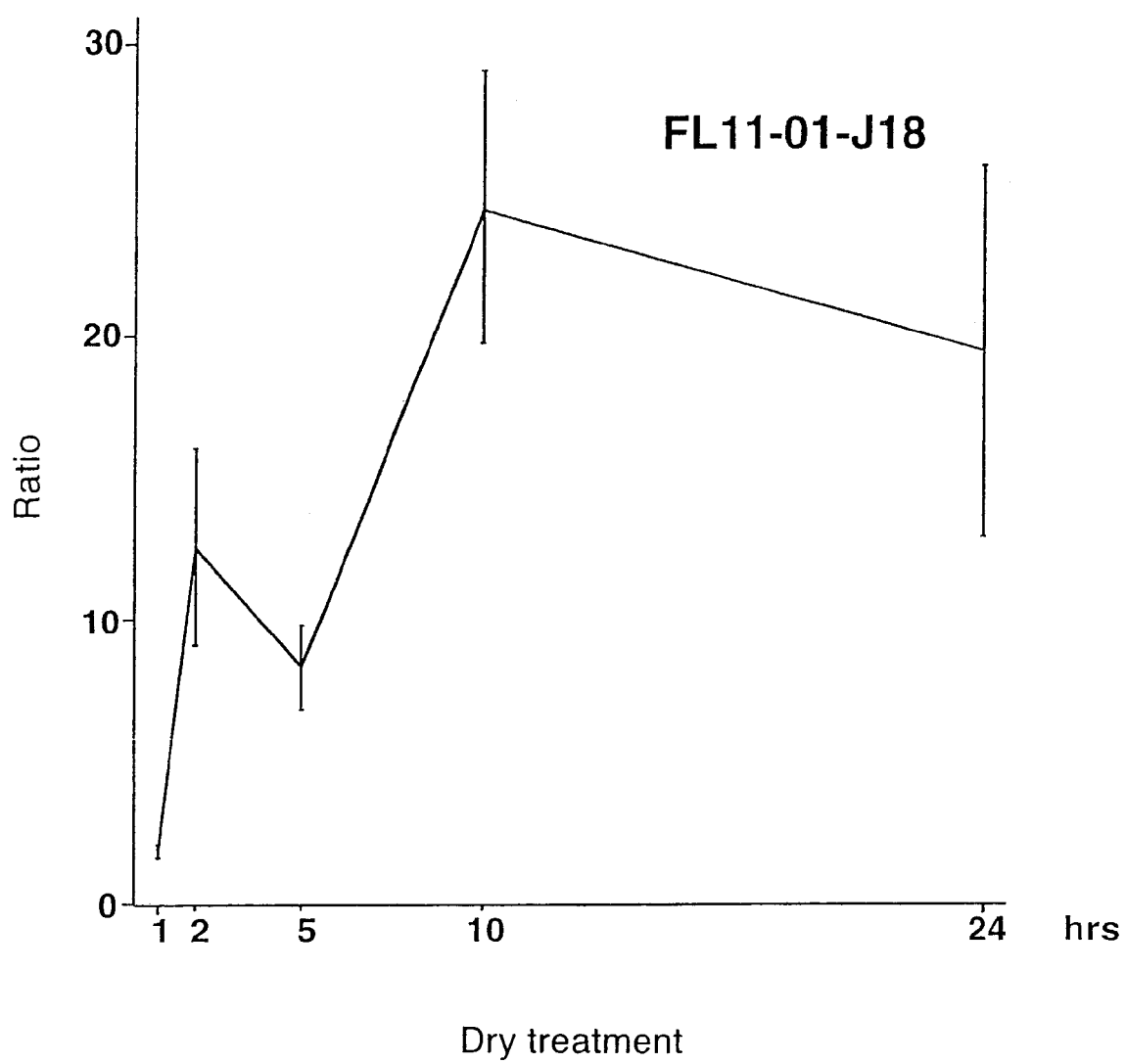
FIG. 101 is a characteristic graph showing the relationship between dehydration treatment time and expression ratio regarding FL11-01-J18.
Figure 102:
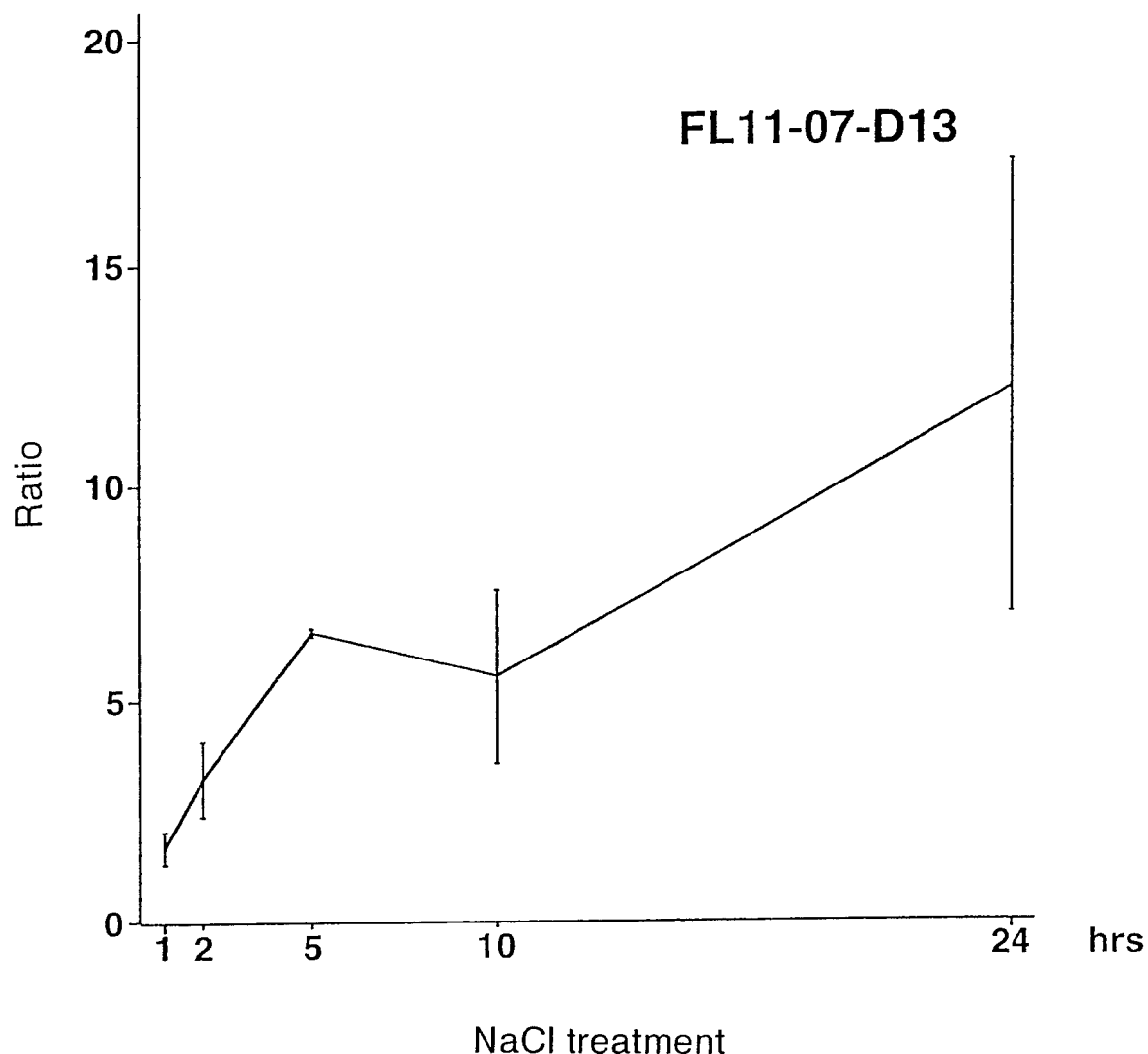
FIG. 102 is a characteristic graph showing the relationship between high salt treatment time and expression ratio regarding FL11-07-D13.
Figure 103:
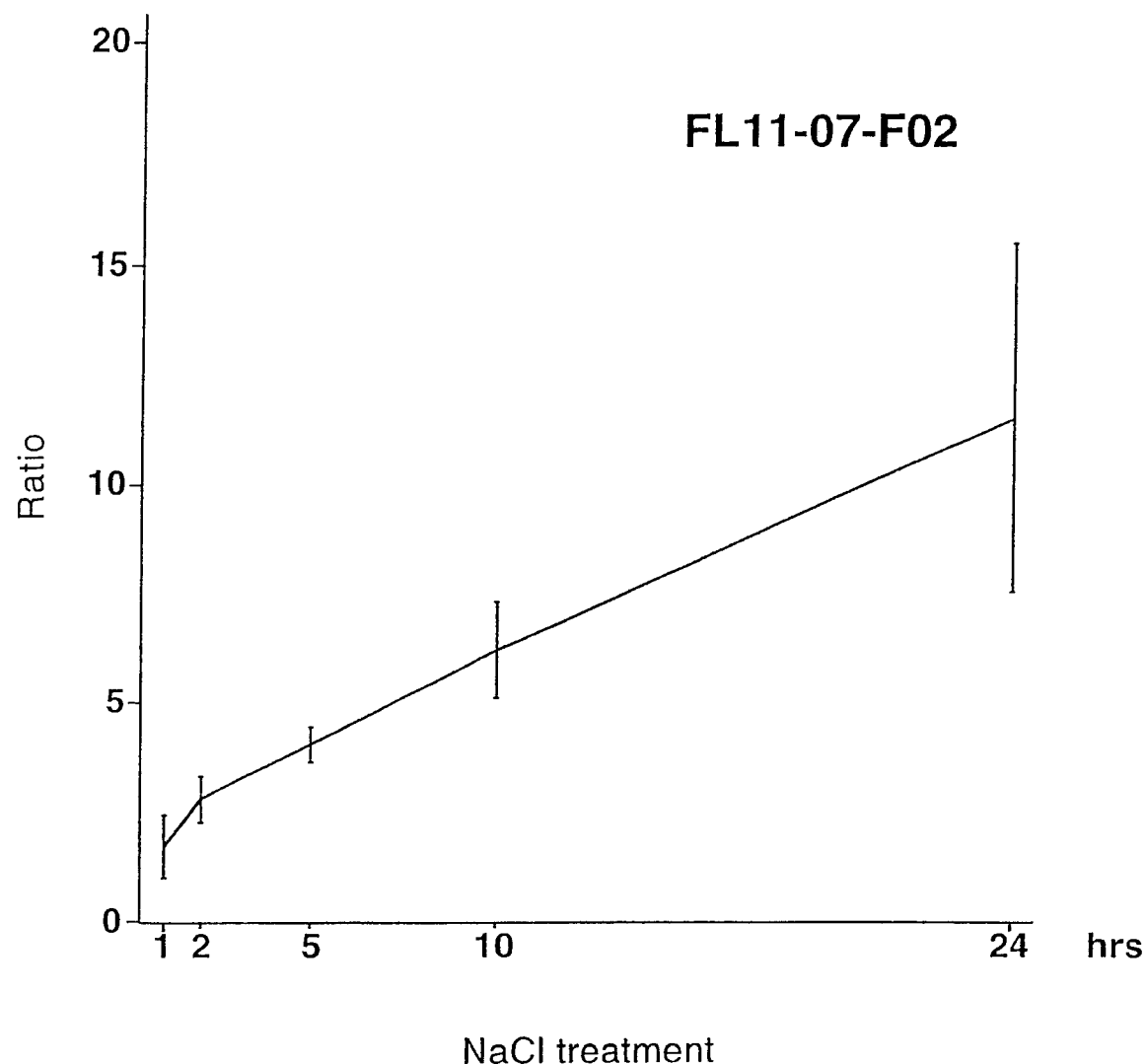
FIG. 103 is a characteristic graph showing the relationship between high salt treatment time and expression ratio regarding FL11-07-F02.
Figure 104:
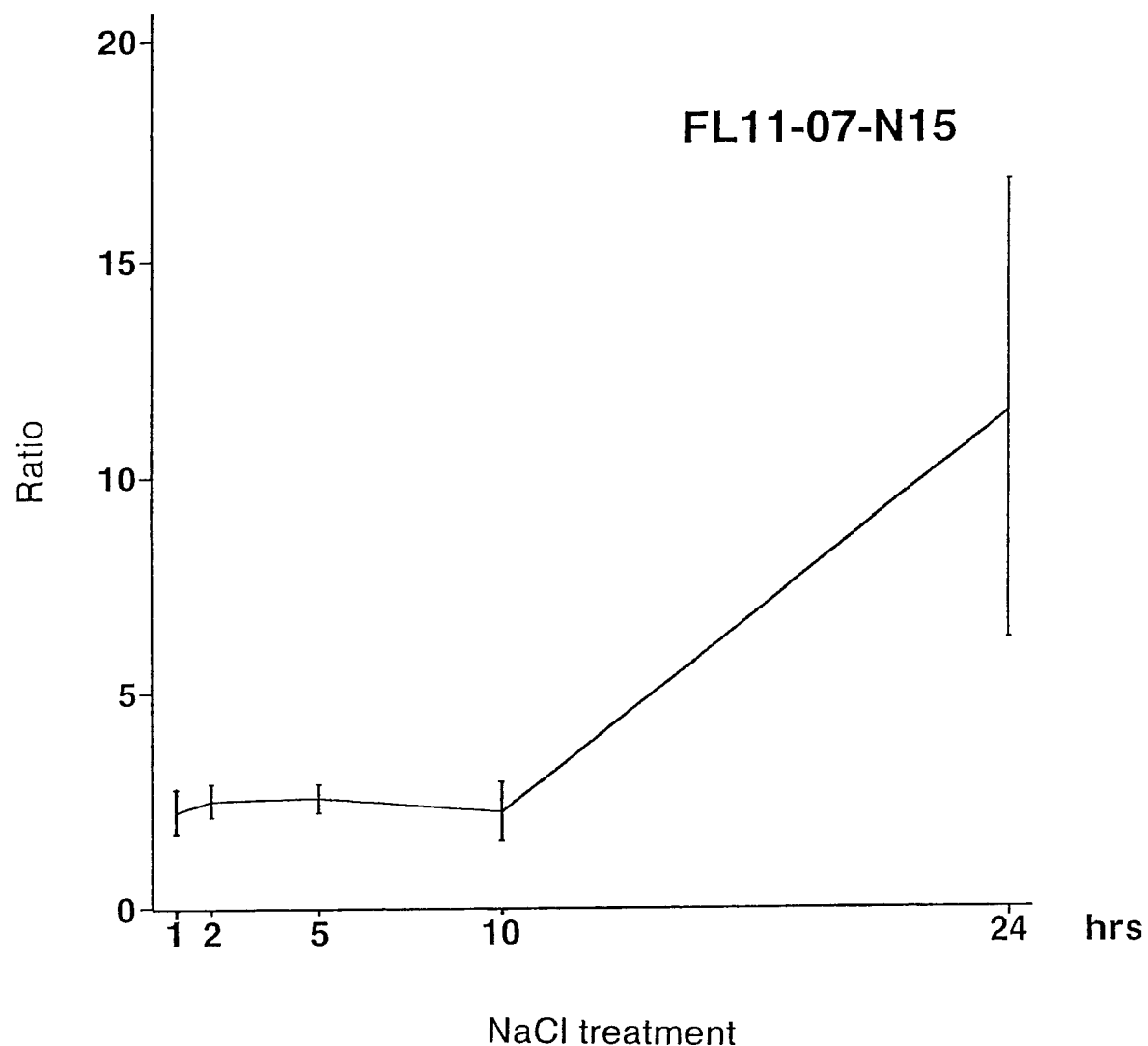
FIG. 104 is a characteristic graph showing the relationship between high salt treatment time and expression ratio regarding FL11-07-N15.

| Name of gene | Type of applied stress | Drawing |
| --- | --- | --- |
| FL06-11-K21 | Dehydration | FIG. 85 |
| FL07-07-G15 | Exposure to a high level salt solution | FIG. 86 |
| FL07-12-D17 | Exposure to a high level salt solution | FIG. 87 |
| FL08-11-C23 | Dehydration | FIG. 88 |
| FL08-13-G20 | Dehydration | FIG. 89 |
| FL08-15-M21 | Dehydration | FIG. 90 |
| FL08-18-N19 | Dehydration | FIG. 91 |
| FL08-19-C07 | Dehydration | FIG. 92 |
| FL08-19-P05 | Exposure to a high level salt solution | FIG. 93 |
| FL09-07-G09 | Exposure to a high level salt solution | FIG. 94 |
| FL09-07-G15 | Dehydration | FIG. 95 |
| FL09-10-J18 | Exposure to a high level salt solution | FIG. 96 |
| FL09-11-I12 | Dehydration | FIG. 97 |
| FL09-12-B03 | Dehydration | FIG. 98 |
| FL09-16-I11 | Exposure to a high level salt solution | FIG. 99 |
| FL09-16-M04 | Exposure to a high level salt solution | FIG. 100 |
| FL11-01-J18 | Dehydration | FIG. 101 |
| FL11-07-D13 | Exposure to a high level salt solution | FIG. 102 |
| FL11-07-F02 | Exposure to a high level salt solution | FIG. 103 |
| FL11-07-N15 | Exposure to a high level salt solution | FIG. 104 |
| FL11-10-D10 | Exposure to a high level salt solution | FIG. 105 |

In FIGS. 1 to 105, the vertical axis shows the expression ratio of a gene, which is calculated as follows:

Expression ratio=[(F1 of a cDNA molecule under stress)/(F1 of a cDNA molecule under no stress)]÷[(F1 of α-tubulin under stress)/(F1 of α-tubulin under no stress)]

where F1 is the intensity of fluorescence.

As shown in FIGS. 1 to 105, the stress inducible genes isolated by a method according to the present invention exhibit different profiles; however, it is found that expression is induced by adding each stress. From this, it is demonstrated that the nucleotide sequences positioned upstream of these 90 types of genes and represented by SEQ ID NO: 1 to 90 serve as stress responsive promoters.

EXAMPLE 2

Isolation of Gene Encoding Environmental Stress Responsive Transcriptional Factor 1. Materials and Methods (1) *Arabidopsis* cDNA Clone A microarray was constructed by using about 7,000 cDNA molecules in total including genes isolated from *Arabidopsis* full-length cDNA libraries, responsive to dehydration (RD) genes, early responsive to dehydration (ERD) genes, kin 1 genes, kin2 genes, and cor15a genes; fragments amplified from λ control template DNA by PCR as an internal standard; and mouse nicotinic acetylcholine receptor epsilon subunit (nAChRD) genes and mouse glucocorticoid receptor homologous genes, as negative controls.

Positive control: dehydration-inducible genes (responsive-to-dehydration genes: rd, and early responsive-to-dehydration genes; erd):

Internal standard: fragments amplified from λ control template DNA by PCR (TX803, manufactured by Takara Shuzo, hereinafter referred to as a "control fragment");

Negative control: mouse nicotinic acetylcholine receptor epsilon subunit (nAChRE) genes and mouse glucocorticoid receptor homologous genes, as negative controls, which do not substantially have homology with any given sequence in an *Arabidopsis* database for analyzing non-specific hybridization.

(2) *Arabidopsis* Full-length cDNA Microarray

The present inventors have constructed full-length cDNA libraries from an *Arabidopsis* plant body under different conditions (e.g., dehydration treatment, cold treatment and non-treatment in different growth stages from budding to maturation of seeds) by the biotinylated CAP trapper method. From the full-length cDNA libraries, the present inventors isolated individually about 7,000 independent *Arabidopsis* full-length cDNA molecules. The cDNA fragments, which were amplified by PCR, were arranged on a slide glass in accordance with a known method (Eisen and Brown, 1999). The present inventors prepared a full-length cDNA microarray containing about 7,000 *Arabidopsis* full-length cDNA molecules, which contain the genes below.

(3) Dehydration-, Cold-, High Salt-inducible Genes Using cDNA Microarray

In this example, dehydration-, cold-, high salt-inducible genes were isolated by using a full-length cDNA microarray containing about 7,000 *Arabidopsis* full-length cDNA molecules.

Probes of a plant treated with different stresses and an untreated plant with stress and labeled with Cy3 and Cy5 fluorescent dyes were mixed. The probes were hybridized with the full-length cDNA microarray containing about 7,000 *Arabidopsis* full-length cDNA molecules. By such a double labeling of a pair of cDNA probes wherein one of the mRNA samples was labeled with Cy3-dUTP and the other was labeled with Cy5-dUTP, hybridization with DNA elements on a microarray can be performed simultaneously, with the result that quantitative determination of gene expression under two different conditions (that is, stressed and unstressed conditions) can be directly and easily performed. The hybridized microarray was scanned by two discrete laser channels for Cy3 and Cy5 emission from each of DNA elements. Subsequently, the intensity ratio between two fluorescent signals from each DNA element was determined. Based on the relative value of the intensity ratio, a change of differential expression of genes represented as a cDNA spot on the microarray was determined. In this example, an α-tubulin gene, whose expression level was almost equivalent under two different experimental conditions was used, as an internal control gene.

In the full-length cDNA microarray containing about 7,000 *Arabidopsis* full-length cDNA molecules, a procedure for identifying dehydration-, cold-, high salt-inducible genes will be explained.

Both mRNA molecules derived from a plant treated with one of the stresses mentioned above and mRNA molecules derived from a wild-type plant unstressed were used to prepare Cy3-labeled cDNA and Cy5-labeled cDNA probes, respectively. These cDNA probes were mixed and hybridized with a cDNA microarray. In this example, a control fragment, which exhibits almost the same expression level under two type conditions, was used as an internal control gene. A gene that exhibits the expression ratio (dehydration/unstressed, cold/unstressed or high salt/unstressed) more than 5 times of that of the control fragment was defined as an inducible gene by a stress given to the gene.

(4) Analysis of Sequence

Plasmid DNA extracted by a DNA extraction device (model Biomek, manufactured by Backman Coulter) and purified by use of a multiscreen 96-hole filter plate (manufactured by Millipore) was sequenced to find homology of gene sequences. The DNA sequence was determined by a dye terminator cycle sequencing method using a DNA sequencer (ABI PRISM 3700. PE Applied Biosystems, CA, USA). Based on the GenBank/EMBL database, the homology of sequences was found by using the BLAST program.

(5) Amplification of cDNA

λZAP and λ FLC-1 were used as a vector for constructing a cDNA library. The cDNA inserted in a vector for the library was amplified by PCR using complementary primers to the sequences of both sides of the cDNA.

The sequence of primers are as follows:

```
FL forward 1224:
5'-CGCCAGGGTTTTCCCAGTCACGA      (SEQ ID NO: 165)

FL reverse 1233:
5'-AGCGGATAACAATTTCACACAGGA     (SEQ ID NO: 166)
```

To 100 μl of a PCR solution mixture (0.25 mM dNTP, 0.2 μM PCR primer, 1×Ex Taq Buffer, and 1.25 U Ex Taq polymerase (manufactured by Takura Shuzo)), a plasmid (1 to 2 ng) was added as a template. PCR was performed under the following conditions: an initial reaction at 94° C. for 3 minutes, 35 cycles each consisting of 95° C. for one minute, 60° C. for 30 seconds and 72° C. for 3 minutes, and a final reaction at 72° C. for 3 minutes. After a PCR product was precipitated with ethanol, the precipitate was dissolved in 25 μl of 3×SSC and subjected to electrophoresis using 0.7% agarose gel. The quality of the DNA obtained and amplification efficiency of PCR were conformed.

(6) Construction of cDNA Microarray

Using a gene tip microarray stamp machine GTMASS SYSTEM (manufactured by Nippon Laser & Electronics Lab.), 0.5 μl of a PCR product (500-1,000 ng/ml) was loaded from a 384-well microtiter plate and form spots of the PCR product (5 nl for each) at intervals of 300 μm on 48 micro slide glasses (model Super Aldehyde substrate, manufactured by Telechem International). After spotting, the slide was dried in an atmosphere having a relative humidity of 30% or less and irradiated with ultraviolet rays for mediating a cross-linking reaction.

Thereafter, the slide was treated in 0.2% SDS with shaking for 2 minutes three times and soaked in distilled water twice. Subsequently, the slides were placed on a slide rack, which was the transferred into a chamber containing hot water and allowed to stand for 2 minutes. Subsequently, to the chamber, a blocking solution (containing 1 g borohydride, 300 ml of PBS, and 90 ml of 100% ethanol) was poured. After the glass chamber housing the slide rack was moderately shaken, the slide rack was transferred to a chamber containing 0.2% SDS and gently shaken for one minute 3 times. Thereafter, the slide rack was transferred to a glass chamber containing distilled water, moderately shaken for one minute, and centrifuged for 20 minutes to dry.

(7) Plant Material and Isolation of RNA

As a plant material, use was made of a wild type *Arabidopsis thaliana* plant body which was seeded on an agar medium and grown for 3 weeks (Yamaguchi-Shinozaki and Shinozaki, 1994) and an *Arabidopsis thaliana* (Colombian species) plant body into which DREB1A cDNA (Kasuga et al., 1999) connected to a 35S promoter of a cauliflower mosaic virus was introduced. Dehydration- and cold-stress treatments were performed in accordance with the method of Yamaguchi-Shinozaki and Shinozaki (1994). More specifically, dehydration treatment was performed by pulling a plant body out of the agar medium, placing it on a filter, and dried at a temperature of 22° C. and a relative humidity of 60%. The cold treatment was performed by transferring a plant body grown at 22° C. to 4° C. High salt stress treatment was performed by growing a plant body at an aqueous solution containing 250 mM NaCl.

After wild type plant bodies were exposed to stress-treatment for 2 or 10 hours, a sample was taken from each of plant bodies and stored in cryogenic conditions with liquid nitrogen. Furthermore, wild type and DREB1A overexpression-type transformants cultured in an agar medium without kanamycin were subjected to an experiment for identifying a DREB1A target gene. The DREB1A overexpression-type transformant was not treated with stresses. The total RNA was isolated from a plant body by using ISOGEN (Nippon gene, Tokyo, Japan) and mRNA was isolated and purified by Oligotex-dT30 mRNA purification kit (Takara, Tokyo, Japan).

(8) Fluorescent Labeling of Probe

Each of the mRNA samples was subjected to a reverse transcription reaction in the presence of Cy3 dUTP or Cy5 dUTP (Amersham Pharmacia). More specifically, the reverse transcription reaction was performed in a total amount of 20 μl of 1×Superscript first-stand buffer (containing 50 mM Tris-HCl, pH 8.3, 75 mM KCl, 3 mM $MgCl_2$, and 20 mM DTT, manufactured by Life Technology), which contained:

1 μg of denatured poly $(A)^+$ which contains 1 ng of λ poly $A^+$RNA-A (TX802, manufactured by Takara Shuzo) serving as an internal standard;

50 ng/μl 12 to 18 mer oligo dT primer (manufactured by Life Technology);

0.5 mM dATP, 0.5 mM dGDP, 0.5 mM dCTP, and 0.2 mM dTTP;

0.1 mM Cy3 dUTP or Cy5 dUTP;

100 U of Rnase inhibitor;

10 mM DTT; and

200 U of Superscript II reverse transcriptase.

After the reaction solution of the aforementioned composition was incubated at 42° C. for 35 minutes, 200 U of Superscript II reverse transcriptase was added and further incubated at 42° C. for 35 minutes. To this reaction mixture, subsequently, 5 μl of 0.5 M EDTA, 10 μl of 1N NaOH, and 20 μof distilled water were added, thereby terminating the enzyme reaction taking place in the reaction solution and simultaneously decomposing a template. The reaction solution was then incubated at 65° C. for 1 hour and thereafter neutralized with 1M Tris-HCL (pH 7.5).

The reaction solution was transferred to a Microcon 30 micro concentrator (manufactured by Amicon), 250 μl of TE buffer was added and centrifuged until the amount of the buffer reached 10 μl. The effluent was discarded. This step was repeated 4 times. Probes contained in the reaction solution were centrifugally collected and several μl of distilled water was added. To the obtained probes, 5.1 μl of 20×SSC, 2 μg/μl of Yeast tRNA, and 4.8 μl of 2% SDS were added. Further, the samples were denatured at 100° C. for 2 minutes, place at room temperature for 5 minutes, and thereafter used in hybridization.

(9) Microarray Hybridization and Scanning

A probe was centrifuged for one minute by a benchtop micro centrifuge. To avoid generation of bubbles, the probe was place at the center of an array and a cover slip was placed thereon. Four drops of 5 μl of 3×SSC were dropped on a slide glass and a chamber was kept at a suitable humidity to prevent the probe from being dried during hybridization. After the slide glass was placed in a cassette for hybridization (THC-1, BM machine) and the cassette was sealed, hybridization treatment was performed at 65° C. for 12 to 16 hours. The slide glass was taken out from the cassette and placed on the slide rack. After the cover slip was carefully removed in solution 1 (2×SSC, 0.03% SDS), the rack was washed while shaking and transferred into solution 2 (1×SSC) to wash for 2 minutes. The rack was further transferred to solution 3 (0.05×SSC), allowed to stand for 2 minutes, and centrifuged at 2500 g for 1 min to dry.

The microarray was scanned at a resolution of 10 µm per pixel by use of a scanning laser microscope (ScanArray 4000; GSI Lumonics, Watertown, Mass.). As a program for analyzing microarray data, QuantArray, Ver. 2.0 (GSI Lumonics) was used. The background fluorescence was obtained through calculation based on fluorescent signals obtained from negative control genes (mouse nicotinic acetylcholine receptor epsilon subunit (nAChRE) gene and mouse glucocorticoid receptor homologous gene). Samples giving a fluorescent signal value of less than 1,000, which is equal to less than twice the background signal value, were not subjected to analysis. The cluster analysis of genes was performed by Genespring (manufactured by Silicon Genetic).

(10) Northern Analysis

Northern analysis was performed using total RNA, (Yamaguchi-Shinozaki and Shinozaki, 1994). DNA fragments were isolated from an *Arabidopsis thaliana* full-length cDNA library by a PCR method and used as probes for Northern hybridization.

(11) Determination of Gene Encoding Transcriptional Factor

Based on the genomic information of *Arabidopsis thaliana* in a data base (GenBank/EMBL, ABRC), a gene encoding transcriptional factor was analyzed by using the BLAST program for gene analysis.

2. Results (1) Identification of Stress-inducible Gene

Fluorescence-labeled cDNA was prepared by subjecting mRNA isolated from unstressed *Arabidopsis thaliana* to a reverse transcription reaction in the presence of Cy5-dUTP. A second probe labeled with Cy3-dUTP was prepared from a plant stress with dehydration, cold or high-salt. Both probes were simultaneously hybridized with a cDNA microarray containing about 7,000 *Arabidopsis thaliana* cDNA clones and pseudo color image was created.

Genes induced and suppressed by a stress are represented by a red signal and a greeen signal, respectively. Genes expressed at virtually the same level in both treatments are represented by a yellow signal. The intensity of each spot corresponds to the absolute value of the expression level of each gene. It is shown that a cold-inducible gene (rd29A) is represented by a red signal, whereas a control fragment (an internal control) is represented by a yellow signal.

As a result of scanning the microarray, 277 genes induced by dehydration treatment, 53 genes induced by cold treatment, and 194 genes induced by high salt treatment were identified. Note that genes whose expression ratio are not less than 5 times as large as that of a control fragment were determined as ones induced by a variety of stresses.

As a result of analysis using a database, 35 transcriptional factors, which were classified into the following families were identified. Note that RAFL05-21-L12 was not classified into the following families. However, when the nucleic acid base sequence, which was searched by the BLAST X based on amino acid sequence data registered in the GenBank Database, it exhibited E-value of $e^{-100}$, which means that RAFL05-21-L12 is homologous to a gene encoding a known transcriptional factor, that is, heat shock transcriptional factor-like protein. As a result, RAFL05-21-L12 was identified as a transcriptional factor. In conclusion, 36 types of transcriptional factors were identified in this example.

(1) DREB family: RAFL05-11-M11, RAFL06-11-K21, RAFL05-16-H23, RAFL08-16-D06;

(2) ERF family: RAFL07-16-G17, RAFL06-08-H20;

(3) Zinc finger family: RAFL07-10-G04, RAFL04-17-D16, RAFL05-19-M20, RAFL08-11-M13; RAFL04-15-K19, RAFL05-11-L01, RAFL05-14-C11, RAFL05-19-G24, RAFL05-20-N02;

(4) WRKY family: RAFL05-18-H12, RAFL05-19-E19, RAFL06-10-D22, RAFL06-12-M01;

(5) MYB family: RAFL05-14-D24, RAFL05-20-N17, RAFL04-17-F21;

(6) bHLH family: RAFL09-12-N16;

(7) NAC family: RAFL05-19-I05, RAFL05-21-I22, RAFL08-11-H20, RAFL05-21-C17, RAFL05-08-D06;

(8) Homeo domain family: RAFL05-20-M16, RAFL11-01-J18; RAFL11-09-C20; and (9) bZIP family: RAFL05-18-N16, RAFL11-10-D10, RAFL04-17-N22, RAFL05-09-G15.

Figure 106:
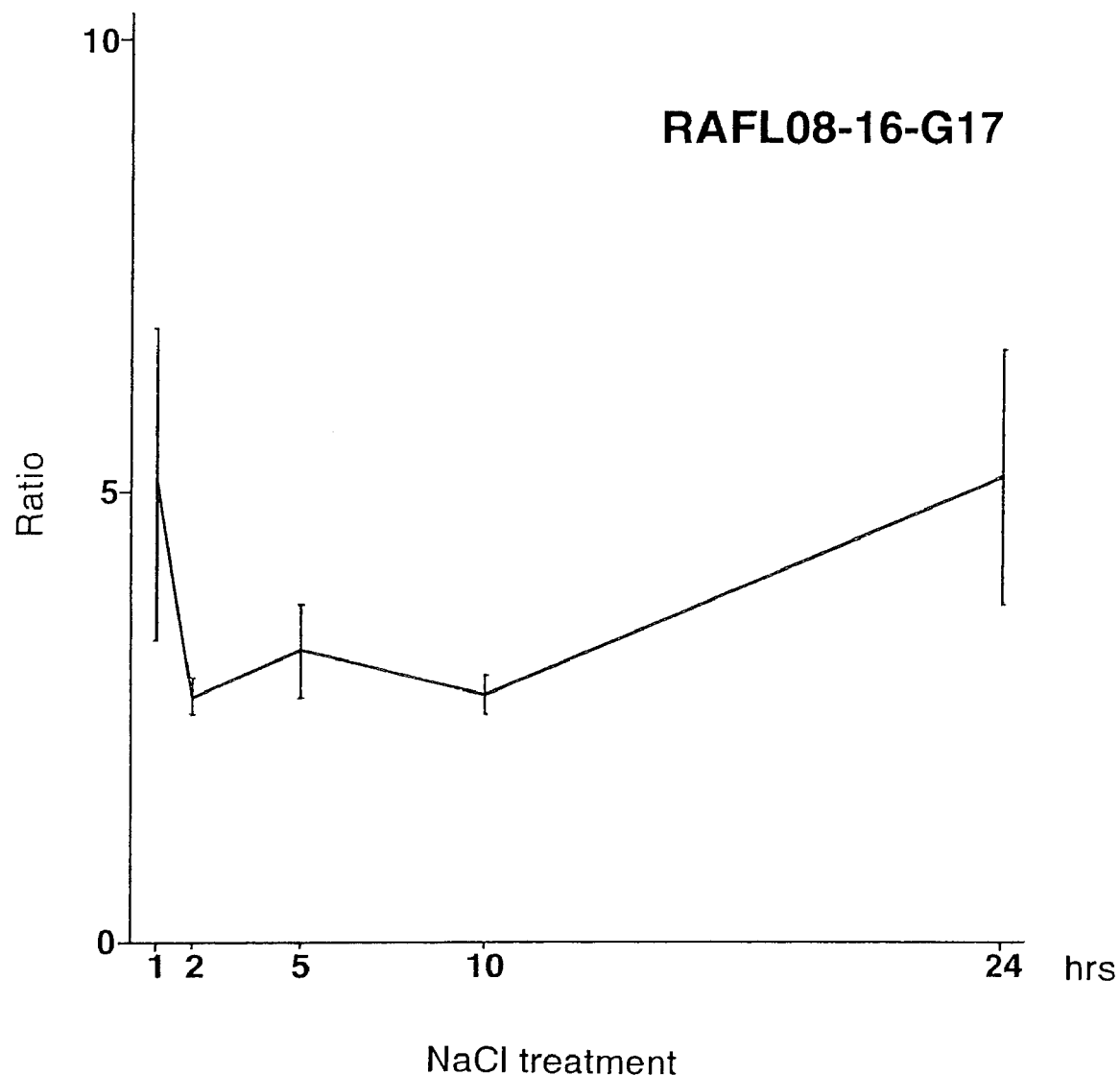
FIG. 106 is a characteristic graph showing the relationship between high salt stress and expression ratio regarding RAFL08-16-G17.

(3) The Relationship Between Treatment Time with Each stress and Expression Ratio Genes encoding 36 types of stress responsive transcriptional factors isolated as described above were analyzed for the relationship between treatment time with each stress and expression ratio. The results are shown in FIGS. 106 to 162. The correspondence between the names of genes and stress treatment shown in FIGS. 106 to 162 is listed in Table 5.

TABLE 5

Figure 107:
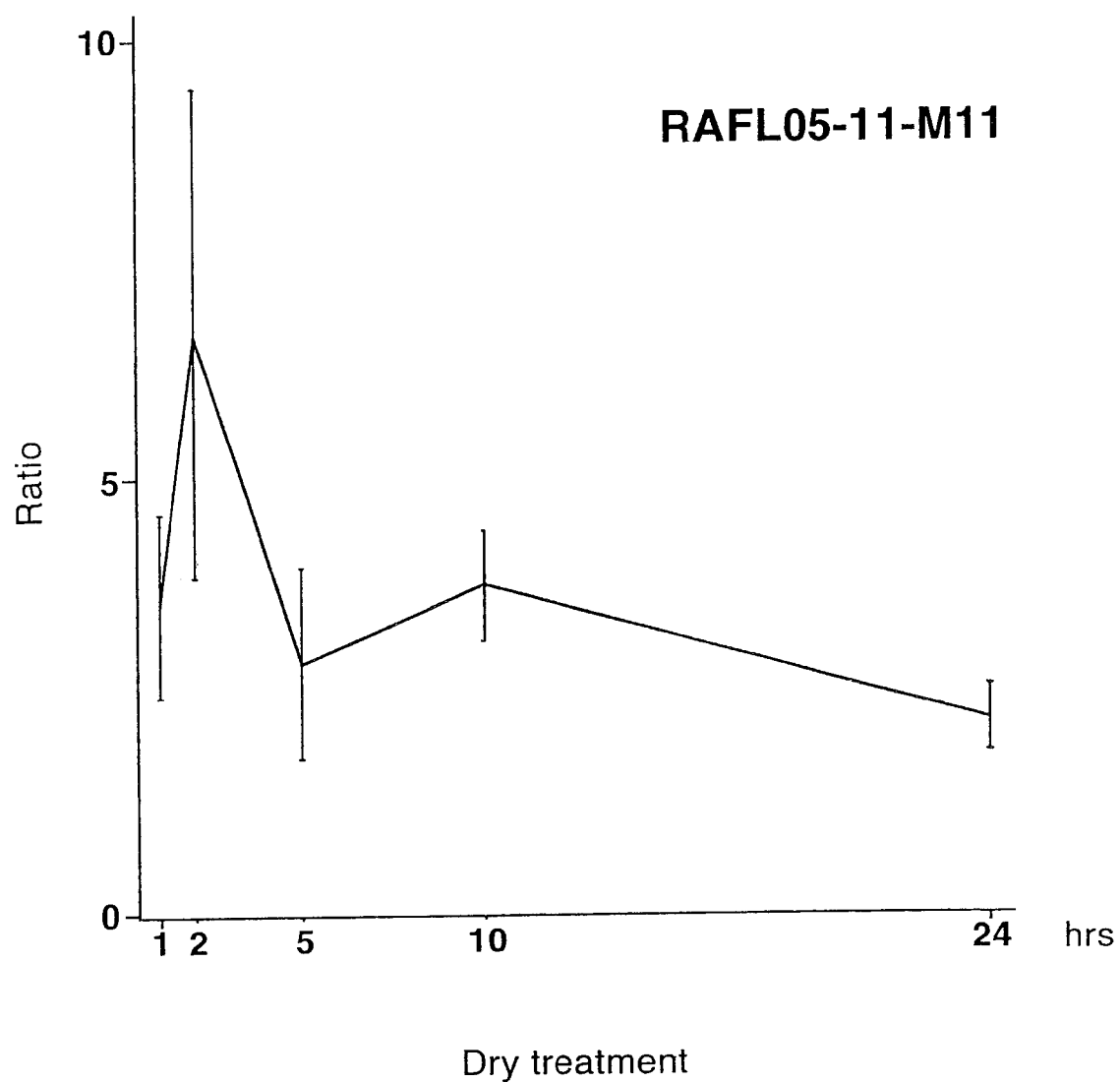
FIG. 107 is a characteristic graph showing the relationship between drought stress and expression ratio regarding RAFL05-11-M11.
Figure 108:
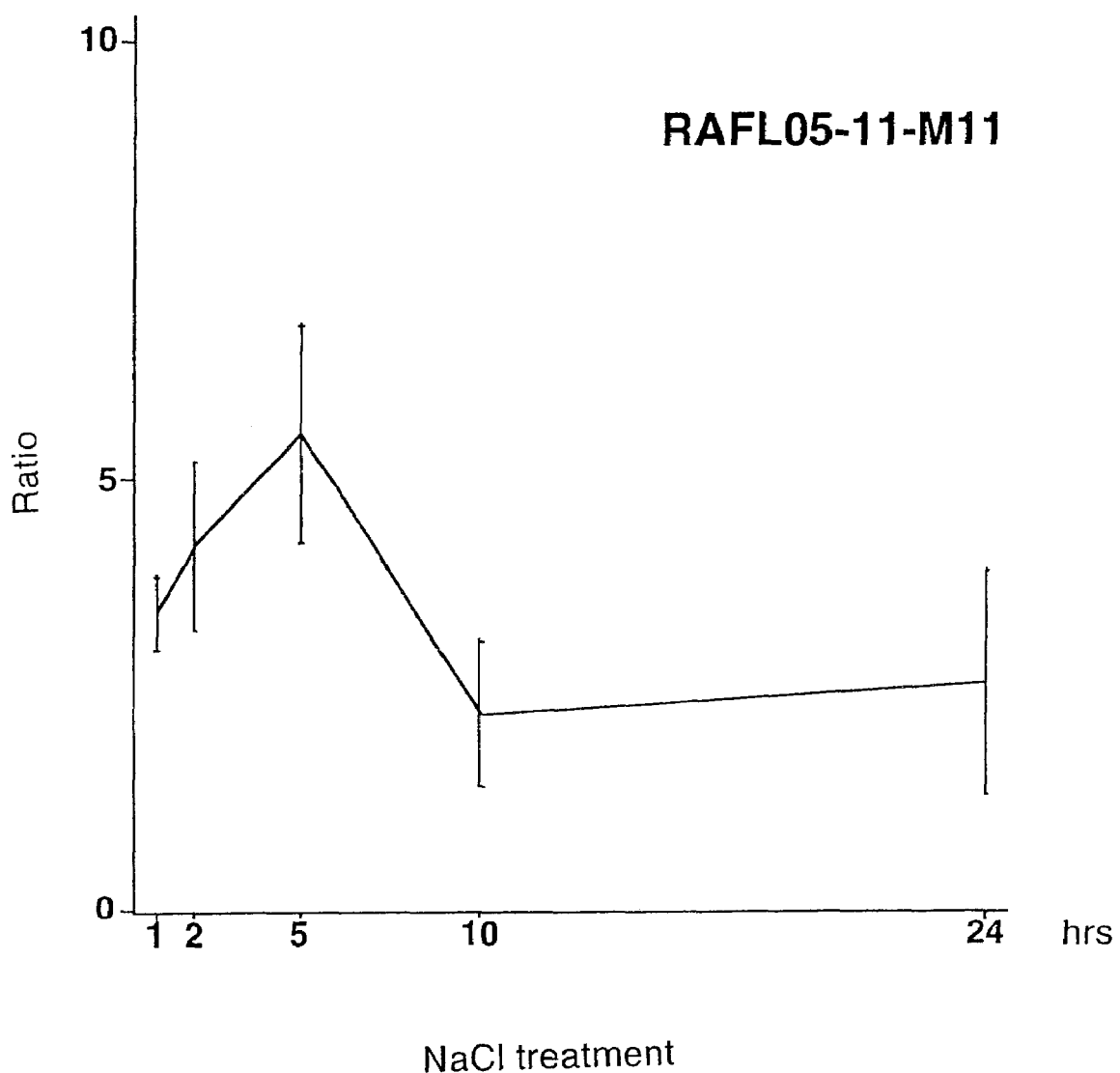
FIG. 108 is a characteristic graph showing the relationship between high salt stress and expression ratio regarding RAFL05-11-M11.
Figure 109:
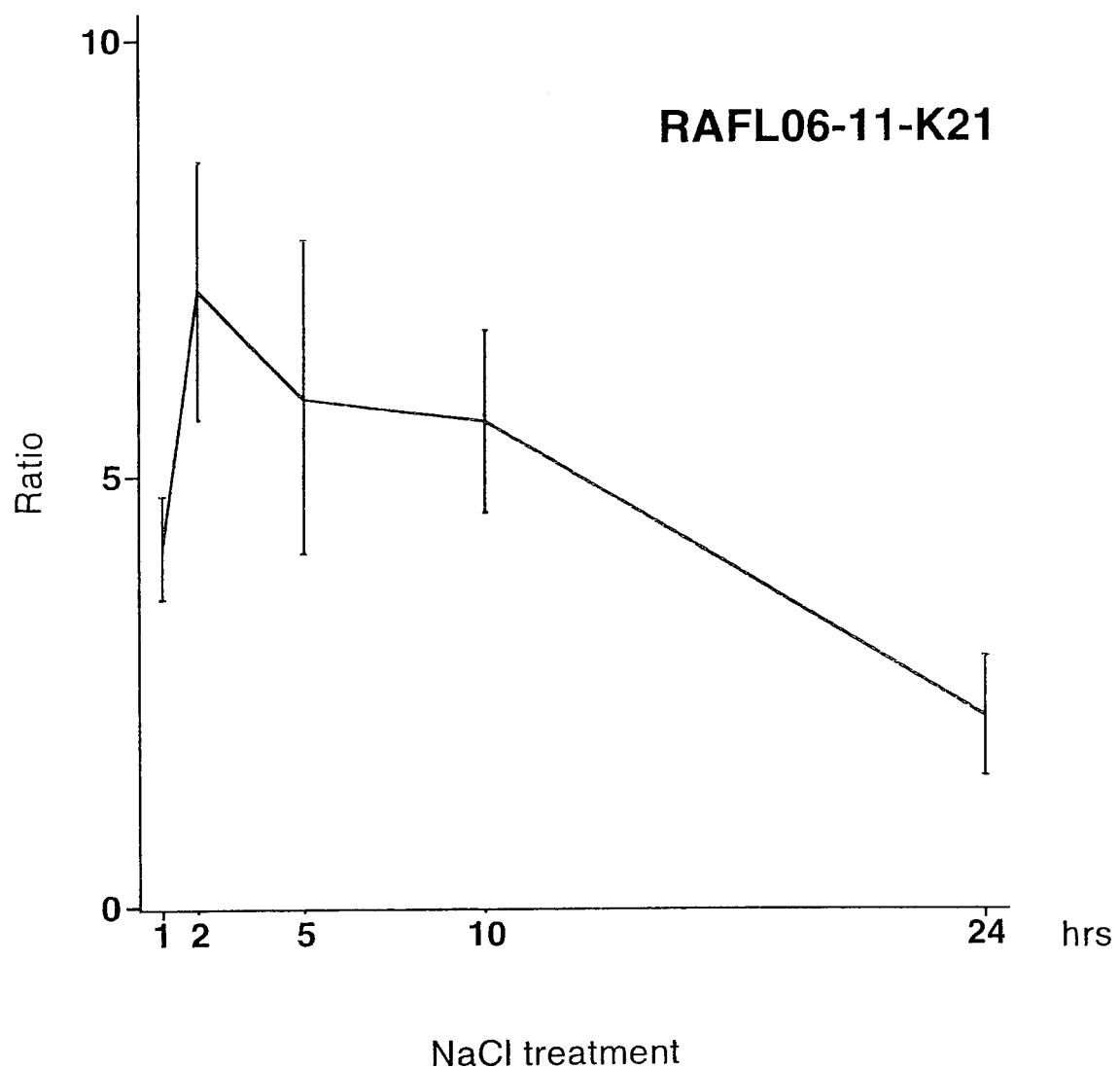
FIG. 109 is a characteristic graph showing the relationship between high salt stress and expression ratio regarding RAFL06-11-K21.
Figure 110:
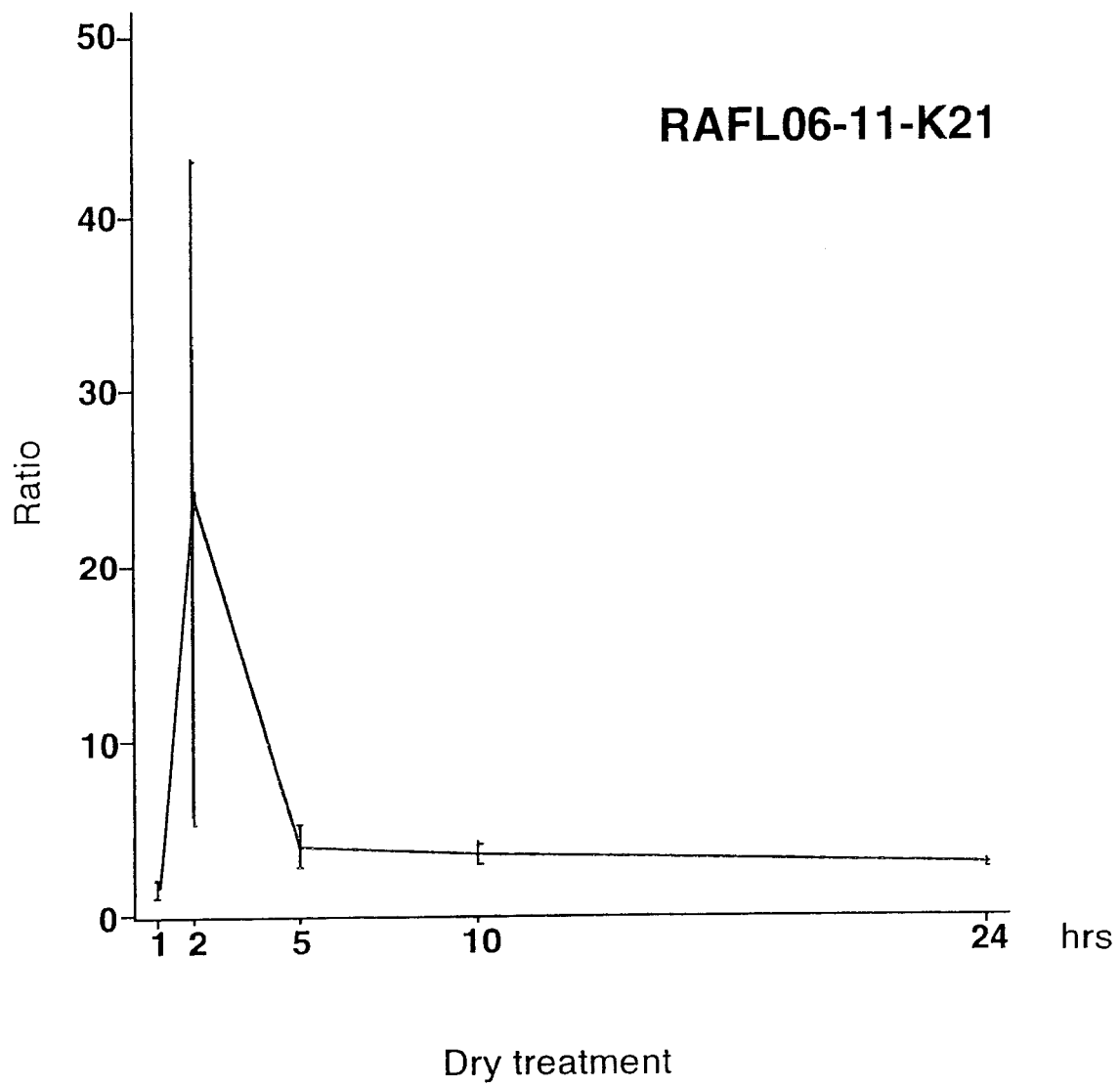
FIG. 110 is a characteristic graph showing the relationship between drought stress and expression ratio regarding RAFL06-11-K21.
Figure 111:
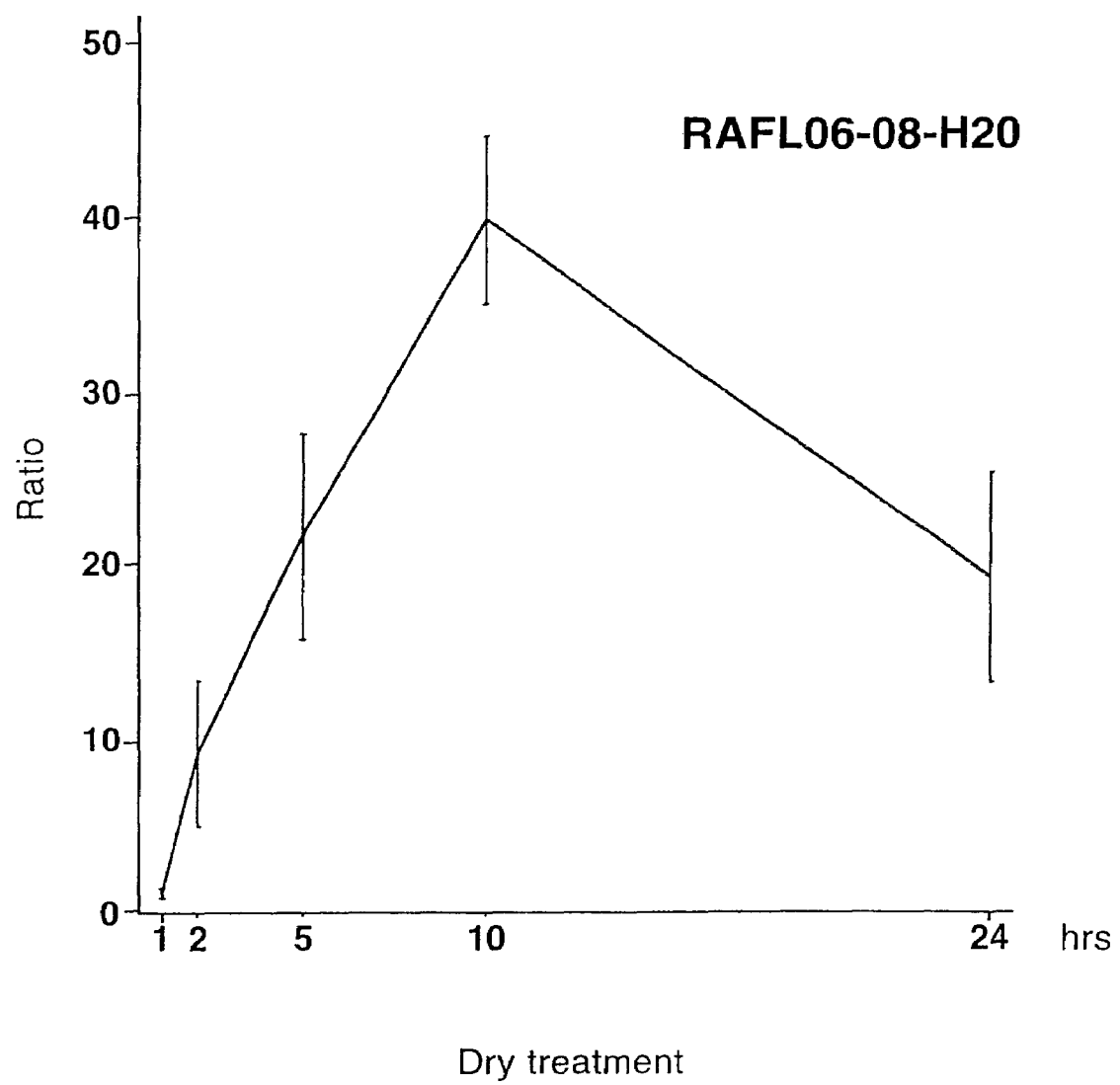
FIG. 111 is a characteristic graph showing the relationship between drought stress and expression ratio regarding RAFL06-08-H20.
Figure 112:
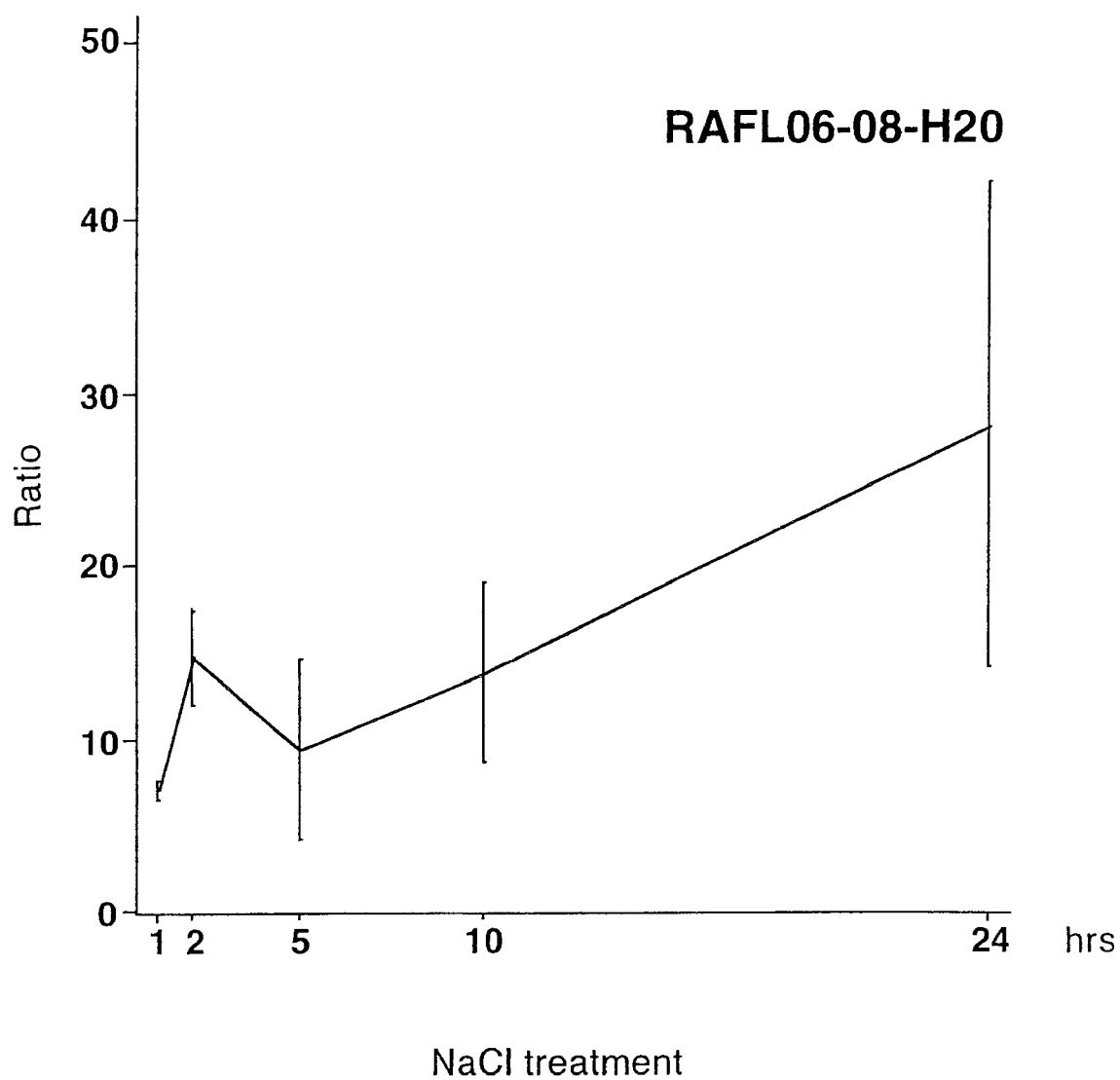
FIG. 112 is a characteristic graph showing the relationship between high salt stress and expression ratio regarding RAFL06-08-H20.
Figure 113:
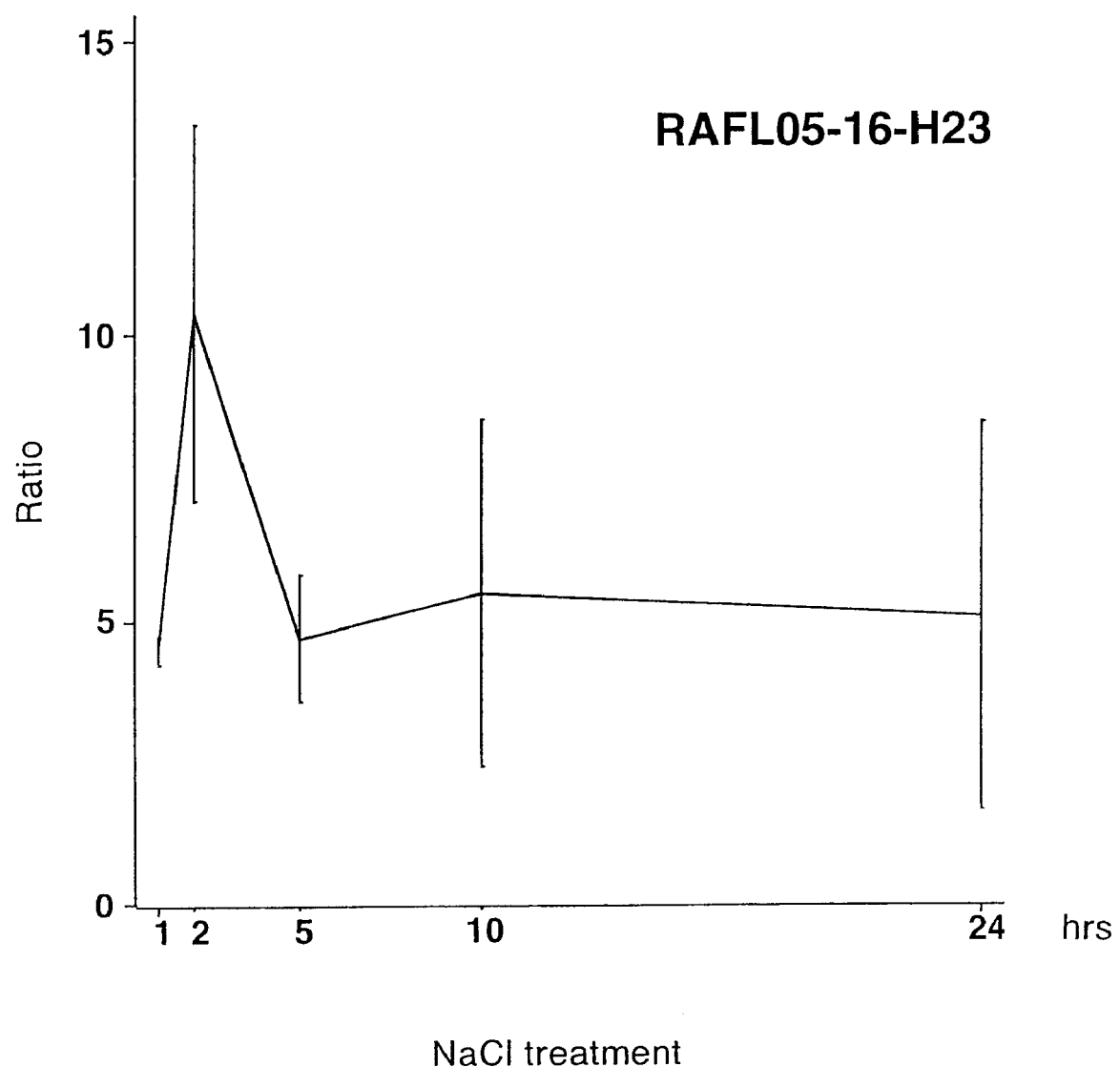
FIG. 113 is a characteristic graph showing the relationship between high salt stress and expression ratio regarding RAFL05-16-H23.
Figure 114:
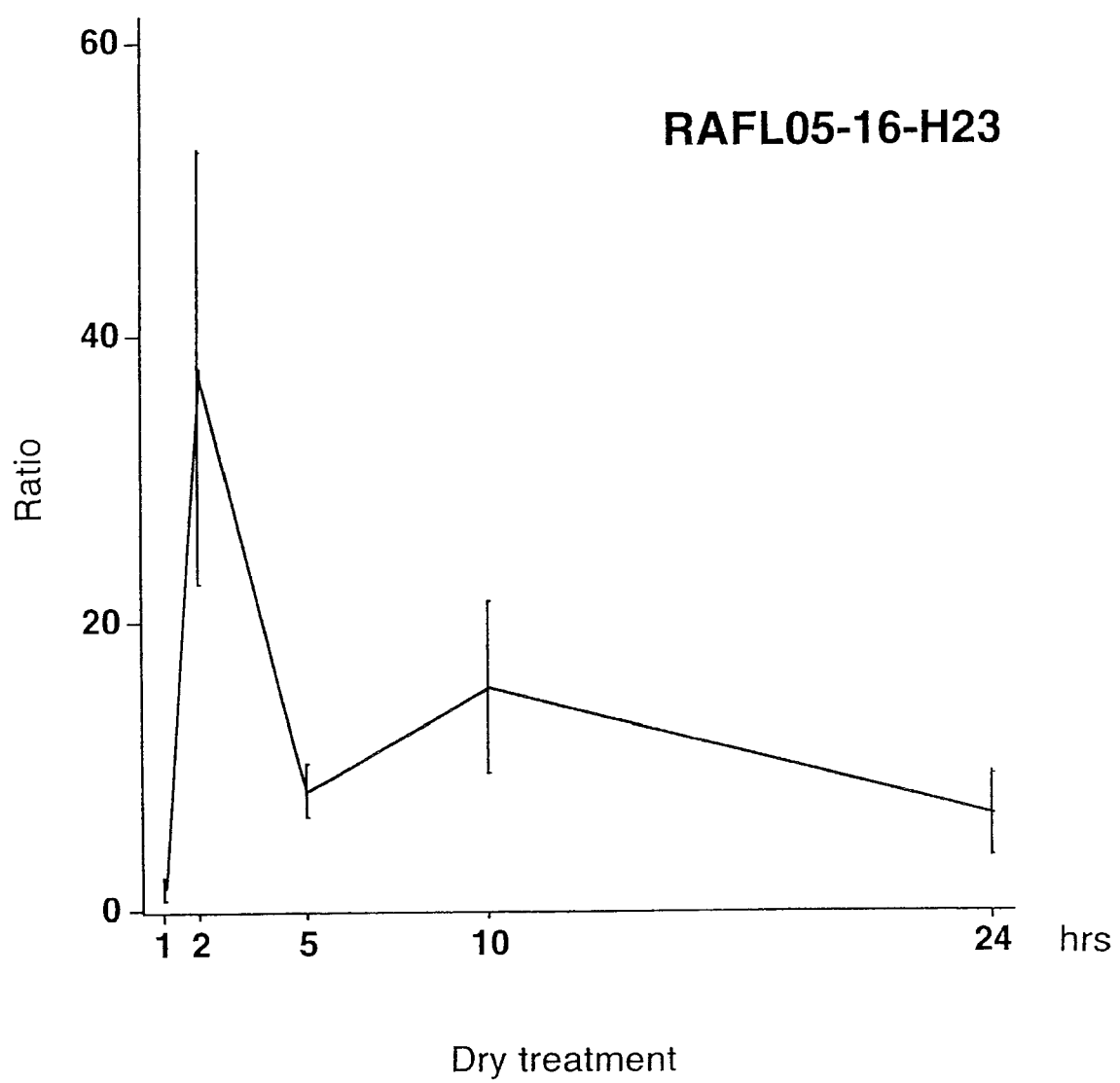
FIG. 114 is a characteristic graph showing the relationship between drought stress and expression ratio regarding RAFL05-16-H23.
Figure 115:
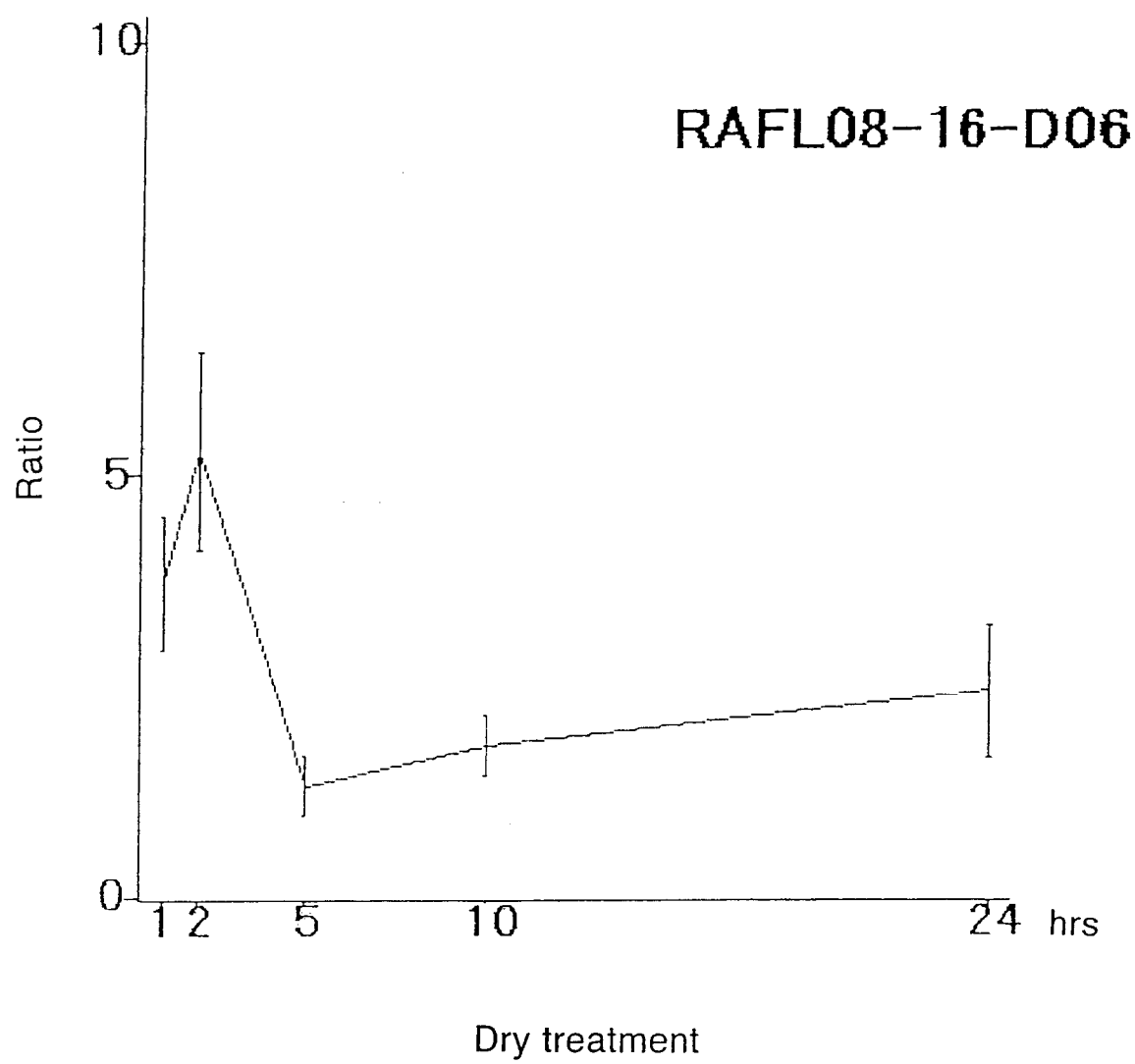
FIG. 115 is a characteristic graph showing the relationship between drought stress and expression ratio regarding RAFL08-16-D06.
Figure 116:
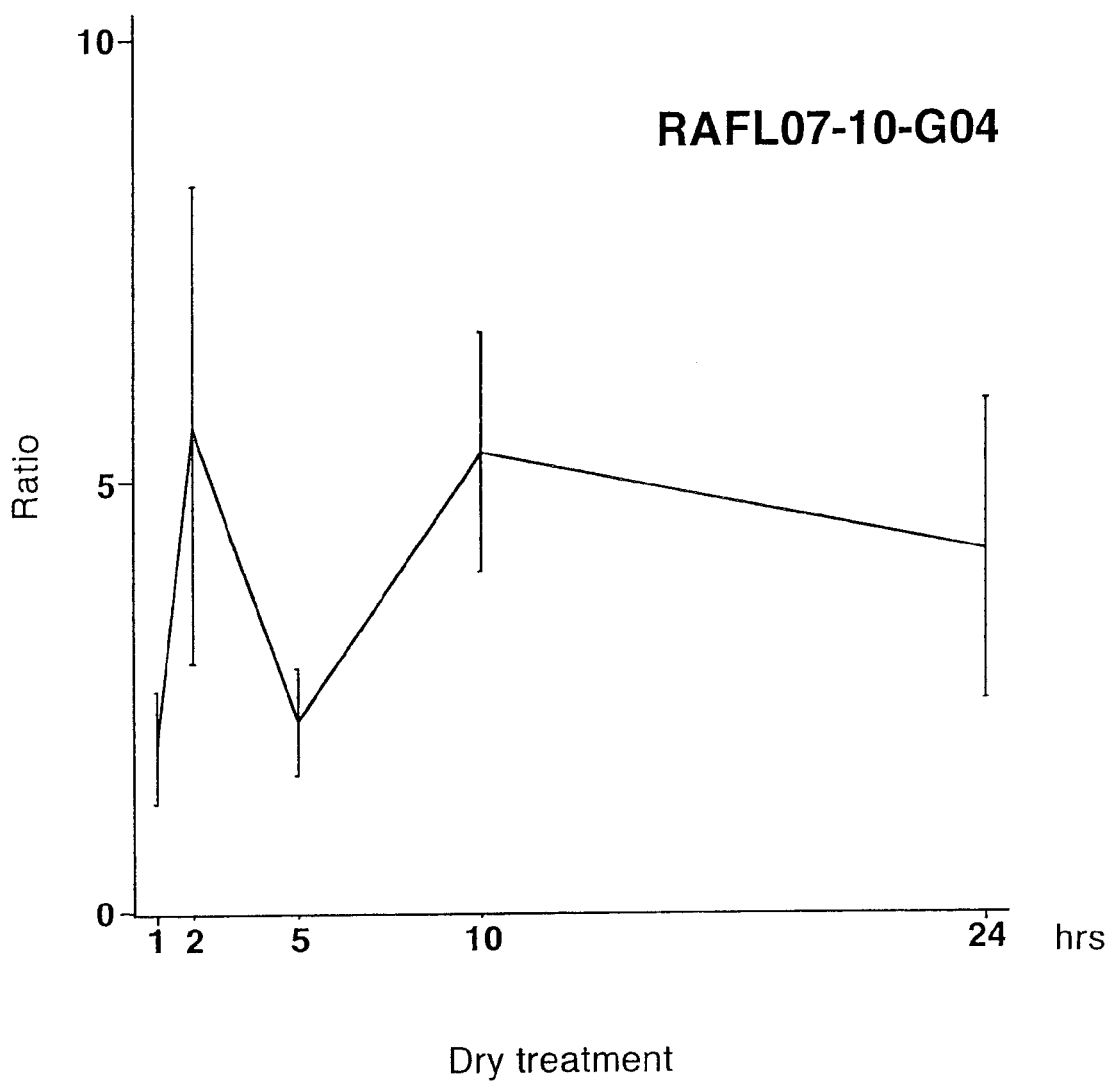
FIG. 116 is a characteristic graph showing the relationship between drought stress and expression ratio regarding RAFL07-10-G04.
Figure 117:
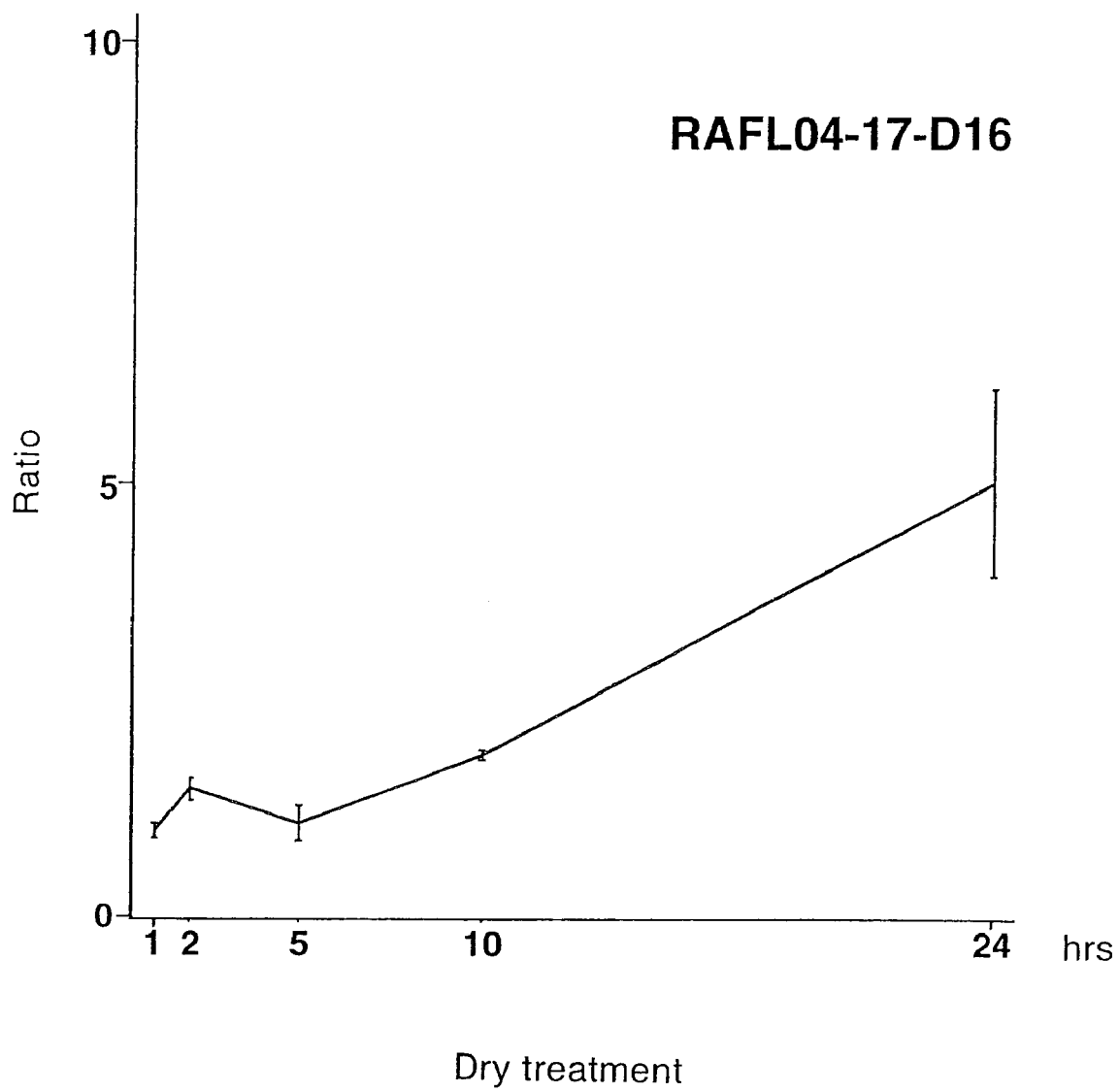
FIG. 117 is a characteristic graph showing the relationship between drought stress and expression ratio regarding RAFL04-17-D16.
Figure 118:
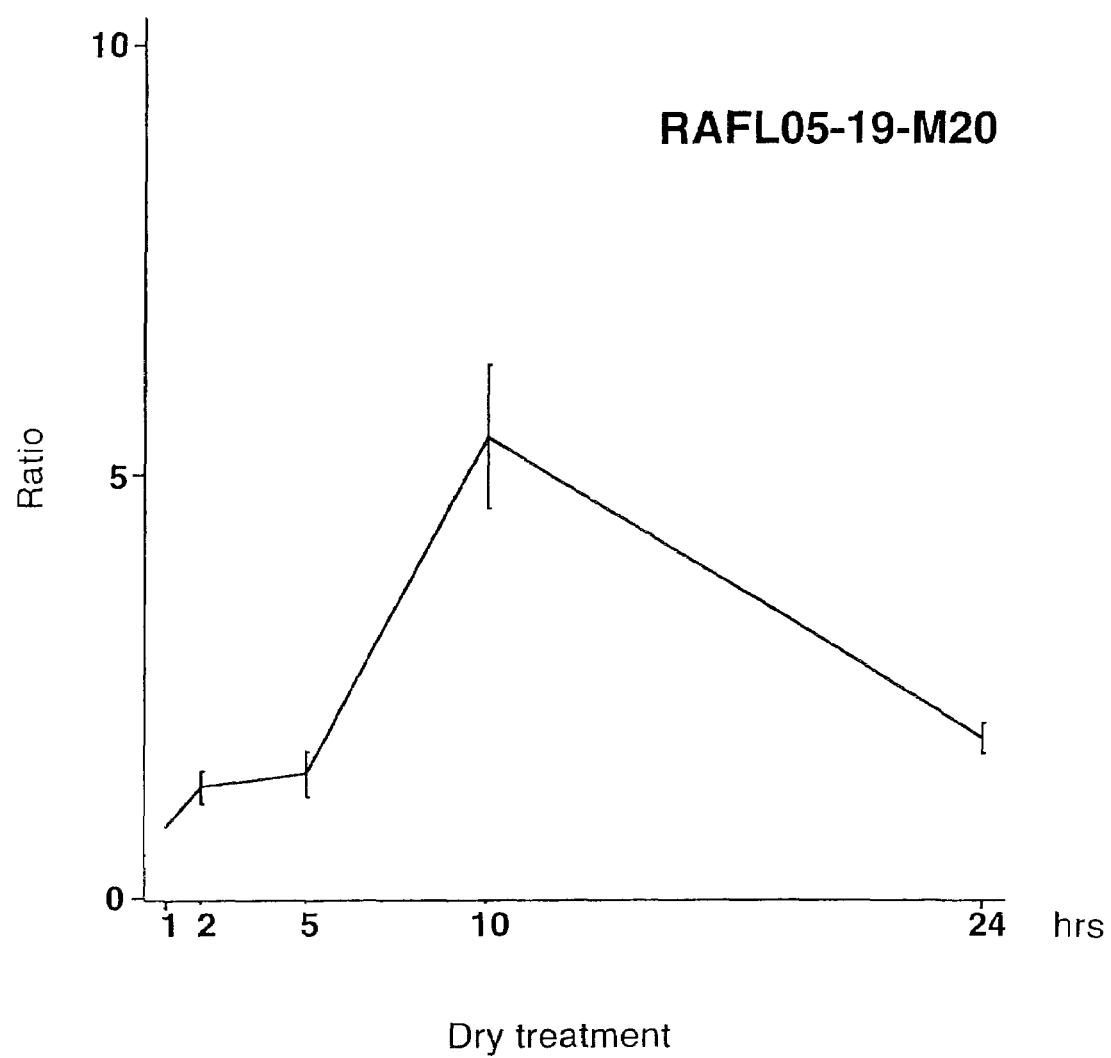
FIG. 118 is a characteristic graph showing the relationship between drought stress treatment time and expression ratio regarding RAFL05-19-M20.
Figure 119:
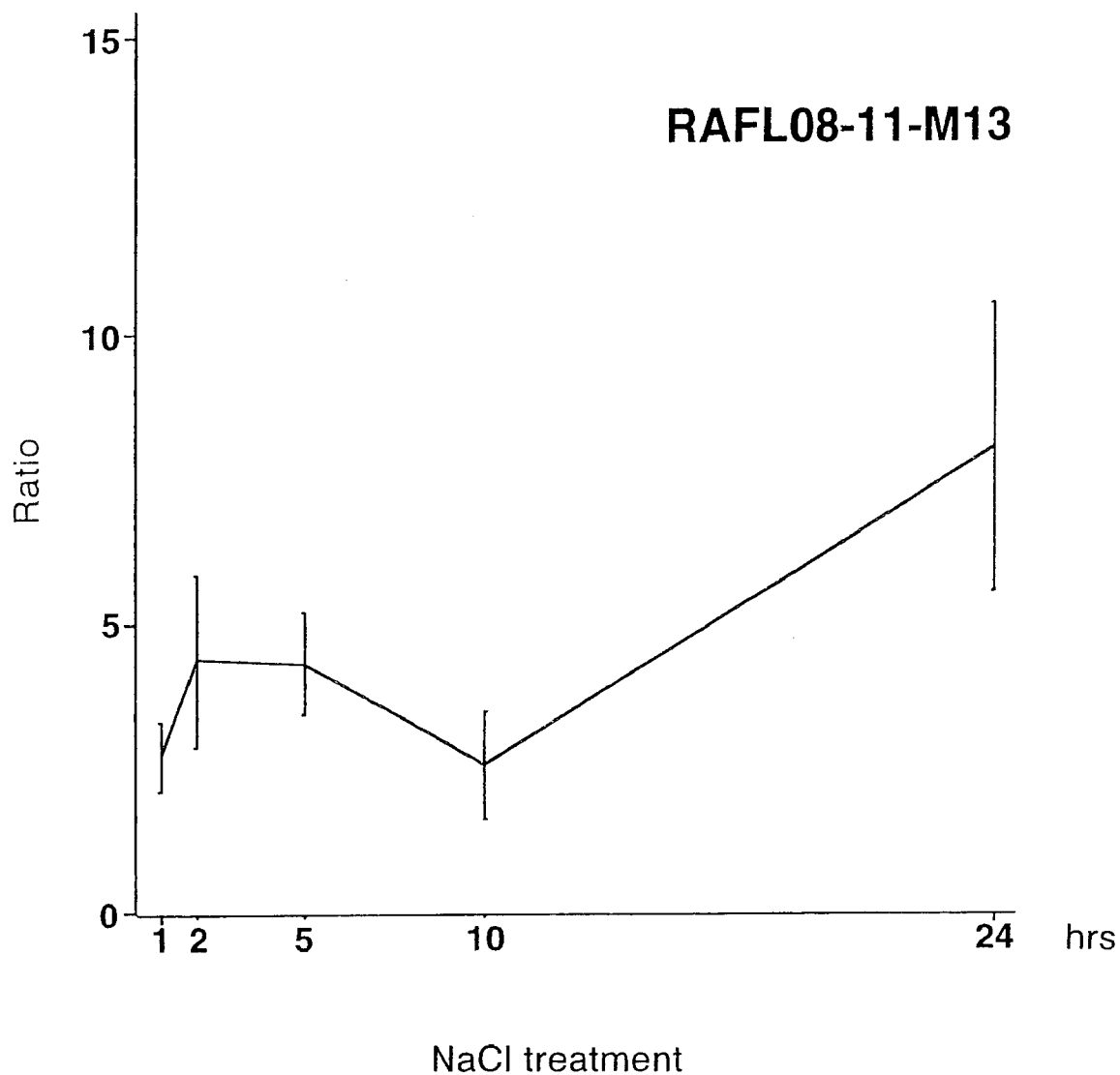
FIG. 119 is a characteristic graph showing the relationship between high salt stress and expression ratio regarding RAFL08-11-M13.
Figure 120:
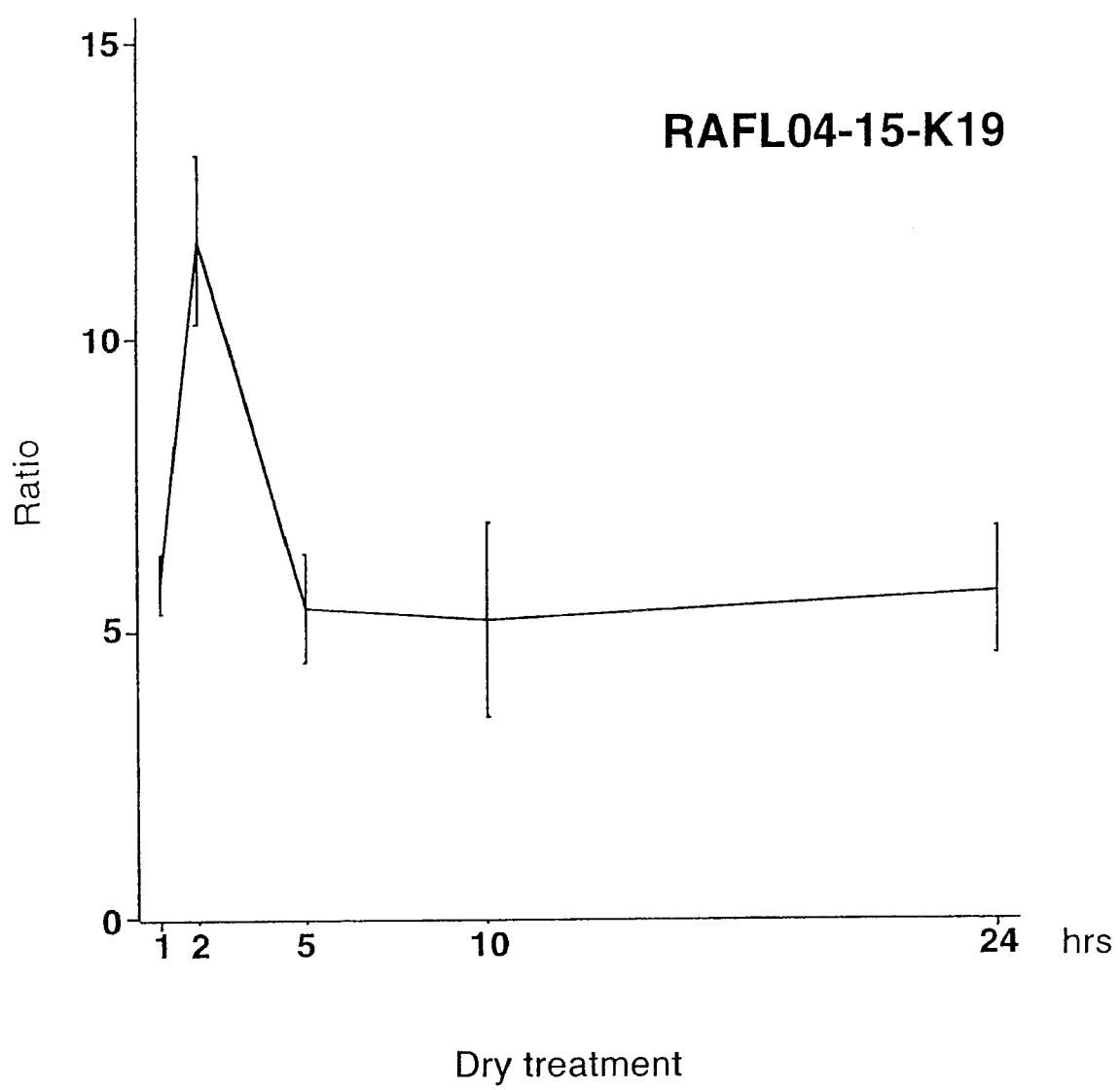
Figure 121:
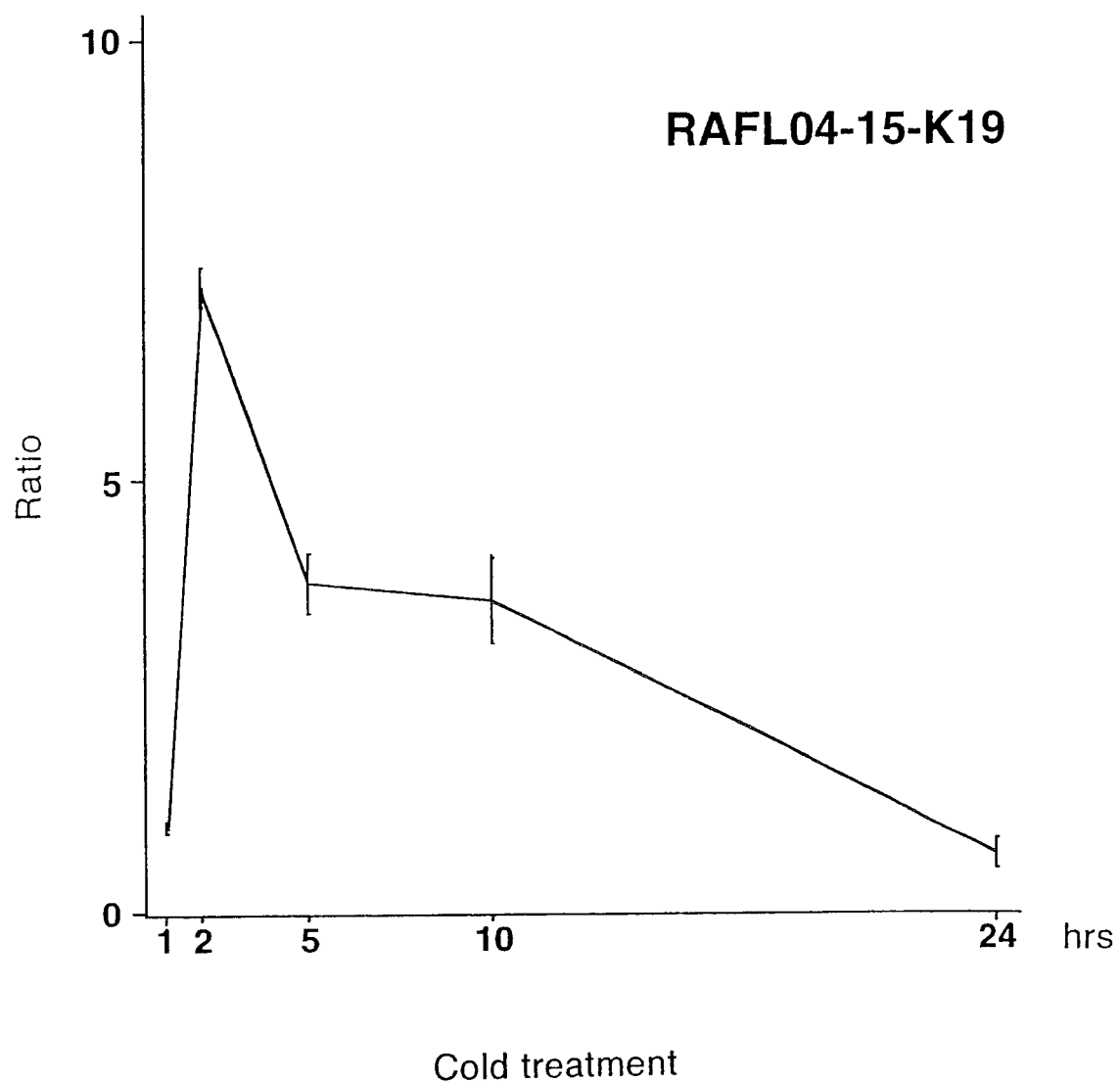
Figure 122:
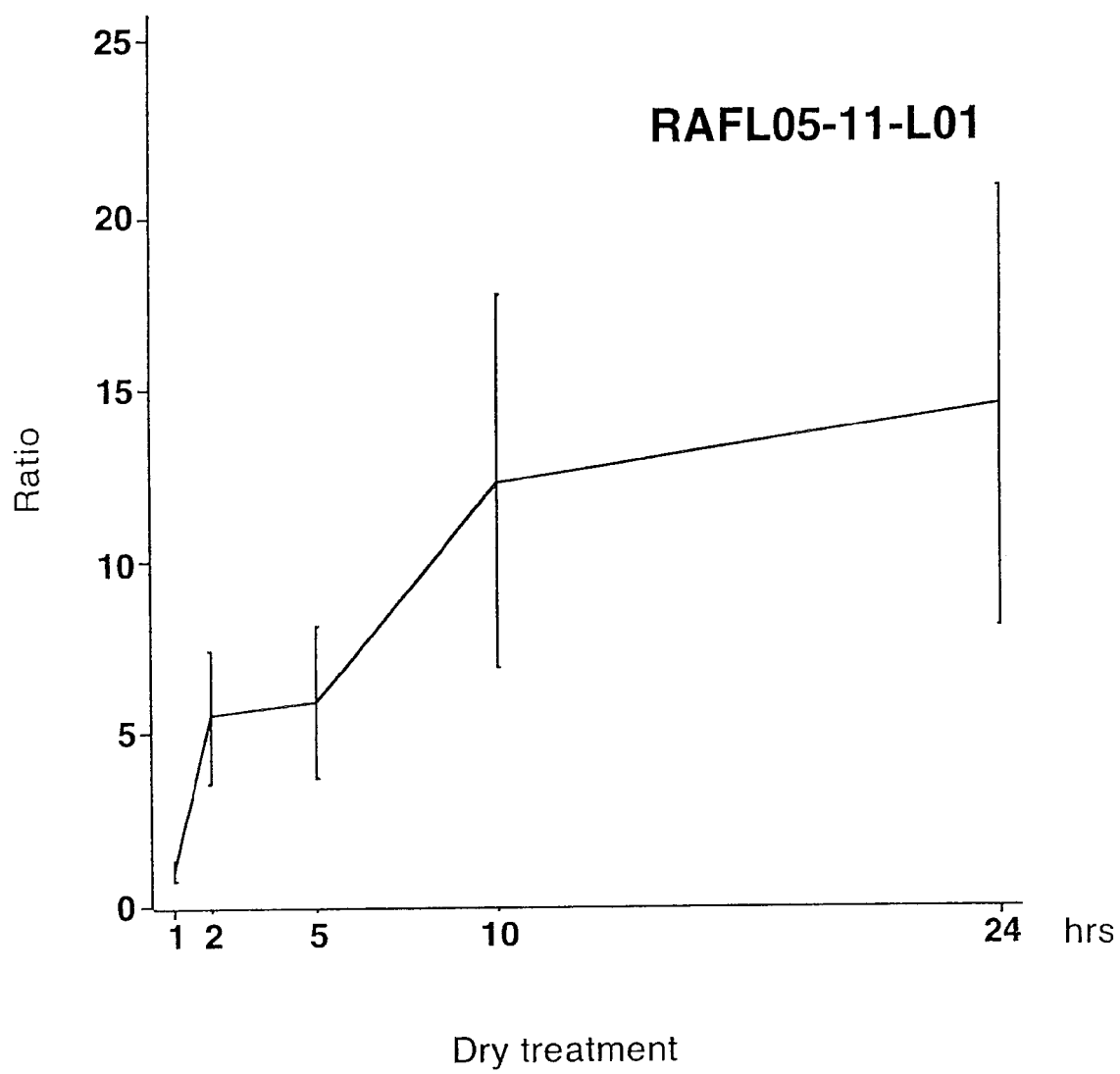
Figure 123:
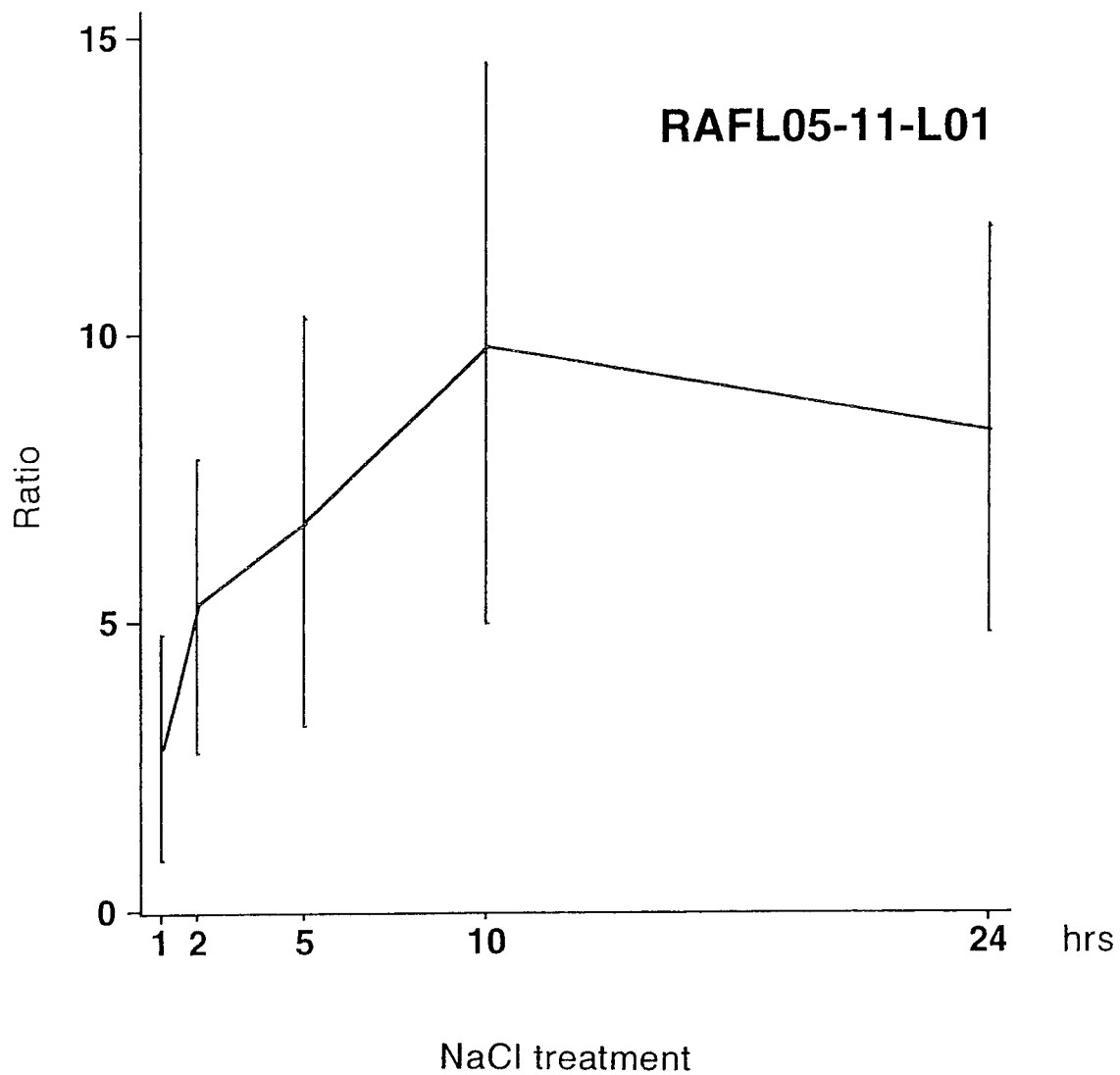
Figure 124:
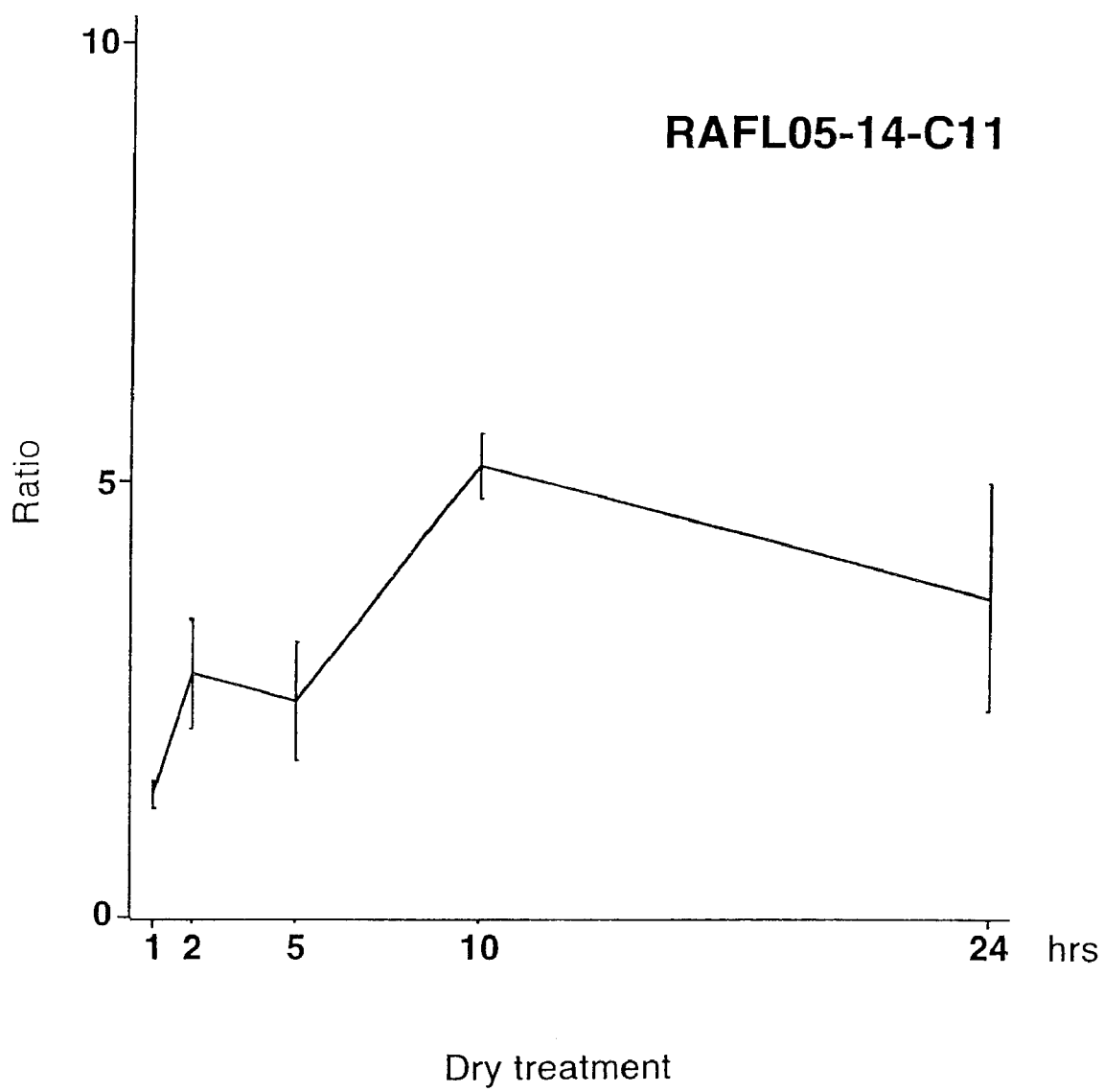
Figure 125:
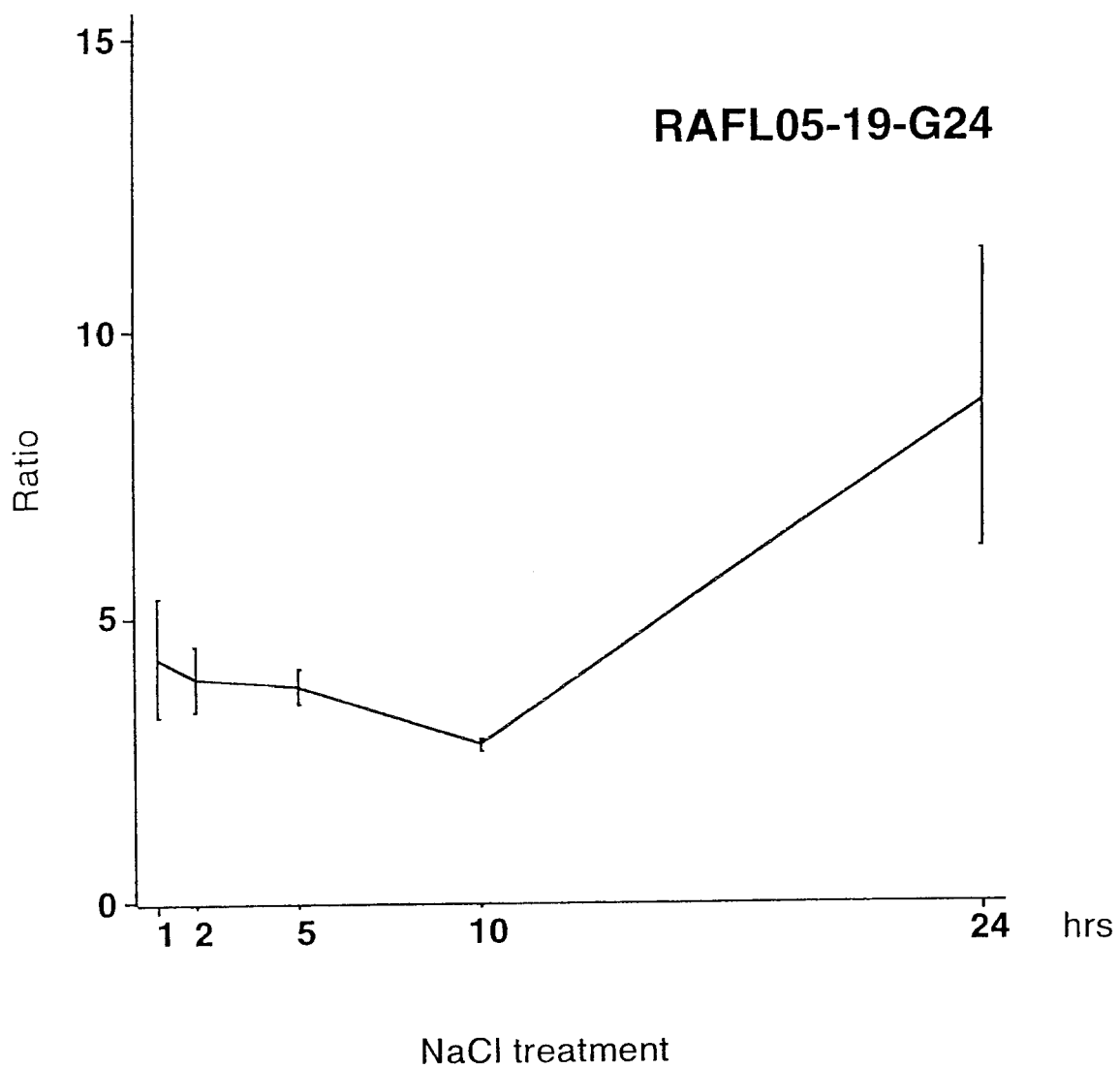
Figure 126:
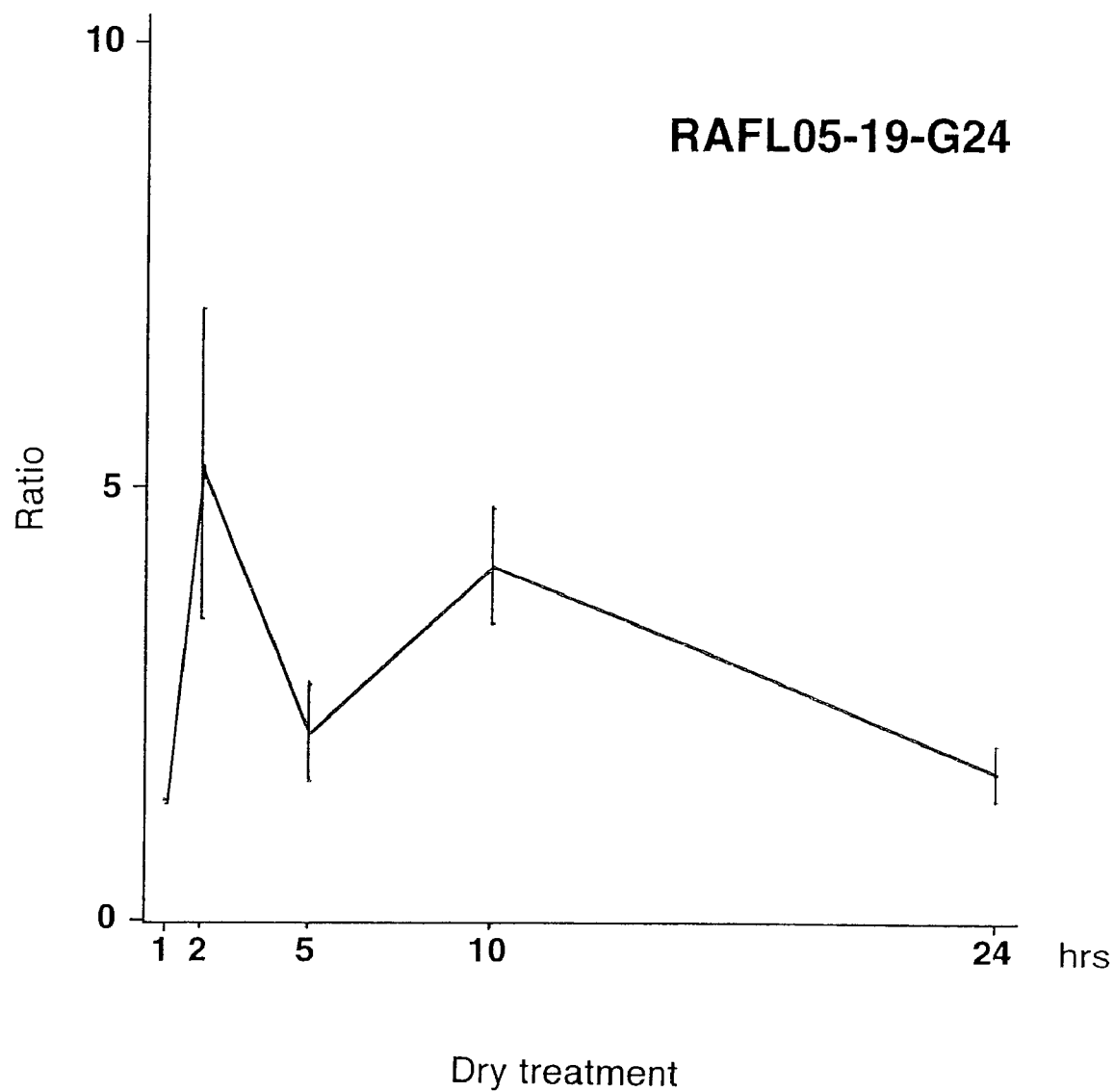
Figure 127:
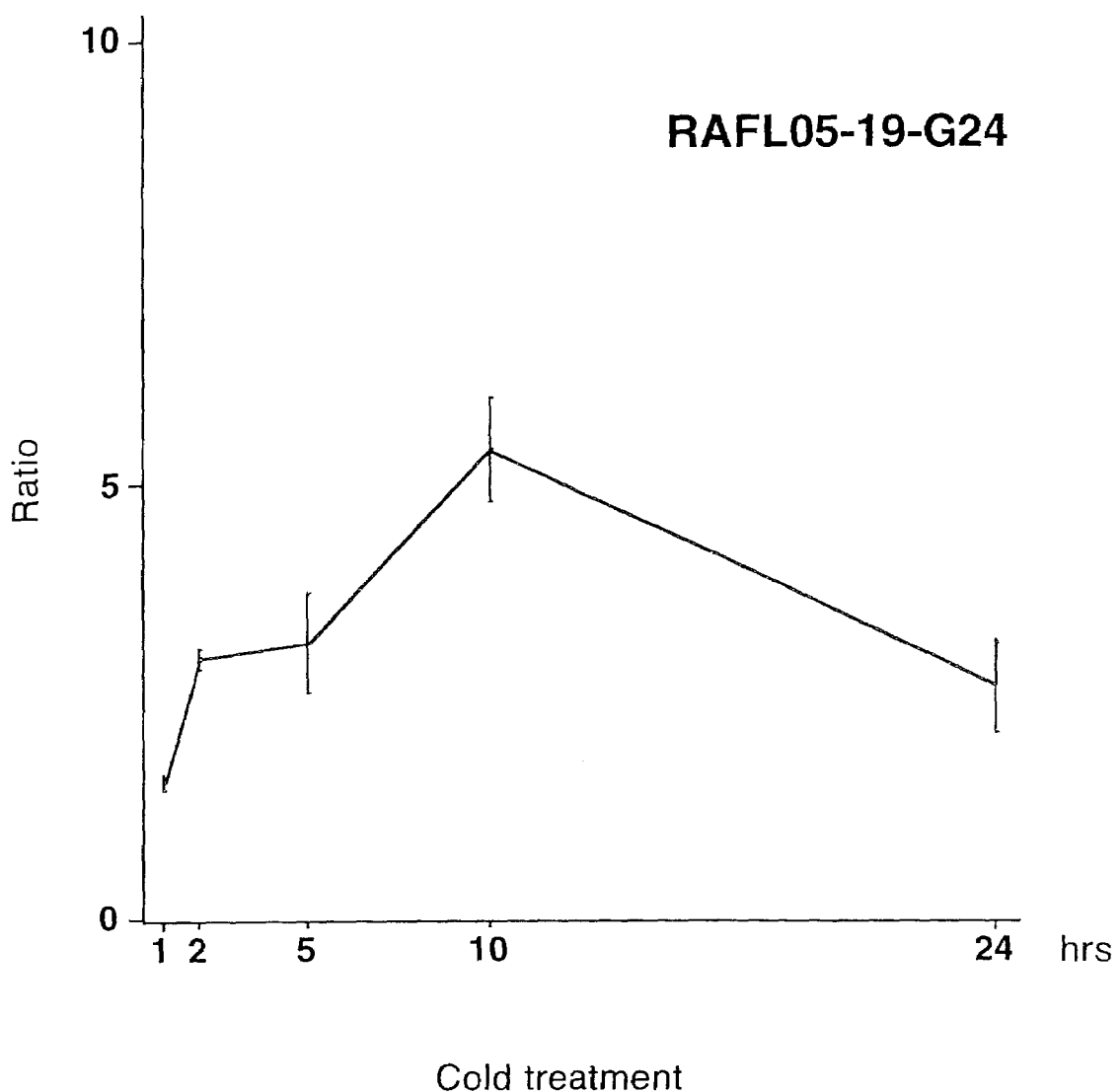
Figure 128:
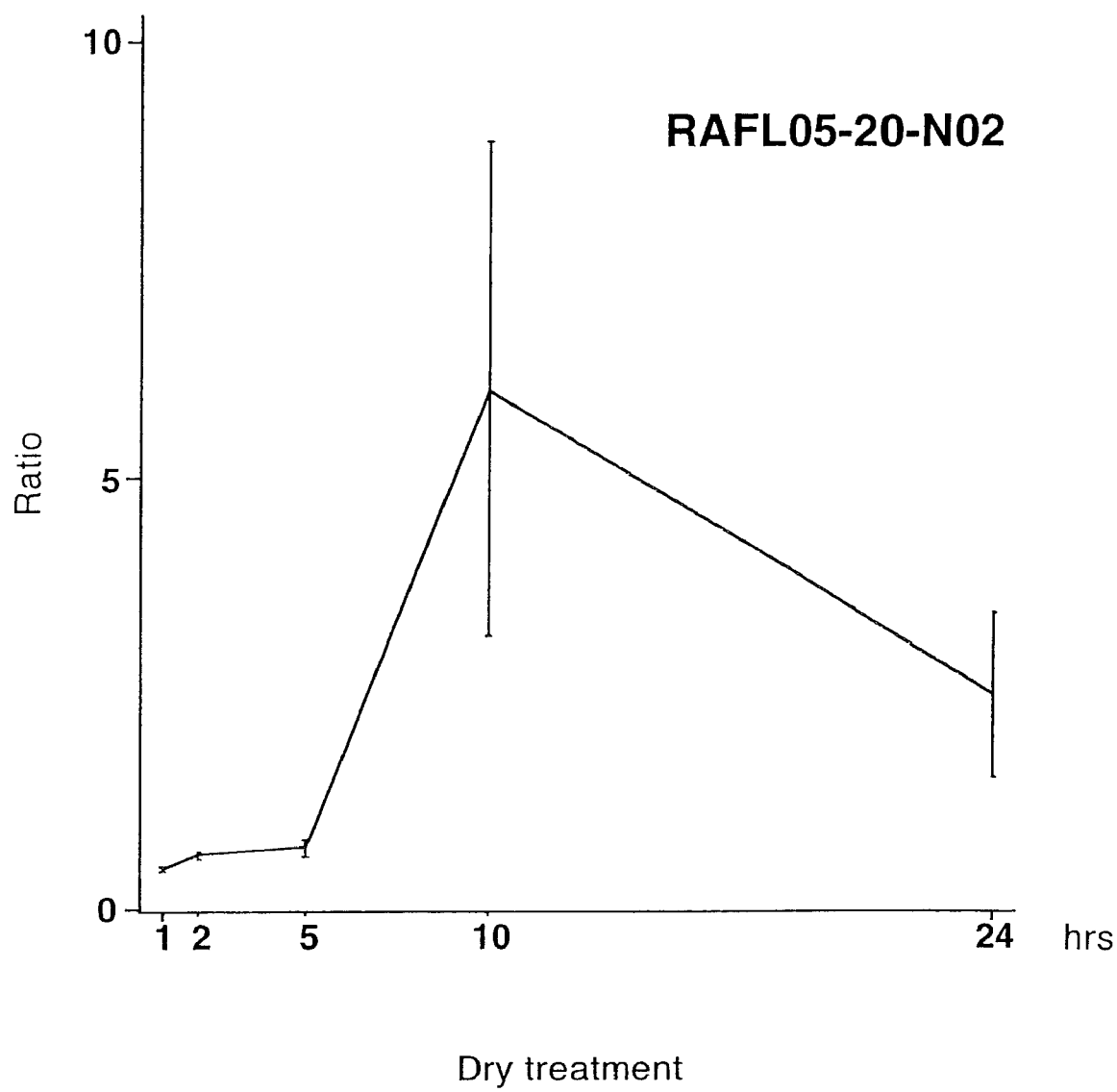
Figure 129:
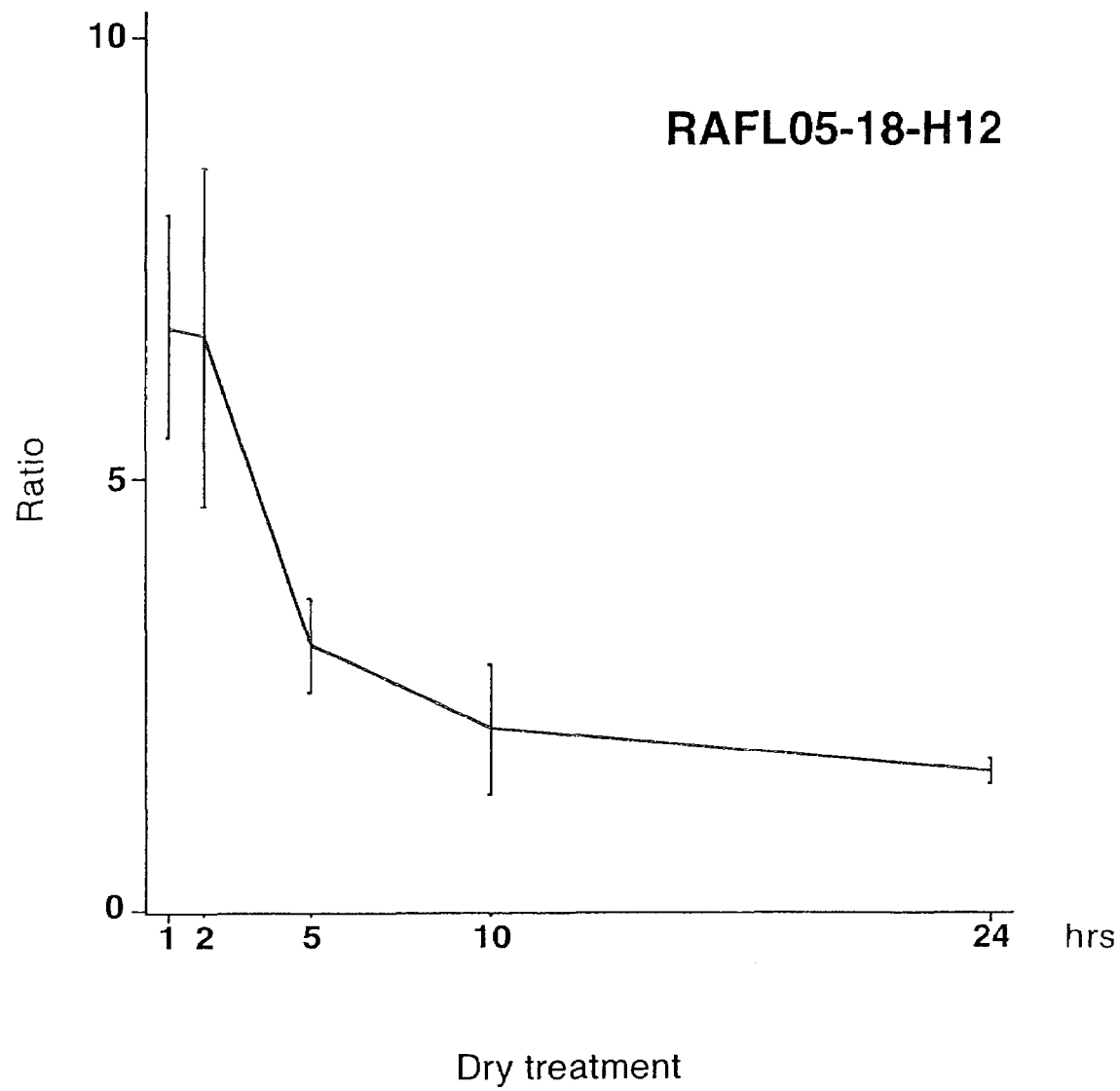
Figure 130:
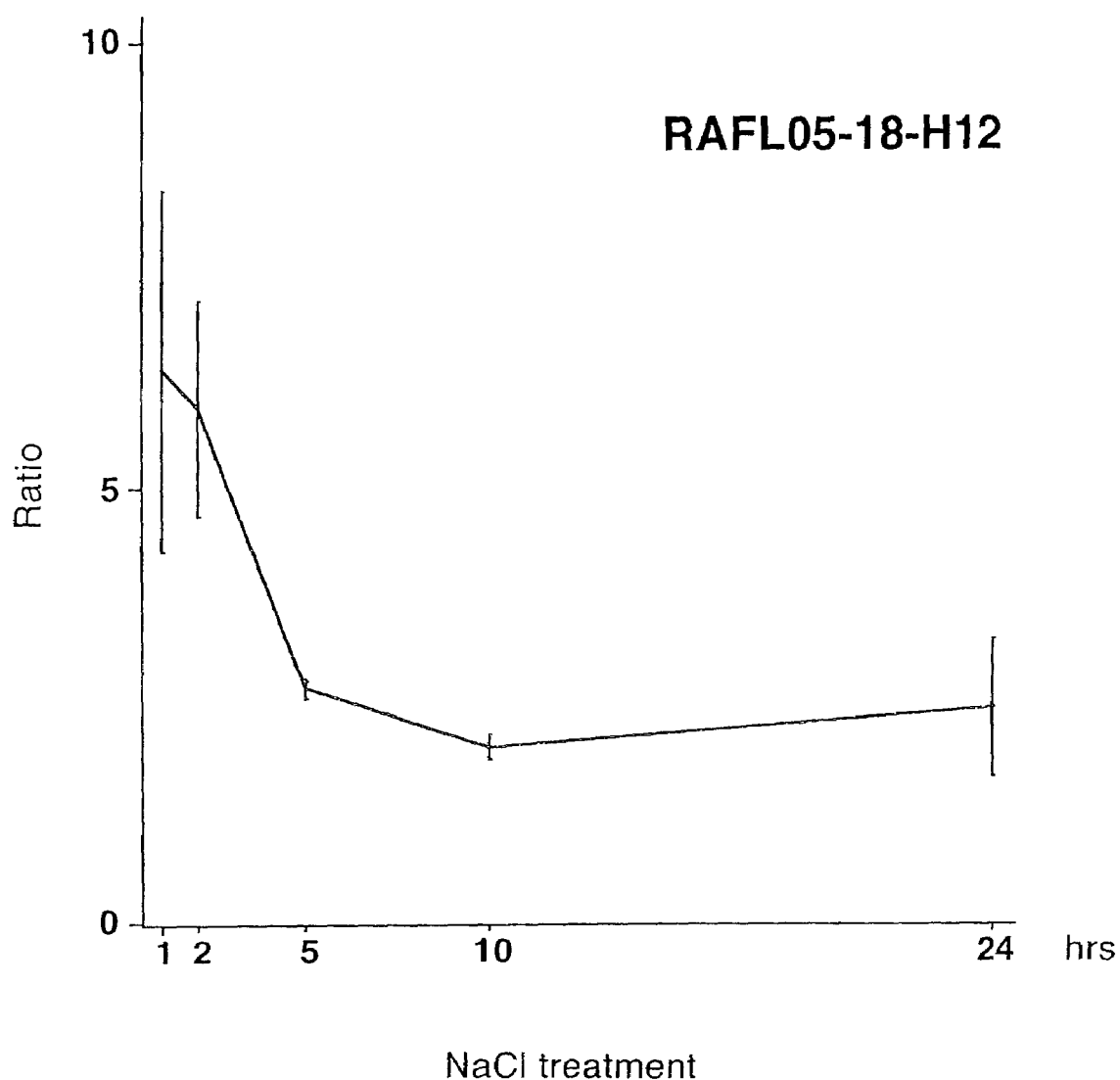
Figure 131:
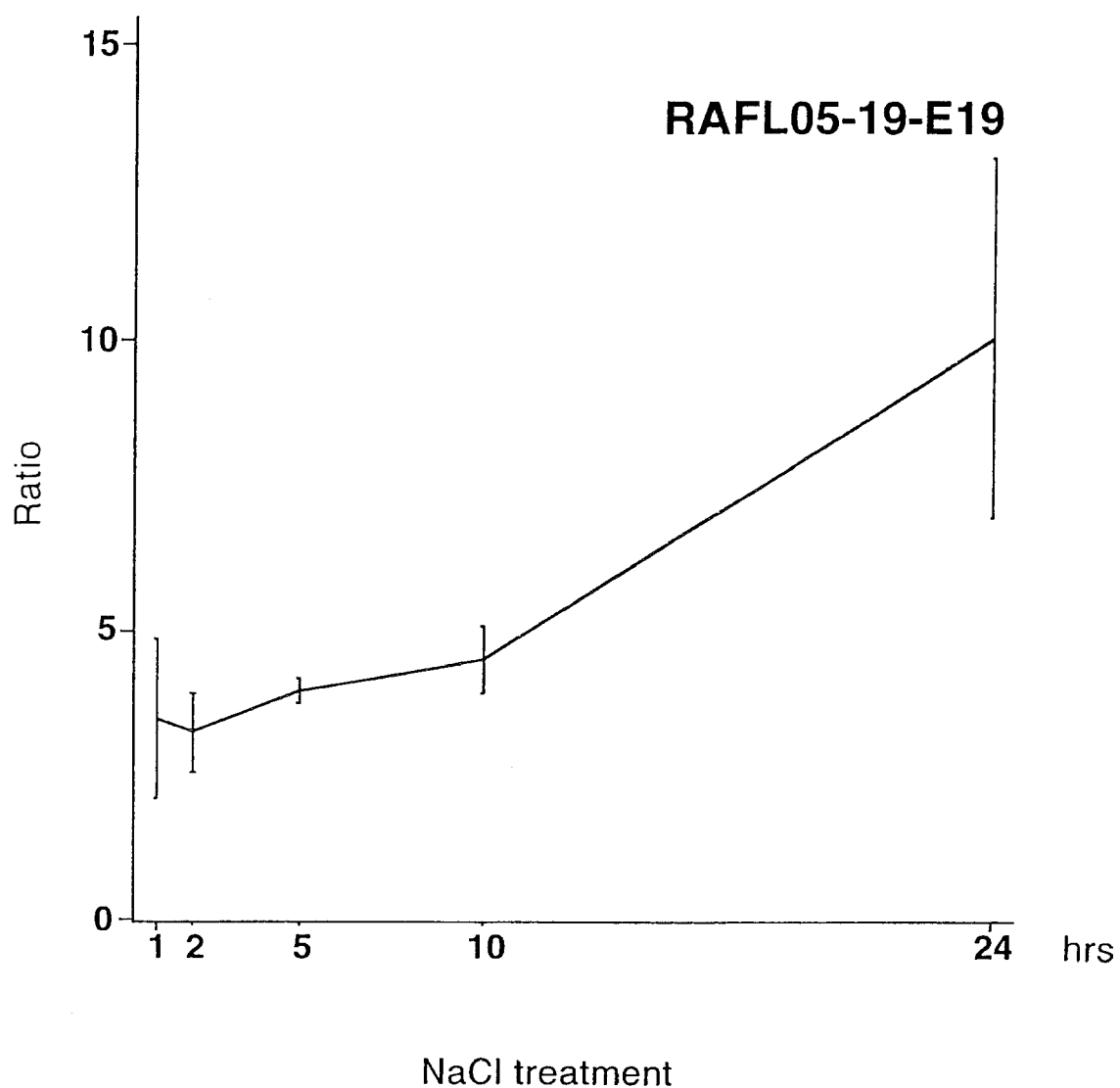

| Number of figure | Name of gene | Type of stress |
|---|---|---|
| FIG. 106 | RAFL08-16-G17 | High level salt solution |
| FIG. 107 | RAFL05-11-M11 | Dehydration |
| FIG. 108 | RAFL05-11-M11 | High level salt solution |
| FIG. 109 | RAFL06-11-K21 | High level salt solution |
| FIG. 110 | RAFL06-11-K21 | Dehydration |
| FIG. 111 | RAFL06-08-H20 | Dehydration |
| FIG. 112 | RAFL06-08-H20 | High level salt solution |
| FIG. 113 | RAFL05-16-H23 | High level salt solution |
| FIG. 114 | RAFL05-16-H23 | Dehydration |
| FIG. 115 | RAFL08-16-D06 | Dehydration |
| FIG. 116 | RAFL07-10-G04 | Dehydration |
| FIG. 117 | RAFL04-17-D16 | Dehydration |
| FIG. 118 | RAFL05-19-M20 | Dehydration |
| FIG. 119 | RAFL08-11-M13 | High level salt solution |
| FIG. 120 | RAFL04-15-K19 | Dehydration |
| FIG. 121 | RAFL04-15-K19 | Cold |
| FIG. 122 | RAFL05-11-L01 | Dehydration |
| FIG. 123 | RAFL05-11-L01 | High level salt solution |
| FIG. 124 | RAFL05-14-C11 | Dehydration |
| FIG. 125 | RAFL05-19-G24 | High level salt solution |
| FIG. 126 | RAFL05-19-G24 | Dehydration |
| FIG. 127 | RAFL05-19-G24 | Cold |
| FIG. 128 | RAFL05-20-N02 | Dehydration |
| FIG. 129 | RAFL05-18-H12 | Dehydration |
| FIG. 130 | RAFL05-18-H12 | High level salt solution |
| FIG. 131 | RAFL05-19-E19 | High level salt solution |
| FIG. 132 | RAFL06-10-D22 | High level salt solution |
| FIG. 133 | RAFL06-12-M01 | High level salt solution |
| FIG. 134 | RAFL06-12-M01 | Dehydration |

TABLE 5-continued

| Number of figure | Name of gene | Type of stress |
|---|---|---|
| FIG. 135 | RAFL05-14-D24 | Dehydration |
| FIG. 136 | RAFL05-14-D24 | High level salt solution |
| FIG. 137 | RAFL05-20-N17 | Cold |
| FIG. 138 | RAFL05-20-N17 | Dehydration |
| FIG. 139 | RAFL04-17-F21 | Dehydration |
| FIG. 140 | RAFL09-12-N16 | Dehydration |
| FIG. 141 | RAFL05-19-I05 | Dehydration |
| FIG. 142 | RAFL05-19-I05 | High level salt solution |
| FIG. 143 | RAFL05-21-I22 | High level salt solution |
| FIG. 144 | RAFL08-11-H20 | Dehydration |
| FIG. 145 | RAFL08-11-H20 | High level salt solution |
| FIG. 146 | RAFL05-21-C17 | High level salt solution |
| FIG. 147 | RAFL05-21-C17 | Dehydration |
| FIG. 148 | RAFL05-08-D06 | High level salt solution |
| FIG. 149 | RAFL05-20-M16 | Dehydration |
| FIG. 150 | RAFL05-20-M16 | High level salt solution |
| FIG. 151 | RAFL11-01-J18 | Dehydration |
| FIG. 152 | RAFL11-01-J18 | High level salt solution |
| FIG. 153 | RAFL11-09-C20 | High level salt solution |
| FIG. 154 | RAFL05-18-N16 | High level salt solution |
| FIG. 155 | RAFL11-10-D10 | Dehydration |
| FIG. 156 | RAFL11-10-D10 | High level salt solution |
| FIG. 157 | RAFL04-17-N22 | Dehydration |
| FIG. 158 | RAFL04-17-N22 | High level salt solution |
| FIG. 159 | RAFL05-09-G15 | Dehydration |
| FIG. 160 | RAFL05-09-G15 | High level salt solution |
| FIG. 161 | RAFL05-21-L12 | Dehydration |
| FIG. 162 | RAFL05-21-L12 | High level salt solution |

In FIGS. 106 to 162, the vertical axis shows the expression ratio of a gene, which is calculated as follows:

Expression ratio=[(F1 of cDNA molecule under stress)/(F1 of cDNA molecule under no stress)]+[(F1 of control fragment under stress)/(F1 of control fragment under no stress)]

where F1 is the intensity of fluorescence.

As shown in FIGS. 106 to 162, the genes encoding stress responsive transcriptional factors isolated by a method according to the present invention exhibit different profiles; however, it is found that expression is induced by adding each stress.

INDUSTRIAL APPLICABILITY

A stress responsive promoter and an environmental stress responsive transcriptional factor are provided by the present invention. The promoter of the present invention is useful in that it can be used for breeding of environmental stress resistant plants in a molecular level.

Sequencing Free Text

SEQ ID NOS: 91, 92, 165 and 166 are synthetic primers.

The invention claimed is:

1. A method of regulating expression of a gene which comprises:
   (a) preparing a recombinant plant cell line, plant tissue or plant comprising an expression vector having an abiotic environmental stress-responsive promoter comprising SEQ ID NO: 27 which is operably linked to the coding sequence of the gene; and
   (b) culturing and cultivating the recombinant plant cell, plant tissue or plant under an abiotic environmental stress, wherein the promoter regulates the expression of the gene under the abiotic environmental stress.

2. The method according to claim 1, wherein the abiotic environmental stress is cold stress, drought stress or salt stress.

3. The method according to claim 1, wherein the gene encodes a polypeptide that can confer increased environmental stress resistance compared to a plant cell line, plant tissue or plant lacking the expression vector.

4. A method according to claim 1, wherein the gene is a plant gene.

* * * * *

SEQUENCE LISTING

<160> NUMBER OF SEQ ID NOS: 166

<210> SEQ ID NO 1
<211> LENGTH: 1000
<212> TYPE: DNA
<213> ORGANISM: Arabidopsis thaliana

<400> SEQUENCE: 1

```
gagaatttta gaaaaagaag ttccgtgaat atcgcaaaca ttaaggcaag aacatttgca      60 aaaaaaaag agaaacaaat tcaacatcca gcagaactgc agaagtaatg ggggtgttta     120
gggcagaaga caagaacatt agcaaaaaaa aggtaaagat tgactggttc catatgcatt     180
catgtcatgc aaaatattga atcgaaccat cacaagcata aacattaagg atttctgtta     240
gacaaattaa cgttgtaagt actaaaacta gctagatttg tgattgtcac atatcaactt     300
gttctacata aagtttgtaa gagctaaaac tttaagcgtg agcttttttgt gaaacaaatg     360 aaagttagat attaaccgtt ctcttattct cgagatgatt ttcaatcgat ggttatgcta     420
caaagttggc tcgttcaata taatgagctc ttgtgtgttc aacatgaata catgatattt     480
ttgtgctcgt taaatactcg gttttttacga aatgaatttt tttaagagtt cgaacctaaa     540
acccgaactt gattgaccaa tgtacattca tagtagaata tttgctttgt acctgaatct     600
gcgtttatga aactacgtct aaagattgaa ccaaacaaat aaaccgagtt aaaccaaaat     660
ctagatccta ccaaatcaaa acgaatgaac attcaattta gaaaccaaaa aaataaaccg     720
gacattcctc attagattct ctatattatt cttttgtctg taattgcgtt tgtacaaaac     780
cacgtttgcg tttagattgt ttaaagatat ttattgaaaa aagaccgcg tgattaaaat     840
```

-continued

| | |
|---|---|
| gtgtaaagaa agttcctccg ttattaccgt ccaagtggat ctctaagaga ccgtacaact | 900 |
| aactccactc acggcggcgc attcccaatc tgctgacacg tttctgctta tcactctctc | 960 |
| tttttcttct cttcttacca cacctggttg actcaaccac | 1000 |

<210> SEQ ID NO 2
<211> LENGTH: 1000
<212> TYPE: DNA
<213> ORGANISM: Arabidopsis thaliana

<400> SEQUENCE: 2

| | |
|---|---|
| tatggtagaa aaatatgaga gagaatgatt atttacataa tgaaaagtga ttgaagttac | 60 |
| cttttaaatg taactaaatt acatgagtta caattctaat ttgtttgaat gacaatgagt | 120 |
| gaagaagaat ataattaata cacaattagt atgatagtta caatttagta ttcaatggtt | 180 |
| gattaataaa tgtgaataaa tttattgttt ttgtgggtta attggagata aatattattc | 240 |
| tatttttatt tttgaaaaat tggttgttaa aaatgagacc ttattttat atatacatga | 300 |
| ttaaactatt ttgaacttga atccatttgt tttggattta ctcacttttc caatgttact | 360 |
| tatagtttcg ccagtggaat ataaggttag aaaatatgag agtaaaaatc aggaattagg | 420 |
| acatgtaaaa tccagaaata tctgaggacg atctcacga ttgattataa gattcgcatt | 480 |
| acattttctc ttcatttttt tcagataaga aaattggatt ctatcaattt gtcgtcctat | 540 |
| tgttctttc ttgtttgata tacaaatacg agtcactgat ttttttagt tgattggtag | 600 |
| agtcttaaag gaaacatcaa attcagacag tccttttaca accatttcat ccatgtcggc | 660 |
| tcattatttc gcaccacaga agaataaccc aaaattatta gaaaacttgg accactataa | 720 |
| gcacttgaac tgtggtcgtg cactgactaa tgtgagcccg ttttggtaat tctcagctgt | 780 |
| gtgcgtaatt gatgtcggcg tcaccttcag aaacttcgaa attatgtgtg atacaccgtg | 840 |
| tttcataaat tcatacacgt cattttagat acaaaattag atattttcat ttgataaaac | 900 |
| cgaaagaaat aataaacttt tcctttcttg ttctcatttt aagtctctct ttatatcact | 960 |
| ttctatatat attgaatcat gcaaggaata cacataaaat | 1000 |

<210> SEQ ID NO 3
<211> LENGTH: 1000
<212> TYPE: DNA
<213> ORGANISM: Arabidopsis thaliana

<400> SEQUENCE: 3

| | |
|---|---|
| tgggtgacca actctttcct actttttctaa cagttttttgg tttgttttgt tcagattcgg | 60 |
| acaaaatgat gagtgttgtg ttgtgaacag agaactggtc cgtttgtaat atttggggtc | 120 |
| ggtggtcttt gtgacggtct aggctttggt tgttgaacta cttcctttga ttaaggttta | 180 |
| tggagttttg ctatatctac acaataaatac ataattgttt tgtattattg acttgaccaa | 240 |
| taacaggtgt cgaaaattct cagttagtac atcatctttt acaagtcttt tgacgttcta | 300 |
| gaccaaatta tgttgatttt tgaatcaatg gtgagttatt ttagtcatct ggttgccgtg | 360 |
| ttttgaaact aagaaaagtt gaattatata ccgtaaagaa gagataata ctaaaaatcc | 420 |
| gaatacgacc tacaatgaaa ctaagaaaat cagtagccaa gaatgatttt gagtcaatgg | 480 |
| tactaaatgg caaaaacat tacaaactaa ataaatgact tttggtggac gtctaataaa | 540 |
| gtaatagcaa tgaataaaag taagttttt gcaatagagt ctttcattta attgtaaatg | 600 |
| gatgtcttgt taaccaaaca atattttgat tgttttcatt gctatgtgct ttattgagag | 660 |
| gatgagagca catgcatgtc ttgttttgta agctgtacct tttttttgtca taactcaaca | 720 |

```
tgatagtaat ggaatggaat ctctttgatc tcttgttaag ttaccaaaac agaacaaccg    780
tgagagagtg gttcatctaa tacaataaca agacatgtat ctaccacaat cctcacatac    840
acatgtacgc atcccattgg ccaattcact tccaccaacg accccaatta acaaaaacca    900
acatgagtta gttattagta gttgacctat actcacttct tttatcttcc ctccactctc    960
tccaatctat aaaaccaaat ccaacaattg cttccttctc                         1000

<210> SEQ ID NO 4
<211> LENGTH: 1000
<212> TYPE: DNA
<213> ORGANISM: Arabidopsis thaliana

<400> SEQUENCE: 4
ttgaattgaa tgaagggtgt ggtcggaaga gaagacgtgt agaagagacg agacaagtaa     60
atttaagcat tggccccatt tacagccaca agtccgctac aacaaattat ttccaagaaa    120
ctctgagata acgtcgtgat gaaacggctc atgctgctgt tgtgattcgt gaattagagg    180
tttatctttt gggttttttga atgttactta attggacggt cgattttttca aactgggtgt    240 gaaatgtgaa tgggtcattc ataatgggct tttgttttaa tgtgaagcca ttcacacact    300
ctttgtcctt cttttctatt attcataact gtcactcttt gttcttcgaa atagtaaaga    360
gcaaatcgat tctttgttga tctgggccgt aaaatttcca tggttgtggg aagtattctc    420
gcagctgatc tgggccgtca atgctacagt ttcatgtcag agagaggtca agaatcaaca    480
cgtggccaac catgatttta aaccaaagca acacacgat tagaccccac attgtttgtt    540 caccaaccccc cgtggaccct cctttagccg acgtgtccac gtcaatagtg gttttttcttc    600 ctttcaaagt acacaaattc cattctttct cattttactt tttggattac gttgttgtta    660
taaactggta aaatgaatta tgaatgcaaa taaatttcat ttaagttttg ttggcttcta    720 atatttttttt cacctaaaat tctaataaac tacacagcca tgagccatcg tatgaaaaga    780
agaagaaaaa aaatgtcttt ttctagaagg atctttcaac gactaaaaaa gatttaagc    840 ttttgactaa ttttgtcaat aatatacaca aatttacact caattatagc catcaaatgt    900
gtgctatgca gaaacaccaa ttatttcatc acacatacgc atacgttacg tttccaactt    960
tctctatata tatatatagt aatacacaca cataaacagc                         1000

<210> SEQ ID NO 5
<211> LENGTH: 1000
<212> TYPE: DNA
<213> ORGANISM: Arabidopsis thaliana

<400> SEQUENCE: 5
tttgtcgaat tggtggggtc ttaaggctaa aaaagggttc accacatgtg tatgaatcga     60
aatctactca tccgctgtcg ggaccaaact acatatcaac taccacgttt ttctcatatg    120
aatattcaaa gctaccgtaa attttttataa aattacgtca ttagcataag aatgtatgta    180
catattaatg actattataa accctaaggc acggatacct tatccttcca ccaccgaatt    240
tcacggattc catatccttt caccggacta gacgaatatg aagctaagat attaatagat    300
tggtgaccaa atttgaatct tttcggataa aacttgtttg gcatactttc ccttagagtc    360
aattattctt caaacaatgt ttaacttaaa tctcaagatc ttatgtagtt aatggtagat    420
atcgtacagt tttttttcgtg tttgtctttt gatcgtgtgt aaagtgttgg aaaatctaac    480
tttgtatata agttctacac ctccaaatta acgttcgagc ttatcggtat tactgctagt    540
```

```
gctttctcaa attccttttt agatcatata gtagcccact aggaaacctt acaccaaaac    600
gcccaaataa tatgaaaagc ccatcatatt gtccatccaa agtaggacaa ttgctgaaaa    660
agcccaacga atcaaacctg cattgttacc ttgcacttgg aaaatgaatt aaacggcgac    720
gcacctatgg atggagacta agttcactca tcaaaaatct aatttcaact ctaattatcg    780
tatttaaggt cattggagat tcaactcttg tacctgtagt ttcttcttct gaaaatcagc    840
aacaaactac aaatcatcca atgatagaat ttcagcttta attatcaaac aaattaaaga    900 taacccccatt gataatatcg ccacgtctca tcggatgaaa tagtactatc tgacacgaca    960
cgaatctctt atgagagaaa cagaagagca cggaatctcc                         1000

<210> SEQ ID NO 6
<211> LENGTH: 1000
<212> TYPE: DNA
<213> ORGANISM: Arabidopsis thaliana

<400> SEQUENCE: 6
attcatttct ccgagaagaa tatgtacttt tttactttcg acaaaagaac catattttta     60
gcttgggaat cttggattaa atattaggac aatattttta acttgagaat cttggtttaa    120
atatgagaac catatttcag aaaaaaaaag tttatatatg tgtaattttg tcggaaccgg    180
atttactaac attcgtaggt agtcggattt ggtcccgtaa aataaaatgg taaataaaac    240
aaaattaata gtaagaaaaa tgaaaaataa tttacaaaca caaattaaat tgaatacaaa    300
ctagctatca taatatttttt caagttggtt ttcatgaaca ttttagagca ctaagctata    360
taacaaaata ataataatta aacatctttt aatcattaag tatttaaaga tccatacaaa    420
tgttggttac ttggtacaac caacaaggca aaggcggtac tgaataagaa tataagatac    480
atgaaaaatt gatctactat actttacaaa acgcgttaga tattatataa ttgctactcg    540
ttcaattcat ggggatgtag ctcagatggt agagcgctcg cttagcatgc gagaggcacg    600
gggatcgata ccccgcatct ccactttat tgttttcttt ttaaggttct tttttctttta    660 atttattttc aatcttctag tcttcaattc tgttttttgtt tctgtcggaa tctcttaaaa    720
gtcaatttaa atactttaaa ttccttgcac aacactcaat tttgatactt tgaattcctt    780
gcacaacaca acacgtcgct atcaatcaca gacaccacaa acttggacac ttatctttag    840
ttctgtctta aactgaatct ccctcttatc aattctgttt ttgtttctgt cggaatatct    900
taaaagtcaa ttttaatact ttgaattcct tgcacaacac aacacgtcgc tctcaatcac    960
agacaccaca aacttcgaca cttatcttta gttccgtctt                         1000

<210> SEQ ID NO 7
<211> LENGTH: 1000
<212> TYPE: DNA
<213> ORGANISM: Arabidopsis thaliana

<400> SEQUENCE: 7 ggttttata ataaaaagtt gaaatttgtg cccttttcaa gtctttcttc atcatcttca      60
ttctcattct catttccatc ctctgcttgc tctcttctca cagccccatc ctctttaatt    120
accatctcca atcccctgaa ccaggattta taccattgcg attccgcaat ccaacactac    180
tatctctcta gttccttttc ttcattagga aagagcaaaa gcattctttt atggtaaagt    240
ttcgattttt caaattcata cactgtcgga ttcataccct tttcgctccg ggtctggaat    300
ttgggttttt gaggtttcta cggagtcaat tcgagtctgc ggaaactcaa tttgatagac    360
tcgtttcaaa atgttgctta agggttttct tttgttcatg gattgaagtt ttgcttaaac    420
```

| | |
|---|---|
| cagttacgag gtttcttggt tcttccatgt atccgtgcgt tatctttgat gacccttcac | 480 |
| tcaaagtctt cgttttttca tgtcaagttg cttcctagac ttagaaaatt ctcgttttta | 540 |
| atggatttt gttcatagaa caaacattta acgtttcatg cttttctgt gagtcacatg | 600 |
| tttttttc ttgagctgat taagtctctt tttttgtttg cagccatcaa ttgaattata | 660 |
| tgtcttttag ccaataattc tgataaacgt caagaggtag gtgagaaaat caaaactctt | 720 |
| gccttgttat cggttttcga taaccacatc tatcaaacga tgtcatttgc ttgtttgttt | 780 |
| ctgcttggac attagtttcc aaattattag agagttttag tcacgtagaa ttatgaagtt | 840 |
| tgtagtatgg cagatggctc gtgagcttgt ttaactttat cttatgaatt tagtggacga | 900 |
| gaaagaagtt gggttgtttt tggttggaca tttattaatt ttcgtctctt tgtgccatgt | 960 |
| tccatgaagt atcatttcat catctctagc ttaatctctg | 1000 |

<210> SEQ ID NO 8
<211> LENGTH: 1000
<212> TYPE: DNA
<213> ORGANISM: Arabidopsis thaliana

<400> SEQUENCE: 8

| | |
|---|---|
| ataaaattt tagatattta tatttataaa tatgactgca gaagttttaa gtttatgata | 60 |
| gtttttaaaa agcaattatg atagttagta acaatttaga aacacgtata atttaatttc | 120 |
| tttgtttatt tttcaaaaat atacaaaaaa tttatgtcag cgattttatt ttattttgta | 180 |
| tggtatatga ctaatttaaa agtggtacta attagtatta taaaaaatta ttaaaaagta | 240 |
| tttttaaccct tacgactcta ttttttaca agttacaaat gtttcataaa attttattgt | 300 |
| taaaacacta tgatctaaga tattgaaacc cacggtcaaa gtattgctaa catggtcatt | 360 |
| acattgaaaa agaaaattaa ttgtctttac tcatgtttat tctatacaaa taaaaatatt | 420 |
| aaccaaccat cgcactaaca aaatagaaat cttattctaa tcacttaatt gttgacaatt | 480 |
| aaatcattga aaatacact taaatgtcaa atattcgttt tgcatacttt tcaatttaaa | 540 |
| tacatttaaa gttcgacaag ttgcgtttac tatcatagaa aactaaatct cctaccaaag | 600 |
| cgaaatgaaa ctactaaagc gacaggcagg ttacataacc taacaaatct ccacgtgtca | 660 |
| attaccaaga gaaaaaaga gaagataagc ggaacacgtg gtagcacaaa aaagataatg | 720 |
| tgatttaaat taaaaaacaa aaacaaagac acgtgacgac ctgacgctgc aacatcccac | 780 |
| cttacaacgt aataaccact gaacataaga cacgtgtacg atcttgtctt tgttttctcg | 840 |
| atgaaaacca cgtgggtgct caaagtcctt gggtcagagt cttccatgat tccacgtgtc | 900 |
| gttaatgcac caaacaaggg tactttcggt attttggctt ccgcaaatta gacaaaacag | 960 |
| cttttttgttt gattgatttt tctcttctct ttttccatct | 1000 |

<210> SEQ ID NO 9
<211> LENGTH: 1000
<212> TYPE: DNA
<213> ORGANISM: Arabidopsis thaliana

<400> SEQUENCE: 9

| | |
|---|---|
| cgtatatagc agatatagtt aaatctgttt tgtatgttga taaactgctt gatataacga | 60 |
| attgttatat ggaagattca aaattgatga tcctatgata aagatcaaca tggatacaag | 120 |
| acacgttttt tcttgcgata gtacttatat ctgacgtcag taatagtcgt ggtggctatg | 180 |
| tcagaagagg acacatctgt gactcatgtt atgtggtcga gaatgaagtc tcgtgaaatt | 240 |

-continued

```
gtatttacac tttgttgtca tgtagggttt gactttactt agtcggcaac gtatatatcc      300
gatttatttt attttcttca aactggaagc ttttagacca aaatttaaac taattttctg      360
aaccacagaa atccaatctt tttttgtcac tgaaagcggt tataatcata aatgtccaaa      420
atgtgatttg ttttttgaaat agttaaaagg aagtgaattt ctaattaacc ttaatccacg     480
taaaaacttt atatacctca aacaaaatcc cagcacaacg aggttaaaat caaatatagc      540
cagcttcaat tttaatttat tctaaaatgt cgaagggtcc ggaaagcagt caaattgtcg      600
cacattcata tttacgttaa ttagagaagt cgcttcttac tcacgtttct cgttccaaac      660
acaatctttt catgtttctc ttttaatttg accgtcattt tttatgatgt gaaatattaa      720
ttgcgcgaat acttcaaacg tacatctgtg atctgtccgt cattttcctt cacgttacga      780
taagtttcaa tctaaaaact aacatcgtcg ccttcgttga atcaatgcat ggattcgtcg      840
cagcatttat tctttattag acaactggcc cttcaagcga aatgagggat acgtgtatat      900
atatgcatcc acataaacaa taagaaaaat ataacccttta tttttggatg ttatataaaa     960
ttgctttacc tatatgtgag ctagcaacat ttactcatac                           1000
```

<210> SEQ ID NO 10
<211> LENGTH: 1000
<212> TYPE: DNA
<213> ORGANISM: Arabidopsis thaliana

<400> SEQUENCE: 10

```
gggaatctag cagaattttt cttcctaata actattttcg agctttctgt ttttgttctt      60 tcttttaaa aaacttatta agttcttatg aataatgact tgtgaagttt gagttcgtct      120
ccttcacaag caagttgtat tggtgttttc tactttatga atatgggttt tatataccta      180
aagacttgtt atgttattat tcttaaatgt tgctgctatg atgattacta ttatcgattt      240
ttactattat atttgttttt tttaacgatt cgttgaaaaa taaacgagat tgacactaat      300
gtagcaaaat gtgcaatatt atcttcaaaa cattacaaaa ttcagttgtc ttaatcttttt      360 tatttccgat gacaaattat ggttacgtaa atagtactat attaaaaaaa aaagaaaaaa      420
aaagacgaaa ataaaacaaa aagggagaat ttgagtatta aaccaaaaaa aaagggagaa      480
gtggactttt gatcaaaaga agagaacaac ttgcatgagt aaattagttt tagagctgac      540
tatttaaaat tttaagaact aaaaagaaag tggtagtata atttaacaaa aggatgatga      600
ctcatatgaa taatagtagg caaaaaaaac ttcaaaacca caatttcttg tttttcactta      660 gaaccttatt ctgccataat tacgtttagt taaattaaga aaaaattgct taaaacgaca      720
gtacaagaag aaggaaacat tttctttcac tcaaaatcct attatcgcgc aacagaggag      780
tctaagtgaa ataataccgt gtcgtttgcg gatcagaaat cgagagaacc acgtatgtgt      840
cttttatgtc ctggtcaaac ggttatccaa cacgtggatc ccaaaactag ccaccgactg      900
cagcaagttt ctcgaaccga tgcacgtgtc ctcgacacgt ggagactccc aagcacgtct      960
ctgggttata aatagcaacc caatgctcca atcatttttcc                           1000
```

<210> SEQ ID NO 11
<211> LENGTH: 1000
<212> TYPE: DNA
<213> ORGANISM: Arabidopsis thaliana

<400> SEQUENCE: 11

```
gtcaacattg attttttcaat ttattaagat tttttttact aatgtaacat agatgaaagt      60
gaggttttct cgttacaata aaaaaaaaag aagctacata gccagtaagc cagagaacta     120
```

```
aacgtttctt gtacatgcat gttgcatgag aactcttcta gtgagagaac tcttggccca      180
aacaatcaat ttttttgaaat attaaattaa gcttacaaat ttgcaagagt gatgattgct     240
atattgcata agaggtattt aacttggatt tttttaaaaa aaaaaacaaa ttgggacgaa      300
aatgtagtct ttcttttttt gtgtgtgtaa agattaatat gttagaagaa tagcttatat     360
attgctaaaa aaaataaaaa tgaatagctt atatataaaa tagcaaaatc aagaaaacga     420
cattactttt aagctgaata gatatgaatt ttttgaaatg ccaaaagtta ttatataata     480
gatgaacaaa gttttttta aaatatagtt ataatttaa aacgtacggg ataaattaaa       540
agatcacttt ttcacgtttt ctttttttaa caaaacttt gttagataat ctgaaatatt      600
actcattatt tcccatattc tattaagtat ttgtgaataa attgtataca gctaaacaca     660
cataaattac aaatttattg atttaatata ctttactact ttggttaaaa agtaaacata     720
ttcaaattcc tttatttctt ctactttgga gctgcattaa caacttcct tgaataatta     780 cgtaattaaa aacaaattac caaatattta gtcaaaaaat aatttagtga atatatcaaa     840
aataaaaaat aaaggaaagt cggacgatac taacaaaatt attaaaggaa gatgaatttc    900
tctttccttg tgcgcaaaat agcaacaagt ctccgcgttt cctctctttc tctctttccc   960
ttatttaaac acacttcgtc ttctacctct aaacaatctc                            1000

<210> SEQ ID NO 12
<211> LENGTH: 1000
<212> TYPE: DNA
<213> ORGANISM: Arabidopsis thaliana

<400> SEQUENCE: 12
caacatgttc agaataataa ttcacagctg ggtaaatttt aatttacaat tattgagttt      60
tttttttttt ttgtttatgt caaactcaaa actagtgcca cgtggaggaa gctaagccta     120
taaacgatta tgaccgacag ttgtcactct agaagtagcg gtccttgtga cggcataagc     180
tggtcataac cgcttagtgg tgatgatttg acgaaattgc ccattaagcg actgtgagat     240
gtcggtagac tacgatggcc acgttccaca gagagtgaca ctaacaacca aaacctattt    300
tattactatt ttttcttttg tcattagtat tttattacta attgtttgaa tatttcctcg     360
tggtctatta ttattaaaca ctctagtcct cttattgttc attaaaattg tctgacgctt     420
gtctcttcct ttcgttttct actagaaaat tcagctattt tcttaatgtt ttatatctcg     480
taaactctta agttgtaaca gtgtttcaat ataatttgaa cacatattga agtttagtcc     540
aaaattcttc ttctccagaa tatatccaaa tcgagtcaca atggaaaaca aattctcctt     600
tgtaggtaaa tagaaacaaa caataattgt ggcattaaag tgttttaaaa cgagatccca     660
ataatttaca tcagtaagat ttcaaaagtg tgtaattaga ataaacaata aacctccaca    720
atttggaaga tattttgttt ccatatttgt cgcgtataat ttattatatt gtcaattctc     780
gagaattttt aacgttttgt tttgaccagg taacgactgt tccggtaaat atgtaggtcc    840
aaaaacttcc cgcggactta actcgttttg aaatccgctg tttggttttc ttttttattt   900
accggctcta accggtccta cccaaaacct tgtcatgtcc tctcattcct ccaccgttta     960
taagtaggcc cttaactcca attcccaccg tttcttcgct                            1000

<210> SEQ ID NO 13
<211> LENGTH: 1000
<212> TYPE: DNA
<213> ORGANISM: Arabidopsis thaliana
```

<400> SEQUENCE: 13

```
tcacgtgtta cggctgagag cttcgaagcc cacgtcattg ctgacatatc ttcattcgta        60
cggatcatgt aatctgttaa atttcccaaa acgtttgcta cctaaacccg tgaattattt       120
ggaagtcaaa cttcctcttt aatttcggaa atatttacaa attcaggtca atctaatgta       180
tttcatacaa cgagtgtaaa tgtattattt tgacaaattt gcgtatcttc tagttgggtt       240
gacaatttaa tatactttta ggtcaatttt gcatagtaga gatatggata agaaagtcta       300
tctatataca cacgcacatc tacgtattat aacaactgta catcacattc acactatata       360
cagaacattc atctaaaaca accgtattta ttgtatccac acgttttact atgggtgtgt       420
ggtcctttta attatcagtt actataaatt ataaacaaaa ttccactagc taatcaatat       480
gaaattacat ttgagtttag aatagtcaat aggaaacgat ttaaccaaaa taaaataact       540
aattcaattt aaatcactgt ttttttttgt atccatcaac aatcatatga accatttgac       600
tacattctct ggtcaatttg aattggtatt tactactact aatagatact cttataccaa       660
tttagataaa taaacttaat cctgagtacg gactaaagga caatttgtac agtgagttaa       720
aaatagaaaa tttacctaac aatactttt aaatcagtca acatttttt gactttaata        780
agaaataata tttaatattg gccttgtaaa acaagactac tctcacaaca gtcaacacac       840
acagctaagc atacgcgtca gcttccggtt taaacaaaaa aaaacacaaa ccgtaatttg       900
gtttccgttt cttcctcttg taacgaccgg ttaaataaaa tgctgacgtc accatcttct       960
tctatatata tcctacctgg aaccaactct gtatatacgc                            1000
```

<210> SEQ ID NO 14
<211> LENGTH: 1000
<212> TYPE: DNA
<213> ORGANISM: Arabidopsis thaliana

<400> SEQUENCE: 14

```
tttatacatt tcacatatta taaatattat aaaacgtttt tccgttaaat attttaaatg        60
tttaactaac tataatattt attttttaata aagtataata ttaataaatt cctaagattt       120
ctcctttta aaagtaatta gaattgatgg aaatatatta gataaagaaa tgctaataat        180
taagaatatt aattagttat aataattaaa tatcaatgac atccactgta aataagtccc       240
aacttaagga tttatttact aaaatagctc caaaaatgta tatatagatg ttatcaaaat       300
tcgaattaaa aagttgtaaa aagactcgga ggcggtcaaa atcaattttt ttattttctt       360
gcataaattt gtgaactcca gagaattaag aatgaccagt gatagagctc cacgtggata       420
gattgggttc caaagtggga cggcgttaaa tataaaaagg ccggaagttg tcgaagtagt       480
cttttttccc attattctg ttttcggttc cttattttgt tcctttgtaa taatgagtga        540
catcaaaaat atttggggac gaattaacag gtaatgtaaa tagaaagaaa tagaaaattt       600
tctttgattt tacaatttgg attcggattg cataagcaat gacatcaaca gtaatacata       660
gctgagaggc tgagatgcag tgtctctctc tcagggaaga tgacaaaaag aatctgatat       720
acacgtacgt atgttgcgag ttacatattg atatatcaca tgtcataagt cacatgctaa       780
cgataaacta ataaactaaa acaattatgt caacatatat cggtgaattg cattatcatc       840
gacctcggtc actgttccgc acatcttggt cgccacggaa catagacaat ttttggattg       900
tagtccaatt aatgagtccc ccaccaaagc cgtagtaaaa tcgaagtcgt tctctaatcc       960
aatcatatat atatccataa cacacaccaa caacacccac                            1000
```

<210> SEQ ID NO 15
<211> LENGTH: 1000
<212> TYPE: DNA
<213> ORGANISM: Arabidopsis thaliana

<400> SEQUENCE: 15

| | | | | | |
|---|---|---|---|---|---|
| tgccaaaacc | cattcttgga | tcctgttgtc | accaactgca | accattactt | ctgcgacaag | 60 |
| tgtgctctaa | aggtaatctt | ttccttacaa | caagtttcgt | aatttctgaa | acacactca | 120 |
| aaacagattt | tccttgttat | ttttttttcat | aatgcagcat | cacactgaga | acgatacttg | 180 |
| ttttgtgtgt | aacgagccaa | ctctagggct | tttcgacaca | gccgtggaga | tcaaggaaag | 240 |
| aatagaggaa | gaacgtgaga | agccagagg | tttgttaaaa | acgcaaaact | ctctgttttg | 300 |
| acaccaaaaa | cctactctta | caaaactcgc | tcggtgatgt | ctctttgtag | ccatggtaaa | 360 |
| ggaagtgaca | gcaatgttag | aaaaggcatc | gacaatggcg | gatgacgcca | agggcgtagc | 420 |
| gcaaaaggtt | gtaaaaatgg | tggaggagat | tgaaacaatg | gtggaaaaag | tggcggctat | 480 |
| ggccacaaag | gcgggagaaa | cggcgacaat | ggcggcagat | atggtgaaag | aagctgagga | 540 |
| gacgatggaa | acagctaaag | ctaatatgtc | caaagccttt | gtggtaatga | agtcggtgaa | 600 |
| ttggaacgtg | taaatcgggt | caaaacagag | ttttattgtg | atctcatgct | gacatcagct | 660 |
| acaatcttta | tctaataaga | tagattctca | caagattctt | ttatctatct | acttttttaga | 720 |
| gaagatgaga | tcatacttcg | gagatagata | ggtgtcgtaa | aaattgggaa | gcttacttgg | 780 |
| caggagaaga | gagatataca | cacgtgctta | aagtcaacag | ctaatccaaa | aaggtagacg | 840 |
| acaaaccagt | taaactaaga | cacgtaatct | atcttaaaga | tttgtcggtt | catcgtaaat | 900 |
| ccgttggtgg | attaatatat | gtcggtgtct | tcgttgattt | tcttagccta | accaaccaaa | 960 |
| cataaataaa | aatcgaagct | ttactttgtt | tgcttctatt | | | 1000 |

<210> SEQ ID NO 16
<211> LENGTH: 1000
<212> TYPE: DNA
<213> ORGANISM: Arabidopsis thaliana

<400> SEQUENCE: 16

| | | | | | |
|---|---|---|---|---|---|
| ataatataat | tctgaaaata | actaataatt | tactctttc | aagtaattat | tcaaaataaa | 60 |
| tttagaaaac | taattcaatg | tatttcctca | ttgtcactct | tttatttccc | tctacaaaat | 120 |
| tatatatatg | aagtagtttt | ttttaaaata | gagccccata | actaacatta | ggggtccata | 180 |
| tatttgcatt | gtaatttata | aacacgtgta | gaacattata | attatttaaa | ataaaattta | 240 |
| gaacaataac | ttaatgtatt | tcctcctcgt | tagttttcct | ttttttccct | ctacaaaatt | 300 |
| acatatatgg | aatagttgtt | ctttacttct | tttaagtaga | gccccttaac | taacacatta | 360 |
| ggggtccata | tatttgcatt | ataatttata | aacacgtgta | gaacctggca | ctgaagtctg | 420 |
| atgaatatat | atccatttgt | tttcacaact | accctagctt | tttgtatcat | cggttacttt | 480 |
| tttttttatca | caagaaattt | ctcgattttg | attttgattt | tcaatgttg | tgaagttgag | 540 |
| aagttcaaca | tgtttggac | agatgttttt | gaacagtaaa | ttagtatttt | aaacatgtga | 600 |
| atctatttgc | aaacgtaatg | acgtgtcgtc | tgaccatttc | ttgaatgtta | gttaattttt | 660 |
| tagctctagt | tttgattaat | ctaccaatta | ggtcattcat | ttcagtttaa | gtcaaatcaa | 720 |
| caattaggct | cgtcctaacg | ttttcattta | gccaaaacaa | aaaaaaagat | ttcaacagta | 780 |
| taaataattc | gtccttatca | aaaaattaat | aaataaaaaa | gatatacatc | attacttacg | 840 |
| taattgtttg | tattttgata | gttttcgata | atttctatgt | gacggttttt | aaaataaaaa | 900 |

```
taaatgttga ataacaaaaa atagtagtac aatagaatac tgaattggtt tgtgtagggt      960
caaaccaaca aatatggaaa gaaaagtatt atttagttac                            1000
```

<210> SEQ ID NO 17
<211> LENGTH: 1000
<212> TYPE: DNA
<213> ORGANISM: Arabidopsis thaliana

<400> SEQUENCE: 17

```
gccctagcct aaatcaaacc agagataact gtggaaatga gactagagga ttcaataaaa       60
acacaaactt ttttggatgt gcaaaaaaat caaaattggt acctcttgtt ccttttaag       120 atcttgttct ggcttaatcc agagaaagta agcaatagtt ccggcgacga cccaagaagc      180
ggcactctga ccacctctaa gacctcccat ggaattaccg atgaaagatc tcacgtttcc      240
aattgatctt ctccagctgc tagccattga ttgatgccca actatacgaa ctggtctaag      300
gttcttctgg atctcttctc tgacaattgc ttgactttga tgatgattcg atttggaact      360
gaaattgcaa gaaagtaaa agcaggcgat tgattttga ttcgcatttg cttggtgaac       420
actgccaaag gctaaaccgg tcgccgagac ggttaatctg atgtttggga ttgacacatc      480
atgcggctgt tgtttctcca cgtaacattt ggagacccgc tcaaatatat tgtgggccgg      540
agaacattgt tttaccatat agggcccata gactttgaat atgtgtaggt aaataaaata      600
caatctgtgg aacaaaaatg gcaaaaatat ttgaagtcag caggattggt taacaatttg      660
agcacagaaa tacatttggt aacatctgag catatcattc atatcatatc gctgtcgaat      720
ttgaaggaaa aaaaaaagac taaggaagtg gatatattgg tgaatgctga tgatgagaaa      780
acttattatt atatacgaaa aatttactaa agacagcaat attccaaaat aatgataggg      840
aagattctga gatggtgtgt ggtcagtgtg gaggcactac agatggtcaa acagtagcat      900
acccacctgg ctatttggac aaggacaagg aagaagaaaa atcgagaacc atcttctcag      960
ccgattttag taaccatctt cttgtttgct ccgaacaatc                            1000
```

<210> SEQ ID NO 18
<211> LENGTH: 1000
<212> TYPE: DNA
<213> ORGANISM: Arabidopsis thaliana

<400> SEQUENCE: 18

```
aataataata actaattagt aattagtggg tattttaaat accattatgc catttagcta       60
aggtaaaaaa tcaattgtta attataacac ccaccaccaa catagattcg tctatggttc      120
attcatcgtg tttaagagtt gaaagaaata aattcgccca tcgtgaataa tagatattta      180
ttcatctcaa acttataact caaatatatt tcaactatat atcgatcaaa tagtatagct      240
tttggttaat gacgaatttt tattctttg atccataatt cttcttcttc tttttttct       300 gtccggatac atgaaattga tgatacacat ttaaaacaac aattcgaatc agggaacaaa      360
ttacagccac aaccagtgat gatagaccat atatatgatt tagtttattt aataaataat      420
gtgtaagcaa atttggcttt gctgtaaaaa agaacacga atttttggcaa aagtttctgt      480 taggaatctg gttctattct cctctgcaac ctccagtctc tcatgaatct ggttcggatt      540
ctctttttcc ttgtttctat ataatttaga tacatggttt tataattcta tcatatgtct      600
attttggata tagtatttta aaaatatata tattttcat aaatggttat ggtctattct      660
atgttaatga taatcattag tcttttttgtc aactatgttt ttttttccaa caaatttagt      720
atgtaaactt tttttttacta ccgttttatt aaatcgacgg ttgatcagat caactccggt      780
```

| ataacacaac ataagtttcg ttatcaaaac aaaaacaaaa acagattttt ttttgtcaac | 840 |
| taccagtgaa gattagtctt acgtgtcaag aaaccggata aaaatatata acgtatttgg | 900 |
| gcaatcagct aagatattaa ctaacgcgga gttcattatt aaaatggagt aatgatgttt | 960 |
| tcagttttct atataaatca cgtcgagacc gtagagtctt | 1000 |

<210> SEQ ID NO 19
<211> LENGTH: 1000
<212> TYPE: DNA
<213> ORGANISM: Arabidopsis thaliana

<400> SEQUENCE: 19

| taattttttt ttctttattc aaattatttc aaaatacaat tatatataat ttattttttg | 60 |
| tttgaacaaa attttacatt tattccgaaa aaaaaaacta tgcaaaagaa aattttaatc | 120 |
| caacttctca tcatcctcaa aataatgata acaatatatc cgcttcatta gtaactgtaa | 180 |
| ccttcttcga tcaaacaact catctgcaaa gactagacta tttcatttat ctaacattac | 240 |
| cgttaacaaa caaaaaacaa aaatttactt gggagtcgaa gaagtcaaat atctagaaga | 300 |
| atacttcttc ttacaaaatt ataaggaaaa tttcccctac tgcttcgaga aatacctttt | 360 |
| tccccattca cgttatgtta tgcaacgtgt gaggataacg agcggacaac acagcccttt | 420 |
| tccttatttt attggtcaac caaccccaaa acagatttta agacggagtg tatttctttt | 480 |
| gtcaactgtt tacatgggtt aaataaaaca gtttcactaa aacttattaa attatcatgt | 540 |
| catattgtca tgtatataag ctatagcata tatacgatg gaatatcgat taaaccattt | 600 |
| tcttttcac cattggacca taatcagata atatacatag attgggaacc ccaaatattt | 660 |
| tcacattttg acatatttag tagcgacatt aaactacttc gtgaaaatac ataggatatt | 720 |
| atgtcaaatt gtcaacgaaa ctttttatat ttaataagaa aacgaaatta ataataatt | 780 |
| aacagaaaat actcacaagt gactttcaat gattttgtct ctaacgtttt caatgtttat | 840 |
| tttttggtct ctgactcttc aaggaaactg gtaaaaccgg tgtcccggta gtcatcactc | 900 |
| acatctcgtc caccacgtgt cactcttaca cgttcataag ttttcccacc tttctacgtc | 960 |
| cgattctgta tttatatacc ctaaacccat cgtcttctat | 1000 |

<210> SEQ ID NO 20
<211> LENGTH: 1000
<212> TYPE: DNA
<213> ORGANISM: Arabidopsis thaliana

<400> SEQUENCE: 20

| gaataatact cttatagaga ttttagtaga ttttcttctg cacccatctt cttttttgcc | 60 |
| actagaaaaa gttacataaa aactgtaagt tgataaataa ataaaactgt aaattccaac | 120 |
| aattagtttg gattttccac ctgaaatctt tatagactat gttattcct cacaataaat | 180 |
| agaagatatg aagaataaca tcacgcatag tcgatatgca cgtgagataa tatgttgaga | 240 |
| tttagttacc aaaaaagaat gattttgtct gagaaatgaa attcctctag ttgtgaattt | 300 |
| ttcaaacttg gtcggtcttg tgagttgagt atcttttga ggggaggtgg gaataataat | 360 |
| aagcaaaaat atcttaaaaa aaagcgaaag ctgagtttga ccaatcaccg acccggaaga | 420 |
| ttgaaactat aattagtact acgtttggtt gtcatcaaaa tggtcattct tatggttatg | 480 |
| ggatattatc ctttgccgcg gctagccgac cattacacca acatcatttt ttttgtctc | 540 |
| cattcaattt gcataaacct cttaaattat agatgttttt tacagtctaa tcttatcttt | 600 |

-continued

```
taactttgta agtggtgtcg ccttacgaaa attaaagctt ggaaaataac taaataaagt        660
tgaaggatat gaactaatga atgccttcac cgtccaaaaa aacagagaat gccacgtatt        720
cgtacggacg ttaatgtttt catctctgcg cgttgtgttt ttatgtgtca atatctctct        780 attttttcaaa tgctcatttt cttaactttc ttattggcca atgaattgga gtaaaagcaa      840
aggaataacc ccaaaaagat agttttgaat agtcgtcaat agatagatgg gacatacaaa       900
ttacaaaagc ggttagcaaa atctttcgtt gaaaaaaata aatatctaat tcttgccctc       960
atatataaac ccatgtagag tcgtctctct cttaccaaat                            1000
```

<210> SEQ ID NO 21
<211> LENGTH: 1000
<212> TYPE: DNA
<213> ORGANISM: Arabidopsis thaliana

<400> SEQUENCE: 21

```
aatggatgaa aggatagatc atacttacgt ttgattcttg attttgattt tgattttcgt        60
tagtttgggt agatgccata attgagagaa tagggtttca atatattgat taggattttc       120
tgataagaat aagatatata gggtttgggt ggaagacata attattttag ttaattaaaa       180
aaaaaaatta acctaaccgc taccgcccgc aaccgcaaac gcttgcggga aggaactttt       240
aaaatatggc gatttcgagc ggtccaaagc ggtatctaac ggttttttatg attggtgtca      300 aacgctaaca actgctacca cccgcaaacg cagcgtttgc gggtgacaga gggagaacca      360
atcaagctct aagactaatc ggaccaattt agcaacttgt gtgcttcgat gtgttggact       420
gggctagatt gggcccaaat agcctgtttt aacattccca aagatccaaa caattccttc      480
ttctttcttc cgaacaattc aatgtagatc cgagcgaatc tcctaaatta ctaaatgca       540 caattgtgct cagcttacca aaaaggccca aaagaccaaa acatattctg attttttctc       600
tttagataca ataaaagtaa tttatataga ttagaggccc aataaggttc acgtaggccc      660
aaacatatta aaagtaactc agaagagatc catcaaaatt ttgattcaca catctgttta      720
ggaattaaaa atattatttg atcggttatt cattccttt catgaaatca tgcaaaaaat       780
caaaaatcat ttttttctct agaaactacg tggcgagaaa gcagagcacc agttgtcttc      840
ttgctctgat tatctcgttg aaaccgcttt caaagcagag caaaagagac gacaccggag       900
cctccactgc tttactttc ctttaaactg tgactgcttt catttatata ataaaataca      960
tacactctca gagtcacatg tactctcctc taacataaac                            1000
```

<210> SEQ ID NO 22
<211> LENGTH: 1000
<212> TYPE: DNA
<213> ORGANISM: Arabidopsis thaliana

<400> SEQUENCE: 22

```
aggacacctc attctcatta cataatgtga cgagattgag ctgtcgtttt gttgtaaata        60
tatggtcggg ggtcaattat tcatatgcag ttttaggtca tttataaaga ccattaaaaa       120
cgtctttaat atttcaacaa tcttataatt caattattaa gaagcatcta gatatggatt      180
cacattagag ttcgtattct ttgacagcaa attcacatta gactttgat atatatattg        240 tacatttgta atatagtata cgaaaatatt acttgaaaac tgatgttatg tgttgccatg       300
atgccattgg tccatgactt ttccacacga aggccaaagc atactcttat attatatgag      360
ttgagtcatt cttttttcct tttgacggca agttgagtaa ttcaattctc ttgtcactta      420
ccggtgatat aagagttaat cttataaata gttttctgaa acttaatata ctataacaat      480
```

-continued

```
gtaaaagtcg tcgctttgtt atttgaagtg aaaattaagc aatgttatga tattttact      540 aattaactca atatgaaaaa caaaatcct cttaactaaa acagaaacat aaaagacgac      600
ttagtttttg ctttagatct agactcataa ctcaaaaaac aatttcatta taaacttttg     660
tagatcttac aattttaaaa taaaatgtac attaatgttg aaaagcaaaa tcttaaatta    720
gtgtatacta ctacttttt tttatcaccg tgatagatca ttagatcctt aacctcaatc    780
cctagagcct gcttattgcc tttaagcatt gtgcaatcac taccaaacac actcaaaact     840
aaataaatat aatttataac ttatcaaata aaataaatac tatcaagtgt gtatgaaatc    900
gatgacaatt tatttattac cttattacca tttgtgtctt gaagtacacg ttaagctatt    960
tttatgtgtt ataaaggctt cttcgtcaac caattacgaa                          1000
```

<210> SEQ ID NO 23
<211> LENGTH: 1000
<212> TYPE: DNA
<213> ORGANISM: Arabidopsis thaliana

<400> SEQUENCE: 23

```
acatgcatga ttgttaacgt tttcttttg tacaaggaaa aaaaaaacg tgtacctcta       60 gacaagagtt agagagaaat gagaaactgg accaggagat gtgaatggtt tcattcctac    120
tttggttaat cattgcaaat gccaataatt atatagaaa cggcgtcaat tttctgcaaa    180
gaaatatctt tactggtact ttttttgtgct acctataaat gtgttggttt aatctagcca    240
tcacacgtat atttctagct atgttagatc tttaatcatt ctcacctaga ctccttaca     300 aaaaccaata tagatgaaac cagtcccacc cctctcattt aagtcatagt atatatttgt    360
gtaacgagaa tacagacaaa acaattaaat tcattgtaat catacttgaa aatatagtca    420
atgaaattaa ttatcctaca tttttgaaaa cagtgtctat aattattatg tacattgaat    480
agatacgtgg gataatttgg attccagttc atatatatgt agattaaaaa taagagagg     540 gcgataaagc ctaagaaaaa tgtacaaatc gtaatgtaat ctagtgatga tttcctctat    600
ataggttgat gttgggtaga cttttggtca ccatgatatt tatctatcgt ctataaagta    660
caaaactgtg gtactaaatg tgatttatga aagctaatta aaaagaaggc gtgaagaaaa    720
tgaaatcgta atagacgacg cgcgtacgag atgagagtag tggaggaaag aagtaagatt    780
gagtgaatga taaaatgcaa acgctaccta ctaatatctc cacttgtcat gcaaccagac    840
tgagttcgtt ttccttttcg agtcttattt ttttgttttt tattctactc aacacgttac    900
acgcttctaa taaactctaa acattaaaat caaaatattt tgactacaat ggttattttg    960
gagctatata taaaccacct gagcctcctc agtttcctcc                         1000
```

<210> SEQ ID NO 24
<211> LENGTH: 1000
<212> TYPE: DNA
<213> ORGANISM: Arabidopsis thaliana

<400> SEQUENCE: 24

```
catacatata ttacgatgca aacaccgtat tttagagcta cccataaaat tgcttacaca     60
aacaatagct gtctgttttc acaaatttat aactccaaac cccacaatta caataaccaa    120
gagacactta accagatttc ggtttacact agaattatat ccccattggt catctggctc    180
ggtccggtag agttccccag gcacaccggt tacatacatg tatttcggcg gaggtggaga    240
tgaagatgac ttgctgcagt atgtcttcct tggtggtggt ggccgcaacg gagttgtaat    300
```

```
tccggtatgt cctccgaggt aagaatcgga attggtttga ttagtgagat agtgtaacac    360
gaggaacatt gagaaaaaga ctagaatcag aggtttaagt tcatcatga tcatgattat    420 tatgattaat gggaaatgtc ttttgatttc aagatttgca aaaataaca catataaagc    480 atacatatat aaacgaaatg catgtgcatg taaagtatat gcagcgtcat atctctacat    540
cacctatatg catttggtgg agaccagatc atacacatta aaatgcaaaa ttgtaaggtt    600
cttcagtttt gaataagtct tagattgacg aggtcaattt tttctggtta ccattagtcc    660
tatataaggt tataggattt ttgtaatgga ctggcctggt tgcttttgaa tccggcctgt    720
tttaaggccc atctctttt cagtgaagaa gctaaaaaaa gagttttaat ttcgtttgaa    780
aattttcggg agcataaaga actatcgaag caacacgtat ccaccttaaa ccacatgtat    840
actctagaac acaacacgtg ttaaagtgaa agatgagaat aatacggacc gaccctacgt    900
acttgataaa aacaattaag aagaagaatt taaaagaga gtgaaatgat tcgcttgagt    960
ctctatataa acatcacaat ccaactctcc atcatcttcc                         1000

<210> SEQ ID NO 25
<211> LENGTH: 1000
<212> TYPE: DNA
<213> ORGANISM: Arabidopsis thaliana

<400> SEQUENCE: 25
aggtagtgat aaatttatta agataagttt gtttgtaatt tattataaat cgtcatttgc     60
tccttgcaca agtggtaatg tgtctatggc cttggcaagg tcaaaggatt ccaaattcgt    120
ctttgcaata ttgttctttt tttgtttaat gtccaaaaca aacatagttg cattactcta    180
acatatttag cagcacaaat atacaatttt gtactgatta aaacacaaaa tattttctg     240 attttcataa actaactcaa acttggaaaa tgatctttta attcttaact caaacaattt    300
tgacatgact gatcgttttt ttggatacgt aaatattatg atagaagtaa taagaaatgt    360
gagaaatttt tagttttaag aagatgaaag acctagtaaa tagatgttca aactttgaat    420
acatcaaaca gatgagttaa tgctagtgag caaaattcca tagtcaagtc ttccaaaaaa    480
aagtcaaaac aatcatgtta taaagtttg taaccaatat ttacatttaa cacatttata    540
aaatgtgaca tcaaaaacgc ggctataaaa taacgttacg atattaaaaa tcaaggact    600 aataaaactc agaatttaat ttggggaaag aaaaataaac cctgcaagat ttgaagtgtt    660
cctcctaatc aaccgtaatt tagaaatggt ccttaatgga cggtggtcgt cgtttcacac    720
tctccgtcca ccattttttt ttttgtttc tcctcctcta aaaagcaatg gtctttcaag    780
ctccatcaat ggctactact acttagcgtc tacgaataat aaccccttta ccataagtcc    840
atagatttat ctctcttctt ctcaccactc atgtcccttt ctttgtcttc ttcctctcac    900
cgccttcaaa gttttcatct ttatccaaat aaaaaaatcg tttctttttt agtttcttct    960
taacatattt aaaggcgtac cctttctctt acttatcctc                         1000

<210> SEQ ID NO 26
<211> LENGTH: 1000
<212> TYPE: DNA
<213> ORGANISM: Arabidopsis thaliana

<400> SEQUENCE: 26
cactaacgcc gtttactttc ccgcttggac gataacaccc ttgatatatg gattagtctc     60
tcttttgctt ttggatatct taatatattt taatatgtcc attttatat tgacgaccat    120 ttaattaggt ctcagtttgt attattgatt tttaggtgcc aagcattact ttcgttacgt    180
```

```
gtaatctttt gattattcaa tcaaattatc atatggttca tggcatttta tcaattgtga      240
cggtcgacat gtgggttgac tttgatgtat gacttttagc ttgtgcctca tttttattcc      300
aactcgacaa ctagcagact ttatatttta atttatttct ttctagatat tagacaattc      360
ttagcttgtc tctctgcatg aatcacgcgt taatatactt ataatagtaa gttttaaaat      420
gtttcgagta taatatcata ttagatttca attataattg taagattatt tagtctcaat      480
gaagagcatt taaaaatgtg aaagagttta ggctttgact gttgactggt tctaacgcgt      540
tttgcttctt atttatacaa aaagatttta ttttatttta attagaaata ttaagtactt      600
tttagacgtg tttaggttga ttaatttctt gttaacatat ccgataaaaa aaaacagcac      660
caaaatcacg acgagaatta tgcctacgtt acgttgataa taaagattag agataaaatg      720
taacctctct tctctttaca tcattacatg catcttgtgt tttatttgac tttattctta      780
ccaacaaaca accaatggat aaattaggct cgtgaaggag ggcaaactcg taatttcaaa      840
gaaacggaaa gcgtcagaac gtggagaaca gtgaaccgag acacattccc gattttctta      900
aagaaacaaa ataaaacacg tgttttttat accataagta aagtagtagt atttattaaa      960
ctattaatat atagctttgt tatattggag gtaggaagaa                            1000

<210> SEQ ID NO 27
<211> LENGTH: 1000
<212> TYPE: DNA
<213> ORGANISM: Arabidopsis thaliana

<400> SEQUENCE: 27
aaataaagtt ggacaaagaa agaaaaaaag tgtttggcat ttaataaaac gtctcattca       60
ttgcgaagag attagatagt agagaggtca aattcaatgt cgcagccgac aatagataag      120
aagagataag gtcttcgtta tattttttg tttgtttttt aactgtcacg tgaaactgat      180
atccacaaag agcgaatgag agacgtagaa gagtcaaaga ttaaaaaccc aacgaacttt      240
gactcatcct ttgaaggtgt tcgttaatta tccattttt ggtctgactc gtggcatgtg      300
gcaactaccg accttagata agcctggtcc tactctcgta ttcgatcacc acgtgtcgat      360
cggcttatcc gacacctcga gtgggagttg tatgttagta actagataac ggtcataggt      420
acgattatga cattgacatg aaatcatatt ccaactatca acgttagtgt ccttgttttt      480
atcccctgta attcagtcaa ttaagccatc gtaccaggtg agtctttgat attgttgttg      540
tctacgaaaa accattagat gatctctaat tgatatttga ttcaacctat ggtaaaatta      600
tcccaaaact caaatattac ttcaattgat atcatcccaa atattaccta gagaggatca      660 agcttttaa tcgtcaattt tggttataca aaacgataaa aaaaaaattg taagccaaaa      720 ataaaagta aaacgaaatt gtgaattttt aataattctt ttgcataata cacaaaagaa      780
aaaaaactca tactccacat gtcaagtgat gacacaataa atgtctaaat ttttacaatc      840
aaaaacaaaa aaatgtataa aaaattcgtg taacctttt tttttgttgt ctaaaaaaat      900
gacatgattt tggtaaatag ccaacaaatt tgtagtagag tagtaaagtt aggtttcatc      960
atccatctct ataaattctc aagaccgacc tatacatttt                            1000

<210> SEQ ID NO 28
<211> LENGTH: 1000
<212> TYPE: DNA
<213> ORGANISM: Arabidopsis thaliana

<400> SEQUENCE: 28
```

```
tcaatcatta atgtatttat gatttgatcg aataacaata atatagctta ttttgttcta      60
ttctatcgta tttgattctt ctttcgtttt tttttgttt gacttaagaa accgattgtt     120
tatagtagta aacatttgtt tttaatgttg ctcgattcca gtgcacatgt ccaggctaga    180
cacttgtcgt tataaaggtt gctttggttc aatattgatc cactagagat gttacaacta    240
ttgttgacat ctgagattgt gtgataagaa aatatgaaac tggatttagt gaaagttaca    300
atatataatc atacatcata gataggaaat aaggaaatgt cagatatact tgaagaatac    360
atcaaataga caaggtcctt tttcttattg tcgactatta tagagccgta cagaaccttt    420
tcacgtcttt agtaattagt acattctcca tttcggctct ctcttatttt ttttccatct    480
cttttacttc tccaaataat aacaataaaa gcttcgattt tgtgtgtgtt tgtatttaca    540
tcttgacatc gatattcttt tcatcaattt tttaccaaaa atgtaataaa aacaaaaaaa    600
aaccaacgct gaacacagac atggtttctc catccgttta tattcatcgt ttgtatgttt    660
acttaacaac ttatttcaaa atagtacata tcatggttgt gtttttaaaa aaagtataca    720
gaacagaaaa gcacatggta gacaaaataa tgaagccaaa attaatacaa agaagaagtt    780
caacttgtat ttattaacac atttttcttc cttgtcaaag acatgcaaat tggttttgtt    840
ttcttattcc catttttttt ttataataaa aagaagaaga gtaaaacaaa aaaactatca    900
tttcttctta tcgcaaaact cttatctaag caagaaaccg acaaaaccta tatctacata   960
tattctcatc aacatctctt gagacatatt cattttggtt                        1000

<210> SEQ ID NO 29
<211> LENGTH: 1000
<212> TYPE: DNA
<213> ORGANISM: Arabidopsis thaliana

<400> SEQUENCE: 29
cttttgtctt tttccagcct ttgtttacgt ggaatctcgg tttctaggac ccactacact     60
ccttaaataa gaggtgcata attttatatt taacaaatac aattagcatt agattagtcc    120
aaatatccgg agtgattttt tttggttttt agaatattta ttttttatt gtaaattata    180 aaaaatgtta tatataattt ttttatagat aattttttta attttattag atttatgata    240
tacaatgtat tctttttta tgttataaat attttttaata aaatttgttt ttaataaaat    300
tttggtgaac gattataatt atattttgtt gtaaattttt tatacattta tttttattaa    360
tctgtaaatt tgtaataaat tataatattt gaaattcgaa ttttaaattt tttggtataa    420
aattattaat aaactttaa tcaattaata gatcaaaaaa atttatgtcc aaattaatta    480
attaaaattt ttttaaccta cactattgtt taatgttatc acaaattata aattttaaa    540 ttaattattt tgtttggtcg gcaaattaag atattattat caaaaacatt ttttttttt    600 tcgcaacaca ttagttacta aatgaactat taagttcact tatcttatcc aatttgtgtc    660 tacccctacat aaaccttgta cttatccccta aatcacttta gataaattgt tgaaaattta    720
atttataaat tttgtatta ccaaattagg aaaacaaata tctgaaaata ttattttta    780 atatcttaac aactcgaaga actgagaaac gcgacaaaac caatcgtcct cttccgatag    840
ccacaaaaca aaaatcagac aagaagaaag aagaacgttt cttctaacag atagagatta    900
caatcaaatt gactcttaat ttctcaattc cgtatctctc atttcatctt cttcttcttc    960
tcctttactt aaggatctct ggtttctctt tctctcctct                        1000

<210> SEQ ID NO 30
<211> LENGTH: 1000
```

```
<212> TYPE: DNA
<213> ORGANISM: Arabidopsis thaliana

<400> SEQUENCE: 30
ttagcaataa tatataaccc aaaaacttat ctctgaacaa attaattagg aagtaacgca      60
caaaagaaa tgcacaaaaa taaatgtcag aagtgggatt tgaacccacg ccctctttcg     120
aagaccagaa cttgagtctg gcgccttaga ccactcggcc atcctgactt tttgttaaac    180
ttatacgtat atagtgtaaa taatcgtata attttcaata tccataccaa tcttcagact    240
cttttttttg gtgacaaagt gtatgtatta ttttcagaag ctatatgttt ttcctataaa    300
acatccaaga ctgcccata catattttta agaaaccta tagtgtgtat atgacttcaa      360
aatttcgaat ggttagtttt tcttcgagg accaaaacaa aaagcccatt caatcactag     420
aaaaatatca ctagtcaatc aatagaccaa aagattgaaa gtaggatata tttgtttaat    480
aatgcctacg attctgcgaa gacaggagaa gccataccct tcaatctaag ccgtcaactt    540
gttcccttac gtgggatcct attatacaat ccaacggttc taaatgagcc acgccttcca   600
gatctaacac agtcatgctt tctacagtct gcacccctt ttttttttagt gttttatcta    660
catttttcc tttgtgttta attttgtgcc aacatctata acttacccct ataaaaatat    720
tcaattatca cagaatacc acaatcgaaa acaaaattta ccggaataat ttaattaaag    780
ctggactata atgacaattc cgaaactatc aaggaataaa ttaaagaaac taaaaaacta   840
aagggcatta gagtaaagaa gcggcaacat cagaattaaa aaactgccga aaaaccaacc   900
tagtagccgt ttatatgaca acacgtacgc aaagtctcgg taatgactca tcagttttca   960
tgtgcaaaca tattaccccc atgaaataaa aaagcagaga                         1000

<210> SEQ ID NO 31
<211> LENGTH: 1000
<212> TYPE: DNA
<213> ORGANISM: Arabidopsis thaliana

<400> SEQUENCE: 31
aagtgagtat aggtcaacta ctaataacta actcatgttg gttttttgtta attggggtcg     60
ttggtggaag tgaattggcc aatgggatgc gtacatgtgt atgtgaggat tgtggtagat    120
acatgtcttg ttattgtatt agatgaacca ctctctcacg gttgttctgt tttggtaact    180
taacaagaga tcaaagagat tccattccat tactatcatg ttgagttatg acaaaaaaag   240
gtacagctta caaacaaga catgcatgtg ctctcatcct ctcaataaag cacatagcaa    300
tgaaaacaat caaaatattg tttggttaac aagacatcca tttacaatta aatgaaagac   360
tctattgcaa aaactttact tttattcatt gctattactt tattagacgt ccaccaaaag   420
tcatttattt agtttgtaat gttttttgcc atttagtacc attgactcaa aatcattctt    480
ggctactgat tttcttagtt tcattgtagg tcgtattcgg attttagta ttatcttctt      540
ctttacggta tataattcaa cttttcttag tttcaaaaca cggcaaccag atgactaaaa    600
taactcacca ttgattcaaa aatcaacata atttggtcta gaacgtcaaa agacttgtaa   660
aagatgatgt actaactgag aattttcgac acctgttatt ggtcaagtca ataatacaaa   720
acaattatgt attattgtgt agatatagca aaactccata aaccttaatc aaaggaagta   780
gttcaacaac caaagcctag accgtcacaa agaccaccga ccccaaatat tacaaacgga   840
ccagttctct gttcacaaca caacactcat cattttgtcc gaatctgaac aaaacaaacc   900
aaaaactgtt agaaaagtag gaaagagttg gtcacccaaa ttaagccacc tttgcttcct   960
```
caattcctta tttataccat caaaagactc cacaatatcc          1000

<210> SEQ ID NO 32
<211> LENGTH: 1000
<212> TYPE: DNA
<213> ORGANISM: Arabidopsis thaliana

<400> SEQUENCE: 32
aaaacatcaa atctaagtac aatgatagac gacaacacag ttcctgcaac catggaactc          60
aaattgaata tgcaatgact cttggttaaa gacagagcct tgggatatt  acatacataa        120
acatataact taagcactaa ttcatgaatt tacatgttat atatgtatga tgacgaagtt        180
ccaattccaa gaaagatcaa aaactacaaa gttacctctt ttacttctgg cggagtcgtt        240
gacggagatt cactccggct cgttcttgct gcgacggtcg aaaaccacag aaaattgtcg        300
caggtgggtc tggttagtgt aaaaaccgat aaggaggga  ttttgacatt tgttttgga         360
ggaggaagac gaggagattt cttgaaccga atgtcccggt ttttctaaaa ccacttctca        420
gactcccggt tcatattaac cagcgcgtgc gtgtcgtctg gttttcatca tgaccaacgg        480
tcaagatcaa aaggatcgcc ttttttagta gatggtgttc gatgaaatgc tcgttagaga        540
cgttaaagtt gtagtgacaa caaattagtg tttatcattt tcagaatcgg tataatggaa        600
atgtcagttt cttcattcat ttgaaattgt gacaagatcc aactccatca tttcaccacg        660
caataactaa actgttaggg acaaaacgca acatgaatga atcaatgtac acaagtgtga        720
gaacctgata ttcctatcat tgaattgtat ggaacatgcc aaacttagag agtaaagtgt        780
acgtgttcta ttttgtaatg caaatatgat gcaattcaaa tcaaacacga gtttatctcc        840
tttggcacgt ttctcaatat agattgctgc accagaaaaa gacaattttt tctgtttgaa        900
gcctcttttg acatgaagcg aaatgcggca agagaaccaa gaagacaata gcattttttgc       960
ttttctttgg ttaccactct ctaacaagat aaagaaatgt                             1000

<210> SEQ ID NO 33
<211> LENGTH: 1000
<212> TYPE: DNA
<213> ORGANISM: Arabidopsis thaliana

<400> SEQUENCE: 33
ccatgttagc taaattgatc catttggaat tttggattct atgtatttag ttcattatca          60
atgattcgtt ccaagagaaa aaaaaaaaca cttaatagat tattagtttt ttttgttttg        120
aacaccaaaa ttttttagaaa ttactcaaca gaaataattt atcttttgtt tttttagtcg        180
acccaaactt gtgcgtttta gtctttctct taatctttgg aaaaaaatat ctgcagtgtt        240
tttatatcta ctcaaaagcc caactttcaa agttctaaaa ttcaaagccc aaagcctaac        300
agttaatcca gttaaaacta agttcggaat ccatgtaagg cttaatggtc cggtcccgtc        360
ccggtctcaa aacggtagtc gtgactcgtg atatcttgca gaatccgtaa ttccgtatac        420
ttgacgaggt gctgtaagta ttagatgtta tcgtgatgtt tctgctcttc ttcgatcgcc        480
acatcaaaat tataccatat ttttgaatct aaagattgtt acgaatgcat aagcatatat        540
gtaagaaaac aataatcacc tatatttatc aaaattaaag atctatcgat tgatctttct        600
gacttgcaaa gagagactcc acataaatgt aaacacggtt aaaatacttg aatacctcaa        660
tcattgtcgt gccacgccga catagtcaat tagtcataac ttgaccctcc aaaaaagcct        720
aacgtaagag agtttcacaa acttatttcc aattatctta agccacgtgt ttagtgacct        780
ttgtgctggc cctgaaacgt gtctatctta tcgacccctc tttaaactca aaactcaaaa        840

```
ataataatta aatagtaaca ggccgacata ataacccaaa aatatctata acgattaaaa      900
atagtaacac actgacccta cgtggaaaca agaaagatat taaaaaaact catatgattc      960
gtctctataa aagatccaac tctcacaaat caaacaaatc                           1000
```

<210> SEQ ID NO 34
<211> LENGTH: 1000
<212> TYPE: DNA
<213> ORGANISM: Arabidopsis thaliana

<400> SEQUENCE: 34

```
ttatccaatc cttttcaggc cattgactta ttttctaatt aacctaatta tatatataag       60
aaaaagctaa ggcatcttat atttatatat acatatatca attgattgct aataatgttt      120
tgattaactc tgcatatggc atgttttcca gcgatttaag ttcacaaaga agattttcgt      180
ttttgtcatc actaaaaatt atctagttct ttctacttttt tcagcgtaca ataatctttt      240
tttctatcaa ttggtacgtt ttttattttc tcaatttttaa ttttgttttc taggtacatt     300
tttaatcgaa ttgcaccaaa atatccaaac aaatcaataa acaggcaga atgaggtatt       360 accgtattag ttaaacgaga agtggctact ttcctcagcg tgattaaaat gcttatgggt      420
tcagtttcat aattctcata acggaacta cgcatttgac ctcatgctct ctataaatat      480
taagatctga tgttgagagc ccattagaac taagtttacg aatgagccca tgatagttta     540
acttgggcct aattagtgtc taatctgctt ctaacgttac cgagtcaaac gcggtctaaa     600
ctaatttgta gagtagtgta tttgtccaaa gcgtacccac acaattgctg agaaacttca    660
aaccctaagt gtgtgtctag tattttgcaa tatacgacgc ataagaaat atcctaacat     720 tgacaacaac aaaaaaaaat cttagcggag atatagacgt gtgagacaag agctcacacg     780
tgttgcacat tcgagacttg ttgataatga cgacaacaag aggttctaga atattcgtgt     840
tggtttcatt attattagca aataagacca agtcaacaaa ctaacttaaa cattgtggat    900
cgtccacttg tccgactctt acgtcaaacc catcattgtt ccacatatct ccacgcgtca    960
atctctctat aaatacgaac aaatgaacac gtatcaattc                          1000
```

<210> SEQ ID NO 35
<211> LENGTH: 1000
<212> TYPE: DNA
<213> ORGANISM: Arabidopsis thaliana

<400> SEQUENCE: 35

```
catctggtac ggatcttcta gtttctatca ataatcagag tacacaagaa ctcatcatct       60
cgaatatgta ttaacgtcta tattgtatgt ttcaattcag aaatcagtaa actctggtat      120
tttgaagatg aaccggtccc taagtctcac atggataaat ttacatcctg gtacgagaat     180
taccgaagtg aaatgtccca agcgatgatg gaaactgata aggttaagag gaatcaatta     240
accaatgaag ttatccagag gtacaagcag gtaagctctc gctcaatcca atgcaaagat     300
ctgaccaata gatttcatga atcacatttt ttgttgatta gtccatataa tgcttcttaa     360
cacaactcat cggttgaacg gtttcttctg tctgtatcag gatttctatg gcgctgcagg     420
gtttgaagac agcaataaaa gtctggaaga actctacccc caagccttgg cactctacaa    480
cgtcgtttac gattatgcca ttcaggaagg tgttgcgaaa tgtacatttg cctggaatgt     540
tgcaggaccg gtcctgtgca aattttacct taagaaaacg aaggataaat cagtagtggc    600
ttcaacgtct gtgcttaaaa agcttttggg ttgaacagac ttacttgtcc tgtttgttgt    660
```

```
cttcatgtat cataagatgc gttagacaag tatctgacct aggtaaccga acttataggc      720
gaagctatgt ggtgtacttc ctttgtttaa gttataactt aagatttgtc atctagtgta      780
caagtaattc cgtgtgtatg tttgcttatg aataaataa agaaaactaa tgcttatatt        840
taatttcaat taattgtacg tggcactttc agagtccatt tggtgtacaa agctgtcttc      900
ttcagtgtga cacctctctg catcctcaag cttccatttg tcttttccag acctttcttc      960
tttccattaa gtttcttcct tgtgatcct agaaaaatct                             1000

<210> SEQ ID NO 36
<211> LENGTH: 1000
<212> TYPE: DNA
<213> ORGANISM: Arabidopsis thaliana

<400> SEQUENCE: 36
cacataatct ctctctacta cccacaggta tattagagaa actacatata acatgcacat       60
aagtctttat tagttctcaa gcctgtcatc ttgttcaggt gtttgaaacg ctggttagca      120
agatgacccg gtcgcaagat tcagttgtga gagcagcatg ctcatcagcc tttgggttac      180
tgctaagatc aagcaagtca acactgtgga gaggagctcg acttgacggg accgactcag      240
gtagaaaagc caatgatctc gaatctgtta agaaataaca tgtgcattac ggtctgtgtg      300
aataccaacc agttactgcc gaaaactttg ggggggtttg cgatatatat ccataggtac      360
agtgtgcaat gagaaaccat ccaggttttt gtgcttgttg taaagtgtat tatgttttca      420
tcttgtaaag gatattgtca ctcgtgtgtc atctctatta ccaaactcag gaaagaaaca      480
ttcacacgaa attgttgtag gctgtggtcc tctttttatt gattataatt tttgaggcta      540
gtgttggata tacttgtctt gacagagtcc aacgtttgat ttatcttcag ttagtgtttc      600
atatgagagt ttaaacggtc tttgaagttt caaacacaca ttagattttg gtaacattgg      660
taatttattt atgtggcctc tatgtttatt ttgattttg agacttgacg atagatgtag       720
ctatcactat cagtgagccc tccaagttgt tgttttgtgt atgtgaatta tcttcgtttt      780
ctttatgaag atatgtttct aaacttttcc tgagaaggaa ggtcactacg atggtcacat      840
acggacaaac taagtagcaa gcacaatctg tggacttaaa aagaggtgtt tggcaagtaa      900
aaaactgttt acgtcatctg ttacgtcttc tgttcactt atgttttact ctccacgcat       960
cttatccttt ataagctcgc acaaatctta accaaaacca                            1000

<210> SEQ ID NO 37
<211> LENGTH: 1000
<212> TYPE: DNA
<213> ORGANISM: Arabidopsis thaliana

<400> SEQUENCE: 37
atacccaata tatctaaact ttaaaactta atttggtcca acaaacgtca atcgatacaa       60
tcatgtgttc ttctagctta tggattctat ttgacgacat catgaagagt ttgtacaaat      120 caattaatt ggatattaca taaactaaaa atatgttgtt tttttttacg gatgatcttt       180
taataactga agatgaaaat taattttagt tagaaatgtc ttgaataata attaatgtca      240
cagaaaagtc agaacgtacc aaagatttcc gcgtgtatta aacttaataa atagacacaa      300
gccaagtctt agcagtgtac tactactaac acacatccac atcaatgtgt catctttgtt      360
gtatgacaca agttagtatg acaatcagtg tttgagtagt gatggtttaa atggaatgtt      420
tgagaatcca atacaattgg cggtctgcta atggccagaa tatctgccaa agttattttt      480
tatctactgc ttataaatcg tacaacaatc tatttagttc tctttagttt tgaccttgaa      540
```

| | |
|---|---|
| gtccatgaat cttaaggacc tcttctccac atcattcaaa ttcacatatc ggaaacacag | 600 |
| tactgcttga atgcccctcc catacaatat gtctatccac tgatccacaa taactcgatg | 660 |
| gtgcatgtgt gtgtgtgtgt gtgtgtgtgt gtgtgaactt cctggctgta ataaatttaa | 720 |
| taaatactta aatagacagg cgaagtcctc gtccactttt ctacacctag catcaatcat | 780 |
| caatgtgcca tcttattgtt tcaattttc ttaccataac tttgtccttg catgtaactt | 840 |
| ttccaattaa atacaagtct gtcttttatt aaccccgag aatttactaa atgatattga | 900 |
| cataatctat tggacggaat gagttgtcaa aaaacgagag ctgtcttttc ctgctccact | 960 |
| gtcctcttat atatcccaca acaatctttg ctacattttc | 1000 |

<210> SEQ ID NO 38
<211> LENGTH: 1000
<212> TYPE: DNA
<213> ORGANISM: Arabidopsis thaliana

<400> SEQUENCE: 38

| | |
|---|---|
| taccttgtag agttccaaaa cattgtcaca aaatatttat aaagaattta ttttaactaa | 60 |
| ttaggtcgtt aattgtccaa gggttttca tagttgatat agttctgttc aaatatagcc | 120 |
| atccttaatc gattcatggg atcgtaaatt actacttcga gtgttgtaaa aaaaatgaa | 180 |
| acttctacat tacaaactcg aatttaatgc atctggagtg atactataaa agtagggatg | 240 |
| ctctcaggtc gcatttgaga gacacagaaa tgatttaat ggaattaata tattttcagt | 300 |
| ttttcacaaa aaaaaattgt gtttataaca actgcagatt caatgctgat tttatgagtc | 360 |
| tcacctatag aatttatatt tctatattca tagaggcagt ataggtgttg acccaacatc | 420 |
| gaaagaacac ttcgtaaaaa attctttgga acaaggctga aaatttactc ccaaatttag | 480 |
| ctatccgatg aagataaatc atttaccgtt tattaaagaa ttatcgagat tttagtccaa | 540 |
| accaaaagag attatgagcc taagattttg aatttgtatt ggtaaaagaa attgaacgaa | 600 |
| aatttcagaa aaaatatta ataaattgaa cgatagagtt cacttactac atagtcaact | 660 |
| agtgcctagc tataatagtt tcaaaagaca aaaaaaaca aaatcggtta actacttccg | 720 |
| tgacataatt ctcattttga ttttgaatc cagtctaatt tgaaaagtat attcaaaatc | 780 |
| tttaaatcca ttaatgataa cttttataat acgttgacac acgcaattgt atatacaata | 840 |
| ttcttgaatt ttaaatgtaa attctagaat atattgcgat caccacacta atcaaaatct | 900 |
| ttgggacaac ttgaacccac atttgacttt tcttggtcaa atattttggc atcatgcatg | 960 |
| atcttctcta taaaaccaa aaggcctcaa cgacattcat | 1000 |

<210> SEQ ID NO 39
<211> LENGTH: 1000
<212> TYPE: DNA
<213> ORGANISM: Arabidopsis thaliana

<400> SEQUENCE: 39

| | |
|---|---|
| ttcactgatt tggaccaaat cgaacgccag gtcattctgg tgagaaaatc ttaaggctat | 60 |
| ttatgccttt tctttcttct attcattcag gagattacac gtggcattac ttgtgtggtt | 120 |
| cgcatgtcgt tgtttctaca ttgcaaattg tcacaaattg gtccataatg agtgtttcta | 180 |
| gtacctttcc ctttgtctgt gtttatttat gaataataat tcatgaatag aataaactat | 240 |
| ttttccaaaa atattcatat atgtccgaaa actcacatcc atattgtaaa tttaatcgaa | 300 |
| tctaatatat tttccaaata atatattagt ttttgccaaa atttaaacag aaaatcctta | 360 |

| | |
|---|---|
| atacagtttc gaaaattctt tttcttttc tgttgaaatc atagtcaaat tcatttattt | 420 |
| gtagatatat atatatagtc aaattttctt tttatacaaa ttgataagaa aataaatgtt | 480 |
| aacctacaaa attaatgtat tatgagctgt caaattatta ttttgacttt atgagttgtc | 540 |
| atattataca tagcatatca ttcttaagaa aaacaaaaac aaaaacaaaa acaaaaaaat | 600 |
| tatcatcaat gatccgcttc ataaagtaac caccaacaca attattttgg acgcctcaaa | 660 |
| tccaaacctt attttcaata attgtgaaaa aaagaaaaa aaaaagctat attgtggtag | 720 |
| gtggttcgaa ccactcaaaa atatttatga taataacacc caaaaacaaa ctaaactatt | 780 |
| atttatttat tgtggtcatg agatagttac agacacagag aatacatctg tcagaaagct | 840 |
| gactcattgt atcttatctt tcccatttcc tcttaccttt tttcctacgt gttgccacaa | 900 |
| aactctcatc ttcacccact caatctccgc cacgtgtact ctctaaccct tcagttcggt | 960 |
| cttttttaagg cttccccaag ccttcgcatc caaatctctc | 1000 |

<210> SEQ ID NO 40
<211> LENGTH: 1000
<212> TYPE: DNA
<213> ORGANISM: Arabidopsis thaliana

<400> SEQUENCE: 40

| | |
|---|---|
| tcatcagaat taaaaaaaaa aagtcagtct aaaaatatac cctaataaac tgacataacct | 60 |
| atttcaacga tacaattcta taatgagtta ttaaattgat ttgatttcgt attctctaaa | 120 |
| atatactcat agacatagca gaaactagtt aatttgctta tatgttcata ttcttgtaca | 180 |
| tcatgtgatc tcacgtggaa taaaaataat gtgaccatct ctaattctct acttcactta | 240 |
| gtatctaagt atccactgtg ataccttgtt ttctgctcaa agttgtacat gcgtagatta | 300 |
| ataaatacat ttcaccccctt caattgatcc caaaagcctc tacaagacag ccaaaacaaa | 360 |
| tcaaggattg cgcaaagcat tcaagtttcg aaacaataat tttttttaatg gttgacaaaa | 420 |
| agcaataatt tgtaaagcga ttcataggtc agcttctaaa tgttctcgaa ataactcgaa | 480 |
| ccaacaccta aaccatttgt tctaacgata atagacgaac gtattagaga ctcgttagga | 540 |
| aaacactact tgtatatatt cacttttaca tacatatttg tttccttcat atatttattt | 600 |
| atttacataa caaaccaata tgaaaaacgt acgtttcatg aaagagaacg ttgtagaaca | 660 |
| ctatcaccgt ttgcttgtaa gaaaaaggct tatctcacct ataaactcgt gagtcatatt | 720 |
| tatactctta acaataataa ataaaataaa actctatttt ggtaaccaca aaaaatattc | 780 |
| tgaggctaaa agcgcgtctg ctggaaagtt cacgcgctct gctaaccca ccgtccattc | 840 |
| tgactctttt agatcttaac cgtgtcttta tccacatcat acgtttatac acgtgtcaca | 900 |
| cgatcaccta ttctataaaa aacattattt taatcttatc cttttatgc ttcccctata | 960 |
| aattatcttc tcttcctcct tctccgatct ctcctccgtc | 1000 |

<210> SEQ ID NO 41
<211> LENGTH: 1000
<212> TYPE: DNA
<213> ORGANISM: Arabidopsis thaliana

<400> SEQUENCE: 41

| | |
|---|---|
| gactaattgt cagtattcta acaacgttaa tttcgtggtg cacgaaaaca aaatgacgat | 60 |
| gtggttgcac aaggtccacg ttcttgtata ttgtttttta atgtgctaat tgtgcgctaa | 120 |
| aataaattta attgtataaa attagtatag tttatatttt tttaatatgt atatgttcat | 180 |
| tcaaaacatt tggataatat atgtttacta tgtgatagac tgatggtgga acattttatc | 240 |

```
catcttatat gcatatgaat aaaaattatt caaaatgttt gttgttgttc agattattaa      300
ttattaaaga attagaaaat tttggaatta caggtatata tgtatgtgtt gtatattgta      360
tatttaaatt attatgtata tttatattta aattttctta ttttcataaa tcgttagtat      420
ataattgtgt cacatctaat attattagaa acaagttgg acttttcata ataaaataaa       480
acatatcttt tatcaaatta accttttcct ttaggtgccc aaatccgtag caccatcaaa      540
tacctaagat atacttttta tttccaaaaa tcctttcgtt tgatctaata ttaataatat      600
aaacgatcaa acaaaacgat ttttagaaat caaacgttca agtttgatcg ttggtcgtcg      660
ctaatttaag tttgatcgac tgctcatgtt ccgtgacaat gttaaaactg aatacatgaa      720
acatgttttt tttttgtgca tttgatttta ataattttt aaaaactgat aacacccgaa       780
aaaaacagca agaaactaaa caaggaagaa aagaacggtc ggtgaggaac tctcgtgaaa      840
gtcttcaaaa gacttttaac ggaaaaacaa aaaacaaaaa acaaaaactc ttgtgaacgt      900
aagtgcatgg accgaattgc acccgatcac gtcggttcca caatcctctc ctatattaag      960
gccttcactg ctccttatca tctcaaactt ctcatttatt                           1000
```

<210> SEQ ID NO 42
<211> LENGTH: 1000
<212> TYPE: DNA
<213> ORGANISM: Arabidopsis thaliana

<400> SEQUENCE: 42

```
aacaaaaatg gatttgatca agtgaaaact ttggtccaca tactccactg agatatttac       60
ttggcttaca acatatgtca caagatatat attccaaaga gatattttac ttggctcaca      120
taattcccaa gatatttcat atgttttggt tttgttttcg atgaagataa gatatttcaa      180
atgcttctcc acctaaaccc aacaactttt gagaattcca aattctgatc aagatagaaa      240
tttttttatat tgtttttcga attaattgtt tttcatatca ctacaaaaca aaatatattat      300
attaattaaa gtataaaaaa tggtactaat ttaaattact caaaataaat gatacacata      360
tacatggtgt tatatcaatt acaataattg acactattat tgaattgttt gacattgatt      420
taataaaatc ggtacaaatt cacattaatt tgcatctttt tcaaaatatt attacaacaa      480
catttaaatc actatgttct taatcgtctt ttcgtaataa taattaaatt ttgaggttt       540
tcgtttttt agataagaaa aaaataatgt aaaaaaaatt gacgagatca tattttggtt       600
gatcacaagt gaggaaaatg aagttattat gtaaagaagg attctataat cgattgacca      660
acattcctcc aaagaaatat attttatttt ataaaaaat ctaataaata attggaaata       720
aaatcatcat tcaccaaact ttatactgtt ttacaaatct acgttttagt caatttcttc      780
cccatacttg acctcatgaa gcaatgaaca caaatctatg tttcgatttt accatggaag      840
agggtcttag tgatatgaat ttaaatgtcg ggataaaata taagattata aaactataaa      900
ggtttatttt gaaatacagc acacacaaga aaaaggccc atcaacctcg cagtcctaat       960
tagataaata cacgtcaact tctctgggaa caaaaaaact                           1000
```

<210> SEQ ID NO 43
<211> LENGTH: 1000
<212> TYPE: DNA
<213> ORGANISM: Arabidopsis thaliana

<400> SEQUENCE: 43

```
agttaaaacg ggcttacgaa accataaaaa acatgaacat ggatgctgat tctgtcttat       60
```

```
ggagttctgt tctcggaagc tgtaaacttc atggagattt tgtgttaggc aaggaaattg      120
cagagtatct cattggacta aacatcaaaa actcaggaat ttatgttctt ctttcgaaca      180
tatatgcatc ggtgggtgat tatgaaggtg ttgcaaaagt gaggaacttg atgaaggaga      240
aaggaatagt gaaggagcct ggtataagca ccatagaaat cgaaaacaaa gttcatgaat      300
tccgagctgg agatagagaa cactcgaaaa gcaaagaaat ttacacaatg ctaagaaaga      360
tcagcgagcg gatcaagtct catggttatg ttccaaatac aaacacagtc ttgcaggatc      420
ttgaagagac agagaaagag caatctctac aagttcacag cgagagactc gcgattgcat      480
acggtctaat cagcaccaaa ccggaagtc ccttgaaaat attcaagaac ctacgagtat      540
gttctgattg tcatacggtg acaaaactga tatcgaaaat cacaggacgg aaaatcgtta      600
tgagagatcg gaataggttc catcatttca cagatggttc ttgctcttgt ggcgatttct      660
ggtaaaacca acaccacac attgtaattt gtacgtgaaa agaagatcaa agtgaacaaa      720
tttagttgga ttatctaaat atcattcttt catgggaatt atgttgaaca cgtggagggc      780
attatttgtg aagttgaaac gaggactatt tttcaaactt tcttgaggaa caagacttga      840
cttttgtaac cataaagata gaatcaagtc agattttgct acttcgagaa cattggtcaa      900
tgagtcaaaa tgtcaaatag tcaatactaa aatcaaaatt gaactttgtt tattaatttt      960
gttctaatct atttaacccc acaaaagttt ccaaaactgc                           1000

<210> SEQ ID NO 44
<211> LENGTH: 1000
<212> TYPE: DNA
<213> ORGANISM: Arabidopsis thaliana

<400> SEQUENCE: 44
acgaatctcg tattcattac tatactgcta atgaatgcat caattttaat ttttattggt       60
tatctatcct taaaaaaaag ttataagaat attttgataa tttgttccaa gatgtagtac      120
tagtagtagt acttggtctc gtaaacgacg acgccgttta ggaaatcaaa cggccaaaaa      180
tgcttccact ttgcgaaatt ttattggtgg gaaacgcaaa tgtatcgata atgatttaaa      240
gaaaaagcgg cgtttctaat tggaccacgt tgcccaatct ctacggctca cgcacgatct      300
gacgtcaaat tggcataata ctataataac cttatcgaga ataaaataat agtcgcatcc      360
aaacaaaaga aaccaacccct tttatatcac gacgagtgtc acgccatgga cacttgtcca      420
tctctctcgc tctgacccct ttcaggtatc ttttatttct caaagaggaa ttattgattt      480
tccatttcca aagaaaaaaa ataaattcga aggtcaggaa aattaacaaa aaacttcctt      540
tttttttttg ttagtttgtg tgactgagct gcttcatttt ttttctttct tttttttttt      600
ggtttgatga atcgattttt gttgtctatt actgattggt tttcttgttc agattcactg      660
attcgaagag aatcatgatt tttttttccc gctgaataat aagcatatga ttgggtgttt      720
tggagatttg tttactgatt aaaaggagat tcctttccat tttcaccatt tgctctgttt      780
gacttcattg tgcttatatt tcatttagat cttttgtttg ggtttagctt tggaactgat      840
aaaaatctga ttttgtctca cggctttgga tttggttctt aaattttggt actttaaaac      900
tggataaaga tcagtgcttt tttagattct tcgtttgttg atgaatttat ggatgtatgt      960
ataattaaac cataatctct ctgcttgttt gttttcttat                           1000

<210> SEQ ID NO 45
<211> LENGTH: 1000
<212> TYPE: DNA
<213> ORGANISM: Arabidopsis thaliana
```

```
<400> SEQUENCE: 45 ttgaattttta tgtaaagtta ttctgttttt aggactttta tcctcactga attatgttgt        60
gttaaagtag tagcttatat ggtcacatat ctcacacgtg tttccatttt ttttctatct       120
aagttttcgg ttttttacatt gtatacaaaa ataaatggca tgccttgggc cttggccact       180
gattcacatg atcacgtaga gtttgtgtgt gattcaaatc ctagatgaga agatcatcca       240
attgatctaa gatgtgtctt tcttatatca cacgttttat tttaataata ctcttcagtt       300
gggtttgatt ccatttatga tttatctatg aaaacagaat atgtcctcat gctgattatt       360
tcgtttgtgg ttgcatttta ccatctgtag ttttttttgt ttactgacaa acaactaaga       420
ttttatgaat tcatttgatg ataaatagtt aatcaaatat attattatga gtgactcgat       480
ggcgaaagct ggtattatct tatggctgct aaagtctact tttagaagaa gaaaaaaaaa       540
gggtctgttg cattaccctg ttgttgcgac tctcctacaa taactctcac gtggcccgtt       600
tcttggtttt tgccctattt tcacaaaagt aaacagagat tttcactagc aaattgggcc       660
caattggaga caacttcatg tggtttgaat cgtatatttc agatagatta gacatctagt       720
cttctttgat gtgcggtgag gatcttaagt cgctataacg ttgtgaaaaa agaaaagaaa       780
aagtcactat aacatagatc gcaactaaac aaataaagga cactatacat gtacgtaata       840
atattcattt attttcaacg acaatgttcc ctagggtggt aacccaagta tttttcatag       900
atattatact tctagcgaaa agccatcaat tgagaaaaaa ggcctccacg tttgacccgt       960
tttgcctata aaaggattct ttaagatatg gaccttactc                           1000

<210> SEQ ID NO 46
<211> LENGTH: 1000
<212> TYPE: DNA
<213> ORGANISM: Arabidopsis thaliana

<400> SEQUENCE: 46
caaagctcct aaatgatata gcttcaagca agattcaca gagactatca catgcgagta        60
tttaatcatg cctactataa aagagaggac aattagctac ataaatcaaa cgctataatc       120
aataaagcga tggataatac cgaaaacgac ggcataatcg ctgttgagga catcaccgca       180
agtgccacca ccaatagggc aaaacgcatc ggagccagtg accttgaggt aagtcaaata       240
cgcagtgtct aacatcccaa taccgccgat tccggtgtac cagttgtatg tcgaactgtt       300
actagtagat acttcacttg tagacgatga ggaggaggaa gacagcgacg gtgccgaatc       360
ctcaccgttt tccggctcag atgaagaaca tttaatcgga atcgcaggaa atctccgatc       420
agagacctaa ttcagaacat ctgacttcaa atgaccgatc acacactact gtcactgaag       480
aaaacacatg acaagaattt acctcgaatc gtctaggata agaagttacc gacggaggag       540
aaacctcacg gaagccgaaa tgaaactgac aagacgacac agaaacaaac ctcgccatca       600
tcgtcgtcga agaatcgcta ttccaccatt gttaacttca tcatcttctc tcctccgctc       660
cactatctca gccacttgtt tcaatattgg gcctaaacga ggcccaaata cgataaatttg       720 gatccataat tagtttatca caattgggcc ttacggtctt cttatccgtc cgagtcagca       780
agttatcctc ttcaacacga ctcacgaggc accgagttgg acttatcatg attcattatc       840
tacgcattgt ttacattttg gaatcgactt tggtacataa ttgaatttat ccatagaaat       900
gatagagact cgaagatcgg acataaaact tgctgacgtg acacccatac ctttgtgtct       960
gtatgtatta tataaacgct atagaactaa gagaagaagt                            1000
```

<210> SEQ ID NO 47
<211> LENGTH: 1000
<212> TYPE: DNA
<213> ORGANISM: Arabidopsis thaliana

<400> SEQUENCE: 47

| | | | | | |
|---|---|---|---|---|---|
| ataccctcgt | gacctttatc | gaaggtttcc | accttcacac | tcaagatact | tctcctagga | 60 |
| tcttctctac | acacattcct | gtagggtcac | tccctgagtc | agttaaggac | tcgtcctgta | 120 |
| aagttgtgta | ttgctgcagg | aacccgaagg | acgcgtttgt | ctcactttgg | catttcatga | 180 |
| aaaatttgat | tgttaaggag | atggttggat | gcacaatgga | ggaaatggtg | aggtttttt | 240 |
| gccgagggtc | tagtatatac | ggacccttt | gggatcatgt | attacagtat | tggaaagaaa | 300 |
| gccgagaaaa | cccgaaaaag | gttatgtttg | taatgtatga | agagatgaga | gagcagcctc | 360 |
| aggagtgggt | gatgcggatc | gccgagttct | tgggatattc | ttttacagaa | gaagagatag | 420 |
| agaatggagt | attggaagat | atcataaagc | tgtgtagtct | tgagaatctg | agtaaattgg | 480 |
| aggttaatga | aagggtaag | ttactgaatg | gaatggagac | taaggcattt | tttaggaaag | 540 |
| gagagattgg | tggatggaga | gatactttaa | ctcctttgtt | agcagaggaa | attgataaaa | 600 |
| ccactaagga | gaaactaatt | ggttctgatt | ttagattctt | ttgctaagaa | tctgctttac | 660 |
| caacttagtt | ctcaatttct | tgagcttttt | tttttcttct | ttttattggc | ttaatacaag | 720 |
| taaggttgtt | gacttgttgt | gatggaccaa | agtcaccaaa | ctggtctgtt | gagaaataaa | 780 |
| actattgttt | ttgagtttta | gacataagag | tcgtgattct | ccttctttct | tgttttgtta | 840 |
| tcttaaata | ttatattcta | cgtgctcttc | aagtaaagga | tgtgttgacc | atttcaccac | 900 |
| ccaaactaat | atcttagaag | caaaagcatt | gtgaaattta | cttgtagaac | aaccttctca | 960 |
| ttcatatata | aaagcagaca | agcattagca | tcatagatac | | | 1000 |

<210> SEQ ID NO 48
<211> LENGTH: 1000
<212> TYPE: DNA
<213> ORGANISM: Arabidopsis thaliana

<400> SEQUENCE: 48

| | | | | | |
|---|---|---|---|---|---|
| cagttgatat | tcataacatt | ttgaaagaac | ataacccaaa | ttagtagtat | atttctattt | 60 |
| tagttcgttg | aagaaactgg | atttatttct | cgaaatatta | ctaaatcgaa | aaagaaatg | 120 |
| aaaacgtgca | catgttgtta | tagtgtttaa | cactgataaa | tttcagtttt | accttcttcc | 180 |
| tttttttaag | gagtctagca | tgacaagaga | tctttgttat | cattcggaat | atgaacgtat | 240 |
| tataagaaaa | tgattgtatt | caaaaataga | ataataaata | aataacgag | aaatgagctg | 300 |
| tgctttctag | aagaacatcg | atatctcttt | ttcgtatttt | tcgtctttaa | ggctggaaac | 360 |
| aaacgaaggc | gtactcctac | gcctcaaatc | tttcatgcct | tttggctttt | cccaattaag | 420 |
| attatacata | ctatttagca | aacaaaacaa | tggtagtagc | aattaatcca | acaaaataag | 480 |
| aattttaga | aacgtaagta | ttcctccaaa | aaagataaaa | taggtgatta | gtttaccttg | 540 |
| ccagacaact | aaataaaatt | aatgtgaaac | ttaagataaa | aggcagacga | gattttttag | 600 |
| gttctgtgaa | gacaaatccc | tttctatttc | gttttgacat | gcatagaagt | taacacatac | 660 |
| tacgaaaatg | ctaaaaaaac | gagatagtgt | cgccatgata | actgcaatgc | tgctgaaacc | 720 |
| ctcaacttta | ttaatgaact | aatgaagcca | aatcattttt | attttatgat | taaaaagttg | 780 |
| ccaagattcg | tgctcactct | gtcaaagaca | acaactttat | cattttttcaa | acaatagttg | 840 |
| attaaactaa | actaaaaatg | ggtatacaaa | atgagttaca | acgataaaga | caacaacgac | 900 |

```
tttcccttg   tttgattatt   taaaacaagt   ccgtgataag   aagaagatcc   cactaatgga    960
aaataaaatg  ttataaaaac  tggcggcaat  acacaattgt                                1000
```

<210> SEQ ID NO 49
<211> LENGTH: 1000
<212> TYPE: DNA
<213> ORGANISM: Arabidopsis thaliana

<400> SEQUENCE: 49

```
tggatgggga  tggcgtacta  tgcatggctg  ttgacatttt  acccacagaa  tttgcaaaag     60
aggtatgtat  gaaggttaca  gttatagtac  ttaagattaa  atctaaagtt  aaaaaccttg    120
tattgagtgg  gagttcttgt  gtcctgaaaa  aggcatccca  gcattttgga  gatattcttt    180
ccggatttgt  cggtagtttg  gcttcaatga  ctgaaatttc  agatctacca  gcacatctga    240
agagggcttg  cataagctat  aggggagaat  tgacatcttt  gtatgagtat  attccacgta    300
tgaggaagtc  aaatccagag  tatgttctgc  ttcgagcgtt  acttcatctg  aaatatttag    360
gcctcttctc  taaactatgt  tttcatcttt  acccactta   actgcagaga  ggcacaagat    420
aatattatcg  ccaacggggt  ttccagccag  agaacattca  acatattggt  tagttttgat    480
gaagaaagta  tatataacta  gtttccgaat  catatgattt  aagctaatga  attaagaaaa    540
tatatagttc  aagacttatg  attcatatct  ctatcaactt  tttgaccaaa  gattgatact    600
ttttcgacat  ctgtcacagc  attttgtgat  gattttgatt  gagacaaatc  atttgtaggt    660
atctctgagc  ggacacctat  ttgataagtt  tctgataaac  gaagctcttg  atatgatcga    720
agcggctggt  ggctcatttc  atttggctaa  atgtgaactg  gggcagagcg  ctgatgctga    780
atcgtactca  gaacttgaag  taagtttctt  tctggataaa  acctaatcat  tcacatggaa    840
caactgtcaa  gagttttaa   tgtcacgttt  aggttcaatg  tccttttcac  taagtctcgt    900
aagttttaa   aacaagtaaa  caaactacaa  gccaaaaaca  ttctggcccc  acattaacct    960
attcccactt  gttaaagaac  ccatcttgca  ttatcttggt                              1000
```

<210> SEQ ID NO 50
<211> LENGTH: 1000
<212> TYPE: DNA
<213> ORGANISM: Arabidopsis thaliana

<400> SEQUENCE: 50

```
gtaatttta   tttaagtttt  ggtttaggtt  tggtttgatt  aaaaaccgta  aaaccgaacg     60
tttttttgt   ttttgattta  aattaaaaat  aattgtatat  atatatatat  aatgttcatt    120
tgataacatg  atatctatca  aactatcgaa  aaacaaaacc  ctaactgtaa  cctaaactaa    180
aattctatat  aaattacatg  ccgtcattta  ggatttgagt  ttacaaatta  gattttgatt    240
ttatttatgc  atcacactta  taatttttt   tggtaaaaac  atgaaaaaac  cggaaccaaa    300
ccggaaccga  tccgaaccaa  aatacatatg  gttttaaat   ggttttaatt  ttttaaaacc    360
aaaaactgta  aaactgttaa  aaccgaaccg  taaccaaacc  gaattttata  tggtttttat    420
atggttttac  ttttcttaaa  atcgaaaaac  cgtaaaacct  aaaaccgaaa  cgaaaccaaa    480
ccgaaaaact  gaacacccag  cccttaaata  taatgaaaat  cgaataaatt  tgtttgaaag    540
aatcgaacaa  aattgacaat  aaaatctaat  taggactatt  ttcgtctaat  tttgacttag    600
ttgaaacaga  atattagcaa  aaatactaaa  acaccacaac  gcgtaataat  acccacacac    660
gatatcatta  aatttgacca  ataagaatct  agctcttggc  gaccacgcaa  gtatcttcca    720
```

```
tcttgctctc caagaaaaat ctacaccggc tttaaattta cataaacacc ctcagtcaaa       780
gaaaagtcgt aaacatagtc tctctcatga ccacaagggt aacacagtca tcctaaatat       840
aaaccacaca agaaaactgt tatactttat acacgtgtca tagtctcatt acatctacgt       900
gaagagtttc gatcatcaac cgttcgtttt cttactatat aaaccttgct cgagacctgc       960
gtgtgaagcg tataaagacg acaaagtaaa ccaaaaaaaa                            1000
```

<210> SEQ ID NO 51
<211> LENGTH: 1000
<212> TYPE: DNA
<213> ORGANISM: Arabidopsis thaliana

<400> SEQUENCE: 51

```
acgaaacaac ttgcattaaa caatttgctt ctactatact tatattgatc tatcgtgggc        60
ggtgagtaaa atgagttggg acatggattt gtcatttagg tcattttag taaatgtgaa       120 acttgtaacc aaaatatgca taaaaacttt agcctttcta aaagctaaaa atggtttgag       180
gaacaccaag acgtaagctc ttttaagcta tttgatgttt gatgtgataa ataactaaa       240 aactatttgt tatgttttttt cctcccctta aagatataag agaagagaag gtaaagaagt       300
tgtgtaagtt agtcacaatc aattgttgga ataaatttg aaaactctgt taaaagtcac       360
ccaaatgagt ttcaaacaag agttaaaaga ttaaaaaaaa aaagtaactg atataaagaa       420
tggtagttta ctttttttttt aaagaatggt agtttttaa aaactattta ggttgatggt       480 attttttgtaa agaaatccaa aaattgtagt tgatacaaga aaattttgat ttgtgttgat       540
ttatttctct tttggcatgt gaatgtaagt aatctttttc cacatgattt ctaattctgg       600
acttgcatgt cttgttacgc cagtcaacat tcgttggata agttacaatg tcatttacaa       660
cttgcagatt aattcggaaa tcaagaagga aaaaatctga attagaaata gtaggttgga       720
tttttcacaa aaaaaaaaaa agtacaatat tttgagatat gaccattaga ttcttaaatt       780
ttacgattct aacttgtaag atttcaaatt aaaccatgta taattcaatt tagggggtaat       840 ttaatacttt agggtagtaa cgataaaata gataattaaa ttgaagttta aggaccatcc       900
tgtaaattca agttcggtac cggaaacacg tcagcattga tctaatagat acgagtcctc       960
ctttctctat aaataacgta atctctctcc cgtcttcatt                            1000
```

<210> SEQ ID NO 52
<211> LENGTH: 1000
<212> TYPE: DNA
<213> ORGANISM: Arabidopsis thaliana

<400> SEQUENCE: 52

```
aatcctactt tttcaaattg ttttttttttt ctttgtatta atgctcccaa gatgtttatt        60
gaactgaaca cactagaatg aattatagct tttgtaatca gtcgagtaga ctagtttttt       120
tttttccgat ttaattttat taaatgtca acataacaaa cttccaaaca gaagtctttt       180
aagaattttg gaggctcaaa gattttttttt tctcgatttt ttttactct aatttggacc       240 atttggtctg ggaatacatt tagaaattga ttcatctcta tctcccgtat atattttaat       300
atatttagaa aaaatgctaa aataaagaaa agtagacgag cttataattt tatatattaa       360
ataaaaactt aaataaaagc ttataatttt atatattaaa taaatcttc accttaaaac       420 tattaaaata aataaatata tatatatata tatatatata tatatatata tatatagttt       480
tgttatcggt attaaagctc tattttgtag tcgaaagaat aaaatcatat aaaacaattt       540
tgctttagct ttatatcgat tttatttttgt gactaaatac tagttttgca aattactatt       600
```

| | |
|---|---:|
| cattatgtta atttaaaata ttttcaaata gaaataaaat aattattaat atttttaaa | 660 |
| aagatataaa aaaaatcgat tacaaacaat gatataacga gaaaggata gcattaaaaa | 720 |
| ttcattccta acaattttgt actcaattat tttccatttt tagaaaaaca actgcttccc | 780 |
| aaatatttga tcttagaata ttttttccaag cttttaaaat ctttttgaca gatacgtggc | 840 |
| acataaaact aggtggtgac atagatatcg acgtgtgtaa cgtttcttgt gtcctaaatc | 900 |
| aattaaaaaa gcctcacatc tctttgtaca ctacaaagaa aagatcattg attcactcac | 960 |
| aactttcatc tatttatagt ctttaacccca tttcagtatc | 1000 |

<210> SEQ ID NO 53
<211> LENGTH: 1000
<212> TYPE: DNA
<213> ORGANISM: Arabidopsis thaliana

<400> SEQUENCE: 53

| | |
|---|---:|
| tttgaaaacg ttaaaaatat aactaaaaga attattgtta taaaatataa ttactcccaa | 60 |
| ccagaacatc aaactaaaaa cagaaactca tgagaaagat ttgatctgat taatgacaat | 120 |
| acctcaggcg atgtaaaaga catcattgta ccatcaggac cgggtctagt cataacactg | 180 |
| tcgtcggcat accacatcat ctgaactacc tcgggataga ctcctagatt caggaagtaa | 240 |
| gattggagaa agcaattggc taatgcttcg gaagtattta agttcgtgaa gtgggattga | 300 |
| ataaagccat tggctaacaa tacgaaagga tcaacatctt tgatcatgga atccatatct | 360 |
| gcaccagtaa ttatgcccta ggggagacga agaaatatcc aaagtaaacc ctagctagat | 420 |
| atcaaaatct cttaaaaaca aacttatctc tctgttgaga tcaaccgctg atctataggc | 480 |
| taaaggaatc accggaagag agagagagag aggaaagagg cggaagttgt gacttgtgag | 540 |
| acggtttgga ttttggaaac ctacgttcca ttgaacttct ttatatattg gttttcatt | 600 |
| atgggatata gtaatatctt tataaaaaaa aaaaaaaaa ttatatatat atatatatct | 660 |
| ttaatacatt attaaattaa ataatatacg gataggaatt actataaatc tttataaaat | 720 |
| aaaaataaaa ggagaagtcc cttttatcta atttggatgg ttaatttgtg aatttttccat | 780 |
| atttatctaa tttcgatttg aaacatatcc aacgttaagt cagattcttg tggtgaaatt | 840 |
| attgcatcat aacataaagt catgagagta ggagagaaag taataagtgg caacatcaaa | 900 |
| acgacgacgt ttttaagcta gtgcgtcagc aacagttaaa ccatatgaag ttaatggtct | 960 |
| gtgttaatga agacaaaaac tatatcctca ggttagcgat | 1000 |

<210> SEQ ID NO 54
<211> LENGTH: 1000
<212> TYPE: DNA
<213> ORGANISM: Arabidopsis thaliana

<400> SEQUENCE: 54

| | |
|---|---:|
| ttataccatc gtaatccaca cgtacacatt gttttaact tttgacaaaa taattgttta | 60 |
| gctacctaac aaattgacat attgtgtggc aaatttataa ataataatt acatatatct | 120 |
| cactgagacg ccatgcagat tcgtatgttt atacaatgcc tcacccatttt cttgaattct | 180 |
| ctcaattgat cttcccatga tgttcattta ttatttgctt tatgtatatc tttgtagaat | 240 |
| ggtagtatta ctattaaagt atcaaattac catgacgacc tatagaaaaa tgtttttaga | 300 |
| aaagcatagg gatatgtgtc ttatggacag tggataagag agtggtccta aaaacagacc | 360 |
| ataaattatg ggatcttccc ttagttcctt tattgttatc atattttaat tactcttatt | 420 |

```
agtattttt  taatggtcaa  gttgtttatt  ggaattacgc  atttaattat  ttttctaatt      480
cgtatacttg  tgagaaacag  aacagcacgc  tttgcttctt  ttactagaca  aacccttaat      540
tagcgatatt  tgaggcagaa  aaaagacaa   ggttgcgtgt  gttttactcc  acaaaagaac      600
tcctaaaacc  aaaacgtta   aaacccactt  cttttttttc  acagtattct  cttttcatgt      660
caagaacaat  tactgttttt  cttggtatgc  aatctgtaaa  tttattgtag  ttttcatttc      720 tactttggg   gtttaggagt  aaaagtggag  tcactctact  ttgctttacc  ttttttctgag     780 tttttttttg  ttcatacaaa  tccaaatttc  cttttctttg  tattcctatt  ttttctcttc      840
tcgtcccttt  cagaatcttt  agagagagag  aacaacaaat  tgagaaagaa  aaaaaggtaa      900
ggctgtgtga  gagagaaccc  accaaagcgt  gcacgagaga  gagaaaaaa   aagctttgat      960 tttgtataaa  atcccaccac  tgctctctta  ccataccttc                            1000

<210> SEQ ID NO 55
<211> LENGTH: 1000
<212> TYPE: DNA
<213> ORGANISM: Arabidopsis thaliana

<400> SEQUENCE: 55
tgtgaaaaca  gccaaaagct  acggagagcg  acactcctcg  acgacgtcca  tgtctcttta      60
gattgtgatt  gcattgttaa  ttatcatatt  tatcaattga  ttagttaagt  cttaagtatc     120
atcacacaag  tttatacatt  aatctataca  gtgtttaaca  ctacaaaact  ccccaaaatc     180
acgtgtttca  tatcatacgt  acatttgtct  accgtcttta  ttaacaatat  taaaacagaa     240
tttatcaatt  ttctagttga  atagactata  tactattata  gagactctta  taaattatga     300
aactcctaat  caattaaaaa  tagttaattt  gaaacatatc  actcgaaact  agggtattag     360
ttggattgac  gatattttc   ttattaatat  caacgagaag  aatcaagtgt  cgttagctca     420
attggtaaaa  aatttaggca  aagcttagag  atgtctattt  gagtgacgct  tggaacaaaa     480
attacatgct  atggtttcag  gcctagagaa  atgcttcgat  ccagaatctc  ttgatattca     540 aaaaaaaaa   aaaaatcaac  aagaagaatg  tataaatggt  ttctatacta  tctaagttat     600 gaaaatatt   tttggttacc  caaattacaa  gatttgtacc  gaagtgtcac  actagattca     660
catgcatgca  tagttataat  taacttaaaa  cataaatgac  ttacaaaaat  acttacaaac     720
aaaaaccaaa  ttaagttatt  tagtggccag  ctttgttact  agagttttag  ccattatcat     780
aattcacaat  aaggtgtagg  aaaaaacatt  aatatatagt  atgtatacat  ccaaaaaaaa     840 cttttttggaa aaaacaaatt  tgggattat   aaaggacacg  tagcccaatc  gatgaacaga     900
ggacggcacc  gaatcaattt  gacttcacct  ttttccca    tatgataaga  gtctcatctc     960
tttcctatat  atatttcgta  cctctcttta  aggaccctac                            1000

<210> SEQ ID NO 56
<211> LENGTH: 1000
<212> TYPE: DNA
<213> ORGANISM: Arabidopsis thaliana

<400> SEQUENCE: 56
aagactatgg  cgtgaagcgc  atgagctgta  tagaaaaatg  caaaagagg   atgggcttat      60 gccaattaag  tagacgtata  aaagaggtaa  atatgagaca  ccttagagat  agcgagttaa     120
gggttcacca  tcaccacaga  tgcgtcttaa  ttttaagttt  ggctgttgta  tgatacgaaa     180
ttggacaaac  attaagctag  gaggcatgat  ggatttaatc  atattttaga  tgggaatgag     240
aggatattaa  ggtaccaacc  ctcaaggcat  attgtagact  ggtttggttt  ggacatgtga     300
```

```
agagttttga agctgaagtg tttggtcact ctagcattag atgttgcagg tgtagttttg      360
tacatacatg taaatgatgt ctcttcctta cgcacatttg ttgacataga gaagctaata      420
tttgcttaag catgttgtaa gctgtaactt tagaatttaa cctccactgt aacatattac      480
atatgcaatc aggcaaacga agattcgatc aaacgggtca ttgcaaatcc agaagtgtga      540
gaagattgac cattaggaaa cttataaagt ggttcagtct tttacaaatt aaatttcctg      600
tttcaaacac caatcaaatc caccgaatta ccaaagattt catgtttgcc tctatccata      660
atggttggaa aattttcaat tttttaagta atagtttgat attgtgggga aaaaatacta      720
ttctaaacgg tagataggtc ttacacgtga gcattccgta actggacaag gatcaaccaa      780
agagaaagca gggagatcca tcacggaaca ttatctttgt aatcaaaatc tgatcgtaca      840
cgtgtacact atgatgtcca ctaacagtcc acatctgttg acctgacatt ctcagacaca      900
cgagaggatc ttttttcttt ctaacctcta aaatatttta attttaaaat aaaataataa      960
aatccgtata tgtgtctatc gttagcttct acagctcaac                          1000
```

<210> SEQ ID NO 57
<211> LENGTH: 1000
<212> TYPE: DNA
<213> ORGANISM: Arabidopsis thaliana

<400> SEQUENCE: 57

```
ctaatctgat ttgattttt tttattttgt ctacgattct tgagttacga aatgttcatc       60
atttgttact tcttgttgtc gggattgagt agttgcattt ttttagttgt ggagctgtga      120
caaagaggcc agctagtgtg tggaatgtgg atcatcatcc tttggttgat tccttgtaga      180
atcctttttg taaacattta aactataata aagtgttatg attaagaaaa ctagttactt      240 attttttag tcatattgac tctgagccat aaactccata aaagtcctcc tcgattcaat      300
tcggaattta aacagtttca gttgaactct gaacaagaaa aaaaaggaa aaagcaaaag      360 gagtccgtgc aagataactc tcattttatt ctctttgttt ttgaactatt tattttgcac      420
aaattaggat tgatattaaa attttaatta aatcaaataa taactattaa ttttgcacca      480
attaggatta atactaaaaa cattaaatta aatcaaataa tagcattttt gtttagtaaa      540
tataaaattt aatctaaaat aattaaaata cacaatacat taaaaaaaaa aaactcaaaa      600
ggcaaagcat aaaagaagaa acagagtgga ccatgtgtcc gcgtggaacc aaagcttcca      660 ataactcga ccgtttagtt tattggaaac gaaaaaagaa aaatcatggc aacacaacgg      720
ccataaacat ccatcacgcg tctactaaac gaacacgcgt acggtccaga ttctcaaatg      780
acagctgtca tagagccgtt agcgccgtag tcaaagggtt taagcccaac cgcgtttctc      840
tttttcacct cttctttttg tagcataata tctcagccgt tagatttaag tcggtcctta      900 cttttttcata tcaacggtca cgattcacta aacacctcaa tacagtgtac cccacttctt      960
ctctctatat aaagaacacc atctcctagg tttcgttaac                          1000
```

<210> SEQ ID NO 58
<211> LENGTH: 1000
<212> TYPE: DNA
<213> ORGANISM: Arabidopsis thaliana

<400> SEQUENCE: 58

```
aaatttcaac tataccatta atacatgtat tatattctag aaaccacggt tcgattcaaa       60
ttttgaccta acaaatatta atataatgtt tggatgtttc gtaatattgt aaccattaat      120
```

| | |
|---|---|
| ggagatgtcg tatatcattt gagttttttt gttaaccatt caaagtacac tataattaat | 180 |
| ttagttactt taatataggt ctattttcct tgcgtcatag tctctatcgt ggttttgtcg | 240 |
| gagatatgcc acgttctaaa actttggact tctgcgtcgc caaagcgttt gcaacacgtc | 300 |
| aaattaggaa acacaaaagc ggcttagata gcaaacgagc gataaataaa gggtcaagta | 360 |
| agccaaacaa tatgtaataa acgaataaat taattaaaag aaatgtttga tgtcctatta | 420 |
| attttataaa ttctttttt ttgtttttt tttaattta taaattcctt atacacaaat | 480 |
| gtggttttt caggaaagtt gttcaatgtg cttattacaa tattaatcat ttgatgatac | 540 |
| atactcacag ttcactaac agttcaatat cctgatggag cttatcacta aaagagaaaa | 600 |
| tctatactac agtattagga actcgaaaca atatcgtcat cctaaaagag acaaaatagc | 660 |
| ctgactaaac atttatattt tcgttaggac aattctcaaa aaaagatact atatattaga | 720 |
| ctaaaaaag gaatgaaaca gtgacataca gctacactaa agacaaaaaa ggagataaaa | 780 |
| taatatctcc gtagacacat aatagtataa taccgtgtta cgtcgatcaa aatgtgatat | 840 |
| aagaaatcaa attaatacta aaagcgatat gtttcgggac agattggtcc ggacccgcca | 900 |
| cctttcctt tctatataca cacacgcaat acccaccaag aacacacaca aacacttaat | 960 |
| tagcaatata aaaagcacat tcacaaactc tttccaacac | 1000 |

<210> SEQ ID NO 59
<211> LENGTH: 1000
<212> TYPE: DNA
<213> ORGANISM: Arabidopsis thaliana

<400> SEQUENCE: 59

| | |
|---|---|
| ccgctataca cttgtgggaa aaggcttctt gtagtacagt ttcgtcacgg cgtcttatta | 60 |
| attgcaaatc tgtgacgtta cggttttcga ttcgggttac tattttaatg gaaatctttt | 120 |
| gataatagct agagcctaga gtatgtaacc ctaaggttag atggtaatac cgaatctacc | 180 |
| taaattttg ttattttcgg tttttcatga gatatataga ctgcgtaatt taaaatctca | 240 |
| aaatttggtt tcactttatt tttatttttt tttagtttcg aggtaggtat acaagcatgg | 300 |
| acctttgac attatttaaa attttcataa tttagaatct tcatgttaaa cgtgtatggc | 360 |
| tacgatcttc ggaactttat tcggtttgta tgctcaaagg ccaacgccat ttattttcta | 420 |
| attgattttt tcccgttacg gaaacaatct ttttgcatta ttgaacttaa ttaccaaagt | 480 |
| ttatgaaaag aaacaataaa gtctaaattg gcctattttg atatactgat cacttacgcg | 540 |
| aaaacatcta cattgttatc tactagacta gtcattaact cgaagataga atttcatttc | 600 |
| ttgaccaaaa aaaaactcaa aagatagtta taatcacaga ttcattattg acttttgctt | 660 |
| ttaacactgt agccatttat gtactattta tacaaatacc taacttttca aatttgtgat | 720 |
| atttttcacc ctacatttta gcctataggt tggatcattt tgtcatattg catcactgtt | 780 |
| tactagtacc aaacttaaat atcacacgag cagtaaattt gctatcaatt ttttcgtttt | 840 |
| cacaaacata tatctagttt ccctaaccaa taattaagtt aaattgcatt aggaatttag | 900 |
| gatttataat aaatagatat ataacccact aacgacaaaa gactatgtct tgctacgtct | 960 |
| ctgcctttat tatcatgcca caagaaaata agagggggaac | 1000 |

<210> SEQ ID NO 60
<211> LENGTH: 1000
<212> TYPE: DNA
<213> ORGANISM: Arabidopsis thaliana

<400> SEQUENCE: 60

```
actcctatga aatcaagcct tagagacact attgttagcc tcaaggagaa atgtcttta     60 tgattctgtt cgtatatttg taactattat gtgtatttt attttgttag tattactaat    120
tcaagtggtt taagttgttg agactcttta aaatctaagc attttataaa caataatata    180
taattattgt ttaggctaaa tttgtcacta attaaggttt ggatacatag tgtctaaact    240
aagctaataa tatcacttaa cgtttacttg taacgctagg tgatgatgtc gtcaagtcaa    300
ttggtacaag gaataaacga gtggtcatat gacattatga ccatatgaat tcaaactcca    360
gtaatccaat ggtaattgga ttcaatgatc aagacttgaa ccacgtaatc caccccttatc   420 cttagaagct cataaatatc actaaaggga caggcaacac ttaaccagta gttgtccaat    480
aatttagttt tccaaaatga aaattattg ttgtcatcta ttttaggtgt tttagttcaa     540
tgtggattcc tcgtcctaac aaatacttga cgaatatatc tagactataa aattggttat    600
gagttctact ttttttttgtt tgtgaaatta tcaaaatttg ttatatttat ttatttattc   660
tcattaattt gagtactaat ttttaaatta tttatactaa aaacaattac taagatacaa    720
aaatggataa gagcatggtg tatagatatt taatgggata gaatatttcc cataattgta    780
tgtgtgtgag aggttttgtt ttcgtaagga aagaaacaaa aaccatttga ccaaagaaaa    840 gcaaagaag gcaaggaatc aaacaacaaa tgttgcaagg cagaaataat ggacgttatg     900
ttaatgtagt gtcgtcacac gtgacttaaa agagacgagt ctgcgtgtca aactaaaaat    960
gtatgcaact ataaaaatgg gatttgatta tcttttagt                           1000
```

<210> SEQ ID NO 61
<211> LENGTH: 1000
<212> TYPE: DNA
<213> ORGANISM: Arabidopsis thaliana

<400> SEQUENCE: 61

```
aaagaacaaa atagtcccgc aggttaaaac ctagtatttt acaaaaatat agacaaataa     60
aataaaaatg aactatcgtg gatttagtta gagaaatcca tacaaaaata aattgcattg    120
agaaacttta tgatgacgact aagtaatata agattttgca ttgagaaagc ttacatgtca    180
ccctaatttc tatcaaaagg gtttctgata ctaattggaa ccatgtgaga aactatccat    240
agaaatgatg atcttatcta gttatcatga gctgatgact ttgaatattc cacagtcact    300
aaacgcatgt ttatttctca gctttatgaa tctgtatgta gacacacttt cgtatttct     360 tcactttgt gtatttgtat tgcccattcc tcttttacca accataaaa aaagcagtct      420 ttttttttgtt tggtcaagca ttggcactct ttgtcaatca attcccaag ggatatataa    480 taataaattg gaataatgaa agtagttcat cataaggttc gtgattatta acttctactt    540
ttgtttatat tcaatagatt aagatgccgt gtatgataag gagagcaaaa gtaatccgat    600
agagatcaca gcaatattca ttacaaaata gttttcaaat aaaaacacat gatcaaaag     660 tgactcacaa aaacacatga tacgtacgtg ggatgctaat cctaaagcaa caaggccaca    720
agggcaaaat atgtagcttt catgctttgg caaagcgaaa actctagtta agcttaccta    780
acagaaaaaa taaccccccaa aaaagcgtta cgttccaaac atttagacag ggtacacgtg    840
aatgactccc acttttttta aaaaataat agtactatca attcaaatgt gtaaacaaca    900
aaaaaaaaaa atgtgtaagt aacgtctgta attgatttga taagataaaa aaatcttgat   960
taatttttct ataaattgaa gcctttcctc tttacatttc                          1000
```

<210> SEQ ID NO 62

```
<211> LENGTH: 1000
<212> TYPE: DNA
<213> ORGANISM: Arabidopsis thaliana

<400> SEQUENCE: 62
ttcatgcatg cattattta  agatattaaa gagtaatagt ctcgtcgaaa ttataacatt    60
aaaaagtgga ttattcgcct cgaagatatc cgatgtcaca attttgtctt cttttagaac   120
ataatgttga atccgagaat cgaggtatac ctgaatatct cgccaatgtg ataatgtgat   180
ataatcgaga tacctgaata cccactgaac cagactcgtg aattgactt  gtccttaagt   240
ttttcaaatt tgatcagcaa tacagatatg tcatttccta ggactataaa agatatcaaa   300
caaatattaa ttaaagatat gtaaaactta tgggtgaatg atcggtgatg tatgtgtata   360
tgttactggc attccataat acacgcgatt caactaggaa aaatatacta taaaagagg    420
cgtatggaac tacgttacac gtttcttgta catttgagct tcgttacgat gatttgtatc   480
aagagtgaaa ataactacg  atttattatt tacagtttca gaatatgatt tgattcgatg   540
tttaatatga tttcttgcac agctagaaac aaccataatt tcaacatttc atattagcaa   600
ttcctccgtt aacagccgtt tgacatttt  aaagtaggct aaaatttggg taaactgatt   660
ttttaactaa tatttttta  ttttatatta actacaacta ttattattat tcgtttataa   720
aaatatacga aattcaattt aaatgctagt agtattttgg tattttacc  aaaaaaaaaa   780
ctgacacaat cgaaagaacg tagtaaaaaa caaagtatat tttttttgta atgagttgtc   840
tctgattcag caataggaga gcgacaaaaa tatcacgatt ttttctagca acttttccat   900
ctccacggaa aaagagtaat aatatgacac gtggcaacat cgcaacggct cttaccaaat   960
ctcctcgcat atataaagcg tcttctccgc caccttcatt                        1000

<210> SEQ ID NO 63
<211> LENGTH: 1000
<212> TYPE: DNA
<213> ORGANISM: Arabidopsis thaliana

<400> SEQUENCE: 63
atagtattgt caattttca  atctgaagta aatatctttt tgtaaggaag gggtcaacaa    60
atgatcacaa cagagttggc aaaaagttat caaatcgcat gcacggaagt tttacgtgtg   120
gtgaaggtaa acttgtatta cacttatcta taaaaattag tttaggcttt gattctaaat   180
caaatctccg attagaaaaa attgcgtaag caaatagctg gaaaaaattg tatcccatca   240
tacttaagtc acaatgtttt gtttttgaga tttgtgatgt aatcaatata tgttttacaa   300
tgcaagtata ataatattaa agtcacattc taagaaaatt atgatttgtg tcatacgtat   360
acaaaaacac ccgtcacaca tcctgacttc tgaacgttaa atctgtcgca cacaatcata   420
aaaatttaaa aattcaccag agatgtactg aaaagaatat aattaatcac atgatgatat   480
atgcatagga gatgaggatt attcatttc  tgaaattccc tatatgaacc attataattg   540
tttagtaatc agttcagaaa tgctaatcat tatatgaacc attataattc ccttcatttt   600
tatttaagat ccacttaaca ggatttgtta atatgcaccc acatcactaa atacattggt   660
acgcaaccgt tgttccattt ccatttcac  atcgaccaga atgtttacta tgcggtaaat   720
tgtgtagtat gcagattttt ttgtatcatt taattttcta acacttgtta agtcgaaact   780
aatttgtca  caagtaaaag aaataaaaaa ggtggaaatt attaatcagt agttagatga   840
ttagtttcga gttgaaatga aactcgactt aacaagtgat agcgacgact ctagaaacag   900
ccaaaatccg ccctattgct acctgtcgac ccacaaatcg tttactcaaa aatgaataaa   960
```
aaatttacga taaagcaaac ccaaagttat atcttattat                         1000

```
<210> SEQ ID NO 64
<211> LENGTH: 1000
<212> TYPE: DNA
<213> ORGANISM: Arabidopsis thaliana

<400> SEQUENCE: 64
```
ttttgtgacg aaccaataaa agaggaactg ctttttttct tcgcatgtcc actatttact    60
gtttggtatg acatcgaatt ggtatgatac attgttgtac caaaaacttc aaaatttggt   120
ggcttgtaat caacattgat ccacttagcc attccaagca gtgaattaca atccgtggaa   180
ggaaaaatta tggtccggca ccaacaaatt atcacctcat ctcccgtcac aaacatatca   240
tctagaagtc ggtatgccac accacataat taaggagcac attactcaca tacccaacca   300
atgtgggaca tatctaataa gctcattctt ggctggtaca tgctctattt catatttatc   360
aaaaaaaaaa atattaggca ttgtaaatag cgttttttgct gttgagcaaa atagttatat   420
ttgaaagtaa cattggtatt tataattata gtataacaat taggcattga agtgtgagtt   480
tttgtttttg tttatttaac attggagtat taggttctta gaaatatatc tatatactat   540
tagtagttta actacagttt gtacttaatt gaaaaaatgt taaagttgt tttaacctag    600
ctaattgcta aaaatgacta aatagacata cacaaagact tgtacatttt cagcttaacg   660
actaatacat ttttccttta tatatatatc tctatcgagt ctagttatta atgttgaaag   720
ttgcaaataa aacagaaatg ctaacatgta aatatcgtag ccaaaaatgc taacatgtgt   780
ataacggtta taaccacaac ttgatggccg acctcttttt tcttttggta accatagaaa   840
tggttacacg taactagtac gaaccaacga aaactcttct tattcgatag ttaaagataa   900
tagcaatgcg caaaaatatc tagcactcac acgtgtagtt ttggattctc attggtcgag   960
agatctataa aacgatacta ttggaggtta gatttttctc                        1000

```
<210> SEQ ID NO 65
<211> LENGTH: 1000
<212> TYPE: DNA
<213> ORGANISM: Arabidopsis thaliana

<400> SEQUENCE: 65
```
aatatccaaa agaaggttac atgcataagc ttagactggt tttgctgatt aggtgcagct    60
gaaagtaatc tcatgaaatt gatttccgtt ttgccgattc ccatttttaag atatctgatc   120
ataggaatgc cacattcaga tggaagccag acaccagaac agaaacaaag ttgaggtaat   180
caaagaagcc atcttgagag caaagtggtt ttgattccaa gaactcatat ttatcagcat   240
aacctctatg ttcatgaaac ccagaagagc acaatacata actatcacca ctcaatctgt   300
tattaccaga actagcagtg ttcaacttca ctcaaatgtg gacgaattac agtaaattgg   360
ctaatcccac tactgaattg accttcaagg taaaccccaa tcatttgcca ctacgatcaa   420
ccaaaaatat agattcttca ttcactctta tcaaaagcta tacatgaaat tcagagtgtt   480
ctcattccta aatatggaaa gttgaattct atcaacacaa tcagatcatg cgacaatgaa   540
ctagaaacca cgaaccagaa attgttggta atcgtttagt ggacgagatt gaatcaaagg   600
ttcaagtggt aatcgttttc tcctgacgca aaatcgaaag aaaaaagatc ggtagcgtcg   660
catcctaatc gggtgacccg gaaccaata gttgattcgt tttagtggcg gtaaaacccg   720
gtttgatgaa caaatattaa tgggcctggc ccatacgagg atgatcgtgg caatgtcgat   780

| | |
|---|---|
| gataacaaca actcctctat tcgggtttat gttgacccgg aaaacgaaag cataggacac | 840 |
| gtgacacatg tgatgtgagt gaagccaaaa ataataatat tgggaaagga tgaacacagc | 900 |
| agctcagctt tcgtcttctc cgtcaatcca ataaaaaaat cagcaaccgt tgtttgtttt | 960 |
| taagctttt ttacaaaaga cgtacacgtc tctctctctc | 1000 |

<210> SEQ ID NO 66
<211> LENGTH: 1000
<212> TYPE: DNA
<213> ORGANISM: Arabidopsis thaliana

<400> SEQUENCE: 66

| | |
|---|---|
| gattgtgggt agaagtagag cgagtgctct tactttagcg gtatcaactt ggaagctacc | 60 |
| ctgcccattg gattggatct aagcttcata tttgtggatt aaaaaggcct tagtgggact | 120 |
| catgtctcct ccggtgggac tagtgtcttt tacaatgtca agtttaaaaa attggataac | 180 |
| aacaccgata aaaattcaca tttgcaaatt ttattcagtc ggaatatata tttgaaacaa | 240 |
| gttttgaaat ccattggacg attaaaattc attgttgaga ggataaatat ggatttgttc | 300 |
| atctgaacca tgtcgttgat tagtgattga ctaccatgaa aaatatgtta tgaaaagtat | 360 |
| aacaactttt gataaatcac atttattaac aataaatcaa gacaaaatat gtcaacaata | 420 |
| atagtagtag aagatattaa ttcaaattca tccgtaacaa caaaaaatca taccacaatt | 480 |
| aagtgtacag aaaaaccttt tggatatatt tattgtcgct tttcaatgat tttcgtgaaa | 540 |
| aggatatatt tgtgtaaaat aagaaggatc ttgacgggtg taaaaacatg cacaattctt | 600 |
| aatttagacc aatcagaaga caacacgaac acttctttat tataagctat taaacaaaat | 660 |
| cttgcctatt tgcttagaa taatatgaag agtgactcat cagggagtgg aaaatatctc | 720 |
| aggatttgct tttagctcta acatgtcaaa ctatctagat gccaacaaca caaagtgcaa | 780 |
| attcttttaa tatgaaaaca acaataatat ttctaataga aaattaaaaa gggaaataaa | 840 |
| atatttttt aaaatataca aagaagaag gaatccatca tcaaagttttt ataaaattgt | 900 |
| aatataatac aaacttgttt gcttccttgt ctctccctct gtctctctca tctctcctat | 960 |
| cttctccata tatacttcat cttcacaccc aaaactccac | 1000 |

<210> SEQ ID NO 67
<211> LENGTH: 1000
<212> TYPE: DNA
<213> ORGANISM: Arabidopsis thaliana

<400> SEQUENCE: 67

| | |
|---|---|
| agtctataac tgataaataa ttagtcaatc agatcaaaca atagagaaat aattagtctg | 60 |
| caatcagcga ttattaaaaa ataaaataaa atagaaacat atctcagcac cgattttca | 120 |
| acagccggcc cacgatccag aaccgtccag cttgaagccg gcgccgcgtc gacttgttcc | 180 |
| accgttcgga tattgccacg tgtgtgagag cacctgccca ttacctcgtg gaacatgttt | 240 |
| tgttagtata agttactaac caagtcgcta tcttcaattc ttcattacct aagagttgaa | 300 |
| taaaaaaaca accatatacg atgagacacg caaataactg atatacgaaa caattattta | 360 |
| ttgatgtaca ttcttctaac tataatacta caagattctg aatagtttta gatgtaaaaa | 420 |
| gtacgagaag agttatgatc agagtaagtt aagtgataag atcatgacac gtaggcagag | 480 |
| gaaataaagt agaaactatc gacaacataa taattgagtg agtacaaaaa ccacgtaata | 540 |
| attaggtgta cactgtagtc tgtagatcga ttgtacaaaa tgaaaaaact atatgattta | 600 |
| aggaactaga tatacatatg catcgactca agaacagttg ctttatgtga agactatcaa | 660 |

```
ttacattatc ggctaaattt ggcttcatgt gttgaataga tggattgtgt gctcaggtag      720
ttgtgtcagt taattataac agtaaacctt cactgcttca catatataaa atttgggtta      780
aaaaaacttt aacattttat tttttttaatt gacaacaaac aaattctgta acggttacat     840
ataatagtgc ttcagttaaa ctcctttttt aggcaactct aattccttta taccCttaat     900
ccattattat tctatcgaac ttatctttttt aaaagcttcc gcgttacgcc atcacttctc     960 caccattttaa atacctaaac cactttcttt caaatttctt                          1000

<210> SEQ ID NO 68
<211> LENGTH: 1000
<212> TYPE: DNA
<213> ORGANISM: Arabidopsis thaliana

<400> SEQUENCE: 68
taaaaactaa gttgtccaac tactaacgca attgacaacc acaaccaaca ccaatattaa       60
gtatgattac cgaccaaatt tgaattttat aaacatatag aattttttttt gccaactcat     120 aatcatattt ttatatgtat tttaatataa ggtgaatgat tatcttttgt ttcatgtcat     180
attgggcata acaaaactag tacaacaaag ttgtgtgaac cactcctttt atatagtttt     240
gttgttgtct tttcttccaa ggaagattac tagacttaga caagtggatt atatatatat     300
atatatatat atatatatat atatatatat atatattaac taatctttca acacttgtgg     360
attgataatt attcatactt ttaataaaaa ttccatagtt caatgaatct gtaacaaaac     420
caagaagtga cgtgatatac ttttggaact ataatcatat tgtgagctca atggataaga     480
attgattgta gtaaatgatg tcggcagtta caagtgtagt tagatatatg caataactca     540
aatcggacat gaactcattt taacttatct aaagagacca ccgacgaatc attttgggtt     600
cacaaaattg tacttcgatt tctaagcctg aatgtgaacg cacgttttttg aatatttcaa     660 cacgtgtttc atatttcatt acatgcatta taacataaat attacatctt tgagtcttta     720
actagttgac caacaaaaaa aaaaactttta actaagtcta gctagttttg ttactacata     780
tataaaaaca aaaccgaaat aaatatttaa aatttataat atatttgtgt ggctaaatca     840
atcaacgtgt catgaaggtc taattcaagt tggtaaggaa atcttttgtt tatgtccatt     900
tcccacgtgt cactatttgt atgacggcta gagaaagaca tgttgaatta actagtgact     960
ccggattata taagcaagca tctactaaaa agataggaac                          1000

<210> SEQ ID NO 69
<211> LENGTH: 1000
<212> TYPE: DNA
<213> ORGANISM: Arabidopsis thaliana

<400> SEQUENCE: 69
gaatcgttct tgatctcaat ttggtttgtg atgagaatga ctttgatatt tatagtgatg       60
aaggaggcta gggttgttgg atctaatatt ttcaaaaata ttcgaaaata tcttgcagga     120
taagttgcaa atcaaagatt ggatcctcac taatgattcg aatttggttt agttcataat     180
gattggctat atttagataa gtggtaaata ttgtttagtt gattatggtt agttttagat     240
ttaagagaat aaatttataa gattttttttc taatttatgg aatgtattat cgtgttatgg     300
tagttagaag aatcgaataa gctcgtctat gtcgatttta tagtgattag tgaggagggt     360
gaatatatga ttgaagattc ttaaaatcgt aattaaatat gcagactatt ttgatggaat     420
atgcgtgtat tagatactaa aaattgttga gatatacaac taatcgtgtt atggttaaga     480
```

| | | |
|---|---|---|
| ttgcattact tgatggtaac ctattatgta gttttacatg tgatcaaaag cccattaaac | 540 | |
| ataactcacc cgtctatgta aaacgcggat cctgtttaat ttagttattt ggtttggacg | 600 | |
| attttacccct tgataaggaa gaacaaaatt caaaattgaa atcaaaattg aggctaaatt | 660 | |
| agacaaaaat ttaatttgta cttctttttt aataataaga ggatatgact atgatacctc | 720 | |
| gcctaattct ggaaataatt ttttaaatta atcaagattt ttttcttaat aggtaagcca | 780 | |
| aagatagaac acgtctcgta ctattacaga aatactcttc aatctgtcac aataaaataa | 840 | |
| gaattagtat catagatggt aacgtatctc catttatctt ttaatattag acgttactta | 900 | |
| attcttagta agagaaatcg taatttactt ttgtacttta attgtggtcc cttgatacca | 960 | |
| cattttcccta taagtaagta cacgcaacag catcaacaac | 1000 | |

<210> SEQ ID NO 70
<211> LENGTH: 1000
<212> TYPE: DNA
<213> ORGANISM: Arabidopsis thaliana

<400> SEQUENCE: 70

| | | |
|---|---|---|
| catatttgga atccatatta tgcaaggaga catcggtttt actaatgcga attgagggggc | 60 | |
| ttgtataaaa tcggtctgct tcagaaaaca ttccattttt caacccttga aagtccattc | 120 | |
| agtttaccat ccaagagttt ttccttgttg tgaatgataa gaaaatccat aacatttatc | 180 | |
| taattttatc gtattggaaa ataatttaa tatttctgaa tacatttatt aaaaatatag | 240 | |
| ttaaaaacga tgtattttta gcgttttata attatttagc attatttaga tgttttcgtt | 300 | |
| attttgttat tacatcattt taattattat tcatgtgact tgaaattaat tactttttaa | 360 | |
| ggtcgaatct tttttacgc ctgcctttac acttcttatt agaaggttat gtatcgaaac | 420 | |
| agccatccaa aatttaaata aattctaaaa gaagttatat atattatgaa tgtatggtga | 480 | |
| tactgacatg ggtagggtac attcttttttc tattgagtta gttgatacgt taagttggat | 540 | |
| gagatataac ttatactatc atataagctt ttttttaattt gtgtgtttca agtttggtcg | 600 | |
| gttttgttta tgtcttttgt aggtggggta tacagaaaaa taagagaaaa aaaaacaaag | 660 | |
| tcaaagctga ctttgacgac aaatcgctaa ccttcgagag atgatgataa caagcctaat | 720 | |
| taaaatacac gttacgtcgc aatcaattgc ttcaatctca ttctcattgc atgtcatcct | 780 | |
| tagccgcggt tagccgacca tactatcaac gatgtgcata ctatcaacaa tgtatttgta | 840 | |
| ataattaagt agaaaaataa agaatgttcc accgtccaaa agaaacacaa gtacggtcct | 900 | |
| gagagggctt gagatatttt gcttagtgat atatgtcaac atcttagtta agccccaccg | 960 | |
| gttctgatat aaaagtgggg aaaatatttc ataaccacac | 1000 | |

<210> SEQ ID NO 71
<211> LENGTH: 1000
<212> TYPE: DNA
<213> ORGANISM: Arabidopsis thaliana

<400> SEQUENCE: 71

| | | |
|---|---|---|
| atctcgagat agcctgattc agctcaaaga aagagtgtac gagaacattg ccacagtgcc | 60 | |
| tctagttgta gagagaatgc gagagagtaa agagagaatc gacaagtcca tttctttcaa | 120 | |
| tggaactact atgcacccgg ctttcacaag gcggaaagct agctaactga tcagtttcta | 180 | |
| cttctcccta ttggctttac cactcaaaga aagctaatgc ataggaggag atatggctgg | 240 | |
| tatttctttc tactatatta gtatcaacca acatctctcg catttagaat aagagtatac | 300 | |
| cataacctct gttttgattg tgttctacat tgaaacaggt ctttctctga ttttaatatg | 360 | |

```
gactcttata gaatcttggg ctgattctac accctgtatg tatatgtaag aatcacataa      420
tcagatggtt gcacaattgt caagaacacc caaatccaag cttgcgattt agcaatctca      480
cccgtgtaag aaacttaaaa ccataaaacc aattgatata agagcttttc tagcaaaaac      540
ttaaaaatat aattaacacc gtcgaaaatg gtggaggcta ctagagcgag atataaactt      600
tatcaccgtt taatcgtgtg ggattttgaa atgatatgaa cctattgcaa aaagacaaaa      660
aaaaaatata aacggaggaa ctaggcagtg ggaccggaga tccaccgacc ggaaacgaag      720
aatccatagt aagatagagc ccaggggttc ggtcgtatcg gaccggtcgg atttggattc      780
taacgacaag tgagtggacc cccagaaacg acagacgtaa gcaatgacaa catcaaactc      840
atcgccacgt cagcaacgga gttctacttg cgaaacgtgt cccggcagcg tcatccaccc      900
acgtgtgttc tagaagctct tctcctcctc cgtatctcga cacgtgtcca ctccctctcc      960
ttatataatt gactttctc tcattctttc caagtttcaa                            1000
```

<210> SEQ ID NO 72
<211> LENGTH: 1000
<212> TYPE: DNA
<213> ORGANISM: Arabidopsis thaliana

<400> SEQUENCE: 72

```
gcggttgttg gatggctgaa ggtaaaagct gctatgagat ggggattctt cataaggagg       60
aaagctgctg agaggagagc acagattgtg gagcttcatg ataataacga tggtaaatga      120
atagtcaggt tgcttgctag tgtatagaag ccatgtacag tttagggatg tataacaaca      180
tcacttaccg atatggattt gcttgattta gcttattaga caagaatata atcgatgaac      240
catgagaaat ttgaagacta accttcagca gcaagacaag aagctgattt tctgtctctt      300
taagtttcaa ctttcaactt gcagatatat tagaagactg actaagtatg ggcctataag      360
cccattaatg tctctactga acgcccaact tgtgaaaaac atgtctctca tctcaatttt      420
gttttctttt cacatcaact taaagctacg agaaccaaac aagtgatgtt tttggtcaaa      480
caggacgaaa catgtataca taaaagagg taattatgtt cgataaacat aggtataaat      540
aaactataag aatttgttac aacattcttt agatttgata ttaactgctg tttacatttg      600
aagaactcag ttagttattt aatattttat tttatagggt ctagaaatta cttgcgtgtg      660
gggactgatc accgattcta aagaaggctc atcctttgga taatagtatg aaacttgtca      720
ataaagataa gtcatcacaa gtagggagat cttagctgtg ttccatacgc ccatctagaa      780
aaagcgacga tggtcaagat taaataactg tatttgaaaa accaaaaccg cgtcaccaac      840
tccaaagcca ttaccattag ccatcacttt ccatcttcca gctgttcgaa tcaggacgcc      900
cctttttctt caccaaaccc atcggccgat aacgaacctt cctctctgac tgcctctgct      960
cttactataa atacaaccaa tacgacctca tccaaaaccc                           1000
```

<210> SEQ ID NO 73
<211> LENGTH: 1000
<212> TYPE: DNA
<213> ORGANISM: Arabidopsis thaliana

<400> SEQUENCE: 73

```
gaccaccggt ttctcaagtt tccagaaata tgcaaggatc tggtggtccc ggcggcagat       60
tctcagggag aggagatcca ggatcaggcc ctgtttcaat ctttggtgct tctacttcca      120
agatcagtgt agatgcttct ttagccggtg ccatcattgg aaaaggtgga atccattcca      180
```

```
aacagatatg ccgtgaaaca ggagcaaaat tatcgattaa agatcatgaa agagacccaa      240
acttgaagat tatcgagctg gaaggaacat ttgaacagat caatgtagcg agtgggatgg      300
tgagagagct tatagggagg cttggatcag tgaagaaacc tcaagggatt ggtggtcctg      360
aagggaaacc acatcctggg agcaactaca aaaccaagat ctgtgatagg tactctaaag      420
ggaactgtac atatggagat agatgccatt ttgctcatgg tgaatctgag ctgcgcaggt      480
caggaatcgc ttagttatgt ctttagactc ttgagaacga attatgcatt gttagctcca      540
ttatcattgt gacttttgc tctctctttt tgttttatca atttgtttta tgcgactcgc       600
tttgaaaact ttagcccatt ctgtattgag ctctgaagat tcgacgagtt ctgtaagtta      660
ccgatcacag ttaaaagact ttgatatgtt aaaaccctta tattacagct acatactatt      720
tttgtcttaa ctcttaagat atcatgcaca ataatatact tgttttgtct taacctatcg      780
attacaaaac cgggttaacc gccgacatga ggcgaactct aaagcctaac acgcgtcaac      840
atctatcttc tcaacgactc aaaggctttc caacacgtgt aggaccaata actgaaacac      900
aaagcctacc acctcttctt cctcttcttt catgacacgt ctcactgacg tgtcgtcaag      960
aacgtaatta aatattaaac tatcgtgacg aacgcgaggc                            1000

<210> SEQ ID NO 74
<211> LENGTH: 1000
<212> TYPE: DNA
<213> ORGANISM: Arabidopsis thaliana

<400> SEQUENCE: 74
taaggtttta ggccaatgat agtgattata cctcttttgt ttgtacttga ttcgtcacca      60
ttattctgct tgcgtttatt ttagaattta gaggtggctt tcggaattaa aaacaacaag      120
acaacaacat tttataattt tgatttgtat actaataata gaaccaaact ctgcttctct      180
cagctattat tatctaagta ctgatatatt tcaaattgta gcataagttc tgtatatgta      240
ttagatagag ttatcttttg atttattatc atatacggat taaatttgca gtttagagca      300
atgtatttgc aattttgtga aaagtgaatt tgctttattt ttgtcttcat tactaaagtt      360
gaattagcgg tttgatgagt cattatcgct attaatttgt ttccgtaata ataatgataa      420
gcaatcatgt cacgaacata ttactaatat tgtggtgatt cttttgccct cctcatccat      480
attcattgat tgtaaaagca cacgtaggtc acatacgtat catcctaaac cccaaattaa      540
aaaaaaaaac taagcaattt ttatacatgg cctttggcga tccaagcatg caaaaatatt      600
ccataaatgg ttaacacaaa atcatcgatt ctgaggggtt aactagggtc cactttatta      660
ccgtatggaa atagagacac gtcaaagcta gtatttggac ctacgtacgc tcatgtattc      720
cgccacgtgt cgtggtttca ctgacataaa acacatgtcg gtcagataat tctagctctc      780
acgacgatga agcaatgtag gctcacttcc actcaccgcc gcctatagca gtgacacacg      840
tcctgtcacc ggcgtgtcac tcaataatta tcagatttc attttaatta aataatgtta      900
tcctatattt gttaggtgga tcccaacggg agggctttat ggtaattacc atttactcct      960
gagaagcttt tatttttgtg tgtggagtag taggagaagt                            1000

<210> SEQ ID NO 75
<211> LENGTH: 1000
<212> TYPE: DNA
<213> ORGANISM: Arabidopsis thaliana

<400> SEQUENCE: 75
cagggtggtg aagcttctcc tgtttggcca accgatgcaa caatgcaatc aatctctact      60
```

```
caaaccactc tcaaatgctt atcccggatg ctagaggaaa gcatactaac cgatgtaatc        120
atccacacag ccgatggaac actctctgct cacaaagcta tcctctcagc tagctcaact        180
gttttcaaaa gcatgttcca ccacgacctc atggaaaagg aatcatccac aatccacata        240
gacgacatgt cgagagaatc ttgcatggct ctactaagtt acctctacgg aaacataacc        300
caagaagagt tctggaaaca caggctcgcc ctcctcggcg ctgcaaacaa gtacgacata        360
acggatttga aagcagcctg cgaggagagc taatggaag atataaactc gagtaatgtg         420
ctcgagaggc tacaagaagc ttggctttat cagctggaga aactgaagaa agggtgtttg        480
atgtatttgt ttgatttcgg aaagatttat gatgtcagag aagaaatcag cagtttcttc        540
aggcaagctg atcgagaact gatgctggag atgtttcaag aggttttgtc tgtgtggaaa        600
ccggtctaat atacacttac acacatactt tgaacatttc agcttgatgg tgttttgttt        660
atagtcttct tgttctcttc tgtgtgtgta actaacaaca actctggatt tgttgtatc         720 actctgtcta atgtatagta ttgagtggat ttgcctctag tttggtgtac cgagcctctc        780
aaatgggccg agcctttcaa atgggctgtg actaggccta atgactgtcg acatcgaatg        840
tcggcacaaa atatgataat tttgtcgatg ttgaaatcgt acgttttttg ttttaattag        900
atgagtcagc atcaggagga tgaagtatcg accgacacgt gtccgttgcg tcccaaagta        960
aagcttataa cgtgaaggca tttgtatcgt ctcttccgcc                             1000
```

<210> SEQ ID NO 76
<211> LENGTH: 1000
<212> TYPE: DNA
<213> ORGANISM: Arabidopsis thaliana

<400> SEQUENCE: 76

```
ttctttattg gtaactttt aatatattca tttggtcaaa gctggcagga aaaagttt           60 caacttataa ttttcttatg aagaagatac tgatacaatg catattaagg tcaaagcaag        120
agtctaacaa tttattattc aaggaatata ataattgtt aggtaggttc ttattgaaat         180
gaagcatttc acaccgtaat aatgatatag ctgtagaata tgaacaatgc gcgtttgctt       240
gactgtttcg ttgtaagttt gtaacaataa tggccaccaa gtaatctgtc actagaatat       300
tgcaacaaaa taaaaccat aaatataact ataatgatct actaatttat taattttaatt       360 aacatgaaaa tatgacagct tttgccagcc cttgctcgta taatcagtcc agataacaca        420
ttacaacgaa acatataaaa taacttttttt caacagaaac gattataata tacatctaaa      480
ataattaaca gttgaaaatt ttgatagaca tactatatat gaatatgaac ttaaataatg       540 acccatttttt cgtataatgt taattatta ctcgtaaacg cgttatttcc acgaaacatt       600
aggcaaaact caagttaatt tacgcctggc attgtaacgc ggttaaccaa aaagcaaatt       660
acgcagagtc aaatcatatc taaaaaccaa tataaacata acacgtgtca atacttaact      720
gatctcagaa ttaacatcgt taagagaaaa cacgtggcag agatctgtgt atccgtttgg     780
tgctccttca tgtagatgat tcttcaagaa aacttcaaaa actcaaacac gtcaagttta     840
agaaagaaaa aagacaacaa ttattttaaa ccgccattga aaagctaagc catgttgtat      900
ttttgtatgt ggttcgcatg attagtgtca caccaataat taattattaa ctatttccca     960
accatcgcgt atatatagag ctctcttctc tcattgttct                            1000
```

<210> SEQ ID NO 77
<211> LENGTH: 1000
<212> TYPE: DNA

<213> ORGANISM: Arabidopsis thaliana

<400> SEQUENCE: 77

```
tacttacaag caattgtgaa agagactctt cgtttgcatc ctgcagctcc tttgatccct     60
agaaaatcag aatccgatgt tcagattatg ggtttccttg ttcctaaaaa cacccaggtt    120
tttctcatac ttatctttat tacaccaaca ttcattactt gagatattac accaataaaa    180
aagtttggtt tggttaaaat cttccacctc tgtttctcga gattaggttg ttgtgaacgt    240
atgggcgata ggacgagacg cgagcgtgtg ggaaaatcca atgaagttcg agccagagag    300
gttcttgtta cgagaaaccg atgtaaaagg cagagatttc gagttgatac cgtttggatc    360
aggaagaagg atgtgtccgg gaatctcgat ggctcttaag acaatgcata tggtgcttgc    420
ctctcttctc tattcctttg actggaagct tcaaaacggt gtcgtccccg aaacattga     480
catgagcgag actttcggtc ttaccttaca caaggccaaa tctctttgtg ccgtacccgt    540
caagaaacct acaatatcgt cttcttatta ataatcgtat caatataaag ttcgtgtacg    600
gatcaatatt aataattgaa gagaatgaaa ttataaaaga tactgctttt tatgtttcaa    660
gtaaaaatgt taatattaga aagtcaagaa agaggaaaca caatgcaatt tgataaggtg    720
ttttatcgtc tccgggattg aattgcgtag gtcaaaaaaa gacatttgcc atttgatatc    780
gacatataat cactcattca cggatacgta tctcttgtga atggtcgtcg gtcaattaca    840
actttactgc tcggctttaa ctgacaagtg gcgcctcctg gtttcattca gaccctaccg    900
gtaggatgta atttggacca taagtaagaa atatttgtga atatttact acacgaatat     960
ctttacgtat ttaagttggc ttttgaagct tgataattc                          1000
```

<210> SEQ ID NO 78
<211> LENGTH: 1000
<212> TYPE: DNA
<213> ORGANISM: Arabidopsis thaliana

<400> SEQUENCE: 78

```
gataaaaaca gatacttta gcgaatactt ataacaacac tgtgttttgt ccaattcagg      60
ggaggttcta cgatcaaccc aatgcaacaa ttctatatgc ttccgtttca taaaaattct    120
gaatatcaat ctaaacctat acaattacat ccttactaat ctagataaag tgtatacaat    180
aaaatgagag caataaggtt cattaatctt tatacttagc tcctccacag gacgatatac    240
tttgagactg acacaaaaca aaataaggaa gaaagcttac gttttgaag gaaaatcaca     300
ggagggacgc ggaagcaaga ttggtctgag aggaaaattg aggaagaggg gttaatcgag    360
atgaaaatgg agtttgaagt aatagagaga acgttgcgca gatcgaggaa gaacagagga    420
taggatcaac acaaggatct tgtgaaaatg aaaatggctg aggaaatgaa ggactatttg    480
ttaaataaga tataatatta tttctgaaat atttccatct gactcctttta atttatacaa   540
gcctcctttt ttgtacatct atttttcagaa gatccaaata attgtttctt ctatttgtgt   600
attttttgata tttaaacgta aatctttgga ttttgatcaa taatagacaa ttagccaagt    660
tcagttttca ttaattagat ttataatttt aattattttt agcattcgtc taaaattaaa    720
taatgcggca aaagaggaga aattaatttt tgttgttatt aattcaaagc gttacaaata    780
aaaaggaaa ttccacgctg gcaataaaat aagcgaaaat tccacgtgac atctacctgt     840
cggatcaaaa agagtggaat tgacatttgt ttctctcaca ctctctctcg aattctctgg    900
tagcttctag ttctatgcaa aaaaacgacg atagttctct atctttccag atgaatctcc    960
ttccatatac aaaagcagtc atgcctcctc gctctctcgc                         1000
```

<210> SEQ ID NO 79
<211> LENGTH: 1000
<212> TYPE: DNA
<213> ORGANISM: Arabidopsis thaliana

<400> SEQUENCE: 79

| | | | | |
|---|---|---|---|---|
| aattcacatg tgatccggta tattaaaata tacatgattt atggatacac tcgaatactt | | | | 60 |
| ctccgatatt catttcgcgg aaagttgcat atgatccact atctcctata tatttgttat | | | | 120 |
| ataacacatg gcaaatctct ctatatatat ttttaaata cacatatatc caaaataggc | | | | 180 |
| ttaactataa cacaaagact tttgtttact gtatattagt aagaagtaaa tgtatttttt | | | | 240 |
| aatattatga taaagtttgt gaaatcacca tttgcaatag ccatataggg tcgtgtttta | | | | 300 |
| attttacagt ttgtattgtt ataattcgat tccaaggttg agaatatgtg tgtactatta | | | | 360 |
| gactatacaa ataataattc gttgacgata ttgaatattt actaattata ggaagagaaa | | | | 420 |
| attatttact aactatagta cgatatattt cttctatatg tgtttttaac gttttttttt | | | | 480 |
| ttttaaattt aagtcttaac tttacttctc attttaatc aaaaggaaaa aaataccaat | | | | 540 |
| caattttttcc taacacagtt tacttatcat tttcatttga aatgtgttca ctttctgata | | | | 600 |
| aaatgctaat cctacaatca aatacaccat tgtcgtgata acacgtgtac ggctctaaag | | | | 660 |
| caatcagaac aatcattgga cagttttttac accgtcagat aagtacctat ccacttgctg | | | | 720 |
| actcagccgg ataaacccta aaccggaagt ttgccccacc gtcaaaattg aagaaaccg | | | | 780 |
| gacaaaagag aatgtaaaga ctaagaagta agaacccatc ggacgtcgta agaaggttaa | | | | 840 |
| ttaacacgtg gaaacagctg gtcagagtta tccggtaact tatccggtta caagtaaaaa | | | | 900 |
| aataaatttgt tcccatacac gactccttca gaacccaaacg cgacatcacg gcgccgttta | | | | 960 |
| gtgtctataa atagagcaat cggtcgtaga aaaccaagac | | | | 1000 |

<210> SEQ ID NO 80
<211> LENGTH: 1000
<212> TYPE: DNA
<213> ORGANISM: Arabidopsis thaliana

<400> SEQUENCE: 80

| | | | | |
|---|---|---|---|---|
| aagagatttt gaaaggtcgt cgaggagtta gtttattatc ttacaattat tatgggattc | | | | 60 |
| ttctgactaa agttttagtg caatagttt ctgagttatt atatattttt cgaaattcat | | | | 120 |
| ccaaaggcta aaactttgta aggtattctg agtctattac gctagaaata gacacgctta | | | | 180 |
| cgttttaag tcattttaat ctgatatata tatatatata tatatactac aattttataa | | | | 240 |
| ccaattatct ttgtttcaga caattatat aaattcatat aaactatcag aaataaagag | | | | 300 |
| acaattggct gtaaaattgt attattttgc atctatgaaa ttttatttc tctttatcaa | | | | 360 |
| aattgaagac gagttgaaat tctatttctt ttttaaaaaa atttatatat gggagtgtca | | | | 420 |
| aaaaataatt ttcctttgta agagaatatt cgtatttgga cgagtcttga tttgtgtttt | | | | 480 |
| ccgttagcgt tccacattag ttgtaaagag cgagaaagat ttaagtgata attaaaagga | | | | 540 |
| caagatatgc attttgaata tactctagat attaatctta agcatttttc atattggtta | | | | 600 |
| tattttatgg tcgaattttg acatccgaaa aatacatccc ttattcttca atttatattg | | | | 660 |
| aatacttaag tttttgatag taaatatgta taaataaatt ttaaacaatt gtcaaaagaa | | | | 720 |
| cattataact tatacggtta tagttgttaa aaaaaaaact tatacggtta taccaataga | | | | 780 |
| taaactgaca ttttagattt gagttttttt ttttttact ttccatgtag atagcgtgga | | | | 840 |

-continued

| | |
|---|---|
| ataatacctc atttatatgt atcgttagtt gaaataattg acaaaaggaa actattcgtt | 900 |
| tgctgttcta gataaaagcc tttaattgag aaaagaaaa tgcctccagc tttgacccgt | 960 |
| tttgcctata aaggattct ctaagatatg gactttcctc | 1000 |

<210> SEQ ID NO 81
<211> LENGTH: 1000
<212> TYPE: DNA
<213> ORGANISM: Arabidopsis thaliana

<400> SEQUENCE: 81

| | |
|---|---|
| aataatcctt cgttgccagc agtctaatgg gactgtgtta taggttaatc tctctttcac | 60 |
| ggactattaa ttttggctc aacctcaatg taatttattt aaattatatt tcaacgcata | 120 |
| cacgtgaatt tatacatctt ttcataggat ttgcaattcc ggattctcat ccgtcctagg | 180 |
| aggttgtata tgtatattat tggtaactac agcattaaac aactttaaca ctaagtacga | 240 |
| tgatattata tgtacatgta cgtatgctat agattgatat aagaaaaaag taagagaga | 300 |
| gcggatgatt gttgattgaa ctaattaaca atagtgtatt aggtaggctt gtatccgaca | 360 |
| gtcaacttaa acttcatagt tgaaaccaat aaaaccagaa gaaaaaaat ttatatacta | 420 |
| atcataatca gcatgatgtt agacgatttg atatctaact ttcttcgtta tgatagagaa | 480 |
| ataatattcg caataaatca catataaaaa aaattacttt acgtcataga ttatcaactt | 540 |
| gcctccaaac acaacaacat gatcccctac gctacaatac ataatatgaa aaataaatta | 600 |
| atcgttgatt aacttaaagt cactccgtta ataacgttat aagcaaagct tattagtttt | 660 |
| tttgaccgtc attatcgacg accaaacaaa gaaagagtcc caacaaatta tgccacgtaa | 720 |
| gtccagaacg acgcctatga aaccaataag acaaaaattc aaaaaccaaa acatccgtga | 780 |
| aaactcttac gtggcggtga catgtgggtc ccttatgtct ccattaacta acataagctt | 840 |
| attgtcgact gtaccttttg tccccgtct cggctacaac cctgtgacaa acaaagatca | 900 |
| agtcaaaata tctaacctaa agtactctcg tccacgtgga cattgctgac gtggaacttc | 960 |
| tcccttctat aaatacaggc ttctcttcgc cgaattatac | 1000 |

<210> SEQ ID NO 82
<211> LENGTH: 1000
<212> TYPE: DNA
<213> ORGANISM: Arabidopsis thaliana

<400> SEQUENCE: 82

| | |
|---|---|
| caagagcttg actcaacagc tcaacaaagg atgagatggg tgcagaggaa ctacatgatc | 60 |
| tataattatt gtacggatgc gaagaggttc cctcaaggtc ttcctaaaga gtgcttagct | 120 |
| gcatagagag agtaaagagt tgagagagga acaagatttt attttctttt gtggttataa | 180 |
| aattctattc attttattgt agatcacgtg aatttattg atttgttttg tagtatactc | 240 |
| tatagttcgt taaagttata atattctctt tgttacaatg tgcttttttg ttttttaag | 300 |
| tctctcgtag ttcgttccgt tatattctcc gagtcagtcc aaaatggcc gcttctgttt | 360 |
| taattttgtt ctagggttcc acagtcaaac tcaaaccaa acccaatgga gcaataacct | 420 |
| ttttttagt tttataatcg aaatcaaacc ggaattttgc atgtaatttg attggtgtcg | 480 |
| ttactttaaa tctttaatcc acaaaacaaa atttactcga ttttagtatt aaccgaacca | 540 |
| attatagttt attgaaattt aatttttaatt ctatcaaatt gcatatgtat tcttgagtta | 600 |
| tttttttataa aaatactgaa accaactaaa ataatagagt ttggcggaac taccgtacca | 660 |
| aatttgattg tatttggagt atcattttg caaacctaat tagcctgaag actgagatat | 720 |

```
ccttgtccac tcttatgaag aaccaattta acaaggtgaa aaccagaatc tctaaaccaa    780
acatggcatc aactgaaccg gatcaggcag acttaaacca aaacaaagaa caagcacacg    840
tagcatgagg caaaattaag cacatgcttg ctttacttca aaacaaaaac cagctgttca    900
cagctaaaac tacacaagag tcacaaacgg cgaactatac tacaaaaaga ctaagacttg    960
cctcccttat ataaaacccc ccaacacata aggtcccaat                         1000
```

<210> SEQ ID NO 83
<211> LENGTH: 1000
<212> TYPE: DNA
<213> ORGANISM: Arabidopsis thaliana

<400> SEQUENCE: 83

```
tctacgacta ttatacattc atactttgaa tttggattac aaaaaaaaat cttcgagtat     60
gagaaaacta ttaaaatagt tttattgaaa aatcatataa aataaaaata aatttagtaa    120
tagtataatt aaatatgtaa aataaaatta aataagaaat atatcattaa cctataaatt    180
agaagttgaa gagcttacat taattatttta atagacacat gtcaaatgct aaagtgatga    240
tgtgtcaatc atatgaagag agttggccaa ctttcatata tatgattctt agtttcgtac    300
caattagttt ctcaattcag tgcatgtgta gtcaaatgtc caaagattg tttctaagca     360 attaaaatct tatcaaaact tcattgccca aaatattacg aaagcttgtt tctgtgtatg    420
atataccggg taaaattaaa atgatcatta tacagaacaa atcagcatga ttttcggata    480
aagatgacac acatttgaaa tcgtagccgt actacgcgaa atacatgcac tcttcgttat    540
gttaacactt taacagtgaa cgtagccata atgttgacca cattcaacag tcaacacaaa    600
cattacttta cacacaaata tatgattata tatacatatg tacatgtaag tgaatgtgag    660
caataatgac gggaatattc agagaagacg atggtgaatg ttagcagtga tcacgggcac    720
attcaaaact gactgtggac aaaaaaagct cctggcctta aatatgattg tgccaaaaat    780
agtacaaaac taagaaccca aaatggaatt cgagacctat ataataatat atatgtatat    840
agtctttcct tggaaagaaa tcttatgtta ttaagaaaaa tactataagt tatctctcta    900
tctagatatg atatatatgt ccaaacattt ccacgtagat gacgtatatt accgaggata    960
atcctctata taaggaagag aagctcgagt aataaatctc                         1000
```

<210> SEQ ID NO 84
<211> LENGTH: 1000
<212> TYPE: DNA
<213> ORGANISM: Arabidopsis thaliana

<400> SEQUENCE: 84

```
gtgtatattt tgtcatgcaa actatatcgt ggagaaaata atgttgctta tgacttttga     60
tagttgggct tacatttgga taatggatag ggtagacaaa gataggagga aagcaataat    120
agcgaaatga agaacgaata tttggggaaa taggacaaat gaatatactt ctctttgaaa    180
tggagattca cctaaattat taatactaaa gccatgcaat gcatccaaac aaatcagtgg    240
tcaagcacac tcaattatat gtccacgaag accttttagaa tcttcacaac caaaagctat    300
tttctacgct acctgataat tctgactcaa ttcttcttca taaaacgtat aatgaagctt    360
tatgaatgat taattataga cacaaccggc cctatctgcg atttctacaa acaatagaac    420
acaaaacttt aaaagttact acaaaatacc gaattgacta tatatatcat attatcagta    480
taaacatgat tagattgatc atgtttatca gtaatcatga aagacaaaga gtgtgactat    540
```

```
tgtaaaccaa attttagaat aaaataaata atttatcata ctatatacag tattttgtta      600
agtatatgtc atccaatagt aacattatca tttaaactga aaaatgtttc agctacttta      660
aggaattata gctttattaa aagtatatac ttttaggtca cgtgtttaga ggtgaagaac      720
aataataatt actcaataag ttcaccagtc acactccaac atcttattca aattcctttt      780
aaaagctttt taaccgtggc tgtttgatga ccatttgaca aaatttagta tattagaaaa      840
aaacaatagg atagggataa tataggacat tagactatta gatggacaaa atgaagtatt      900
atttaatttt ccaatgtacc aaccaataag aaagaagtga cgcacagtaa acgacaaaaa      960
gctcaagcat aaaaacccaa accttctctg ctttctaaac                          1000

<210> SEQ ID NO 85
<211> LENGTH: 1000
<212> TYPE: DNA
<213> ORGANISM: Arabidopsis thaliana

<400> SEQUENCE: 85
gtaatcttaa accattcatt aattatgcga ataaacgta aaaaacgtta tcaggtttca       60
actttattta ggctgcaatg ggaactatgg atggcataat tgatacagtt tctgcatcgc      120
attcgatttc acctttgatt ggactactca aatccaacgg taaacttgtt ctactcggtg      180
caacggagaa gccatttgat atatctgcat tttccttaat attgggtatg catatataac      240
cctacgtaat agaacgttat attagtcttt cacatctaga ctatgtatcg agtatgatga      300
aaccatgatg cgacaggacg aaaatcgata gcgggaagtg gtattggagg aatgcaagag      360
acacaagaga tgattgactt tgcggcagag catggcataa aagcagaaat tgagatcata      420
tccatggatt atgtgaacac cgccatggat agacttgcca aaggggatgt tagatatcga      480
tttgtcattg acatttctaa tacattggct gctactcgat cttaattaaa gtcgatgttc      540
tatatgtatt caaaataatc tggatttcaa tcccacaaaa cttaaggata tatatatata      600
tatatatata gtctatttta tataaatgga gtatagtcaa ataaatatgc attatcaacg      660
atatatagtc ttctattaca tagatacgtg ggagttcacc caacgtagat acgttcggtt      720
gaaacaagtc aatttcatca atgcctcttc caaaaaaaaa acaaattgca ttattgatga      780
acacatgcat cattatcaaa taggttggtt aaaatgacca agatgactaa agccaatcac      840
actactacca gatcgagtaa ccattaggga ccattaattc acgtggacgt agtgaatatg      900
gtccttgtga attaatgagt acgtaattgt cctcattcat atatggatcg gttccacaaa      960
catttcctgt ataaaattct acatctttcc tctcattatt                          1000

<210> SEQ ID NO 86
<211> LENGTH: 1000
<212> TYPE: DNA
<213> ORGANISM: Arabidopsis thaliana

<400> SEQUENCE: 86
cagcttacca catgcggcca caattttaac catgattaat cttcttttgg aatttagcga       60
gataaatcaa gagtaggttt attttagaac atagtatata atacactaat gaaaagtctc      120
gttaaaacgt gtttcacgta accgacctct aaagtatggc gtgcgagtaa cgacaaatga      180
aatctcaaat gaaaatggag attattttaa tcttaattat aacacactaa ttaacacccg      240
tcaaacatcc tgatatgtga acgtggaatc tcgttacaca atcgaataaa attattgctt      300
aatacgatcc gtctttctct ctctttcgta atgattatct atcaatatta tcttgactaa      360
taaaagtatc gcaaggcctt ggcagtcaca tgttaaatga tgatatacgt tgttgcatgt      420
```

```
taaaacatag tacaacgatc atctaggctg ctgctaaatt ctattttcaa aaatgccttt      480
tatatgcaag aaaagcaaaa taatcgagtt tttttttttg tttcattata aactgcttca      540
tttttcttag gaacggccaa actgttaaaa agtaaaatat gtatggtgat taattgatgt      600
aaccaaagcc agttcgcccg tttgattgtc aacccacgtt atcattcact tgatcacttc      660
catgaaacat ataaaagctg ataatactta tattataaag gaaaaaaagt atgaaaatat      720
tatcagtagt tagatgatta gttcacatct aaatgaaata cgacttaaac tgaaagagac      780
atgagccaat tcgtgtcgag ccacaaattt tggacgtata ttttttagccc gtggttccac      840 aatatttgca ggtcttttta ttcaatgagt ttattttgtc ttggttgaat aatgaaattt      900
ccaaatataa aaataatag aaatccgagg ccctacacaa gcacacatag taactcccac      960
attatatata agcggccaat atcagcaact cagagattcc                          1000
```

<210> SEQ ID NO 87
<211> LENGTH: 1000
<212> TYPE: DNA
<213> ORGANISM: Arabidopsis thaliana

<400> SEQUENCE: 87

```
gagataggac atagtattca tcactttaaa acactcttat tgataaatcc aagagtcact       60 taacttttc tggtaatcgc tgttaaagac tccaactcaa aaacaatcac attattccaa      120
gtcttaacat tctgatacga ttcattacaa gaaactgagt ttatctaaga tttctttctc      180
acttgtgcat taacatatat acacacaaca taacacagat atgatacaat ttcacttctt      240
tgaagaacgc ttgggagtaa cagcattaaa gatagcttca atctcttctt tcagtcgttg      300
aaagaaacca ggtcctttca cataatcaat tggagtgctc tcatcaatgt cgtcacttgt      360
tccatgagtc tctttgtcat ggtgacgact cttggacttt tcatgatgac ccattgcctc      420
tatttcttct ttaactcgtt caaacacatt tggcgatttc acagtcttct cctctgtgga      480
aatacccaat taaacaaag ggtttagatt cgtgtttcat aagagacaaa acagagcaac      540
gaatcaaaaa tagacttatc atggcgtgtt tctattgttt ctttagagaa atttccgatc      600 aaaccatcc attaatagac gtgtaatttt gattgtgaaa tttgaggaaa cgaacataac      660
ttgatcaaaa agtcttcctt tttaacaata tgcataaacc tatgatgaga tctgatcgtt      720
cattgtgttt acctgatcgg ttttgatccg ccatcgatgg ttttgtctt cttgatcttg      780 cagctttcta ttttttggttc ctgattcggt ggcgttttgc gtcagatgca aaagagtctt      840
tacagtataa atcaaaatcg atttcaactt aaatgggcct tgttgggtta taatgggcct      900
ttttgtttgt aagtgagtcc aaggaaaaaa aacaccagac cagattgaaa ttgaatcact      960
tgcaaaagca aaattgatta ctctgttttg gttttggatc                          1000
```

<210> SEQ ID NO 88
<211> LENGTH: 1000
<212> TYPE: DNA
<213> ORGANISM: Arabidopsis thaliana

<400> SEQUENCE: 88

```
aaagtaaagc tcaaagactg tcctcactta tagtttatga atcagcaaaa gaggaactta       60
ccggcaaagc aactaaatca taaacttgat cagcacattt cgagataaga acatcagcaa      120
gcaatctggt ccctgaggat ccttcaacct ctagcttctg ctccacagaa gcaacagtaa      180
catcagcacc agctcgccgt aaaacatcaa ctaacacaac agcttctatt tcctccgtcc      240
```

-continued

```
catatccaat tggaacaagc acctacatag tttctcagtt atctccaatc tcaatctctc      300
tacacaaaca agctggacaa ttttagttat agataacaag aaaaaaggag aaaccttttt      360
agtagttgca gaagacccga cgccaacatc ggaatctagc gttgttacca tacccggaga      420
catggaagat ctaagcttta aagttcggtc cctccttgtt gtccctagtg aagaagaaac      480
tacagagact gaagaaaaac taggagcaac agtcatcgag acacaaccca tcgaagagat      540
aagccttgac tccatcaaag ttggactcag cgaagctatc attgaaatcg aatatcctaa      600 agacccatt gacgatagct aatgcagcag tctgataatc ccgccgctag acggagagtg       660
agttgcgtct tatctactag tatacacttc ttgaagaaag ctaaaaacgt cgtcgtatcg      720
ttgtcttatt gcttgattgg ataaagcttc aattttttcc tccattttt gtcgaaaatg       780 taacatttt tttgctttcc actgtgagat tgtcacacac gattctctaa agaaatgaga       840
cgaattttga aaacgattta taaaaatagt attttgttt ccttgagctt atctcctctt       900
ttctctttgg tttgagatat gaattacaga caatcaagta gtcagtcaca acagtgtgta      960
taaatatgtc ttttaagtga aatcggtttc gagagacagt                           1000

<210> SEQ ID NO 89
<211> LENGTH: 1000
<212> TYPE: DNA
<213> ORGANISM: Arabidopsis thaliana

<400> SEQUENCE: 89
ttgtgtttat ctcaatgttt agatgttgaa aagtatatat gctgattaat aaataacaat       60
ttcttagtca acaactcaat gatagaatgt tatataactc tcttacatca tttacatttt      120
taaattgaat gaattctcat actatgcaat ctacctggtt agggtgaagt cacaacaaca      180
acaacattaa ctaataacaa caatttaagc tgcatgtcct aatcagaatc tcggttattg      240
gtcgctcata agaacagtta gaggtctttc agtcacaatt gagagacgac atacataatt      300
ggatgggaat caaaatcagt ttaattgcgc tatacgcaac ttgaaacgtc attatacacc      360
gataagcttt aaaaataaaa tgttgtgatg gacacgcgca ctatatatgt atgtgtttgg      420
acatgattga agctaaacaa gataatatttt attaagaaga aaatacataa ttattactaa      480
ataatgtgta ttattatacg attccaactt ttatttgata atgattttg agcaaatcag       540 gttgataggt atgattgaga ccatcgccca aactacacct taaggtctta ctattagaaa      600
caaacaattc atttgggaat tgaaaccaaa gtcatctatg gaagtaacct caaaatttat      660
ctaagaaaca gtgatgtatt agaatggtca agtcaactta ttcacaaaat tacaaaacta      720
tcgtttataa atatataatc tattttttcac ttgtgttaca cgattcctct tttgatatgc     780
aggaagaaga gaagatctta caacggctag aaatagaaaa cttaatgtgc tattaattac      840
aacttaccaa ctaattagaa cttttctatat gaaccggatc ttctacagca atcacggtc      900 aattcaaaat attcatctct ctctctctct ccacatggac aagacatgat taagaaagta      960
tataaaagaa acagagcaga gaaagacatt ttgttccggt                           1000

<210> SEQ ID NO 90
<211> LENGTH: 1000
<212> TYPE: DNA
<213> ORGANISM: Arabidopsis thaliana

<400> SEQUENCE: 90
gtgagcagat aaggatcgtg tattttcaag tattatatta attaataaat tatcgcccat       60
cttctattgt tttgtatttt catttgaaaa gaaagcaggg ctggcttatc aatatataca      120
```

```
gtctctttct tttagtttac taaaatcatt tcagataaga cccacacaaa agtaatatca      180
aatggaattt tgctttcaac atggataatt ttctttaata ataaaattgt caaccatgtt      240
aagcgtaatc tctaaatccc caaaattaaa aacactaaaa atagtcggtc attgctccac      300
gtttaacctg tccaattcca aaagaacttc gtgtttcatt gacgatatag tttacgtacg      360
tatgattctt tctaaatgag gtattttttgt cccattagca atttaaaatt taaaatggtt     420
gtgtaacttt ttgaaatgct tagtagttaa aaccgaacta agaagaaata atgatcggaa      480
cgtgtttatg tcagctaatg cattacccac tgacattaac tgatccagtt tactgatttt      540
agacaatcat actctatttt tactggagtt gcagaaaaag ggacttacaa aacgatgaat      600
taaatttgga caagtatata tacataatta gaaggttata gaatctagtt ttcgtaggat      660
atttcttgaa ttatcctacg agtgtgacaa ctaaatgcac aacaaaacaa caatttaaat      720
gctaaaaagc aaaaatagta attactggtc acctattaag gaacaacacc aacacctatt      780
tagctgttat gtcctaataa aaataaaata aaataaaaac aataaaccaa aaaagtaaaa      840
aataaaaatg tttgactaaa attctctttc ttttccgatt cgtcattcga tgaatcttcc      900
tttcttatac aatttggata atcttttcta atgtaaaaat tcgagatttt tttttataat      960
gttaaatcta taaataagag caacctaaaa cgaacaactt                          1000

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 91
cgccagggtt ttcccagtca cga                                               23

<210> SEQ ID NO 92
<211> LENGTH: 24
<212> TYPE: DNA
<213> ORGANISM: Artificial Sequence
<220> FEATURE:

<223> OTHER INFORMATION: Description of Artificial Sequence:primer

<400> SEQUENCE: 92
agcggataac aatttcacac agga                                              24

<210> SEQ ID NO 93
<211> LENGTH: 588
<212> TYPE: DNA
<213> ORGANISM: Arabidopsis thaliana
<220> FEATURE:
<221> NAME/KEY: CDS
<222> LOCATION: (1)..(585)

<400> SEQUENCE: 93 atg gtg aag caa gcg atg aag gaa gag gag aag aag aga aac acg gcg      48
Met Val Lys Gln Ala Met Lys Glu Glu Glu Lys Lys Arg Asn Thr Ala
 1               5                  10                  15 atg cag tca aag tac aaa gga gtg agg aag agg aaa tgg gga aaa tgg      96
Met Gln Ser Lys Tyr Lys Gly Val Arg Lys Arg Lys Trp Gly Lys Trp
            20                  25                  30 gta tcg gag atc aga ctt cca cac agc aga gaa cga att tgg tta ggc     144
Val Ser Glu Ile Arg Leu Pro His Ser Arg Glu Arg Ile Trp Leu Gly
        35                  40                  45
```

```
tct tac gac act ccc gag aag gcg gcg cgt gct ttc gac gcc gct caa      192
Ser Tyr Asp Thr Pro Glu Lys Ala Ala Arg Ala Phe Asp Ala Ala Gln
 50                  55                  60 ttt tgt ctc cgc ggc ggc gat gct aat ttc aat ttc cct aat aat cca      240
Phe Cys Leu Arg Gly Gly Asp Ala Asn Phe Asn Phe Pro Asn Asn Pro
 65                  70                  75                  80 ccg tcg atc tcc gta gaa aag tcg ttg acg cct ccg gag att cag gaa      288
Pro Ser Ile Ser Val Glu Lys Ser Leu Thr Pro Pro Glu Ile Gln Glu
                 85                  90                  95 gct gct gct aga ttc gct aac aca ttc caa gac att gtc aag gga gaa      336
Ala Ala Ala Arg Phe Ala Asn Thr Phe Gln Asp Ile Val Lys Gly Glu
            100                 105                 110 gaa gaa tcg ggt tta gta ccc gga tcc gag atc cga cca gag tct cct      384
Glu Glu Ser Gly Leu Val Pro Gly Ser Glu Ile Arg Pro Glu Ser Pro
        115                 120                 125 tct aca tct gca tct gtt gct aca tcg acg gtg gat tat gat ttt tcg      432
Ser Thr Ser Ala Ser Val Ala Thr Ser Thr Val Asp Tyr Asp Phe Ser
130                 135                 140 ttt ttg gat ttg ctt ccg atg aat ttc ggg ttt gat tcc ttc tcc gac      480
Phe Leu Asp Leu Leu Pro Met Asn Phe Gly Phe Asp Ser Phe Ser Asp
145                 150                 155                 160 gac ttc tct ggc ttc tcc ggt ggt gat cga ttt aca gag att tta ccc      528
Asp Phe Ser Gly Phe Ser Gly Gly Asp Arg Phe Thr Glu Ile Leu Pro
                165                 170                 175 atc gaa gat tac gga gga gag agt tta tta gat gaa tct ttg att ctt      576
Ile Glu Asp Tyr Gly Gly Glu Ser Leu Leu Asp Glu Ser Leu Ile Leu
            180                 185                 190 tgg gat ttt tga                                                      588
Trp Asp Phe
        195

<210> SEQ ID NO 94
<211> LENGTH: 195
<212> TYPE: PRT
<213> ORGANISM: Arabidopsis thaliana

<400> SEQUENCE: 94

Met Val Lys Gln Ala Met Lys Glu Glu Lys Lys Arg Asn Thr Ala
  1               5                  10                  15

Met Gln Ser Lys Tyr Lys Gly Val Arg Lys Arg Lys Trp Gly Lys Trp
                 20                  25                  30

Val Ser Glu Ile Arg Leu Pro His Ser Arg Glu Arg Ile Trp Leu Gly
             35                  40                  45

Ser Tyr Asp Thr Pro Glu Lys Ala Ala Arg Ala Phe Asp Ala Ala Gln
 50                  55                  60

Phe Cys Leu Arg Gly Gly Asp Ala Asn Phe Asn Phe Pro Asn Asn Pro
 65                  70                  75                  80

Pro Ser Ile Ser Val Glu Lys Ser Leu Thr Pro Pro Glu Ile Gln Glu
                 85                  90                  95

Ala Ala Ala Arg Phe Ala Asn Thr Phe Gln Asp Ile Val Lys Gly Glu
            100                 105                 110

Glu Glu Ser Gly Leu Val Pro Gly Ser Glu Ile Arg Pro Glu Ser Pro
        115                 120                 125

Ser Thr Ser Ala Ser Val Ala Thr Ser Thr Val Asp Tyr Asp Phe Ser
130                 135                 140

Phe Leu Asp Leu Leu Pro Met Asn Phe Gly Phe Asp Ser Phe Ser Asp
145                 150                 155                 160
```

```
                Asp Phe Ser Gly Phe Ser Gly Gly Asp Arg Phe Thr Glu Ile Leu Pro
                                165                 170                 175

Ile Glu Asp Tyr Gly Gly Glu Ser Leu Leu Asp Glu Ser Leu Ile Leu
                            180                 185                 190

Trp Asp Phe
                        195

<210> SEQ ID NO 95
<211> LENGTH: 1290
<212> TYPE: DNA
<213> ORGANISM: Arabidopsis thaliana
<220> FEATURE:
<221> NAME/KEY: CDS
<222> LOCATION: (81)..(1088)

<400> SEQUENCE: 95
aacaaatctc tctgtttctc ccgctcttgc tctgttttct caaagacaaa agaggacatc       60
gtcgttgact cctcttctct atg gct act gct aag aac aag gga aaa tca atc     113
                     Met Ala Thr Ala Lys Asn Lys Gly Lys Ser Ile
                       1               5                  10 agg gtc ctt ggt acc agt gaa gca gag aaa aag gat gag atg gag ttg        161
Arg Val Leu Gly Thr Ser Glu Ala Glu Lys Lys Asp Glu Met Glu Leu
             15                  20                  25 gag gag gag ttc cag ttt agt agc ggc aag tat aaa gat tcg ggt cct        209
Glu Glu Glu Phe Gln Phe Ser Ser Gly Lys Tyr Lys Asp Ser Gly Pro
         30                  35                  40 ggc tcg gac atg tgg tta gga gat gct tcc tct acg tct cca aga agt        257
Gly Ser Asp Met Trp Leu Gly Asp Ala Ser Ser Thr Ser Pro Arg Ser
     45                  50                  55 ctt agg aag act aga acc ttt gac cga cat aat ccc tat ctc gta tct        305
Leu Arg Lys Thr Arg Thr Phe Asp Arg His Asn Pro Tyr Leu Val Ser
 60                  65                  70                  75 tct tat gct act cct cag ccg cca aca aca act aca tgc tct gtc tct        353
Ser Tyr Ala Thr Pro Gln Pro Pro Thr Thr Thr Thr Cys Ser Val Ser
                 80                  85                  90 ttt ccc ttt tac ctc cct cca gcg att caa aat caa caa cga ttt tta        401
Phe Pro Phe Tyr Leu Pro Pro Ala Ile Gln Asn Gln Gln Arg Phe Leu
             95                 100                 105 cac ccg aat gac cct tca gga caa aga cag caa caa atg atc tcg ttt        449
His Pro Asn Asp Pro Ser Gly Gln Arg Gln Gln Gln Met Ile Ser Phe
        110                 115                 120 gat cct caa caa cag gtg caa cca tat gtt gca caa cag cag caa caa        497
Asp Pro Gln Gln Gln Val Gln Pro Tyr Val Ala Gln Gln Gln Gln Gln
    125                 130                 135 caa caa cat cta ttg cag tac tgg aga gac att ctg aag ctg agt ccg        545
Gln Gln His Leu Leu Gln Tyr Trp Arg Asp Ile Leu Lys Leu Ser Pro
140                 145                 150                 155 agc gga aga atg atg atg atg aac atg tta aga caa gaa agc gat ctg        593
Ser Gly Arg Met Met Met Met Asn Met Leu Arg Gln Glu Ser Asp Leu
                160                 165                 170 cca ctg acg agg cca ccg gtt caa ccc ttc agc gcc acc aag cta tat        641
Pro Leu Thr Arg Pro Pro Val Gln Pro Phe Ser Ala Thr Lys Leu Tyr
            175                 180                 185 aga ggt gtc agg caa cgc cac tgg gga aaa tgg gtt gcc gag atc cgt        689
Arg Gly Val Arg Gln Arg His Trp Gly Lys Trp Val Ala Glu Ile Arg
        190                 195                 200 aag cca cga aac agg aca cgt ctc tgg cta ggg aca ttc gat aca gca        737
Lys Pro Arg Asn Arg Thr Arg Leu Trp Leu Gly Thr Phe Asp Thr Ala
    205                 210                 215 gaa gaa gcc gcc atg gcc tac gac cgc gag gcc ttc aag ttg agg gga        785
Glu Glu Ala Ala Met Ala Tyr Asp Arg Glu Ala Phe Lys Leu Arg Gly
```

```
Glu Glu Ala Ala Met Ala Tyr Asp Arg Glu Ala Phe Lys Leu Arg Gly
220                 225                 230                 235 gag acc gct agg ctc aat ttc cct gaa ctt ttt ctc aat aaa caa gag      833
Glu Thr Ala Arg Leu Asn Phe Pro Glu Leu Phe Leu Asn Lys Gln Glu
                240                 245                 250 cca act ccc gtg cat cag aaa caa tgt gag acg ggg act act agt gaa      881
Pro Thr Pro Val His Gln Lys Gln Cys Glu Thr Gly Thr Thr Ser Glu
                255                 260                 265 gac tca agc aga aga gga gag gat gat tcg agc acg gca ttg gca gta      929
Asp Ser Ser Arg Arg Gly Glu Asp Asp Ser Ser Thr Ala Leu Ala Val
            270                 275                 280 gga ggg gtg agt gag gag acg ggt tgg gct gag gca tgg ttc aat gca      977
Gly Gly Val Ser Glu Glu Thr Gly Trp Ala Glu Ala Trp Phe Asn Ala
        285                 290                 295 att cca gag gaa tgg gga cct gga agc cct cta tgg gat gat tac cac     1025
Ile Pro Glu Glu Trp Gly Pro Gly Ser Pro Leu Trp Asp Asp Tyr His
300                 305                 310                 315 ttt ccc att tct aac cat aag gac gat ctt gac gcc aca caa aac tct     1073
Phe Pro Ile Ser Asn His Lys Asp Asp Leu Asp Ala Thr Gln Asn Ser
                320                 325                 330 tct tct gat aca att taggaccttt gttagaatat agatatgctt agttgtatga     1128
Ser Ser Asp Thr Ile
                335 ctgatctagc ttgtgttttt tttttgggtg gagacagttt ttgtcatctt ccacatttta   1188 gattctattt tcgaccatca ttttttttctt gatcggtgac tatgaatcta atggggtcaa  1248 tcatttttcac atataaaact taagtatttg gtgtttgtac tt                     1290

<210> SEQ ID NO 96
<211> LENGTH: 336
<212> TYPE: PRT
<213> ORGANISM: Arabidopsis thaliana

<400> SEQUENCE: 96

Met Ala Thr Ala Lys Asn Lys Gly Lys Ser Ile Arg Val Leu Gly Thr
1               5                   10                  15

Ser Glu Ala Glu Lys Lys Asp Glu Met Glu Leu Glu Glu Glu Phe Gln
                20                  25                  30

Phe Ser Ser Gly Lys Tyr Lys Asp Ser Gly Pro Gly Ser Asp Met Trp
            35                  40                  45

Leu Gly Asp Ala Ser Ser Thr Ser Pro Arg Ser Leu Arg Lys Thr Arg
50                  55                  60

Thr Phe Asp Arg His Asn Pro Tyr Leu Val Ser Ser Tyr Ala Thr Pro
65                  70                  75                  80

Gln Pro Pro Thr Thr Thr Cys Ser Val Ser Phe Pro Phe Tyr Leu
                85                  90                  95

Pro Pro Ala Ile Gln Asn Gln Gln Arg Phe Leu His Pro Asn Asp Pro
            100                 105                 110

Ser Gly Gln Arg Gln Gln Gln Met Ile Ser Phe Asp Pro Gln Gln Gln
        115                 120                 125

Val Gln Pro Tyr Val Ala Gln Gln Gln Gln Gln His Leu Leu
130                 135                 140

Gln Tyr Trp Arg Asp Ile Leu Lys Leu Ser Pro Ser Gly Arg Met Met
145                 150                 155                 160

Met Met Asn Met Leu Arg Gln Glu Ser Asp Leu Pro Leu Thr Arg Pro
                165                 170                 175

Pro Val Gln Pro Phe Ser Ala Thr Lys Leu Tyr Arg Gly Val Arg Gln
```

-continued

```
                    180                 185                 190
Arg His Trp Gly Lys Trp Val Ala Glu Ile Arg Lys Pro Arg Asn Arg
                195                 200                 205

Thr Arg Leu Trp Leu Gly Thr Phe Asp Thr Ala Glu Glu Ala Ala Met
210                 215                 220

Ala Tyr Asp Arg Glu Ala Phe Lys Leu Arg Gly Glu Thr Ala Arg Leu
225                 230                 235                 240

Asn Phe Pro Glu Leu Phe Leu Asn Lys Gln Glu Pro Thr Pro Val His
                245                 250                 255

Gln Lys Gln Cys Glu Thr Gly Thr Thr Ser Glu Asp Ser Ser Arg Arg
                260                 265                 270

Gly Glu Asp Asp Ser Ser Thr Ala Leu Ala Val Gly Val Ser Glu
                275                 280                 285

Glu Thr Gly Trp Ala Glu Ala Trp Phe Asn Ala Ile Pro Glu Glu Trp
290                 295                 300

Gly Pro Gly Ser Pro Leu Trp Asp Asp Tyr His Phe Pro Ile Ser Asn
305                 310                 315                 320

His Lys Asp Asp Leu Asp Ala Thr Gln Asn Ser Ser Ser Asp Thr Ile
                325                 330                 335
```

<210> SEQ ID NO 97
<211> LENGTH: 879
<212> TYPE: DNA
<213> ORGANISM: Arabidopsis thaliana
<220> FEATURE:
<221> NAME/KEY: CDS
<222> LOCATION: (1)..(876)

<400> SEQUENCE: 97

```
atg gac ttt gac gag gag cta aat ctt tgt att acg aaa ggt aaa aat      48
Met Asp Phe Asp Glu Glu Leu Asn Leu Cys Ile Thr Lys Gly Lys Asn
  1               5                  10                  15 gtt gat cat tct ttt gga gga gaa gct tct tcc acg tcc cca aga tct      96
Val Asp His Ser Phe Gly Gly Glu Ala Ser Ser Thr Ser Pro Arg Ser
             20                  25                  30 atg aag aaa atg aag agt cct agt cgt cct aaa ccc tat ttc caa tcc     144
Met Lys Lys Met Lys Ser Pro Ser Arg Pro Lys Pro Tyr Phe Gln Ser
         35                  40                  45 tct tct tct cct tat tcg tta gag gct ttc cct ttt tct ctc gat cca     192
Ser Ser Ser Pro Tyr Ser Leu Glu Ala Phe Pro Phe Ser Leu Asp Pro
     50                  55                  60 aca ctt cag aat cag caa caa caa ctc gga tca tac gtt ccg gta ctt     240
Thr Leu Gln Asn Gln Gln Gln Gln Leu Gly Ser Tyr Val Pro Val Leu
 65                  70                  75                  80 gag caa cga caa gac ccg aca atg caa ggc cag aag caa atg atc tcc     288
Glu Gln Arg Gln Asp Pro Thr Met Gln Gly Gln Lys Gln Met Ile Ser
                 85                  90                  95 ttt agt cct caa caa caa caa cag cag cag tat atg gcc cag tac         336
Phe Ser Pro Gln Gln Gln Gln Gln Gln Gln Tyr Met Ala Gln Tyr
            100                 105                 110 tgg agt gac aca ttg aat ctg agt cca aga gga aga atg atg atg atg     384
Trp Ser Asp Thr Leu Asn Leu Ser Pro Arg Gly Arg Met Met Met Met
        115                 120                 125 atg agc caa gaa gct gtt caa cct tac atc gca acg aag ctg tac aga     432
Met Ser Gln Glu Ala Val Gln Pro Tyr Ile Ala Thr Lys Leu Tyr Arg
    130                 135                 140 gga gtg aga caa cgt caa tgg gga aaa tgg gtc gca gag atc cgt aag     480
Gly Val Arg Gln Arg Gln Trp Gly Lys Trp Val Ala Glu Ile Arg Lys
145                 150                 155                 160
```

```
cca cga agc agg gca cgt ctt tgg ctt ggt acc ttt gat aca gct gaa    528
Pro Arg Ser Arg Ala Arg Leu Trp Leu Gly Thr Phe Asp Thr Ala Glu
            165                 170                 175 gaa gct gcc atg gcc tac gac cgc caa gcc ttc aaa tta cga ggc cac    576
Glu Ala Ala Met Ala Tyr Asp Arg Gln Ala Phe Lys Leu Arg Gly His
        180                 185                 190 agc gca aca ctg aat ttc ccg gag cat ttt gtg aat aag gaa agc gag    624
Ser Ala Thr Leu Asn Phe Pro Glu His Phe Val Asn Lys Glu Ser Glu
    195                 200                 205 ctg cat gat tca aac tcg tcg gat cag aaa gaa cct gaa acg cca cag    672
Leu His Asp Ser Asn Ser Ser Asp Gln Lys Glu Pro Glu Thr Pro Gln
210                 215                 220 cca agc gag gtt aac ttg gag agc aag gaa cta ccg gtg att gat gtt    720
Pro Ser Glu Val Asn Leu Glu Ser Lys Glu Leu Pro Val Ile Asp Val
225                 230                 235                 240 ggg aga gag gaa ggt atg gct gag gca tgg tac aat gcc att aca tcg    768
Gly Arg Glu Glu Gly Met Ala Glu Ala Trp Tyr Asn Ala Ile Thr Ser
                245                 250                 255 gga tgg ggt cct gaa agt cct ctt tgg gat gat ttg gat agt tct cat    816
Gly Trp Gly Pro Glu Ser Pro Leu Trp Asp Asp Leu Asp Ser Ser His
            260                 265                 270 cag ttt tca tca gaa agc tca tct tct tct cct ctc tct tgt cct atg    864
Gln Phe Ser Ser Glu Ser Ser Ser Ser Ser Pro Leu Ser Cys Pro Met
275                 280                 285 agg cct ttc ttt tga                                                879
Arg Pro Phe Phe
    290

<210> SEQ ID NO 98
<211> LENGTH: 292
<212> TYPE: PRT
<213> ORGANISM: Arabidopsis thaliana

<400> SEQUENCE: 98

Met Asp Phe Asp Glu Glu Leu Asn Leu Cys Ile Thr Lys Gly Lys Asn
1               5                   10                  15

Val Asp His Ser Phe Gly Gly Glu Ala Ser Ser Thr Ser Pro Arg Ser
            20                  25                  30

Met Lys Lys Met Lys Ser Pro Ser Arg Pro Lys Pro Tyr Phe Gln Ser
        35                  40                  45

Ser Ser Ser Pro Tyr Ser Leu Glu Ala Phe Pro Phe Ser Leu Asp Pro
    50                  55                  60

Thr Leu Gln Asn Gln Gln Gln Leu Gly Ser Tyr Val Pro Val Leu
65                  70                  75                  80

Glu Gln Arg Gln Asp Pro Thr Met Gln Gly Gln Lys Gln Met Ile Ser
                85                  90                  95

Phe Ser Pro Gln Gln Gln Gln Gln Gln Gln Tyr Met Ala Gln Tyr
            100                 105                 110

Trp Ser Asp Thr Leu Asn Leu Ser Pro Arg Gly Arg Met Met Met Met
        115                 120                 125

Met Ser Gln Glu Ala Val Gln Pro Tyr Ile Ala Thr Lys Leu Tyr Arg
    130                 135                 140

Gly Val Arg Gln Arg Gln Trp Gly Lys Trp Val Ala Glu Ile Arg Lys
145                 150                 155                 160

Pro Arg Ser Arg Ala Arg Leu Trp Leu Gly Thr Phe Asp Thr Ala Glu
                165                 170                 175

Glu Ala Ala Met Ala Tyr Asp Arg Gln Ala Phe Lys Leu Arg Gly His
```

```
                180             185             190
Ser Ala Thr Leu Asn Phe Pro Glu His Phe Val Asn Lys Glu Ser Glu
            195                 200                 205
Leu His Asp Ser Asn Ser Ser Asp Gln Lys Glu Pro Glu Thr Pro Gln
        210                 215                 220
Pro Ser Glu Val Asn Leu Glu Ser Lys Glu Leu Pro Val Ile Asp Val
225                 230                 235                 240
Gly Arg Glu Glu Gly Met Ala Glu Ala Trp Tyr Asn Ala Ile Thr Ser
                245                 250                 255
Gly Trp Gly Pro Glu Ser Pro Leu Trp Asp Asp Leu Asp Ser Ser His
            260                 265                 270
Gln Phe Ser Ser Glu Ser Ser Ser Ser Pro Leu Ser Cys Pro Met
        275                 280                 285
Arg Pro Phe Phe
    290

<210> SEQ ID NO 99
<211> LENGTH: 1499
<212> TYPE: DNA
<213> ORGANISM: Arabidopsis thaliana
<220> FEATURE:
<221> NAME/KEY: CDS
<222> LOCATION: (644)..(1222)

<400> SEQUENCE: 99
tggtatcggt gaggctgaga gttattcact tacaaaaaaa aaaaaaaact tgagtgtaac      60
caaaaaaaaa aagttgatat actttctggt tttctcctta acttttattc tttacaaatc     120
catccccctt agatctgttt atttcccgct actttgattc atttctgtta gtaatctgtc     180
tttcgtatag aagaaaactg atttcttggt ttgtattttc ttaaagagat caatcttttt     240
ttatttttga tcttcttgtg tttttttttc tttgtagaat taatcgtttg tgagggtatt     300
tttttaattc cctcctctca gaaatctaca cagaggtttt ttatttata aacctctttt      360 ttcgattttc ttgaaaacaa aaaatcctgt tctttacttt tttacaaga caagggaaa       420 aaaatttctt tttattagaa atgacaactt ctatggattt ttacagtaac aaaacgtttc     480
aacaatctga tccattcggt ggtgaattaa tggaagcgct ttacctttta tcaaaagccc     540
ttccaacgat tcatccgcgt ttgcgttctc tctacccgct ccaatttcat acgggtcgga     600
tctccactca ttttctcacc atcttagtcc taaaccggtc tca atg aaa caa acc       655
                                              Met Lys Gln Thr
                                                1 ggt act tcc gcg gct aaa ccg acg aag cta tac aga gga gtg aga caa      703
Gly Thr Ser Ala Ala Lys Pro Thr Lys Leu Tyr Arg Gly Val Arg Gln
  5                  10                  15                  20 cgt cac tgg gga aaa tgg gtg gct gag att cgt tta ccg agg aat cga      751
Arg His Trp Gly Lys Trp Val Ala Glu Ile Arg Leu Pro Arg Asn Arg
                 25                  30                  35 act cga ctt tgg ctc gga aca ttc gac acg gcg gag gaa gct gct tta      799
Thr Arg Leu Trp Leu Gly Thr Phe Asp Thr Ala Glu Glu Ala Ala Leu
             40                  45                  50 gct tat gac aag gcg gcg tat aag ctc cga gga gat ttt gcg cgg ctt      847
Ala Tyr Asp Lys Ala Ala Tyr Lys Leu Arg Gly Asp Phe Ala Arg Leu
         55                  60                  65 aat ttc cct gat ctc cgt cat aac gac gag tat caa cct ctt caa tca      895
Asn Phe Pro Asp Leu Arg His Asn Asp Glu Tyr Gln Pro Leu Gln Ser
     70                  75                  80 tca gtc gac gct aag ctt gaa gct att tgt caa aac tta gct gag acg      943
```

```
                                     -continued

Ser Val Asp Ala Lys Leu Glu Ala Ile Cys Gln Asn Leu Ala Glu Thr
 85                  90                  95                 100 acg cag aaa cag gtg aga tca acg aag aag tct tct tct cgg aaa cgt    991
Thr Gln Lys Gln Val Arg Ser Thr Lys Lys Ser Ser Ser Arg Lys Arg
                105                 110                 115 tca tca acc gtc gca gtg aaa cta ccg gag gag gac tac tct agc gcc   1039
Ser Ser Thr Val Ala Val Lys Leu Pro Glu Glu Asp Tyr Ser Ser Ala
            120                 125                 130 gga tct tcg ccg ctg tta acg gag agt tat gga tct ggt gga tct tct   1087
Gly Ser Ser Pro Leu Leu Thr Glu Ser Tyr Gly Ser Gly Gly Ser Ser
        135                 140                 145 tcg ccg ttg tcg gag ctg acg ttt ggt gat acg gag gag gag att cag   1135
Ser Pro Leu Ser Glu Leu Thr Phe Gly Asp Thr Glu Glu Glu Ile Gln
150                 155                 160 ccg ccg tgg aac gag aac gcg ttg gag aag tat ccg tcg tac gag atc   1183
Pro Pro Trp Asn Glu Asn Ala Leu Glu Lys Tyr Pro Ser Tyr Glu Ile
165                 170                 175                 180 gat tgg gat tcg att ctt cag tgt tcg agt ctt gta aat tagatgttgc    1232
Asp Trp Asp Ser Ile Leu Gln Cys Ser Ser Leu Val Asn
                185                 190 cataggggta ttttagggac tttagagctc tctgcgatgg agttttggt cattgcagag  1292 attttattat tattaagggg gtttgttatg ttaatatcaa ataagtttat ctactttgat  1352
gttaattagt gttaatctct gcgtcggtcc aagctgtttt ttttggcat gcttcgaccg   1412 tgtgagattt cttatgtaat ttttgtagtt ccttgatttt cttagttcaa gttaaattgg  1472
cacaaaagag caaaaaaaaa aaaaaaa                                      1499

<210> SEQ ID NO 100
<211> LENGTH: 193
<212> TYPE: PRT
<213> ORGANISM: Arabidopsis thaliana

<400> SEQUENCE: 100

Met Lys Gln Thr Gly Thr Ser Ala Ala Lys Pro Thr Lys Leu Tyr Arg
  1               5                  10                  15

Gly Val Arg Gln Arg His Trp Gly Lys Trp Val Ala Glu Ile Arg Leu
             20                  25                  30

Pro Arg Asn Arg Thr Arg Leu Trp Leu Gly Thr Phe Asp Thr Ala Glu
         35                  40                  45

Glu Ala Ala Leu Ala Tyr Asp Lys Ala Ala Tyr Lys Leu Arg Gly Asp
     50                  55                  60

Phe Ala Arg Leu Asn Phe Pro Asp Leu Arg His Asn Asp Glu Tyr Gln
 65                  70                  75                  80

Pro Leu Gln Ser Ser Val Asp Ala Lys Leu Glu Ala Ile Cys Gln Asn
                 85                  90                  95

Leu Ala Glu Thr Thr Gln Lys Gln Val Arg Ser Thr Lys Lys Ser Ser
            100                 105                 110

Ser Arg Lys Arg Ser Ser Thr Val Ala Val Lys Leu Pro Glu Glu Asp
        115                 120                 125

Tyr Ser Ser Ala Gly Ser Ser Pro Leu Leu Thr Glu Ser Tyr Gly Ser
    130                 135                 140

Gly Gly Ser Ser Ser Pro Leu Ser Glu Leu Thr Phe Gly Asp Thr Glu
145                 150                 155                 160

Glu Glu Ile Gln Pro Pro Trp Asn Glu Asn Ala Leu Glu Lys Tyr Pro
                165                 170                 175

Ser Tyr Glu Ile Asp Trp Asp Ser Ile Leu Gln Cys Ser Ser Leu Val
```

Asn

<210> SEQ ID NO 101
<211> LENGTH: 962
<212> TYPE: DNA
<213> ORGANISM: Arabidopsis thaliana
<220> FEATURE:
<221> NAME/KEY: CDS
<222> LOCATION: (77)..(880)

<400> SEQUENCE: 101

```
acaccggaca ttttgaaatc tcaacaagaa ccaaaccaaa caacaaaaaa acattcttaa        60
taattatctt tctgtt atg tcg atg acg gcg gat tct caa tct gat tat gct       112
               Met Ser Met Thr Ala Asp Ser Gln Ser Asp Tyr Ala
                 1               5                  10 ttt ctt gag tcc ata cga cga cac tta cta gga gaa tcg gag ccg ata         160
Phe Leu Glu Ser Ile Arg Arg His Leu Leu Gly Glu Ser Glu Pro Ile
             15                  20                  25 ctc agt gag tcg aca gcg agt tcg gtt act caa tct tgt gta acc ggt         208
Leu Ser Glu Ser Thr Ala Ser Ser Val Thr Gln Ser Cys Val Thr Gly
         30                  35                  40 cag agc att aaa ccg gtg tac gga cga aac cct agc ttt agc aaa ctg         256
Gln Ser Ile Lys Pro Val Tyr Gly Arg Asn Pro Ser Phe Ser Lys Leu
 45                  50                  55                  60 tat cct tgc ttc acc gag agc tgg gga gat ttg ccg ttg aaa gaa aac         304
Tyr Pro Cys Phe Thr Glu Ser Trp Gly Asp Leu Pro Leu Lys Glu Asn
                 65                  70                  75 gat tct gag gat atg tta gtt tac ggt atc ctc aac gac gcc ttt cac         352
Asp Ser Glu Asp Met Leu Val Tyr Gly Ile Leu Asn Asp Ala Phe His
             80                  85                  90 ggc ggt tgg gag ccg tct tct tcg tct tcc gac gaa gat cgt agc tct         400
Gly Gly Trp Glu Pro Ser Ser Ser Ser Ser Asp Glu Asp Arg Ser Ser
         95                 100                 105 ttc ccg agt gtt aag atc gag act ccg gag agt ttc gcg gcg gtg gat         448
Phe Pro Ser Val Lys Ile Glu Thr Pro Glu Ser Phe Ala Ala Val Asp
110                 115                 120 tct gtt ccg gtc aag aag gag aag acg agt cct gtt tcg gcg gcg gtg         496
Ser Val Pro Val Lys Lys Glu Lys Thr Ser Pro Val Ser Ala Ala Val
125                 130                 135                 140 acg gcg gcg aag gga aag cat tat aga gga gtg aga caa agg ccg tgg         544
Thr Ala Ala Lys Gly Lys His Tyr Arg Gly Val Arg Gln Arg Pro Trp
                145                 150                 155 ggg aaa ttt gcg gcg gag att aga gac ccg gcg aag aac gga gct agg         592
Gly Lys Phe Ala Ala Glu Ile Arg Asp Pro Ala Lys Asn Gly Ala Arg
            160                 165                 170 gtt tgg tta gga acg ttt gag acg gcg gag gac gcg gcg ttg gct tac         640
Val Trp Leu Gly Thr Phe Glu Thr Ala Glu Asp Ala Ala Leu Ala Tyr
        175                 180                 185 gac aga gct gct ttc agg atg cgt ggt tcc cgc gct ttg ttg aat ttt         688
Asp Arg Ala Ala Phe Arg Met Arg Gly Ser Arg Ala Leu Leu Asn Phe
    190                 195                 200 ccg ttg aga gtt aat tca gga gaa ccc gac ccg gtt cga atc aag tcc         736
Pro Leu Arg Val Asn Ser Gly Glu Pro Asp Pro Val Arg Ile Lys Ser
205                 210                 215                 220 aag aga tct tct ttt tct tct tct aac gag aac gga gct ccg aag aag         784
Lys Arg Ser Ser Phe Ser Ser Ser Asn Glu Asn Gly Ala Pro Lys Lys
                225                 230                 235 agg aga acg gtg gcc gcc ggt ggt gga atg gat aag gga ttg acg gtg         832
Arg Arg Thr Val Ala Ala Gly Gly Gly Met Asp Lys Gly Leu Thr Val
```

```
                      240              245              250
aag tgc gag gtt gtt gaa gtg gca cgt ggc gat cgt tta ttg gtt tta      880
Lys Cys Glu Val Val Glu Val Ala Arg Gly Asp Arg Leu Leu Val Leu
        255              260              265 taatttgat tttctttgt tggatgatta tatgattctt caaaaagaa gaacgttaat       940 aaaaaaattc gtttattatt gt                                             962
```

<210> SEQ ID NO 102
<211> LENGTH: 268
<212> TYPE: PRT
<213> ORGANISM: Arabidopsis thaliana

<400> SEQUENCE: 102

```
Met Ser Met Thr Ala Asp Ser Gln Ser Asp Tyr Ala Phe Leu Glu Ser
 1               5                  10                  15

Ile Arg Arg His Leu Leu Gly Glu Ser Glu Pro Ile Leu Ser Glu Ser
            20                  25                  30

Thr Ala Ser Ser Val Thr Gln Ser Cys Val Thr Gly Gln Ser Ile Lys
        35                  40                  45

Pro Val Tyr Gly Arg Asn Pro Ser Phe Ser Lys Leu Tyr Pro Cys Phe
    50                  55                  60

Thr Glu Ser Trp Gly Asp Leu Pro Leu Lys Glu Asn Asp Ser Glu Asp
65                  70                  75                  80

Met Leu Val Tyr Gly Ile Leu Asn Asp Ala Phe His Gly Gly Trp Glu
                85                  90                  95

Pro Ser Ser Ser Ser Asp Glu Asp Arg Ser Ser Phe Pro Ser Val
            100                 105                 110

Lys Ile Glu Thr Pro Glu Ser Phe Ala Ala Val Asp Ser Val Pro Val
        115                 120                 125

Lys Lys Glu Lys Thr Ser Pro Val Ser Ala Ala Val Thr Ala Ala Lys
    130                 135                 140

Gly Lys His Tyr Arg Gly Val Arg Gln Arg Pro Trp Gly Lys Phe Ala
145                 150                 155                 160

Ala Glu Ile Arg Asp Pro Ala Lys Asn Gly Ala Arg Val Trp Leu Gly
                165                 170                 175

Thr Phe Glu Thr Ala Glu Asp Ala Ala Leu Ala Tyr Asp Arg Ala Ala
            180                 185                 190

Phe Arg Met Arg Gly Ser Arg Ala Leu Leu Asn Phe Pro Leu Arg Val
        195                 200                 205

Asn Ser Gly Glu Pro Asp Pro Val Arg Ile Lys Ser Lys Arg Ser Ser
    210                 215                 220

Phe Ser Ser Asn Glu Asn Gly Ala Pro Lys Lys Arg Arg Thr Val
225                 230                 235                 240

Ala Ala Gly Gly Gly Met Asp Lys Gly Leu Thr Val Lys Cys Glu Val
                245                 250                 255

Val Glu Val Ala Arg Gly Asp Arg Leu Leu Val Leu
            260                 265
```

<210> SEQ ID NO 103
<211> LENGTH: 834
<212> TYPE: DNA
<213> ORGANISM: Arabidopsis thaliana
<220> FEATURE:
<221> NAME/KEY: CDS
<222> LOCATION: (171)..(746)

<400> SEQUENCE: 103

```
aacacaattt gattacactg agcaacacaa aactggcgaa ccaacgtgac tctaacgaag    60
aaaccggcaa tggccagtat cactacaatg ccgaagaaat aacaagaatc ataaacgagc   120
cagaatatta tcccccgggt tacaacttgt ctaccaccgc aatttcaaac atg gtg      176
                                                        Met Val
                                                          1 tct atg ctg act aat gtt gtc tct ggt gag acc gaa ccc tcg gca tct    224
Ser Met Leu Thr Asn Val Val Ser Gly Glu Thr Glu Pro Ser Ala Ser
        5                  10                 15 gcg aca tgg acg atg ggt cat aag aga gaa aga gaa gag ttt tct ttg    272
Ala Thr Trp Thr Met Gly His Lys Arg Glu Arg Glu Glu Phe Ser Leu
 20                  25                 30 cct cct caa cca ttg att acc ggt tca gct gtg act aaa gaa tgt gaa    320
Pro Pro Gln Pro Leu Ile Thr Gly Ser Ala Val Thr Lys Glu Cys Glu
 35              40                  45                 50 agc tca atg tcc ttg gag agg cca aaa aaa tat aga gga gta agg caa    368
Ser Ser Met Ser Leu Glu Arg Pro Lys Lys Tyr Arg Gly Val Arg Gln
             55                  60                 65 cga cca tgg gga aaa tgg gcg gcg gag att cga gac cca cac aag gcg    416
Arg Pro Trp Gly Lys Trp Ala Ala Glu Ile Arg Asp Pro His Lys Ala
                 70                  75                 80 aca cgt gta tgg ctt ggg aca ttc gag aca gcc gag gcc gcc gca aga    464
Thr Arg Val Trp Leu Gly Thr Phe Glu Thr Ala Glu Ala Ala Ala Arg
             85                  90                 95 gcc tat gat gcg gca gca ctt cgc ttt aga gga agc aaa gca aag ctt    512
Ala Tyr Asp Ala Ala Ala Leu Arg Phe Arg Gly Ser Lys Ala Lys Leu
100                 105                 110 aat ttc ccc gaa aat gtt gga act cag acg att caa cga aat tct cat    560
Asn Phe Pro Glu Asn Val Gly Thr Gln Thr Ile Gln Arg Asn Ser His
115                 120                 125                 130 ttc ttg caa aac tct atg caa cct tct ctg aca tac atc gat caa tgt    608
Phe Leu Gln Asn Ser Met Gln Pro Ser Leu Thr Tyr Ile Asp Gln Cys
                135                 140                 145 cca act cta tta tct tac tct cga tgt atg gag caa caa caa cca tta    656
Pro Thr Leu Leu Ser Tyr Ser Arg Cys Met Glu Gln Gln Gln Pro Leu
            150                 155                 160 gta ggc atg ttg cag cca aca gaa gag gaa aat cac ttt ttc gaa aaa    704
Val Gly Met Leu Gln Pro Thr Glu Glu Glu Asn His Phe Phe Glu Lys
                165                 170                 175 cca tgg acc gaa tat gat caa tac aat tac tcc tct ttt ggt            746
Pro Trp Thr Glu Tyr Asp Gln Tyr Asn Tyr Ser Ser Phe Gly
                180                 185                 190 taactaacat attgtcaacg ctttgtattt ctacttattc gatctaccaa tttttctct    806 cccaatacaa cttcagtctg attattgc                                     834

<210> SEQ ID NO 104
<211> LENGTH: 192
<212> TYPE: PRT
<213> ORGANISM: Arabidopsis thaliana

<400> SEQUENCE: 104

Met Val Ser Met Leu Thr Asn Val Val Ser Gly Glu Thr Glu Pro Ser
 1               5                  10                 15

Ala Ser Ala Thr Trp Thr Met Gly His Lys Arg Glu Arg Glu Glu Phe
                 20                 25                 30

Ser Leu Pro Pro Gln Pro Leu Ile Thr Gly Ser Ala Val Thr Lys Glu
             35                 40                 45

Cys Glu Ser Ser Met Ser Leu Glu Arg Pro Lys Lys Tyr Arg Gly Val
```

```
            50                  55                  60
Arg Gln Arg Pro Trp Gly Lys Trp Ala Ala Glu Ile Arg Asp Pro His
 65                  70                  75                  80

Lys Ala Thr Arg Val Trp Leu Gly Thr Phe Glu Thr Ala Glu Ala Ala
                 85                  90                  95

Ala Arg Ala Tyr Asp Ala Ala Ala Leu Arg Phe Arg Gly Ser Lys Ala
                100                 105                 110

Lys Leu Asn Phe Pro Glu Asn Val Gly Thr Gln Thr Ile Gln Arg Asn
            115                 120                 125

Ser His Phe Leu Gln Asn Ser Met Gln Pro Ser Leu Thr Tyr Ile Asp
        130                 135                 140

Gln Cys Pro Thr Leu Leu Ser Tyr Ser Arg Cys Met Glu Gln Gln Gln
145                 150                 155                 160

Pro Leu Val Gly Met Leu Gln Pro Thr Glu Glu Asn His Phe Phe
                165                 170                 175

Glu Lys Pro Trp Thr Glu Tyr Asp Gln Tyr Asn Tyr Ser Ser Phe Gly
                180                 185                 190

<210> SEQ ID NO 105
<211> LENGTH: 1085
<212> TYPE: DNA
<213> ORGANISM: Arabidopsis thaliana
<220> FEATURE:
<221> NAME/KEY: CDS
<222> LOCATION: (120)..(953)

<400> SEQUENCE: 105
acttcactct ctaatttcct tctctctatc tctcaccata ttcgcgatta aaaactctca      60
acttttctct caaatttctg atcctttgat ccaacagtta gaagaagatt catctgatc     119 atg gcc ctc gaa gcg atg aac act cca act tct tct ttc acc aga atc     167
Met Ala Leu Glu Ala Met Asn Thr Pro Thr Ser Ser Phe Thr Arg Ile
  1               5                  10                  15 gaa acg aaa gaa gat ttg atg aac gac gcc gtt ttc att gag ccg tgg     215
Glu Thr Lys Glu Asp Leu Met Asn Asp Ala Val Phe Ile Glu Pro Trp
             20                  25                  30 ctt aaa cgc aaa cgc tcc aaa cgt cag cgt tct cac agc cct tct tcg     263
Leu Lys Arg Lys Arg Ser Lys Arg Gln Arg Ser His Ser Pro Ser Ser
         35                  40                  45 tct tcc tcc tca ccg cct cga tct cga ccc aaa tcc cag aat caa gat     311
Ser Ser Ser Ser Pro Pro Arg Ser Arg Pro Lys Ser Gln Asn Gln Asp
     50                  55                  60 ctt acg gaa gaa gag tat ctc gct ctt tgt ctc ctc atg ctc gct aaa     359
Leu Thr Glu Glu Glu Tyr Leu Ala Leu Cys Leu Leu Met Leu Ala Lys
 65                  70                  75                  80 gat caa ccg tcg caa acg cga ttt cat caa cag tcg caa tcg tta acg     407
Asp Gln Pro Ser Gln Thr Arg Phe His Gln Gln Ser Gln Ser Leu Thr
                 85                  90                  95 ccg ccg cca gaa tca aag aac ctt ccg tac aag tgt aac gtc tgt gaa     455
Pro Pro Pro Glu Ser Lys Asn Leu Pro Tyr Lys Cys Asn Val Cys Glu
                100                 105                 110 aaa gcg ttt cct tcc tat cag gct tta ggc ggt cac aaa gca agt cac     503
Lys Ala Phe Pro Ser Tyr Gln Ala Leu Gly Gly His Lys Ala Ser His
            115                 120                 125 cga atc aaa cca cca acc gta atc tca aca acc gcc gat gat tca aca     551
Arg Ile Lys Pro Pro Thr Val Ile Ser Thr Thr Ala Asp Asp Ser Thr
        130                 135                 140 gct ccg acc atc tcc atc gtc gcc gga gaa aaa cat ccg att gct gcc     599
Ala Pro Thr Ile Ser Ile Val Ala Gly Glu Lys His Pro Ile Ala Ala
```

```
                                                                         -continued 145                 150                 155                 160 tcc gga aag atc cac gag tgt tca atc tgt cat aaa gtg ttt ccg acg          647
Ser Gly Lys Ile His Glu Cys Ser Ile Cys His Lys Val Phe Pro Thr
                165                 170                 175 ggt caa gct tta ggc ggt cac aaa cgt tgt cac tac gaa ggc aac ctc          695
Gly Gln Ala Leu Gly Gly His Lys Arg Cys His Tyr Glu Gly Asn Leu
            180                 185                 190 ggc ggc gga gga gga gga gga agc aaa tca atc agt cac agt gga agc          743
Gly Gly Gly Gly Gly Gly Gly Ser Lys Ser Ile Ser His Ser Gly Ser
        195                 200                 205 gtg tcg agc acg gta tcg gaa gaa agg agc cac cgt gga ttc atc gat          791
Val Ser Ser Thr Val Ser Glu Glu Arg Ser His Arg Gly Phe Ile Asp
    210                 215                 220 cta aac cta ccg gcg tta cct gaa ctc agc ctt cat cac aat cca atc          839
Leu Asn Leu Pro Ala Leu Pro Glu Leu Ser Leu His His Asn Pro Ile
225                 230                 235                 240 gtc gac gaa gag atc ttg agt ccg ttg acc ggt aaa aaa acc gct ttt          887
Val Asp Glu Glu Ile Leu Ser Pro Leu Thr Gly Lys Lys Thr Ala Phe
                245                 250                 255 gtt gac cga tca cga cca agt cat caa gaa aga aga ttt atc ttt aaa          935
Val Asp Arg Ser Arg Pro Ser His Gln Glu Arg Arg Phe Ile Phe Lys
            260                 265                 270 aat cta ata ctc gac tat taattcttgt gtgattttt tcgttacaac                  983
Asn Leu Ile Leu Asp Tyr
        275 catagtttca ttttcatttt tttagttaca aattttaat tgttctgatt tggattgaat        1043 attggtatat tgttaggggt tgatacaaaa aaaaaaaaaa aa                          1085

<210> SEQ ID NO 106
<211> LENGTH: 278
<212> TYPE: PRT
<213> ORGANISM: Arabidopsis thaliana

<400> SEQUENCE: 106

Met Ala Leu Glu Ala Met Asn Thr Pro Thr Ser Ser Phe Thr Arg Ile
  1               5                  10                  15

Glu Thr Lys Glu Asp Leu Met Asn Asp Ala Val Phe Ile Glu Pro Trp
            20                  25                  30

Leu Lys Arg Lys Arg Ser Lys Arg Gln Arg Ser His Ser Pro Ser Ser
        35                  40                  45

Ser Ser Ser Ser Pro Pro Arg Ser Arg Pro Lys Ser Gln Asn Gln Asp
    50                  55                  60

Leu Thr Glu Glu Glu Tyr Leu Ala Leu Cys Leu Leu Met Leu Ala Lys
 65                  70                  75                  80

Asp Gln Pro Ser Gln Thr Arg Phe His Gln Gln Ser Gln Ser Leu Thr
                85                  90                  95

Pro Pro Pro Glu Ser Lys Asn Leu Pro Tyr Lys Cys Asn Val Cys Glu
            100                 105                 110

Lys Ala Phe Pro Ser Tyr Gln Ala Leu Gly Gly His Lys Ala Ser His
        115                 120                 125

Arg Ile Lys Pro Pro Thr Val Ile Ser Thr Thr Ala Asp Asp Ser Thr
    130                 135                 140

Ala Pro Thr Ile Ser Ile Val Ala Gly Glu Lys His Pro Ile Ala Ala
145                 150                 155                 160

Ser Gly Lys Ile His Glu Cys Ser Ile Cys His Lys Val Phe Pro Thr
                165                 170                 175
```

```
Gly Gln Ala Leu Gly Gly His Lys Arg Cys His Tyr Glu Gly Asn Leu
                180                 185                 190

Gly Gly Gly Gly Gly Gly Ser Lys Ser Ile Ser His Ser Gly Ser
            195                 200                 205

Val Ser Ser Thr Val Ser Glu Glu Arg Ser His Arg Gly Phe Ile Asp
        210                 215                 220

Leu Asn Leu Pro Ala Leu Pro Glu Leu Ser Leu His His Asn Pro Ile
225                 230                 235                 240

Val Asp Glu Glu Ile Leu Ser Pro Leu Thr Gly Lys Lys Thr Ala Phe
                245                 250                 255

Val Asp Arg Ser Arg Pro Ser His Gln Glu Arg Arg Phe Ile Phe Lys
            260                 265                 270

Asn Leu Ile Leu Asp Tyr
            275

<210> SEQ ID NO 107
<211> LENGTH: 1783
<212> TYPE: DNA
<213> ORGANISM: Arabidopsis thaliana
<220> FEATURE:
<221> NAME/KEY: CDS
<222> LOCATION: (162)..(1529)

<400> SEQUENCE: 107
attgttaaaa gctctcacac aaccaccgtt ctccgtcacg gtggcgcttt attctctcat    60
cggagcgcct caccggtggc agacggtgtc gttgttcctc tcctaaaacc tccatcaatc   120
accatctctt tacacagagc tctaaccaaa atcttcgaga g atg ggg cag agt atg   176
                                            Met Gly Gln Ser Met
                                              1               5 agc tgt gga agt cga ccg gag cac gga ata ttc gcc tct gta cag tgc    224
Ser Cys Gly Ser Arg Pro Glu His Gly Ile Phe Ala Ser Val Gln Cys
             10                  15                  20 ggc gat atc atc act atc cgt cgt gtg atg gcg acg gag cct agt ctg    272
Gly Asp Ile Ile Thr Ile Arg Arg Val Met Ala Thr Glu Pro Ser Leu
         25                  30                  35 ttg aat caa act act cct tat gat cgt cac tct gtt ctt cat gtc gct    320
Leu Asn Gln Thr Thr Pro Tyr Asp Arg His Ser Val Leu His Val Ala
     40                  45                  50 gct gct aat ggt cag atc gag att ttg tca ttg ctt ttg gaa cga ttt    368
Ala Ala Asn Gly Gln Ile Glu Ile Leu Ser Leu Leu Leu Glu Arg Phe
 55                  60                  65 acg aat cca gat ttg ttg aat cgt cac aag cag act ccg tta atg ttg    416
Thr Asn Pro Asp Leu Leu Asn Arg His Lys Gln Thr Pro Leu Met Leu
 70                  75                  80                  85 gct gcg atg tat gga aga atc tct tgt gtg aag aag cta gct gaa gtt    464
Ala Ala Met Tyr Gly Arg Ile Ser Cys Val Lys Lys Leu Ala Glu Val
                 90                  95                 100 gga gct aat att ttg atg ttt gat tct gtg aat cga aga aca tgt ttg    512
Gly Ala Asn Ile Leu Met Phe Asp Ser Val Asn Arg Arg Thr Cys Leu
            105                 110                 115 cat tac gct gct tat tat gga cat gct aat tgt gtt caa gct att ctc    560
His Tyr Ala Ala Tyr Tyr Gly His Ala Asn Cys Val Gln Ala Ile Leu
        120                 125                 130 tct gct gct caa tca agt cct gtt gct gtc cat tgg gga tat gcg aga    608
Ser Ala Ala Gln Ser Ser Pro Val Ala Val His Trp Gly Tyr Ala Arg
    135                 140                 145 ttt gtg aac ata aga gat gat aaa gga gcg act ccg ttg cat tta gct    656
Phe Val Asn Ile Arg Asp Asp Lys Gly Ala Thr Pro Leu His Leu Ala
150                 155                 160                 165
```

```
gct cga cag aga cga cct gaa tgt gtg aat gtt ttg ttg gat agt ggt      704
Ala Arg Gln Arg Arg Pro Glu Cys Val Asn Val Leu Leu Asp Ser Gly
            170                 175                 180 tct ctt gtt tgt gca tct act agt gta tat ggt tct cca gga agc aca      752
Ser Leu Val Cys Ala Ser Thr Ser Val Tyr Gly Ser Pro Gly Ser Thr
            185                 190                 195 cct ctt cat tta gca gct aga agt gga tct ata gat tgt gtc aga aag      800
Pro Leu His Leu Ala Ala Arg Ser Gly Ser Ile Asp Cys Val Arg Lys
            200                 205                 210 ttg ctt gct tgg ggt gct gat cgt ctt caa cga gac gct tct ggg aga      848
Leu Leu Ala Trp Gly Ala Asp Arg Leu Gln Arg Asp Ala Ser Gly Arg
    215                 220                 225 ata cct tat gtg gtt gcg atg aag cat aag cat gga gca tgt gga gcc      896
Ile Pro Tyr Val Val Ala Met Lys His Lys His Gly Ala Cys Gly Ala
230                 235                 240                 245 tta ctt aat ccg tcc tct gca gag cca ctt gtt tgg cca tca cca tta      944
Leu Leu Asn Pro Ser Ser Ala Glu Pro Leu Val Trp Pro Ser Pro Leu
                250                 255                 260 aag ttc atc agt gag ctt aat gac gag gcg aaa ctt ctc tta gag cag      992
Lys Phe Ile Ser Glu Leu Asn Asp Glu Ala Lys Leu Leu Leu Glu Gln
            265                 270                 275 gct tta atg gag gct aac agg gag aga gag aaa acc atc ctc aaa gga     1040
Ala Leu Met Glu Ala Asn Arg Glu Arg Glu Lys Thr Ile Leu Lys Gly
            280                 285                 290 aca gct tat tcc tta cca tca ccc tct ttc tct gac acg gat gat aac     1088
Thr Ala Tyr Ser Leu Pro Ser Pro Ser Phe Ser Asp Thr Asp Asp Asn
            295                 300                 305 atg tcc gag gtg agt gat acg gaa ctg tgc tgc att tgc ttt gag caa     1136
Met Ser Glu Val Ser Asp Thr Glu Leu Cys Cys Ile Cys Phe Glu Gln
310                 315                 320                 325 gta tgt aca att gaa gtt aaa gac tgt ggt cac caa atg tgt gca caa     1184
Val Cys Thr Ile Glu Val Lys Asp Cys Gly His Gln Met Cys Ala Gln
                330                 335                 340 tgc aca ctt gca ctg tgc tgt cac aac aaa cca aac cca acg acc tca     1232
Cys Thr Leu Ala Leu Cys Cys His Asn Lys Pro Asn Pro Thr Thr Ser
            345                 350                 355 acc gtg act cca ccg gtc tgt ccg ttc tgt aga agc acc att gca tgt     1280
Thr Val Thr Pro Pro Val Cys Pro Phe Cys Arg Ser Thr Ile Ala Cys
            360                 365                 370 tta gtc gtc gcc cag aac aac aac aac aac aac gaa aag agc aaa agc     1328
Leu Val Val Ala Gln Asn Asn Asn Asn Asn Asn Glu Lys Ser Lys Ser
            375                 380                 385 cta gat gat gtt gtt gtt gtt gat cgt gag gca ggt gat gtt agc tcc     1376
Leu Asp Asp Val Val Val Val Asp Arg Glu Ala Gly Asp Val Ser Ser
390                 395                 400                 405 tcc aaa ttc aga aaa cat aga aga tca ata aac ctt ggc gaa gaa agc     1424
Ser Lys Phe Arg Lys His Arg Arg Ser Ile Asn Leu Gly Glu Glu Ser
            410                 415                 420 agc agc ttc atg gga cta tca act att gga tca ttc ggt agg ata acc     1472
Ser Ser Phe Met Gly Leu Ser Thr Ile Gly Ser Phe Gly Arg Ile Thr
            425                 430                 435 ggc cgt ggc tcg gga agg atc gca gcc gaa aac gag ctg atg gac aaa     1520
Gly Arg Gly Ser Gly Arg Ile Ala Ala Glu Asn Glu Leu Met Asp Lys
            440                 445                 450 cca ata ttg tgagggatcg attccgtttt aagggacatt ttggggcatg            1569
Pro Ile Leu
    455 ggggagcaat aaaaaagatg aggggatgaa attgtgagaa tgtataaaat atagatgaat   1629
```

-continued

```
ttatgttaga tcttttgttg aagggaggaa gattgaaata aggaaaaaga tgtggggagg    1689
tgtgtaatgc aaggatttgt tgtttctttg attaagtttg gccaaaattg tttgttgttg    1749
ttattatttg gttacttgat atgaaaggga aacc                                1783
```

<210> SEQ ID NO 108
<211> LENGTH: 456
<212> TYPE: PRT
<213> ORGANISM: Arabidopsis thaliana

<400> SEQUENCE: 108

```
Met Gly Gln Ser Met Ser Cys Gly Ser Arg Pro Glu His Gly Ile Phe
  1               5                  10                  15

Ala Ser Val Gln Cys Gly Asp Ile Ile Thr Ile Arg Arg Val Met Ala
                 20                  25                  30

Thr Glu Pro Ser Leu Leu Asn Gln Thr Thr Pro Tyr Asp Arg His Ser
             35                  40                  45

Val Leu His Val Ala Ala Asn Gly Gln Ile Glu Ile Leu Ser Leu
         50                  55                  60

Leu Leu Glu Arg Phe Thr Asn Pro Asp Leu Leu Asn Arg His Lys Gln
 65                  70                  75                  80

Thr Pro Leu Met Leu Ala Ala Met Tyr Gly Arg Ile Ser Cys Val Lys
                 85                  90                  95

Lys Leu Ala Glu Val Gly Ala Asn Ile Leu Met Phe Asp Ser Val Asn
            100                 105                 110

Arg Arg Thr Cys Leu His Tyr Ala Ala Tyr Gly His Ala Asn Cys
            115                 120                 125

Val Gln Ala Ile Leu Ser Ala Ala Gln Ser Ser Pro Val Ala Val His
        130                 135                 140

Trp Gly Tyr Ala Arg Phe Val Asn Ile Arg Asp Asp Lys Gly Ala Thr
145                 150                 155                 160

Pro Leu His Leu Ala Ala Arg Gln Arg Arg Pro Glu Cys Val Asn Val
                165                 170                 175

Leu Leu Asp Ser Gly Ser Leu Val Cys Ala Ser Thr Ser Val Tyr Gly
            180                 185                 190

Ser Pro Gly Ser Thr Pro Leu His Leu Ala Ala Arg Ser Gly Ser Ile
        195                 200                 205

Asp Cys Val Arg Lys Leu Leu Ala Trp Gly Ala Asp Arg Leu Gln Arg
    210                 215                 220

Asp Ala Ser Gly Arg Ile Pro Tyr Val Val Ala Met Lys His Lys His
225                 230                 235                 240

Gly Ala Cys Gly Ala Leu Leu Asn Pro Ser Ser Ala Glu Pro Leu Val
                245                 250                 255

Trp Pro Ser Pro Leu Lys Phe Ile Ser Glu Leu Asn Asp Glu Ala Lys
            260                 265                 270

Leu Leu Leu Glu Gln Ala Leu Met Glu Ala Asn Arg Glu Arg Glu Lys
        275                 280                 285

Thr Ile Leu Lys Gly Thr Ala Tyr Ser Leu Pro Ser Pro Ser Phe Ser
    290                 295                 300

Asp Thr Asp Asp Asn Met Ser Glu Val Ser Asp Thr Glu Leu Cys Cys
305                 310                 315                 320

Ile Cys Phe Glu Gln Val Cys Thr Ile Glu Val Lys Asp Cys Gly His
                325                 330                 335

Gln Met Cys Ala Gln Cys Thr Leu Ala Leu Cys Cys His Asn Lys Pro
            340                 345                 350
```

```
Asn Pro Thr Thr Ser Thr Val Thr Pro Pro Val Cys Pro Phe Cys Arg
        355                 360                 365

Ser Thr Ile Ala Cys Leu Val Val Ala Gln Asn Asn Asn Asn Asn Asn
        370                 375                 380

Glu Lys Ser Lys Ser Leu Asp Asp Val Val Val Asp Arg Glu Ala
385                 390                 395                 400

Gly Asp Val Ser Ser Lys Phe Arg Lys His Arg Arg Ser Ile Asn
                405                 410                 415

Leu Gly Glu Glu Ser Ser Ser Phe Met Gly Leu Ser Thr Ile Gly Ser
            420                 425                 430

Phe Gly Arg Ile Thr Gly Arg Gly Ser Gly Arg Ile Ala Ala Glu Asn
        435                 440                 445

Glu Leu Met Asp Lys Pro Ile Leu
        450                 455

<210> SEQ ID NO 109
<211> LENGTH: 714
<212> TYPE: DNA
<213> ORGANISM: Arabidopsis thaliana
<220> FEATURE:
<221> NAME/KEY: CDS
<222> LOCATION: (1)..(711)

<400> SEQUENCE: 109
```

| | | | | | | | | | | | | | | | | |
|---|---|---|---|---|---|---|---|---|---|---|---|---|---|---|---|---|
| atg aag ata caa tgt gat gtg tgt gag aaa gct ccg gcc acg ctt ata | | | | | | | | | | | | | | | | 48 |
| Met Lys Ile Gln Cys Asp Val Cys Glu Lys Ala Pro Ala Thr Leu Ile | | | | | | | | | | | | | | | | |
| 1 | | | | 5 | | | | | 10 | | | | | 15 | | |
| tgt tgt gct gat gaa gct gct ctc tgc gct aaa tgt gac gtt gag gtt | | | | | | | | | | | | | | | | 96 |
| Cys Cys Ala Asp Glu Ala Ala Leu Cys Ala Lys Cys Asp Val Glu Val | | | | | | | | | | | | | | | | |
| | | | | 20 | | | | | 25 | | | | | 30 | | |
| cat gct gct aat aaa ctc gct agc aaa cac caa cgc ctt ttt ctt gac | | | | | | | | | | | | | | | | 144 |
| His Ala Ala Asn Lys Leu Ala Ser Lys His Gln Arg Leu Phe Leu Asp | | | | | | | | | | | | | | | | |
| | | | 35 | | | | | 40 | | | | | 45 | | | |
| tct ctc tca act aaa ttc cct ccc tgc gac atc tgc ctt gag aag gca | | | | | | | | | | | | | | | | 192 |
| Ser Leu Ser Thr Lys Phe Pro Pro Cys Asp Ile Cys Leu Glu Lys Ala | | | | | | | | | | | | | | | | |
| | | 50 | | | | | 55 | | | | | 60 | | | | |
| gct ttc ata ttc tgt gta gag gat agg gct ctg ctc tgc aga gat tgc | | | | | | | | | | | | | | | | 240 |
| Ala Phe Ile Phe Cys Val Glu Asp Arg Ala Leu Leu Cys Arg Asp Cys | | | | | | | | | | | | | | | | |
| 65 | | | | | 70 | | | | | 75 | | | | | 80 | |
| gat gag gcg acc cat gcg cca aat act cgc tct gct aat cac cag agg | | | | | | | | | | | | | | | | 288 |
| Asp Glu Ala Thr His Ala Pro Asn Thr Arg Ser Ala Asn His Gln Arg | | | | | | | | | | | | | | | | |
| | | | | | 85 | | | | | 90 | | | | | 95 | |
| ttc tta gcc act gga atc cga gtt gct ctt agt tcc act agt tgc aat | | | | | | | | | | | | | | | | 336 |
| Phe Leu Ala Thr Gly Ile Arg Val Ala Leu Ser Ser Thr Ser Cys Asn | | | | | | | | | | | | | | | | |
| | | | | 100 | | | | | 105 | | | | | 110 | | |
| caa gaa gtg gaa aag aat cac ttt gac cca tct aat cag cag agt ctc | | | | | | | | | | | | | | | | 384 |
| Gln Glu Val Glu Lys Asn His Phe Asp Pro Ser Asn Gln Gln Ser Leu | | | | | | | | | | | | | | | | |
| | | | 115 | | | | | 120 | | | | | 125 | | | |
| tct aaa ccg cca act cag caa ccc gct gct cca tct cct ttg tgg gct | | | | | | | | | | | | | | | | 432 |
| Ser Lys Pro Pro Thr Gln Gln Pro Ala Ala Pro Ser Pro Leu Trp Ala | | | | | | | | | | | | | | | | |
| | | 130 | | | | | 135 | | | | | 140 | | | | |
| acc gat gaa ttc ttc agc tac tct gat ctt gac tgc agt aat aag aaa | | | | | | | | | | | | | | | | 480 |
| Thr Asp Glu Phe Phe Ser Tyr Ser Asp Leu Asp Cys Ser Asn Lys Lys | | | | | | | | | | | | | | | | |
| 145 | | | | | 150 | | | | | 155 | | | | | 160 | |
| gag caa ctc gat ctc ggg gag ctg gat tgg ctt gca gag atg ggt ctg | | | | | | | | | | | | | | | | 528 |
| Glu Gln Leu Asp Leu Gly Glu Leu Asp Trp Leu Ala Glu Met Gly Leu | | | | | | | | | | | | | | | | |
| | | | | | 165 | | | | | 170 | | | | | 175 | |
| ttt ggt gac cag cct gat caa gag gct cta ccg gta gcc gaa gtt ccc | | | | | | | | | | | | | | | | 576 |
| Phe Gly Asp Gln Pro Asp Gln Glu Ala Leu Pro Val Ala Glu Val Pro | | | | | | | | | | | | | | | | |

```
                     180             185             190
gag ctt tcc ttt tca cat ttg gct cat gct cat tcc tac aac aga cct     624
Glu Leu Ser Phe Ser His Leu Ala His Ala His Ser Tyr Asn Arg Pro
        195                 200                 205 atg aag tcc aat gta ccc aac aag aag cag agg ctt gag tac cgg tat     672
Met Lys Ser Asn Val Pro Asn Lys Lys Gln Arg Leu Glu Tyr Arg Tyr
    210                 215                 220 gat gat gaa gaa gag cac ttc cta gtc ccc gac cta ggc taa             714
Asp Asp Glu Glu Glu His Phe Leu Val Pro Asp Leu Gly
225                 230                 235
```

<210> SEQ ID NO 110
<211> LENGTH: 237
<212> TYPE: PRT
<213> ORGANISM: Arabidopsis thaliana

<400> SEQUENCE: 110

```
Met Lys Ile Gln Cys Asp Val Cys Glu Lys Ala Pro Ala Thr Leu Ile
 1               5                  10                  15

Cys Cys Ala Asp Glu Ala Ala Leu Cys Ala Lys Cys Asp Val Glu Val
                20                  25                  30

His Ala Ala Asn Lys Leu Ala Ser Lys His Gln Arg Leu Phe Leu Asp
            35                  40                  45

Ser Leu Ser Thr Lys Phe Pro Pro Cys Asp Ile Cys Leu Glu Lys Ala
    50                  55                  60

Ala Phe Ile Phe Cys Val Glu Asp Arg Ala Leu Leu Cys Arg Asp Cys
65                  70                  75                  80

Asp Glu Ala Thr His Ala Pro Asn Thr Arg Ser Ala Asn His Gln Arg
                85                  90                  95

Phe Leu Ala Thr Gly Ile Arg Val Ala Leu Ser Ser Thr Ser Cys Asn
            100                 105                 110

Gln Glu Val Glu Lys Asn His Phe Asp Pro Ser Asn Gln Gln Ser Leu
    115                 120                 125

Ser Lys Pro Pro Thr Gln Gln Pro Ala Ala Pro Ser Pro Leu Trp Ala
130                 135                 140

Thr Asp Glu Phe Phe Ser Tyr Ser Asp Leu Asp Cys Ser Asn Lys Lys
145                 150                 155                 160

Glu Gln Leu Asp Leu Gly Glu Leu Asp Trp Leu Ala Glu Met Gly Leu
                165                 170                 175

Phe Gly Asp Gln Pro Asp Gln Glu Ala Leu Pro Val Ala Glu Val Pro
            180                 185                 190

Glu Leu Ser Phe Ser His Leu Ala His Ala His Ser Tyr Asn Arg Pro
    195                 200                 205

Met Lys Ser Asn Val Pro Asn Lys Lys Gln Arg Leu Glu Tyr Arg Tyr
210                 215                 220

Asp Asp Glu Glu Glu His Phe Leu Val Pro Asp Leu Gly
225                 230                 235
```

<210> SEQ ID NO 111
<211> LENGTH: 829
<212> TYPE: DNA
<213> ORGANISM: Arabidopsis thaliana
<220> FEATURE:
<221> NAME/KEY: CDS
<222> LOCATION: (99)..(584)

<400> SEQUENCE: 111
atcacaacta ctatcacacc aaactcaaaa aacacaaacc acaagaggat catttcattt    60

```
tttattgttt cgttttaatc atcatcatca gaagaaaa atg gtt gcg ata tcg gag        116
                                         Met Val Ala Ile Ser Glu
                                           1               5 atc aag tcg acg gtg gat gtc acg gcg gcg aat tgt ttg atg ctt tta         164
Ile Lys Ser Thr Val Asp Val Thr Ala Ala Asn Cys Leu Met Leu Leu
         10                  15                  20 tct aga gtt gga caa gaa aac gtt gac ggt ggc gat caa aaa cgc gtt         212
Ser Arg Val Gly Gln Glu Asn Val Asp Gly Gly Asp Gln Lys Arg Val
     25                  30                  35 ttc aca tgt aaa acg tgt ttg aag cag ttt cat tcg ttc caa gcc tta         260
Phe Thr Cys Lys Thr Cys Leu Lys Gln Phe His Ser Phe Gln Ala Leu
 40                  45                  50 gga ggt cac cgt gcg agt cac aag aag cct aac aac gac gct ttg tcg         308
Gly Gly His Arg Ala Ser His Lys Lys Pro Asn Asn Asp Ala Leu Ser
 55                  60                  65                  70 tct gga ttg atg aag aag gtg aaa acg tcg tcg cat cct tgt ccc ata         356
Ser Gly Leu Met Lys Lys Val Lys Thr Ser Ser His Pro Cys Pro Ile
         75                  80                  85 tgt gga gtg gag ttt ccg atg gga caa gct ttg gga gga cac atg agg         404
Cys Gly Val Glu Phe Pro Met Gly Gln Ala Leu Gly Gly His Met Arg
     90                  95                 100 aga cac agg aac gag agt ggg gct gct ggt ggc gcg ttg gtt aca cgc         452
Arg His Arg Asn Glu Ser Gly Ala Ala Gly Gly Ala Leu Val Thr Arg
        105                 110                 115 gct ttg ttg ccg gag ccc acg gtg act acg ttg aag aaa tct agc agt         500
Ala Leu Leu Pro Glu Pro Thr Val Thr Thr Leu Lys Lys Ser Ser Ser
    120                 125                 130 ggg aag aga gtg gct tgt ttg gat ctg agt cta ggg atg gtg gac aat         548
Gly Lys Arg Val Ala Cys Leu Asp Leu Ser Leu Gly Met Val Asp Asn
135                 140                 145                 150 ttg aat ctc aag ttg gag ctt gga aga aca gtt tat tgattttatt             594
Leu Asn Leu Lys Leu Glu Leu Gly Arg Thr Val Tyr
                155                 160 tattttcctt aaattttctg aatatatttg tttctctcat tctttgaatt tttcttaata       654
ttctagatta tacatacatc cgcagattta ggaaactttc atagagtgta atcttttctt       714
tctgtaaaaa tatattttac ttgtagcatt ggagatttgt tatgagatta tcttacttag       774
catttagtga ataatctatt agcctatttt gccgacgcga aaaaaaaaaa aaaaa           829

<210> SEQ ID NO 112
<211> LENGTH: 162
<212> TYPE: PRT
<213> ORGANISM: Arabidopsis thaliana

<400> SEQUENCE: 112

Met Val Ala Ile Ser Glu Ile Lys Ser Thr Val Asp Val Thr Ala Ala
  1               5                  10                  15

Asn Cys Leu Met Leu Leu Ser Arg Val Gly Gln Glu Asn Val Asp Gly
             20                  25                  30

Gly Asp Gln Lys Arg Val Phe Thr Cys Lys Thr Cys Leu Lys Gln Phe
         35                  40                  45

His Ser Phe Gln Ala Leu Gly Gly His Arg Ala Ser His Lys Lys Pro
     50                  55                  60

Asn Asn Asp Ala Leu Ser Ser Gly Leu Met Lys Lys Val Lys Thr Ser
 65                  70                  75                  80

Ser His Pro Cys Pro Ile Cys Gly Val Glu Phe Pro Met Gly Gln Ala
             85                  90                  95
```

```
Leu Gly Gly His Met Arg Arg His Arg Asn Glu Ser Gly Ala Ala Gly
            100                 105                 110

Gly Ala Leu Val Thr Arg Ala Leu Leu Pro Glu Pro Thr Val Thr Thr
        115                 120                 125

Leu Lys Lys Ser Ser Gly Lys Arg Val Ala Cys Leu Asp Leu Ser
    130                 135                 140

Leu Gly Met Val Asp Asn Leu Asn Leu Lys Leu Glu Leu Gly Arg Thr
145                 150                 155                 160

Val Tyr

<210> SEQ ID NO 113
<211> LENGTH: 881
<212> TYPE: DNA
<213> ORGANISM: Arabidopsis thaliana
<220> FEATURE:
<221> NAME/KEY: CDS
<222> LOCATION: (89)..(769)

<400> SEQUENCE: 113
agcaattaaa caatttcttc actgcaattc acaagcaacc ttcaaactaa aactcgagag      60
acaagaaatc ctcagaatct ttaactta atg gcg ctc gag gct ctt aca tca       112
                                Met Ala Leu Glu Ala Leu Thr Ser
                                  1               5 cca aga tta gct tct ccg att cct cct ttg ttc gaa gat tct tca gtc      160
Pro Arg Leu Ala Ser Pro Ile Pro Pro Leu Phe Glu Asp Ser Ser Val
     10                  15                  20 ttc cat gga gtc gag cac tgg aca aag ggt aag cga tct aag aga tca      208
Phe His Gly Val Glu His Trp Thr Lys Gly Lys Arg Ser Lys Arg Ser
 25                  30                  35                  40 aga tcc gat ttc cac cac caa aac ctc act gag gaa gag tat cta gct      256
Arg Ser Asp Phe His His Gln Asn Leu Thr Glu Glu Glu Tyr Leu Ala
                 45                  50                  55 ttt tgc ctc atg ctt ctc gct cgc gac aac cgt cag cct cct cct cct      304
Phe Cys Leu Met Leu Leu Ala Arg Asp Asn Arg Gln Pro Pro Pro Pro
             60                  65                  70 ccg gcg gtg gag aag ttg agc tac aag tgt agc gtc tgc gac aag acg      352
Pro Ala Val Glu Lys Leu Ser Tyr Lys Cys Ser Val Cys Asp Lys Thr
         75                  80                  85 ttc tct tct tac caa gct ctc ggt ggt cac aag gca agc cac cgt aag      400
Phe Ser Ser Tyr Gln Ala Leu Gly Gly His Lys Ala Ser His Arg Lys
     90                  95                 100 aac tta tca cag act ctc tcc ggc gga gga gat gat cat tca acc tcg      448
Asn Leu Ser Gln Thr Leu Ser Gly Gly Gly Asp Asp His Ser Thr Ser
105                 110                 115                 120 tcg gcg aca acc aca tcc gcc gtg act act gga agt ggg aaa tca cac      496
Ser Ala Thr Thr Thr Ser Ala Val Thr Thr Gly Ser Gly Lys Ser His
                125                 130                 135 gtt tgc acc atc tgt aac aag tct ttt cct tcc ggt caa gct ctc ggc      544
Val Cys Thr Ile Cys Asn Lys Ser Phe Pro Ser Gly Gln Ala Leu Gly
            140                 145                 150 gga cac aag cgg tgc cac tac gaa gga aac aac aac atc aac act agt      592
Gly His Lys Arg Cys His Tyr Glu Gly Asn Asn Asn Ile Asn Thr Ser
        155                 160                 165 agc gtg tcc aac tcc gaa ggt gcg ggg tcc act agc cac gtt agc agt      640
Ser Val Ser Asn Ser Glu Gly Ala Gly Ser Thr Ser His Val Ser Ser
    170                 175                 180 agc cac cgt ggg ttt gac ctc aac atc cct ccg atc cct gaa ttc tcg      688
Ser His Arg Gly Phe Asp Leu Asn Ile Pro Pro Ile Pro Glu Phe Ser
185                 190                 195                 200
```

```
atg gtc aac gga gac gac gaa gtc atg agc cct atg ccg gcg aag aag      736
Met Val Asn Gly Asp Asp Glu Val Met Ser Pro Met Pro Ala Lys Lys
            205                 210                 215 cct cgg ttt gac ttt ccg gtc aaa ctt caa ctt taaggaaatt tacttagacg    789
Pro Arg Phe Asp Phe Pro Val Lys Leu Gln Leu
        220                 225 ataagatttc gtttgtatac tgttgagagt tgtgtaggaa tttgttgact gtacatacca   849
aattggactt tgactcaaaa aaaaaaaaaa aa                                  881

<210> SEQ ID NO 114
<211> LENGTH: 227
<212> TYPE: PRT
<213> ORGANISM: Arabidopsis thaliana

<400> SEQUENCE: 114

Met Ala Leu Glu Ala Leu Thr Ser Pro Arg Leu Ala Ser Pro Ile Pro
1               5                   10                  15

Pro Leu Phe Glu Asp Ser Ser Val Phe His Gly Val Glu His Trp Thr
            20                  25                  30

Lys Gly Lys Arg Ser Lys Arg Ser Arg Ser Asp Phe His His Gln Asn
        35                  40                  45

Leu Thr Glu Glu Glu Tyr Leu Ala Phe Cys Leu Met Leu Leu Ala Arg
    50                  55                  60

Asp Asn Arg Gln Pro Pro Pro Pro Ala Val Glu Lys Leu Ser Tyr
65                  70                  75                  80

Lys Cys Ser Val Cys Asp Lys Thr Phe Ser Ser Tyr Gln Ala Leu Gly
                85                  90                  95

Gly His Lys Ala Ser His Arg Lys Asn Leu Ser Gln Thr Leu Ser Gly
            100                 105                 110

Gly Gly Asp Asp His Ser Thr Ser Ser Ala Thr Thr Ser Ala Val
        115                 120                 125

Thr Thr Gly Ser Gly Lys Ser His Val Cys Thr Ile Cys Asn Lys Ser
130                 135                 140

Phe Pro Ser Gly Gln Ala Leu Gly Gly His Lys Arg Cys His Tyr Glu
145                 150                 155                 160

Gly Asn Asn Asn Ile Asn Thr Ser Ser Val Ser Asn Ser Glu Gly Ala
                165                 170                 175

Gly Ser Thr Ser His Val Ser Ser Ser His Arg Gly Phe Asp Leu Asn
            180                 185                 190

Ile Pro Pro Ile Pro Glu Phe Ser Met Val Asn Gly Asp Asp Glu Val
        195                 200                 205

Met Ser Pro Met Pro Ala Lys Lys Pro Arg Phe Asp Phe Pro Val Lys
    210                 215                 220

Leu Gln Leu
225

<210> SEQ ID NO 115
<211> LENGTH: 1107
<212> TYPE: DNA
<213> ORGANISM: Arabidopsis thaliana
<220> FEATURE:
<221> NAME/KEY: CDS
<222> LOCATION: (139)..(957)

<400> SEQUENCE: 115
aactcggtcc gagtcgactc ggtccgacaa gcgattttcg tgactccgtc gtcaccacgc     60
ctatgttaag tgagtaaatc cgactcttct ccgtagagat ttctcctact ttcaggctct    120
```

```
cttgtgaatt tggaagac atg agc ttt gtt ttc cgg gga agt aga gga gat       171
                    Met Ser Phe Val Phe Arg Gly Ser Arg Gly Asp
                     1               5                  10 tta gaa agc gga ttc tcg ggt ggt ttt cta ccc gaa aga cga gct atg       219
Leu Glu Ser Gly Phe Ser Gly Gly Phe Leu Pro Glu Arg Arg Ala Met
         15                  20                  25 cgt gtt cat gga gct cga cca gtt aat tct aat tcc ctc gct ttt ctg       267
Arg Val His Gly Ala Arg Pro Val Asn Ser Asn Ser Leu Ala Phe Leu
             30                  35                  40 gtt aca gtt ctt ttg ctg ttt atg att ctc aat tcg cat cag atg cct       315
Val Thr Val Leu Leu Leu Phe Met Ile Leu Asn Ser His Gln Met Pro
         45                  50                  55 cct aat ttc ctg ctg tgg ctt gtg ctt ggg gtg ttt ttg atg gca acg       363
Pro Asn Phe Leu Leu Trp Leu Val Leu Gly Val Phe Leu Met Ala Thr
 60              65                  70                  75 acg ctt agg atg tat gct act tgc caa caa ctt caa gct cat gct cag       411
Thr Leu Arg Met Tyr Ala Thr Cys Gln Gln Leu Gln Ala His Ala Gln
                 80                  85                  90 gct cag gct gca gca gca agt ggc ctc ttt agc cat act gag ctg agg       459
Ala Gln Ala Ala Ala Ala Ser Gly Leu Phe Ser His Thr Glu Leu Arg
             95                  100                 105 ttg cat gtg cct cct tcc att gct ctt gct acg aga ggg cgt ctt cag       507
Leu His Val Pro Pro Ser Ile Ala Leu Ala Thr Arg Gly Arg Leu Gln
         110                 115                 120 gga ctt agg ctc cag ctg gct ctt ctt gat cgg gaa ttt gat gac tta       555
Gly Leu Arg Leu Gln Leu Ala Leu Leu Asp Arg Glu Phe Asp Asp Leu
     125                 130                 135 gat tat gaa act tta aga gca ctt gat tct gat aat gtt tcc aca act       603
Asp Tyr Glu Thr Leu Arg Ala Leu Asp Ser Asp Asn Val Ser Thr Thr
140             145                 150                 155 tct atg agc gag gaa gag ata aat gca ctt cca gtt cac aag tac aag       651
Ser Met Ser Glu Glu Glu Ile Asn Ala Leu Pro Val His Lys Tyr Lys
                 160                 165                 170 gtg ttg gat cct gaa aat ggt tgc tct ttg gca aag caa gcg tca acc       699
Val Leu Asp Pro Glu Asn Gly Cys Ser Leu Ala Lys Gln Ala Ser Thr
             175                 180                 185 tca tcc tca gct gag aag atg cta gat tct gcc aat gaa agt aaa aaa       747
Ser Ser Ser Ala Glu Lys Met Leu Asp Ser Ala Asn Glu Ser Lys Lys
         190                 195                 200 gga aca gaa gat gag ctc aca tgt agt gtt tgc cta gaa caa gtt acc       795
Gly Thr Glu Asp Glu Leu Thr Cys Ser Val Cys Leu Glu Gln Val Thr
     205                 210                 215 gta ggg gaa atc gtt cgc acc tta cct tgt ttg cat cag ttt cat gca       843
Val Gly Glu Ile Val Arg Thr Leu Pro Cys Leu His Gln Phe His Ala
220             225                 230                 235 gga tgt atc gat cca tgg ttg aga cag caa gga aca tgt cct gtc tgt       891
Gly Cys Ile Asp Pro Trp Leu Arg Gln Gln Gly Thr Cys Pro Val Cys
                 240                 245                 250 aaa ttt aga gct cat tca gga tgg caa gaa caa gat gag att gat gat       939
Lys Phe Arg Ala His Ser Gly Trp Gln Glu Gln Asp Glu Ile Asp Asp
             255                 260                 265 gat gct tcc gac atg gtt tgaaaagttt ggtttcgaac acttgtttat             987
Asp Ala Ser Asp Met Val
         270 gttattaatg tgcgtgcgaa ttaaacccca aacaaatcat gtaatggtca ataactcaat   1047 atgatgtaac tgatgactct cccttttcca aagtttgatt tagattcatc atgaaaaagt   1107

<210> SEQ ID NO 116
```

<211> LENGTH: 273
<212> TYPE: PRT
<213> ORGANISM: Arabidopsis thaliana

<400> SEQUENCE: 116

Met Ser Phe Val Phe Arg Gly Ser Arg Gly Asp Leu Glu Ser Gly Phe
1               5                   10                  15

Ser Gly Gly Phe Leu Pro Glu Arg Arg Ala Met Arg Val His Gly Ala
            20                  25                  30

Arg Pro Val Asn Ser Asn Ser Leu Ala Phe Leu Val Thr Val Leu Leu
        35                  40                  45

Leu Phe Met Ile Leu Asn Ser His Gln Met Pro Pro Asn Phe Leu Leu
    50                  55                  60

Trp Leu Val Leu Gly Val Phe Leu Met Ala Thr Thr Leu Arg Met Tyr
65                  70                  75                  80

Ala Thr Cys Gln Gln Leu Gln Ala His Ala Gln Ala Gln Ala Ala Ala
                85                  90                  95

Ala Ser Gly Leu Phe Ser His Thr Glu Leu Arg Leu His Val Pro Pro
            100                 105                 110

Ser Ile Ala Leu Ala Thr Arg Gly Arg Leu Gln Gly Leu Arg Leu Gln
        115                 120                 125

Leu Ala Leu Leu Asp Arg Glu Phe Asp Asp Leu Asp Tyr Glu Thr Leu
    130                 135                 140

Arg Ala Leu Asp Ser Asp Asn Val Ser Thr Thr Ser Met Ser Glu Glu
145                 150                 155                 160

Glu Ile Asn Ala Leu Pro Val His Lys Tyr Lys Val Leu Asp Pro Glu
                165                 170                 175

Asn Gly Cys Ser Leu Ala Lys Gln Ala Ser Thr Ser Ser Ser Ala Glu
            180                 185                 190

Lys Met Leu Asp Ser Ala Asn Glu Ser Lys Lys Gly Thr Glu Asp Glu
        195                 200                 205

Leu Thr Cys Ser Val Cys Leu Glu Gln Val Thr Val Gly Glu Ile Val
    210                 215                 220

Arg Thr Leu Pro Cys Leu His Gln Phe His Ala Gly Cys Ile Asp Pro
225                 230                 235                 240

Trp Leu Arg Gln Gln Gly Thr Cys Pro Val Cys Lys Phe Arg Ala His
                245                 250                 255

Ser Gly Trp Gln Glu Gln Asp Glu Ile Asp Asp Ala Ser Asp Met
            260                 265                 270

Val

<210> SEQ ID NO 117
<211> LENGTH: 531
<212> TYPE: DNA
<213> ORGANISM: Arabidopsis thaliana
<220> FEATURE:
<221> NAME/KEY: CDS
<222> LOCATION: (1)..(528)

<400> SEQUENCE: 117 atg gga tcg gaa caa aac gat agc aca agc ttc acg caa tcg caa gct      48
Met Gly Ser Glu Gln Asn Asp Ser Thr Ser Phe Thr Gln Ser Gln Ala
1               5                   10                  15 tca gag cca aag cta tgt gtt aaa gga tgt ggt ttc ttt gga tca cca      96
Ser Glu Pro Lys Leu Cys Val Lys Gly Cys Gly Phe Phe Gly Ser Pro
            20                  25                  30 tca aac atg gat ctc tgt tct aaa tgt tac aga ggc att tgt gct gag     144

-continued

```
                Ser Asn Met Asp Leu Cys Ser Lys Cys Tyr Arg Gly Ile Cys Ala Glu
                            35                  40                  45 gaa gct caa aca gca gtt gct aaa gct gct gtt gaa aaa tct ttc aag           192
Glu Ala Gln Thr Ala Val Ala Lys Ala Ala Val Glu Lys Ser Phe Lys
     50                  55                  60 cct tct cct cct cgt agt ctc ttc ata gca gaa cct cct gct gtt gtt           240
Pro Ser Pro Pro Arg Ser Leu Phe Ile Ala Glu Pro Pro Ala Val Val
 65                  70                  75                  80 gtg gaa ccc aaa ccc gaa aag gcg gca gtt gtt gtt tcg gcc gag               288
Val Glu Pro Lys Pro Glu Lys Ala Ala Val Val Val Ser Ala Glu
                 85                  90                  95 cca tct tcc tcg gcg gtt cct gag gcg aac gag cca tcg aga cct gca           336
Pro Ser Ser Ser Ala Val Pro Glu Ala Asn Glu Pro Ser Arg Pro Ala
                100                 105                 110 cga acc aac cgg tgt ttg tgt tgt aac aag aag gtt ggg atc atg ggg           384
Arg Thr Asn Arg Cys Leu Cys Cys Asn Lys Lys Val Gly Ile Met Gly
            115                 120                 125 ttt aag tgc aaa tgc ggg agc act ttc tgc ggc gaa cat cgg tac ccg           432
Phe Lys Cys Lys Cys Gly Ser Thr Phe Cys Gly Glu His Arg Tyr Pro
        130                 135                 140 gag act cat gat tgc agc ttt gat ttc aaa gaa gtt gga cgt gga gag           480
Glu Thr His Asp Cys Ser Phe Asp Phe Lys Glu Val Gly Arg Gly Glu
145                 150                 155                 160 att gcc aaa gct aat cct gtg gtt aag gct gat aaa att caa agg ttc           528
Ile Ala Lys Ala Asn Pro Val Val Lys Ala Asp Lys Ile Gln Arg Phe
                165                 170                 175 tga                                                                       531

<210> SEQ ID NO 118
<211> LENGTH: 176
<212> TYPE: PRT
<213> ORGANISM: Arabidopsis thaliana

<400> SEQUENCE: 118

Met Gly Ser Glu Gln Asn Asp Ser Thr Ser Phe Thr Gln Ser Gln Ala
 1               5                  10                  15

Ser Glu Pro Lys Leu Cys Val Lys Gly Cys Gly Phe Phe Gly Ser Pro
             20                  25                  30

Ser Asn Met Asp Leu Cys Ser Lys Cys Tyr Arg Gly Ile Cys Ala Glu
         35                  40                  45

Glu Ala Gln Thr Ala Val Ala Lys Ala Ala Val Glu Lys Ser Phe Lys
     50                  55                  60

Pro Ser Pro Pro Arg Ser Leu Phe Ile Ala Glu Pro Pro Ala Val Val
 65                  70                  75                  80

Val Glu Pro Lys Pro Glu Lys Ala Ala Val Val Val Ser Ala Glu
                 85                  90                  95

Pro Ser Ser Ser Ala Val Pro Glu Ala Asn Glu Pro Ser Arg Pro Ala
                100                 105                 110

Arg Thr Asn Arg Cys Leu Cys Cys Asn Lys Lys Val Gly Ile Met Gly
            115                 120                 125

Phe Lys Cys Lys Cys Gly Ser Thr Phe Cys Gly Glu His Arg Tyr Pro
        130                 135                 140

Glu Thr His Asp Cys Ser Phe Asp Phe Lys Glu Val Gly Arg Gly Glu
145                 150                 155                 160

Ile Ala Lys Ala Asn Pro Val Val Lys Ala Asp Lys Ile Gln Arg Phe
                165                 170                 175
```

<210> SEQ ID NO 119
<211> LENGTH: 1068
<212> TYPE: DNA
<213> ORGANISM: Arabidopsis thaliana
<220> FEATURE:
<221> NAME/KEY: CDS
<222> LOCATION: (1)..(1065)

<400> SEQUENCE: 119

| atg | ttg | aaa | gta | gag | agt | aac | tgg | gca | caa | gcc | tgt | gat | aca | tgc | cga | 48 |
|---|---|---|---|---|---|---|---|---|---|---|---|---|---|---|---|---|
| Met | Leu | Lys | Val | Glu | Ser | Asn | Trp | Ala | Gln | Ala | Cys | Asp | Thr | Cys | Arg | |
| 1 | | | | 5 | | | | | 10 | | | | | 15 | | |

| tca | gcc | gcc | tgc | acc | gtg | tac | tgc | cgg | gct | gat | tct | gcc | tac | ttg | tgc | 96 |
|---|---|---|---|---|---|---|---|---|---|---|---|---|---|---|---|---|
| Ser | Ala | Ala | Cys | Thr | Val | Tyr | Cys | Arg | Ala | Asp | Ser | Ala | Tyr | Leu | Cys | |
| | | | 20 | | | | | 25 | | | | | 30 | | | |

| tcc | agt | tgt | gat | gct | caa | gtt | cat | gct | gcc | aat | cgt | ctt | gct | tcc | cgc | 144 |
|---|---|---|---|---|---|---|---|---|---|---|---|---|---|---|---|---|
| Ser | Ser | Cys | Asp | Ala | Gln | Val | His | Ala | Ala | Asn | Arg | Leu | Ala | Ser | Arg | |
| | | 35 | | | | | 40 | | | | | 45 | | | | |

| cat | gaa | cgt | gtt | cga | gtc | tgt | caa | tca | tgt | gag | cga | gcc | ccg | gct | gcc | 192 |
|---|---|---|---|---|---|---|---|---|---|---|---|---|---|---|---|---|
| His | Glu | Arg | Val | Arg | Val | Cys | Gln | Ser | Cys | Glu | Arg | Ala | Pro | Ala | Ala | |
| 50 | | | | | 55 | | | | | 60 | | | | | | |

| ttt | ttc | tgc | aag | gca | gat | gct | gca | tct | cta | tgc | aca | acc | tgt | gat | tca | 240 |
|---|---|---|---|---|---|---|---|---|---|---|---|---|---|---|---|---|
| Phe | Phe | Cys | Lys | Ala | Asp | Ala | Ala | Ser | Leu | Cys | Thr | Thr | Cys | Asp | Ser | |
| 65 | | | | 70 | | | | | 75 | | | | | 80 | | |

| gag | att | cat | tcc | gca | aac | cca | ctt | gct | aga | cgc | cat | caa | cga | gtt | cca | 288 |
|---|---|---|---|---|---|---|---|---|---|---|---|---|---|---|---|---|
| Glu | Ile | His | Ser | Ala | Asn | Pro | Leu | Ala | Arg | Arg | His | Gln | Arg | Val | Pro | |
| | | | 85 | | | | | 90 | | | | | 95 | | | |

| att | ctg | ccc | att | tct | gag | tac | tct | tac | agt | tcc | acg | gcc | act | aac | cat | 336 |
|---|---|---|---|---|---|---|---|---|---|---|---|---|---|---|---|---|
| Ile | Leu | Pro | Ile | Ser | Glu | Tyr | Ser | Tyr | Ser | Ser | Thr | Ala | Thr | Asn | His | |
| | | 100 | | | | | 105 | | | | | 110 | | | | |

| tca | tgt | gag | aca | aca | gtg | aca | gat | cca | gag | aac | aga | ctt | gtg | ctt | ggt | 384 |
|---|---|---|---|---|---|---|---|---|---|---|---|---|---|---|---|---|
| Ser | Cys | Glu | Thr | Thr | Val | Thr | Asp | Pro | Glu | Asn | Arg | Leu | Val | Leu | Gly | |
| | 115 | | | | | 120 | | | | | 125 | | | | | |

| caa | gaa | gaa | gag | gat | gaa | gat | gaa | gca | gag | gcg | gct | tca | tgg | ttg | ttg | 432 |
|---|---|---|---|---|---|---|---|---|---|---|---|---|---|---|---|---|
| Gln | Glu | Glu | Glu | Asp | Glu | Asp | Glu | Ala | Glu | Ala | Ala | Ser | Trp | Leu | Leu | |
| | 130 | | | | | 135 | | | | | 140 | | | | | |

| cct | aat | tca | ggg | aaa | aac | agt | ggt | aac | aac | aat | ggc | ttc | tcg | att | ggg | 480 |
|---|---|---|---|---|---|---|---|---|---|---|---|---|---|---|---|---|
| Pro | Asn | Ser | Gly | Lys | Asn | Ser | Gly | Asn | Asn | Asn | Gly | Phe | Ser | Ile | Gly | |
| 145 | | | | | 150 | | | | | 155 | | | | | 160 | |

| gat | gag | ttt | ctg | aac | ctt | gtt | gat | tat | agt | tcg | agt | gat | aag | caa | ttc | 528 |
|---|---|---|---|---|---|---|---|---|---|---|---|---|---|---|---|---|
| Asp | Glu | Phe | Leu | Asn | Leu | Val | Asp | Tyr | Ser | Ser | Ser | Asp | Lys | Gln | Phe | |
| | | | | 165 | | | | | 170 | | | | | 175 | | |

| aca | gat | caa | tcc | aat | cag | tat | caa | cta | gac | tgc | aac | gta | cct | cag | agg | 576 |
|---|---|---|---|---|---|---|---|---|---|---|---|---|---|---|---|---|
| Thr | Asp | Gln | Ser | Asn | Gln | Tyr | Gln | Leu | Asp | Cys | Asn | Val | Pro | Gln | Arg | |
| | | | 180 | | | | | 185 | | | | | 190 | | | |

| agc | tat | ggg | gaa | gat | gga | gtt | gtt | cca | ctt | caa | att | gaa | gta | tca | aag | 624 |
|---|---|---|---|---|---|---|---|---|---|---|---|---|---|---|---|---|
| Ser | Tyr | Gly | Glu | Asp | Gly | Val | Val | Pro | Leu | Gln | Ile | Glu | Val | Ser | Lys | |
| | | 195 | | | | | 200 | | | | | 205 | | | | |

| ggc | atg | tac | caa | gag | caa | cag | aac | ttt | cag | ctg | agt | atc | aac | tgt | ggc | 672 |
|---|---|---|---|---|---|---|---|---|---|---|---|---|---|---|---|---|
| Gly | Met | Tyr | Gln | Glu | Gln | Gln | Asn | Phe | Gln | Leu | Ser | Ile | Asn | Cys | Gly | |
| | 210 | | | | | 215 | | | | | 220 | | | | | |

| tcc | tgg | gga | gct | ctt | cga | agc | tcc | aat | ggt | tcc | ctc | agt | cat | atg | gtg | 720 |
|---|---|---|---|---|---|---|---|---|---|---|---|---|---|---|---|---|
| Ser | Trp | Gly | Ala | Leu | Arg | Ser | Ser | Asn | Gly | Ser | Leu | Ser | His | Met | Val | |
| 225 | | | | | 230 | | | | | 235 | | | | | 240 | |

| aat | gtt | tca | tct | atg | gac | ctg | gga | gtt | gtg | ccg | gag | tca | aca | acg | agt | 768 |
|---|---|---|---|---|---|---|---|---|---|---|---|---|---|---|---|---|
| Asn | Val | Ser | Ser | Met | Asp | Leu | Gly | Val | Val | Pro | Glu | Ser | Thr | Thr | Ser | |
| | | | | 245 | | | | | 250 | | | | | 255 | | |

| gac | gca | aca | gta | tca | aac | cca | aga | tcg | ccc | aaa | gcg | gta | aca | gac | caa | 816 |
|---|---|---|---|---|---|---|---|---|---|---|---|---|---|---|---|---|
| Asp | Ala | Thr | Val | Ser | Asn | Pro | Arg | Ser | Pro | Lys | Ala | Val | Thr | Asp | Gln | |
| | | | 260 | | | | | 265 | | | | | 270 | | | |

| cca | cct | tac | cct | cca | gct | cag | atg | ctc | agt | cca | agg | gac | aga | gaa | gct | 864 |

```
Pro Pro Tyr Pro Pro Ala Gln Met Leu Ser Pro Arg Asp Arg Glu Ala
        275                 280                 285 aga gtc ctg aga tac aga gag aag aag aag atg agg aaa ttt gag aag      912
Arg Val Leu Arg Tyr Arg Glu Lys Lys Lys Met Arg Lys Phe Glu Lys
    290                 295                 300 acg ata aga tat gct tca agg aaa gcg tat gca gag aaa aga cca cgg      960
Thr Ile Arg Tyr Ala Ser Arg Lys Ala Tyr Ala Glu Lys Arg Pro Arg
305                 310                 315                 320 atc aag ggc cgg ttt gca aag aag aaa gat gtc gat gaa gag gca aac     1008
Ile Lys Gly Arg Phe Ala Lys Lys Lys Asp Val Asp Glu Glu Ala Asn
                325                 330                 335 caa gct ttc tcc aca atg ata aca ttt gac acc gga tat gga att gtt     1056
Gln Ala Phe Ser Thr Met Ile Thr Phe Asp Thr Gly Tyr Gly Ile Val
            340                 345                 350 cca tca ttc tga                                                     1068
Pro Ser Phe
        355

<210> SEQ ID NO 120
<211> LENGTH: 355
<212> TYPE: PRT
<213> ORGANISM: Arabidopsis thaliana

<400> SEQUENCE: 120

Met Leu Lys Val Glu Ser Asn Trp Ala Gln Ala Cys Asp Thr Cys Arg
 1               5                  10                  15

Ser Ala Ala Cys Thr Val Tyr Cys Arg Ala Asp Ser Ala Tyr Leu Cys
            20                  25                  30

Ser Ser Cys Asp Ala Gln Val His Ala Ala Asn Arg Leu Ala Ser Arg
        35                  40                  45

His Glu Arg Val Arg Val Cys Gln Ser Cys Glu Arg Ala Pro Ala Ala
    50                  55                  60

Phe Phe Cys Lys Ala Asp Ala Ala Ser Leu Cys Thr Thr Cys Asp Ser
65                  70                  75                  80

Glu Ile His Ser Ala Asn Pro Leu Ala Arg Arg His Gln Arg Val Pro
                85                  90                  95

Ile Leu Pro Ile Ser Glu Tyr Ser Tyr Ser Ser Thr Ala Thr Asn His
            100                 105                 110

Ser Cys Glu Thr Thr Val Thr Asp Pro Glu Asn Arg Leu Val Leu Gly
        115                 120                 125

Gln Glu Glu Glu Asp Glu Asp Glu Ala Glu Ala Ala Ser Trp Leu Leu
    130                 135                 140

Pro Asn Ser Gly Lys Asn Ser Gly Asn Asn Gly Phe Ser Ile Gly
145                 150                 155                 160

Asp Glu Phe Leu Asn Leu Val Asp Tyr Ser Ser Ser Asp Lys Gln Phe
                165                 170                 175

Thr Asp Gln Ser Asn Gln Tyr Gln Leu Asp Cys Asn Val Pro Gln Arg
            180                 185                 190

Ser Tyr Gly Glu Asp Gly Val Val Pro Leu Gln Ile Glu Val Ser Lys
        195                 200                 205

Gly Met Tyr Gln Glu Gln Gln Asn Phe Gln Leu Ser Ile Asn Cys Gly
    210                 215                 220

Ser Trp Gly Ala Leu Arg Ser Ser Asn Gly Ser Leu Ser His Met Val
225                 230                 235                 240

Asn Val Ser Ser Met Asp Leu Gly Val Val Pro Glu Ser Thr Thr Ser
                245                 250                 255
```

```
Asp Ala Thr Val Ser Asn Pro Arg Ser Pro Lys Ala Val Thr Asp Gln
            260                 265                 270

Pro Pro Tyr Pro Pro Ala Gln Met Leu Ser Pro Arg Asp Arg Glu Ala
        275                 280                 285

Arg Val Leu Arg Tyr Arg Glu Lys Lys Met Arg Lys Phe Glu Lys
    290                 295                 300

Thr Ile Arg Tyr Ala Ser Arg Lys Ala Tyr Ala Glu Lys Arg Pro Arg
305                 310                 315                 320

Ile Lys Gly Arg Phe Ala Lys Lys Asp Val Asp Glu Glu Ala Asn
                325                 330                 335

Gln Ala Phe Ser Thr Met Ile Thr Phe Asp Thr Gly Tyr Gly Ile Val
            340                 345                 350

Pro Ser Phe
        355

<210> SEQ ID NO 121
<211> LENGTH: 1116
<212> TYPE: DNA
<213> ORGANISM: Arabidopsis thaliana
<220> FEATURE:
<221> NAME/KEY: CDS
<222> LOCATION: (191)..(934)

<400> SEQUENCE: 121
atcccaccta cttgttcccc acaaaacact ctctccctct tgttctttc atcttctcta        60 agctctttct ctgaacctac gcttctgcta agctattcta agagaagcca gactagcaat      120
aaacccttca ttttaagcat tctgtttcct tcttgagaaa cctagatatt tggtttctt      180 gtatccggtg atg aag ata cag tgt gat gtg tgt gag aaa gct ccg gcg         229
            Met Lys Ile Gln Cys Asp Val Cys Glu Lys Ala Pro Ala
              1               5                  10 acg gtg att tgt tgc gcc gac gaa gct gct ctc tgt cct caa tgc gac        277
Thr Val Ile Cys Cys Ala Asp Glu Ala Ala Leu Cys Pro Gln Cys Asp
 15                  20                  25 atc gag att cac gcc gct aac aaa ctc gct agc aag cac caa cgt ctt        325
Ile Glu Ile His Ala Ala Asn Lys Leu Ala Ser Lys His Gln Arg Leu
 30                  35                  40                  45 cat ctt aat tcc ctc tcc acc aaa ttc cct cgt tgc gat atc tgc caa        373
His Leu Asn Ser Leu Ser Thr Lys Phe Pro Arg Cys Asp Ile Cys Gln
                 50                  55                  60 gag aag gca gct ttc att ttc tgt gta gag gat aga gct ctg ctt tgc        421
Glu Lys Ala Ala Phe Ile Phe Cys Val Glu Asp Arg Ala Leu Leu Cys
             65                  70                  75 agg gac tgc gat gaa tcc atc cac gtg gct aat tct cga tct gct aat        469
Arg Asp Cys Asp Glu Ser Ile His Val Ala Asn Ser Arg Ser Ala Asn
         80                  85                  90 cac cag agg ttc tta gcc act ggg atc aaa gta gct ctg acc tca act        517
His Gln Arg Phe Leu Ala Thr Gly Ile Lys Val Ala Leu Thr Ser Thr
     95                 100                 105 ata tgt agt aaa gaa att gag aag aat caa cct gag cct tcc aac aac        565
Ile Cys Ser Lys Glu Ile Glu Lys Asn Gln Pro Glu Pro Ser Asn Asn
110                 115                 120                 125 caa cag aag gct aat cag att cct gct aaa tcc aca agc cag cag caa        613
Gln Gln Lys Ala Asn Gln Ile Pro Ala Lys Ser Thr Ser Gln Gln Gln
                130                 135                 140 caa caa cct tct tct gct act cca ctt ccc tgg gct gtt gac gat ttc        661
Gln Gln Pro Ser Ser Ala Thr Pro Leu Pro Trp Ala Val Asp Asp Phe
            145                 150                 155 ttt cac ttc tct gat att gaa tcc acc gac aag aaa gga cag ctt gat        709
```

```
                Phe His Phe Ser Asp Ile Glu Ser Thr Asp Lys Lys Gly Gln Leu Asp
                        160                 165                 170 ctt ggg gca ggg gag ttg gat tgg ttt tca gac atg gga ttc ttc ggt        757
Leu Gly Ala Gly Glu Leu Asp Trp Phe Ser Asp Met Gly Phe Phe Gly
        175                 180                 185 gat cag att aat gac aag gct ctt cct gca gct gaa gtt cct gag ctt        805
Asp Gln Ile Asn Asp Lys Ala Leu Pro Ala Ala Glu Val Pro Glu Leu
190                 195                 200                 205 tct gtt tcg cat tta ggt cat gtt cat tca tac aaa cct atg aag tca        853
Ser Val Ser His Leu Gly His Val His Ser Tyr Lys Pro Met Lys Ser
            210                 215                 220 aat gtt tca cac aag aag ccg agg ttt gag acc aga tat gat gat gat        901
Asn Val Ser His Lys Lys Pro Arg Phe Glu Thr Arg Tyr Asp Asp Asp
                225                 230                 235 gat gag gaa cac ttc att gtc cct gat ctt ggc taaaaagcta tatgtaatct      954
Asp Glu Glu His Phe Ile Val Pro Asp Leu Gly
                240                 245 atgtgtagac attcttcaat gtaaaagaac aaacaagaaa cctatctgca tgtgtggagt     1014
taatgtcata tacattttag ttttgtctta agttgtgtaa gatatgttga gagcttataa     1074
caaatgtctg tgtttgagtt ttgttcaaaa aaaaaaaaa aa                         1116

<210> SEQ ID NO 122
<211> LENGTH: 248
<212> TYPE: PRT
<213> ORGANISM: Arabidopsis thaliana

<400> SEQUENCE: 122

Met Lys Ile Gln Cys Asp Val Cys Glu Lys Ala Pro Ala Thr Val Ile
1               5                   10                  15

Cys Cys Ala Asp Glu Ala Ala Leu Cys Pro Gln Cys Asp Ile Glu Ile
            20                  25                  30

His Ala Ala Asn Lys Leu Ala Ser Lys His Gln Arg Leu His Leu Asn
        35                  40                  45

Ser Leu Ser Thr Lys Phe Pro Arg Cys Asp Ile Cys Gln Glu Lys Ala
    50                  55                  60

Ala Phe Ile Phe Cys Val Glu Asp Arg Ala Leu Leu Cys Arg Asp Cys
65                  70                  75                  80

Asp Glu Ser Ile His Val Ala Asn Ser Arg Ser Ala Asn His Gln Arg
                85                  90                  95

Phe Leu Ala Thr Gly Ile Lys Val Ala Leu Thr Ser Thr Ile Cys Ser
            100                 105                 110

Lys Glu Ile Glu Lys Asn Gln Pro Glu Pro Ser Asn Asn Gln Gln Lys
        115                 120                 125

Ala Asn Gln Ile Pro Ala Lys Ser Thr Ser Gln Gln Gln Gln Gln Pro
    130                 135                 140

Ser Ser Ala Thr Pro Leu Pro Trp Ala Val Asp Asp Phe Phe His Phe
145                 150                 155                 160

Ser Asp Ile Glu Ser Thr Asp Lys Lys Gly Gln Leu Asp Leu Gly Ala
                165                 170                 175

Gly Glu Leu Asp Trp Phe Ser Asp Met Gly Phe Phe Gly Asp Gln Ile
            180                 185                 190

Asn Asp Lys Ala Leu Pro Ala Ala Glu Val Pro Glu Leu Ser Val Ser
        195                 200                 205

His Leu Gly His Val His Ser Tyr Lys Pro Met Lys Ser Asn Val Ser
    210                 215                 220
```

```
His Lys Lys Pro Arg Phe Glu Thr Arg Tyr Asp Asp Asp Glu Glu
225                 230                 235                 240

His Phe Ile Val Pro Asp Leu Gly
                245

<210> SEQ ID NO 123
<211> LENGTH: 909
<212> TYPE: DNA
<213> ORGANISM: Arabidopsis thaliana
<220> FEATURE:
<221> NAME/KEY: CDS
<222> LOCATION: (1)..(906)

<400> SEQUENCE: 123 atg gat cag tac tca tcc tct ttg gtc gat act tca tta gat ctc act      48
Met Asp Gln Tyr Ser Ser Ser Leu Val Asp Thr Ser Leu Asp Leu Thr
1               5                   10                  15 att ggc gtt act cgt atg cga gtt gaa gaa gat cca ccg aca agt gct      96
Ile Gly Val Thr Arg Met Arg Val Glu Glu Asp Pro Pro Thr Ser Ala
            20                  25                  30 ttg gtg gaa gaa tta aac cga gtt agt gct gag aac aag aag ctc tcg     144
Leu Val Glu Glu Leu Asn Arg Val Ser Ala Glu Asn Lys Lys Leu Ser
        35                  40                  45 gag atg cta act ttg atg tgt gac aac tac aac gtc ttg agg aag caa     192
Glu Met Leu Thr Leu Met Cys Asp Asn Tyr Asn Val Leu Arg Lys Gln
    50                  55                  60 ctt atg gaa tat gtt aac aag agc aac ata acc gag agg gat caa atc     240
Leu Met Glu Tyr Val Asn Lys Ser Asn Ile Thr Glu Arg Asp Gln Ile
65                  70                  75                  80 agc cct ccc aag aaa cgc aaa tcc ccg gcg aga gag gac gca ttc agc     288
Ser Pro Pro Lys Lys Arg Lys Ser Pro Ala Arg Glu Asp Ala Phe Ser
                85                  90                  95 tgc gcg gtt att ggc gga gtg tcg gag agt agc tca acg gat caa gat     336
Cys Ala Val Ile Gly Gly Val Ser Glu Ser Ser Ser Thr Asp Gln Asp
            100                 105                 110 gag tat ttg tgt aag aag cag aga gaa gag act gtc gtg aag gag aaa     384
Glu Tyr Leu Cys Lys Lys Gln Arg Glu Glu Thr Val Val Lys Glu Lys
        115                 120                 125 gtc tca agg gtc tat tac aag acc gaa gct tct gac act acc ctc gtt     432
Val Ser Arg Val Tyr Tyr Lys Thr Glu Ala Ser Asp Thr Thr Leu Val
    130                 135                 140 gtg aaa gat ggg tat caa tgg agg aaa tat gga cag aaa gtg act aga     480
Val Lys Asp Gly Tyr Gln Trp Arg Lys Tyr Gly Gln Lys Val Thr Arg
145                 150                 155                 160 gac aat cca tct cca aga gct tac ttc aaa tgt gct tgt gct cca agc     528
Asp Asn Pro Ser Pro Arg Ala Tyr Phe Lys Cys Ala Cys Ala Pro Ser
                165                 170                 175 tgt tct gtc aaa aag aag gtt cag aga agt gtg gag gat cag tcc gtg     576
Cys Ser Val Lys Lys Lys Val Gln Arg Ser Val Glu Asp Gln Ser Val
            180                 185                 190 tta gtt gca act tat gag ggt gaa cac aac cat cca atg cca tcg cag     624
Leu Val Ala Thr Tyr Glu Gly Glu His Asn His Pro Met Pro Ser Gln
        195                 200                 205 atc gat tca aac aat ggc tta aac cgc cac atc tct cat ggt ggt tca     672
Ile Asp Ser Asn Asn Gly Leu Asn Arg His Ile Ser His Gly Gly Ser
    210                 215                 220 gct tca aca ccc gtt gca gca aac aga aga agt agc ttg act gtg ccg     720
Ala Ser Thr Pro Val Ala Ala Asn Arg Arg Ser Ser Leu Thr Val Pro
225                 230                 235                 240 gtg act acc gta gat atg att gaa tcg aag aaa gtg acg agc cca acg     768
Val Thr Thr Val Asp Met Ile Glu Ser Lys Lys Val Thr Ser Pro Thr
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     |     | 245 |     |     |     | 250 |     |     |     | 255 |     |     |     |
| tca | aga | atc | gat | ttt | ccc | caa | gtt | cag | aaa | ctt | ttg | gtg | gag | caa | atg | 816 |
| Ser | Arg | Ile | Asp | Phe | Pro | Gln | Val | Gln | Lys | Leu | Leu | Val | Glu | Gln | Met |
|     |     |     | 260 |     |     |     | 265 |     |     |     | 270 |     |     |     |     |
| gct | tct | tcc | tta | acc | aaa | gat | cct | aac | ttt | aca | gca | gct | tta | gca | gca | 864 |
| Ala | Ser | Ser | Leu | Thr | Lys | Asp | Pro | Asn | Phe | Thr | Ala | Ala | Leu | Ala | Ala |
|     |     | 275 |     |     |     | 280 |     |     |     | 285 |     |     |     |     |     |
| gct | gtt | acc | gga | aaa | ttg | tat | caa | cag | aat | cat | acc | gag | aaa | tag |     | 909 |
| Ala | Val | Thr | Gly | Lys | Leu | Tyr | Gln | Gln | Asn | His | Thr | Glu | Lys |     |     |
|     | 290 |     |     |     |     | 295 |     |     |     |     | 300 |     |     |     |     |

<210> SEQ ID NO 124
<211> LENGTH: 302
<212> TYPE: PRT
<213> ORGANISM: Arabidopsis thaliana

<400> SEQUENCE: 124

Met Asp Gln Tyr Ser Ser Leu Val Asp Thr Ser Leu Asp Leu Thr
1               5                   10                  15

Ile Gly Val Thr Arg Met Arg Val Glu Glu Asp Pro Thr Ser Ala
            20                  25                  30

Leu Val Glu Glu Leu Asn Arg Val Ser Ala Glu Asn Lys Lys Leu Ser
            35                  40                  45

Glu Met Leu Thr Leu Met Cys Asp Asn Tyr Asn Val Leu Arg Lys Gln
    50                  55                  60

Leu Met Glu Tyr Val Asn Lys Ser Asn Ile Thr Glu Arg Asp Gln Ile
65                  70                  75                  80

Ser Pro Pro Lys Lys Arg Lys Ser Pro Ala Arg Glu Asp Ala Phe Ser
                85                  90                  95

Cys Ala Val Ile Gly Gly Val Ser Glu Ser Ser Thr Asp Gln Asp
            100                 105                 110

Glu Tyr Leu Cys Lys Lys Gln Arg Glu Glu Thr Val Val Lys Glu Lys
    115                 120                 125

Val Ser Arg Val Tyr Tyr Lys Thr Glu Ala Ser Asp Thr Thr Leu Val
    130                 135                 140

Val Lys Asp Gly Tyr Gln Trp Arg Lys Tyr Gly Gln Lys Val Thr Arg
145                 150                 155                 160

Asp Asn Pro Ser Pro Arg Ala Tyr Phe Lys Cys Ala Cys Ala Pro Ser
                165                 170                 175

Cys Ser Val Lys Lys Lys Val Gln Arg Ser Val Glu Asp Gln Ser Val
            180                 185                 190

Leu Val Ala Thr Tyr Glu Gly Glu His Asn His Pro Met Pro Ser Gln
    195                 200                 205

Ile Asp Ser Asn Asn Gly Leu Asn Arg His Ile Ser His Gly Gly Ser
    210                 215                 220

Ala Ser Thr Pro Val Ala Ala Asn Arg Arg Ser Ser Leu Thr Val Pro
225                 230                 235                 240

Val Thr Thr Val Asp Met Ile Glu Ser Lys Lys Val Thr Ser Pro Thr
                245                 250                 255

Ser Arg Ile Asp Phe Pro Gln Val Gln Lys Leu Leu Val Glu Gln Met
            260                 265                 270

Ala Ser Ser Leu Thr Lys Asp Pro Asn Phe Thr Ala Ala Leu Ala Ala
    275                 280                 285

Ala Val Thr Gly Lys Leu Tyr Gln Gln Asn His Thr Glu Lys
    290                 295                 300

```
<210> SEQ ID NO 125
<211> LENGTH: 1462
<212> TYPE: DNA
<213> ORGANISM: Arabidopsis thaliana
<220> FEATURE:
<221> NAME/KEY: CDS
<222> LOCATION: (382)..(1161)

<400> SEQUENCE: 125
accgaccttc ttggttcttc cggcgttgac tgttacgaag atgatgaaga cttgagagtt      60
tctgggtcga gttttggtgg gtactatcca gagagaaccg ggtctggttt acctaagttc     120
aagacggctc aaccaccacc tcttccgatt tcacaatctt ctcataactt cactttctcc     180
gattaccttg attctcctct gcttctcagc tcctcacaca gtttgatatc tccaacaaca     240
ggaacgtttc cattgcaagg ctttaatgga acaacaaaca atcactcaga ttttccctgg     300
cagctacaat ctcaaccatc aaacgcttct tctgctttgc aagaaacata tggtgttcaa     360
gatcacgaga agaagcagga g atg att cct aat gag att gca aca caa aac       411
                        Met Ile Pro Asn Glu Ile Ala Thr Gln Asn
                          1               5                  10 aac aat caa agt ttt gga aca gaa cgt cag ata aag ata cca gca tac       459
Asn Asn Gln Ser Phe Gly Thr Glu Arg Gln Ile Lys Ile Pro Ala Tyr
             15                  20                  25 atg gtg agt agg aac tct aat gat ggt tat ggt tgg aga aaa tac ggt       507
Met Val Ser Arg Asn Ser Asn Asp Gly Tyr Gly Trp Arg Lys Tyr Gly
         30                  35                  40 cag aaa caa gtg aag aag agc gaa aac cct agg agt tac ttc aag tgt       555
Gln Lys Gln Val Lys Lys Ser Glu Asn Pro Arg Ser Tyr Phe Lys Cys
     45                  50                  55 acg tat cct gat tgt gtt tcc aag aag att gtt gag acg gct tct gat       603
Thr Tyr Pro Asp Cys Val Ser Lys Lys Ile Val Glu Thr Ala Ser Asp
 60                  65                  70 gga cag atc act gag atc att tat aaa ggt ggt cat aat cat cct aag       651
Gly Gln Ile Thr Glu Ile Ile Tyr Lys Gly Gly His Asn His Pro Lys
             75                  80                  85                  90 cct gag ttc acc aag aga cca tct caa tct tca tta cca tca tcg gtt       699
Pro Glu Phe Thr Lys Arg Pro Ser Gln Ser Ser Leu Pro Ser Ser Val
                 95                 100                 105 aat ggg agg cgc ttg ttt aat cct gct tct gtt gtt agt gaa cct cat       747
Asn Gly Arg Arg Leu Phe Asn Pro Ala Ser Val Val Ser Glu Pro His
            110                 115                 120 gat caa tca gag aac tct tcg att tcg ttt gac tat agt gat ctt gag       795
Asp Gln Ser Glu Asn Ser Ser Ile Ser Phe Asp Tyr Ser Asp Leu Glu
        125                 130                 135 cag aaa agt ttt aaa tca gag tat ggt gag ata gat gaa gag gag gaa       843
Gln Lys Ser Phe Lys Ser Glu Tyr Gly Glu Ile Asp Glu Glu Glu Glu
    140                 145                 150 caa cct gag atg aag agg atg aaa aga gaa ggt gaa gat gaa ggg atg       891
Gln Pro Glu Met Lys Arg Met Lys Arg Glu Gly Glu Asp Glu Gly Met
155                 160                 165                 170 tct ata gaa gta agc aaa gga gtt aaa gag cca aga gtt gtg gtt cag       939
Ser Ile Glu Val Ser Lys Gly Val Lys Glu Pro Arg Val Val Val Gln
                175                 180                 185 aca ata agt gat att gat gtt ctt ata gat ggc ttt aga tgg agg aaa       987
Thr Ile Ser Asp Ile Asp Val Leu Ile Asp Gly Phe Arg Trp Arg Lys
            190                 195                 200 tat ggt caa aaa gtt gtc aaa gga aat act aat cca agg agc tac tac      1035
Tyr Gly Gln Lys Val Val Lys Gly Asn Thr Asn Pro Arg Ser Tyr Tyr
        205                 210                 215
```

```
aag tgc aca ttc caa ggt tgt gga gtg aag aag caa gtg gaa aga tcc      1083
Lys Cys Thr Phe Gln Gly Cys Gly Val Lys Lys Gln Val Glu Arg Ser
220                 225                 230 gca gca gac gag aga gca gtt ctc act acc tat gaa gga aga cac aat      1131
Ala Ala Asp Glu Arg Ala Val Leu Thr Thr Tyr Glu Gly Arg His Asn
235                 240                 245                 250 cac gat atc cca acc gcg cta cgt cgc tcg tgaaattatt gggacttagt        1181
His Asp Ile Pro Thr Ala Leu Arg Arg Ser
                255                 260 cactagtaat atgatttagg ctttctaaaa acaaaaaatc ttactatggc ttatcttttg    1241
tgctcattca cagtttgttt atttgttgt tacacagtca atactttgtt ttgtacagag     1301
tggtgcttag tagtgttttt attattatct tggccttata gaataaccctc tcttctcatc  1361 tgtgtgactt taaacacttg agagtccatt ttatagttct tgtgtattgg tcttttgttt   1421
gatttatgta cattttaat attcgaaaaa aaaaaaaaaa a                        1462
```

<210> SEQ ID NO 126
<211> LENGTH: 260
<212> TYPE: PRT
<213> ORGANISM: Arabidopsis thaliana

<400> SEQUENCE: 126

```
Met Ile Pro Asn Glu Ile Ala Thr Gln Asn Asn Gln Ser Phe Gly
 1               5                  10                  15

Thr Glu Arg Gln Ile Lys Ile Pro Ala Tyr Met Val Ser Arg Asn Ser
                20                  25                  30

Asn Asp Gly Tyr Gly Trp Arg Lys Tyr Gly Gln Lys Gln Val Lys Lys
            35                  40                  45

Ser Glu Asn Pro Arg Ser Tyr Phe Lys Cys Thr Tyr Pro Asp Cys Val
        50                  55                  60

Ser Lys Lys Ile Val Glu Thr Ala Ser Asp Gly Gln Ile Thr Glu Ile
 65                  70                  75                  80

Ile Tyr Lys Gly Gly His Asn His Pro Lys Pro Glu Phe Thr Lys Arg
                85                  90                  95

Pro Ser Gln Ser Ser Leu Pro Ser Ser Val Asn Gly Arg Arg Leu Phe
            100                 105                 110

Asn Pro Ala Ser Val Val Ser Glu Pro His Asp Gln Ser Glu Asn Ser
        115                 120                 125

Ser Ile Ser Phe Asp Tyr Ser Asp Leu Glu Gln Lys Ser Phe Lys Ser
    130                 135                 140

Glu Tyr Gly Glu Ile Asp Glu Glu Glu Gln Pro Glu Met Lys Arg
145                 150                 155                 160

Met Lys Arg Glu Gly Glu Asp Glu Gly Met Ser Ile Glu Val Ser Lys
                165                 170                 175

Gly Val Lys Glu Pro Arg Val Val Gln Thr Ile Ser Asp Ile Asp
            180                 185                 190

Val Leu Ile Asp Gly Phe Arg Trp Arg Lys Tyr Gly Gln Lys Val Val
        195                 200                 205

Lys Gly Asn Thr Asn Pro Arg Ser Tyr Tyr Lys Cys Thr Phe Gln Gly
    210                 215                 220

Cys Gly Val Lys Lys Gln Val Glu Arg Ser Ala Ala Asp Glu Arg Ala
225                 230                 235                 240

Val Leu Thr Thr Tyr Glu Gly Arg His Asn His Asp Ile Pro Thr Ala
                245                 250                 255

Leu Arg Arg Ser
```

```
<210> SEQ ID NO 127
<211> LENGTH: 438
<212> TYPE: DNA
<213> ORGANISM: Arabidopsis thaliana
<220> FEATURE:
<221> NAME/KEY: CDS
<222> LOCATION: (1)..(435)

<400> SEQUENCE: 127 atg gag gga tat gat aat ggg tcg ttg tat gct cct ttt ttg tcg ttg      48
Met Glu Gly Tyr Asp Asn Gly Ser Leu Tyr Ala Pro Phe Leu Ser Leu
 1               5                  10                  15 aaa tct cat tcg aaa cca gag ctg cat caa ggc gaa gaa gag agc tca      96
Lys Ser His Ser Lys Pro Glu Leu His Gln Gly Glu Glu Glu Ser Ser
             20                  25                  30 aag gtt aga tca gaa ggt tgt tcg aaa agc gtg gag tcg tcg aaa aag     144
Lys Val Arg Ser Glu Gly Cys Ser Lys Ser Val Glu Ser Ser Lys Lys
         35                  40                  45 aag ggg aag aaa caa agg tat gcg ttt caa aca agg agc caa gtg gat     192
Lys Gly Lys Lys Gln Arg Tyr Ala Phe Gln Thr Arg Ser Gln Val Asp
     50                  55                  60 att ctt gat gat ggt tat cga tgg agg aaa tat ggc caa aag gcc gtc     240
Ile Leu Asp Asp Gly Tyr Arg Trp Arg Lys Tyr Gly Gln Lys Ala Val
 65                  70                  75                  80 aag aac aac aag ttc cct agg agt tac tat agg tgt aca tat gga gga     288
Lys Asn Asn Lys Phe Pro Arg Ser Tyr Tyr Arg Cys Thr Tyr Gly Gly
                 85                  90                  95 tgc aat gtg aag aag caa gtg caa aga tta aca gtg gac caa gaa gtg     336
Cys Asn Val Lys Lys Gln Val Gln Arg Leu Thr Val Asp Gln Glu Val
            100                 105                 110 gtc gtg aca acc tac gaa gga gtg cat tcg cat ccc atc gag aaa tcc     384
Val Val Thr Thr Tyr Glu Gly Val His Ser His Pro Ile Glu Lys Ser
        115                 120                 125 acc gaa aac ttc gag cat att ctc act caa atg caa atc tac tct tct     432
Thr Glu Asn Phe Glu His Ile Leu Thr Gln Met Gln Ile Tyr Ser Ser
    130                 135                 140 ttc tag                                                              438
Phe
145

<210> SEQ ID NO 128
<211> LENGTH: 145
<212> TYPE: PRT
<213> ORGANISM: Arabidopsis thaliana

<400> SEQUENCE: 128

Met Glu Gly Tyr Asp Asn Gly Ser Leu Tyr Ala Pro Phe Leu Ser Leu
 1               5                  10                  15

Lys Ser His Ser Lys Pro Glu Leu His Gln Gly Glu Glu Glu Ser Ser
             20                  25                  30

Lys Val Arg Ser Glu Gly Cys Ser Lys Ser Val Glu Ser Ser Lys Lys
         35                  40                  45

Lys Gly Lys Lys Gln Arg Tyr Ala Phe Gln Thr Arg Ser Gln Val Asp
     50                  55                  60

Ile Leu Asp Asp Gly Tyr Arg Trp Arg Lys Tyr Gly Gln Lys Ala Val
 65                  70                  75                  80

Lys Asn Asn Lys Phe Pro Arg Ser Tyr Tyr Arg Cys Thr Tyr Gly Gly
                 85                  90                  95
```

```
Cys Asn Val Lys Lys Gln Val Gln Arg Leu Thr Val Asp Gln Glu Val
            100                 105                 110

Val Val Thr Thr Tyr Glu Gly Val His Ser His Pro Ile Glu Lys Ser
        115                 120                 125

Thr Glu Asn Phe Glu His Ile Leu Thr Gln Met Gln Ile Tyr Ser Ser
    130                 135                 140

Phe
145

<210> SEQ ID NO 129
<211> LENGTH: 1254
<212> TYPE: DNA
<213> ORGANISM: Arabidopsis thaliana
<220> FEATURE:
<221> NAME/KEY: CDS
<222> LOCATION: (137)..(1090)

<400> SEQUENCE: 129
aaaagtccaa gcaccaatct agacctctta ggaaaaaaac ctaaaaacct aatccccaaa      60
cctaaaaggc ttatctcatc tcttcttctt tgtcttcttt actctttttt tacctctctc     120
```

| | | | | | | | | | | | |
|---|---|---|---|---|---|---|---|---|---|---|---|
| ttcattgttc ttcacc atg tct aat gaa acc aga gat ctc tac aac tac caa | | | | | | | | | | | 172 |
| | Met Ser Asn Glu Thr Arg Asp Leu Tyr Asn Tyr Gln | | | | | | | | | | |
| | 1 | | | 5 | | | | | 10 | | |

```
tac cct tca tcg ttt tcg ttg cac gaa atg atg aat ctg cct act tca     220
Tyr Pro Ser Ser Phe Ser Leu His Glu Met Met Asn Leu Pro Thr Ser
        15                  20                  25 aat cca tct tct tat gga aac ctc cca tca caa aac ggt ttt aat cca     268
Asn Pro Ser Ser Tyr Gly Asn Leu Pro Ser Gln Asn Gly Phe Asn Pro
    30                  35                  40 tct act tat tcc ttc acc gat tgt ctc caa agt tct cca gca gcg tat     316
Ser Thr Tyr Ser Phe Thr Asp Cys Leu Gln Ser Ser Pro Ala Ala Tyr
45                  50                  55                  60 gaa tct cta ctt cag aaa act ttt ggt ctt tct ccc tct tcc tca gag     364
Glu Ser Leu Leu Gln Lys Thr Phe Gly Leu Ser Pro Ser Ser Ser Glu
                65                  70                  75 gtt ttc aat tct tcg atc gat caa gaa ccg aac cgt gat gtt act aat     412
Val Phe Asn Ser Ser Ile Asp Gln Glu Pro Asn Arg Asp Val Thr Asn
            80                  85                  90 gac gta atc aat ggt ggt gca tgc aac gag act gaa act agg gtt tct     460
Asp Val Ile Asn Gly Gly Ala Cys Asn Glu Thr Glu Thr Arg Val Ser
        95                  100                 105 cct tct aat tct tcc tct agt gag gct gat cac ccc ggt gaa gat tcc     508
Pro Ser Asn Ser Ser Ser Ser Glu Ala Asp His Pro Gly Glu Asp Ser
    110                 115                 120 ggt aag agc cgg agg aaa cga gag tta gtc ggt gaa gaa gat caa att     556
Gly Lys Ser Arg Arg Lys Arg Glu Leu Val Gly Glu Glu Asp Gln Ile
125                 130                 135                 140 tcc aaa aaa gtt ggg aaa acg aaa aag act gag gtg aag aaa caa aga     604
Ser Lys Lys Val Gly Lys Thr Lys Lys Thr Glu Val Lys Lys Gln Arg
                145                 150                 155 gag cca cga gtc tcg ttt atg act aaa agt gaa gtt gat cat ctt gaa     652
Glu Pro Arg Val Ser Phe Met Thr Lys Ser Glu Val Asp His Leu Glu
            160                 165                 170 gat ggt tat aga tgg aga aaa tac ggc caa aag gct gta aaa aat agc     700
Asp Gly Tyr Arg Trp Arg Lys Tyr Gly Gln Lys Ala Val Lys Asn Ser
        175                 180                 185 cct tat cca agg agt tac tat aga tgt aca aca caa aag tgc aac gtg     748
Pro Tyr Pro Arg Ser Tyr Tyr Arg Cys Thr Thr Gln Lys Cys Asn Val
    190                 195                 200
```

```
aag aaa cga gtg gag aga tcg ttc caa gat cca acg gtt gtg att aca       796
Lys Lys Arg Val Glu Arg Ser Phe Gln Asp Pro Thr Val Val Ile Thr
205                 210                 215                 220 act tac gag ggt caa cac aac cac ccg att ccg act aat ctt cga gga       844
Thr Tyr Glu Gly Gln His Asn His Pro Ile Pro Thr Asn Leu Arg Gly
                225                 230                 235 agt tct gcc gcg gct gct atg ttc tcc gca gac ctc atg act cca aga       892
Ser Ser Ala Ala Ala Ala Met Phe Ser Ala Asp Leu Met Thr Pro Arg
            240                 245                 250 agc ttt gca cat gat atg ttt agg acg gca gct tat act aac ggc ggt       940
Ser Phe Ala His Asp Met Phe Arg Thr Ala Ala Tyr Thr Asn Gly Gly
        255                 260                 265 tct gtg gcg gcg gct ttg gat tat gga tat gga caa agt ggt tat ggt       988
Ser Val Ala Ala Ala Leu Asp Tyr Gly Tyr Gly Gln Ser Gly Tyr Gly
    270                 275                 280 agt gtg aat tca aac cct agt tct cac caa gtg tat cat caa ggg ggt      1036
Ser Val Asn Ser Asn Pro Ser Ser His Gln Val Tyr His Gln Gly Gly
285                 290                 295                 300 gag tat gag ctc ttg agg gag att ttt cct tca att ttc ttt aag caa      1084
Glu Tyr Glu Leu Leu Arg Glu Ile Phe Pro Ser Ile Phe Phe Lys Gln
                305                 310                 315 gag cct tgatcgatca ttgttataac tacatatatt atatatattg agagagagag       1140
Glu Pro gtagagaaaa aaaaaactta tatgtaactt aagatcttat tttgtctctc ttatttgcat    1200
gtacatattt tttcatgaaa gaatgagaca gttgggcttg cttaaaaaaa aaat          1254

<210> SEQ ID NO 130
<211> LENGTH: 318
<212> TYPE: PRT
<213> ORGANISM: Arabidopsis thaliana

<400> SEQUENCE: 130

Met Ser Asn Glu Thr Arg Asp Leu Tyr Asn Tyr Gln Tyr Pro Ser Ser
1               5                   10                  15

Phe Ser Leu His Glu Met Met Asn Leu Pro Thr Ser Asn Pro Ser Ser
            20                  25                  30

Tyr Gly Asn Leu Pro Ser Gln Asn Gly Phe Asn Pro Ser Thr Tyr Ser
        35                  40                  45

Phe Thr Asp Cys Leu Gln Ser Ser Pro Ala Ala Tyr Glu Ser Leu Leu
    50                  55                  60

Gln Lys Thr Phe Gly Leu Ser Pro Ser Ser Glu Val Phe Asn Ser
65                  70                  75                  80

Ser Ile Asp Gln Glu Pro Asn Arg Asp Val Thr Asn Asp Val Ile Asn
                85                  90                  95

Gly Gly Ala Cys Asn Glu Thr Glu Thr Arg Val Ser Pro Ser Asn Ser
            100                 105                 110

Ser Ser Ser Glu Ala Asp His Pro Gly Glu Asp Ser Gly Lys Ser Arg
        115                 120                 125

Arg Lys Arg Glu Leu Val Gly Glu Asp Gln Ile Ser Lys Lys Val
    130                 135                 140

Gly Lys Thr Lys Lys Thr Glu Val Lys Lys Gln Arg Glu Pro Arg Val
145                 150                 155                 160

Ser Phe Met Thr Lys Ser Glu Val Asp His Leu Glu Asp Gly Tyr Arg
                165                 170                 175

Trp Arg Lys Tyr Gly Gln Lys Ala Val Lys Asn Ser Pro Tyr Pro Arg
            180                 185                 190
```

```
Ser Tyr Tyr Arg Cys Thr Thr Gln Lys Cys Asn Val Lys Lys Arg Val
        195                 200                 205

Glu Arg Ser Phe Gln Asp Pro Thr Val Val Ile Thr Thr Tyr Glu Gly
    210                 215                 220

Gln His Asn His Pro Ile Pro Thr Asn Leu Arg Gly Ser Ser Ala Ala
225                 230                 235                 240

Ala Ala Met Phe Ser Ala Asp Leu Met Thr Pro Arg Ser Phe Ala His
            245                 250                 255

Asp Met Phe Arg Thr Ala Ala Tyr Thr Asn Gly Gly Ser Val Ala Ala
            260                 265                 270

Ala Leu Asp Tyr Gly Tyr Gly Gln Ser Gly Tyr Gly Ser Val Asn Ser
        275                 280                 285

Asn Pro Ser Ser His Gln Val Tyr His Gln Gly Gly Glu Tyr Glu Leu
    290                 295                 300

Leu Arg Glu Ile Phe Pro Ser Ile Phe Phe Lys Gln Glu Pro
305                 310                 315

<210> SEQ ID NO 131
<211> LENGTH: 1148
<212> TYPE: DNA
<213> ORGANISM: Arabidopsis thaliana
<220> FEATURE:
<221> NAME/KEY: CDS
<222> LOCATION: (104)..(1075)

<400> SEQUENCE: 131
acgtctctct ctttctctct actctctgtt tcctcataat tcaatcacta tattttttta      60
aaaacatttg acttcatcga tcggttaaca attaatcaaa aag atg gga cga tca     115
                                              Met Gly Arg Ser
                                                1 cca tgt tgt gag aag aag aat ggt ctc aag aaa gga cca tgg act cct     163
Pro Cys Cys Glu Lys Lys Asn Gly Leu Lys Lys Gly Pro Trp Thr Pro
  5              10                  15                  20 gag gag gat caa aag ctc att gat tat atc aat ata cat ggt tat gga     211
Glu Glu Asp Gln Lys Leu Ile Asp Tyr Ile Asn Ile His Gly Tyr Gly
             25                  30                  35 aat tgg aga act ctt ccc aag aat gct ggg tta caa aga tgt ggt aag     259
Asn Trp Arg Thr Leu Pro Lys Asn Ala Gly Leu Gln Arg Cys Gly Lys
         40                  45                  50 agt tgt cgt ctc cgg tgg acc aac tat ctc cga cca gat att aag cgt     307
Ser Cys Arg Leu Arg Trp Thr Asn Tyr Leu Arg Pro Asp Ile Lys Arg
     55                  60                  65 gga aga ttc tct ttt gaa gaa gaa gaa acc att att caa ctt cac agc     355
Gly Arg Phe Ser Phe Glu Glu Glu Glu Thr Ile Ile Gln Leu His Ser
 70                  75                  80 atc atg gga aac aag tgg tct gcg att gcg gct cgt ttg cct gga aga     403
Ile Met Gly Asn Lys Trp Ser Ala Ile Ala Ala Arg Leu Pro Gly Arg
 85                  90                  95                 100 aca gac aac gag atc aaa aac tat tgg aac act cac atc aga aaa aga     451
Thr Asp Asn Glu Ile Lys Asn Tyr Trp Asn Thr His Ile Arg Lys Arg
                105                 110                 115 ctt cta aag atg gga atc gac ccg gtt aca cac act cca cgt ctt gat     499
Leu Leu Lys Met Gly Ile Asp Pro Val Thr His Thr Pro Arg Leu Asp
            120                 125                 130 ctt ctc gat atc tcc tcc att ctc agc tca tct atc tac aac tct tcg     547
Leu Leu Asp Ile Ser Ser Ile Leu Ser Ser Ser Ile Tyr Asn Ser Ser
        135                 140                 145 cat cat cat cat cat cat cat caa caa cat atg aac atg tcg agg ctc     595
His His His His His His His Gln Gln His Met Asn Met Ser Arg Leu
```

-continued

```
                      150                 155                 160
atg atg agt gat ggt aat cat caa cca ttg gtt aac ccc gag ata ctc    643
Met Met Ser Asp Gly Asn His Gln Pro Leu Val Asn Pro Glu Ile Leu
165                 170                 175                 180 aaa ctc gca acc tct ctc ttt tca aac caa aac cac ccc aac aac aca    691
Lys Leu Ala Thr Ser Leu Phe Ser Asn Gln Asn His Pro Asn Asn Thr
                185                 190                 195 cac gag aac aac acg gtt aac caa acc gaa gta aac caa tac caa acc    739
His Glu Asn Asn Thr Val Asn Gln Thr Glu Val Asn Gln Tyr Gln Thr
            200                 205                 210 ggt tac aac atg cct ggt aat gaa gaa tta caa tct tgg ttc cct atc    787
Gly Tyr Asn Met Pro Gly Asn Glu Glu Leu Gln Ser Trp Phe Pro Ile
        215                 220                 225 atg gat caa ttc acg aat ttc caa gac ctc atg cca atg aag acg acg    835
Met Asp Gln Phe Thr Asn Phe Gln Asp Leu Met Pro Met Lys Thr Thr
    230                 235                 240 gtc caa aat tca ttg tca tac gat gat gat tgt tcg aag tcc aat ttt    883
Val Gln Asn Ser Leu Ser Tyr Asp Asp Asp Cys Ser Lys Ser Asn Phe
245                 250                 255                 260 gta tta gaa cct tat tac tcc gac ttt gct tca gtc ttg acc aca cct    931
Val Leu Glu Pro Tyr Tyr Ser Asp Phe Ala Ser Val Leu Thr Thr Pro
                265                 270                 275 tct tca agc ccg act ccg tta aac tca agt tcc tca act tac atc aat    979
Ser Ser Ser Pro Thr Pro Leu Asn Ser Ser Ser Thr Tyr Ile Asn
            280                 285                 290 agt agc act tgc agc acc gag gat gaa aaa gag agt tat tac agt gat   1027
Ser Ser Thr Cys Ser Thr Glu Asp Glu Lys Glu Ser Tyr Tyr Ser Asp
        295                 300                 305 aat atc act aat tat tcg ttt gat gtt aat ggt ttt ctc caa ttc caa   1075
Asn Ile Thr Asn Tyr Ser Phe Asp Val Asn Gly Phe Leu Gln Phe Gln
    310                 315                 320 taaacaaaac gccattggaa tagagttatg taaacatgca atcattgtat tgttatata   1135 gattttgtta cat                                                     1148

<210> SEQ ID NO 132
<211> LENGTH: 324
<212> TYPE: PRT
<213> ORGANISM: Arabidopsis thaliana

<400> SEQUENCE: 132

Met Gly Arg Ser Pro Cys Cys Glu Lys Lys Asn Gly Leu Lys Lys Gly
1               5                   10                  15

Pro Trp Thr Pro Glu Glu Asp Gln Lys Leu Ile Asp Tyr Ile Asn Ile
            20                  25                  30

His Gly Tyr Gly Asn Trp Arg Thr Leu Pro Lys Asn Ala Gly Leu Gln
        35                  40                  45

Arg Cys Gly Lys Ser Cys Arg Leu Arg Trp Thr Asn Tyr Leu Arg Pro
    50                  55                  60

Asp Ile Lys Arg Gly Arg Phe Ser Phe Glu Glu Glu Thr Ile Ile
65                  70                  75                  80

Gln Leu His Ser Ile Met Gly Asn Lys Trp Ser Ala Ile Ala Ala Arg
                85                  90                  95

Leu Pro Gly Arg Thr Asp Asn Glu Ile Lys Asn Tyr Trp Asn Thr His
            100                 105                 110

Ile Arg Lys Arg Leu Leu Lys Met Gly Ile Asp Pro Val Thr His Thr
        115                 120                 125

Pro Arg Leu Asp Leu Leu Asp Ile Ser Ser Ile Leu Ser Ser Ser Ile
```

```
                  130                 135                 140
Tyr Asn Ser Ser His His His His His Gln Gln His Met Asn
145                 150                 155                 160

Met Ser Arg Leu Met Met Ser Asp Gly Asn His Gln Pro Leu Val Asn
                165                 170                 175

Pro Glu Ile Leu Lys Leu Ala Thr Ser Leu Phe Ser Asn Gln Asn His
                180                 185                 190

Pro Asn Asn Thr His Glu Asn Asn Thr Val Asn Gln Thr Glu Val Asn
            195                 200                 205

Gln Tyr Gln Thr Gly Tyr Asn Met Pro Gly Asn Glu Glu Leu Gln Ser
210                 215                 220

Trp Phe Pro Ile Met Asp Gln Phe Thr Asn Phe Gln Asp Leu Met Pro
225                 230                 235                 240

Met Lys Thr Thr Val Gln Asn Ser Leu Ser Tyr Asp Asp Cys Ser
                245                 250                 255

Lys Ser Asn Phe Val Leu Glu Pro Tyr Tyr Ser Asp Phe Ala Ser Val
                260                 265                 270

Leu Thr Thr Pro Ser Ser Ser Pro Thr Pro Leu Asn Ser Ser Ser Ser
            275                 280                 285

Thr Tyr Ile Asn Ser Ser Thr Cys Ser Thr Glu Asp Glu Lys Glu Ser
        290                 295                 300

Tyr Tyr Ser Asp Asn Ile Thr Asn Tyr Ser Phe Asp Val Asn Gly Phe
305                 310                 315                 320

Leu Gln Phe Gln

<210> SEQ ID NO 133
<211> LENGTH: 2684
<212> TYPE: DNA
<213> ORGANISM: Arabidopsis thaliana
<220> FEATURE:
<221> NAME/KEY: CDS
<222> LOCATION: (898)..(2475)

<400> SEQUENCE: 133
acttcttctt cttcttcttc tcgatttctt actgttttct tatccaacga aatctggaat      60
taaaaatgga atctttatcg aatccaagct gattttgttt ctttcattga atcatctctc     120
taaagtggaa ttttgtaaag agaagatctg aagttgtgta gaggagctta gtgatggaga     180
caaattcgtc tggagaagat ctggttatta agactcggaa gccatatacg ataacaaagc     240
aacgtgaaag gtggactgag gaagaacata atagattcat tgaagctttg aggctttatg     300
gtagagcatg gcagaagatt gaagaacatg tagcaacaaa aactgctgtc cagataagaa     360
gtcacgctca gaattttttc tccaaggtaa aatcggttaa ttttgaaatg atgttctcat     420
cttcattggc ttaatgctta agacttattg aaagccaggc aagttttctg cttcttttgc     480
ttcttagtca ggagatagat agattacgtt tttagagttt agtaatgagc aataagtctt     540
aaaatagttg gagaaatgac gagatgtaat cgtttctttt tgtttatgcc tatatcttgt     600
taatccacaa acatgtacat agattcttca gaagaatgtt agtttcttta gattcttcag     660
ataaacttgt gtcttcttac cgattctgag gtagtggcaa aagtgggctg agtgctagaa     720
atttttgaat gttccttgtg ataagccata gaggtaaacc atttttgatt ttccagttct     780
gtcatttaaa cttgttagtg tcattagatt tttgtttgtt tacgtttgtt tagagggtaa     840
caaaactact ctcatctctc tcaggtagag aaagaggctg aagctaaagg tgtagct         897 atg ggt caa gcg cta gac ata gct att cct cct cca cgg cct aag cgt       945
```

```
Met Gly Gln Ala Leu Asp Ile Ala Ile Pro Pro Arg Pro Lys Arg
 1               5                  10                  15 aaa cca aac aat cct tat cct cga aag acg gga agt gga acg atc ctt      993
Lys Pro Asn Asn Pro Tyr Pro Arg Lys Thr Gly Ser Gly Thr Ile Leu
             20                  25                  30 atg tca aaa acg ggt gtg aat gat gga aaa gag tcc ctt gga tca gaa     1041
Met Ser Lys Thr Gly Val Asn Asp Gly Lys Glu Ser Leu Gly Ser Glu
         35                  40                  45 aaa gtg tcg cat cct gag atg gcc aat gaa gat cga caa caa tca aag     1089
Lys Val Ser His Pro Glu Met Ala Asn Glu Asp Arg Gln Gln Ser Lys
     50                  55                  60 cct gaa gag aaa act ctg cag gaa gac aac tgt tca gat tgt ttc act     1137
Pro Glu Glu Lys Thr Leu Gln Glu Asp Asn Cys Ser Asp Cys Phe Thr
 65                  70                  75                  80 cat cag tat ctc tct gct gca tcc tcc atg aat aaa agt tgt ata gag     1185
His Gln Tyr Leu Ser Ala Ala Ser Ser Met Asn Lys Ser Cys Ile Glu
                 85                  90                  95 aca tca aac gca agc act ttc cgc gag ttc ttg cct tca cgg gaa gag     1233
Thr Ser Asn Ala Ser Thr Phe Arg Glu Phe Leu Pro Ser Arg Glu Glu
            100                 105                 110 gga agt cag aat aac agg gta aga aag gag tca aac tca gat ttg aat     1281
Gly Ser Gln Asn Asn Arg Val Arg Lys Glu Ser Asn Ser Asp Leu Asn
        115                 120                 125 gca aaa tct ctg gaa aac ggt aat gag caa gga cct cag act tat ccg     1329
Ala Lys Ser Leu Glu Asn Gly Asn Glu Gln Gly Pro Gln Thr Tyr Pro
    130                 135                 140 atg cat atc cct gtg cta gtg cca ttg ggg agc tca ata aca agt tct     1377
Met His Ile Pro Val Leu Val Pro Leu Gly Ser Ser Ile Thr Ser Ser
145                 150                 155                 160 cta tca cat cct cct tca gag cca gat agt cat ccc cac aca gtt gca     1425
Leu Ser His Pro Pro Ser Glu Pro Asp Ser His Pro His Thr Val Ala
                165                 170                 175 gga gat tat cag tcg ttt cct aat cat ata atg tca acc ctt tta caa     1473
Gly Asp Tyr Gln Ser Phe Pro Asn His Ile Met Ser Thr Leu Leu Gln
            180                 185                 190 aca ccg gct ctt tat act gcc gca act ttc gcc tca tca ttt tgg cct     1521
Thr Pro Ala Leu Tyr Thr Ala Ala Thr Phe Ala Ser Ser Phe Trp Pro
        195                 200                 205 ccc gat tct agt ggt ggc tca cct gtt cca ggg aac tca cct ccg aat     1569
Pro Asp Ser Ser Gly Gly Ser Pro Val Pro Gly Asn Ser Pro Pro Asn
    210                 215                 220 ctg gct gcc atg gcc gca gcc act gtt gca gct gct agt gct tgg tgg     1617
Leu Ala Ala Met Ala Ala Ala Thr Val Ala Ala Ala Ser Ala Trp Trp
225                 230                 235                 240 gct gcc aat gga tta tta cct tta tgt gct cct ctt agt tca ggt ggt     1665
Ala Ala Asn Gly Leu Leu Pro Leu Cys Ala Pro Leu Ser Ser Gly Gly
                245                 250                 255 ttc act agt cat cct cca tct act ttt gga cca tca tgt gat gta gag     1713
Phe Thr Ser His Pro Pro Ser Thr Phe Gly Pro Ser Cys Asp Val Glu
            260                 265                 270 tac aca aaa gca agc act tta caa cat ggt tct gtg cag agc cga gag     1761
Tyr Thr Lys Ala Ser Thr Leu Gln His Gly Ser Val Gln Ser Arg Glu
        275                 280                 285 caa gaa cac ttc gag gca tca aag gct cga tct tca ctg gac tca gag     1809
Gln Glu His Phe Glu Ala Ser Lys Ala Arg Ser Ser Leu Asp Ser Glu
    290                 295                 300 gat gtt gaa aat aag agt aaa cca gtt tgt cat gag cag cct tct gca     1857
Asp Val Glu Asn Lys Ser Lys Pro Val Cys His Glu Gln Pro Ser Ala
305                 310                 315                 320
```

-continued

```
aca cct gag agt gat gca aag ggt tca gat gga gca gga gac aga aaa    1905
Thr Pro Glu Ser Asp Ala Lys Gly Ser Asp Gly Ala Gly Asp Arg Lys
            325                 330                 335 caa gtt gac cgg tcc tcg tgt ggc tca aac act ccg tcg agt agt gat    1953
Gln Val Asp Arg Ser Ser Cys Gly Ser Asn Thr Pro Ser Ser Ser Asp
        340                 345                 350 gat gtt gag gcg gat gca tca gaa agg caa gag gat ggc acc aat ggt    2001
Asp Val Glu Ala Asp Ala Ser Glu Arg Gln Glu Asp Gly Thr Asn Gly
    355                 360                 365 gag gtg aaa gaa acg aat gaa gac act aat aaa cct caa act tca gag    2049
Glu Val Lys Glu Thr Asn Glu Asp Thr Asn Lys Pro Gln Thr Ser Glu
370                 375                 380 tcc aat gca cgc cgc agt aga atc agc tcc aat ata acc gat cca tgg    2097
Ser Asn Ala Arg Arg Ser Arg Ile Ser Ser Asn Ile Thr Asp Pro Trp
385                 390                 395                 400 aag tct gtg tct gac gag ggt cga att gcc ttc caa gct ctc ttc tcc    2145
Lys Ser Val Ser Asp Glu Gly Arg Ile Ala Phe Gln Ala Leu Phe Ser
            405                 410                 415 aga gag gta ttg ccg caa agt ttt aca tat cga gaa gaa cac aga gag    2193
Arg Glu Val Leu Pro Gln Ser Phe Thr Tyr Arg Glu Glu His Arg Glu
        420                 425                 430 gaa gaa caa caa caa caa gaa caa aga tat cca atg gca ctt gat ctt    2241
Glu Glu Gln Gln Gln Gln Glu Gln Arg Tyr Pro Met Ala Leu Asp Leu
    435                 440                 445 aac ttc aca gct cag tta aca cca gtt gat gat caa gag gag aag aga    2289
Asn Phe Thr Ala Gln Leu Thr Pro Val Asp Asp Gln Glu Glu Lys Arg
450                 455                 460 aac aca gga ttt ctt gga atc gga tta gat gct tca aag cta atg agt    2337
Asn Thr Gly Phe Leu Gly Ile Gly Leu Asp Ala Ser Lys Leu Met Ser
465                 470                 475                 480 aga gga aga aca ggt ttt aaa cca tac aaa aga tgt tcc atg gaa gcc    2385
Arg Gly Arg Thr Gly Phe Lys Pro Tyr Lys Arg Cys Ser Met Glu Ala
            485                 490                 495 aaa gaa agt aga atc ctc aac aac aat cct atc att cat gtg gaa cag    2433
Lys Glu Ser Arg Ile Leu Asn Asn Asn Pro Ile Ile His Val Glu Gln
        500                 505                 510 aaa gat ccc aaa cgg atg cgg ttg gaa act caa gct tcc aca           2475
Lys Asp Pro Lys Arg Met Arg Leu Glu Thr Gln Ala Ser Thr
    515                 520                 525 tgagactcta ttttcatctg atctgttgtt tgtactctgt ttttaagttt tcaagaccac   2535
tgctacattt tcttttttctt ttgaggcctt tgtatttgtt tccttgtcca tagtcttcct  2595
gtaacatttg actctgtatt attcaacaaa tcataaactg tttaatcttt ttttttccag   2655
aaaaaaaaaa aagaaaaaaa aaaaaaaaa                                    2684
```

<210> SEQ ID NO 134
<211> LENGTH: 526
<212> TYPE: PRT
<213> ORGANISM: Arabidopsis thaliana

<400> SEQUENCE: 134

```
Met Gly Gln Ala Leu Asp Ile Ala Ile Pro Pro Arg Pro Lys Arg
  1               5                  10                  15

Lys Pro Asn Asn Pro Tyr Pro Arg Lys Thr Gly Ser Gly Thr Ile Leu
             20                  25                  30

Met Ser Lys Thr Gly Val Asn Asp Gly Lys Glu Ser Leu Gly Ser Glu
         35                  40                  45

Lys Val Ser His Pro Glu Met Ala Asn Glu Asp Arg Gln Gln Ser Lys
     50                  55                  60
```

-continued

```
Pro Glu Glu Lys Thr Leu Gln Glu Asp Asn Cys Ser Asp Cys Phe Thr
 65                  70                  75                  80

His Gln Tyr Leu Ser Ala Ala Ser Ser Met Asn Lys Ser Cys Ile Glu
                 85                  90                  95

Thr Ser Asn Ala Ser Thr Phe Arg Glu Phe Leu Pro Ser Arg Glu Glu
            100                 105                 110

Gly Ser Gln Asn Asn Arg Val Arg Lys Glu Ser Asn Ser Asp Leu Asn
            115                 120                 125

Ala Lys Ser Leu Glu Asn Gly Asn Glu Gln Gly Pro Gln Thr Tyr Pro
130                 135                 140

Met His Ile Pro Val Leu Val Pro Leu Gly Ser Ser Ile Thr Ser Ser
145                 150                 155                 160

Leu Ser His Pro Pro Ser Glu Pro Asp Ser His Pro His Thr Val Ala
                165                 170                 175

Gly Asp Tyr Gln Ser Phe Pro Asn His Ile Met Ser Thr Leu Leu Gln
            180                 185                 190

Thr Pro Ala Leu Tyr Thr Ala Ala Thr Phe Ala Ser Ser Phe Trp Pro
            195                 200                 205

Pro Asp Ser Ser Gly Gly Ser Pro Val Pro Gly Asn Ser Pro Pro Asn
210                 215                 220

Leu Ala Ala Met Ala Ala Ala Thr Val Ala Ala Ala Ser Ala Trp Trp
225                 230                 235                 240

Ala Ala Asn Gly Leu Leu Pro Leu Cys Ala Pro Leu Ser Ser Gly Gly
                245                 250                 255

Phe Thr Ser His Pro Pro Ser Thr Phe Gly Pro Ser Cys Asp Val Glu
            260                 265                 270

Tyr Thr Lys Ala Ser Thr Leu Gln His Gly Ser Val Gln Ser Arg Glu
            275                 280                 285

Gln Glu His Phe Glu Ala Ser Lys Ala Arg Ser Ser Leu Asp Ser Glu
            290                 295                 300

Asp Val Glu Asn Lys Ser Lys Pro Val Cys His Glu Gln Pro Ser Ala
305                 310                 315                 320

Thr Pro Glu Ser Asp Ala Lys Gly Ser Asp Gly Ala Gly Asp Arg Lys
                325                 330                 335

Gln Val Asp Arg Ser Ser Cys Gly Ser Asn Thr Pro Ser Ser Ser Asp
            340                 345                 350

Asp Val Glu Ala Asp Ala Ser Glu Arg Gln Glu Asp Gly Thr Asn Gly
            355                 360                 365

Glu Val Lys Glu Thr Asn Glu Asp Thr Asn Lys Pro Gln Thr Ser Glu
370                 375                 380

Ser Asn Ala Arg Arg Ser Arg Ile Ser Ser Asn Ile Thr Asp Pro Trp
385                 390                 395                 400

Lys Ser Val Ser Asp Glu Gly Arg Ile Ala Phe Gln Ala Leu Phe Ser
                405                 410                 415

Arg Glu Val Leu Pro Gln Ser Phe Thr Tyr Arg Glu Glu His Arg Glu
            420                 425                 430

Glu Glu Gln Gln Gln Gln Glu Gln Arg Tyr Pro Met Ala Leu Asp Leu
            435                 440                 445

Asn Phe Thr Ala Gln Leu Thr Pro Val Asp Asp Gln Glu Glu Lys Arg
            450                 455                 460

Asn Thr Gly Phe Leu Gly Ile Gly Leu Asp Ala Ser Lys Leu Met Ser
465                 470                 475                 480
```

```
Arg Gly Arg Thr Gly Phe Lys Pro Tyr Lys Arg Cys Ser Met Glu Ala
                485                 490                 495

Lys Glu Ser Arg Ile Leu Asn Asn Pro Ile Ile His Val Glu Gln
            500                 505                 510

Lys Asp Pro Lys Arg Met Arg Leu Glu Thr Gln Ala Ser Thr
        515                 520                 525

<210> SEQ ID NO 135
<211> LENGTH: 1938
<212> TYPE: DNA
<213> ORGANISM: Arabidopsis thaliana
<220> FEATURE:
<221> NAME/KEY: CDS
<222> LOCATION: (1)..(1935)

<400> SEQUENCE: 135
```

| | | | | | | | | | | | | | | | | |
|---|---|---|---|---|---|---|---|---|---|---|---|---|---|---|---|---|
| atg | act | aat | aca | tct | gga | gaa | gaa | tta | tta | gct | aag | gca | aga | aag | | 48 |
| Met | Asp | Thr | Asn | Thr | Ser | Gly | Glu | Glu | Leu | Leu | Ala | Lys | Ala | Arg | Lys | |
| 1 | | | | 5 | | | | | 10 | | | | | 15 | | |
| cca | tat | aca | ata | aca | aag | cag | cga | gag | cga | tgg | act | gag | gat | gag | cat | 96 |
| Pro | Tyr | Thr | Ile | Thr | Lys | Gln | Arg | Glu | Arg | Trp | Thr | Glu | Asp | Glu | His | |
| | | | 20 | | | | | 25 | | | | | 30 | | | |
| gag | agg | ttt | cta | gaa | gcc | ttg | agg | ctt | tat | gga | aga | gct | tgg | caa | cga | 144 |
| Glu | Arg | Phe | Leu | Glu | Ala | Leu | Arg | Leu | Tyr | Gly | Arg | Ala | Trp | Gln | Arg | |
| | 35 | | | | | 40 | | | | | 45 | | | | | |
| att | gaa | gaa | cat | att | ggg | aca | aag | act | gct | gtt | cag | atc | aga | agt | cat | 192 |
| Ile | Glu | Glu | His | Ile | Gly | Thr | Lys | Thr | Ala | Val | Gln | Ile | Arg | Ser | His | |
| 50 | | | | | 55 | | | | | 60 | | | | | | |
| gca | caa | aag | ttc | ttc | aca | aag | ttg | gag | aaa | gag | gct | gaa | gtt | aaa | ggc | 240 |
| Ala | Gln | Lys | Phe | Phe | Thr | Lys | Leu | Glu | Lys | Glu | Ala | Glu | Val | Lys | Gly | |
| 65 | | | | | 70 | | | | | 75 | | | | | 80 | |
| atc | cct | gtt | tgc | caa | gct | ttg | gac | ata | gaa | att | ccg | cct | cct | cgt | cct | 288 |
| Ile | Pro | Val | Cys | Gln | Ala | Leu | Asp | Ile | Glu | Ile | Pro | Pro | Pro | Arg | Pro | |
| | | | | 85 | | | | | 90 | | | | | 95 | | |
| aaa | cga | aaa | ccc | aat | act | cct | tat | cct | cga | aag | cct | ggg | aac | aac | ggt | 336 |
| Lys | Arg | Lys | Pro | Asn | Thr | Pro | Tyr | Pro | Arg | Lys | Pro | Gly | Asn | Asn | Gly | |
| | | | 100 | | | | | 105 | | | | | 110 | | | |
| aca | tct | tcc | tct | caa | gta | tca | tca | gca | aaa | gat | gca | aaa | ctt | gtt | tca | 384 |
| Thr | Ser | Ser | Ser | Gln | Val | Ser | Ser | Ala | Lys | Asp | Ala | Lys | Leu | Val | Ser | |
| | | 115 | | | | | 120 | | | | | 125 | | | | |
| tcg | gcc | tct | tct | tca | cag | ttg | aat | cag | gcg | ttc | ttg | gat | ttg | gaa | aaa | 432 |
| Ser | Ala | Ser | Ser | Ser | Gln | Leu | Asn | Gln | Ala | Phe | Leu | Asp | Leu | Glu | Lys | |
| | 130 | | | | | 135 | | | | | 140 | | | | | |
| atg | ccg | ttc | tct | gag | aaa | aca | tca | act | gga | aaa | gaa | aat | caa | gat | gag | 480 |
| Met | Pro | Phe | Ser | Glu | Lys | Thr | Ser | Thr | Gly | Lys | Glu | Asn | Gln | Asp | Glu | |
| 145 | | | | | 150 | | | | | 155 | | | | | 160 | |
| aat | tgc | tcg | ggt | gtt | tct | act | gtg | aac | aag | tat | ccc | tta | cca | acg | aaa | 528 |
| Asn | Cys | Ser | Gly | Val | Ser | Thr | Val | Asn | Lys | Tyr | Pro | Leu | Pro | Thr | Lys | |
| | | | | 165 | | | | | 170 | | | | | 175 | | |
| cag | gta | agt | ggc | gac | att | gaa | aca | agt | aag | acc | tca | act | gtg | gac | aac | 576 |
| Gln | Val | Ser | Gly | Asp | Ile | Glu | Thr | Ser | Lys | Thr | Ser | Thr | Val | Asp | Asn | |
| | | | 180 | | | | | 185 | | | | | 190 | | | |
| gcg | gtt | caa | gat | gtt | ccc | aag | aag | aac | aaa | gac | aaa | gat | ggt | aac | gat | 624 |
| Ala | Val | Gln | Asp | Val | Pro | Lys | Lys | Asn | Lys | Asp | Lys | Asp | Gly | Asn | Asp | |
| | | 195 | | | | | 200 | | | | | 205 | | | | |
| ggt | act | act | gtg | cac | agc | atg | caa | aac | tac | cct | tgg | cat | ttc | cac | gca | 672 |
| Gly | Thr | Thr | Val | His | Ser | Met | Gln | Asn | Tyr | Pro | Trp | His | Phe | His | Ala | |
| | 210 | | | | | 215 | | | | | 220 | | | | | |
| gat | att | gtg | aac | ggg | aat | ata | gca | aaa | tgc | cct | caa | aat | cat | ccc | tca | 720 |
| Asp | Ile | Val | Asn | Gly | Asn | Ile | Ala | Lys | Cys | Pro | Gln | Asn | His | Pro | Ser | |
| 225 | | | | | 230 | | | | | 235 | | | | | 240 | |

|  |  |
|---|---|
| ggt atg gta tct caa gac ttc atg ttt cat cct atg aga gaa gaa act<br>Gly Met Val Ser Gln Asp Phe Met Phe His Pro Met Arg Glu Glu Thr<br>245 250 255 | 768 |
| cac ggg cac gca aat ctt caa gct aca aca gca tct gct act act aca<br>His Gly His Ala Asn Leu Gln Ala Thr Thr Ala Ser Ala Thr Thr Thr<br>260 265 270 | 816 |
| gct tct cat caa gcg ttt cca gct tgt cat tca cag gat gat tac cgt<br>Ala Ser His Gln Ala Phe Pro Ala Cys His Ser Gln Asp Asp Tyr Arg<br>275 280 285 | 864 |
| tcg ttt ctc cag ata tca tct act ttc tcc aat ctt att atg tca act<br>Ser Phe Leu Gln Ile Ser Ser Thr Phe Ser Asn Leu Ile Met Ser Thr<br>290 295 300 | 912 |
| ctc cta cag aat cct gca gct cat gct gca gct aca ttc gct gct tcg<br>Leu Leu Gln Asn Pro Ala Ala His Ala Ala Ala Thr Phe Ala Ala Ser<br>305 310 315 320 | 960 |
| gtc tgg cct tat gcg agt gtc ggg aat tct ggt gat tca tca acc cca<br>Val Trp Pro Tyr Ala Ser Val Gly Asn Ser Gly Asp Ser Ser Thr Pro<br>325 330 335 | 1008 |
| atg agc tct tct cct cca agt ata act gcc att gcc gct gct aca gta<br>Met Ser Ser Ser Pro Pro Ser Ile Thr Ala Ile Ala Ala Ala Thr Val<br>340 345 350 | 1056 |
| gct gct gca act gct tgg tgg gct tct cat gga ctt ctt cct gta tgc<br>Ala Ala Ala Thr Ala Trp Trp Ala Ser His Gly Leu Leu Pro Val Cys<br>355 360 365 | 1104 |
| gct cca gct cca ata aca tgt gtt cca ttc tca act gtt gca gtt cca<br>Ala Pro Ala Pro Ile Thr Cys Val Pro Phe Ser Thr Val Ala Val Pro<br>370 375 380 | 1152 |
| act cca gca atg act gaa atg gat acc gtt gaa aat act caa ccg ttt<br>Thr Pro Ala Met Thr Glu Met Asp Thr Val Glu Asn Thr Gln Pro Phe<br>385 390 395 400 | 1200 |
| gag aaa caa aac aca gct ctg caa gat caa aac ttg gct tcg aaa tct<br>Glu Lys Gln Asn Thr Ala Leu Gln Asp Gln Asn Leu Ala Ser Lys Ser<br>405 410 415 | 1248 |
| cca gct tca tca tct gat gat tca gat gag act gga gta acc aag cta<br>Pro Ala Ser Ser Ser Asp Asp Ser Asp Glu Thr Gly Val Thr Lys Leu<br>420 425 430 | 1296 |
| aat gcc gac tca aaa acc aat gat gat aaa att gag gag gtt gtt gtt<br>Asn Ala Asp Ser Lys Thr Asn Asp Asp Lys Ile Glu Glu Val Val Val<br>435 440 445 | 1344 |
| act gcc gct gtg cat gac tca aac act gcc cag aag aaa aat ctt gtg<br>Thr Ala Ala Val His Asp Ser Asn Thr Ala Gln Lys Lys Asn Leu Val<br>450 455 460 | 1392 |
| gac cgc tca tcc tgt ggc tca aat aca cct tca ggg agt gac gca gaa<br>Asp Arg Ser Ser Cys Gly Ser Asn Thr Pro Ser Gly Ser Asp Ala Glu<br>465 470 475 480 | 1440 |
| act gat gca tta gat aaa atg gag aaa gat aaa gag gat gtg aag gag<br>Thr Asp Ala Leu Asp Lys Met Glu Lys Asp Lys Glu Asp Val Lys Glu<br>485 490 495 | 1488 |
| aca gat gag aat cag cca gat gtt att gag tta aat aac cgt aag att<br>Thr Asp Glu Asn Gln Pro Asp Val Ile Glu Leu Asn Asn Arg Lys Ile<br>500 505 510 | 1536 |
| aaa atg aga gac aac aac agc aac aac aat gca act act gat tcg tgg<br>Lys Met Arg Asp Asn Asn Ser Asn Asn Asn Ala Thr Thr Asp Ser Trp<br>515 520 525 | 1584 |
| aag gaa gtc tcc gaa gag ggt cgt ata gcg ttt cag gct ctc ttt gca<br>Lys Glu Val Ser Glu Glu Gly Arg Ile Ala Phe Gln Ala Leu Phe Ala<br>530 535 540 | 1632 |
| aga gaa aga ttg cct caa agc ttt tcg cct cct caa gtg gca gag aat<br>Arg Glu Arg Leu Pro Gln Ser Phe Ser Pro Pro Gln Val Ala Glu Asn | 1680 |

```
                545                 550                 555                 560
gtg aat aga aaa caa agt gac acg tca atg cca ttg gct cct aat ttc       1728
Val Asn Arg Lys Gln Ser Asp Thr Ser Met Pro Leu Ala Pro Asn Phe
            565                 570                 575 aaa agc cag gat tct tgt gct gca gac caa gaa gga gta gta atg atc       1776
Lys Ser Gln Asp Ser Cys Ala Ala Asp Gln Glu Gly Val Val Met Ile
                580                 585                 590 ggt gtt gga aca tgc aag agt ctt aaa acg aga cag aca gga ttt aag       1824
Gly Val Gly Thr Cys Lys Ser Leu Lys Thr Arg Gln Thr Gly Phe Lys
            595                 600                 605 cca tac aag aga tgt tca atg gaa gtg aaa gag agc caa gtt ggg aac       1872
Pro Tyr Lys Arg Cys Ser Met Glu Val Lys Glu Ser Gln Val Gly Asn
        610                 615                 620 ata aac aat caa agt gat gaa aaa gtc tgc aaa agg ctt cga ttg gaa       1920
Ile Asn Asn Gln Ser Asp Glu Lys Val Cys Lys Arg Leu Arg Leu Glu
625                 630                 635                 640 gga gaa gct tct aca tga                                                1938
Gly Glu Ala Ser Thr
            645

<210> SEQ ID NO 136
<211> LENGTH: 645
<212> TYPE: PRT
<213> ORGANISM: Arabidopsis thaliana

<400> SEQUENCE: 136

Met Asp Thr Asn Thr Ser Gly Glu Glu Leu Leu Ala Lys Ala Arg Lys
1               5                   10                  15

Pro Tyr Thr Ile Thr Lys Gln Arg Glu Arg Trp Thr Glu Asp Glu His
            20                  25                  30

Glu Arg Phe Leu Glu Ala Leu Arg Leu Tyr Gly Arg Ala Trp Gln Arg
        35                  40                  45

Ile Glu Glu His Ile Gly Thr Lys Thr Ala Val Gln Ile Arg Ser His
    50                  55                  60

Ala Gln Lys Phe Phe Thr Lys Leu Glu Lys Glu Ala Glu Val Lys Gly
65                  70                  75                  80

Ile Pro Val Cys Gln Ala Leu Asp Ile Glu Ile Pro Pro Arg Pro
                85                  90                  95

Lys Arg Lys Pro Asn Thr Pro Tyr Pro Arg Lys Pro Gly Asn Asn Gly
            100                 105                 110

Thr Ser Ser Ser Gln Val Ser Ser Ala Lys Asp Ala Lys Leu Val Ser
        115                 120                 125

Ser Ala Ser Ser Gln Leu Asn Gln Ala Phe Leu Asp Leu Glu Lys
    130                 135                 140

Met Pro Phe Ser Glu Lys Thr Ser Thr Gly Lys Glu Asn Gln Asp Glu
145                 150                 155                 160

Asn Cys Ser Gly Val Ser Thr Val Asn Lys Tyr Pro Leu Pro Thr Lys
                165                 170                 175

Gln Val Ser Gly Asp Ile Glu Thr Ser Lys Thr Ser Thr Val Asp Asn
            180                 185                 190

Ala Val Gln Asp Val Pro Lys Lys Asn Lys Asp Lys Asp Gly Asn Asp
        195                 200                 205

Gly Thr Thr Val His Ser Met Gln Asn Tyr Pro Trp His Phe His Ala
    210                 215                 220

Asp Ile Val Asn Gly Asn Ile Ala Lys Cys Pro Gln Asn His Pro Ser
225                 230                 235                 240
```

-continued

```
Gly Met Val Ser Gln Asp Phe Met Phe His Pro Met Arg Glu Glu Thr
                245                 250                 255

His Gly His Ala Asn Leu Gln Ala Thr Thr Ala Ser Ala Thr Thr Thr
            260                 265                 270

Ala Ser His Gln Ala Phe Pro Ala Cys His Ser Gln Asp Asp Tyr Arg
        275                 280                 285

Ser Phe Leu Gln Ile Ser Ser Thr Phe Ser Asn Leu Ile Met Ser Thr
    290                 295                 300

Leu Leu Gln Asn Pro Ala Ala His Ala Ala Thr Phe Ala Ala Ser
305                 310                 315                 320

Val Trp Pro Tyr Ala Ser Val Gly Asn Ser Gly Asp Ser Ser Thr Pro
                325                 330                 335

Met Ser Ser Pro Pro Ser Ile Thr Ala Ile Ala Ala Thr Val
            340                 345                 350

Ala Ala Ala Thr Ala Trp Trp Ala Ser His Gly Leu Leu Pro Val Cys
            355                 360                 365

Ala Pro Ala Pro Ile Thr Cys Val Pro Phe Ser Thr Val Ala Val Pro
        370                 375                 380

Thr Pro Ala Met Thr Glu Met Asp Thr Val Glu Asn Thr Gln Pro Phe
385                 390                 395                 400

Glu Lys Gln Asn Thr Ala Leu Gln Asp Gln Asn Leu Ala Ser Lys Ser
                405                 410                 415

Pro Ala Ser Ser Ser Asp Asp Ser Asp Glu Thr Gly Val Thr Lys Leu
            420                 425                 430

Asn Ala Asp Ser Lys Thr Asn Asp Asp Lys Ile Glu Glu Val Val Val
        435                 440                 445

Thr Ala Ala Val His Asp Ser Asn Thr Ala Gln Lys Lys Asn Leu Val
450                 455                 460

Asp Arg Ser Ser Cys Gly Ser Asn Thr Pro Ser Gly Ser Asp Ala Glu
465                 470                 475                 480

Thr Asp Ala Leu Asp Lys Met Glu Lys Asp Lys Glu Asp Val Lys Glu
                485                 490                 495

Thr Asp Glu Asn Gln Pro Asp Val Ile Glu Leu Asn Asn Arg Lys Ile
            500                 505                 510

Lys Met Arg Asp Asn Asn Ser Asn Asn Ala Thr Thr Asp Ser Trp
        515                 520                 525

Lys Glu Val Ser Glu Glu Gly Arg Ile Ala Phe Gln Ala Leu Phe Ala
530                 535                 540

Arg Glu Arg Leu Pro Gln Ser Phe Ser Pro Gln Val Ala Glu Asn
545                 550                 555                 560

Val Asn Arg Lys Gln Ser Asp Thr Ser Met Pro Leu Ala Pro Asn Phe
                565                 570                 575

Lys Ser Gln Asp Ser Cys Ala Ala Asp Gln Glu Gly Val Val Met Ile
            580                 585                 590

Gly Val Gly Thr Cys Lys Ser Leu Lys Thr Arg Gln Thr Gly Phe Lys
        595                 600                 605

Pro Tyr Lys Arg Cys Ser Met Glu Val Lys Glu Ser Gln Val Gly Asn
    610                 615                 620

Ile Asn Asn Gln Ser Asp Glu Lys Val Cys Lys Arg Leu Arg Leu Glu
625                 630                 635                 640

Gly Glu Ala Ser Thr
                645
```

<210> SEQ ID NO 137
<211> LENGTH: 1989
<212> TYPE: DNA
<213> ORGANISM: Arabidopsis thaliana
<220> FEATURE:
<221> NAME/KEY: CDS
<222> LOCATION: (1)..(1986)

<400> SEQUENCE: 137

| | | | | | | | | | | | | | | | | |
|---|---|---|---|---|---|---|---|---|---|---|---|---|---|---|---|---|
| atg | aat | atg | agt | gat | tta | ggt | tgg | gat | gat | gaa | gat | aaa | tcg | gtg | gtt | 48 |
| Met | Asn | Met | Ser | Asp | Leu | Gly | Trp | Asp | Asp | Glu | Asp | Lys | Ser | Val | Val | |
| 1 | | | | 5 | | | | | 10 | | | | | 15 | | |
| agt | gct | gtt | tta | ggg | cat | tta | gct | tct | gat | ttt | ctt | cga | gca | aac | tct | 96 |
| Ser | Ala | Val | Leu | Gly | His | Leu | Ala | Ser | Asp | Phe | Leu | Arg | Ala | Asn | Ser | |
| | | | 20 | | | | | 25 | | | | | 30 | | | |
| aat | tcg | aat | cag | aat | ctc | ttt | ctt | gtt | atg | gga | act | gat | gat | act | ctg | 144 |
| Asn | Ser | Asn | Gln | Asn | Leu | Phe | Leu | Val | Met | Gly | Thr | Asp | Asp | Thr | Leu | |
| | | 35 | | | | | 40 | | | | | 45 | | | | |
| aat | aag | aag | ctc | tct | agt | ctc | gtt | gat | tgg | cca | aac | tcg | gag | aat | ttc | 192 |
| Asn | Lys | Lys | Leu | Ser | Ser | Leu | Val | Asp | Trp | Pro | Asn | Ser | Glu | Asn | Phe | |
| | 50 | | | | | 55 | | | | | 60 | | | | | |
| agc | tgg | aac | tac | gct | att | ttc | tgg | caa | caa | acc | atg | tct | aga | tcc | gga | 240 |
| Ser | Trp | Asn | Tyr | Ala | Ile | Phe | Trp | Gln | Gln | Thr | Met | Ser | Arg | Ser | Gly | |
| 65 | | | | | 70 | | | | | 75 | | | | | 80 | |
| caa | caa | gtc | tta | ggt | tgg | gga | gat | ggg | tgt | tgt | cga | gag | cct | aat | gag | 288 |
| Gln | Gln | Val | Leu | Gly | Trp | Gly | Asp | Gly | Cys | Cys | Arg | Glu | Pro | Asn | Glu | |
| | | | | 85 | | | | | 90 | | | | | 95 | | |
| gaa | gag | gaa | tca | aaa | gtt | gtt | agg | tct | tat | aat | ttt | aac | aac | atg | ggg | 336 |
| Glu | Glu | Glu | Ser | Lys | Val | Val | Arg | Ser | Tyr | Asn | Phe | Asn | Asn | Met | Gly | |
| | | | 100 | | | | | 105 | | | | | 110 | | | |
| gca | gag | gaa | gag | aca | tgg | caa | gat | atg | agg | aag | aga | gtg | ttg | cag | aag | 384 |
| Ala | Glu | Glu | Glu | Thr | Trp | Gln | Asp | Met | Arg | Lys | Arg | Val | Leu | Gln | Lys | |
| | | 115 | | | | | 120 | | | | | 125 | | | | |
| ctt | cat | agg | ttg | ttt | ggt | gga | tct | gat | gaa | gac | aat | tat | gct | ttg | agc | 432 |
| Leu | His | Arg | Leu | Phe | Gly | Gly | Ser | Asp | Glu | Asp | Asn | Tyr | Ala | Leu | Ser | |
| | 130 | | | | | 135 | | | | | 140 | | | | | |
| tta | gag | aaa | gtt | act | gct | act | gag | att | ttc | ttc | tta | gct | tcc | atg | tat | 480 |
| Leu | Glu | Lys | Val | Thr | Ala | Thr | Glu | Ile | Phe | Phe | Leu | Ala | Ser | Met | Tyr | |
| 145 | | | | | 150 | | | | | 155 | | | | | 160 | |
| ttc | ttc | ttc | aat | cac | ggt | gaa | ggc | ggt | cct | ggg | agg | tgt | tat | tct | tca | 528 |
| Phe | Phe | Phe | Asn | His | Gly | Glu | Gly | Gly | Pro | Gly | Arg | Cys | Tyr | Ser | Ser | |
| | | | | 165 | | | | | 170 | | | | | 175 | | |
| ggg | aaa | cat | gtg | tgg | ctc | tct | gat | gca | gtt | aac | tct | gag | tct | gac | tat | 576 |
| Gly | Lys | His | Val | Trp | Leu | Ser | Asp | Ala | Val | Asn | Ser | Glu | Ser | Asp | Tyr | |
| | | | 180 | | | | | 185 | | | | | 190 | | | |
| tgt | ttc | agg | tct | ttt | atg | gcg | aaa | tct | gcg | gga | atc | aga | acg | atc | gtt | 624 |
| Cys | Phe | Arg | Ser | Phe | Met | Ala | Lys | Ser | Ala | Gly | Ile | Arg | Thr | Ile | Val | |
| | | 195 | | | | | 200 | | | | | 205 | | | | |
| atg | gtt | cct | act | gat | gct | ggt | gtt | ctt | gag | ctt | ggt | tct | gtt | tgg | tct | 672 |
| Met | Val | Pro | Thr | Asp | Ala | Gly | Val | Leu | Glu | Leu | Gly | Ser | Val | Trp | Ser | |
| | 210 | | | | | 215 | | | | | 220 | | | | | |
| ttg | cct | gaa | aac | att | ggc | ttg | gtt | aag | tct | gtt | caa | gct | ttg | ttc | atg | 720 |
| Leu | Pro | Glu | Asn | Ile | Gly | Leu | Val | Lys | Ser | Val | Gln | Ala | Leu | Phe | Met | |
| 225 | | | | | 230 | | | | | 235 | | | | | 240 | |
| agg | aga | gtt | acg | caa | cca | gta | atg | gtg | act | tca | aac | act | aac | atg | act | 768 |
| Arg | Arg | Val | Thr | Gln | Pro | Val | Met | Val | Thr | Ser | Asn | Thr | Asn | Met | Thr | |
| | | | | 245 | | | | | 250 | | | | | 255 | | |
| gga | ggg | att | cac | aag | ctt | ttc | ggg | cag | gat | ttg | agt | gga | gct | cac | gcg | 816 |
| Gly | Gly | Ile | His | Lys | Leu | Phe | Gly | Gln | Asp | Leu | Ser | Gly | Ala | His | Ala | |
| | | | 260 | | | | | 265 | | | | | 270 | | | |
| tat | cct | aag | aag | ctc | gaa | gtg | aga | aga | aac | ttg | gat | gag | aga | ttc | act | 864 |

```
                Tyr Pro Lys Lys Leu Glu Val Arg Arg Asn Leu Asp Glu Arg Phe Thr
                        275                 280                 285 cct caa agt tgg gaa ggc tat aat aac aat aaa ggt cca aca ttt ggt    912
Pro Gln Ser Trp Glu Gly Tyr Asn Asn Asn Lys Gly Pro Thr Phe Gly
    290                 295                 300 tac aca cct cag agg gat gat gtg aaa gtg cta gag aat gtg aat atg    960
Tyr Thr Pro Gln Arg Asp Asp Val Lys Val Leu Glu Asn Val Asn Met
305                 310                 315                 320 gtt gta gat aat aac aat tac aag acg cag att gag ttt gcg gga tca   1008
Val Val Asp Asn Asn Asn Tyr Lys Thr Gln Ile Glu Phe Ala Gly Ser
                325                 330                 335 tca gtt gct gct tct tcg aat cca tct aca aac act cag caa gaa aaa   1056
Ser Val Ala Ala Ser Ser Asn Pro Ser Thr Asn Thr Gln Gln Glu Lys
        340                 345                 350 tca gaa tct tgt aca gag aaa aga cca gtg agc ttg tta gca gga gca   1104
Ser Glu Ser Cys Thr Glu Lys Arg Pro Val Ser Leu Leu Ala Gly Ala
    355                 360                 365 gga ata gtt tct gtt gtt gat gag aag aga ccg aga aag aga ggg aga   1152
Gly Ile Val Ser Val Val Asp Glu Lys Arg Pro Arg Lys Arg Gly Arg
370                 375                 380 aag cct gca aac gga aga gaa gag cca ttg aac cat gtg gaa gct gag   1200
Lys Pro Ala Asn Gly Arg Glu Glu Pro Leu Asn His Val Glu Ala Glu
385                 390                 395                 400 agg cag aga cgc gag aag ctt aac caa aga ttc tac gct tta cga tca   1248
Arg Gln Arg Arg Glu Lys Leu Asn Gln Arg Phe Tyr Ala Leu Arg Ser
                405                 410                 415 gtt gtt cca aac att tct aaa atg gac aag gct tct cta ctt gga gac   1296
Val Val Pro Asn Ile Ser Lys Met Asp Lys Ala Ser Leu Leu Gly Asp
        420                 425                 430 gca att tct tac atc aaa gag ctt caa gag aaa gtc aag ata atg gaa   1344
Ala Ile Ser Tyr Ile Lys Glu Leu Gln Glu Lys Val Lys Ile Met Glu
    435                 440                 445 gat gaa aga gta gga aca gat aag agc tta tca gaa tca aac aca ata   1392
Asp Glu Arg Val Gly Thr Asp Lys Ser Leu Ser Glu Ser Asn Thr Ile
450                 455                 460 aca gta gaa gaa agt cca gaa gtt gac att caa gct atg aat gaa gag   1440
Thr Val Glu Glu Ser Pro Glu Val Asp Ile Gln Ala Met Asn Glu Glu
465                 470                 475                 480 gtt gtt gta aga gta atc tcg cct ttg gat tca cat cca gct tca aga   1488
Val Val Val Arg Val Ile Ser Pro Leu Asp Ser His Pro Ala Ser Arg
                485                 490                 495 atc ata caa gca atg aga aac tca aat gtt agt cta atg gag gct aag   1536
Ile Ile Gln Ala Met Arg Asn Ser Asn Val Ser Leu Met Glu Ala Lys
        500                 505                 510 tta tca tta gct gaa gac aca atg ttt cac act ttt gtg ata aag tct   1584
Leu Ser Leu Ala Glu Asp Thr Met Phe His Thr Phe Val Ile Lys Ser
    515                 520                 525 aac aac ggg tcg gat cca ttg acg aaa gag aag ctt ata gca gcg ttt   1632
Asn Asn Gly Ser Asp Pro Leu Thr Lys Glu Lys Leu Ile Ala Ala Phe
530                 535                 540 tac ccc gag acc agc tcg acg caa ccg cca ttg cct tct tct agt tca   1680
Tyr Pro Glu Thr Ser Ser Thr Gln Pro Pro Leu Pro Ser Ser Ser Ser
545                 550                 555                 560 cag gtc tct ggg ttt gtt tct ccg atc aga tcc aat ttc aat cct tct   1728
Gln Val Ser Gly Phe Val Ser Pro Ile Arg Ser Asn Phe Asn Pro Ser
                565                 570                 575 ccg tca gat tat ctc ctc ggc cac gat gtc tct ccg ccg cac tat cct   1776
Pro Ser Asp Tyr Leu Leu Gly His Asp Val Ser Pro Pro His Tyr Pro
        580                 585                 590
```

```
cga tct cca ccg tca aac cca gag agc cac tct ctc aaa gtc tct acc   1824
Arg Ser Pro Pro Ser Asn Pro Glu Ser His Ser Leu Lys Val Ser Thr
            595                 600                 605 ttt ctc gat gag tca cat ctc ctc cgc atc cgc cac cgc cgc cgt gag   1872
Phe Leu Asp Glu Ser His Leu Leu Arg Ile Arg His Arg Arg Arg Glu
    610                 615                 620 aaa ccc act ggg aag aga cct ctc ttc aat ccc ctt cgc aca agc cca   1920
Lys Pro Thr Gly Lys Arg Pro Leu Phe Asn Pro Leu Arg Thr Ser Pro
625                 630                 635                 640 gaa act gaa acc aga ttc aac caa tct cgt cac cga tcg ctc gat ttc   1968
Glu Thr Glu Thr Arg Phe Asn Gln Ser Arg His Arg Ser Leu Asp Phe
                645                 650                 655 gtc ttc aat tgg gca atc tga                                       1989
Val Phe Asn Trp Ala Ile
            660
```

<210> SEQ ID NO 138
<211> LENGTH: 662
<212> TYPE: PRT
<213> ORGANISM: Arabidopsis thaliana

<400> SEQUENCE: 138

```
Met Asn Met Ser Asp Leu Gly Trp Asp Asp Glu Asp Lys Ser Val Val
1               5                   10                  15

Ser Ala Val Leu Gly His Leu Ala Ser Asp Phe Leu Arg Ala Asn Ser
                20                  25                  30

Asn Ser Asn Gln Asn Leu Phe Leu Val Met Gly Thr Asp Asp Thr Leu
            35                  40                  45

Asn Lys Lys Leu Ser Ser Leu Val Asp Trp Pro Asn Ser Glu Asn Phe
        50                  55                  60

Ser Trp Asn Tyr Ala Ile Phe Trp Gln Gln Thr Met Ser Arg Ser Gly
65                  70                  75                  80

Gln Gln Val Leu Gly Trp Gly Asp Gly Cys Cys Arg Glu Pro Asn Glu
                85                  90                  95

Glu Glu Glu Ser Lys Val Val Arg Ser Tyr Asn Phe Asn Asn Met Gly
            100                 105                 110

Ala Glu Glu Glu Thr Trp Gln Asp Met Arg Lys Arg Val Leu Gln Lys
        115                 120                 125

Leu His Arg Leu Phe Gly Gly Ser Asp Glu Asp Asn Tyr Ala Leu Ser
    130                 135                 140

Leu Glu Lys Val Thr Ala Thr Glu Ile Phe Phe Leu Ala Ser Met Tyr
145                 150                 155                 160

Phe Phe Phe Asn His Gly Glu Gly Gly Pro Gly Arg Cys Tyr Ser Ser
                165                 170                 175

Gly Lys His Val Trp Leu Ser Asp Ala Val Asn Ser Glu Ser Asp Tyr
            180                 185                 190

Cys Phe Arg Ser Phe Met Ala Lys Ser Ala Gly Ile Arg Thr Ile Val
        195                 200                 205

Met Val Pro Thr Asp Ala Gly Val Leu Glu Leu Gly Ser Val Trp Ser
    210                 215                 220

Leu Pro Glu Asn Ile Gly Leu Val Lys Ser Val Gln Ala Leu Phe Met
225                 230                 235                 240

Arg Arg Val Thr Gln Pro Val Met Val Thr Ser Asn Thr Asn Met Thr
                245                 250                 255

Gly Gly Ile His Lys Leu Phe Gly Gln Asp Leu Ser Gly Ala His Ala
            260                 265                 270
```

Tyr Pro Lys Lys Leu Glu Val Arg Arg Asn Leu Asp Glu Arg Phe Thr
            275                 280                 285

Pro Gln Ser Trp Glu Gly Tyr Asn Asn Lys Gly Pro Thr Phe Gly
        290                 295                 300

Tyr Thr Pro Gln Arg Asp Asp Val Lys Val Leu Glu Asn Val Asn Met
305                 310                 315                 320

Val Val Asp Asn Asn Tyr Lys Thr Gln Ile Glu Phe Ala Gly Ser
            325                 330                 335

Ser Val Ala Ala Ser Ser Asn Pro Ser Thr Asn Thr Gln Gln Glu Lys
            340                 345                 350

Ser Glu Ser Cys Thr Glu Lys Arg Pro Val Ser Leu Ala Gly Ala
            355                 360                 365

Gly Ile Val Ser Val Val Asp Glu Lys Arg Pro Arg Lys Arg Gly Arg
            370                 375                 380

Lys Pro Ala Asn Gly Arg Glu Glu Pro Leu Asn His Val Glu Ala Glu
385                 390                 395                 400

Arg Gln Arg Arg Glu Lys Leu Asn Gln Arg Phe Tyr Ala Leu Arg Ser
            405                 410                 415

Val Val Pro Asn Ile Ser Lys Met Asp Lys Ala Ser Leu Leu Gly Asp
            420                 425                 430

Ala Ile Ser Tyr Ile Lys Glu Leu Gln Glu Lys Val Lys Ile Met Glu
            435                 440                 445

Asp Glu Arg Val Gly Thr Asp Lys Ser Leu Ser Glu Ser Asn Thr Ile
            450                 455                 460

Thr Val Glu Glu Ser Pro Glu Val Asp Ile Gln Ala Met Asn Glu Glu
465                 470                 475                 480

Val Val Val Arg Val Ile Ser Pro Leu Asp Ser His Pro Ala Ser Arg
            485                 490                 495

Ile Ile Gln Ala Met Arg Asn Ser Asn Val Ser Leu Met Glu Ala Lys
            500                 505                 510

Leu Ser Leu Ala Glu Asp Thr Met Phe His Thr Phe Val Ile Lys Ser
            515                 520                 525

Asn Asn Gly Ser Asp Pro Leu Thr Lys Glu Lys Leu Ile Ala Ala Phe
            530                 535                 540

Tyr Pro Glu Thr Ser Ser Thr Gln Pro Pro Leu Pro Ser Ser Ser Ser
545                 550                 555                 560

Gln Val Ser Gly Phe Val Ser Pro Ile Arg Ser Asn Phe Asn Pro Ser
            565                 570                 575

Pro Ser Asp Tyr Leu Leu Gly His Asp Val Ser Pro Pro His Tyr Pro
            580                 585                 590

Arg Ser Pro Pro Ser Asn Pro Glu Ser His Ser Leu Lys Val Ser Thr
            595                 600                 605

Phe Leu Asp Glu Ser His Leu Leu Arg Ile Arg His Arg Arg Glu
            610                 615                 620

Lys Pro Thr Gly Lys Arg Pro Leu Phe Asn Pro Leu Arg Thr Ser Pro
625                 630                 635                 640

Glu Thr Glu Thr Arg Phe Asn Gln Ser Arg His Arg Ser Leu Asp Phe
            645                 650                 655

Val Phe Asn Trp Ala Ile
            660

<210> SEQ ID NO 139
<211> LENGTH: 870
<212> TYPE: DNA

<213> ORGANISM: Arabidopsis thaliana
<220> FEATURE:
<221> NAME/KEY: CDS
<222> LOCATION: (1)..(867)

<400> SEQUENCE: 139

```
atg tca gaa tta tta cag ttg cct cca ggt ttc cga ttt cac cct acc      48
Met Ser Glu Leu Leu Gln Leu Pro Pro Gly Phe Arg Phe His Pro Thr
1               5                   10                  15 gat gaa gag ctt gtc atg cac tat ctc tgc cgc aaa tgt gcc tct cag      96
Asp Glu Glu Leu Val Met His Tyr Leu Cys Arg Lys Cys Ala Ser Gln
            20                  25                  30 tcc atc gcc gtt ccg atc atc gct gag atc gat ctc tac aaa tac gat     144
Ser Ile Ala Val Pro Ile Ile Ala Glu Ile Asp Leu Tyr Lys Tyr Asp
        35                  40                  45 cca tgg gag ctt cct ggt tta gcc ttg tat ggt gag aag gaa tgg tac     192
Pro Trp Glu Leu Pro Gly Leu Ala Leu Tyr Gly Glu Lys Glu Trp Tyr
    50                  55                  60 ttc ttc tct ccc agg gac aga aaa tat ccc aac ggt tcg cgt cct aac     240
Phe Phe Ser Pro Arg Asp Arg Lys Tyr Pro Asn Gly Ser Arg Pro Asn
65                  70                  75                  80 cgg tcc gct ggt tct ggt tac tgg aaa gct acc gga gct gat aaa ccg     288
Arg Ser Ala Gly Ser Gly Tyr Trp Lys Ala Thr Gly Ala Asp Lys Pro
                85                  90                  95 atc gga cta cct aaa ccg gtc gga att aag aaa gct ctt gtt ttc tac     336
Ile Gly Leu Pro Lys Pro Val Gly Ile Lys Lys Ala Leu Val Phe Tyr
            100                 105                 110 gcc ggc aaa gct cca aag gga gag aaa acc aat tgg atc atg cac gag     384
Ala Gly Lys Ala Pro Lys Gly Glu Lys Thr Asn Trp Ile Met His Glu
        115                 120                 125 tac cgt ctc gcc gac gtt gac cgg tcc gtt cgc aag aag aag aat agt     432
Tyr Arg Leu Ala Asp Val Asp Arg Ser Val Arg Lys Lys Lys Asn Ser
    130                 135                 140 ctc agg ctg gat gat tgg gtt ctc tgc cgg att tac aac aaa aaa gga     480
Leu Arg Leu Asp Asp Trp Val Leu Cys Arg Ile Tyr Asn Lys Lys Gly
145                 150                 155                 160 gct acc gag agg cgg gga cca ccg cct ccg gtt gtt tac ggc gac gaa     528
Ala Thr Glu Arg Arg Gly Pro Pro Pro Pro Val Val Tyr Gly Asp Glu
                165                 170                 175 atc atg gag gag aag ccg aag gtg acg gag atg gtt atg cct ccg ccg     576
Ile Met Glu Glu Lys Pro Lys Val Thr Glu Met Val Met Pro Pro Pro
            180                 185                 190 ccg caa cag aca agt gag ttc gcg tat ttc gac acg tcg gat tcg gtg     624
Pro Gln Gln Thr Ser Glu Phe Ala Tyr Phe Asp Thr Ser Asp Ser Val
        195                 200                 205 ccg aag ctg cat act acg gat tcg agt tgc tcg gag cag gtg gtg tcg     672
Pro Lys Leu His Thr Thr Asp Ser Ser Cys Ser Glu Gln Val Val Ser
    210                 215                 220 ccg gag ttc acg agc gag gtt cag agc gag ccc aag tgg aaa gat tgg     720
Pro Glu Phe Thr Ser Glu Val Gln Ser Glu Pro Lys Trp Lys Asp Trp
225                 230                 235                 240 tcg gcc gta agt aat gac aat aac aat acc ctt gat ttt ggg ttt aat     768
Ser Ala Val Ser Asn Asp Asn Asn Asn Thr Leu Asp Phe Gly Phe Asn
                245                 250                 255 tac att gat gcc acc gtg gat aac gcg ttt gga gga gga ggg agt agt     816
Tyr Ile Asp Ala Thr Val Asp Asn Ala Phe Gly Gly Gly Gly Ser Ser
            260                 265                 270 aat cag atg ttt ccg cta cag gat atg ttc atg tac atg cag aag cct     864
Asn Gln Met Phe Pro Leu Gln Asp Met Phe Met Tyr Met Gln Lys Pro
        275                 280                 285
```

```
tac tag                                                                 870
Tyr <210> SEQ ID NO 140
<211> LENGTH: 289
<212> TYPE: PRT
<213> ORGANISM: Arabidopsis thaliana

<400> SEQUENCE: 140

Met Ser Glu Leu Leu Gln Leu Pro Pro Gly Phe Arg Phe His Pro Thr
  1               5                  10                  15

Asp Glu Glu Leu Val Met His Tyr Leu Cys Arg Lys Cys Ala Ser Gln
             20                  25                  30

Ser Ile Ala Val Pro Ile Ile Ala Glu Ile Asp Leu Tyr Lys Tyr Asp
         35                  40                  45

Pro Trp Glu Leu Pro Gly Leu Ala Leu Tyr Gly Lys Glu Trp Tyr
     50                  55                  60

Phe Phe Ser Pro Arg Asp Arg Lys Tyr Pro Asn Gly Ser Arg Pro Asn
 65                  70                  75                  80

Arg Ser Ala Gly Ser Gly Tyr Trp Lys Ala Thr Gly Ala Asp Lys Pro
                 85                  90                  95

Ile Gly Leu Pro Lys Pro Val Gly Ile Lys Lys Ala Leu Val Phe Tyr
            100                 105                 110

Ala Gly Lys Ala Pro Lys Gly Glu Lys Thr Asn Trp Ile Met His Glu
        115                 120                 125

Tyr Arg Leu Ala Asp Val Asp Arg Ser Val Arg Lys Lys Lys Asn Ser
130                 135                 140

Leu Arg Leu Asp Asp Trp Val Leu Cys Arg Ile Tyr Asn Lys Lys Gly
145                 150                 155                 160

Ala Thr Glu Arg Arg Gly Pro Pro Pro Val Val Tyr Gly Asp Glu
                165                 170                 175

Ile Met Glu Glu Lys Pro Lys Val Thr Glu Met Val Met Pro Pro Pro
            180                 185                 190

Pro Gln Gln Thr Ser Glu Phe Ala Tyr Phe Asp Thr Ser Asp Ser Val
        195                 200                 205

Pro Lys Leu His Thr Thr Asp Ser Ser Cys Ser Glu Gln Val Val Ser
    210                 215                 220

Pro Glu Phe Thr Ser Glu Val Gln Ser Glu Pro Lys Trp Lys Asp Trp
225                 230                 235                 240

Ser Ala Val Ser Asn Asp Asn Asn Thr Leu Asp Phe Gly Phe Asn
                245                 250                 255

Tyr Ile Asp Ala Thr Val Asp Asn Ala Phe Gly Gly Gly Ser Ser
            260                 265                 270

Asn Gln Met Phe Pro Leu Gln Asp Met Phe Met Tyr Met Gln Lys Pro
        275                 280                 285

Tyr

<210> SEQ ID NO 141
<211> LENGTH: 1202
<212> TYPE: DNA
<213> ORGANISM: Arabidopsis thaliana
<220> FEATURE:
<221> NAME/KEY: CDS
<222> LOCATION: (112)..(918)

<400> SEQUENCE: 141
tcctcgattt caatctttga gataaaccac aaagatcctc cgattcgaag gtttataaaa     60
```

-continued

| | |
|---|---|
| actcaaaatc gaatcttatc cacaagaaaa caacaaggta cttttccaaa a atg aag<br>                                                                                                        Met Lys<br>                                                                                                            1 | 117 |
| gcg gag ttg aat ttg ccg gcg gga ttc cga ttt cat ccg acg gac gaa<br>Ala Glu Leu Asn Leu Pro Ala Gly Phe Arg Phe His Pro Thr Asp Glu<br>         5                        10                          15 | 165 |
| gag ctt gtc aag ttc tat ctt tgc cgg aga tgt gcg tca gaa ccg att<br>Glu Leu Val Lys Phe Tyr Leu Cys Arg Arg Cys Ala Ser Glu Pro Ile<br>  20                       25                         30 | 213 |
| aac gtt ccg gtt atc gca gag att gac ttg tac aaa ttc aat cca agg<br>Asn Val Pro Val Ile Ala Glu Ile Asp Leu Tyr Lys Phe Asn Pro Arg<br> 35                      40                       45                       50 | 261 |
| gag ctt cca gaa atg gcg ttg tac ggt gag aaa gaa tgg tac ttc ttc<br>Glu Leu Pro Glu Met Ala Leu Tyr Gly Glu Lys Glu Trp Tyr Phe Phe<br>                   55                       60                       65 | 309 |
| tcg cat aga gac cgg aaa tac cca aac ggg tcg aga cca aac cgg gca<br>Ser His Arg Asp Arg Lys Tyr Pro Asn Gly Ser Arg Pro Asn Arg Ala<br>        70                       75                       80 | 357 |
| gct gga acc ggt tat tgg aaa gcg act gga gct gat aaa ccg atc gga<br>Ala Gly Thr Gly Tyr Trp Lys Ala Thr Gly Ala Asp Lys Pro Ile Gly<br>             85                       90                      95 | 405 |
| aaa ccg aag acg tta ggg att aag aaa gca ctc gtc ttc tac gca gga<br>Lys Pro Lys Thr Leu Gly Ile Lys Lys Ala Leu Val Phe Tyr Ala Gly<br>100                       105                      110 | 453 |
| aaa gct ccg aaa ggg att aaa acg aat tgg att atg cac gag tat cgt<br>Lys Ala Pro Lys Gly Ile Lys Thr Asn Trp Ile Met His Glu Tyr Arg<br>115                  120                  125                  130 | 501 |
| ctc gct aat gtc gat cga tct gct tct acc aac aag aag aac aac tta<br>Leu Ala Asn Val Asp Arg Ser Ala Ser Thr Asn Lys Lys Asn Asn Leu<br>                   135                      140                       145 | 549 |
| aga ctt gat gat tgg gtt ttg tgt cgg ata tac aat aag aaa gga aca<br>Arg Leu Asp Asp Trp Val Leu Cys Arg Ile Tyr Asn Lys Lys Gly Thr<br>              150                      155                      160 | 597 |
| atg gag aag tat tta ccg gcg gcg gct gag aaa ccg acg gaa aag atg<br>Met Glu Lys Tyr Leu Pro Ala Ala Ala Glu Lys Pro Thr Glu Lys Met<br>         165                     170                    175 | 645 |
| agt acg tcg gac tca aga tgc tca agt cac gtg att tca ccg gac gtc<br>Ser Thr Ser Asp Ser Arg Cys Ser Ser His Val Ile Ser Pro Asp Val<br>180                       185                      190 | 693 |
| acg tgt tct gat aac tgg gag gtt gag agt gag ccc aaa tgg att aat<br>Thr Cys Ser Asp Asn Trp Glu Val Glu Ser Glu Pro Lys Trp Ile Asn<br>195                  200                  205                  210 | 741 |
| ctg gaa gac gcg tta gag gca ttt aat gat gac acg tcc atg ttt agt<br>Leu Glu Asp Ala Leu Glu Ala Phe Asn Asp Asp Thr Ser Met Phe Ser<br>                   215                      220                       225 | 789 |
| tcc att ggt ttg ttg caa aat gac gcc ttt gtt cct cag ttt cag tac<br>Ser Ile Gly Leu Leu Gln Asn Asp Ala Phe Val Pro Gln Phe Gln Tyr<br>              230                      235                      240 | 837 |
| cag tcc tcc gat ttc gtc gat tcg ttt cag gac ccg ttc gag cag aaa<br>Gln Ser Ser Asp Phe Val Asp Ser Phe Gln Asp Pro Phe Glu Gln Lys<br>         245                     250                    255 | 885 |
| ccg ttc ttg aat tgg aat ttt gct cct caa ggg taaaaataat cggcaaaaag<br>Pro Phe Leu Asn Trp Asn Phe Ala Pro Gln Gly<br>         260                     265 | 938 |
| ttgaagcttt tcagagtctt cgatcaccgg cattgtgtcg gatcctgacc cggagaccaa | 998 |
| gtcgggtcat acgattacat aatcgggtta ttgagatttc cacatttgga tttccgagac | 1058 |
| taaccaactt aacggattct ggggtaattg gggggttttg cacaggtgaa tcacactgag | 1118 |

```
tcagcaagtt tcgattttt  ggttttgttt tgtaatgatt gattaaatgt ctaaagatat   1178
cacgaagtta aaaaaaaaaa aaaa                                           1202
```

<210> SEQ ID NO 142
<211> LENGTH: 269
<212> TYPE: PRT
<213> ORGANISM: Arabidopsis thaliana

<400> SEQUENCE: 142

```
Met Lys Ala Glu Leu Asn Leu Pro Ala Gly Phe Arg Phe His Pro Thr
  1               5                  10                  15

Asp Glu Glu Leu Val Lys Phe Tyr Leu Cys Arg Arg Cys Ala Ser Glu
                 20                  25                  30

Pro Ile Asn Val Pro Val Ile Ala Glu Ile Asp Leu Tyr Lys Phe Asn
             35                  40                  45

Pro Arg Glu Leu Pro Glu Met Ala Leu Tyr Gly Glu Lys Glu Trp Tyr
         50                  55                  60

Phe Phe Ser His Arg Asp Arg Lys Tyr Pro Asn Gly Ser Arg Pro Asn
 65                  70                  75                  80

Arg Ala Ala Gly Thr Gly Tyr Trp Lys Ala Thr Gly Ala Asp Lys Pro
                 85                  90                  95

Ile Gly Lys Pro Lys Thr Leu Gly Ile Lys Lys Ala Leu Val Phe Tyr
            100                 105                 110

Ala Gly Lys Ala Pro Lys Gly Ile Lys Thr Asn Trp Ile Met His Glu
        115                 120                 125

Tyr Arg Leu Ala Asn Val Asp Arg Ser Ala Ser Thr Asn Lys Lys Asn
    130                 135                 140

Asn Leu Arg Leu Asp Asp Trp Val Leu Cys Arg Ile Tyr Asn Lys Lys
145                 150                 155                 160

Gly Thr Met Glu Lys Tyr Leu Pro Ala Ala Glu Lys Pro Thr Glu
                165                 170                 175

Lys Met Ser Thr Ser Asp Ser Arg Cys Ser Ser His Val Ile Ser Pro
                180                 185                 190

Asp Val Thr Cys Ser Asp Asn Trp Glu Val Glu Ser Glu Pro Lys Trp
            195                 200                 205

Ile Asn Leu Glu Asp Ala Leu Glu Ala Phe Asn Asp Asp Thr Ser Met
        210                 215                 220

Phe Ser Ser Ile Gly Leu Leu Gln Asn Asp Ala Phe Val Pro Gln Phe
225                 230                 235                 240

Gln Tyr Gln Ser Ser Asp Phe Val Asp Ser Phe Gln Asp Pro Phe Glu
                245                 250                 255

Gln Lys Pro Phe Leu Asn Trp Asn Phe Ala Pro Gln Gly
            260                 265
```

<210> SEQ ID NO 143
<211> LENGTH: 1188
<212> TYPE: DNA
<213> ORGANISM: Arabidopsis thaliana
<220> FEATURE:
<221> NAME/KEY: CDS
<222> LOCATION: (124)..(978)

<400> SEQUENCE: 143

```
aaaaacctca actttcttct ctcttctcaa aaacccttcc ctcttcgtct ccaaacaaca    60
acaaacacaa caacaacaaa atcttacaa  gaagatcatt tttagaaacc ctattaggat   120 aaa atg gat tac gag gca tca aga atc gtc gaa atg gta gaa gat gaa     168
```

```
          Met Asp Tyr Glu Ala Ser Arg Ile Val Glu Met Val Glu Asp Glu
            1               5                  10                  15 gaa cat ata gat cta cca cca gga ttc aga ttt cac cct act gat gaa       216
Glu His Ile Asp Leu Pro Pro Gly Phe Arg Phe His Pro Thr Asp Glu
                 20                  25                  30 gaa ctc ata act cac tac ctc aaa cca aag gtt ttc aac act ttc ttc       264
Glu Leu Ile Thr His Tyr Leu Lys Pro Lys Val Phe Asn Thr Phe Phe
                     35                  40                  45 tct gct act gcc att ggt gaa gtt gat ctc aac aag att gag cct tgg       312
Ser Ala Thr Ala Ile Gly Glu Val Asp Leu Asn Lys Ile Glu Pro Trp
                 50                  55                  60 gac tta cca tgg aag gct aag atg gga gaa aaa gaa tgg tat ttc ttc       360
Asp Leu Pro Trp Lys Ala Lys Met Gly Glu Lys Glu Trp Tyr Phe Phe
            65                  70                  75 tgt gtg aga gac cgg aaa tac ccg acc ggt tta agg aca aac cgg gcg       408
Cys Val Arg Asp Arg Lys Tyr Pro Thr Gly Leu Arg Thr Asn Arg Ala
 80                  85                  90                  95 aca gaa gcc ggt tat tgg aaa gcc aca gga aaa gac aaa gag ata ttc       456
Thr Glu Ala Gly Tyr Trp Lys Ala Thr Gly Lys Asp Lys Glu Ile Phe
                    100                 105                 110 aag gga aaa tca ctt gtg ggt atg aag aaa act ttg gtt ttc tat aaa       504
Lys Gly Lys Ser Leu Val Gly Met Lys Lys Thr Leu Val Phe Tyr Lys
                115                 120                 125 gga aga gct cct aaa gga gtt aaa acc aat tgg gtt atg cat gaa tat       552
Gly Arg Ala Pro Lys Gly Val Lys Thr Asn Trp Val Met His Glu Tyr
            130                 135                 140 cgt tta gaa ggc aaa tat tgt att gaa aat ctt ccc caa aca gct aag       600
Arg Leu Glu Gly Lys Tyr Cys Ile Glu Asn Leu Pro Gln Thr Ala Lys
145                 150                 155 aac gaa tgg gtt ata tgt cgt gtt ttc caa aaa cgt gcc gat ggt aca       648
Asn Glu Trp Val Ile Cys Arg Val Phe Gln Lys Arg Ala Asp Gly Thr
160                 165                 170                 175 aag gtt cca atg tca atg ctt gat cca cac att aac cga atg gaa cca       696
Lys Val Pro Met Ser Met Leu Asp Pro His Ile Asn Arg Met Glu Pro
                180                 185                 190 gcc ggt tta cct tcg tta atg gat tgt tct caa cga gac tcc ttc acc       744
Ala Gly Leu Pro Ser Leu Met Asp Cys Ser Gln Arg Asp Ser Phe Thr
                195                 200                 205 ggt tcg tcg tct cac gtg acc tgc ttc tcc gac caa gaa acc gaa gac       792
Gly Ser Ser Ser His Val Thr Cys Phe Ser Asp Gln Glu Thr Glu Asp
            210                 215                 220 aaa aga ctt gtc cac gag tcc aaa gac ggt ttt ggt tct ctg ttt tac       840
Lys Arg Leu Val His Glu Ser Lys Asp Gly Phe Gly Ser Leu Phe Tyr
225                 230                 235 tcg gat cct ctg ttt tta caa gac aat tat tcg cta atg aag ctg ttg       888
Ser Asp Pro Leu Phe Leu Gln Asp Asn Tyr Ser Leu Met Lys Leu Leu
240                 245                 250                 255 ctt gac ggt caa gaa act caa ttc tcc ggc aaa cct ttc gac ggt cgt       936
Leu Asp Gly Gln Glu Thr Gln Phe Ser Gly Lys Pro Phe Asp Gly Arg
                260                 265                 270 gat tcg tcc ggt aca gaa gaa ttg gat tgc gtt tgg aat ttc                978
Asp Ser Ser Gly Thr Glu Glu Leu Asp Cys Val Trp Asn Phe
            275                 280                 285 tgagttgtat aagttatgtt gtagacttgt agtagtcatg tgttcgtgtg tgtgaatgaa     1038
tattcttgtt acattttttt gtaaaaaagg agaaaaaaat atgctagaaa gtcaattgct     1098
tttgttatgt agcattagtg ttttttatgt actcaataga cttcctaatt aaataaaaat     1158
cttaatttat ttgcaaaaaa aaaaaaaaaa                                      1188
```

<210> SEQ ID NO 144
<211> LENGTH: 285
<212> TYPE: PRT
<213> ORGANISM: Arabidopsis thaliana

<400> SEQUENCE: 144

Met Asp Tyr Glu Ala Ser Arg Ile Val Glu Met Val Glu Asp Glu Glu
1               5                   10                  15

His Ile Asp Leu Pro Pro Gly Phe Arg Phe His Pro Thr Asp Glu Glu
            20                  25                  30

Leu Ile Thr His Tyr Leu Lys Pro Lys Val Phe Asn Thr Phe Phe Ser
        35                  40                  45

Ala Thr Ala Ile Gly Glu Val Asp Leu Asn Lys Ile Glu Pro Trp Asp
    50                  55                  60

Leu Pro Trp Lys Ala Lys Met Gly Glu Lys Glu Trp Tyr Phe Phe Cys
65                  70                  75                  80

Val Arg Asp Arg Lys Tyr Pro Thr Gly Leu Arg Thr Asn Arg Ala Thr
                85                  90                  95

Glu Ala Gly Tyr Trp Lys Ala Thr Gly Lys Asp Lys Glu Ile Phe Lys
            100                 105                 110

Gly Lys Ser Leu Val Gly Met Lys Lys Thr Leu Val Phe Tyr Lys Gly
        115                 120                 125

Arg Ala Pro Lys Gly Val Lys Thr Asn Trp Val Met His Glu Tyr Arg
    130                 135                 140

Leu Glu Gly Lys Tyr Cys Ile Glu Asn Leu Pro Gln Thr Ala Lys Asn
145                 150                 155                 160

Glu Trp Val Ile Cys Arg Val Phe Gln Lys Arg Ala Asp Gly Thr Lys
                165                 170                 175

Val Pro Met Ser Met Leu Asp Pro His Ile Asn Arg Met Glu Pro Ala
            180                 185                 190

Gly Leu Pro Ser Leu Met Asp Cys Ser Gln Arg Asp Ser Phe Thr Gly
        195                 200                 205

Ser Ser Ser His Val Thr Cys Phe Ser Asp Gln Glu Thr Glu Asp Lys
    210                 215                 220

Arg Leu Val His Glu Ser Lys Asp Gly Phe Gly Ser Leu Phe Tyr Ser
225                 230                 235                 240

Asp Pro Leu Phe Leu Gln Asp Asn Tyr Ser Leu Met Lys Leu Leu Leu
                245                 250                 255

Asp Gly Gln Glu Thr Gln Phe Ser Gly Lys Pro Phe Asp Gly Arg Asp
            260                 265                 270

Ser Ser Gly Thr Glu Glu Leu Asp Cys Val Trp Asn Phe
        275                 280                 285

<210> SEQ ID NO 145
<211> LENGTH: 894
<212> TYPE: DNA
<213> ORGANISM: Arabidopsis thaliana
<220> FEATURE:
<221> NAME/KEY: CDS
<222> LOCATION: (1)..(891)

<400> SEQUENCE: 145 atg ggt gtt aga gag aaa gat ccg tta gcc cag ttg agt ttg cca cca    48
Met Gly Val Arg Glu Lys Asp Pro Leu Ala Gln Leu Ser Leu Pro Pro
1               5                   10                  15 ggt ttt aga ttt tat ccg aca gat gaa gag ctt ctt gtt cag tat cta    96
Gly Phe Arg Phe Tyr Pro Thr Asp Glu Glu Leu Leu Val Gln Tyr Leu -continued

```
                20                  25                  30
tgt cgg aaa gtt gca ggc tat cat ttc tct ctc cag gtc atc gga gac    144
Cys Arg Lys Val Ala Gly Tyr His Phe Ser Leu Gln Val Ile Gly Asp
         35                  40                  45 atc gat ctc tac aag ttc gat cct tgg gat ttg cca agt aag gct ttg    192
Ile Asp Leu Tyr Lys Phe Asp Pro Trp Asp Leu Pro Ser Lys Ala Leu
 50                  55                  60 ttt gga gag aag gaa tgg tat ttc ttt agc cca aga gat cgg aaa tat    240
Phe Gly Glu Lys Glu Trp Tyr Phe Phe Ser Pro Arg Asp Arg Lys Tyr
 65                  70                  75                  80 ccg aac ggg tca aga ccc aat aga gta gcc ggg tcg ggt tat tgg aaa    288
Pro Asn Gly Ser Arg Pro Asn Arg Val Ala Gly Ser Gly Tyr Trp Lys
                 85                  90                  95 gca acg ggt act gac aaa att atc acg gcg gat ggt cgt cgt gtc ggg    336
Ala Thr Gly Thr Asp Lys Ile Ile Thr Ala Asp Gly Arg Arg Val Gly
            100                 105                 110 att aaa aaa gct ctg gtc ttt tac gcc gga aaa gct ccc aaa ggc act    384
Ile Lys Lys Ala Leu Val Phe Tyr Ala Gly Lys Ala Pro Lys Gly Thr
        115                 120                 125 aaa acc aac tgg att atg cac gag tat cgc tta ata gaa cat tct cgt    432
Lys Thr Asn Trp Ile Met His Glu Tyr Arg Leu Ile Glu His Ser Arg
    130                 135                 140 agc cat gga agc tcc aag ttg gat gat tgg gtg ttg tgt cga att tac    480
Ser His Gly Ser Ser Lys Leu Asp Asp Trp Val Leu Cys Arg Ile Tyr
145                 150                 155                 160 aag aaa aca tct gga tct cag aga caa gct gtt act cct gtt caa gct    528
Lys Lys Thr Ser Gly Ser Gln Arg Gln Ala Val Thr Pro Val Gln Ala
                165                 170                 175 tgt cgt gaa gag cat agc acg aat ggg tcg tca tcg tct tct tca tca    576
Cys Arg Glu Glu His Ser Thr Asn Gly Ser Ser Ser Ser Ser Ser Ser
            180                 185                 190 cag ctt gac gac gtt ctt gat tcg ttc ccg gag ata aaa gac cag tct    624
Gln Leu Asp Asp Val Leu Asp Ser Phe Pro Glu Ile Lys Asp Gln Ser
        195                 200                 205 ttt aat ctt cct cgg atg aat tcg ctc agg acg att ctt aac ggg aac    672
Phe Asn Leu Pro Arg Met Asn Ser Leu Arg Thr Ile Leu Asn Gly Asn
    210                 215                 220 ttt gat tgg gct agc ttg gca ggt ctt aat cca att cca gag cta gct    720
Phe Asp Trp Ala Ser Leu Ala Gly Leu Asn Pro Ile Pro Glu Leu Ala
225                 230                 235                 240 ccg acc aat gga tta ccg agt tac ggt ggt tac gat gcg ttt cga gcg    768
Pro Thr Asn Gly Leu Pro Ser Tyr Gly Gly Tyr Asp Ala Phe Arg Ala
                245                 250                 255 gcg gaa ggt gag gcg gag agt ggg cat gtg aat cgg cag cag aac tcg    816
Ala Glu Gly Glu Ala Glu Ser Gly His Val Asn Arg Gln Gln Asn Ser
            260                 265                 270 agc ggg ttg act cag agt ttc ggg tac agc tcg agt ggg ttt ggt gtt    864
Ser Gly Leu Thr Gln Ser Phe Gly Tyr Ser Ser Ser Gly Phe Gly Val
        275                 280                 285 tcg ggt caa aca ttc gag ttt agg caa tga                            894
Ser Gly Gln Thr Phe Glu Phe Arg Gln
    290                 295
```

<210> SEQ ID NO 146
<211> LENGTH: 297
<212> TYPE: PRT
<213> ORGANISM: Arabidopsis thaliana

<400> SEQUENCE: 146

Met Gly Val Arg Glu Lys Asp Pro Leu Ala Gln Leu Ser Leu Pro Pro

```
                1               5                10               15
Gly Phe Arg Phe Tyr Pro Thr Asp Glu Glu Leu Leu Val Gln Tyr Leu
                    20                  25                  30

Cys Arg Lys Val Ala Gly Tyr His Phe Ser Leu Gln Val Ile Gly Asp
                35                  40                  45

Ile Asp Leu Tyr Lys Phe Asp Pro Trp Asp Leu Pro Ser Lys Ala Leu
     50                  55                  60

Phe Gly Glu Lys Glu Trp Tyr Phe Phe Ser Pro Arg Asp Arg Lys Tyr
65                  70                  75                  80

Pro Asn Gly Ser Arg Pro Asn Arg Val Ala Gly Ser Gly Tyr Trp Lys
                85                  90                  95

Ala Thr Gly Thr Asp Lys Ile Ile Thr Ala Asp Gly Arg Arg Val Gly
                    100                 105                 110

Ile Lys Lys Ala Leu Val Phe Tyr Ala Gly Lys Ala Pro Lys Gly Thr
                115                 120                 125

Lys Thr Asn Trp Ile Met His Glu Tyr Arg Leu Ile Glu His Ser Arg
     130                 135                 140

Ser His Gly Ser Ser Lys Leu Asp Asp Trp Val Leu Cys Arg Ile Tyr
145                 150                 155                 160

Lys Lys Thr Ser Gly Ser Gln Arg Gln Ala Val Thr Pro Val Gln Ala
                165                 170                 175

Cys Arg Glu Glu His Ser Thr Asn Gly Ser Ser Ser Ser Ser Ser Ser
                180                 185                 190

Gln Leu Asp Asp Val Leu Asp Ser Phe Pro Glu Ile Lys Asp Gln Ser
     195                 200                 205

Phe Asn Leu Pro Arg Met Asn Ser Leu Arg Thr Ile Leu Asn Gly Asn
     210                 215                 220

Phe Asp Trp Ala Ser Leu Ala Gly Leu Asn Pro Ile Pro Glu Leu Ala
225                 230                 235                 240

Pro Thr Asn Gly Leu Pro Ser Tyr Gly Gly Tyr Asp Ala Phe Arg Ala
                245                 250                 255

Ala Glu Gly Glu Ala Glu Ser Gly His Val Asn Arg Gln Gln Asn Ser
                260                 265                 270

Ser Gly Leu Thr Gln Ser Phe Gly Tyr Ser Ser Ser Gly Phe Gly Val
     275                 280                 285

Ser Gly Gln Thr Phe Glu Phe Arg Gln
     290                 295

<210> SEQ ID NO 147
<211> LENGTH: 1920
<212> TYPE: DNA
<213> ORGANISM: Arabidopsis thaliana
<220> FEATURE:
<221> NAME/KEY: CDS
<222> LOCATION: (62)..(1645)

<400> SEQUENCE: 147
acagaaaaat cgaaactttt tagggttttt ttttttttgtg ataacgagag agaaaaaagt      60 g atg gac ttg tcg gtt gag aac gga ggt tta gct cca ggt ttt agg ttt     109
  Met Asp Leu Ser Val Glu Asn Gly Gly Leu Ala Pro Gly Phe Arg Phe
  1               5                   10                  15 cat ccg acg gac gaa gaa ctt gtc gtc tat tat ctc aaa aga aag atc      157
His Pro Thr Asp Glu Glu Leu Val Val Tyr Tyr Leu Lys Arg Lys Ile
                20                  25                  30 cgt cgg aaa aaa ctc aga gtc gaa gca atc ggc gag act gat gtc tat      205
Arg Arg Lys Lys Leu Arg Val Glu Ala Ile Gly Glu Thr Asp Val Tyr
```

-continued

|  |  |  |  |
|---|---|---|---|
| 35 | 40 | 45 | |
| aag ttt gat cct gag gaa tta cct gag aaa gcg ttg tat aag act aga<br>Lys Phe Asp Pro Glu Glu Leu Pro Glu Lys Ala Leu Tyr Lys Thr Arg<br>50              55                  60 | | | 253 |
| gat cgt caa tgg ttc ttt ttc agc tta agg gat agg aaa cat gga agt<br>Asp Arg Gln Trp Phe Phe Phe Ser Leu Arg Asp Arg Lys His Gly Ser<br>65              70                  75                  80 | | | 301 |
| agg tca agt aga gct act gaa cgt ggc tat tgg aaa gca aca ggg aag<br>Arg Ser Ser Arg Ala Thr Glu Arg Gly Tyr Trp Lys Ala Thr Gly Lys<br>                85                  90                  95 | | | 349 |
| gat aga gtc att cat tgt gat tcg aga ccc gtt gga gag aag aag act<br>Asp Arg Val Ile His Cys Asp Ser Arg Pro Val Gly Glu Lys Lys Thr<br>100                  105                110 | | | 397 |
| ctt gtt ttc cat aga ggc agg gca cct aat ggc gaa cgg act aat tgg<br>Leu Val Phe His Arg Gly Arg Ala Pro Asn Gly Glu Arg Thr Asn Trp<br>            115                  120                125 | | | 445 |
| gtg atg cat gag tat aca ttg cac aaa gag gag ctc aag agg tgt ggt<br>Val Met His Glu Tyr Thr Leu His Lys Glu Glu Leu Lys Arg Cys Gly<br>    130                  135                140 | | | 493 |
| ggt gaa gat gtt aag gat gct tat gtt ctt tac aag att tat aag aaa<br>Gly Glu Asp Val Lys Asp Ala Tyr Val Leu Tyr Lys Ile Tyr Lys Lys<br>145                  150                155                160 | | | 541 |
| agt ggg tct ggt cct aag aat ggt gag caa tat gga gct cct ttt att<br>Ser Gly Ser Gly Pro Lys Asn Gly Glu Gln Tyr Gly Ala Pro Phe Ile<br>                165                  170                175 | | | 589 |
| gaa gaa gaa tgg gct gaa gat gat gat gat gat gtt gat gag cct gct<br>Glu Glu Glu Trp Ala Glu Asp Asp Asp Asp Asp Val Asp Glu Pro Ala<br>            180                  185                190 | | | 637 |
| aat cag ctc gtt gtt tcg gct agt gtt gat aat agt tta tgg ggg aaa<br>Asn Gln Leu Val Val Ser Ala Ser Val Asp Asn Ser Leu Trp Gly Lys<br>    195                  200                205 | | | 685 |
| ggg ctt aac caa tct gaa ttg gat gat aat gat att gaa gag ctg atg<br>Gly Leu Asn Gln Ser Glu Leu Asp Asp Asn Asp Ile Glu Glu Leu Met<br>210                  215                220 | | | 733 |
| agt cag gtt aga gat cag tct ggt cca aca ttg cag cag aat ggg gtg<br>Ser Gln Val Arg Asp Gln Ser Gly Pro Thr Leu Gln Gln Asn Gly Val<br>225                  230                  235                240 | | | 781 |
| tct gga ctg aac tct cat gta gac acg tat aat ctg gag aac ctg gag<br>Ser Gly Leu Asn Ser His Val Asp Thr Tyr Asn Leu Glu Asn Leu Glu<br>                245                  250                255 | | | 829 |
| gaa gat atg tat ttg gaa atc aat gat ctt atg gaa cct gaa cct gga<br>Glu Asp Met Tyr Leu Glu Ile Asn Asp Leu Met Glu Pro Glu Pro Gly<br>            260                  265                270 | | | 877 |
| cca act tct gtg gaa gtc atg gag aat aac tgg aac gag gat ggt tct<br>Pro Thr Ser Val Glu Val Met Glu Asn Asn Trp Asn Glu Asp Gly Ser<br>    275                  280                285 | | | 925 |
| ggt ctc ctg aat gat gat gat ttc gtt ggt gct gat tca tat ttc ctt<br>Gly Leu Leu Asn Asp Asp Asp Phe Val Gly Ala Asp Ser Tyr Phe Leu<br>290                  295                300 | | | 973 |
| gat ttg gga gtg aca aat cct cag tta gat ttt gtt agt ggt gat ttg<br>Asp Leu Gly Val Thr Asn Pro Gln Leu Asp Phe Val Ser Gly Asp Leu<br>305                  310                  315                320 | | | 1021 |
| aaa aat ggg ttt gca caa agt ctt cag gtg aat act tct tta atg act<br>Lys Asn Gly Phe Ala Gln Ser Leu Gln Val Asn Thr Ser Leu Met Thr<br>                325                  330                335 | | | 1069 |
| tac cag gcc aat aat aac cag ttc cag cag caa tca ggg aag aac caa<br>Tyr Gln Ala Asn Asn Asn Gln Phe Gln Gln Gln Ser Gly Lys Asn Gln<br>            340                  345                350 | | | 1117 |
| gct agt aac tgg cca ctc cgt aac agc tat acc aga cag ata aac aat | | | 1165 |

```
Ala Ser Asn Trp Pro Leu Arg Asn Ser Tyr Thr Arg Gln Ile Asn Asn
            355                 360                 365 gga tca tcg tgg gtg cag gag cta aac aat gac gga ctt acc gtt acc    1213
Gly Ser Ser Trp Val Gln Glu Leu Asn Asn Asp Gly Leu Thr Val Thr
        370                 375                 380 cgg ttt ggt gag gcg cct ggt aca ggt gat tca tct gaa ttc cta aac    1261
Arg Phe Gly Glu Ala Pro Gly Thr Gly Asp Ser Ser Glu Phe Leu Asn
385                 390                 395                 400 cct gtt cct tct ggt ata agt aca act aat gaa gat gac ccg tca aaa    1309
Pro Val Pro Ser Gly Ile Ser Thr Thr Asn Glu Asp Asp Pro Ser Lys
                405                 410                 415 gac gag tct agt aag ttt gct tct agt gta tgg act ttc ctg gaa tcc    1357
Asp Glu Ser Ser Lys Phe Ala Ser Ser Val Trp Thr Phe Leu Glu Ser
            420                 425                 430 att cct gca aag cca gca tat gca tca gag aat cca ttt gtg aag ctg    1405
Ile Pro Ala Lys Pro Ala Tyr Ala Ser Glu Asn Pro Phe Val Lys Leu
        435                 440                 445 aac ctt gtt aga atg tca acc agt ggt ggt cgt ttc agg ttt act tct    1453
Asn Leu Val Arg Met Ser Thr Ser Gly Gly Arg Phe Arg Phe Thr Ser
    450                 455                 460 aaa agc aca ggt aat aat gtt gtt gtt atg gat agt gac tca gca gtg    1501
Lys Ser Thr Gly Asn Asn Val Val Val Met Asp Ser Asp Ser Ala Val
465                 470                 475                 480 aag agg aac aag tct gga gga aac aac gat aag aag aag aag aag aac    1549
Lys Arg Asn Lys Ser Gly Gly Asn Asn Asp Lys Lys Lys Lys Lys Asn
                485                 490                 495 aaa ggt ttc ttt tgc tta tcg atc att ggg gct tta tgt gct ttg ttt    1597
Lys Gly Phe Phe Cys Leu Ser Ile Ile Gly Ala Leu Cys Ala Leu Phe
            500                 505                 510 tgg gtg atc ata gga aca atg gga ggt tca ggg agg cct ttg tta tgg    1645
Trp Val Ile Ile Gly Thr Met Gly Gly Ser Gly Arg Pro Leu Leu Trp
        515                 520                 525 tgagaaccga aaaatccaag aggttaagag acataaaggc ttggttttgt gtgaaccatt    1705
agagagtcaa gtcattgtaa ttattctctt ggattattag attcagaagc tgtttagtat    1765
cacagtttat gcttggaagt tttctctggt attgttaaaa aagtaccaat agaaataagc    1825
aaaagaattt tcttatcttt taggatattt gaacaaatga tgttacttaa ctagattatt    1885
aacttggagg ttgttgtaca aaaaaaaaaa aaaaa                                1920

<210> SEQ ID NO 148
<211> LENGTH: 528
<212> TYPE: PRT
<213> ORGANISM: Arabidopsis thaliana

<400> SEQUENCE: 148

Met Asp Leu Ser Val Glu Asn Gly Gly Leu Ala Pro Gly Phe Arg Phe
1               5                   10                  15

His Pro Thr Asp Glu Glu Leu Val Val Tyr Tyr Leu Lys Arg Lys Ile
            20                  25                  30

Arg Arg Lys Lys Leu Arg Val Glu Ala Ile Gly Glu Thr Asp Val Tyr
        35                  40                  45

Lys Phe Asp Pro Glu Glu Leu Pro Glu Lys Ala Leu Tyr Lys Thr Arg
    50                  55                  60

Asp Arg Gln Trp Phe Phe Phe Ser Leu Arg Asp Arg Lys His Gly Ser
65                  70                  75                  80

Arg Ser Ser Arg Ala Thr Glu Arg Gly Tyr Trp Lys Ala Thr Gly Lys
                85                  90                  95
```

-continued

```
Asp Arg Val Ile His Cys Asp Ser Arg Pro Val Gly Glu Lys Lys Thr
                100                 105                 110
Leu Val Phe His Arg Gly Arg Ala Pro Asn Gly Glu Arg Thr Asn Trp
            115                 120                 125
Val Met His Glu Tyr Thr Leu His Lys Glu Glu Leu Lys Arg Cys Gly
        130                 135                 140
Gly Glu Asp Val Lys Asp Ala Tyr Val Leu Tyr Lys Ile Tyr Lys Lys
145                 150                 155                 160
Ser Gly Ser Gly Pro Lys Asn Gly Glu Gln Tyr Gly Ala Pro Phe Ile
                165                 170                 175
Glu Glu Glu Trp Ala Glu Asp Asp Asp Val Asp Glu Pro Ala
            180                 185                 190
Asn Gln Leu Val Val Ser Ala Ser Val Asp Asn Ser Leu Trp Gly Lys
        195                 200                 205
Gly Leu Asn Gln Ser Glu Leu Asp Asp Asn Asp Ile Glu Glu Leu Met
210                 215                 220
Ser Gln Val Arg Asp Gln Ser Gly Pro Thr Leu Gln Gln Asn Gly Val
225                 230                 235                 240
Ser Gly Leu Asn Ser His Val Asp Thr Tyr Asn Leu Glu Asn Leu Glu
                245                 250                 255
Glu Asp Met Tyr Leu Glu Ile Asn Asp Leu Met Glu Pro Glu Pro Gly
            260                 265                 270
Pro Thr Ser Val Glu Val Met Glu Asn Asn Trp Asn Glu Asp Gly Ser
        275                 280                 285
Gly Leu Leu Asn Asp Asp Phe Val Gly Ala Asp Ser Tyr Phe Leu
290                 295                 300
Asp Leu Gly Val Thr Asn Pro Gln Leu Asp Phe Val Ser Gly Asp Leu
305                 310                 315                 320
Lys Asn Gly Phe Ala Gln Ser Leu Gln Val Asn Thr Ser Leu Met Thr
                325                 330                 335
Tyr Gln Ala Asn Asn Asn Gln Phe Gln Gln Ser Gly Lys Asn Gln
            340                 345                 350
Ala Ser Asn Trp Pro Leu Arg Asn Ser Tyr Thr Arg Gln Ile Asn Asn
        355                 360                 365
Gly Ser Ser Trp Val Gln Glu Leu Asn Asn Asp Gly Leu Thr Val Thr
370                 375                 380
Arg Phe Gly Glu Ala Pro Gly Thr Gly Asp Ser Ser Glu Phe Leu Asn
385                 390                 395                 400
Pro Val Pro Ser Gly Ile Ser Thr Thr Asn Glu Asp Asp Pro Ser Lys
                405                 410                 415
Asp Glu Ser Ser Lys Phe Ala Ser Val Trp Thr Phe Leu Glu Ser
            420                 425                 430
Ile Pro Ala Lys Pro Ala Tyr Ala Ser Glu Asn Pro Phe Val Lys Leu
        435                 440                 445
Asn Leu Val Arg Met Ser Thr Ser Gly Gly Arg Phe Arg Phe Thr Ser
450                 455                 460
Lys Ser Thr Gly Asn Asn Val Val Val Met Asp Ser Asp Ser Ala Val
465                 470                 475                 480
Lys Arg Asn Lys Ser Gly Gly Asn Asn Asp Lys Lys Lys Lys Asn
                485                 490                 495
Lys Gly Phe Phe Cys Leu Ser Ile Ile Gly Ala Leu Cys Ala Leu Phe
            500                 505                 510
Trp Val Ile Ile Gly Thr Met Gly Gly Ser Gly Arg Pro Leu Leu Trp
```

<210> SEQ ID NO 149
<211> LENGTH: 1219
<212> TYPE: DNA
<213> ORGANISM: Arabidopsis thaliana
<220> FEATURE:
<221> NAME/KEY: CDS
<222> LOCATION: (177)..(950)

<400> SEQUENCE: 149

```
atgctaagga gccctcccaa aaagaacaa caaatcacat ttttatataa ctgttaacat      60
aataatctca gcctcatcaa cacacatata tagatagcca acatcacaca aacatagaga    120
ttccaaaaaa taaaataaa gaaaacataa atcctctgag gaaaaattcc gatgag atg    179
                                                                Met
                                                                  1 aca gaa ggt gga gaa tat tct ccg gcg atg atg tca gca gag cca ttc      227
Thr Glu Gly Gly Glu Tyr Ser Pro Ala Met Met Ser Ala Glu Pro Phe
          5                  10                  15 ttg acc atg aag aag atg aag aag agc aac cac aac aag aac aat cag      275
Leu Thr Met Lys Lys Met Lys Lys Ser Asn His Asn Lys Asn Asn Gln
         20                  25                  30 aga agg ttt agc gac gag cag atc aag tca ctg gag atg atg ttt gag      323
Arg Arg Phe Ser Asp Glu Gln Ile Lys Ser Leu Glu Met Met Phe Glu
     35                  40                  45 tct gag aca agg ctt gag cca agg aag aag gtt caa tta gct aga gag      371
Ser Glu Thr Arg Leu Glu Pro Arg Lys Lys Val Gln Leu Ala Arg Glu
 50                  55                  60                  65 cta ggg ttg cag ccg agg caa gtg gct ata tgg ttt cag aac aag agg      419
Leu Gly Leu Gln Pro Arg Gln Val Ala Ile Trp Phe Gln Asn Lys Arg
                 70                  75                  80 gct cgt tgg aaa tcc aag cag ctc gag act gag tac aac att ctc aga      467
Ala Arg Trp Lys Ser Lys Gln Leu Glu Thr Glu Tyr Asn Ile Leu Arg
             85                  90                  95 caa aac tac gac aac ttg gct tct cag ttc gag tcc tta aag aaa gaa      515
Gln Asn Tyr Asp Asn Leu Ala Ser Gln Phe Glu Ser Leu Lys Lys Glu
        100                 105                 110 aaa caa gct tta gtc tct gag ttg cag agg cta aaa gag gcg acg caa      563
Lys Gln Ala Leu Val Ser Glu Leu Gln Arg Leu Lys Glu Ala Thr Gln
    115                 120                 125 aag aag aca cag gag gag gaa agg cag tgt agt gga gat caa gcg gtg      611
Lys Lys Thr Gln Glu Glu Glu Arg Gln Cys Ser Gly Asp Gln Ala Val
130                 135                 140                 145 gtt gct cta agc agc aca cat cat gaa tca gaa aac gaa gag aac cgg      659
Val Ala Leu Ser Ser Thr His His Glu Ser Glu Asn Glu Glu Asn Arg
                150                 155                 160 agg cgt aaa ccg gaa gag gtt aga ccg gag atg gag atg aaa gat gat      707
Arg Arg Lys Pro Glu Glu Val Arg Pro Glu Met Glu Met Lys Asp Asp
            165                 170                 175 aag ggt cat cat ggg gtt atg tgt gat cat cat gat tat gaa gat gat      755
Lys Gly His His Gly Val Met Cys Asp His His Asp Tyr Glu Asp Asp
        180                 185                 190 gat aat ggt tat agt aac aac atc aag aga gag tat ttt ggt ggg ttt      803
Asp Asn Gly Tyr Ser Asn Asn Ile Lys Arg Glu Tyr Phe Gly Gly Phe
    195                 200                 205 gag gaa gaa cca gat cac tta atg aac att gtt gaa cca gct gat agt      851
Glu Glu Glu Pro Asp His Leu Met Asn Ile Val Glu Pro Ala Asp Ser
210                 215                 220                 225 tgt ttg aca tca tct gat gat tgg aga ggt ttc aaa tca gat act act      899
Cys Leu Thr Ser Ser Asp Asp Trp Arg Gly Phe Lys Ser Asp Thr Thr
```

```
                230             235             240
act ctc ttg gac caa tcc agc aac aat tac cct tgg cgg gat ttt tgg    947
Thr Leu Leu Asp Gln Ser Ser Asn Asn Tyr Pro Trp Arg Asp Phe Trp
            245                 250                 255 tca tgaaaacaat aaactctaaa caagaagatg aaacagattg agactaaaga         1000
Ser ttggatatat acatattcaa atcgaaattt accggtctac atcgcatgaa ccgagccacg  1060
gatatagaga tattcggtcc agcaaatgac tcgtttctca gcgagaattt tgcaggattt  1120
tgagctgaaa ttgtatggtt ttgtctgtat aaatgatgtg tttagaaaga cgtatattct  1180
caaaaaaaaa aaaaaaaaa aagaaaaaaa aaaaaaaa                           1219

<210> SEQ ID NO 150
<211> LENGTH: 258
<212> TYPE: PRT
<213> ORGANISM: Arabidopsis thaliana

<400> SEQUENCE: 150
```

Met Thr Glu Gly Gly Glu Tyr Ser Pro Ala Met Met Ser Ala Glu Pro
1               5                   10                  15

Phe Leu Thr Met Lys Lys Met Lys Lys Ser Asn His Asn Lys Asn Asn
                20                  25                  30

Gln Arg Arg Phe Ser Asp Glu Gln Ile Lys Ser Leu Glu Met Met Phe
            35                  40                  45

Glu Ser Glu Thr Arg Leu Glu Pro Arg Lys Lys Val Gln Leu Ala Arg
        50                  55                  60

Glu Leu Gly Leu Gln Pro Arg Gln Val Ala Ile Trp Phe Gln Asn Lys
65                  70                  75                  80

Arg Ala Arg Trp Lys Ser Lys Gln Leu Glu Thr Glu Tyr Asn Ile Leu
                85                  90                  95

Arg Gln Asn Tyr Asp Asn Leu Ala Ser Gln Phe Glu Ser Leu Lys Lys
            100                 105                 110

Glu Lys Gln Ala Leu Val Ser Glu Leu Gln Arg Leu Lys Glu Ala Thr
        115                 120                 125

Gln Lys Lys Thr Gln Glu Glu Arg Gln Cys Ser Gly Asp Gln Ala
    130                 135                 140

Val Val Ala Leu Ser Ser Thr His His Glu Ser Glu Asn Glu Glu Asn
145                 150                 155                 160

Arg Arg Arg Lys Pro Glu Glu Val Arg Pro Glu Met Glu Met Lys Asp
                165                 170                 175

Asp Lys Gly His His Gly Val Met Cys Asp His His Asp Tyr Glu Asp
            180                 185                 190

Asp Asp Asn Gly Tyr Ser Asn Asn Ile Lys Arg Glu Tyr Phe Gly Gly
        195                 200                 205

Phe Glu Glu Glu Pro Asp His Leu Met Asn Ile Val Glu Pro Ala Asp
    210                 215                 220

Ser Cys Leu Thr Ser Ser Asp Asp Trp Arg Gly Phe Lys Ser Asp Thr
225                 230                 235                 240

Thr Thr Leu Leu Asp Gln Ser Ser Asn Asn Tyr Pro Trp Arg Asp Phe
                245                 250                 255

Trp Ser

```
<210> SEQ ID NO 151
<211> LENGTH: 978
<212> TYPE: DNA
```

```
<213> ORGANISM: Arabidopsis thaliana
<220> FEATURE:
<221> NAME/KEY: CDS
<222> LOCATION: (89)..(793)

<400> SEQUENCE: 151
aaagaaagaa agaaaaaaaa gaaacaaata attccaaaac cttctctctt aatcaaaatc      60
aagaaactta caagatctgg tgaaaacc atg gaa gaa gga gat ttt ttc aac       112
                                Met Glu Glu Gly Asp Phe Phe Asn
                                  1               5 tgc tgt ttc agc gag att agt agt ggc atg acc atg aat aag aag aag      160
Cys Cys Phe Ser Glu Ile Ser Ser Gly Met Thr Met Asn Lys Lys Lys
     10                  15                  20 atg aag aag agc aat aac caa aag agg ttt agc gag gaa cag atc aag      208
Met Lys Lys Ser Asn Asn Gln Lys Arg Phe Ser Glu Glu Gln Ile Lys
 25                  30                  35                  40 tca ctt gag ctt ata ttt gag tct gag acg agg ctt gag ccg agg aag      256
Ser Leu Glu Leu Ile Phe Glu Ser Glu Thr Arg Leu Glu Pro Arg Lys
                 45                  50                  55 aag gtt cag gta gct aga gag cta ggg ctg caa cca aga caa gtg gct      304
Lys Val Gln Val Ala Arg Glu Leu Gly Leu Gln Pro Arg Gln Val Ala
             60                  65                  70 ata tgg ttt caa aac aag agg gct cga tgg aaa act aag caa ctt gag      352
Ile Trp Phe Gln Asn Lys Arg Ala Arg Trp Lys Thr Lys Gln Leu Glu
         75                  80                  85 aaa gag tat aac act ctt aga gcc aat tac aac aat ttg gct tca caa      400
Lys Glu Tyr Asn Thr Leu Arg Ala Asn Tyr Asn Asn Leu Ala Ser Gln
     90                  95                 100 ttt gaa atc atg aag aaa gaa aag caa tct ctg gtc tct gag ctg cag      448
Phe Glu Ile Met Lys Lys Glu Lys Gln Ser Leu Val Ser Glu Leu Gln
105                 110                 115                 120 aga cta aac gaa gag atg caa agg cct aaa gaa gaa aag cat cat gag      496
Arg Leu Asn Glu Glu Met Gln Arg Pro Lys Glu Glu Lys His His Glu
                125                 130                 135 tgt tgt ggt gat caa gga ctg gct cta agc agc agc aca gag tcg cat      544
Cys Cys Gly Asp Gln Gly Leu Ala Leu Ser Ser Ser Thr Glu Ser His
            140                 145                 150 aat gga aag agt gag cca gaa ggg agg tta gac caa ggg agt gtt cta      592
Asn Gly Lys Ser Glu Pro Glu Gly Arg Leu Asp Gln Gly Ser Val Leu
        155                 160                 165 tgt aat gat ggt gat tac aac aac aac att aaa aca gag tat ttt ggg      640
Cys Asn Asp Gly Asp Tyr Asn Asn Asn Ile Lys Thr Glu Tyr Phe Gly
    170                 175                 180 ttc gag gaa gag act gat cat gag ctg atg aac att gtg gag aaa gct      688
Phe Glu Glu Glu Thr Asp His Glu Leu Met Asn Ile Val Glu Lys Ala
185                 190                 195                 200 gat gat agt tgc ttg aca tct tct gag aat tgg gga ggt ttc aat tct      736
Asp Asp Ser Cys Leu Thr Ser Ser Glu Asn Trp Gly Gly Phe Asn Ser
                205                 210                 215 gat tct ctc tta gac caa tct agc agc aat tac cct aac tgg tgg gag      784
Asp Ser Leu Leu Asp Gln Ser Ser Ser Asn Tyr Pro Asn Trp Trp Glu
            220                 225                 230 ttt tgg tca taaaagcata taagaaaaaa acagaacata agcgaagaga             833
Phe Trp Ser
        235 aagagtgtga atagtttgta aattatgtgt taagaaaaat aaatttagtt tagtttaaat   893 cttgtttcga tctatgtatc tactatgttc aatactcttt gtagctaatt agtagcttat   953 aatgagacta gaaaagtttt gaagc                                          978
```

<210> SEQ ID NO 152
<211> LENGTH: 235
<212> TYPE: PRT
<213> ORGANISM: Arabidopsis thaliana

<400> SEQUENCE: 152

Met Glu Glu Gly Asp Phe Phe Asn Cys Cys Phe Ser Glu Ile Ser Ser
1               5                   10                  15

Gly Met Thr Met Asn Lys Lys Met Lys Lys Ser Asn Asn Gln Lys
            20                  25                  30

Arg Phe Ser Glu Glu Gln Ile Lys Ser Leu Glu Leu Ile Phe Glu Ser
        35                  40                  45

Glu Thr Arg Leu Glu Pro Arg Lys Lys Val Gln Val Ala Arg Glu Leu
    50                  55                  60

Gly Leu Gln Pro Arg Gln Val Ala Ile Trp Phe Gln Asn Lys Arg Ala
65                  70                  75                  80

Arg Trp Lys Thr Lys Gln Leu Glu Lys Glu Tyr Asn Thr Leu Arg Ala
                85                  90                  95

Asn Tyr Asn Asn Leu Ala Ser Gln Phe Glu Ile Met Lys Lys Glu Lys
            100                 105                 110

Gln Ser Leu Val Ser Glu Leu Gln Arg Leu Asn Glu Glu Met Gln Arg
        115                 120                 125

Pro Lys Glu Glu Lys His His Glu Cys Cys Gly Asp Gln Gly Leu Ala
    130                 135                 140

Leu Ser Ser Ser Thr Glu Ser His Asn Gly Lys Ser Glu Pro Glu Gly
145                 150                 155                 160

Arg Leu Asp Gln Gly Ser Val Leu Cys Asn Asp Gly Asp Tyr Asn Asn
                165                 170                 175

Asn Ile Lys Thr Glu Tyr Phe Gly Phe Glu Glu Thr Asp His Glu
            180                 185                 190

Leu Met Asn Ile Val Glu Lys Ala Asp Asp Ser Cys Leu Thr Ser Ser
        195                 200                 205

Glu Asn Trp Gly Gly Phe Asn Ser Asp Ser Leu Leu Asp Gln Ser Ser
    210                 215                 220

Ser Asn Tyr Pro Asn Trp Trp Glu Phe Trp Ser
225                 230                 235

<210> SEQ ID NO 153
<211> LENGTH: 2043
<212> TYPE: DNA
<213> ORGANISM: Arabidopsis thaliana
<220> FEATURE:
<221> NAME/KEY: CDS
<222> LOCATION: (1)..(2040)

<400> SEQUENCE: 153 atg gct gct tac ttt cac gga aac cca ccg gag atc tct gcc gga tcc      48
Met Ala Ala Tyr Phe His Gly Asn Pro Pro Glu Ile Ser Ala Gly Ser
1               5                   10                  15 gac ggt ggt ctt caa acg ttg atc ctc atg aat cca act act tac gtt      96
Asp Gly Gly Leu Gln Thr Leu Ile Leu Met Asn Pro Thr Thr Tyr Val
            20                  25                  30 cag tac acc caa caa gac aac gac tcg aac aac aac aac agc aac           144
Gln Tyr Thr Gln Gln Asp Asn Asp Ser Asn Asn Asn Asn Ser Asn
        35                  40                  45 aat agc aac aac aac aac aca aac aca aac aca aac aac aac agt           192
Asn Ser Asn Asn Asn Asn Thr Asn Thr Asn Thr Asn Asn Asn Ser
    50                  55                  60

```
agt ttc gtt ttc ctc gat tcc cac gcg ccg cag cca aac gcg agc cag       240
Ser Phe Val Phe Leu Asp Ser His Ala Pro Gln Pro Asn Ala Ser Gln
 65                  70                  75                  80 cag ttc gtc gga ata cca ctc tca ggt cac gaa gct gct tcc att aca       288
Gln Phe Val Gly Ile Pro Leu Ser Gly His Glu Ala Ala Ser Ile Thr
                 85                  90                  95 gcc gcc gac aac atc tcc gta ctt cac ggt tat cct ccg cgc gtg cag       336
Ala Ala Asp Asn Ile Ser Val Leu His Gly Tyr Pro Pro Arg Val Gln
            100                 105                 110 tac agt ctc tac ggt agc cac caa gtg gat ccc act cac cag caa gcc       384
Tyr Ser Leu Tyr Gly Ser His Gln Val Asp Pro Thr His Gln Gln Ala
        115                 120                 125 gcg tgt gag acg cca cgc gcg cag caa ggc ctc tct tta acc ctc tcg       432
Ala Cys Glu Thr Pro Arg Ala Gln Gln Gly Leu Ser Leu Thr Leu Ser
    130                 135                 140 tct caa cag cag cag caa cag caa cat cat caa caa cac cag cct att       480
Ser Gln Gln Gln Gln Gln Gln Gln His His Gln Gln His Gln Pro Ile
145                 150                 155                 160 cac gtc gga ttc ggg tcc gga cat gga gaa gat atc cgg gtc ggg tct       528
His Val Gly Phe Gly Ser Gly His Gly Glu Asp Ile Arg Val Gly Ser
                165                 170                 175 ggc tct aca gga tcg ggg gta aca aac ggt ata gct aat ctt gtt agc       576
Gly Ser Thr Gly Ser Gly Val Thr Asn Gly Ile Ala Asn Leu Val Ser
            180                 185                 190 tcc aag tac ttg aag gca gca caa gag ctt ctt gac gaa gta gtc aac       624
Ser Lys Tyr Leu Lys Ala Ala Gln Glu Leu Leu Asp Glu Val Val Asn
        195                 200                 205 gct gat tcc gat gac atg aac gct aaa tcc caa cta ttc tca tcg aaa       672
Ala Asp Ser Asp Asp Met Asn Ala Lys Ser Gln Leu Phe Ser Ser Lys
    210                 215                 220 aag ggt agt tgc gga aat gat aaa cct gtc gga gaa tca tcg gcc ggc       720
Lys Gly Ser Cys Gly Asn Asp Lys Pro Val Gly Glu Ser Ser Ala Gly
225                 230                 235                 240 gct gga gga gaa ggt tcc ggt ggc gga gca gaa gca gcc ggg aaa cgt       768
Ala Gly Gly Glu Gly Ser Gly Gly Gly Ala Glu Ala Ala Gly Lys Arg
                245                 250                 255 ccg gtg gag cta ggc acg gca gag aga caa gaa ata cag atg aag aaa       816
Pro Val Glu Leu Gly Thr Ala Glu Arg Gln Glu Ile Gln Met Lys Lys
            260                 265                 270 gca aaa ctt agt aac atg ctt cat gag gtg gag cag aga tat aga cag       864
Ala Lys Leu Ser Asn Met Leu His Glu Val Glu Gln Arg Tyr Arg Gln
        275                 280                 285 tac cac cag cag atg cag atg gtg atc tct tcg ttc gag caa gcg gca       912
Tyr His Gln Gln Met Gln Met Val Ile Ser Ser Phe Glu Gln Ala Ala
    290                 295                 300 ggg ata gga tca gcg aag tca tac acg tcg cta gca ttg aaa acc ata       960
Gly Ile Gly Ser Ala Lys Ser Tyr Thr Ser Leu Ala Leu Lys Thr Ile
305                 310                 315                 320 tca aga cag ttc cgt tgc ttg aaa gag gcg atc gct ggt cag ata aaa      1008
Ser Arg Gln Phe Arg Cys Leu Lys Glu Ala Ile Ala Gly Gln Ile Lys
                325                 330                 335 gcg gcc aac aag agt ctt ggg gag gaa gat tca gtg tct ggt gtt ggg      1056
Ala Ala Asn Lys Ser Leu Gly Glu Glu Asp Ser Val Ser Gly Val Gly
            340                 345                 350 agg ttt gag ggg tcg agg ctc aag ttc gtg gac cac cac ttg aga cag      1104
Arg Phe Glu Gly Ser Arg Leu Lys Phe Val Asp His His Leu Arg Gln
        355                 360                 365 caa aga gct ctt caa caa ctg gga atg att caa cat cct tcc aat aat      1152
Gln Arg Ala Leu Gln Gln Leu Gly Met Ile Gln His Pro Ser Asn Asn
```

-continued

```
              370                 375                 380
gct tgg aga cct caa cgt ggt ctc cca gaa cga gcc gtc tca gtt ctc    1200
Ala Trp Arg Pro Gln Arg Gly Leu Pro Glu Arg Ala Val Ser Val Leu
385                 390                 395                 400 cgt gct tgg ctc ttc gaa cac ttt ctt cat cca tac cct aag gat tcg    1248
Arg Ala Trp Leu Phe Glu His Phe Leu His Pro Tyr Pro Lys Asp Ser
            405                 410                 415 gac aag cac atg cta gct aag caa aca gga ctc act cgt agc cag gtg    1296
Asp Lys His Met Leu Ala Lys Gln Thr Gly Leu Thr Arg Ser Gln Val
                420                 425                 430 tcg aac tgg ttt ata aac gcg aga gtt cgg tta tgg aaa cca atg gtg    1344
Ser Asn Trp Phe Ile Asn Ala Arg Val Arg Leu Trp Lys Pro Met Val
            435                 440                 445 gag gag atg tac atg gag gaa atg aag gag cag gca aag aac atg gga    1392
Glu Glu Met Tyr Met Glu Glu Met Lys Glu Gln Ala Lys Asn Met Gly
                450                 455                 460 tcc atg gaa aag act cct ttg gat caa agc aac gaa gat tct gct tca    1440
Ser Met Glu Lys Thr Pro Leu Asp Gln Ser Asn Glu Asp Ser Ala Ser
465                 470                 475                 480 aag tca aca agt aac caa gaa aag agc cca atg gcg gac act aat tac    1488
Lys Ser Thr Ser Asn Gln Glu Lys Ser Pro Met Ala Asp Thr Asn Tyr
            485                 490                 495 cat atg aat ccc aat cac aac ggt gac cta gaa ggc gtc act gga atg    1536
His Met Asn Pro Asn His Asn Gly Asp Leu Glu Gly Val Thr Gly Met
                500                 505                 510 caa gga agc ccc aag aga cta aga acc agc gac gag aca atg atg cag    1584
Gln Gly Ser Pro Lys Arg Leu Arg Thr Ser Asp Glu Thr Met Met Gln
            515                 520                 525 cca ata aat gcg gat ttc agc tcc aac gag aag ctc acg atg aag att    1632
Pro Ile Asn Ala Asp Phe Ser Ser Asn Glu Lys Leu Thr Met Lys Ile
530                 535                 540 cta gaa gaa cgg caa ggg ata aga tca gat ggt ggc tac cct ttc atg    1680
Leu Glu Glu Arg Gln Gly Ile Arg Ser Asp Gly Gly Tyr Pro Phe Met
545                 550                 555                 560 ggt aat ttc ggg caa tac caa atg gat gag atg tca aga ttt gat gta    1728
Gly Asn Phe Gly Gln Tyr Gln Met Asp Glu Met Ser Arg Phe Asp Val
            565                 570                 575 gtc tca gac cag gag ctc atg gcg caa agg tac tca gga aac aac aat    1776
Val Ser Asp Gln Glu Leu Met Ala Gln Arg Tyr Ser Gly Asn Asn Asn
                580                 585                 590 ggc gtg tcc ctc acg tta ggt tta cct cat tgt gat agc ttg tcg tcc    1824
Gly Val Ser Leu Thr Leu Gly Leu Pro His Cys Asp Ser Leu Ser Ser
            595                 600                 605 acg cac cat cag ggt ttc atg cag acc cac cat ggg att cct ata ggg    1872
Thr His His Gln Gly Phe Met Gln Thr His His Gly Ile Pro Ile Gly
610                 615                 620 aga aga gtg aaa ata gga gaa aca gag gaa tat gga ccc gcc acc atc    1920
Arg Arg Val Lys Ile Gly Glu Thr Glu Glu Tyr Gly Pro Ala Thr Ile
625                 630                 635                 640 aat ggt ggt agc tcg acc aca acc gca cat tca tca gcg gca gct gcc    1968
Asn Gly Gly Ser Ser Thr Thr Thr Ala His Ser Ser Ala Ala Ala Ala
            645                 650                 655 gcg gct tac aat ggg atg aac ata cag aac cag aag aga tat gtg gct    2016
Ala Ala Tyr Asn Gly Met Asn Ile Gln Asn Gln Lys Arg Tyr Val Ala
                660                 665                 670 cag tta ttg ccc gac ttc gtt gca taa                                2043
Gln Leu Leu Pro Asp Phe Val Ala
            675                 680
```

<210> SEQ ID NO 154
<211> LENGTH: 680
<212> TYPE: PRT
<213> ORGANISM: Arabidopsis thaliana

<400> SEQUENCE: 154

```
Met Ala Ala Tyr Phe His Gly Asn Pro Pro Glu Ile Ser Ala Gly Ser
  1               5                  10                  15

Asp Gly Gly Leu Gln Thr Leu Ile Leu Met Asn Pro Thr Thr Tyr Val
             20                  25                  30

Gln Tyr Thr Gln Gln Asp Asn Asp Ser Asn Asn Asn Asn Asn Ser Asn
         35                  40                  45

Asn Ser Asn Asn Asn Asn Thr Asn Thr Asn Thr Asn Asn Asn Asn Ser
 50                  55                  60

Ser Phe Val Phe Leu Asp Ser His Ala Pro Gln Pro Asn Ala Ser Gln
 65                  70                  75                  80

Gln Phe Val Gly Ile Pro Leu Ser Gly His Glu Ala Ala Ser Ile Thr
                 85                  90                  95

Ala Ala Asp Asn Ile Ser Val Leu His Gly Tyr Pro Pro Arg Val Gln
            100                 105                 110

Tyr Ser Leu Tyr Gly Ser His Gln Val Asp Pro Thr His Gln Gln Ala
        115                 120                 125

Ala Cys Glu Thr Pro Arg Ala Gln Gln Gly Leu Ser Leu Thr Leu Ser
    130                 135                 140

Ser Gln Gln Gln Gln Gln Gln His His Gln Gln His Gln Pro Ile
145                 150                 155                 160

His Val Gly Phe Gly Ser Gly His Gly Glu Asp Ile Arg Val Gly Ser
                165                 170                 175

Gly Ser Thr Gly Ser Gly Val Thr Asn Gly Ile Ala Asn Leu Val Ser
            180                 185                 190

Ser Lys Tyr Leu Lys Ala Ala Gln Glu Leu Leu Asp Glu Val Val Asn
        195                 200                 205

Ala Asp Ser Asp Asp Met Asn Ala Lys Ser Gln Leu Phe Ser Ser Lys
    210                 215                 220

Lys Gly Ser Cys Gly Asn Asp Lys Pro Val Gly Glu Ser Ser Ala Gly
225                 230                 235                 240

Ala Gly Gly Glu Gly Ser Gly Gly Ala Glu Ala Ala Gly Lys Arg
                245                 250                 255

Pro Val Glu Leu Gly Thr Ala Glu Arg Gln Glu Ile Gln Met Lys Lys
            260                 265                 270

Ala Lys Leu Ser Asn Met Leu His Glu Val Glu Gln Arg Tyr Arg Gln
        275                 280                 285

Tyr His Gln Gln Met Gln Met Val Ile Ser Ser Phe Glu Gln Ala Ala
    290                 295                 300

Gly Ile Gly Ser Ala Lys Ser Tyr Thr Ser Leu Ala Leu Lys Thr Ile
305                 310                 315                 320

Ser Arg Gln Phe Arg Cys Leu Lys Glu Ala Ile Ala Gly Gln Ile Lys
                325                 330                 335

Ala Ala Asn Lys Ser Leu Gly Glu Glu Asp Ser Val Ser Gly Val Gly
            340                 345                 350

Arg Phe Glu Gly Ser Arg Leu Lys Phe Val Asp His His Leu Arg Gln
        355                 360                 365

Gln Arg Ala Leu Gln Gln Leu Gly Met Ile Gln His Pro Ser Asn Asn
    370                 375                 380
```

```
Ala Trp Arg Pro Gln Arg Gly Leu Pro Glu Arg Ala Val Ser Val Leu
385                 390                 395                 400

Arg Ala Trp Leu Phe Glu His Phe Leu His Pro Tyr Pro Lys Asp Ser
            405                 410                 415

Asp Lys His Met Leu Ala Lys Gln Thr Gly Leu Thr Arg Ser Gln Val
        420                 425                 430

Ser Asn Trp Phe Ile Asn Ala Arg Val Arg Leu Trp Lys Pro Met Val
    435                 440                 445

Glu Glu Met Tyr Met Glu Glu Met Lys Glu Gln Ala Lys Asn Met Gly
450                 455                 460

Ser Met Glu Lys Thr Pro Leu Asp Gln Ser Asn Glu Asp Ser Ala Ser
465                 470                 475                 480

Lys Ser Thr Ser Asn Gln Glu Lys Ser Pro Met Ala Asp Thr Asn Tyr
                485                 490                 495

His Met Asn Pro Asn His Asn Gly Asp Leu Glu Gly Val Thr Gly Met
            500                 505                 510

Gln Gly Ser Pro Lys Arg Leu Arg Thr Ser Asp Glu Thr Met Met Gln
        515                 520                 525

Pro Ile Asn Ala Asp Phe Ser Ser Asn Glu Lys Leu Thr Met Lys Ile
    530                 535                 540

Leu Glu Glu Arg Gln Gly Ile Arg Ser Asp Gly Gly Tyr Pro Phe Met
545                 550                 555                 560

Gly Asn Phe Gly Gln Tyr Gln Met Asp Glu Met Ser Arg Phe Asp Val
                565                 570                 575

Val Ser Asp Gln Glu Leu Met Ala Gln Arg Tyr Ser Gly Asn Asn Asn
            580                 585                 590

Gly Val Ser Leu Thr Leu Gly Leu Pro His Cys Asp Ser Leu Ser Ser
        595                 600                 605

Thr His His Gln Gly Phe Met Gln Thr His His Gly Ile Pro Ile Gly
    610                 615                 620

Arg Arg Val Lys Ile Gly Glu Thr Glu Glu Tyr Gly Pro Ala Thr Ile
625                 630                 635                 640

Asn Gly Gly Ser Ser Thr Thr Thr Ala His Ser Ser Ala Ala Ala Ala
                645                 650                 655

Ala Ala Tyr Asn Gly Met Asn Ile Gln Asn Gln Lys Arg Tyr Val Ala
            660                 665                 670

Gln Leu Leu Pro Asp Phe Val Ala
        675                 680

<210> SEQ ID NO 155
<211> LENGTH: 1162
<212> TYPE: DNA
<213> ORGANISM: Arabidopsis thaliana
<220> FEATURE:
<221> NAME/KEY: CDS
<222> LOCATION: (49)..(933)

<400> SEQUENCE: 155
aaattcgctt tttttttct tctttgtata ttttttttt ttttgacc atg gcg gag      57
                                                   Met Ala Glu
                                                     1 gaa ttt gga agc ata gat tta ctc gga gat gaa gat ttc ttc ttc gat    105
Glu Phe Gly Ser Ile Asp Leu Leu Gly Asp Glu Asp Phe Phe Phe Asp
     5                  10                  15 ttc gat cct tca atc gta att gat tct ctt ccg gcg gag gat ttt ctt    153
Phe Asp Pro Ser Ile Val Ile Asp Ser Leu Pro Ala Glu Asp Phe Leu
 20                  25                  30                  35
```

```
cag tct tca ccg gat tca tgg atc gga gaa atc gag aat caa ttg atg      201
Gln Ser Ser Pro Asp Ser Trp Ile Gly Glu Ile Glu Asn Gln Leu Met
                40                  45                  50 aac gat gag aat cat caa gag gag agt ttt gtg gaa ttg gat cag caa      249
Asn Asp Glu Asn His Gln Glu Glu Ser Phe Val Glu Leu Asp Gln Gln
            55                  60                  65 tcg gtt tca gat ttc ata gcg gat cta ctc gtt gat tat cca act agc      297
Ser Val Ser Asp Phe Ile Ala Asp Leu Leu Val Asp Tyr Pro Thr Ser
        70                  75                  80 gat tct ggc tcc gtt gat ttg gcg gct gat aaa gtt cta acc gtc gat      345
Asp Ser Gly Ser Val Asp Leu Ala Ala Asp Lys Val Leu Thr Val Asp
    85                  90                  95 tct ccc gcc gcc gct gat gat tcc ggg aag gag aat tcg gat ttg gtt      393
Ser Pro Ala Ala Ala Asp Asp Ser Gly Lys Glu Asn Ser Asp Leu Val
100                 105                 110                 115 gtt gag aag aag tct aat gat tct ggt agc gag att cat gat gat gat      441
Val Glu Lys Lys Ser Asn Asp Ser Gly Ser Glu Ile His Asp Asp Asp
                120                 125                 130 gac gaa gaa gga gac gat gat gct gtg gct aaa aaa cga aga agg aga      489
Asp Glu Glu Gly Asp Asp Asp Ala Val Ala Lys Lys Arg Arg Arg Arg
            135                 140                 145 gta aga aat aga gat gcg gcg gtt aga tcg aga gag agg aag aag gaa      537
Val Arg Asn Arg Asp Ala Ala Val Arg Ser Arg Glu Arg Lys Lys Glu
        150                 155                 160 tat gta caa gat tta gag aag aag agt aag tat ctc gaa aga gaa tgc      585
Tyr Val Gln Asp Leu Glu Lys Lys Ser Lys Tyr Leu Glu Arg Glu Cys
    165                 170                 175 ttg aga cta gga cgt atg ctt gag tgc ttc gtt gct gaa aac cag tct      633
Leu Arg Leu Gly Arg Met Leu Glu Cys Phe Val Ala Glu Asn Gln Ser
180                 185                 190                 195 cta cgt tac tgt ttg caa aag ggt aat ggc aat aat act acc atg atg      681
Leu Arg Tyr Cys Leu Gln Lys Gly Asn Gly Asn Asn Thr Thr Met Met
                200                 205                 210 tcg aag cag gag tct gct gtg ctc ttg ttg gaa tcc ctg ctg ttg ggt      729
Ser Lys Gln Glu Ser Ala Val Leu Leu Leu Glu Ser Leu Leu Leu Gly
            215                 220                 225 tcc ctg ctt tgg ctt ctg gga gta aac ttc att tgc cta ttc cct tat      777
Ser Leu Leu Trp Leu Leu Gly Val Asn Phe Ile Cys Leu Phe Pro Tyr
        230                 235                 240 atg tcc cac aca aag tgt tgc ctc cta cgt cca gaa cca gaa aag ctg      825
Met Ser His Thr Lys Cys Cys Leu Leu Arg Pro Glu Pro Glu Lys Leu
    245                 250                 255 gtt cta aac ggg ctc ggg agt agt agc aaa ccg tct tat acc ggc gtt      873
Val Leu Asn Gly Leu Gly Ser Ser Ser Lys Pro Ser Tyr Thr Gly Val
260                 265                 270                 275 agt cgg aga tgt aag ggt tcg agg cct agg atg aaa tac caa atc tta      921
Ser Arg Arg Cys Lys Gly Ser Arg Pro Arg Met Lys Tyr Gln Ile Leu
                280                 285                 290 acc ctt gcg gcg tgacaacgcc tttttaact gcttcttttg cgcattttga           973
Thr Leu Ala Ala
            295 gttgtagatg agtgtctttt agttttctct ctcttgtttt gtatttcgct gttgaaagtt   1033 ttctgtctaa tatcgataag ttaacagtga atgtgggtct tatggttatg gatgatatct   1093 atctaataat gcttctgcct ttaaaatgtt gattttgagg cataacttca ggcaaaaaaa   1153 aaaaagaaa                                                           1162

<210> SEQ ID NO 156
```

<211> LENGTH: 295
<212> TYPE: PRT
<213> ORGANISM: Arabidopsis thaliana

<400> SEQUENCE: 156

Met Ala Glu Glu Phe Gly Ser Ile Asp Leu Leu Gly Asp Glu Asp Phe
1               5                   10                  15

Phe Phe Asp Phe Asp Pro Ser Ile Val Ile Asp Ser Leu Pro Ala Glu
            20                  25                  30

Asp Phe Leu Gln Ser Ser Pro Asp Ser Trp Ile Gly Glu Ile Glu Asn
        35                  40                  45

Gln Leu Met Asn Asp Glu Asn His Gln Glu Ser Phe Val Glu Leu
    50                  55                  60

Asp Gln Gln Ser Val Ser Asp Phe Ile Ala Asp Leu Leu Val Asp Tyr
65              70                  75                  80

Pro Thr Ser Asp Ser Gly Ser Val Asp Leu Ala Ala Asp Lys Val Leu
                85                  90                  95

Thr Val Asp Ser Pro Ala Ala Ala Asp Asp Ser Gly Lys Glu Asn Ser
            100                 105                 110

Asp Leu Val Val Glu Lys Lys Ser Asn Asp Ser Gly Ser Glu Ile His
        115                 120                 125

Asp Asp Asp Asp Glu Glu Gly Asp Asp Asp Ala Val Ala Lys Lys Arg
130                 135                 140

Arg Arg Arg Val Arg Asn Arg Asp Ala Ala Val Arg Ser Arg Glu Arg
145                 150                 155                 160

Lys Lys Glu Tyr Val Gln Asp Leu Glu Lys Ser Lys Tyr Leu Glu
            165                 170                 175

Arg Glu Cys Leu Arg Leu Gly Arg Met Leu Glu Cys Phe Val Ala Glu
        180                 185                 190

Asn Gln Ser Leu Arg Tyr Cys Leu Gln Lys Gly Asn Gly Asn Asn Thr
    195                 200                 205

Thr Met Met Ser Lys Gln Glu Ser Ala Val Leu Leu Glu Ser Leu
210                 215                 220

Leu Leu Gly Ser Leu Leu Trp Leu Leu Gly Val Asn Phe Ile Cys Leu
225                 230                 235                 240

Phe Pro Tyr Met Ser His Thr Lys Cys Cys Leu Leu Arg Pro Glu Pro
                245                 250                 255

Glu Lys Leu Val Leu Asn Gly Leu Gly Ser Ser Ser Lys Pro Ser Tyr
            260                 265                 270

Thr Gly Val Ser Arg Arg Cys Lys Gly Ser Arg Pro Arg Met Lys Tyr
        275                 280                 285

Gln Ile Leu Thr Leu Ala Ala
    290                 295

<210> SEQ ID NO 157
<211> LENGTH: 438
<212> TYPE: DNA
<213> ORGANISM: Arabidopsis thaliana
<220> FEATURE:
<221> NAME/KEY: CDS
<222> LOCATION: (1)..(435)

<400> SEQUENCE: 157 atg gca aac gca gag aag aca agt tca ggt tcc gac ata gat gag aag    48
Met Ala Asn Ala Glu Lys Thr Ser Ser Gly Ser Asp Ile Asp Glu Lys
1               5                   10                  15 aaa aga aaa cgc aag tta tca aac cgc gaa tct gca agg agg tcg cgt    96

```
                                                          -continued

Lys Arg Lys Arg Lys Leu Ser Asn Arg Glu Ser Ala Arg Arg Ser Arg
            20                  25                  30 ttg aag aaa cag aag tta atg gaa gac acg att cat gag atc tcc agt       144
Leu Lys Lys Gln Lys Leu Met Glu Asp Thr Ile His Glu Ile Ser Ser
        35                  40                  45 ctt gaa cga cga atc aaa gag aac agt gag aga tgt cga gct gta aaa       192
Leu Glu Arg Arg Ile Lys Glu Asn Ser Glu Arg Cys Arg Ala Val Lys
    50                  55                  60 cag agg ctt gac tcg gtc gaa acg gag aac gcg ggt ctt aga tcg gag       240
Gln Arg Leu Asp Ser Val Glu Thr Glu Asn Ala Gly Leu Arg Ser Glu
65                  70                  75                  80 aag att tgg ctc tcg agt tac gtt agc gat tta gag aat atg att gct       288
Lys Ile Trp Leu Ser Ser Tyr Val Ser Asp Leu Glu Asn Met Ile Ala
                85                  90                  95 acg acg agt tta acg ctg acg cag agt ggt ggt ggc gat tgt gtc gac       336
Thr Thr Ser Leu Thr Leu Thr Gln Ser Gly Gly Gly Asp Cys Val Asp
            100                 105                 110 gat cag aac gca aac gcg gga ata gcg gtt gga gat tgt aga cgt aca       384
Asp Gln Asn Ala Asn Ala Gly Ile Ala Val Gly Asp Cys Arg Arg Thr
        115                 120                 125 ccg tgg aaa ttg agt tgt ggt tct cta caa cca atg gcg tcc ttt aag       432
Pro Trp Lys Leu Ser Cys Gly Ser Leu Gln Pro Met Ala Ser Phe Lys
    130                 135                 140 aca tga                                                                438
Thr
145

<210> SEQ ID NO 158
<211> LENGTH: 145
<212> TYPE: PRT
<213> ORGANISM: Arabidopsis thaliana

<400> SEQUENCE: 158

Met Ala Asn Ala Glu Lys Thr Ser Ser Gly Ser Asp Ile Asp Glu Lys
1               5                   10                  15

Lys Arg Lys Arg Lys Leu Ser Asn Arg Glu Ser Ala Arg Arg Ser Arg
            20                  25                  30

Leu Lys Lys Gln Lys Leu Met Glu Asp Thr Ile His Glu Ile Ser Ser
        35                  40                  45

Leu Glu Arg Arg Ile Lys Glu Asn Ser Glu Arg Cys Arg Ala Val Lys
    50                  55                  60

Gln Arg Leu Asp Ser Val Glu Thr Glu Asn Ala Gly Leu Arg Ser Glu
65                  70                  75                  80

Lys Ile Trp Leu Ser Ser Tyr Val Ser Asp Leu Glu Asn Met Ile Ala
                85                  90                  95

Thr Thr Ser Leu Thr Leu Thr Gln Ser Gly Gly Gly Asp Cys Val Asp
            100                 105                 110

Asp Gln Asn Ala Asn Ala Gly Ile Ala Val Gly Asp Cys Arg Arg Thr
        115                 120                 125

Pro Trp Lys Leu Ser Cys Gly Ser Leu Gln Pro Met Ala Ser Phe Lys
    130                 135                 140

Thr
145

<210> SEQ ID NO 159
<211> LENGTH: 1697
<212> TYPE: DNA
<213> ORGANISM: Arabidopsis thaliana
<220> FEATURE:
```

```
<221> NAME/KEY: CDS
<222> LOCATION: (74)..(1435)

<400> SEQUENCE: 159
ccaaagaaaa aaaataaatt cgaaggtaaa tatccagaag cttgatcctc ctagttgtac      60
gaaagcttga gta atg ggg tct aga tta aac ttc aag agc ttt gtt gat       109
            Met Gly Ser Arg Leu Asn Phe Lys Ser Phe Val Asp
              1               5                  10 ggt gtg agt gag cag cag cca acg gtg ggg act agt ctt cca ttg act      157
Gly Val Ser Glu Gln Gln Pro Thr Val Gly Thr Ser Leu Pro Leu Thr
             15                  20                  25 agg cag aac tct gtg ttc tcg tta acc ttt gat gag ttt cag aac tca      205
Arg Gln Asn Ser Val Phe Ser Leu Thr Phe Asp Glu Phe Gln Asn Ser
 30                  35                  40 tgg ggt ggt gga att ggg aaa gat ttt ggg tct atg aac atg gat gag      253
Trp Gly Gly Gly Ile Gly Lys Asp Phe Gly Ser Met Asn Met Asp Glu
 45                  50                  55                  60 ctc ttg aag aac att tgg act gca gag gaa agt cat tca atg atg gga      301
Leu Leu Lys Asn Ile Trp Thr Ala Glu Glu Ser His Ser Met Met Gly
             65                  70                  75 aac aat acc agt tac acc aac atc agc aat ggt aat agt gga aac act      349
Asn Asn Thr Ser Tyr Thr Asn Ile Ser Asn Gly Asn Ser Gly Asn Thr
             80                  85                  90 gtt att aac ggc ggt ggc aac aac att ggt ggg tta gct gtt ggt gtg      397
Val Ile Asn Gly Gly Gly Asn Asn Ile Gly Gly Leu Ala Val Gly Val
         95                 100                 105 gga gga gaa agt ggt ggt ttt ttc act ggt ggg agt ttg cag aga caa      445
Gly Gly Glu Ser Gly Gly Phe Phe Thr Gly Gly Ser Leu Gln Arg Gln
110                 115                 120 ggt tca ctt acc ttg cct cgg acg att agt cag aaa agg gtt gat gat      493
Gly Ser Leu Thr Leu Pro Arg Thr Ile Ser Gln Lys Arg Val Asp Asp
125                 130                 135                 140 gtc tgg aag gag ctg atg aag gag gat gac att gga aat ggt gtt gtt      541
Val Trp Lys Glu Leu Met Lys Glu Asp Asp Ile Gly Asn Gly Val Val
                145                 150                 155 aat ggt ggg aca agc gga att ccg cag agg caa caa acg ctg gga gag      589
Asn Gly Gly Thr Ser Gly Ile Pro Gln Arg Gln Gln Thr Leu Gly Glu
            160                 165                 170 atg act ttg gag gag ttt ttg gtc agg gct ggt gtg gtt agg gaa gaa      637
Met Thr Leu Glu Glu Phe Leu Val Arg Ala Gly Val Val Arg Glu Glu
                175                 180                 185 cct caa ccg gtg gag agt gta act aac ttc aat ggc gga ttc tat gga      685
Pro Gln Pro Val Glu Ser Val Thr Asn Phe Asn Gly Gly Phe Tyr Gly
            190                 195                 200 ttt ggc agt aat gga ggt ctt ggg aca gct agt aat ggg ttt gtt gca      733
Phe Gly Ser Asn Gly Gly Leu Gly Thr Ala Ser Asn Gly Phe Val Ala
205                 210                 215                 220 aac caa cct caa gat ttg tca gga aat gga gta gcg gtg aga cag gat      781
Asn Gln Pro Gln Asp Leu Ser Gly Asn Gly Val Ala Val Arg Gln Asp
            225                 230                 235 ctg ctg act gct caa act cag cca cta cag atg cag cag cca cag atg      829
Leu Leu Thr Ala Gln Thr Gln Pro Leu Gln Met Gln Gln Pro Gln Met
            240                 245                 250 gtg cag cag cca cag atg gtg cag cag ccg caa caa ctg ata cag acg      877
Val Gln Gln Pro Gln Met Val Gln Gln Pro Gln Gln Leu Ile Gln Thr
            255                 260                 265 cag gag agg cct ttt ccc aaa cag acc act ata gca ttt tcc aac act      925
Gln Glu Arg Pro Phe Pro Lys Gln Thr Thr Ile Ala Phe Ser Asn Thr
            270                 275                 280
```

-continued

```
gtt gat gtg gtt aac cgt tct caa cct gca aca cag tgc cag gaa gtg      973
Val Asp Val Val Asn Arg Ser Gln Pro Ala Thr Gln Cys Gln Glu Val
285                 290                 295                 300 aag cct tca ata ctt gga att cat aac cat cct atg aac aac aat cta     1021
Lys Pro Ser Ile Leu Gly Ile His Asn His Pro Met Asn Asn Asn Leu
            305                 310                 315 ctg caa gct gtc gat ttt aaa aca gga gta acg gtt gca gca gta tct     1069
Leu Gln Ala Val Asp Phe Lys Thr Gly Val Thr Val Ala Ala Val Ser
        320                 325                 330 cct gga agc cag atg tca cct gat ctg act cca aag agc gcc ctg gat     1117
Pro Gly Ser Gln Met Ser Pro Asp Leu Thr Pro Lys Ser Ala Leu Asp
    335                 340                 345 gca tct ttg tcc cct gtt cct tac atg ttt ggg cga gtg aga aaa aca     1165
Ala Ser Leu Ser Pro Val Pro Tyr Met Phe Gly Arg Val Arg Lys Thr
350                 355                 360 ggt gca gtt ctg gag aaa gtg att gag aga agg caa aaa agg atg ata     1213
Gly Ala Val Leu Glu Lys Val Ile Glu Arg Arg Gln Lys Arg Met Ile
365                 370                 375                 380 aag aat agg gaa tca gct gca aga tcc cgc gct cgc aag caa gct tat     1261
Lys Asn Arg Glu Ser Ala Ala Arg Ser Arg Ala Arg Lys Gln Ala Tyr
            385                 390                 395 acg atg gaa ctg gaa gca gaa att gcg caa ctc aaa gaa ttg aat gaa     1309
Thr Met Glu Leu Glu Ala Glu Ile Ala Gln Leu Lys Glu Leu Asn Glu
        400                 405                 410 gag ttg cag aag aaa caa gtt gaa atc atg gaa aag cag aaa aat cag     1357
Glu Leu Gln Lys Lys Gln Val Glu Ile Met Glu Lys Gln Lys Asn Gln
    415                 420                 425 ctt ctg gag cct ctg cgc cag cca tgg gga atg gga tgc aaa agg caa     1405
Leu Leu Glu Pro Leu Arg Gln Pro Trp Gly Met Gly Cys Lys Arg Gln
430                 435                 440 tgc ttg cga agg aca ttg acg ggt ccc tgg tagagcttat aatggcgtct      1455
Cys Leu Arg Arg Thr Leu Thr Gly Pro Trp
445                 450 aaggaaccca acaaagcgcc gaagttatag aacaactcag aagatagaaa gctagctttg   1515
tacgtagttt aggcaggttc tgtgggtgat tgtaaatctt gaagtgtggc ggatttgaca   1575
gagatagata aacacatatc tgttctattt tcctaaatct tttggtttta tcttcctgat   1635
gtaatggatc tttatcattt gtcttgaaca tctttgtgac ttaaccagag tgaatttatc   1695
tt                                                                 1697
```

<210> SEQ ID NO 160
<211> LENGTH: 454
<212> TYPE: PRT
<213> ORGANISM: Arabidopsis thaliana

<400> SEQUENCE: 160

```
Met Gly Ser Arg Leu Asn Phe Lys Ser Phe Val Asp Gly Val Ser Glu
 1               5                  10                  15

Gln Gln Pro Thr Val Gly Thr Ser Leu Pro Leu Thr Arg Gln Asn Ser
            20                  25                  30

Val Phe Ser Leu Thr Phe Asp Glu Phe Gln Asn Ser Trp Gly Gly Gly
        35                  40                  45

Ile Gly Lys Asp Phe Gly Ser Met Asn Met Asp Glu Leu Leu Lys Asn
    50                  55                  60

Ile Trp Thr Ala Glu Glu Ser His Ser Met Met Gly Asn Asn Thr Ser
65                  70                  75                  80

Tyr Thr Asn Ile Ser Asn Gly Asn Ser Gly Asn Thr Val Ile Asn Gly
                85                  90                  95
```

```
Gly Gly Asn Asn Ile Gly Gly Leu Ala Val Gly Val Gly Gly Glu Ser
            100                 105                 110
Gly Gly Phe Phe Thr Gly Gly Ser Leu Gln Arg Gln Gly Ser Leu Thr
        115                 120                 125
Leu Pro Arg Thr Ile Ser Gln Lys Arg Val Asp Asp Val Trp Lys Glu
    130                 135                 140
Leu Met Lys Glu Asp Asp Ile Gly Asn Gly Val Val Asn Gly Gly Thr
145                 150                 155                 160
Ser Gly Ile Pro Gln Arg Gln Gln Thr Leu Gly Glu Met Thr Leu Glu
                165                 170                 175
Glu Phe Leu Val Arg Ala Gly Val Val Arg Glu Glu Pro Gln Pro Val
            180                 185                 190
Glu Ser Val Thr Asn Phe Asn Gly Gly Phe Tyr Gly Phe Gly Ser Asn
        195                 200                 205
Gly Gly Leu Gly Thr Ala Ser Asn Gly Phe Val Ala Asn Gln Pro Gln
    210                 215                 220
Asp Leu Ser Gly Asn Gly Val Ala Val Arg Gln Asp Leu Leu Thr Ala
225                 230                 235                 240
Gln Thr Gln Pro Leu Gln Met Gln Gln Pro Gln Met Val Gln Gln Pro
                245                 250                 255
Gln Met Val Gln Gln Pro Gln Gln Leu Ile Gln Thr Gln Glu Arg Pro
            260                 265                 270
Phe Pro Lys Gln Thr Thr Ile Ala Phe Ser Asn Thr Val Asp Val Val
        275                 280                 285
Asn Arg Ser Gln Pro Ala Thr Gln Cys Gln Glu Val Lys Pro Ser Ile
    290                 295                 300
Leu Gly Ile His Asn His Pro Met Asn Asn Asn Leu Leu Gln Ala Val
305                 310                 315                 320
Asp Phe Lys Thr Gly Val Thr Val Ala Ala Val Ser Pro Gly Ser Gln
                325                 330                 335
Met Ser Pro Asp Leu Thr Pro Lys Ser Ala Leu Asp Ala Ser Leu Ser
            340                 345                 350
Pro Val Pro Tyr Met Phe Gly Arg Val Arg Lys Thr Gly Ala Val Leu
        355                 360                 365
Glu Lys Val Ile Glu Arg Arg Gln Lys Arg Met Ile Lys Asn Arg Glu
    370                 375                 380
Ser Ala Ala Arg Ser Arg Ala Arg Lys Gln Ala Tyr Thr Met Glu Leu
385                 390                 395                 400
Glu Ala Glu Ile Ala Gln Leu Lys Glu Leu Asn Glu Glu Leu Gln Lys
                405                 410                 415
Lys Gln Val Glu Ile Met Glu Lys Gln Lys Asn Gln Leu Leu Glu Pro
            420                 425                 430
Leu Arg Gln Pro Trp Gly Met Gly Cys Lys Arg Gln Cys Leu Arg Arg
        435                 440                 445
Thr Leu Thr Gly Pro Trp
    450
```

<210> SEQ ID NO 161
<211> LENGTH: 1717
<212> TYPE: DNA
<213> ORGANISM: Arabidopsis thaliana
<220> FEATURE:
<221> NAME/KEY: CDS
<222> LOCATION: (234)..(1379)

<400> SEQUENCE: 161

```
aaaaaaaaaa aaaactgaac tcttttcgc tctggttttt ttagagagag agaaagatga      60
aaatgcgttt aattgctgtt taggtttcga attcgcgatt taaatttctg ggtttctctc     120
tgtttaagct tcttcttctt catcttctgc ttacgtttct tcttcaagga gctttcggat     180
tcttgtagaa agagtcattg ttctcttgag tgggaaacct tgaaaccatt cct atg        236
                                                            Met
                                                            1 gga aat agc agc gag gaa cca aag cct cct acc aaa tca gat aaa cca       284
Gly Asn Ser Ser Glu Glu Pro Lys Pro Pro Thr Lys Ser Asp Lys Pro
            5                  10                  15 tct tca ccc ccg gtg gat caa aca aat gtt cat gtc tac cct gat tgg       332
Ser Ser Pro Pro Val Asp Gln Thr Asn Val His Val Tyr Pro Asp Trp
        20                  25                  30 gca gct atg cag gca tat tat ggt cca aga gta gca atg cct cct tat       380
Ala Ala Met Gln Ala Tyr Tyr Gly Pro Arg Val Ala Met Pro Pro Tyr
    35                  40                  45 tac aat tca gct atg gct gca tct ggt cat cct cct cct cct tac atg       428
Tyr Asn Ser Ala Met Ala Ala Ser Gly His Pro Pro Pro Pro Tyr Met
50                  55                  60                  65 tgg aat cct cag cat atg atg tca cca tat gga gca ccc tat gct gct       476
Trp Asn Pro Gln His Met Met Ser Pro Tyr Gly Ala Pro Tyr Ala Ala
                70                  75                  80 gtt tat cct cat gga gga gga gtt tac gct cat ccc ggt att ccc atg       524
Val Tyr Pro His Gly Gly Gly Val Tyr Ala His Pro Gly Ile Pro Met
            85                  90                  95 gga tca ctg cct caa ggt caa aag gat cca cct tta aca act ccg ggg       572
Gly Ser Leu Pro Gln Gly Gln Lys Asp Pro Pro Leu Thr Thr Pro Gly
        100                 105                 110 acg ctt ttg agc atc gac act cct act aaa tct aca ggg aac aca gac       620
Thr Leu Leu Ser Ile Asp Thr Pro Thr Lys Ser Thr Gly Asn Thr Asp
    115                 120                 125 aat gga ttg atg aag aag ctg aaa gag ttt gat ggg ctt gct atg tct       668
Asn Gly Leu Met Lys Lys Leu Lys Glu Phe Asp Gly Leu Ala Met Ser
130                 135                 140                 145 cta gga aat ggg aat cct gaa aat ggt gca gat gaa cat aaa cga tca       716
Leu Gly Asn Gly Asn Pro Glu Asn Gly Ala Asp Glu His Lys Arg Ser
                150                 155                 160 cgg aac agc tca gaa act gat ggt tct act gat gga agt gat ggg aat       764
Arg Asn Ser Ser Glu Thr Asp Gly Ser Thr Asp Gly Ser Asp Gly Asn
            165                 170                 175 aca act ggg gca gat gaa ccg aaa ctt aaa aga agt cga gag gga act       812
Thr Thr Gly Ala Asp Glu Pro Lys Leu Lys Arg Ser Arg Glu Gly Thr
        180                 185                 190 cca aca aaa gat ggg aaa caa ttg gtt caa gct agc tca ttt cat tct       860
Pro Thr Lys Asp Gly Lys Gln Leu Val Gln Ala Ser Ser Phe His Ser
    195                 200                 205 gtt tct ccg tca agt ggt gat acc ggc gta aaa ctc att caa gga tct       908
Val Ser Pro Ser Ser Gly Asp Thr Gly Val Lys Leu Ile Gln Gly Ser
210                 215                 220                 225 gga gct ata ctc tct cct ggt gta agt gca aat tcc aac ccc ttc atg       956
Gly Ala Ile Leu Ser Pro Gly Val Ser Ala Asn Ser Asn Pro Phe Met
                230                 235                 240 tca caa tct tta gcc atg gtt cct cct gaa act tgg ctt cag aac gag      1004
Ser Gln Ser Leu Ala Met Val Pro Pro Glu Thr Trp Leu Gln Asn Glu
            245                 250                 255 aga gaa ctg aaa cgg gag cga agg aaa cag tct aat aga gaa tct gct      1052
Arg Glu Leu Lys Arg Glu Arg Arg Lys Gln Ser Asn Arg Glu Ser Ala
        260                 265                 270
```

```
aga agg tca aga tta agg aaa cag gcc gag aca gaa gaa ctt gct agg      1100
Arg Arg Ser Arg Leu Arg Lys Gln Ala Glu Thr Glu Glu Leu Ala Arg
    275                 280                 285 aaa gtg gaa gcc ttg aca gcc gaa aac atg gca tta aga tct gaa cta      1148
Lys Val Glu Ala Leu Thr Ala Glu Asn Met Ala Leu Arg Ser Glu Leu
290                 295                 300                 305 aac caa ctt aat gag aaa tct gat aaa cta aga gga gca aat gca acc      1196
Asn Gln Leu Asn Glu Lys Ser Asp Lys Leu Arg Gly Ala Asn Ala Thr
                310                 315                 320 ttg ttg gac aaa ctg aaa tgc tcg gaa ccc gaa aag aga gtc ccc gca      1244
Leu Leu Asp Lys Leu Lys Cys Ser Glu Pro Glu Lys Arg Val Pro Ala
            325                 330                 335 aat atg ttg tct aga gtt aag aac tca gga gct gga gat aag aac aag      1292
Asn Met Leu Ser Arg Val Lys Asn Ser Gly Ala Gly Asp Lys Asn Lys
        340                 345                 350 aac caa gga gac aat gat tct aac tct aca agc aaa ttg cat caa ctg      1340
Asn Gln Gly Asp Asn Asp Ser Asn Ser Thr Ser Lys Leu His Gln Leu
    355                 360                 365 ctc gat acg aag cct cga gct aaa gca gta gct gca ggc tgatcgatgg      1389
Leu Asp Thr Lys Pro Arg Ala Lys Ala Val Ala Ala Gly
370                 375                 380 taattcatgt cgatttctac ttaatttgtc gacataaaca aagaaaataa gtgctactaa    1449
tttcagaaaa acttgataga tagtatagta gagagagaga gagagagaga ggtgtgatga    1509
ttattgatct ataaattttc ggagagagag agggagaaag agaaacttt cctccagatg     1569 aaaatttggt gttatggttt gttactgtta atatagagag gctttctttt ttttataaaa    1629
tggcttcctt tgttgcattt ccttgtttta gacctgatgt aatttatga atcggtgtt      1689 attgctttgc gtaaaaaaaa aaaaaaaa                                       1717

<210> SEQ ID NO 162
<211> LENGTH: 382
<212> TYPE: PRT
<213> ORGANISM: Arabidopsis thaliana

<400> SEQUENCE: 162

Met Gly Asn Ser Ser Glu Glu Pro Lys Pro Thr Lys Ser Asp Lys
1               5                   10                  15

Pro Ser Ser Pro Pro Val Asp Gln Thr Asn Val His Val Tyr Pro Asp
                20                  25                  30

Trp Ala Ala Met Gln Ala Tyr Tyr Gly Pro Arg Val Ala Met Pro Pro
            35                  40                  45

Tyr Tyr Asn Ser Ala Met Ala Ala Ser Gly His Pro Pro Pro Tyr
        50                  55                  60

Met Trp Asn Pro Gln His Met Met Ser Pro Tyr Gly Ala Pro Tyr Ala
65                  70                  75                  80

Ala Val Tyr Pro His Gly Gly Val Tyr Ala His Pro Gly Ile Pro
                85                  90                  95

Met Gly Ser Leu Pro Gln Gly Gln Lys Asp Pro Pro Leu Thr Thr Pro
            100                 105                 110

Gly Thr Leu Leu Ser Ile Asp Thr Pro Thr Lys Ser Thr Gly Asn Thr
        115                 120                 125

Asp Asn Gly Leu Met Lys Lys Leu Lys Glu Phe Asp Gly Leu Ala Met
    130                 135                 140

Ser Leu Gly Asn Gly Asn Pro Glu Asn Gly Ala Asp Glu His Lys Arg
145                 150                 155                 160
```

Ser Arg Asn Ser Ser Glu Thr Asp Gly Ser Thr Asp Gly Ser Asp Gly
                165                 170                 175

Asn Thr Thr Gly Ala Asp Glu Pro Lys Leu Lys Arg Ser Arg Glu Gly
            180                 185                 190

Thr Pro Thr Lys Asp Gly Lys Gln Leu Val Gln Ala Ser Ser Phe His
        195                 200                 205

Ser Val Ser Pro Ser Ser Gly Asp Thr Gly Val Lys Leu Ile Gln Gly
    210                 215                 220

Ser Gly Ala Ile Leu Ser Pro Gly Val Ser Ala Asn Ser Asn Pro Phe
225                 230                 235                 240

Met Ser Gln Ser Leu Ala Met Val Pro Pro Glu Thr Trp Leu Gln Asn
                245                 250                 255

Glu Arg Glu Leu Lys Arg Glu Arg Lys Gln Ser Asn Arg Glu Ser
            260                 265                 270

Ala Arg Arg Ser Arg Leu Arg Lys Gln Ala Glu Thr Glu Glu Leu Ala
        275                 280                 285

Arg Lys Val Glu Ala Leu Thr Ala Glu Asn Met Ala Leu Arg Ser Glu
    290                 295                 300

Leu Asn Gln Leu Asn Glu Lys Ser Asp Lys Leu Arg Gly Ala Asn Ala
305                 310                 315                 320

Thr Leu Leu Asp Lys Leu Lys Cys Ser Glu Pro Glu Lys Arg Val Pro
                325                 330                 335

Ala Asn Met Leu Ser Arg Val Lys Asn Ser Gly Ala Gly Asp Lys Asn
            340                 345                 350

Lys Asn Gln Gly Asp Asn Asp Ser Asn Ser Thr Ser Lys Leu His Gln
        355                 360                 365

Leu Leu Asp Thr Lys Pro Arg Ala Lys Ala Val Ala Ala Gly
    370                 375                 380

<210> SEQ ID NO 163
<211> LENGTH: 1554
<212> TYPE: DNA
<213> ORGANISM: Arabidopsis thaliana
<220> FEATURE:
<221> NAME/KEY: CDS
<222> LOCATION: (162)..(1379)

<400> SEQUENCE: 163
acaaaatatc tctccctcta tctgcaaatt ttccaaagtt gcatcctttc aatttccact     60
cctctctaat ataattcaca ttttcccact attgctgatt cattttttt tgtgaattat    120 ttcaaaccca cataaaaaaa tctttgttta aatttaaaac c atg gat cct tca ttt   176
                                              Met Asp Pro Ser Phe
                                                1               5 agg ttc att aaa gag gag ttt cct gct gga ttc agt gat tct cca tca    224
Arg Phe Ile Lys Glu Glu Phe Pro Ala Gly Phe Ser Asp Ser Pro Ser
            10                  15                  20 cca cct tct tct tct tca tac ctt tat tca tct tcc atg gct gaa gca    272
Pro Pro Ser Ser Ser Ser Tyr Leu Tyr Ser Ser Ser Met Ala Glu Ala
        25                  30                  35 gcc ata aat gat cca aca aca ttg agc tat cca caa cca tta gaa ggt    320
Ala Ile Asn Asp Pro Thr Thr Leu Ser Tyr Pro Gln Pro Leu Glu Gly
    40                  45                  50 ctc cat gaa tca ggg cca cct cca ttt ttg aca aag aca tat gac ttg    368
Leu His Glu Ser Gly Pro Pro Pro Phe Leu Thr Lys Thr Tyr Asp Leu
55                  60                  65 gtg gaa gat tca aga acc aat cat gtc gtg tct tgg agc aaa tcc aat    416
Val Glu Asp Ser Arg Thr Asn His Val Val Ser Trp Ser Lys Ser Asn -continued

```
              70                  75                  80                  85
aac agc ttc att gtc tgg gat cca cag gcc ttt tct gta act ctc ctt        464
Asn Ser Phe Ile Val Trp Asp Pro Gln Ala Phe Ser Val Thr Leu Leu
                    90                  95                 100 ccc aga ttc ttc aag cac aat aac ttc tcc agt ttt gtc cgc cag ctc        512
Pro Arg Phe Phe Lys His Asn Asn Phe Ser Ser Phe Val Arg Gln Leu
               105                 110                 115 aac aca tat ggt ttc aga aag gtg aat ccg gat cgg tgg gag ttt gca        560
Asn Thr Tyr Gly Phe Arg Lys Val Asn Pro Asp Arg Trp Glu Phe Ala
           120                 125                 130 aac gaa ggg ttt ctt aga ggg caa aag cat ctc ctc aag aac ata agg        608
Asn Glu Gly Phe Leu Arg Gly Gln Lys His Leu Leu Lys Asn Ile Arg
       135                 140                 145 aga aga aaa aca agt aat aat agt aat caa atg caa caa cct caa agt        656
Arg Arg Lys Thr Ser Asn Asn Ser Asn Gln Met Gln Gln Pro Gln Ser
150                 155                 160                 165 tct gaa caa caa tct cta gac aat ttt tgc ata gaa gtg ggt agg tac        704
Ser Glu Gln Gln Ser Leu Asp Asn Phe Cys Ile Glu Val Gly Arg Tyr
                170                 175                 180 ggt cta gat gga gag atg gac agc cta agg cga gac aag caa gtg ttg        752
Gly Leu Asp Gly Glu Met Asp Ser Leu Arg Arg Asp Lys Gln Val Leu
            185                 190                 195 atg atg gag cta gtg aga cta aga cag caa caa caa agc acc aaa atg        800
Met Met Glu Leu Val Arg Leu Arg Gln Gln Gln Gln Ser Thr Lys Met
        200                 205                 210 tat ctc aca ttg att gaa gag aag ctc aag aag acc gag tca aaa caa        848
Tyr Leu Thr Leu Ile Glu Glu Lys Leu Lys Lys Thr Glu Ser Lys Gln
    215                 220                 225 aaa caa atg atg agc ttc ctt gcc cgc gca atg cag aat cca gat ttt        896
Lys Gln Met Met Ser Phe Leu Ala Arg Ala Met Gln Asn Pro Asp Phe
230                 235                 240                 245 att cag cag cta gta gag cag aag gaa aag agg aaa gag atc gaa gag        944
Ile Gln Gln Leu Val Glu Gln Lys Glu Lys Arg Lys Glu Ile Glu Glu
                250                 255                 260 gcg atc agc aag aag aga caa aga ccg atc gat caa gga aaa aga aat        992
Ala Ile Ser Lys Lys Arg Gln Arg Pro Ile Asp Gln Gly Lys Arg Asn
            265                 270                 275 gtg gaa gat tat ggt gat gaa agt ggt tat ggg aat gat gtt gca gcc       1040
Val Glu Asp Tyr Gly Asp Glu Ser Gly Tyr Gly Asn Asp Val Ala Ala
        280                 285                 290 tca tcc tca gca ttg att ggt atg agt cag gaa tat aca tat gga aac       1088
Ser Ser Ser Ala Leu Ile Gly Met Ser Gln Glu Tyr Thr Tyr Gly Asn
    295                 300                 305 atg tct gaa ttc gag atg tcg gag ttg gac aaa ctt gct atg cac att       1136
Met Ser Glu Phe Glu Met Ser Glu Leu Asp Lys Leu Ala Met His Ile
310                 315                 320                 325 caa gga ctt gga gat aat tcc agt gct agg gaa gaa gtc ttg aat gtg       1184
Gln Gly Leu Gly Asp Asn Ser Ser Ala Arg Glu Glu Val Leu Asn Val
                330                 335                 340 gaa aaa gga aat gat gag gaa gaa gta gaa gat caa caa caa ggg tac       1232
Glu Lys Gly Asn Asp Glu Glu Glu Val Glu Asp Gln Gln Gln Gly Tyr
            345                 350                 355 cat aag gag aac aat gag att tat ggt gaa ggt ttt tgg gaa gat ttg       1280
His Lys Glu Asn Asn Glu Ile Tyr Gly Glu Gly Phe Trp Glu Asp Leu
        360                 365                 370 tta aat gaa ggt caa aat ttt gat ttt gaa gga gat caa gaa aat gtt       1328
Leu Asn Glu Gly Gln Asn Phe Asp Phe Glu Gly Asp Gln Glu Asn Val
    375                 380                 385 gat gtg tta att cag caa ctt ggt tat ttg ggt tct agt tca cac act       1376
```

```
Asp Val Leu Ile Gln Gln Leu Gly Tyr Leu Gly Ser Ser His Thr
390                 395                 400                 405 aat taagaagaaa ttgaaatgat gactacttta agcatttgaa tcaacttgtt         1429
Asn tcctattagt aatttggctt tgtttcaatc aagtgagtcg tggactaact tattgaattt  1489
gggggttaaa tccgtttctt attttggaa ataaaattgc ttttgttta aaaaaaaaa     1549 aaaaa                                                              1554

<210> SEQ ID NO 164
<211> LENGTH: 406
<212> TYPE: PRT
<213> ORGANISM: Arabidopsis thaliana

<400> SEQUENCE: 164

Met Asp Pro Ser Phe Arg Phe Ile Lys Glu Glu Phe Pro Ala Gly Phe
 1               5                  10                  15

Ser Asp Ser Pro Ser Pro Ser Ser Ser Tyr Leu Tyr Ser Ser
             20                  25                  30

Ser Met Ala Glu Ala Ala Ile Asn Asp Pro Thr Thr Leu Ser Tyr Pro
         35                  40                  45

Gln Pro Leu Glu Gly Leu His Glu Ser Gly Pro Pro Phe Leu Thr
     50                  55                  60

Lys Thr Tyr Asp Leu Val Glu Asp Ser Arg Thr Asn His Val Val Ser
 65                  70                  75                  80

Trp Ser Lys Ser Asn Asn Ser Phe Ile Val Trp Asp Pro Gln Ala Phe
                 85                  90                  95

Ser Val Thr Leu Leu Pro Arg Phe Phe Lys His Asn Asn Phe Ser Ser
            100                 105                 110

Phe Val Arg Gln Leu Asn Thr Tyr Gly Phe Arg Lys Val Asn Pro Asp
        115                 120                 125

Arg Trp Glu Phe Ala Asn Glu Gly Phe Leu Arg Gly Gln Lys His Leu
    130                 135                 140

Leu Lys Asn Ile Arg Arg Arg Lys Thr Ser Asn Asn Ser Asn Gln Met
145                 150                 155                 160

Gln Gln Pro Gln Ser Ser Glu Gln Gln Ser Leu Asp Asn Phe Cys Ile
                165                 170                 175

Glu Val Gly Arg Tyr Gly Leu Asp Gly Glu Met Asp Ser Leu Arg Arg
            180                 185                 190

Asp Lys Gln Val Leu Met Met Glu Leu Val Arg Leu Arg Gln Gln Gln
        195                 200                 205

Gln Ser Thr Lys Met Tyr Leu Thr Leu Ile Glu Glu Lys Leu Lys Lys
    210                 215                 220

Thr Glu Ser Lys Gln Lys Gln Met Met Ser Phe Leu Ala Arg Ala Met
225                 230                 235                 240

Gln Asn Pro Asp Phe Ile Gln Leu Val Glu Gln Lys Glu Lys Arg
                245                 250                 255

Lys Glu Ile Glu Glu Ala Ile Ser Lys Lys Arg Gln Arg Pro Ile Asp
            260                 265                 270

Gln Gly Lys Arg Asn Val Glu Asp Tyr Gly Asp Glu Ser Gly Tyr Gly
        275                 280                 285

Asn Asp Val Ala Ala Ser Ser Ala Leu Ile Gly Met Ser Gln Glu
    290                 295                 300

Tyr Thr Tyr Gly Asn Met Ser Glu Phe Glu Met Ser Glu Leu Asp Lys
305                 310                 315                 320
```

```
Leu Ala Met His Ile Gln Gly Leu Gly Asp Asn Ser Ser Ala Arg Glu
            325                 330                 335

Glu Val Leu Asn Val Glu Lys Gly Asn Asp Glu Glu Glu Val Glu Asp
            340                 345                 350

Gln Gln Gln Gly Tyr His Lys Glu Asn Asn Glu Ile Tyr Gly Glu Gly
            355                 360                 365

Phe Trp Glu Asp Leu Leu Asn Glu Gly Gln Asn Phe Asp Phe Glu Gly
        370                 375                 380

Asp Gln Glu Asn Val Asp Val Leu Ile Gln Gln Leu Gly Tyr Leu Gly
385                 390                 395                 400

Ser Ser Ser His Thr Asn
            405

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 165
cgccagggtt ttcccagtca cga                                          23

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 166
agcggataac aatttcacac agga                                         24
```